US012433160B2

(12) United States Patent
Parham et al.

(10) Patent No.: US 12,433,160 B2
(45) Date of Patent: Sep. 30, 2025

(54) MATERIALS FOR ORGANIC ELECTROLUMINESCENT DEVICES

(71) Applicant: Merck Patent GmbH, Darmstadt (DE)

(72) Inventors: Amir Hossain Parham, Darmstadt (DE); Philipp Stoessel, Darmstadt (DE); Christian Ehrenreich, Darmstadt (DE)

(73) Assignee: Merck Patent GmbH, Damstadt (DE)

( * ) Notice: Subject to any disclaimer, the term of this patent is extended or adjusted under 35 U.S.C. 154(b) by 80 days.

(21) Appl. No.: 18/021,560

(22) PCT Filed: Aug. 16, 2021

(86) PCT No.: PCT/EP2021/072662
§ 371 (c)(1),
(2) Date: Feb. 16, 2023

(87) PCT Pub. No.: WO2022/038065
PCT Pub. Date: Feb. 24, 2022

(65) Prior Publication Data
US 2024/0090327 A1    Mar. 14, 2024

(30) Foreign Application Priority Data

Aug. 18, 2020 (EP) .................... 20191436

(51) Int. Cl.
| H10K 85/60 | (2023.01) |
| C07D 209/56 | (2006.01) |
| C07D 307/77 | (2006.01) |
| C07D 403/04 | (2006.01) |
| C07D 403/10 | (2006.01) |
| C07D 403/14 | (2006.01) |
| C07D 405/04 | (2006.01) |
| C07D 405/10 | (2006.01) |
| C07D 405/14 | (2006.01) |
| C07D 409/10 | (2006.01) |
| C07D 409/14 | (2006.01) |
| C07D 471/04 | (2006.01) |
| C07D 491/048 | (2006.01) |
| C07D 519/00 | (2006.01) |
| C09K 11/02 | (2006.01) |

(52) U.S. Cl.
CPC ....... *H10K 85/6572* (2023.02); *C07D 209/56* (2013.01); *C07D 307/77* (2013.01); *C07D 403/04* (2013.01); *C07D 403/10* (2013.01); *C07D 403/14* (2013.01); *C07D 405/04* (2013.01); *C07D 405/10* (2013.01); *C07D 405/14* (2013.01); *C07D 409/10* (2013.01); *C07D 409/14* (2013.01); *C07D 471/04* (2013.01); *C07D 491/048* (2013.01); *C07D 519/00* (2013.01); *C09K 11/02* (2013.01); *H10K 85/615* (2023.02); *H10K 85/626* (2023.02); *H10K 85/654* (2023.02); *H10K 85/657* (2023.02); *H10K 85/6574* (2023.02); *H10K 85/6576* (2023.02); *C07B 2200/05* (2013.01)

(58) Field of Classification Search
CPC .............. H01K 85/6572; C07D 403/14; C07D 405/10; C07D 405/14; C07D 221/18; H10K 85/6572
See application file for complete search history.

(56) References Cited

U.S. PATENT DOCUMENTS

| 2013/0200359 A1 | 8/2013 | Stoessel et al. |
| 2014/0361268 A1 | 12/2014 | Hwang et al. |
| 2019/0036059 A1 | 1/2019 | Ji et al. |
| 2019/0315759 A1 | 10/2019 | Ji et al. |

FOREIGN PATENT DOCUMENTS

| CN | 103180407 A | 6/2013 |
| CN | 107722021 A | 2/2018 |
| CN | 109305974 A | 2/2019 |
| CN | 110330481 A | 10/2019 |
| CN | 110437241 A | 11/2019 |
| CN | 110437242 A | 11/2019 |
| CN | 110724105 A | 1/2020 |
| CN | 110862381 A | 3/2020 |
| JP | 2004-018665 A | 1/2004 |
| KR | 2015-0037703 A | 4/2015 |
| WO | 2011/116865 A1 | 9/2011 |
| WO | 2011/137951 A1 | 11/2011 |
| WO | 2012/048781 A1 | 4/2012 |
| WO | 2013/064206 A1 | 5/2013 |
| WO | 2021/030287 A1 | 2/2021 |

OTHER PUBLICATIONS

International Search Report received for PCT Patent Application No. PCT/EP2021/072662, mailed on Jan. 19, 2022, 12 pages (5 pages of English Translation and 7 pages of Original Document).
Laatsch et al., "Zur Struktur cyclotrimerer 1,4-Chinone, On the Structure of Cyclotrimeric 1,4-Quinones", LIEB/GS Annalen Der Chemie, Verlag Chemie GMBH, vol. 1992, No. 11, Nov. 20, 1992, pp. 1125-1130.
Laatsch,. "Dimere Naphthochinone. XIV. Zwischenstufen der cyclo Trimerisierung von Naphthochinon: Synthese von Hydroxyhepta[2.2.2]starphenchinonen", LIEB/GS Annalen Der Chemie, vol. 3, 1985, pp. 605-619.
Naomichi et al., "Photochemical Synthesis and Electrochemical Behavior of Triphenyleno[4.5-bcd]thiophene and Triphenyleno[4.5-bcd]selenophene Derivatives", Heterocycles, vol. 35, No. 1, Jan. 1, 1993, p. 53.
Pummerer et al., Polymerization processes. Condensation of 1,4-naphthoquinone to triphthaloylbenzene with pyridine, Berichte der Deutschen Chemischen Gesellschaft [Abteilung] B, Abhandlungen, 1938, 71B, pp. 2569-2583.

(Continued)

*Primary Examiner* — Khanh T Nguyen

(74) *Attorney, Agent, or Firm* — Faegre Drinker Biddle & Reath LLP

(57) ABSTRACT

The invention relates to compounds which are suitable for use in electronic devices, and electronic devices, in particular organic electroluminescent devices, containing said compounds.

11 Claims, No Drawings

(56) References Cited

OTHER PUBLICATIONS

Radulescu et al., "Spirans. XXIV. Ring additions in dispirans with 1,3-indandione groups; a new highly condensed aromatic hydrocarbon, benzonaphthanthracene", Bul. Chim., Soc. Chim. Romania [2], 1, pp. 7-17 (1939). English Abstract, CAplus Accession No. 1943:25230, ON 37:25230.
Thuß et al., "Identification and quantification of thiaarenes in the flu gas oflignite-fired domestic heating", Journal of High Resolution Chromatography, vol. 23(7/8), pp. 457-473 (2000).
Zhukov et al., "Morphological-functional changes in internal organs under sulfotrinaphthylenefuran intoxication in subacute experiment," XP055855909, Retrieve from CAplus, STN Database accession No. 1986:63697, vol. 102, Jan. 1, 1984, pp. 134-137.
STN Registry Database, CAS: 857551-26-9, 2005, pp. 1-4.

MATERIALS FOR ORGANIC ELECTROLUMINESCENT DEVICES

CROSS-REFERENCE TO RELATED APPLICATIONS

This application is a National stage application (under 35 U.S.C. § 371) of PCT/EP2021/072662, filed Aug. 16, 2021, which claims benefit of European Application No. 20191436.3, filed Aug. 18, 2020, both of which are incorporated herein by reference in their entirety.

The present invention relates to materials for use in electronic devices, especially in organic electroluminescent devices, and to electronic devices, especially organic electroluminescent devices comprising these materials.

Emitting materials used in organic electroluminescent devices (OLEDs) are frequently phosphorescent organometallic complexes. In general terms, there is still a need for improvement in OLEDs, especially also in OLEDs which exhibit triplet emission (phosphorescence), for example with regard to efficiency, operating voltage and lifetime. The properties of phosphorescent OLEDs are not just determined by the triplet emitters used. More particularly, the other materials used, such as matrix materials, are also of particular significance here. Improvements to these materials can thus also lead to improvements in the OLED properties. Suitable matrix materials for OLEDs are, for example, aromatic lactams as disclosed, for example, in WO 2011/116865, WO 2011/137951, WO 2013/064206 or KR 2015-037703.

It is an object of the present invention to provide compounds which are suitable for use in an OLED, especially as matrix material for phosphorescent emitters or as electron transport material, and which lead to improved properties therein.

It has been found that, surprisingly, this object is achieved by particular compounds described in detail hereinafter that are of good suitability for use in OLEDs. These OLEDs especially have a long lifetime, high efficiency and relatively low operating voltage. The present invention therefore provides these compounds and electronic devices, especially organic electroluminescent devices, comprising these compounds.

The present invention provides a compound of formula (1)

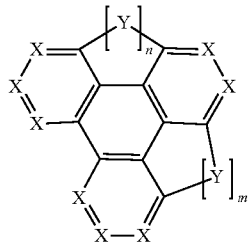

Formula (1)

where the symbols and indices used are as follows:
X is the same or different at each instance and is CR or N, with the proviso that not more than two X groups per cycle are N, and also with the proviso that two adjacent X groups that are part of the same six-membered ring are CR, where the adjacent R radicals form an aromatic or heteroaromatic ring system which has 4 to 8 ring atoms, is fused onto the cycle and may be substituted by one or more R radicals;

Y is BR, $C(R)_2$, C=O, $Si(R)_2$, NR, $NAr^1$, O, S, Se, SO, $SO_2$, PR or P(=O)R, where, in the case that m or n is 0, the carbon atoms that bind to Y are each X;

m and n are 0 or 1, where m+n is 1;

$Ar^1$ is an aromatic ring system which has 6 to 40 aromatic ring atoms and may be substituted by one or more $R^1$ radicals, or a heteroaromatic ring system which has 5 to 40 aromatic ring atoms and may be substituted by one or more $R^1$ radicals;

R is the same or different at each instance and is H, D, F, Cl, Br, I, $N(Ar')_2$, $N(R^1)_2$, $OAr'$, $SAr'$, $B(OR^1)_2$, CHO, C(=O)$R^1$, $CR^1$=C$(R^1)_2$, CN, C(=O)$OR^1$, C(=O)$NR^1$, $Si(R^1)_3$, $Ge(R^1)_3$, $NO_2$, P(=O)$(R^1)_2$, $OSO_2R^1$, $OR^1$, S(=O)$R^1$, S(=O)$_2R^1$, $SR^1$, a straight-chain alkyl group having 1 to 20 carbon atoms or an alkenyl or alkynyl group having 2 to 20 carbon atoms or a branched or cyclic alkyl group having 3 to 20 carbon atoms, where the alkyl, alkenyl or alkynyl group may be substituted in each case by one or more $R^1$ radicals, where one or more nonadjacent $CH_2$ groups may be replaced by —$R^1$C=C$R^1$—, —C≡C—, $Si(R^1)_2$, $NR^1$, $CONR^1$, C=O, C=S, —C(=O)O—, P(=O)($R^1$), —O—, —S—, SO or $SO_2$, or an aromatic or heteroaromatic ring system which has 5 to 60 aromatic ring atoms, preferably 5 to 40 aromatic ring atoms, and may be substituted in each case by one or more $R^1$ radicals, where two or more R radicals bonded to the same cycle may together form an aliphatic, heteroaliphatic, aromatic or heteroaromatic ring system which may be substituted by one or more $R^1$ radicals, and where two R radicals bonded to the same carbon or silicon atom may together form a monocyclic or polycyclic, aliphatic, aromatic or heteroaromatic ring system which may be substituted by one or more $R^1$ radicals;

Ar' is the same or different at each instance and is an aromatic or heteroaromatic ring system which has 5 to 40 aromatic ring atoms and may be substituted by one or more $R^1$ radicals;

$R^1$ is the same or different at each instance and is H, D, F, I, $B(OR^2)_2$, $N(R^2)_2$, CHO, C(=O)$R^2$, $CR^2$=C$(R^2)_2$, CN, C(=O)$OR^2$, $Si(R^2)_3$, $NO_2$, P(=O)$(R^2)_2$, $OSO_2R^2$, $SR^2$, $OR^2$, S(=O)$R^2$, S(=O)$_2R^2$, a straight-chain alkyl group having 1 to 20 carbon atoms or an alkenyl or alkynyl group having 2 to 20 carbon atoms or a branched or cyclic alkyl group having 3 to 20 carbon atoms, where the alkyl, alkenyl or alkynyl group may in each case be substituted by one or more $R^2$ radicals and where one or more $CH_2$ groups in the abovementioned groups may be replaced by —$R^2$C=C$R^2$—, —C≡C—, $Si(R^2)_2$, C=O, C=S, —C(=O)O—, $NR^2$, $CONR^2$, P(=O)($R^2$), —O—, —S—, SO or $SO_2$, and where one or more hydrogen atoms in the abovementioned groups may be replaced by D, F, Cl, Br, I, CN or $NO_2$, or an aromatic or heteroaromatic ring system which has 5 to 30 aromatic ring atoms and may be substituted in each case by one or more $R^2$ radicals, where two or more $R^1$ radicals together may form an aliphatic, heteroaliphatic, aromatic or heteroaromatic ring system;

$R^2$ is the same or different at each instance and is H, D, F, CN or an aliphatic, aromatic or heteroaromatic organic radical having 1 to 20 carbon atoms, in which one or more hydrogen atoms may also be replaced by D or F; at the same time, two or more $R^2$ substituents may be joined to one another and may form a ring.

An aryl group in the context of this invention contains 6 to 40 carbon atoms; a heteroaryl group in the context of this invention contains 2 to 40 carbon atoms and at least one heteroatom, with the proviso that the sum total of carbon atoms and heteroatoms is at least 5. The heteroatoms are preferably selected from N, O and/or S. An aryl group or heteroaryl group is understood here to mean either a simple aromatic cycle, i.e. benzene, or a simple heteroaromatic cycle, for example pyridine, pyrimidine, thiophene, etc., or a fused (annelated) aryl or heteroaryl group, for example naphthalene, anthracene, phenanthrene, quinoline, isoquinoline, etc. Aromatics joined to one another by a single bond, for example biphenyl, by contrast, are not referred to as an aryl or heteroaryl group but as an aromatic ring system.

An aromatic ring system in the context of this invention contains 6 to 60 carbon atoms, preferably 6 to 40 carbon atoms, in the ring system. A heteroaromatic ring system in the context of this invention contains 2 to 60 carbon atoms, preferably 2 to 40 carbon atoms, and at least one heteroatom in the ring system, with the proviso that the sum total of carbon atoms and heteroatoms is at least 5. The heteroatoms are preferably selected from N, O and/or S. An aromatic or heteroaromatic ring system in the context of this invention shall be understood to mean a system which does not necessarily contain only aryl or heteroaryl groups, but in which it is also possible for two or more aryl or heteroaryl groups to be joined by a non-aromatic unit, for example a carbon, nitrogen or oxygen atom. These shall likewise be understood to mean systems in which two or more aryl or heteroaryl groups are joined directly to one another, for example biphenyl, terphenyl, bipyridine or phenylpyridine. For example, systems such as fluorene, 9,9'-spirobifluorene, 9,9-diarylfluorene, triarylamine, diaryl ethers, stilbene, etc. shall also be regarded as aromatic ring systems in the context of this invention, and likewise systems in which two or more aryl groups are joined, for example, by a short alkyl group.

Preferred aromatic or heteroaromatic ring systems are simple aryl or heteroaryl groups and groups in which two or more aryl or heteroaryl groups are joined directly to one another, for example biphenyl or bipyridine, and also fluorene or spirobifluorene.

An electron-rich heteroaromatic ring system is characterized in that it is a heteroaromatic ring system containing no electron-deficient heteroaryl groups. An electron-deficient heteroaryl group is a six-membered heteroaryl group having at least one having at least one nitrogen atom or a five-membered heteroaryl group having at least two heteroatoms, one of which is a nitrogen atom and the other is oxygen, sulfur or a substituted nitrogen atom, where further aryl or heteroaryl groups may also be fused onto these groups in each case. By contrast, electron-rich heteroaryl groups are five-membered heteroaryl groups having exactly one heteroatom selected from oxygen, sulfur and substituted nitrogen, to which may be fused further aryl groups and/or further electron-rich five-membered heteroaryl groups. Thus, examples of electron-rich heteroaryl groups are pyrrole, furan, thiophene, indole, benzofuran, benzothiophene, carbazole, dibenzofuran, dibenzothiophene or indenocarbazole. An electron-rich heteroaryl group is also referred to as an electron-rich heteroaromatic radical.

An electron-deficient heteroaromatic ring system is characterized in that it contains at least one electron-deficient heteroaryl group, and especially preferably no electron-rich heteroaryl groups.

In the context of the present invention, the term "alkyl group" is used as an umbrella term both for linear and branched alkyl groups and for cyclic alkyl groups. Analogously, the terms "alkenyl group" and "alkynyl group" are used as umbrella terms both for linear or branched alkenyl or alkynyl groups and for cyclic alkenyl or alkynyl groups.

In the context of the present invention, an aliphatic hydrocarbyl radical or an alkyl group or an alkenyl or alkynyl group which may contain 1 to 40 carbon atoms and in which individual hydrogen atoms or $CH_2$ groups may also be substituted by the abovementioned groups is preferably understood to mean the methyl, ethyl, n-propyl, i-propyl, n-butyl, i-butyl, s-butyl, t-butyl, 2-methylbutyl, n-pentyl, s-pentyl, neopentyl, cyclopentyl, n-hexyl, neohexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl, heptynyl or octynyl radicals. An alkoxy group $OR^1$ having 1 to 40 carbon atoms is preferably understood to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy and 2,2,2-trifluoroethoxy. A thioalkyl group $SR^1$ having 1 to 40 carbon atoms is understood to mean especially methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio. In general, alkyl, alkoxy or thioalkyl groups according to the present invention may be straight-chain, branched or cyclic, where one or more nonadjacent $CH_2$ groups may be replaced by the abovementioned groups; in addition, it is also possible for one or more hydrogen atoms to be replaced by D, F, Cl, Br, I, CN or $NO_2$, preferably F, Cl or CN, more preferably F or CN.

An aromatic or heteroaromatic ring system which has 5-60 aromatic ring atoms and may also be substituted in each case by the abovementioned $R^2$ radicals or a hydrocarbyl radical and which may be joined to the aromatic or heteroaromatic system via any desired positions is understood to mean especially groups derived from benzene, naphthalene, anthracene, benzanthracene, phenanthrene, pyrene, chrysene, perylene, fluoranthene, naphthacene, pentacene, benzopyrene, biphenyl, biphenylene, terphenyl, triphenylene, fluorene, spirobifluorene, dihydrophenanthrene, dihydropyrene, tetrahydropyrene, cis- or trans-indenofluorene, cis- or trans-indenocarbazole, cis- or trans-indolocarbazole, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, hexaazatriphenylene, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole, or groups derived from a combination of these systems.

The wording that two or more radicals together may form a ring system, in the context of the present description, should be understood to mean, inter alia, that the two radicals are joined to one another by a chemical bond with formal elimination of two hydrogen atoms. This is illustrated by the following scheme:

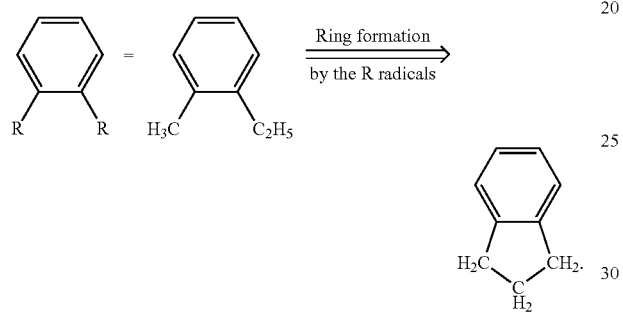

In addition, however, the abovementioned wording shall also be understood to mean that, if one of the two radicals is hydrogen, the second radical binds to the position to which the hydrogen atom was bonded, forming a ring. This will be illustrated by the following scheme:

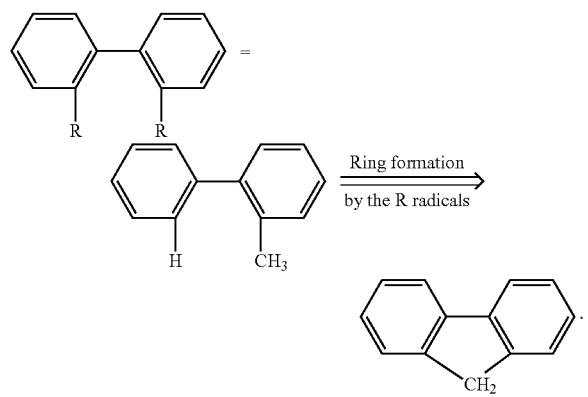

In a preferred embodiment, the compound comprises a structure of the abovementioned formula (1) and formula (2)

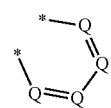

Formula (2)

where the symbols used have the definitions given above, and in addition:

X is the same or different at each instance and is CR or N, with the proviso that not more than two X groups per cycle are N, and also with the proviso that two adjacent X groups that are part of the same cycle are C, at which a group of the formula (2), via the bonds identified by *, forms an aromatic or heteroaromatic ring system fused onto the cycle;

Q is the same or different at each instance and is $CR^1$ or N, with the proviso that at most two Q groups per ring are N.

Further preferred embodiments are shown by the following formulae (3) and (4):

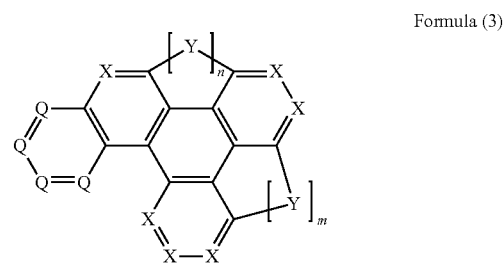

Formula (3)

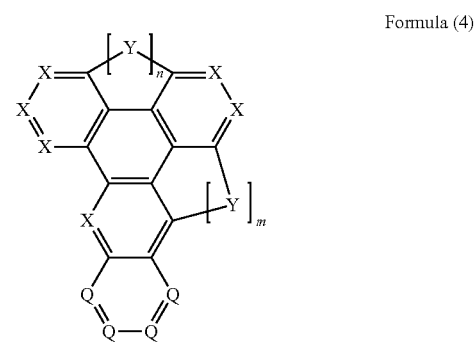

Formula (4)

where the symbols and indices used have the definitions given above for formula (1) and (2).

In a preferred embodiment of the invention, Y in the preceding and subsequent embodiments is $C(R)_2$, $NAr^1$, O or S, more preferably $NAr^1$, O or S, and most preferably $NAr^1$.

In a preferred embodiment, at least one R radical in the symbols Y, X and/or Q in the formulae (3) and (4) is an aromatic or heteroaromatic ring system which has 5 to 60 aromatic ring atoms, preferably 5 to 40 aromatic ring atoms and more preferably 6 to 24 aromatic ring atoms, and may be substituted in each case by one or more $R^1$ radicals, where the $R^1$ radicals are preferably nonaromatic.

In a preferred embodiment of the invention, not more than one symbol X per cycle is N, more preferably no symbol X.

In a preferred embodiment of the invention, X and Q are CR.

Further preferred embodiments are shown by the following formulae (5) to (8):

Formula (5)
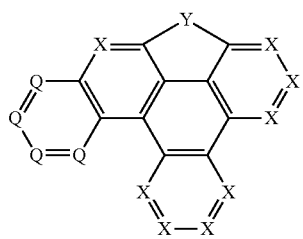

Formula (6)
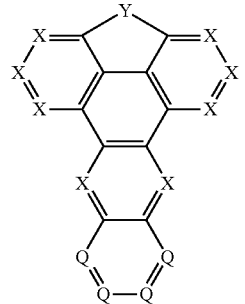

Formula (7)
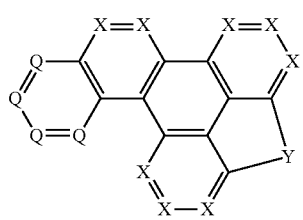

Formula (8)
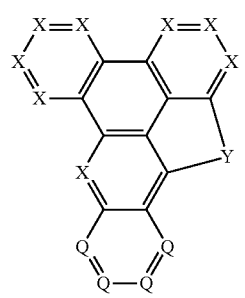

where the symbols used have the definitions given above for formula (2).

Preferred embodiments of the compounds of the formulae (5) to (8) are thus the following compounds of the formulae (5-1) to (8-1):

Formula (5-1)
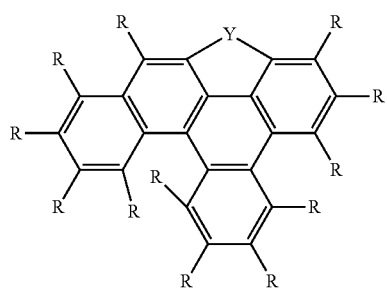

Formula (6-1)
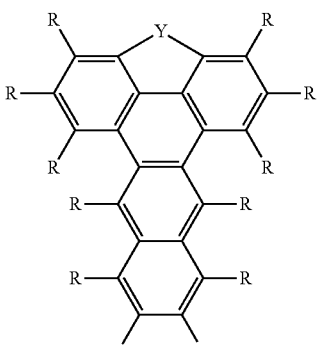

Formula (7-1)
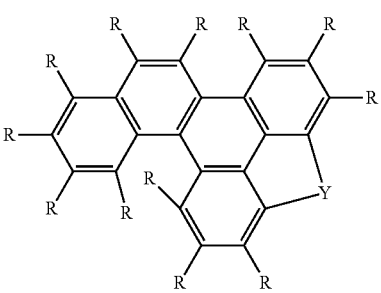

Formula (8-1)
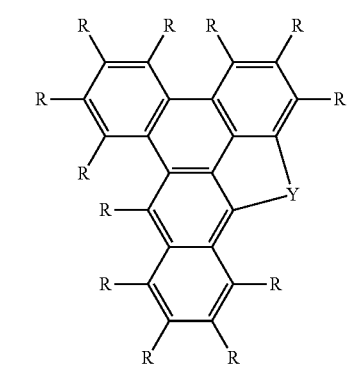

where the symbols, if present, have the definitions given for the formulae (5) to (8).

In a preferred embodiment of the invention, not more than 4 R groups in the formulae (5) to (8), preferably in the formulae (5-1) to (8-1), are not H, CN or D, more preferably not more than 3 R groups and most preferably not more than two R groups.

In a preferred embodiment of the invention, not more than 4 R groups in the formulae (5) to (8), preferably in the formulae (5-1) to (8-1), are not H, CN or D, preferably not more than 3 R groups and most preferably not more than one R group, in which case R is an aromatic or heteroaromatic ring system which has 5 to 60 aromatic ring atoms, preferably 5 to 40 aromatic ring atoms and more preferably 6 to 24 aromatic ring atoms, and may be substituted in each case by one or more $R^1$ radicals.

If Y=NAr$^1$, especially in the formulae (5) to (8), preferably in the formulae (5-1) to (8-1), in a preferred embodiment, not more than one R radical and more preferably no R is an aromatic or heteroaromatic ring system which has 5 to 60 aromatic ring atoms, preferably 5 to 40 aromatic ring atoms, more preferably 6 to 24 aromatic ring atoms; in particular, all R are H, D or CN, preferably H or D; it is more preferable when Ar$^1$ is an electron-deficient heteroaromatic ring system, especially an electron-deficient heteroaromatic.

In the case that Y=NAr¹ where Ar¹ is an aromatic ring system or an electron-rich heteroaromatic ring system, in a preferred embodiment, not more than 2 R radicals, preferably not more than one R radical, is an aromatic or heteroaromatic ring system which has 5 to 60 aromatic ring atoms, preferably 5 to 40 aromatic ring atoms, more preferably 6 to 24 aromatic ring atoms, where the two R radicals are not bonded to the same cycle.

In the case that Y=O or S, in a preferred embodiment, not more than 3 R groups, preferably not more than two R radicals, especially only one R radical, are an aromatic or heteroaromatic ring system having 5 to 60 aromatic ring atoms, preferably having 5 to 40 aromatic ring atoms, more preferably having 6 to 24 aromatic ring atoms, where all R radicals are bonded to a different cycle.

Further preferred embodiments of the formulae (5) to (8) are shown by the following formulae (5-1-1) to (8-1-4):

Formula (5-1-1)
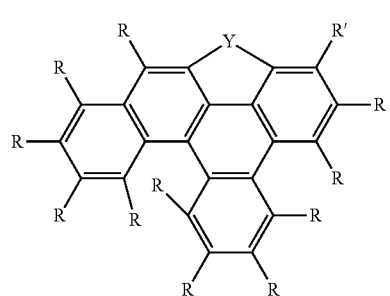

Formula (5-1-2)
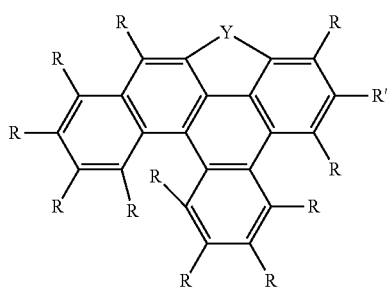

Formula (5-1-3)
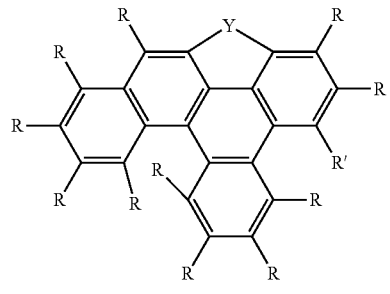

Formula (5-1-4)
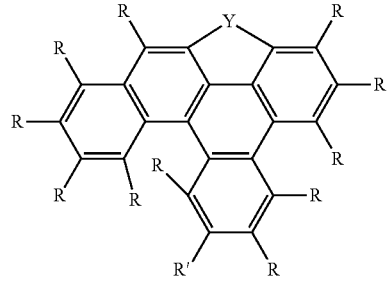

Formula (5-1-5)
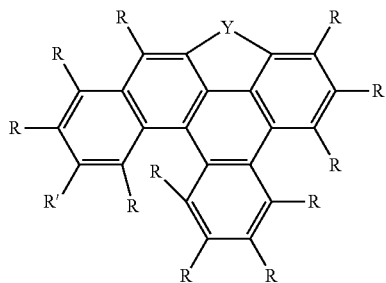

(6-1-1)
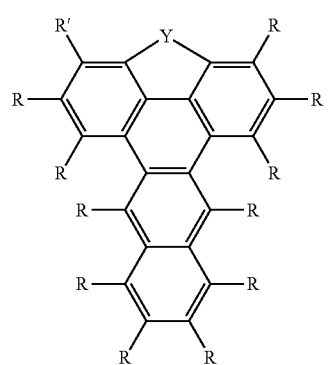

(6-1-2)
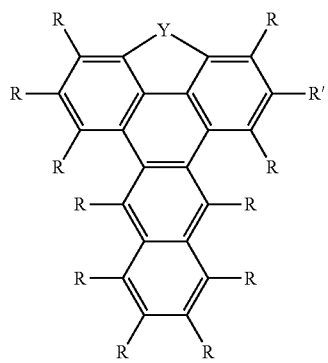

(6-1-3)
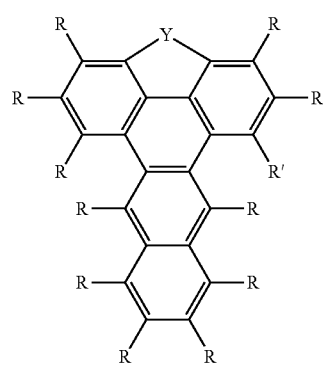

-continued
(6-1-4)
(7-1-1)
(7-1-2)
(7-1-3)
(7-1-4)
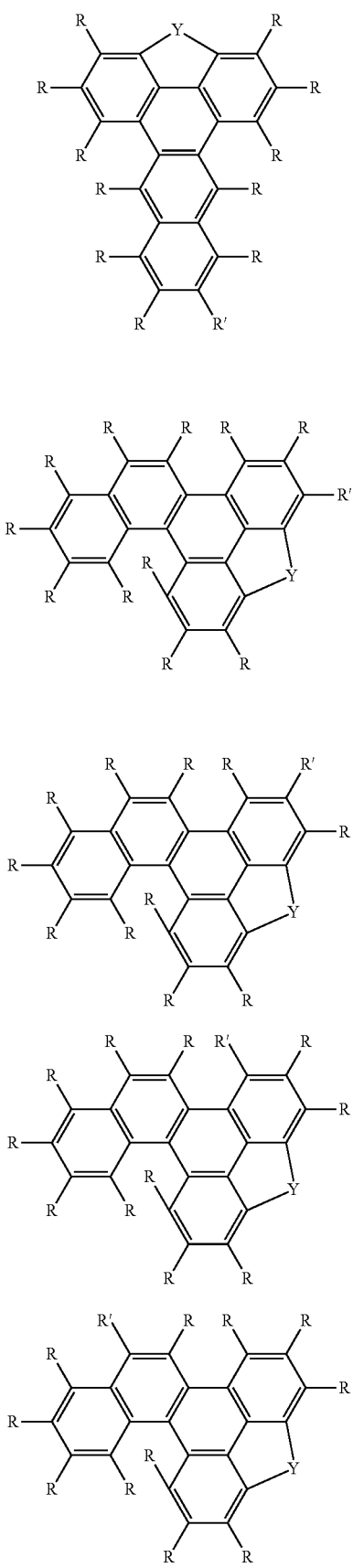
-continued
(8-1-1)
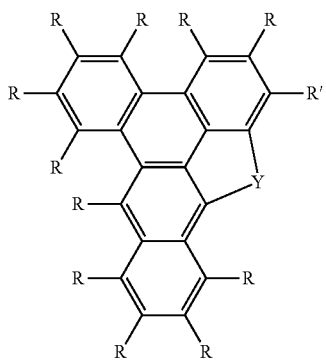
(8-1-2)
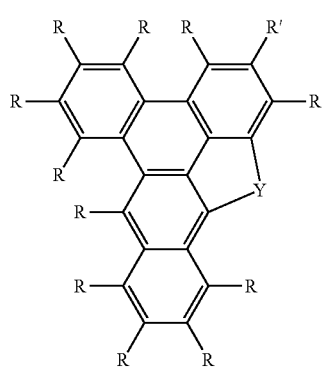
(8-1-3)
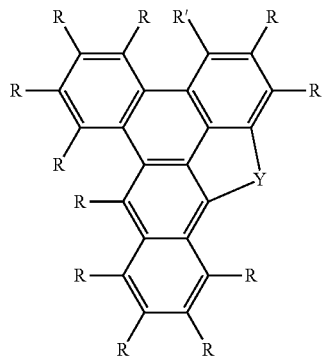
(8-1-4)
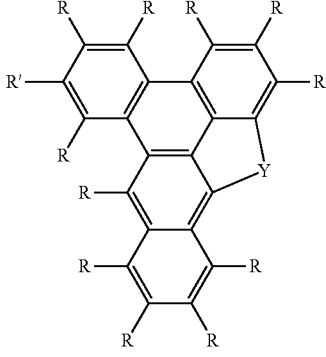
where the symbols, if present, have the definitions given for the formulae (5) to (8), and in addition:
R' is the same or different at each instance or is an aromatic or heteroaromatic ring system which has 5 to 60 aromatic ring atoms, preferably 6 to 40 aromatic ring atoms, and may be substituted in each case by one or more $R^1$ groups.

In a preferred embodiment, only up to 2 further R in the formulae (5-1-1) to (8-1-4) are the same or different at each instance and are an aromatic or heteroaromatic ring system which has 5 to 60 aromatic ring atoms, preferably 5 to 40 aromatic ring atoms and more preferably 6 to 24 aromatic ring atoms, and may be substituted in each case by one or more $R^1$ groups.

In the case that Y=NAr' where $Ar^1$ is an aromatic or electron-rich heteroaromatic ring system having 5 to 60 aromatic ring atoms, preferably having 5 to 40 aromatic ring atoms and more preferably having 6 to 24 aromatic ring atoms, preference is given to compounds of the formulae (5-1-1), (5-1-2), (5-1-3), (6-1-1), (6-1-2), (6-1-3), (7-1-1), (7-1-2), (7-1-3), (7-1-4), (8-1-1), (8-1-2) and (8-1-3), where preferably only not more than one R radical is an aromatic or heteroaromatic ring system having 5 to 60 aromatic ring atoms, preferably having 6 to 40 aromatic ring atoms and more preferably having 6 to 24 aromatic ring atoms, where this R does not bind the same cycle as R'.

In the case that Y=O or S, preferably O, preference is given to compounds of the formulae (5-1-1), (5-1-2), (5-1-4), (5-1-5), (6-1-1), (6-1-2), (6-1-4), (7-1-1), (7-1-2), (7-1-3), (8-1-1), (8-1-2) and (8-1-4), where preferably only not more than one R radical is an aromatic or heteroaromatic ring system having 5 to 60 aromatic ring atoms, preferably having 6 to 40 aromatic ring atoms and more preferably having 6 to 24 aromatic ring atoms, where this R does not bind the same cycle as R'.

There follows a description of preferred substituents R, $Ar^1$, Ar', $R^1$ and $R^2$. In a particularly preferred embodiment of the invention, the preferences specified hereinafter for R, $Ar^1$, Ar', $R^1$ and $R^2$ occur simultaneously and are applicable to the structures of the formula (1) and to all preferred embodiments detailed above.

In a preferred embodiment of the invention, $Ar^1$ is an aromatic ring system which has 6 to 30 aromatic ring atoms and may be substituted by one or more R radicals, or a heteroaromatic ring system which has 6 to 30 aromatic ring atoms and may be substituted by one or more R radicals. In a particularly preferred embodiment of the invention, Ar is an aromatic or heteroaromatic ring system which has 6 to 24 aromatic ring atoms and may be substituted by one or more preferably nonaromatic $R^1$ radicals.

Suitable aromatic or heteroaromatic ring systems $Ar^1$ are the same or different at each instance and are selected from phenyl, biphenyl, especially ortho-, meta- or para-biphenyl, terphenyl, especially ortho-, meta- or para-terphenyl or branched terphenyl, quaterphenyl, especially ortho-, meta- or para-quaterphenyl or branched quaterphenyl, fluorene which may be joined via the 1, 2, 3 or 4 position, spirobifluorene which may be joined via the 1, 2, 3 or 4 position, naphthalene which may be joined via the 1 or 2 position, indole, benzofuran, benzothiophene, dibenzofuran, carbazole which may be joined via the 1, 2, 3 or 4 position, dibenzofuran which may be joined via the 1, 2, 3 or 4 position, dibenzothiophene which may be joined via the 1, 2, 3 or 4 position, indenocarbazole, indolocarbazole, phenanthrene, triphenylene or a combination of two or three of these groups, each of which may be substituted by one or more $R^1$ radicals, preferably nonaromatic $R^1$ radicals.

Further preferred embodiments of $Ar^1$, when these represent a heteroaromatic ring system, are selected from the group consisting of pyridine, pyrimidine, pyrazine, pyridazine, triazine, quinoline, quinazoline, quinoxaline and benzimidazole or a combination of these groups with one of the abovementioned groups, each of which may be substituted by one or more $R^1$ radicals. When $Ar^1$ is a heteroaryl group, especially triazine, pyrimidine, quinazoline or quinoxaline, preference may also be given to aromatic or heteroaromatic $R^1$ radicals on this heteroaryl group.

In a preferred embodiment of the invention, R is the same or different at each instance and is selected from the group consisting of H, D, F, CN, $OR^1$, a straight-chain alkyl group having 1 to 10 carbon atoms or an alkenyl group having 2 to 10 carbon atoms or a branched or cyclic alkyl group having 3 to 10 carbon atoms, where the alkyl or alkenyl group may each be substituted by one or more $R^1$ radicals, but is preferably unsubstituted, and where one or more nonadjacent $CH_2$ groups may be replaced by O, or an aromatic or heteroaromatic ring system which has 6 to 30 aromatic ring atoms and may be substituted in each case by one or more $R^1$ radicals; at the same time, two R radicals together may also form an aliphatic, aromatic or heteroaromatic ring system. More preferably, R is the same or different at each instance and is selected from the group consisting of H, a straight-chain alkyl group having 1 to 6 carbon atoms, especially having 1, 2, 3 or 4 carbon atoms, or a branched or cyclic alkyl group having 3 to 6 carbon atoms, where the alkyl group in each case may be substituted by one or more $R^1$ radicals, but is preferably unsubstituted, or an aromatic or heteroaromatic ring system which has 6 to 24 aromatic ring atoms and may be substituted in each case by one or more $R^1$ radicals, preferably nonaromatic $R^1$ radicals. Most preferably, R is the same or different at each instance and is selected from the group consisting of H or an aromatic or heteroaromatic ring system which has 6 to 24 aromatic ring atoms and may be substituted in each case by one or more $R^2$ radicals, preferably nonaromatic $R^1$ radicals.

Suitable aromatic or heteroaromatic ring systems R are selected from phenyl, biphenyl, especially ortho-, meta- or para-biphenyl, terphenyl, especially ortho-, meta- or para-terphenyl or branched terphenyl, quaterphenyl, especially ortho-, meta- or para-quaterphenyl or branched quaterphenyl, fluorene which may be joined via the 1, 2, 3 or 4 position, spirobifluorene which may be joined via the 1, 2, 3 or 4 position, naphthalene which may be joined via the 1 or 2 position, indole, benzofuran, benzothiophene which may be joined via the 1, 2, 3 or 4 position, dibenzofuran, carbazole which may be joined via the 1, 2, 3 or 4 position, dibenzothiophene which may be joined via the 1, 2, 3 or 4 position, indenocarbazole, indolocarbazole, pyridine, pyrimidine, pyrazine, pyridazine, triazine, quinoline, quinazoline, benzimidazole, phenanthrene, triphenylene or a combination of two or three of these groups, each of which may be substituted by one or more $R^1$ radicals. When R is a heteroaryl group, especially triazine, pyrimidine or quinazoline, preference may also be given to aromatic or heteroaromatic $R^1$ radicals on this heteroaryl group.

The R groups here, or $Ar^1$ when they are an aromatic or heteroaromatic ring system, are preferably selected from the groups of the following formulae R-1 to R-82:

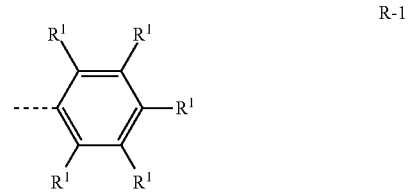

R-1

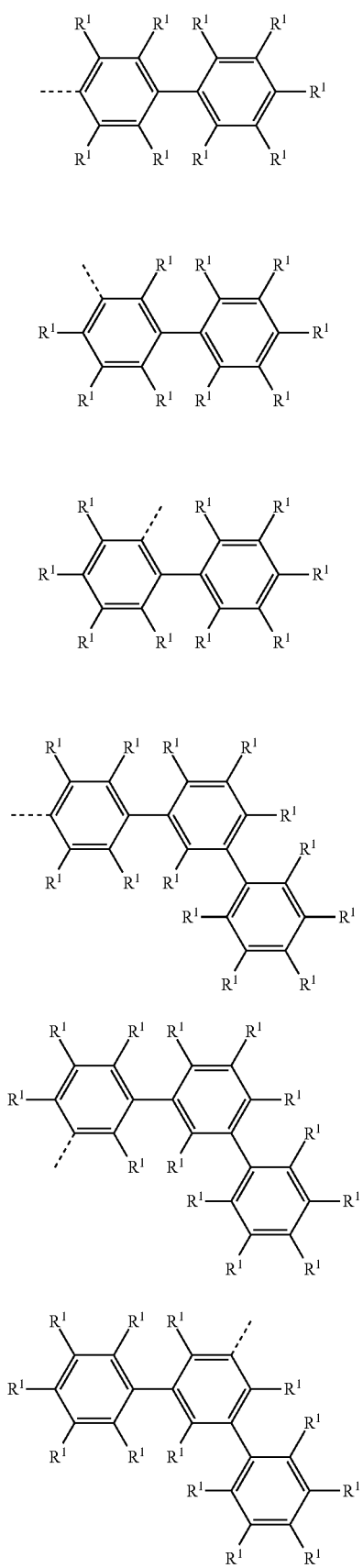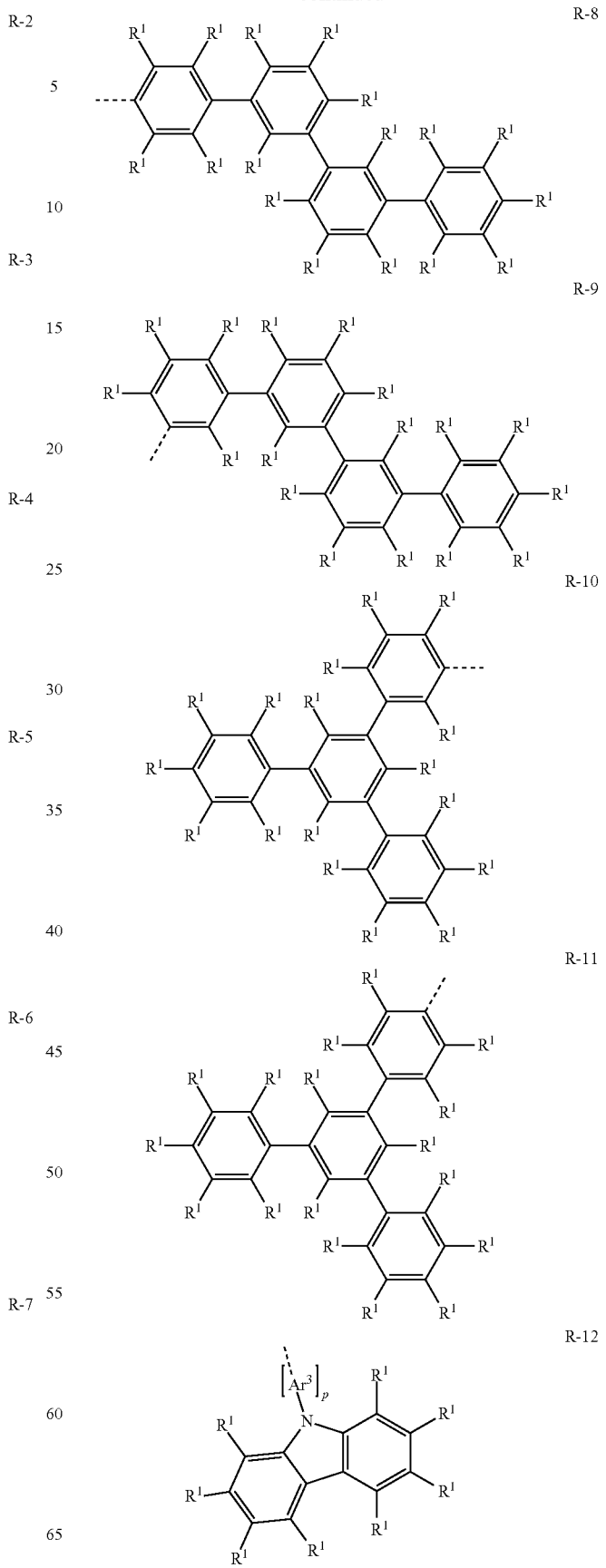

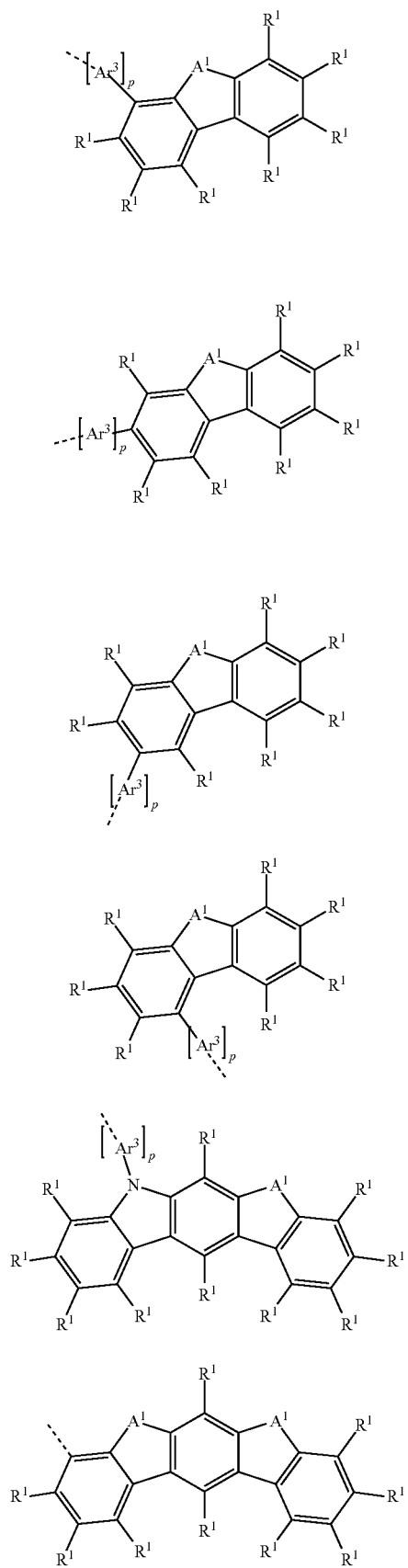
R-13
R-14
R-15
R-16
R-17
R-18
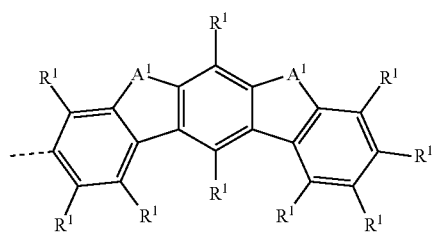
R-19
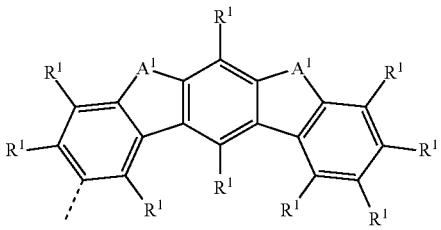
R-20
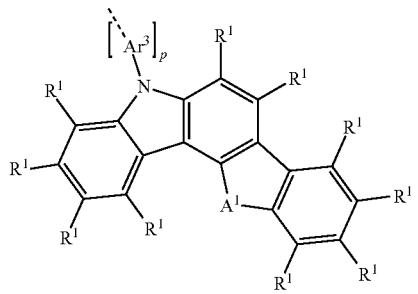
R-21
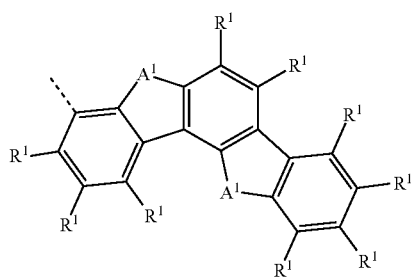
R-22
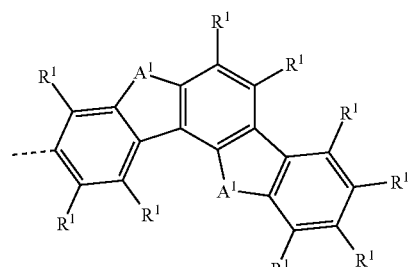
R-23
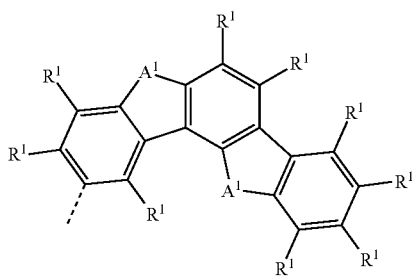
R-24

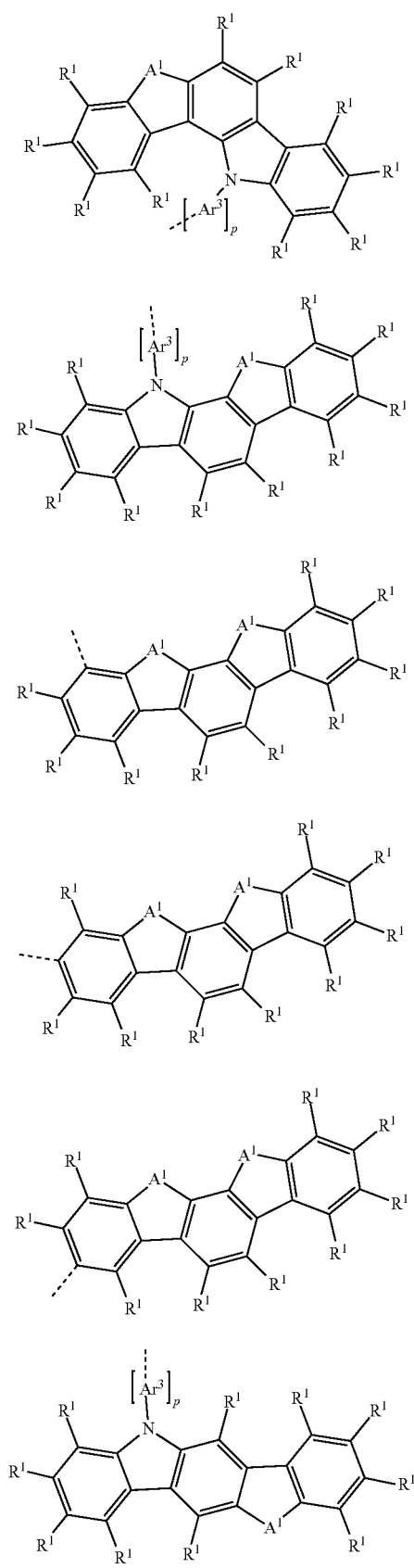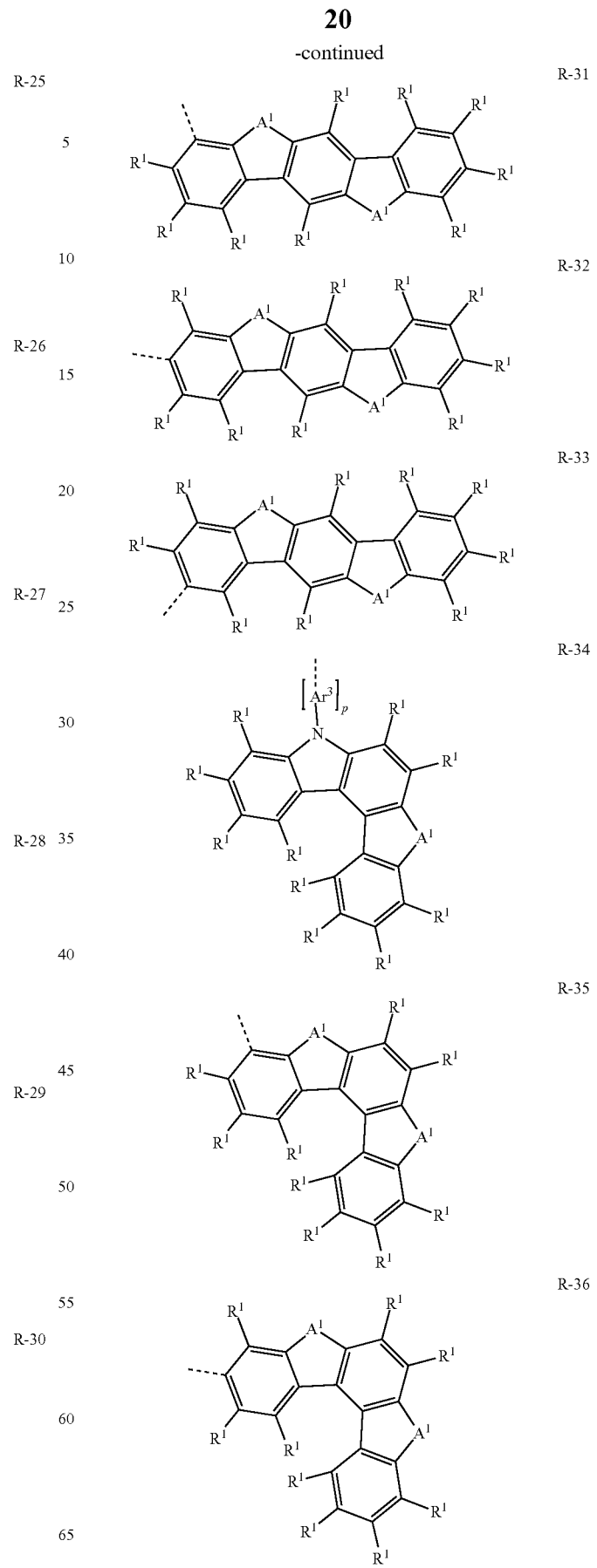

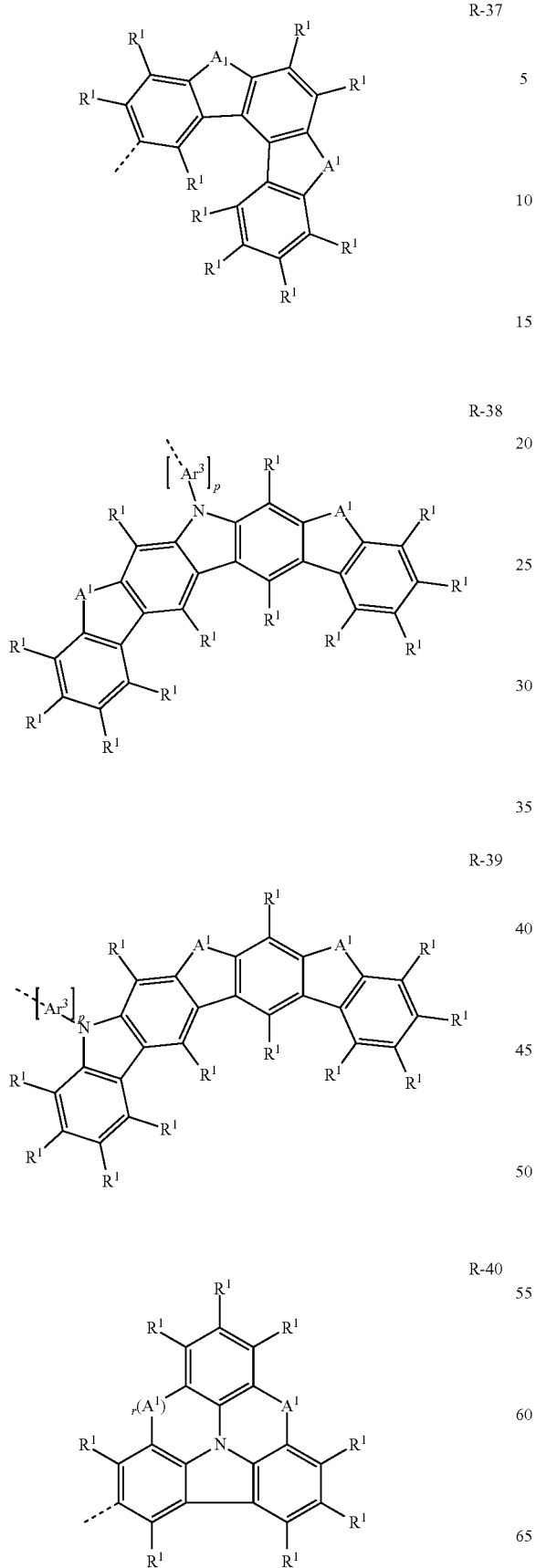
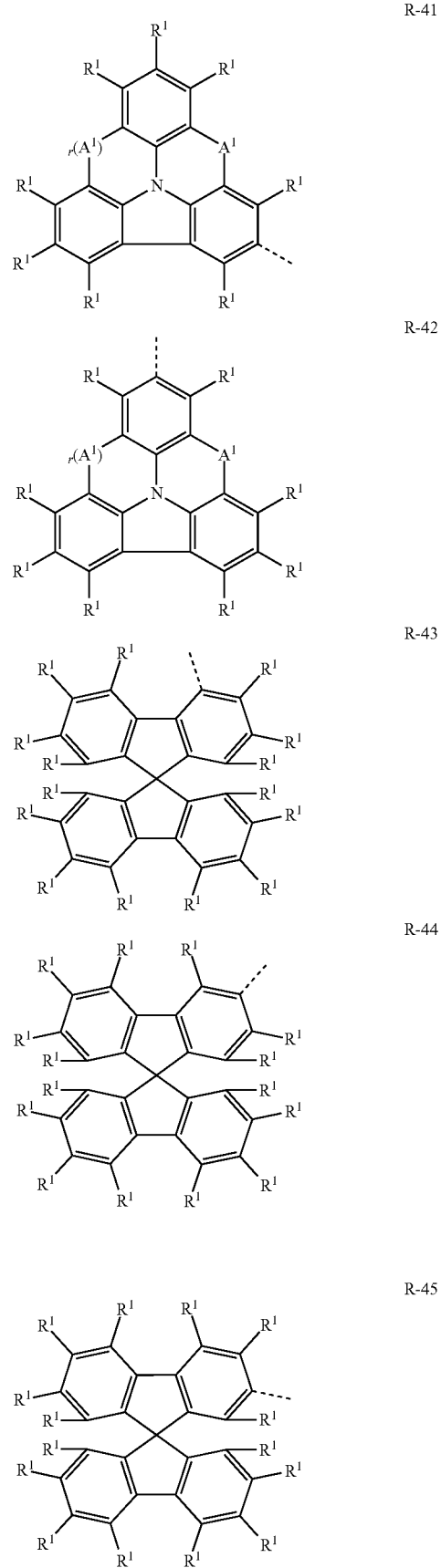

-continued
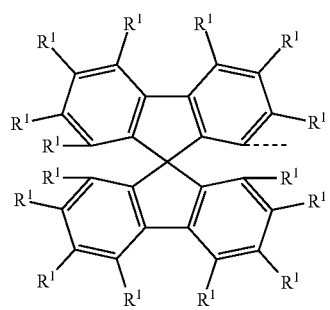
R-46
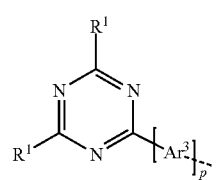
R-47
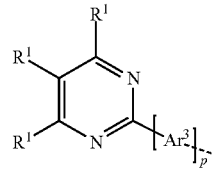
R-48
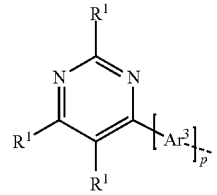
R-49
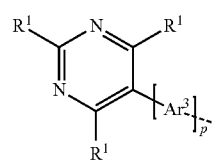
R-50
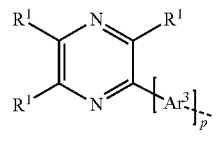
R-51
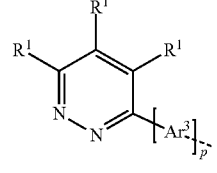
R-52
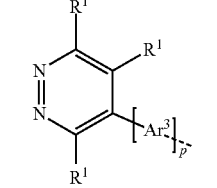
R-53
-continued
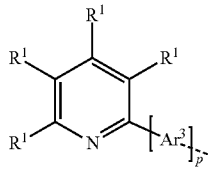
R-54
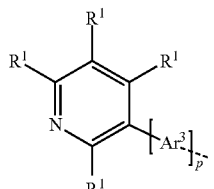
R-55
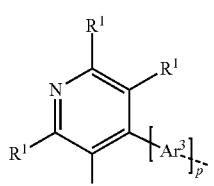
R-56
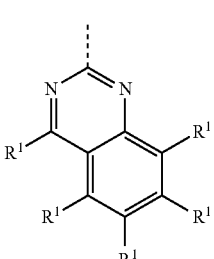
R-57
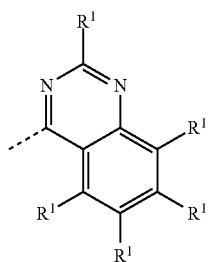
R-58
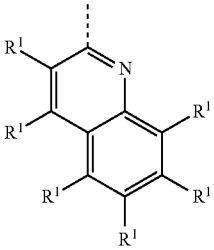
R-59
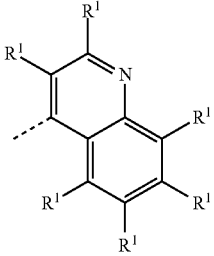
R-60

-continued
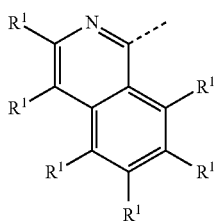
R-61
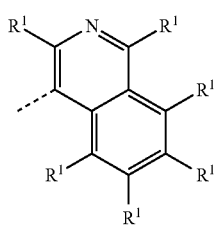
R-62
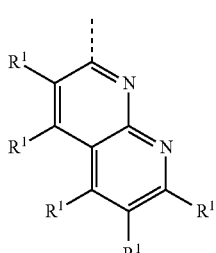
R-63
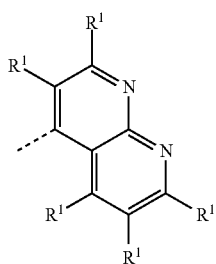
R-64
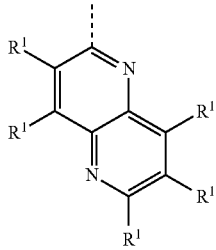
R-65
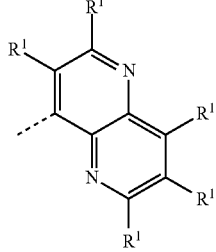
R-66
-continued
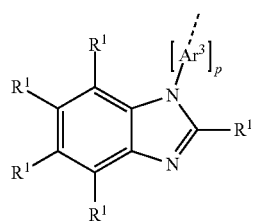
R-67
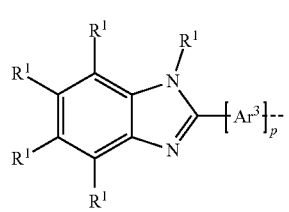
R-68
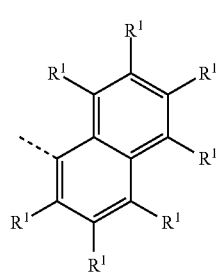
R-69
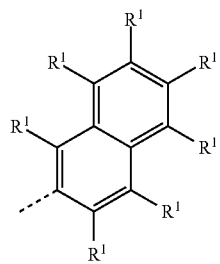
R-70
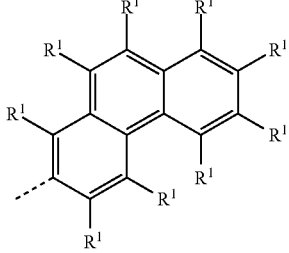
R-71
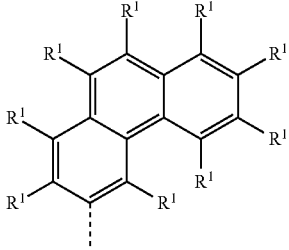
R-72

R-73
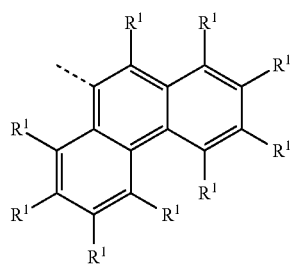

R-74
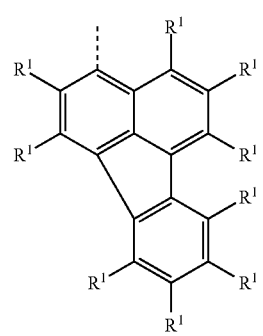

R-75
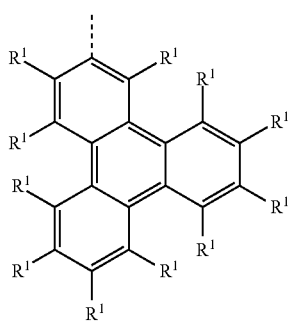

R-76
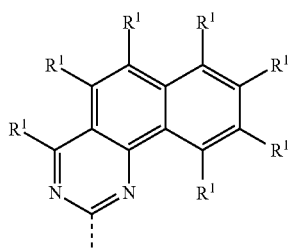

R-77
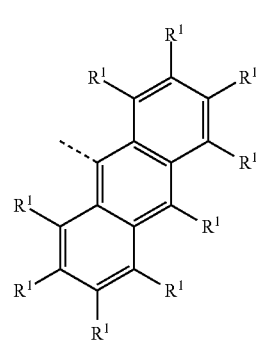

R-78
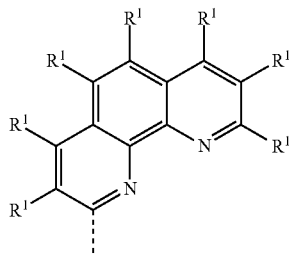

R-79
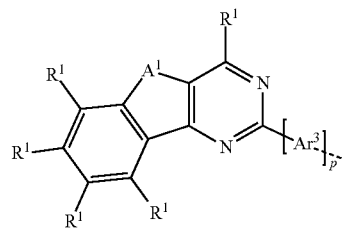

R-80
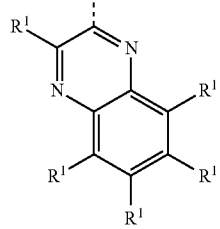

R-81
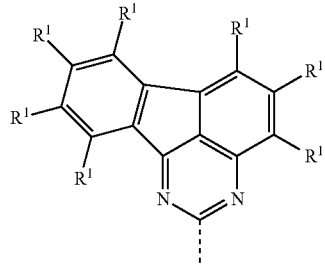

R-82
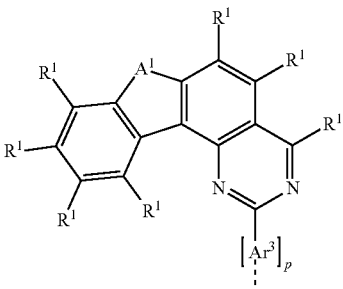

where $R^1$ has the definitions given above, the dotted bond represents the bond to a carbon atom of the base skeleton in formula (1) or in the preferred embodiments, or to a heteroatom of the $N(Ar')_2$ or $NR_2$ group and, in addition:

$Ar^3$ is the same or different at each instance and is a bivalent aromatic or heteroaromatic ring system which has 6 to 18 aromatic ring atoms and may be substituted in each case by one or more $R^1$ radicals;

$A^1$ is the same or different at each instance and is $C(R^1)_2$, $NR^1$, O or S, preferably O or S;

p is 0 or 1, where m=0 means that the $Ar^3$ group is absent and that the corresponding aromatic or heteroaromatic group is bonded directly to a carbon atom of the base skeleton in formula (1) or in the preferred embodiments, or to the nitrogen atom in the $N(Ar^1)_2$ group; with the proviso that m=1 for the structures R-12, R-17, R-21, R-25, R-26, R-30, R-34, R-38, R-39 and R-67 when these groups are embodiments of $Ar^1$;

r is 0 or 1, where r=0 means that no A group is bonded at this position and $R^1$ radicals are bonded to the corresponding carbon atoms in its place.

In a preferred embodiment, $Ar^3$ comprises bivalent aromatic or heteroaromatic ring systems based on the groups of R-1 to R-82, where m=0 and the dotted bond and an $R^1$ represents the bond to the aromatic or heteroaromatic group according to R-1 to R 82.

When the abovementioned R-1 to R-82 groups for R, or $Ar^1$, have two or more $A^1$ groups, possible options for these include all combinations from the definition of $A^1$. Preferred embodiments in that case are those in which one $A^1$ group is O or S and the other $A^1$ group is $C(R^1)_2$ or in which both $A^1$ groups are S or O or in which both $A^1$ groups are O or S.

When $A^1$ is $NR^1$, the substituent $R^1$ bonded to the nitrogen atom is preferably an aromatic or heteroaromatic ring system which has 5 to 24 aromatic ring atoms and may also be substituted by one or more $R^2$ radicals. In a particularly preferred embodiment, this $R^1$ substituent is the same or different at each instance and is an aromatic or heteroaromatic ring system which has 6 to 24 aromatic ring atoms, preferably 6 to 12 aromatic ring atoms, and which does not have any fused aryl groups or heteroaryl groups in which two or more aromatic or heteroaromatic 6-membered ring groups are fused directly to one another, and which may also be substituted in each case by one or more $R^2$ radicals. Particular preference is given to phenyl, biphenyl, terphenyl and quaterphenyl having bonding patterns as listed above for R-1 to R-11, where these structures may be substituted by one or more $R^1$ radicals, but are preferably unsubstituted.

When $A^1$ is $C(R^1)_2$, the substituents $R^1$ bonded to this carbon atom are preferably the same or different at each instance and are a linear alkyl group having 1 to 10 carbon atoms or a branched or cyclic alkyl group having 3 to 10 carbon atoms or an aromatic or heteroaromatic ring system having 5 to 24 aromatic ring atoms, which may also be substituted by one or more $R^2$ radicals. Most preferably, $R^1$ is a methyl group or a phenyl group. In this case, the $R^1$ radicals together may also form a ring system, which leads to a spiro system.

When Y is $CR_2$, the substituents R bonded to this carbon atom are preferably the same or different at each instance and are a linear alkyl group having 1 to 10 carbon atoms or a branched or cyclic alkyl group having 3 to 10 carbon atoms or an aromatic or electron-deficient heteroaromatic ring system having 5 to 24 aromatic ring atoms, which may also be substituted by one or more $R^1$ radicals. Most preferably, these substituents R are a methyl group or a phenyl group. In this case, the R radicals together may also form a ring system, which leads to a spiro system.

In one embodiment of the invention, at least one R or $Ar^1$ radical is an electron-rich heteroaromatic ring system. This electron-rich heteroaromatic ring system is preferably selected from the above-depicted R-13 to R-42 groups, where, in the R-13 to R-16, R-18 to R-20, R-22 to R-24, R-27 to R-29, R-31 to R-33 and R-35 to R-37 groups, at least one $A^1$ group is $NR^1$ where $R^1$ is preferably an aromatic or heteroaromatic ring system, especially an aromatic ring system.

In a further particularly preferred embodiment of the invention, at least one R, or $Ar^1$, radical is an electron-deficient heteroaromatic ring system. This electron-deficient heteroaromatic ring system is preferably selected from the above-depicted R-47 to R-50, R-57, R-58, R-76; R-79, R-80, R-81 and R-82 groups.

In a further preferred embodiment of the invention, $R^1$ is the same or different at each instance and is selected from the group consisting of H, D, F, CN, $OR^2$, a straight-chain alkyl group having 1 to 10 carbon atoms or an alkenyl group having 2 to 10 carbon atoms or a branched or cyclic alkyl group having 3 to 10 carbon atoms, where the alkyl or alkenyl group may in each case be substituted by one or more $R^2$ radicals, and where one or more nonadjacent $CH_2$ groups may be replaced by O, or an aromatic or heteroaromatic ring system which has 6 to 30 aromatic ring atoms and may be substituted in each case by one or more $R^2$ radicals; at the same time, two or more $R^1$ radicals together may form an aliphatic ring system. In a particularly preferred embodiment of the invention, $R^1$ is the same or different at each instance and is selected from the group consisting of H, a straight-chain alkyl group having 1 to 6 carbon atoms, especially having 1, 2, 3 or 4 carbon atoms, or a branched or cyclic alkyl group having 3 to 6 carbon atoms, where the alkyl group may be substituted by one or more $R^2$ radicals, but is preferably unsubstituted, or an aromatic or heteroaromatic ring system which has 6 to 24 aromatic ring atoms and may be substituted in each case by one or more $R^2$ radicals, but is preferably unsubstituted.

In a further preferred embodiment of the invention, $R^2$ is the same or different at each instance and is H, F, an alkyl group having 1 to 4 carbon atoms or an aryl group having 6 to 10 carbon atoms, which may be substituted by an alkyl group having 1 to 4 carbon atoms, but is preferably unsubstituted.

In a further preferred embodiment of the invention, all $R^1$ radicals, if they are an aromatic or heteroaromatic ring system, or $R^2$ radicals, if they are aromatic or heteroaromatic groups, are selected from the R-1 to R-82 groups, in which case these, however, are correspondingly substituted by $R^2$ rather than by $R^1$, or by the groups mentioned for $R^2$.

In a preferred embodiment, the R radicals apart from the group of the formula (2) do not form any further aromatic or heteroaromatic groups fused to the base skeleton of the formula (1).

At the same time, the alkyl groups in compounds of the invention which are processed by vacuum evaporation preferably have not more than five carbon atoms, more preferably not more than 4 carbon atoms, most preferably not more than 1 carbon atom. For compounds that are processed from solution, suitable compounds are also those substituted by alkyl groups, especially branched alkyl groups, having up to 10 carbon atoms or those substituted by oligoarylene groups, for example ortho-, meta- or para-terphenyl or branched terphenyl or quaterphenyl groups.

When the compounds of the formula (1) or the preferred embodiments are used as matrix material for a phosphorescent emitter or in a layer directly adjoining a phosphorescent layer, it is further preferable when the compound does not contain any fused aryl or heteroaryl groups in which more than two six-membered rings are fused directly to one another. It is especially preferable when the Ar, R, $R^1$ and $R^2$ radicals do not contain any fused aryl or heteroaryl groups in which two or more six-membered rings are fused directly to one another. An exception to this is formed by phenanthrene, triphenylene, quinazoline and quinoxaline, which, because of their high triplet energy, may be preferable in spite of the presence of fused aromatic six-membered rings.

The abovementioned preferred embodiments may be combined with one another as desired within the restrictions defined in claim 1. In a particularly preferred embodiment of the invention, the abovementioned preferences occur simultaneously.

Examples of preferred compounds according to the embodiments detailed above are the compounds detailed in the following table:

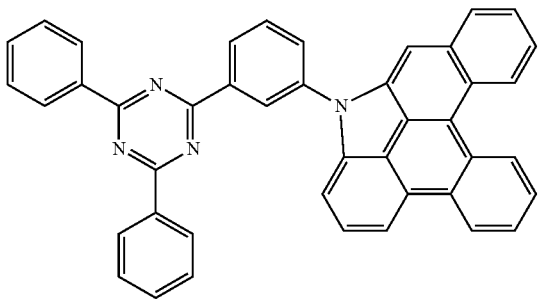

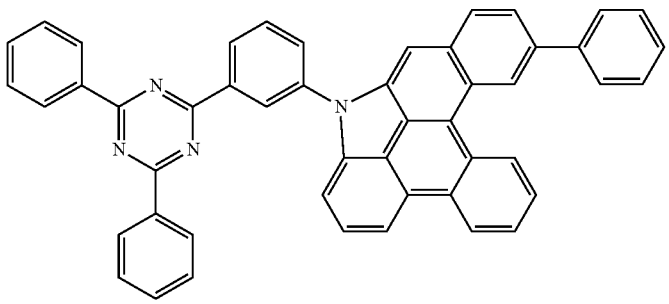

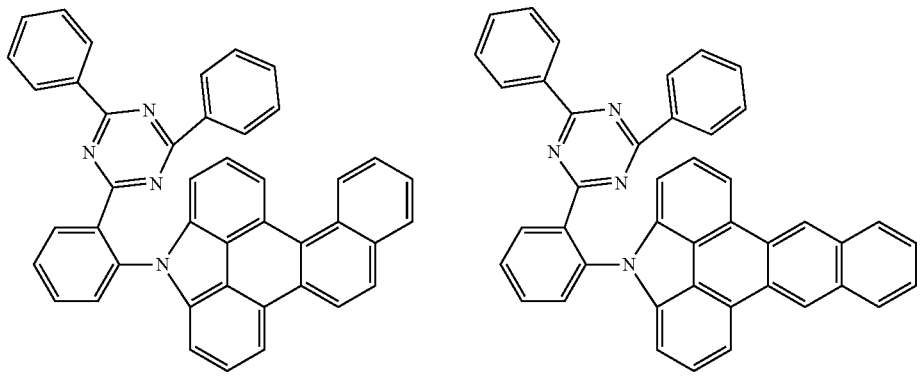

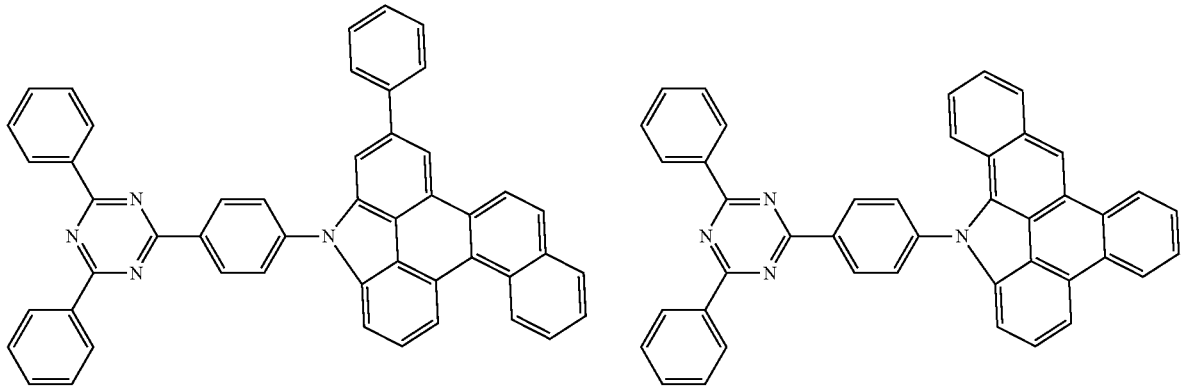

-continued
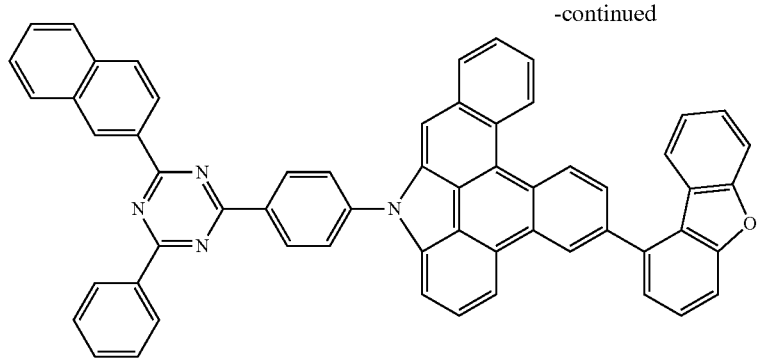
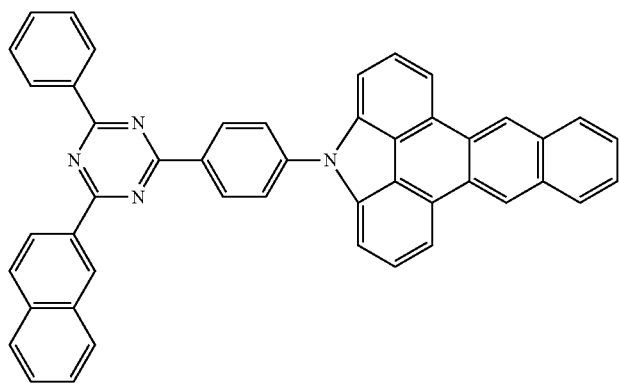
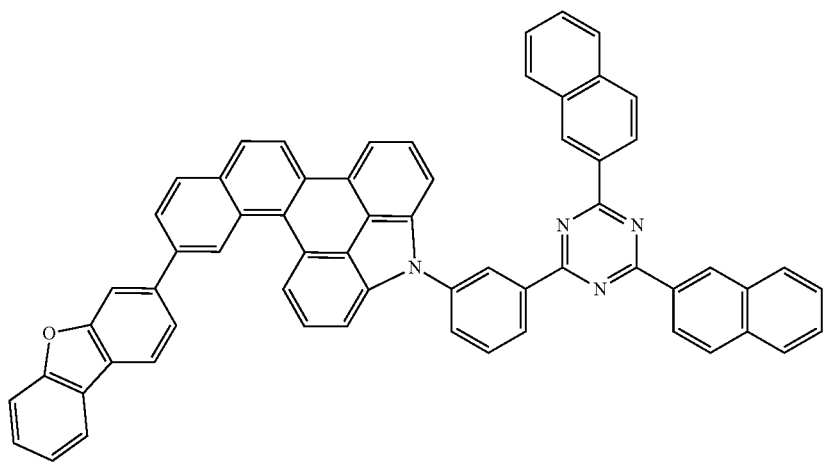
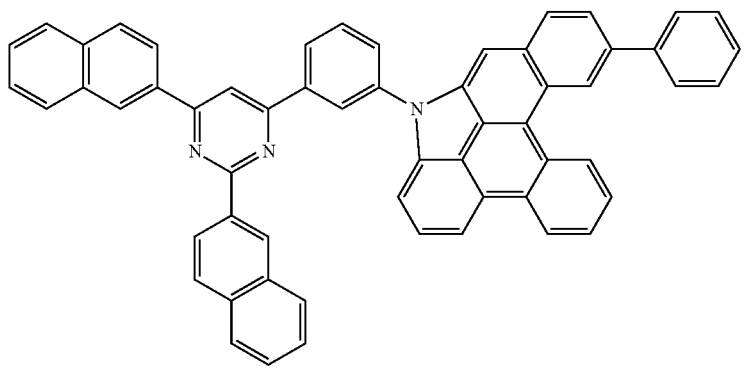

-continued
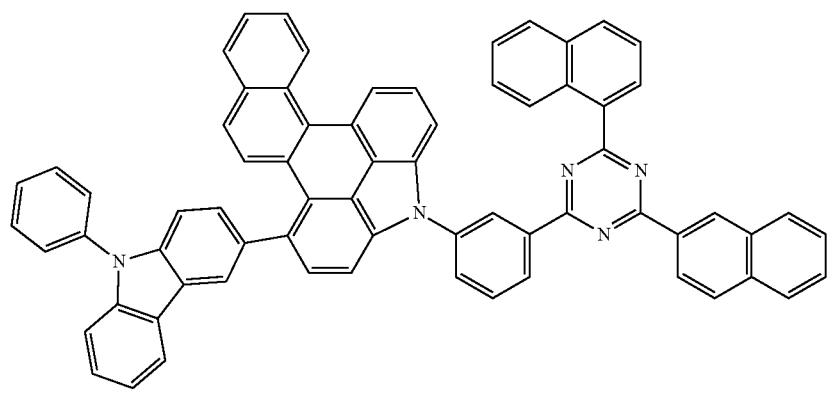
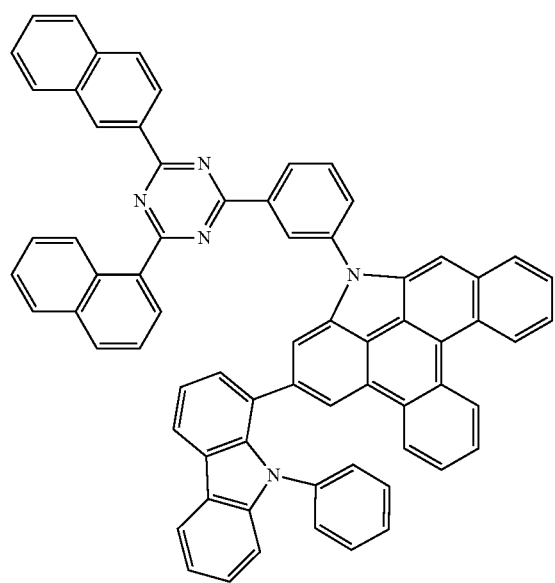
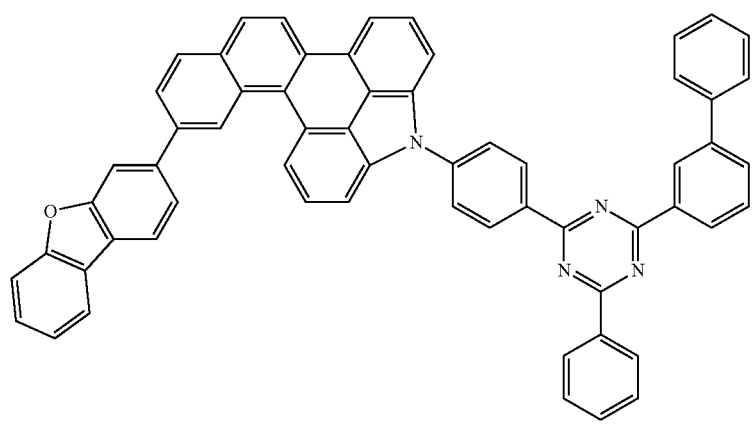

-continued
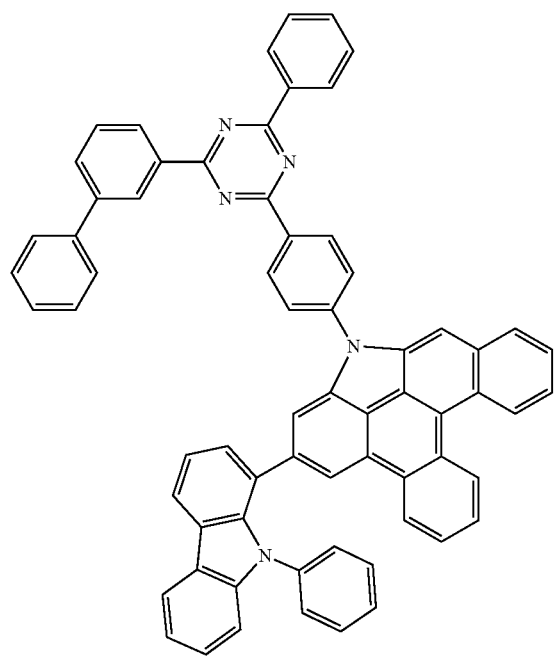
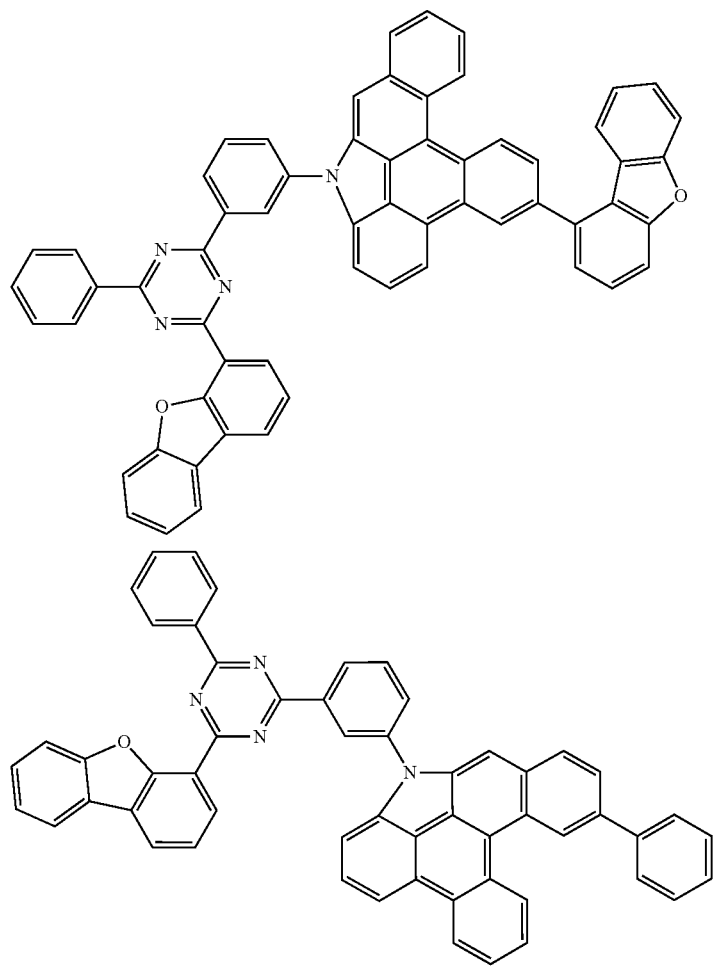

-continued
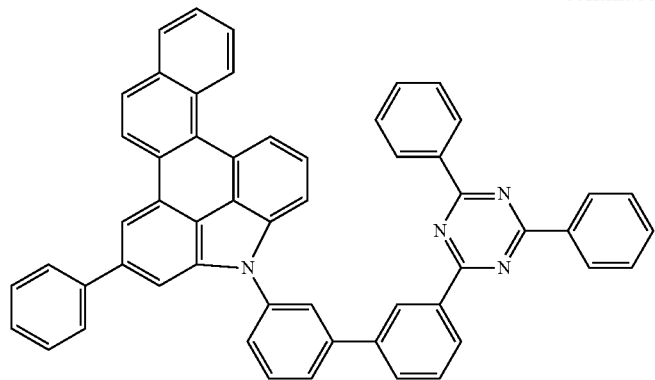
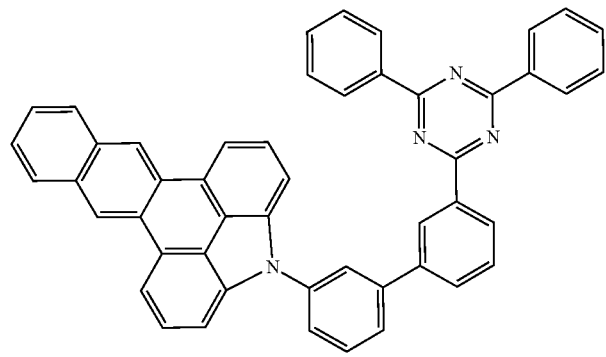
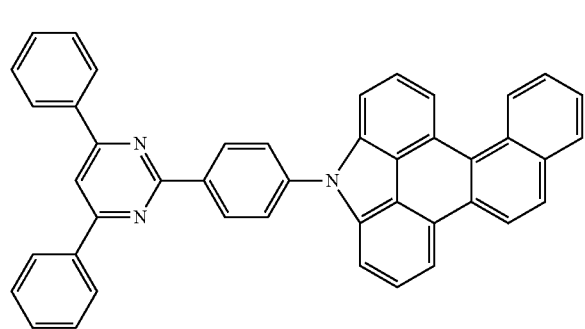
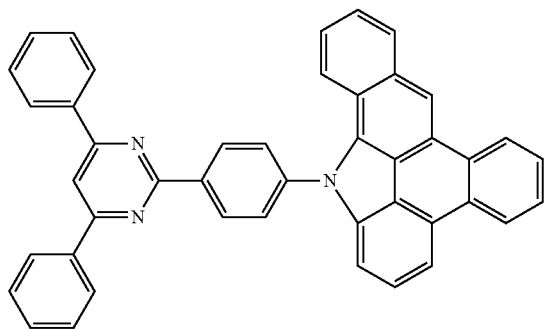
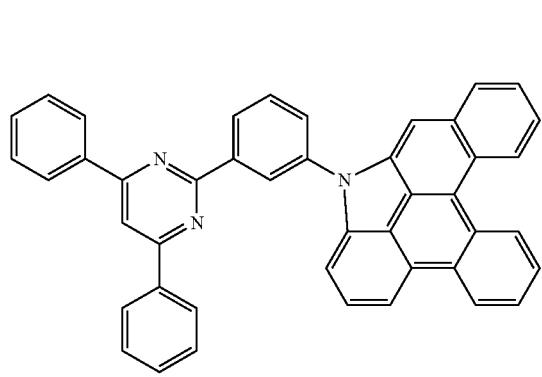
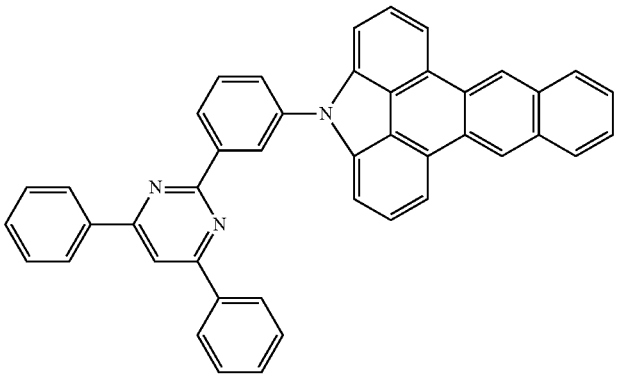

-continued
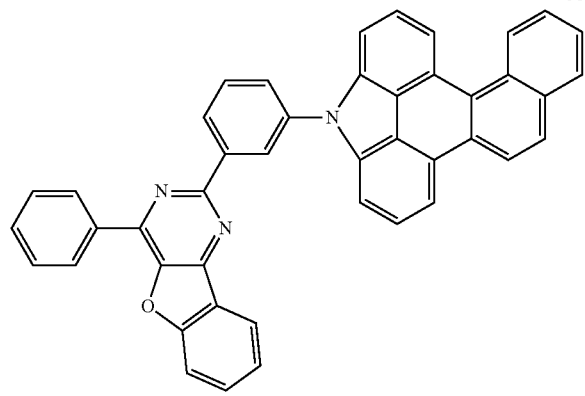
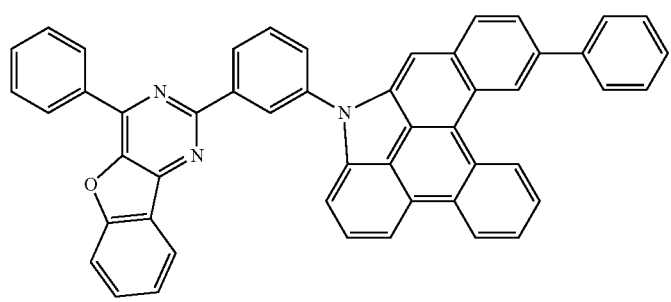
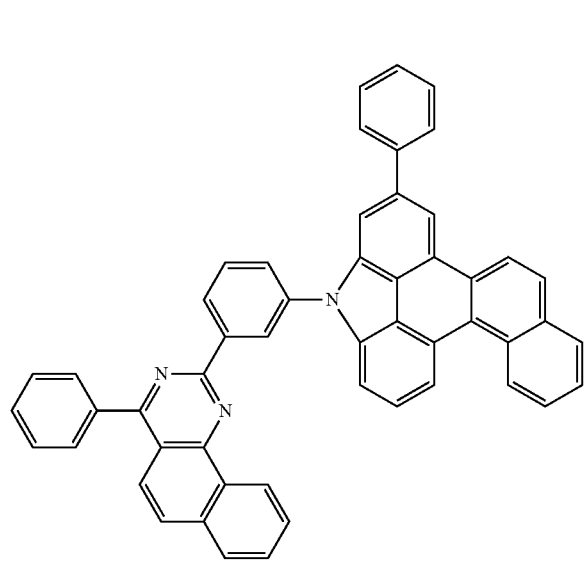
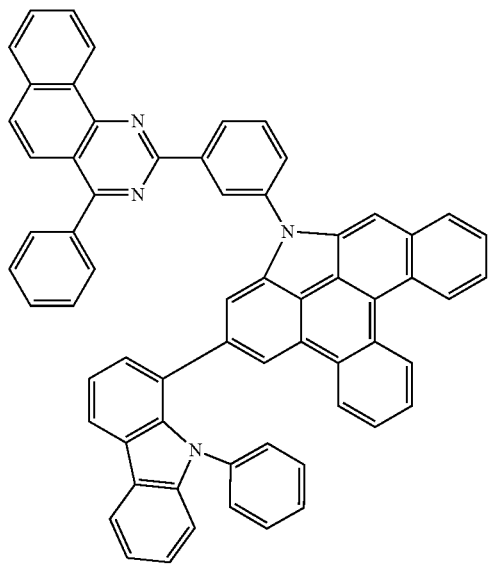
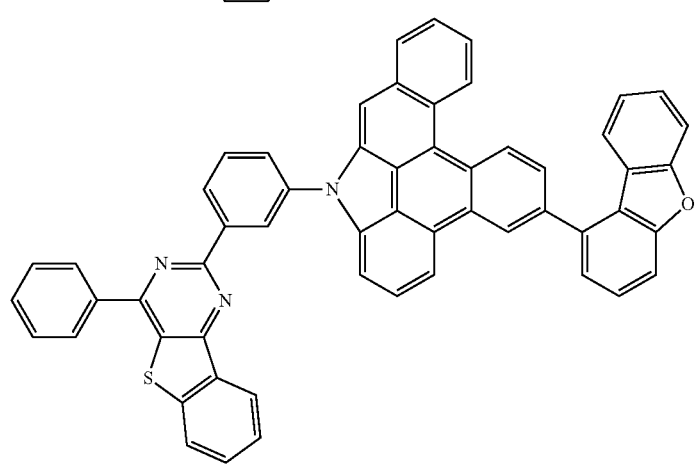

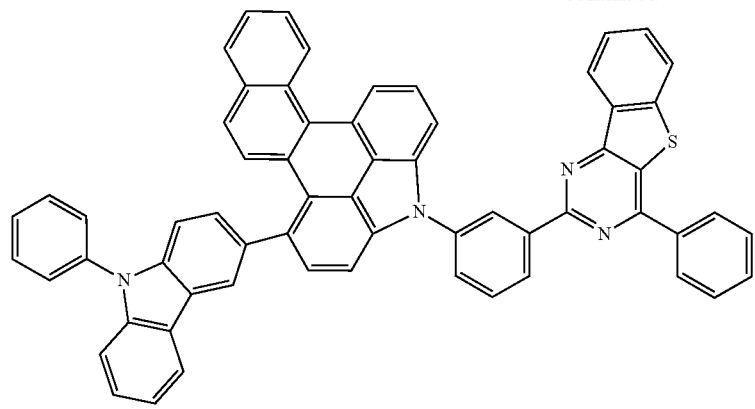
-continued

-continued
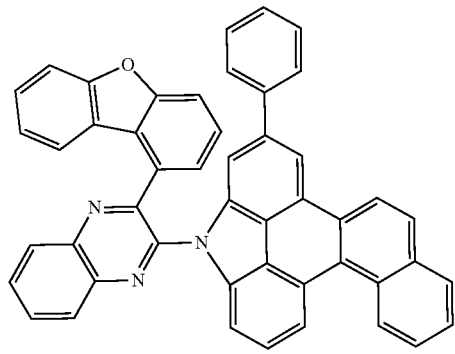 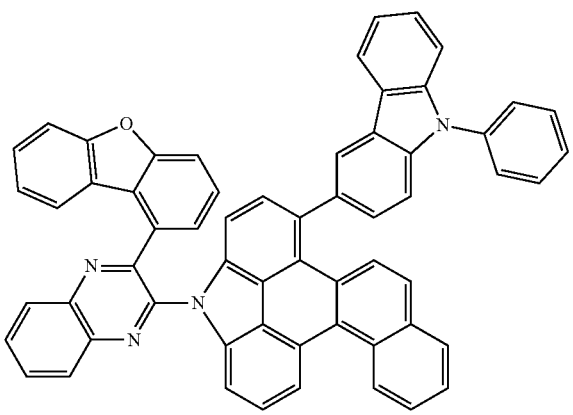
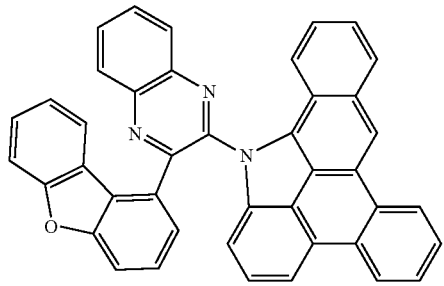 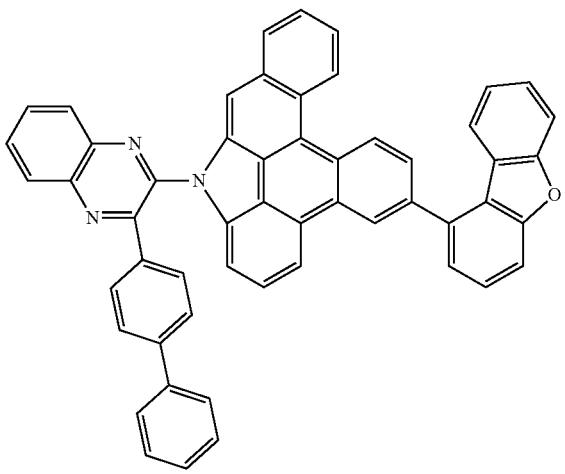
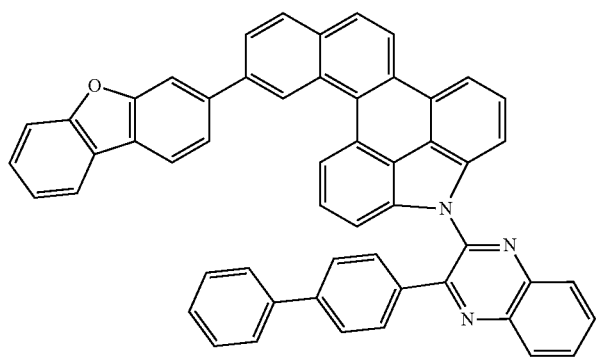

-continued
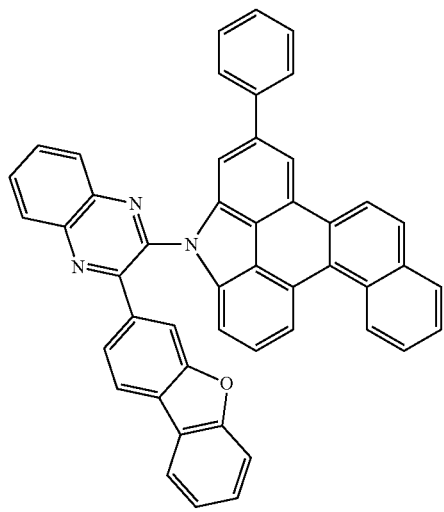
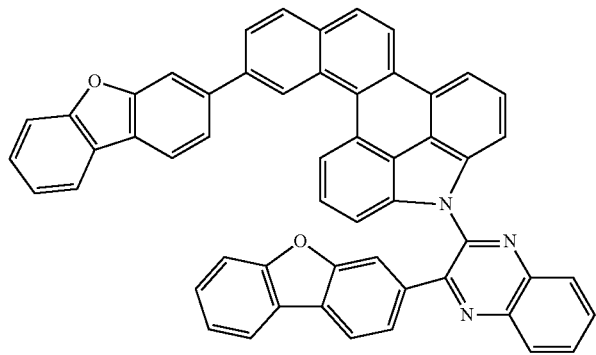
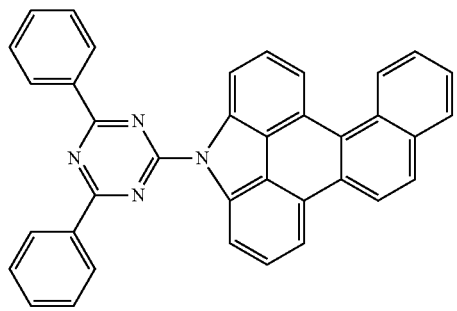
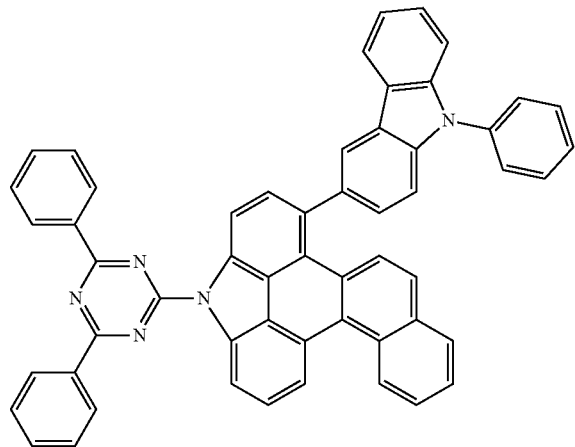
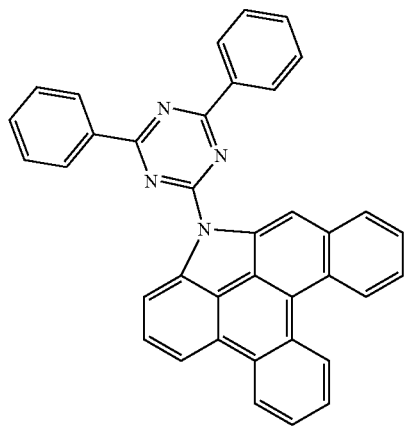
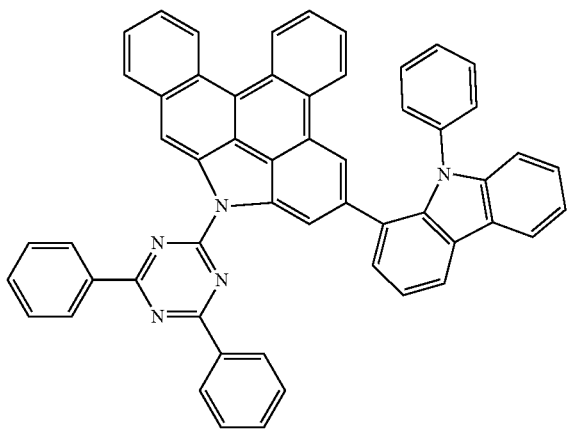

-continued
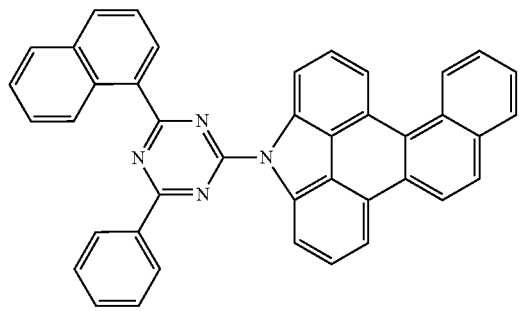
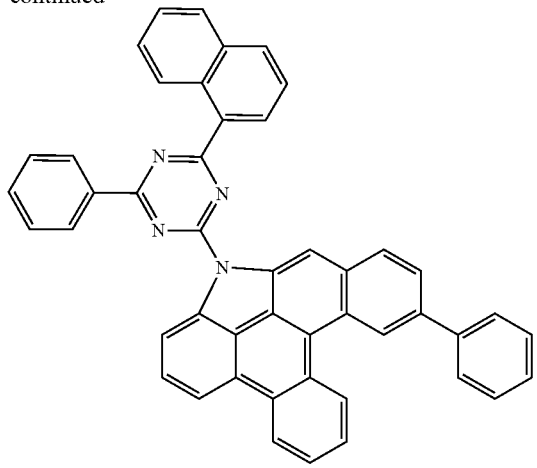
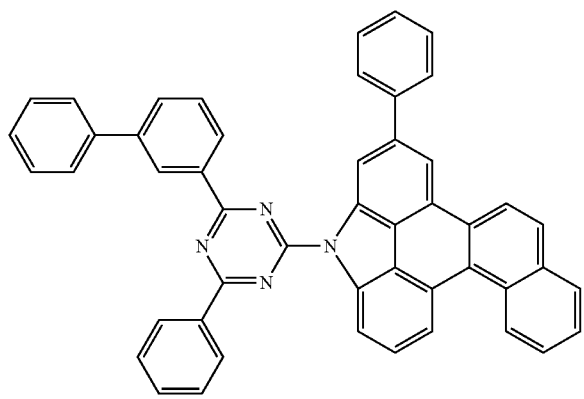
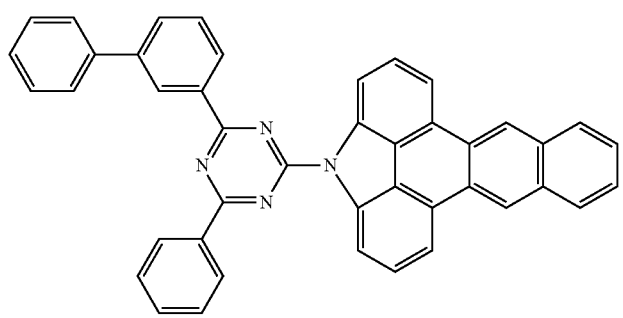
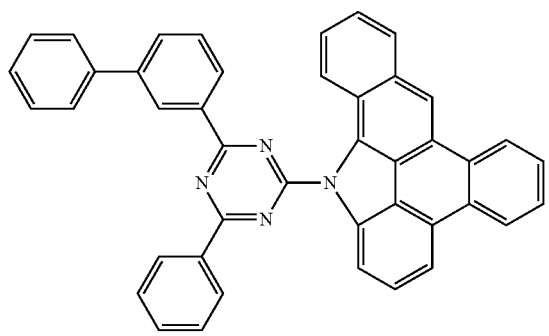
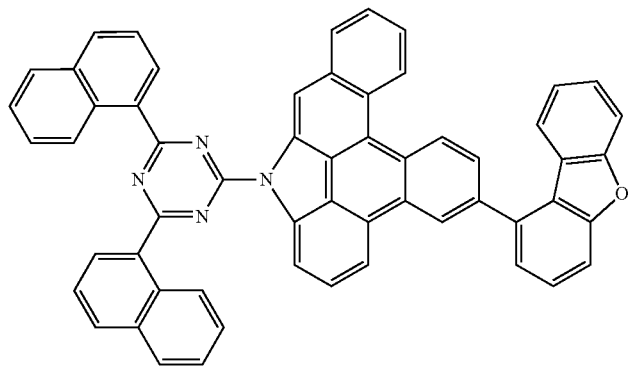

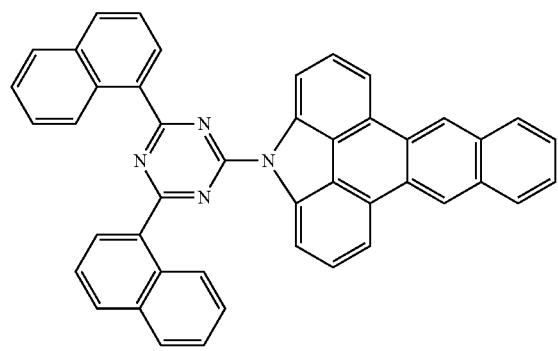
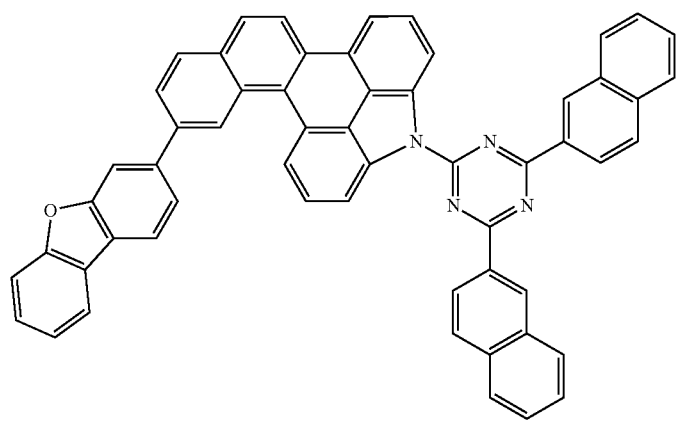
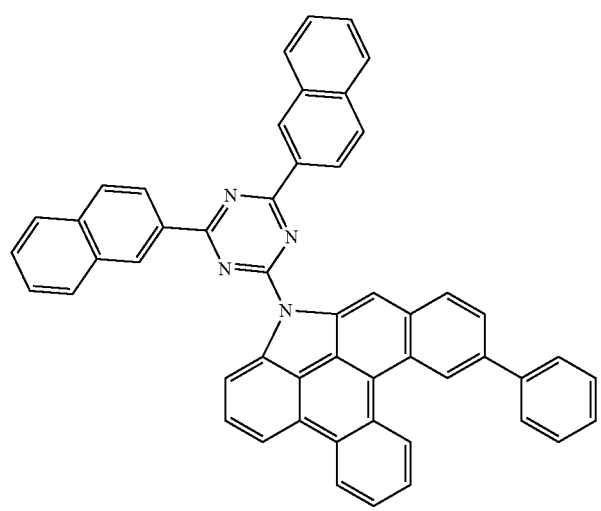

-continued
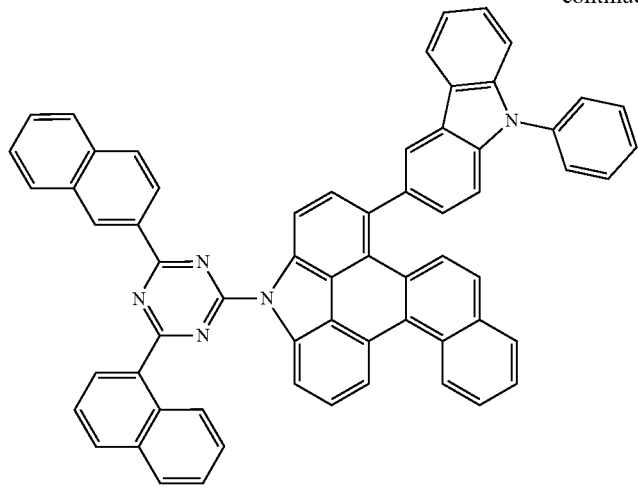
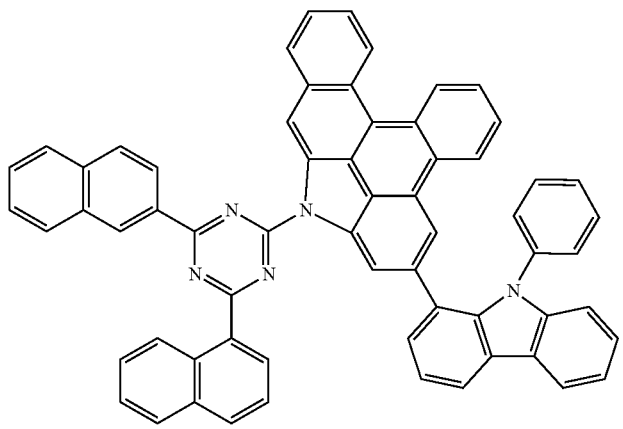
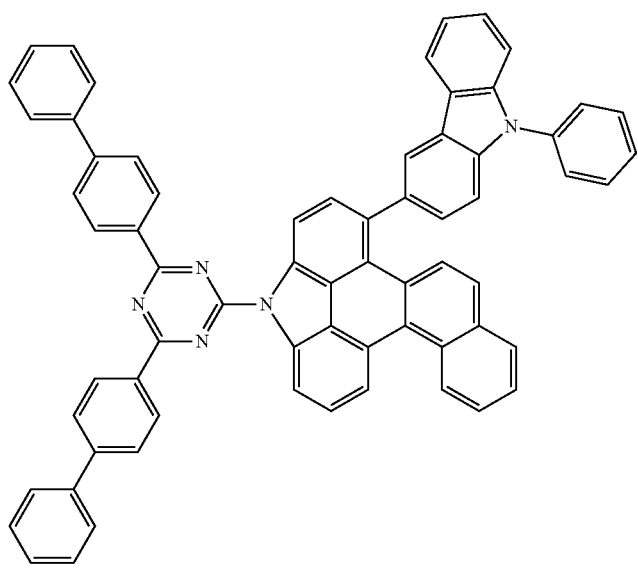

-continued
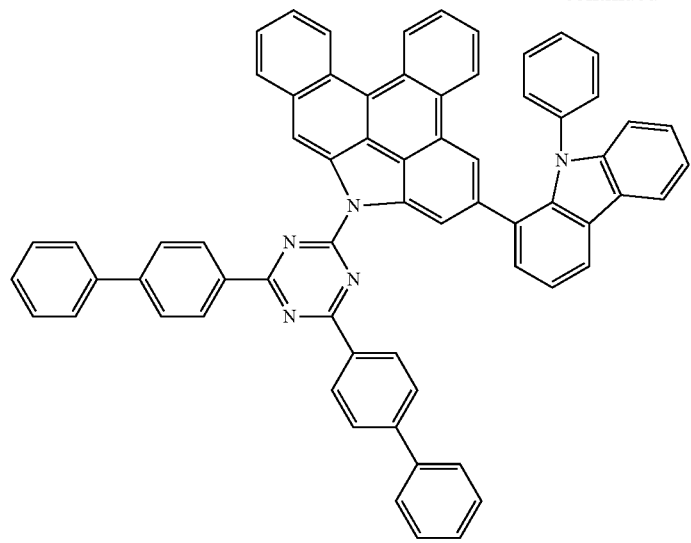
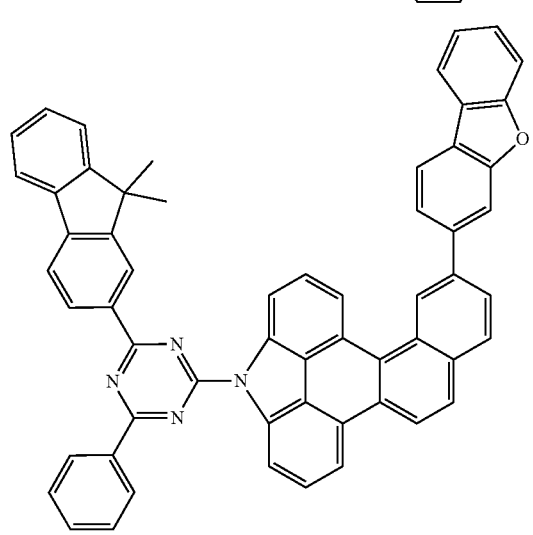
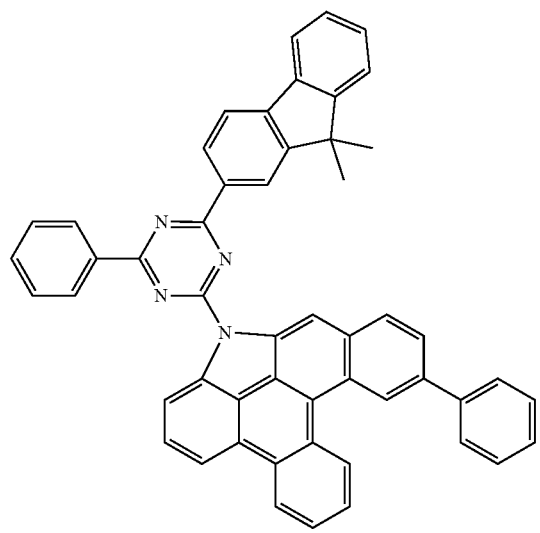
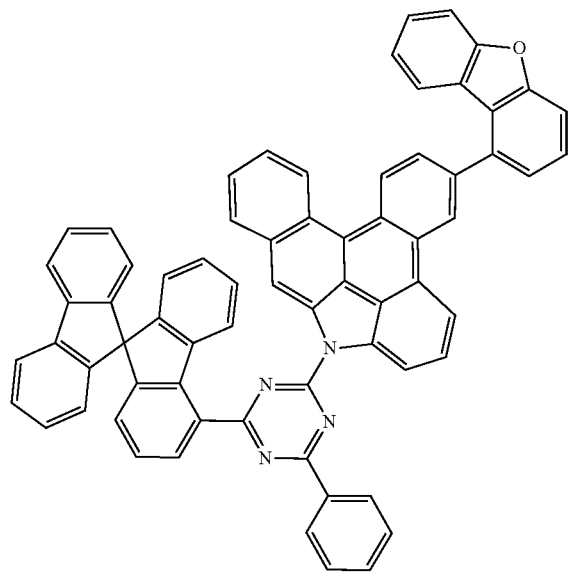
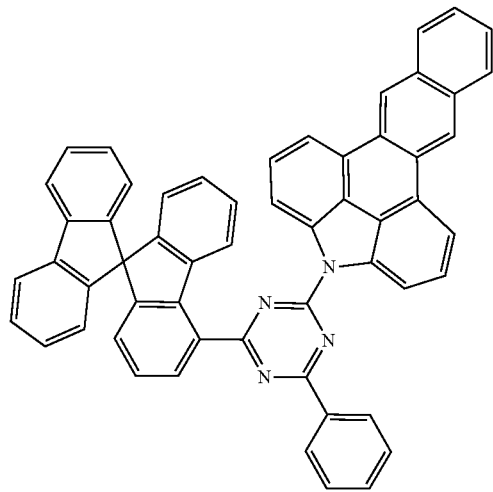

-continued
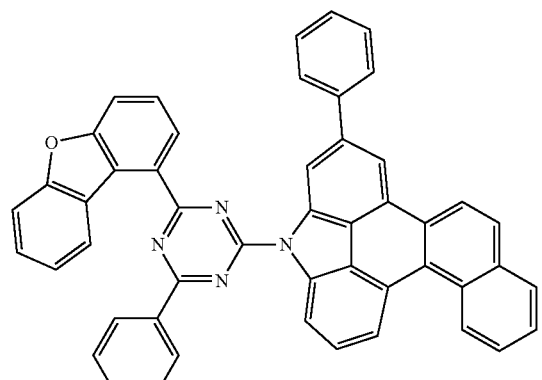 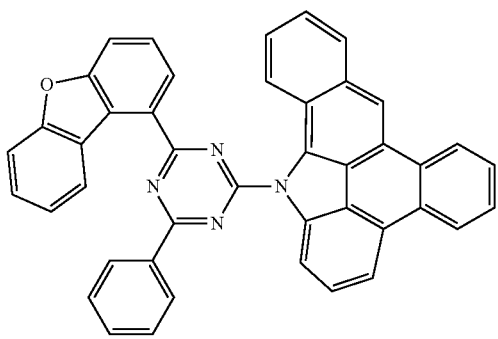
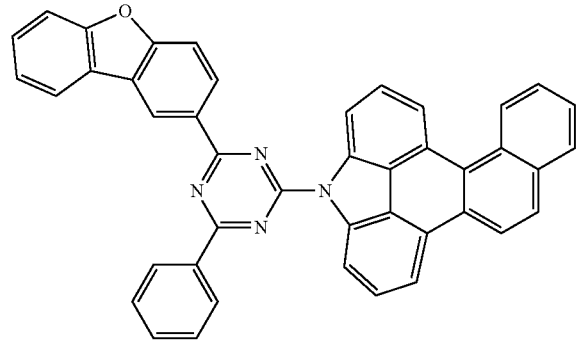 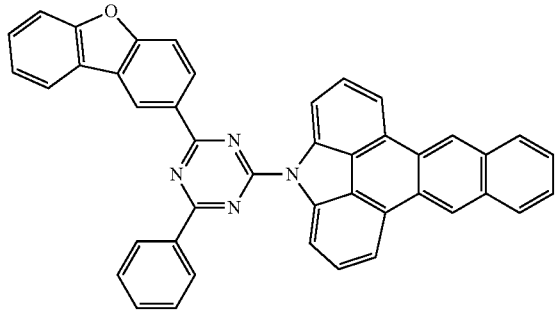
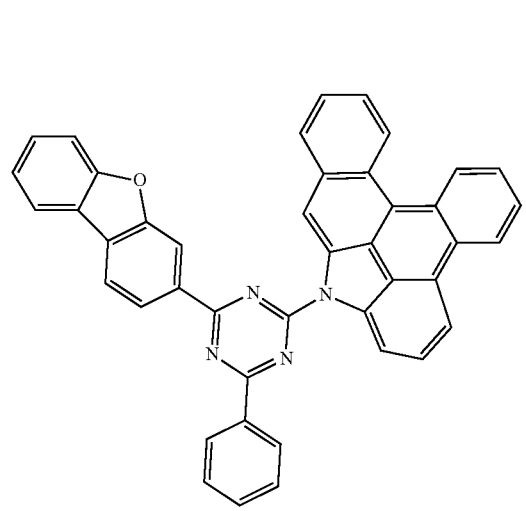 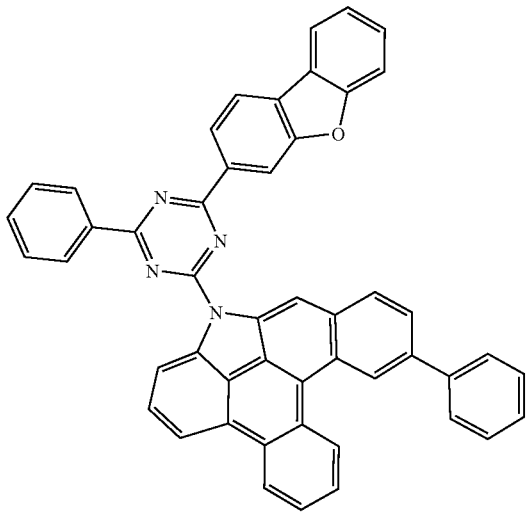
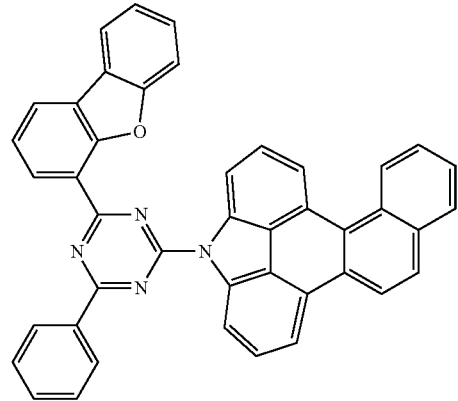 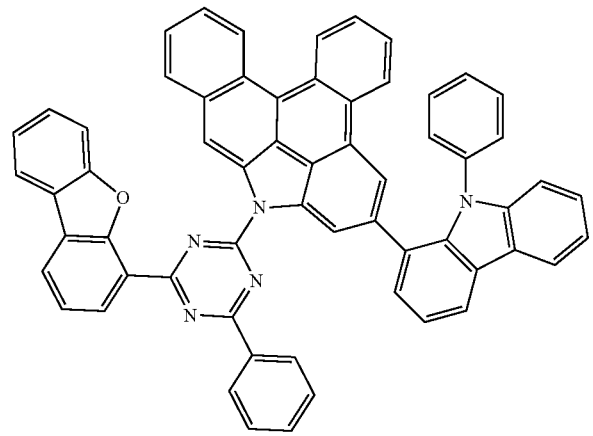

-continued
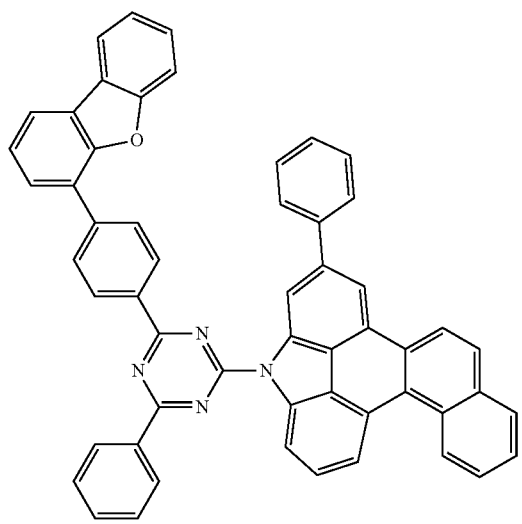
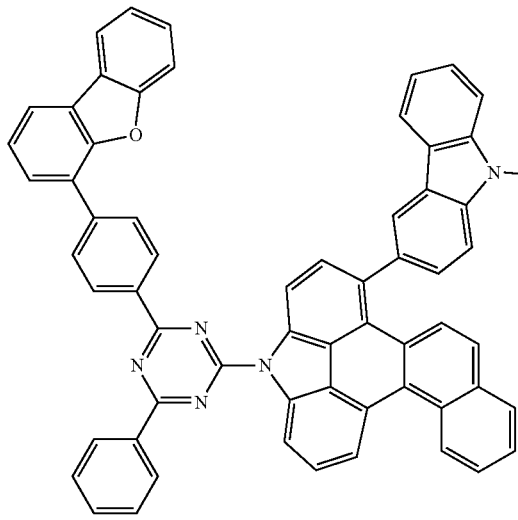
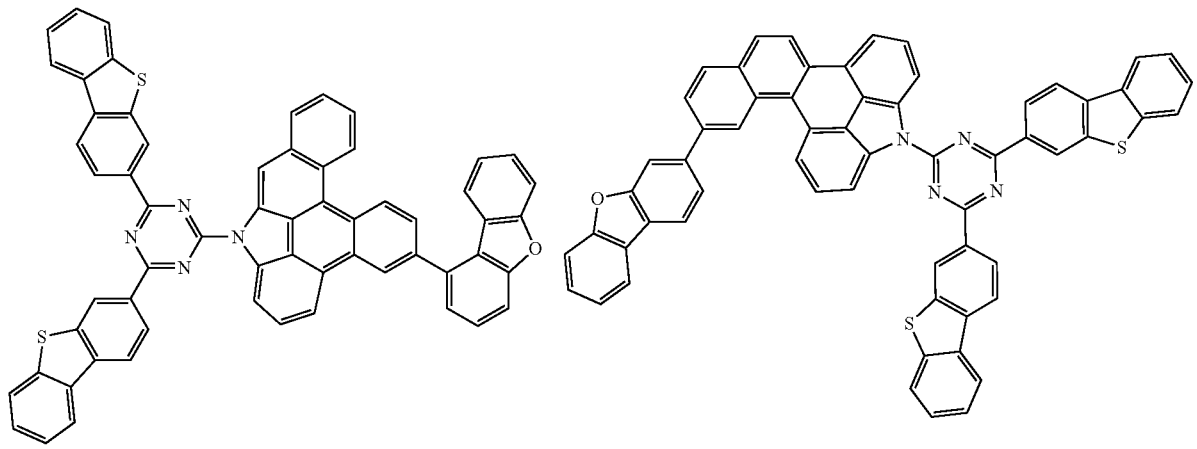
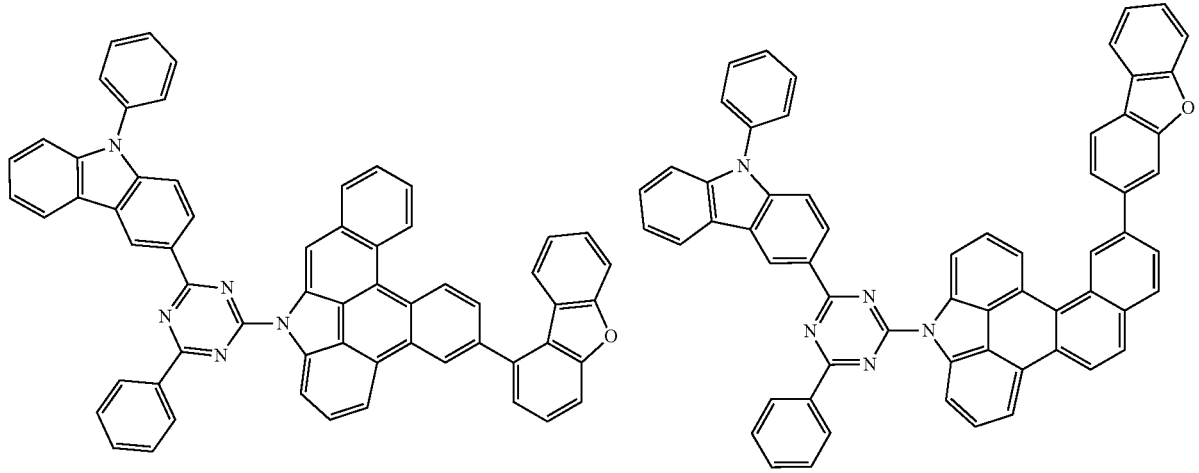

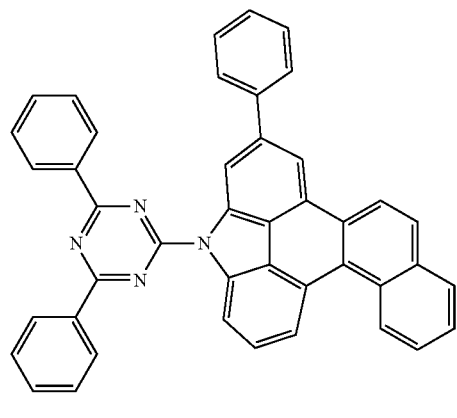
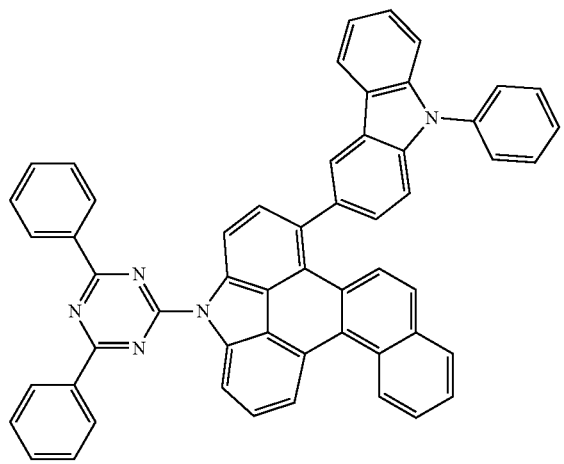
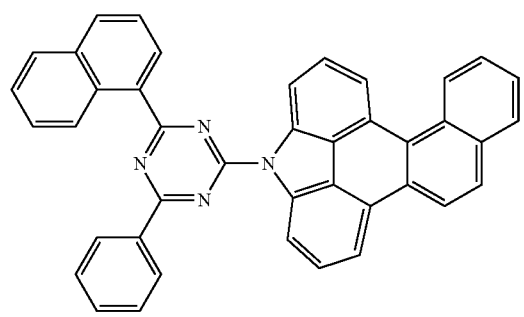
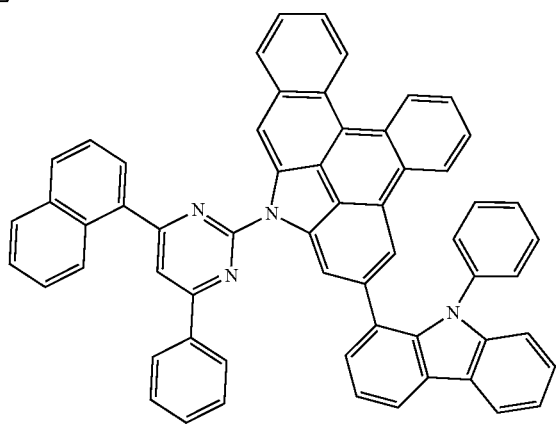
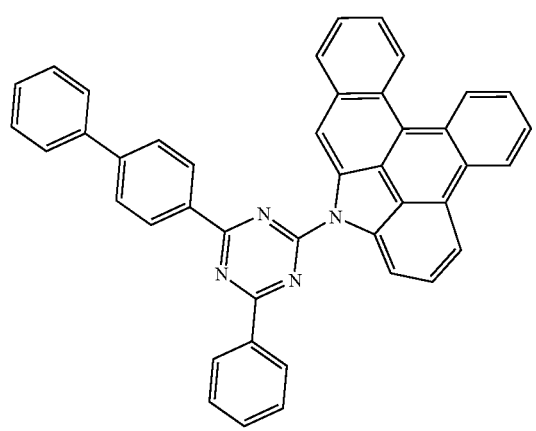
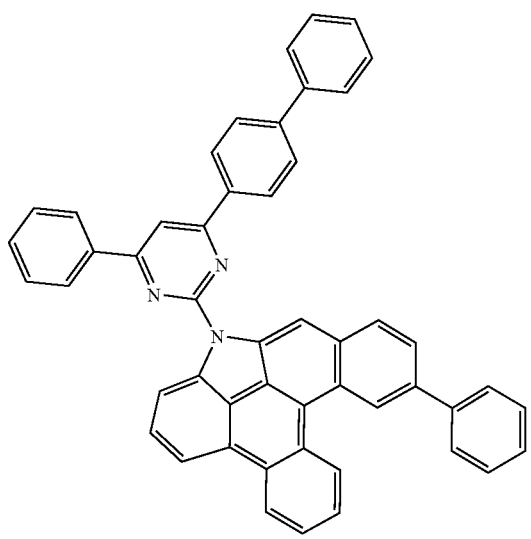
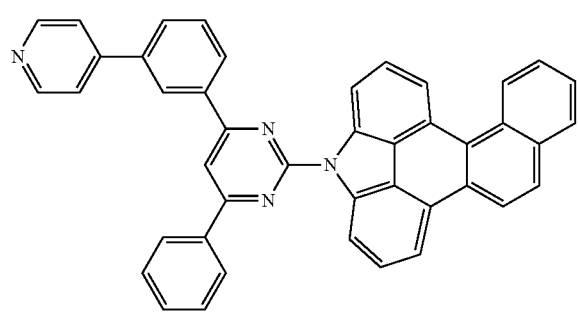
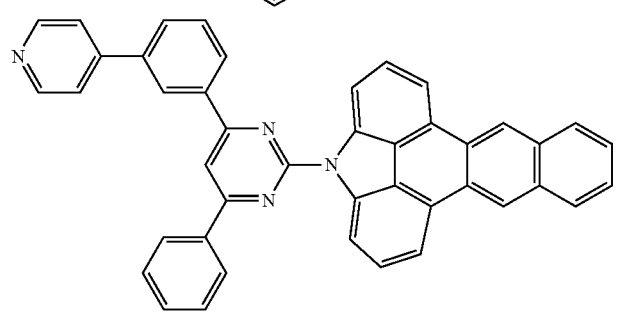

-continued
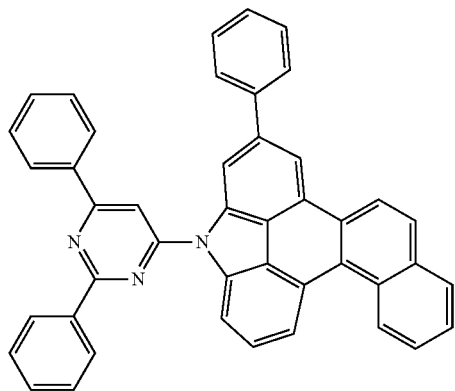
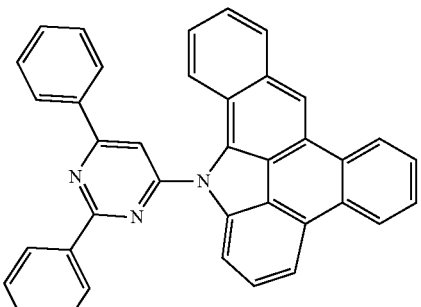
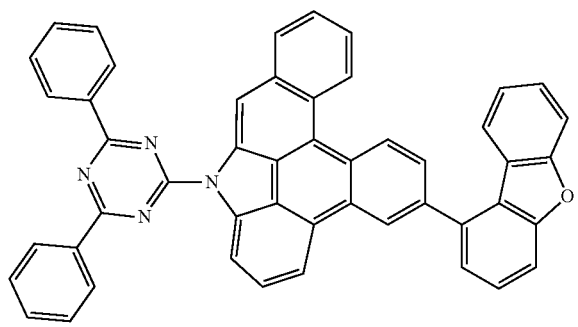
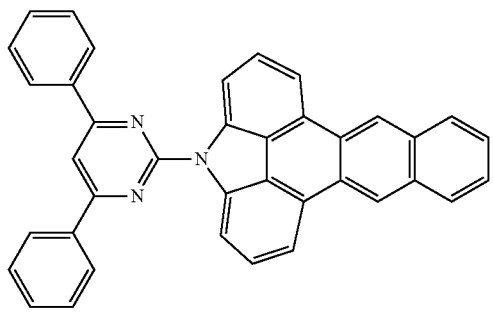
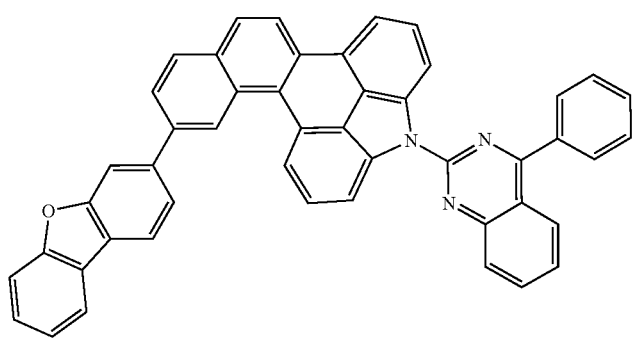
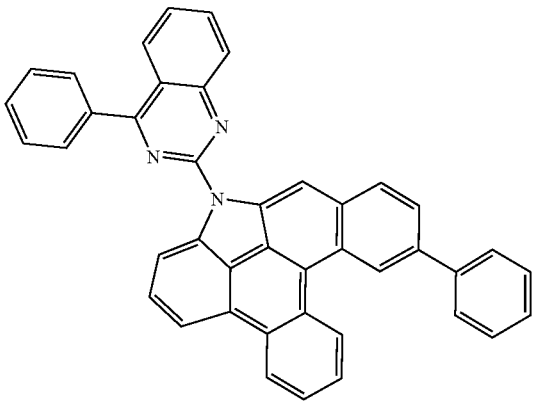
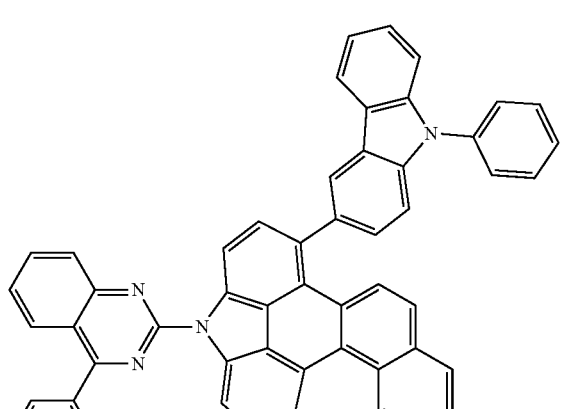
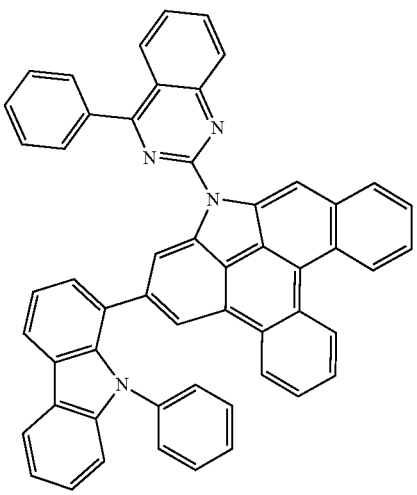

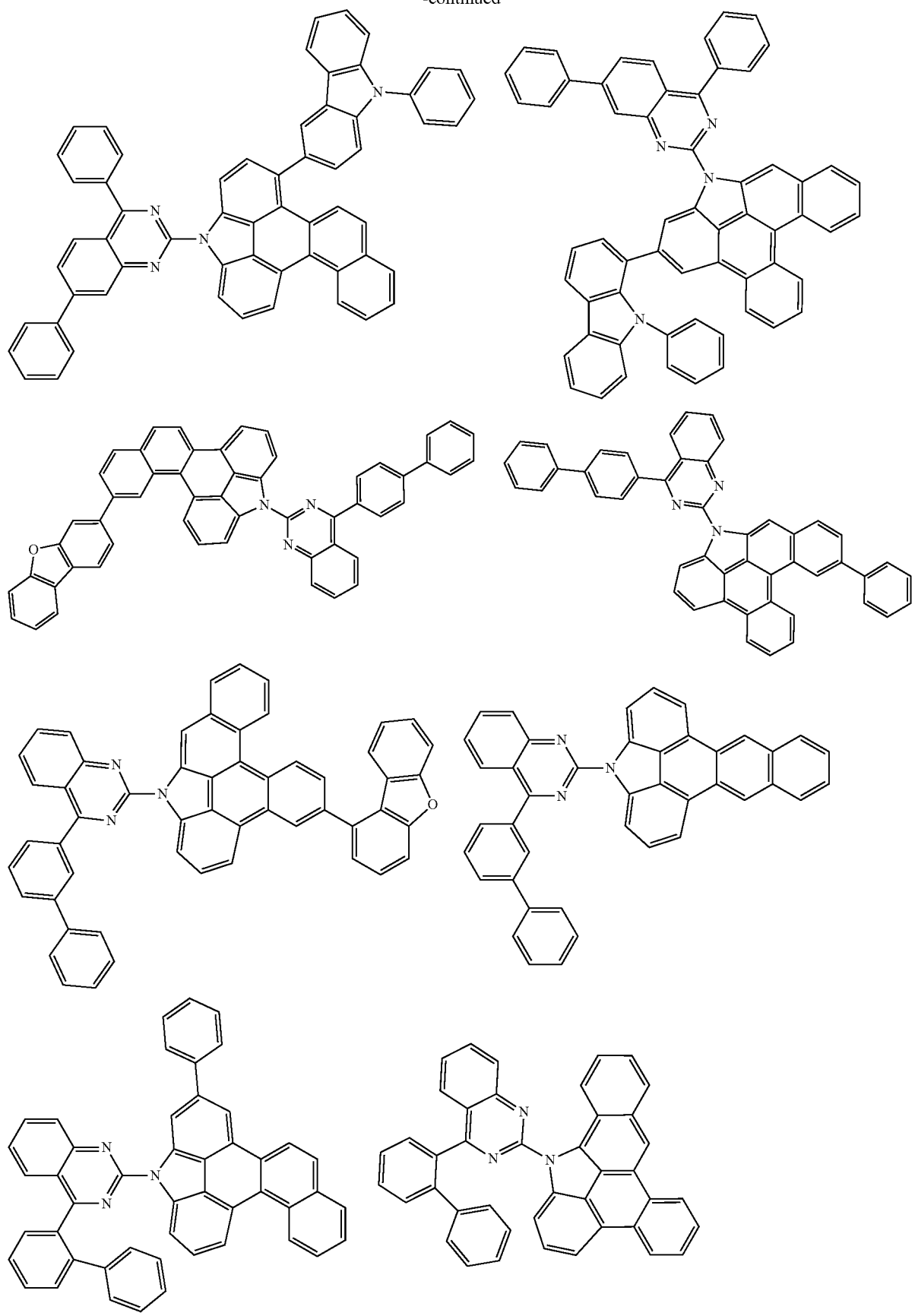

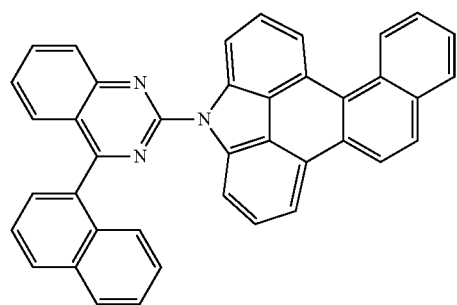 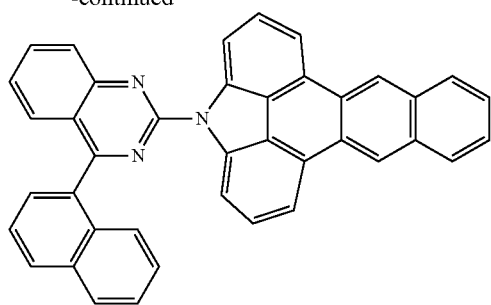
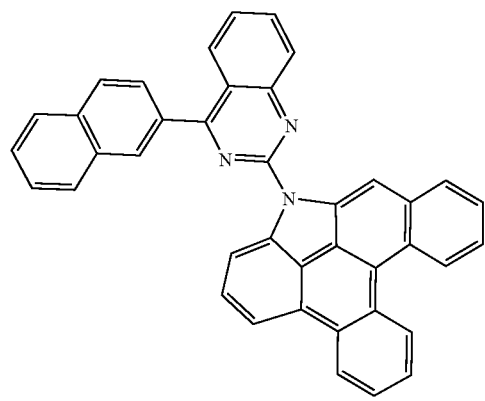 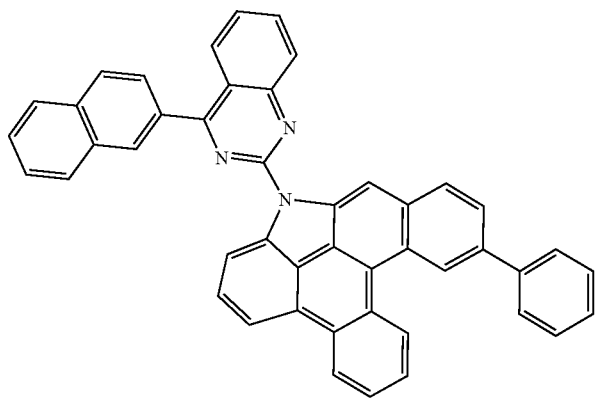
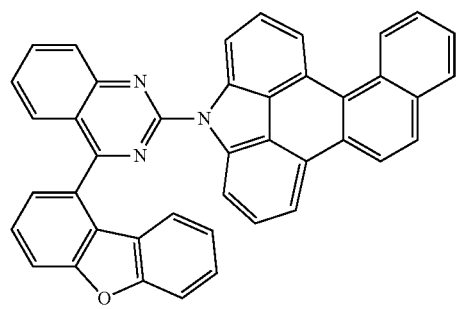 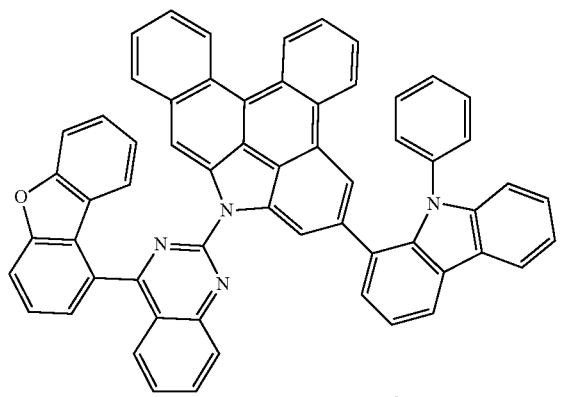
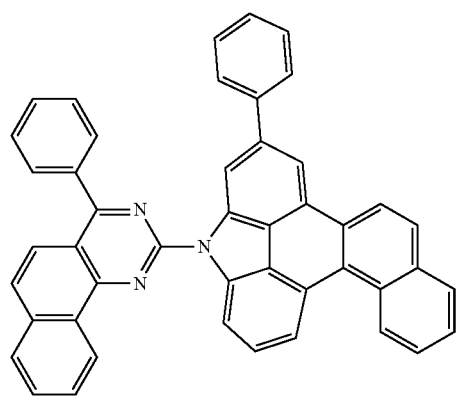 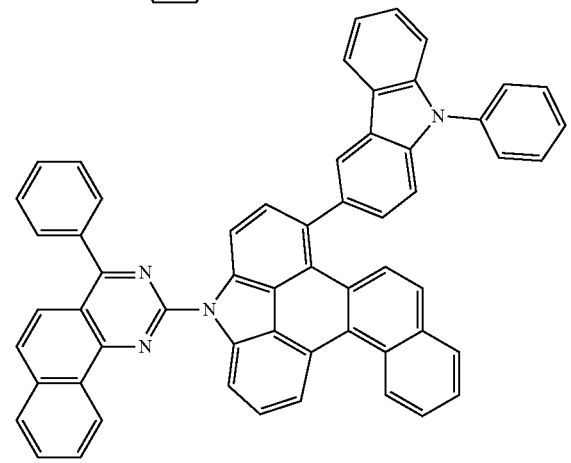

-continued
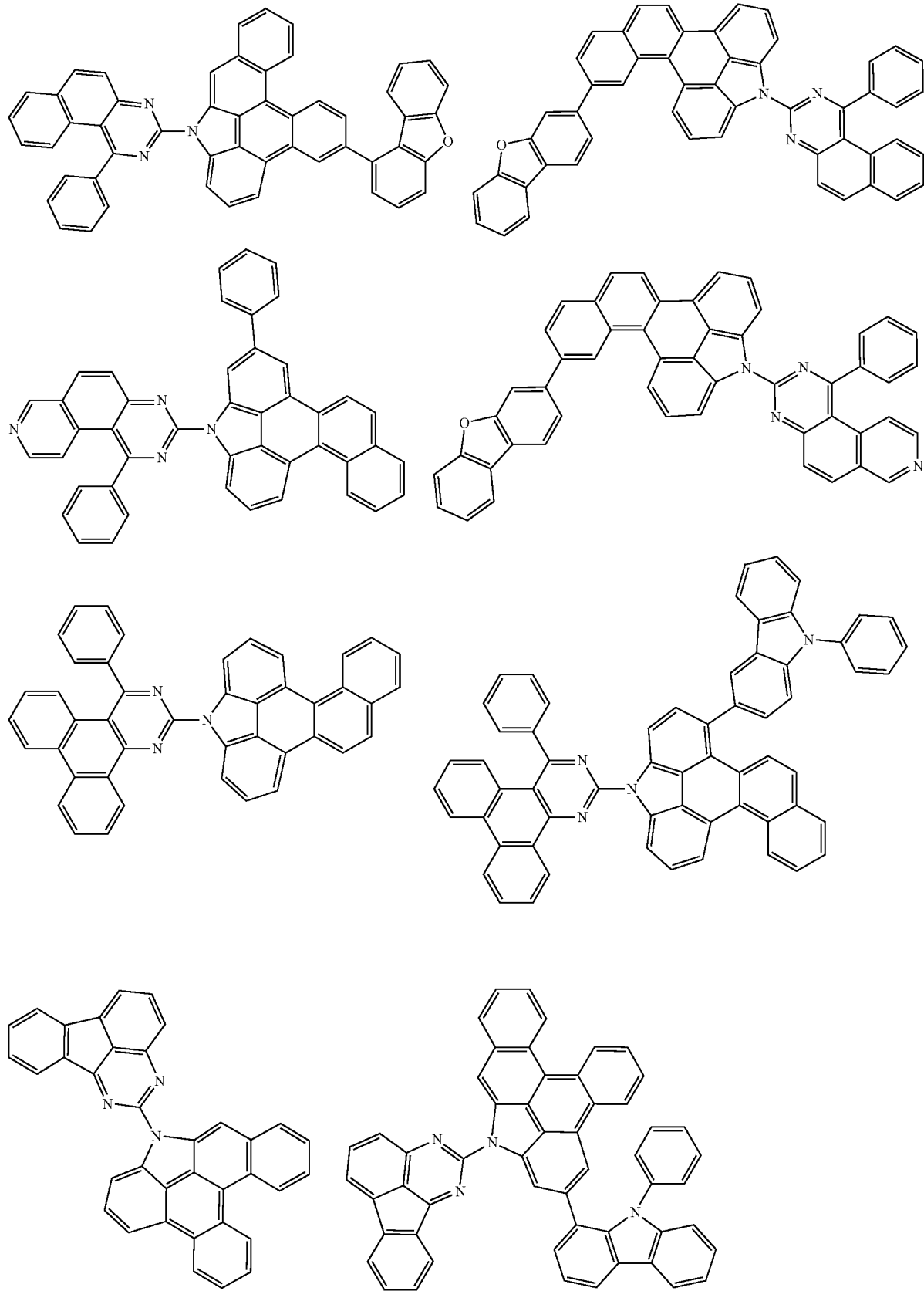

-continued
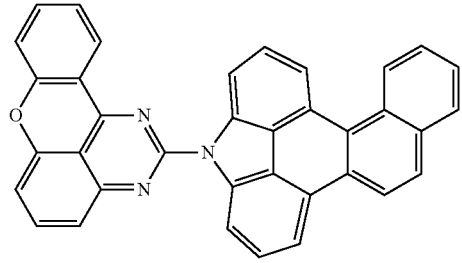
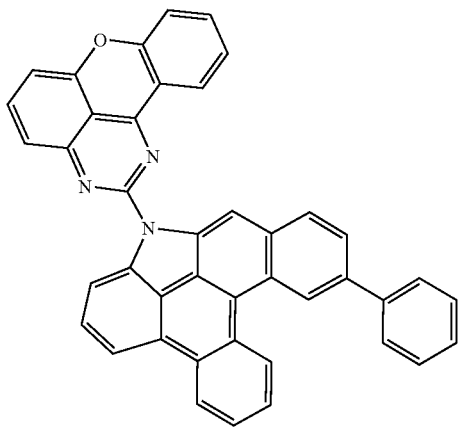
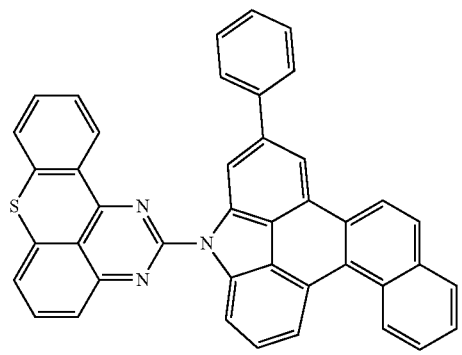
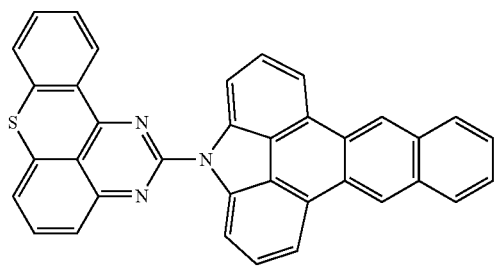
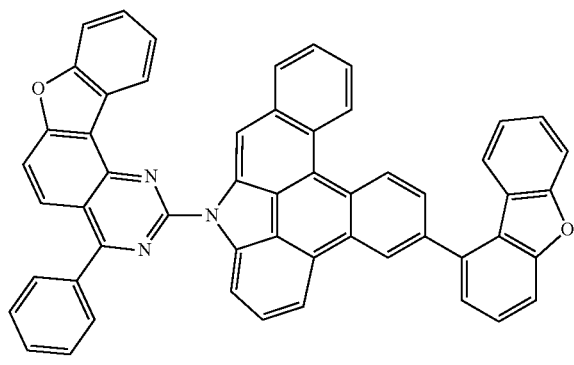
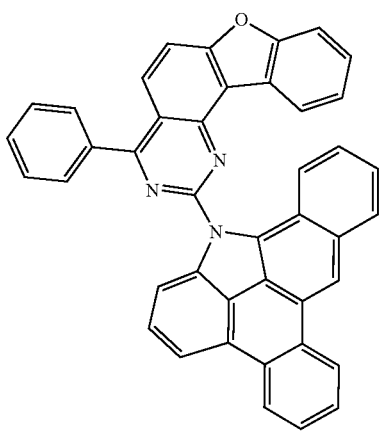
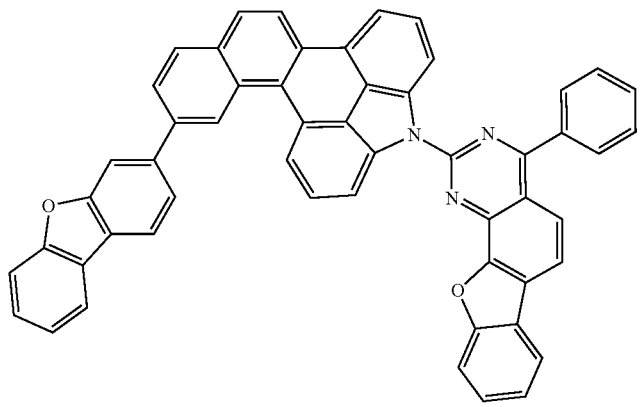
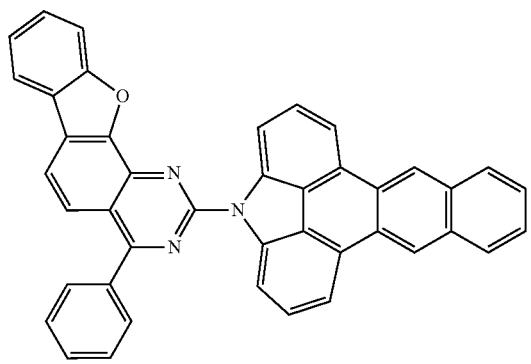

-continued
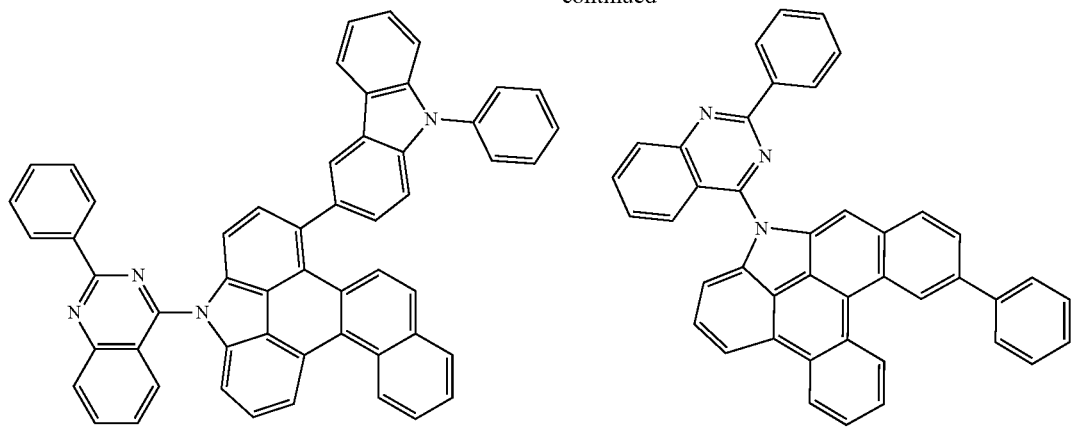
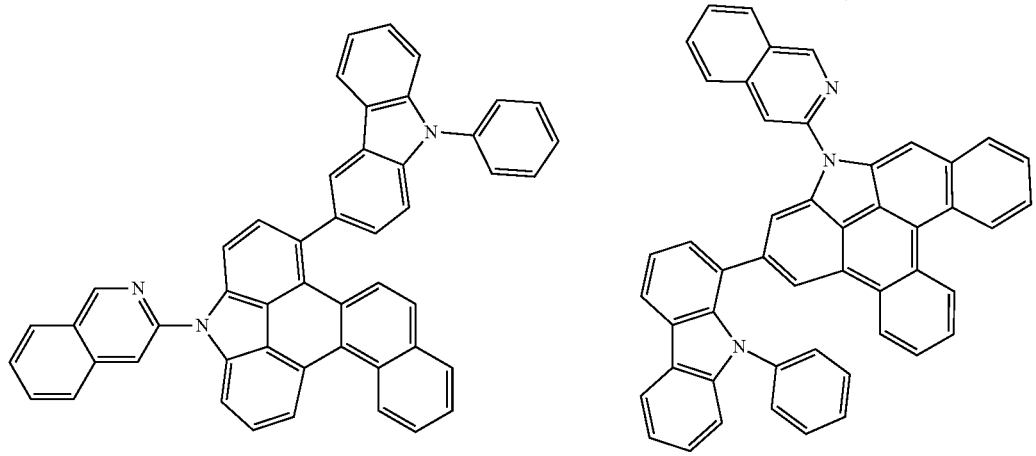
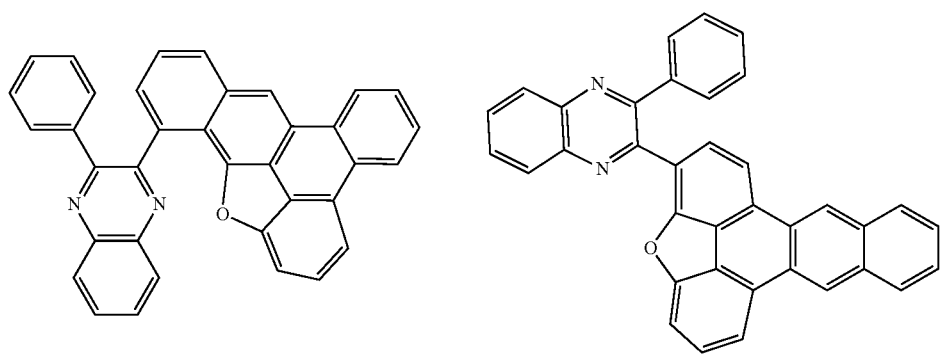
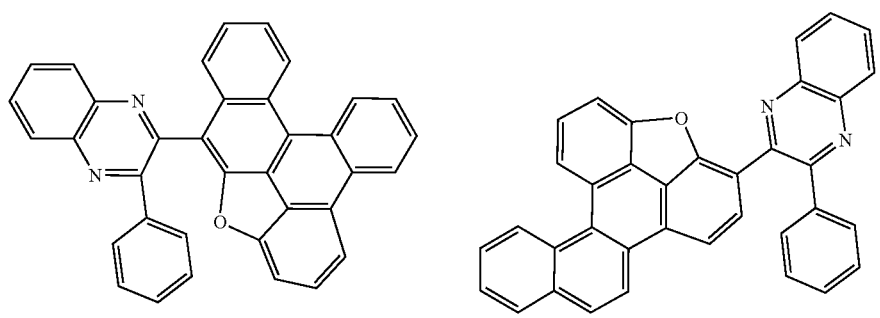

-continued
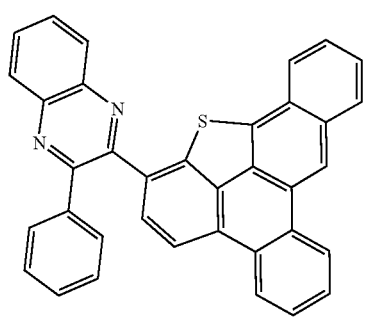
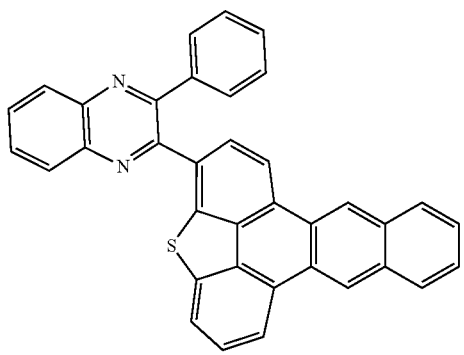
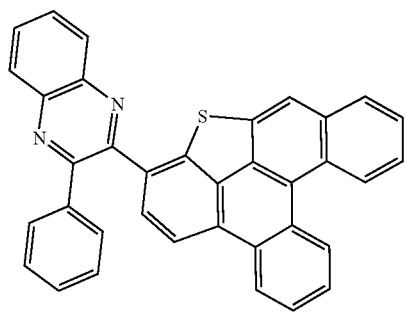
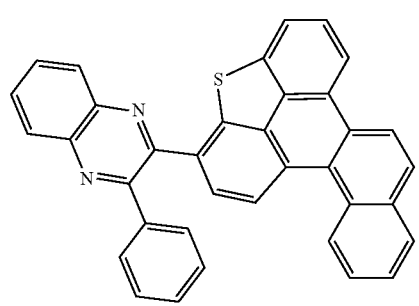
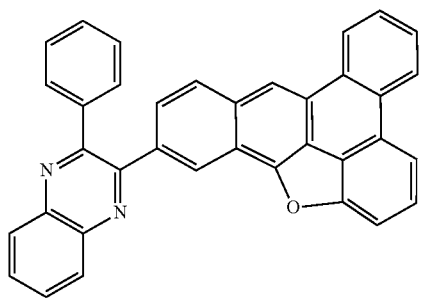
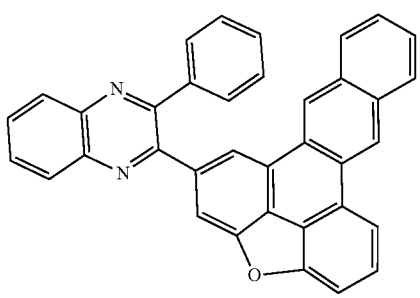
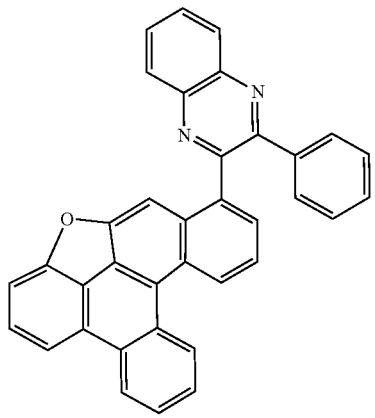
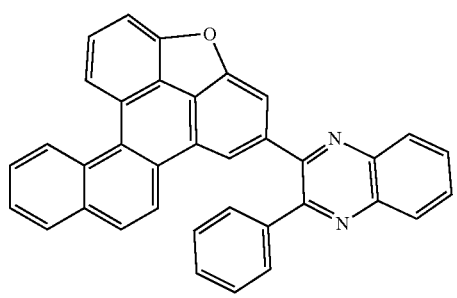
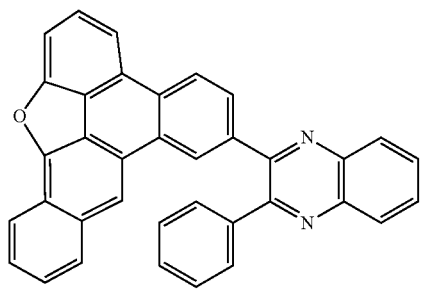
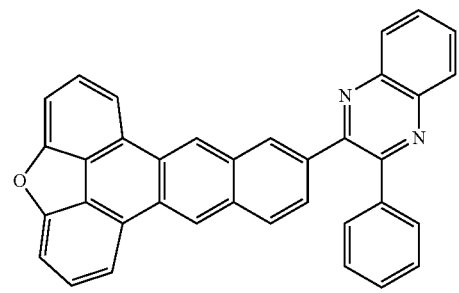

-continued
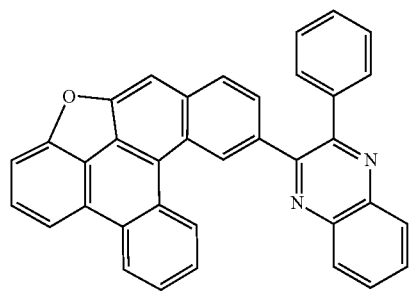 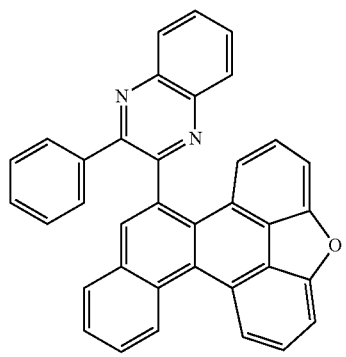
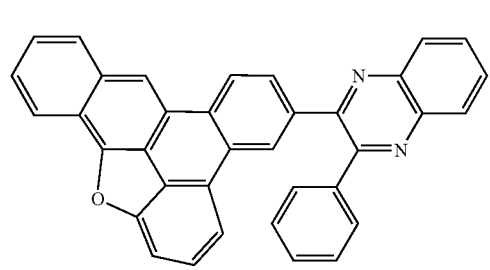 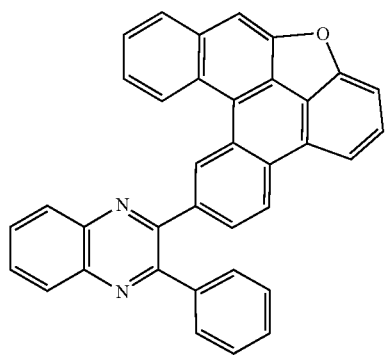
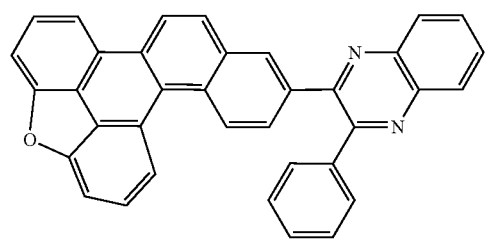 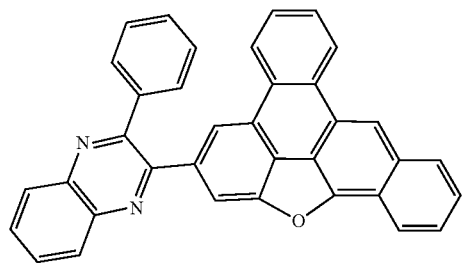
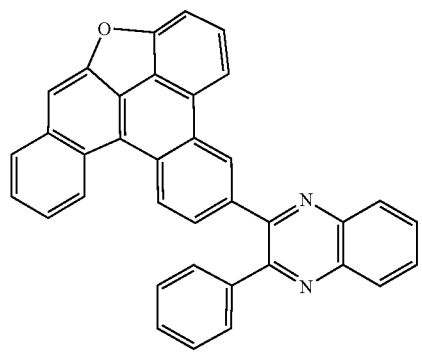 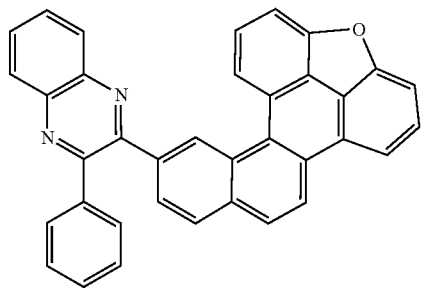
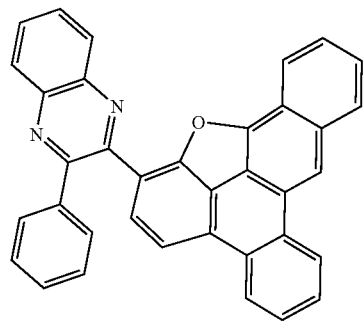 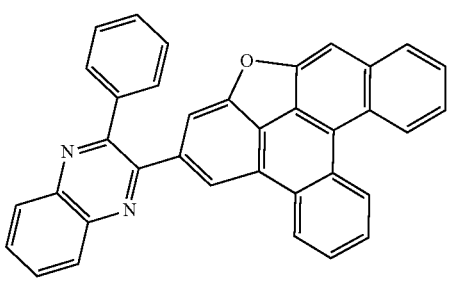

-continued
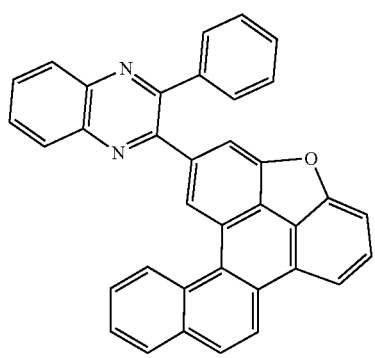
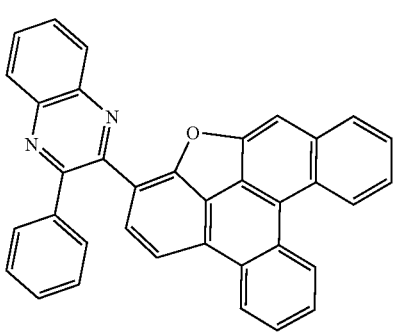
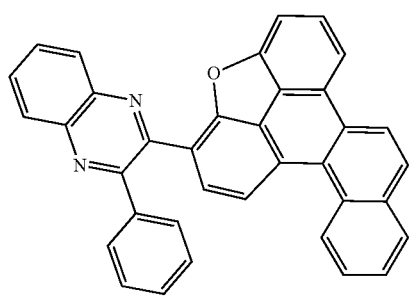
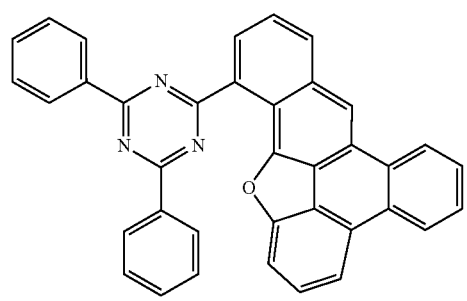
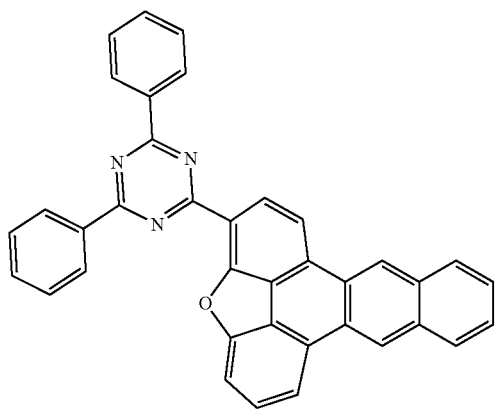
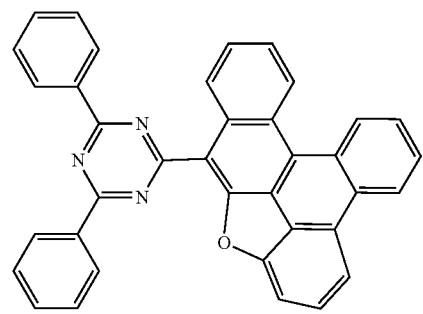
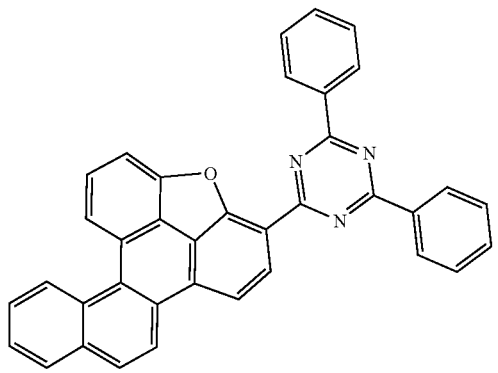
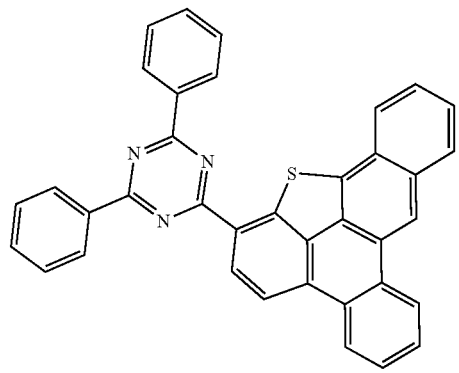

-continued
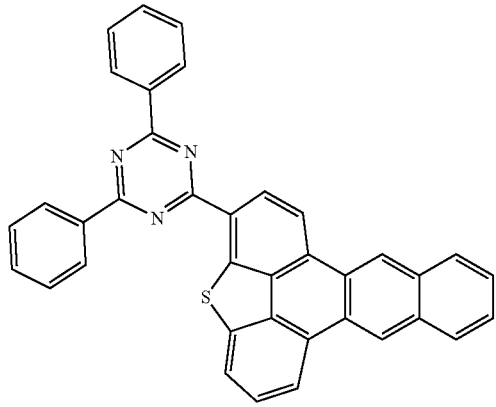
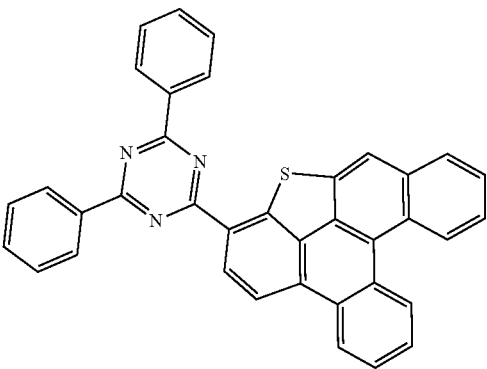
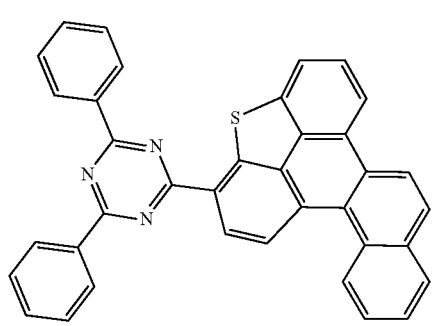
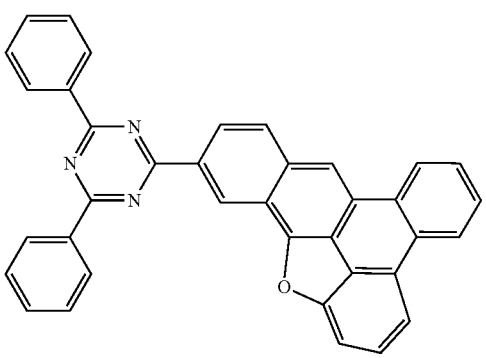
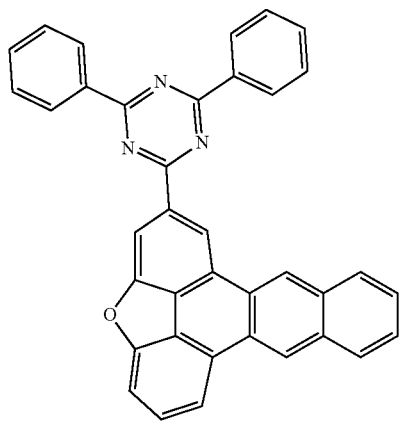
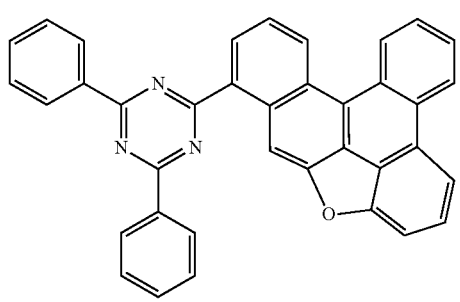
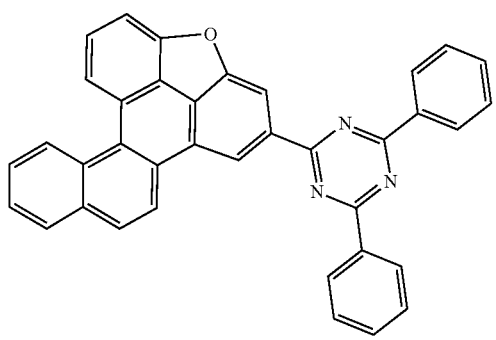
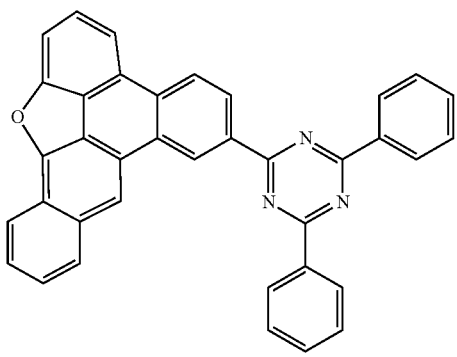

-continued
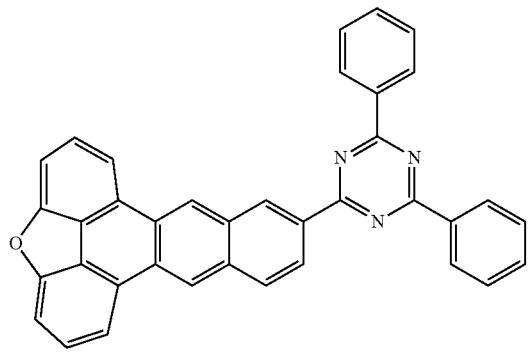
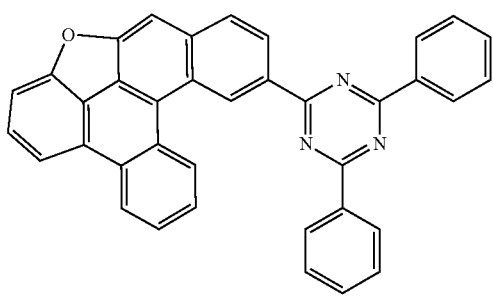
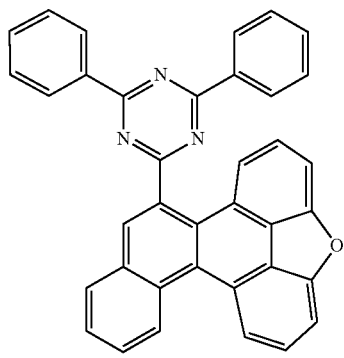
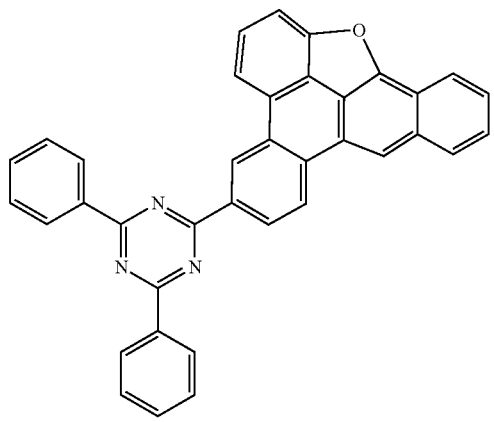
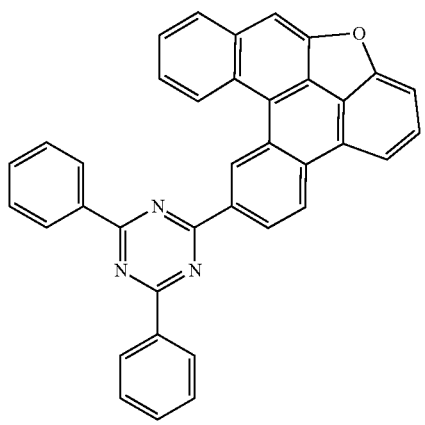
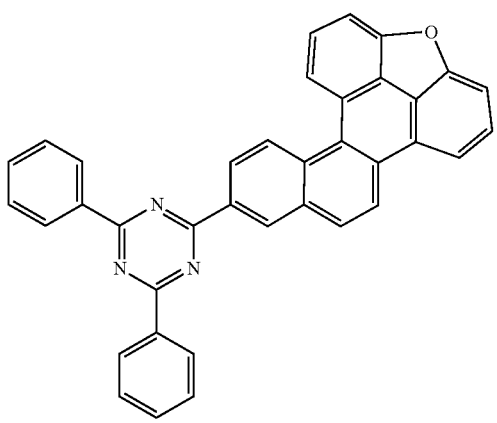
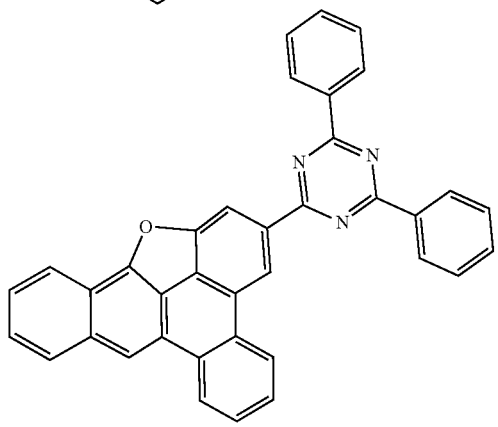
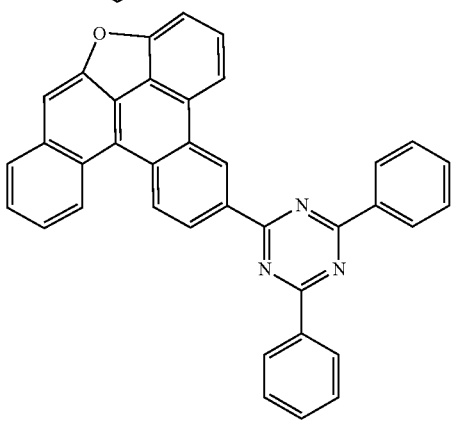

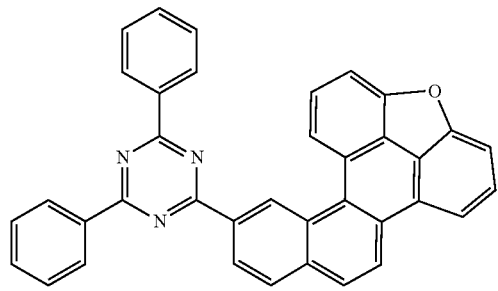
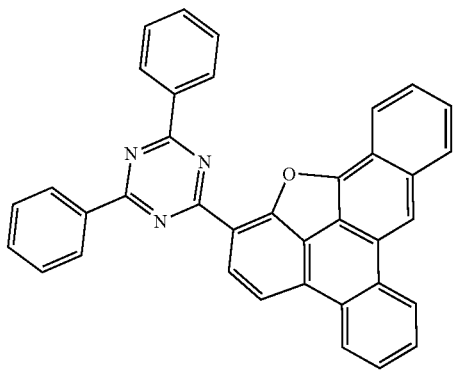
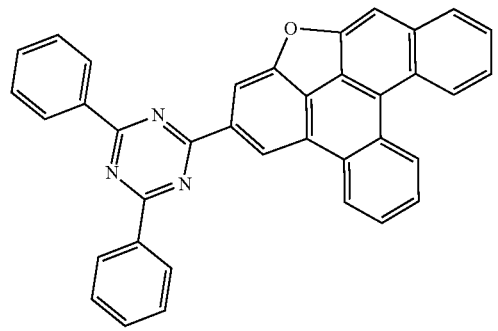
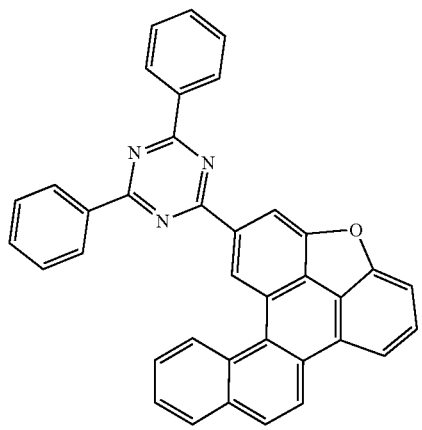
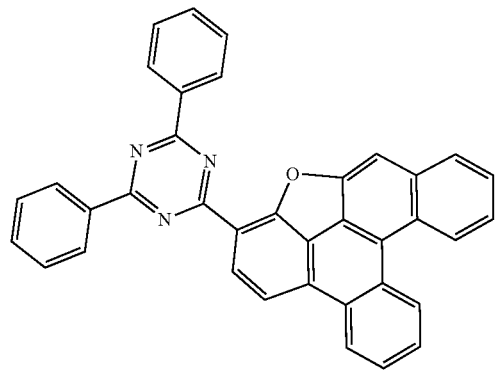
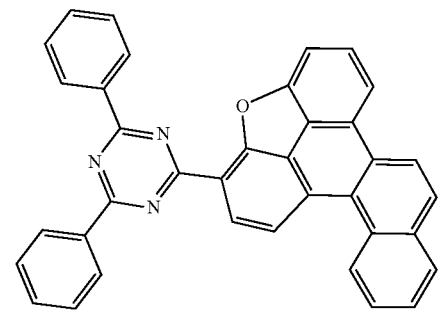
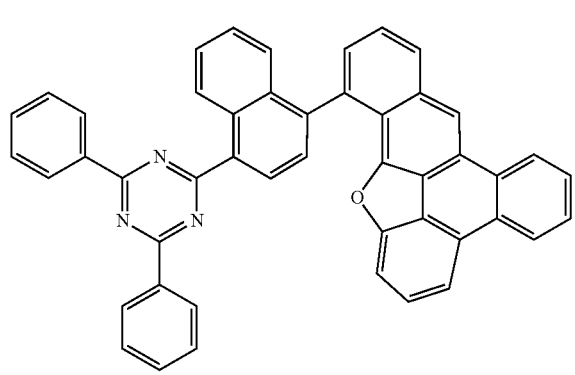
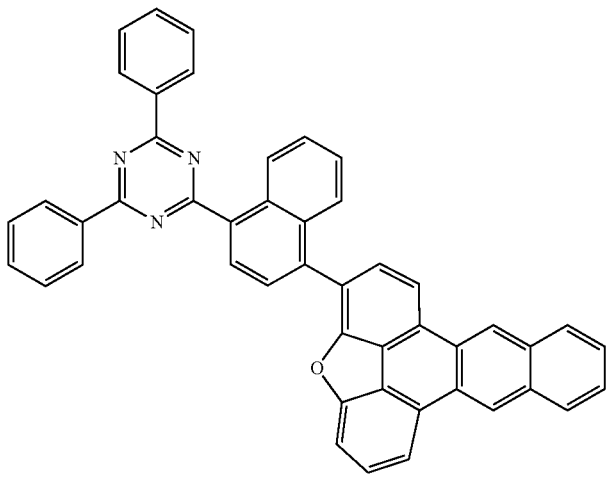

87 88
-continued
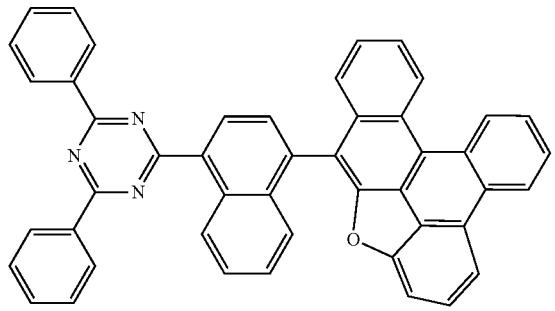
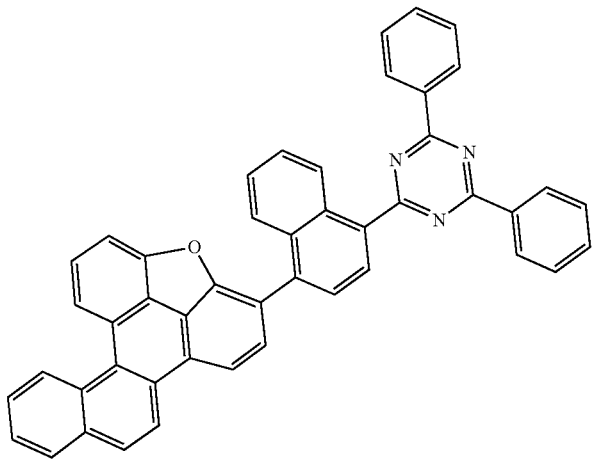
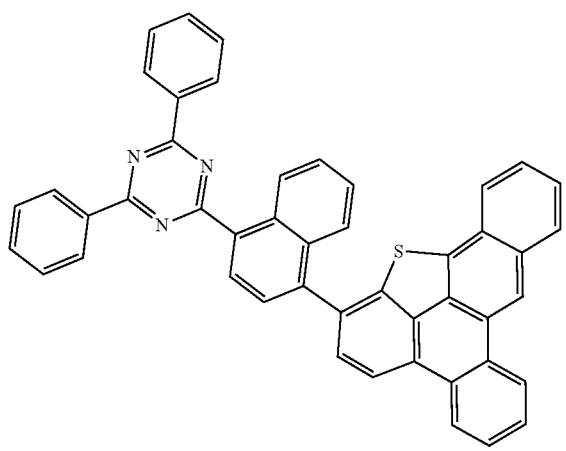
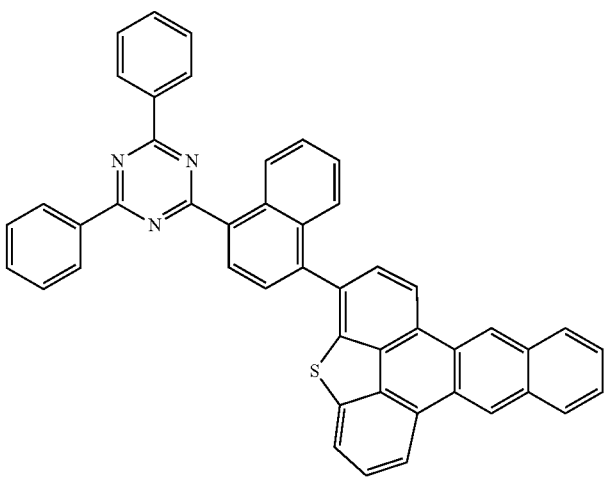
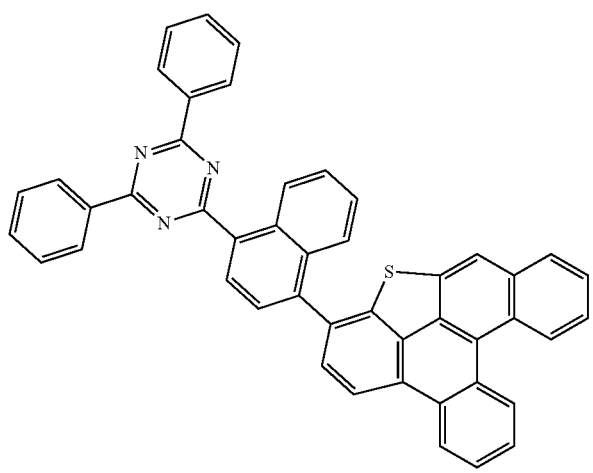
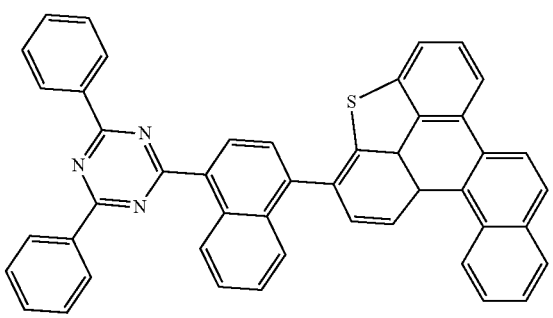

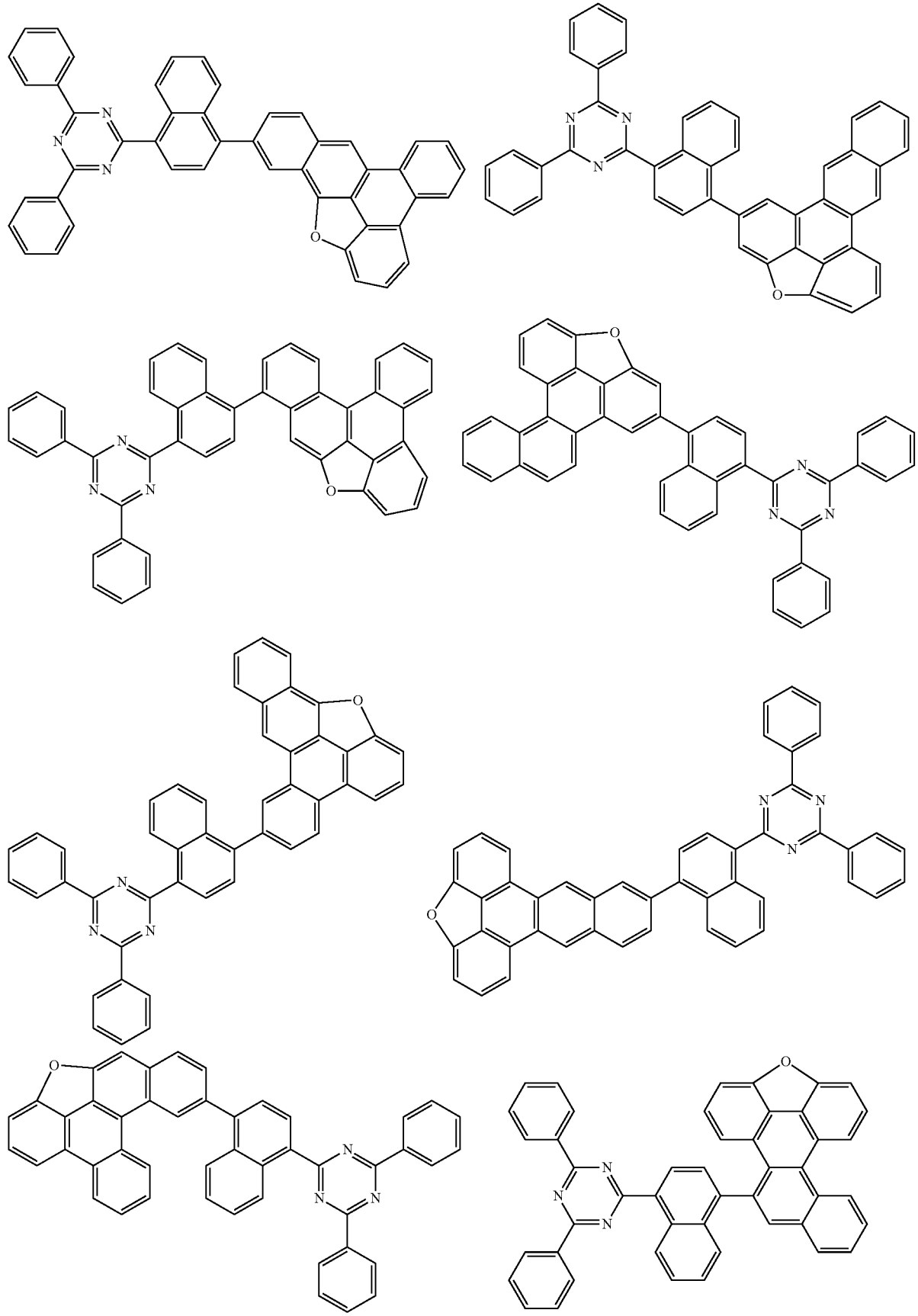

91
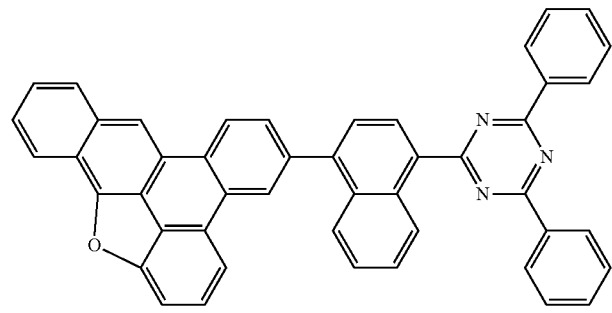
92
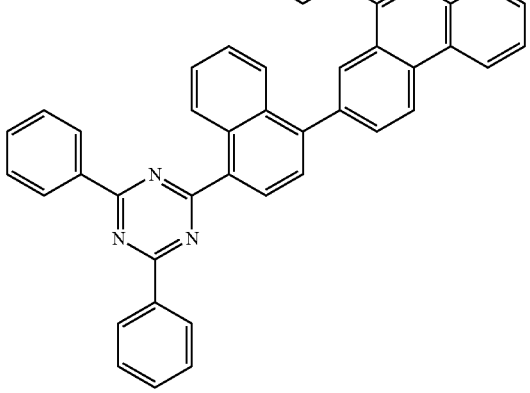
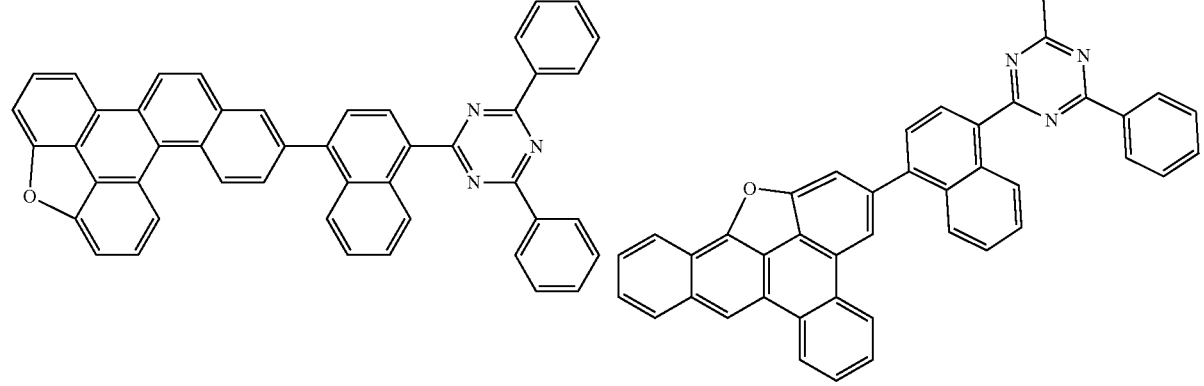
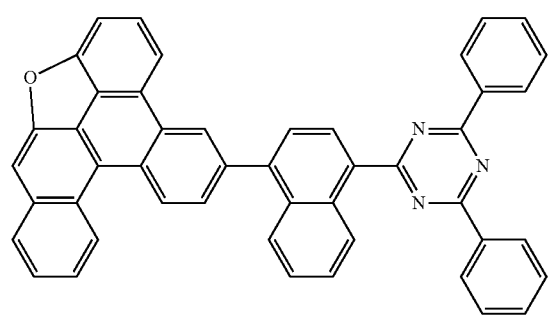
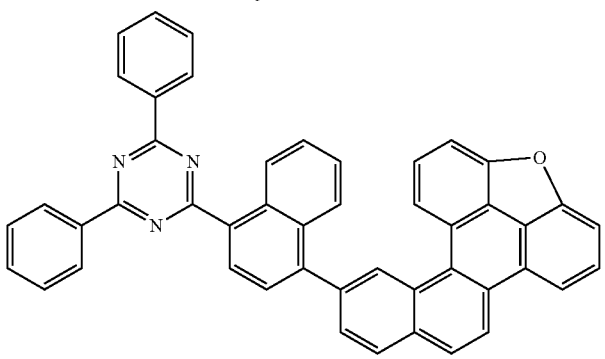
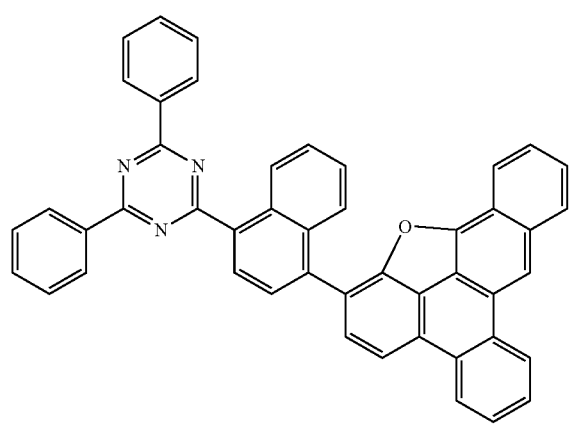
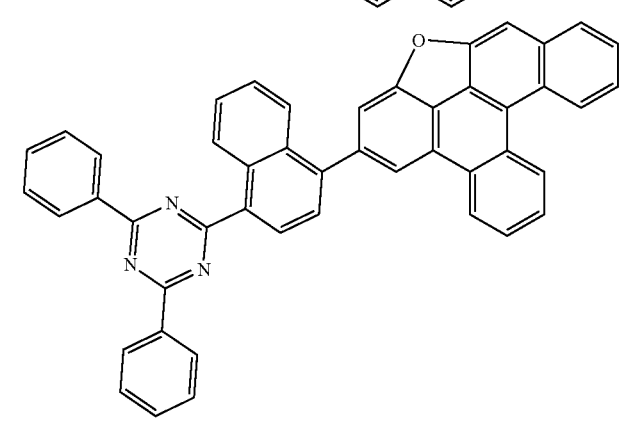

-continued
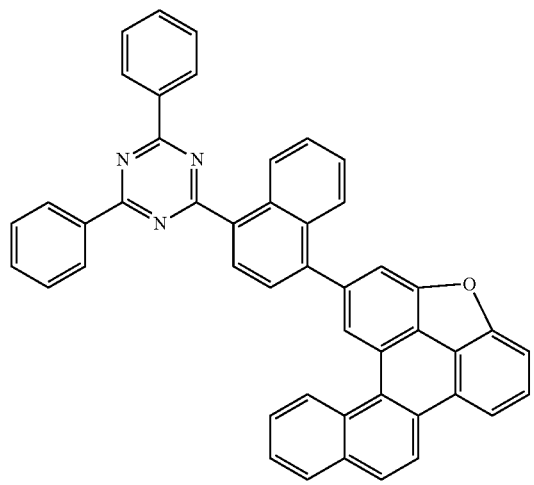
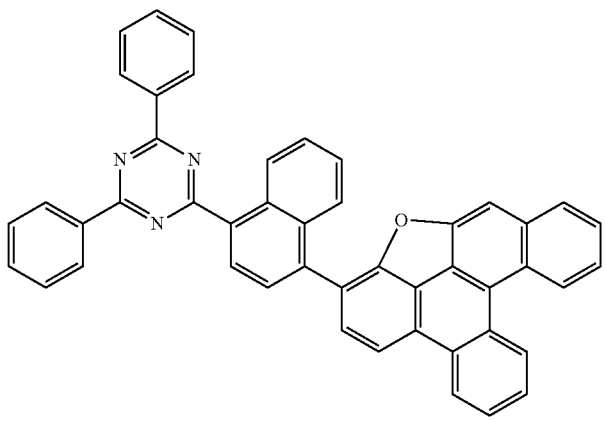
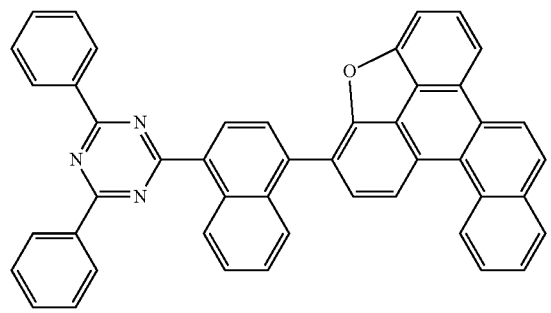
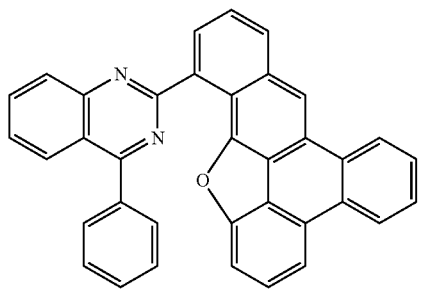
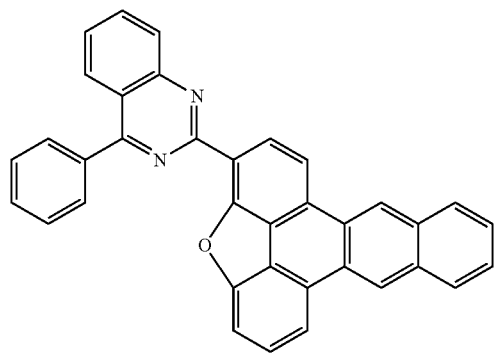
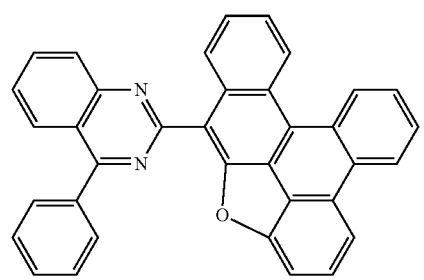
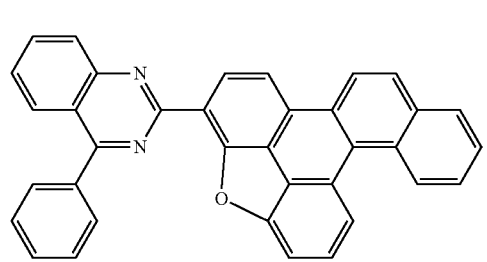
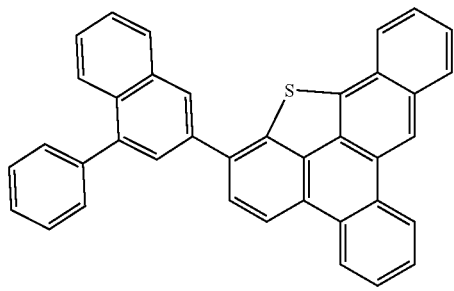

-continued
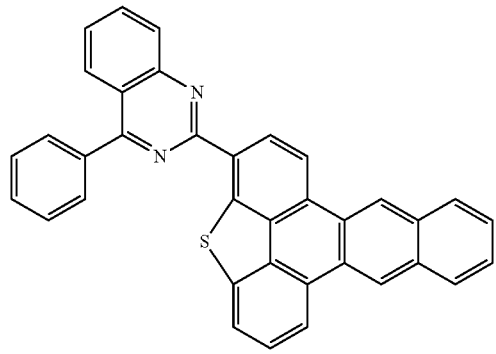
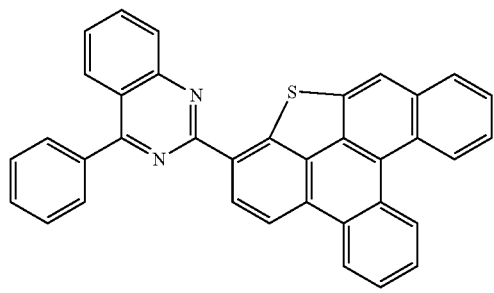
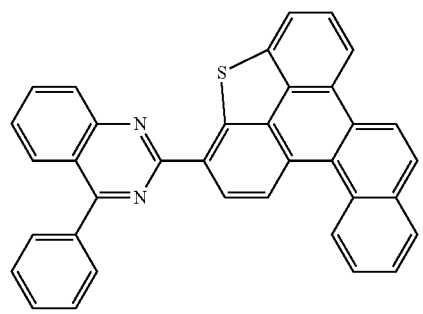
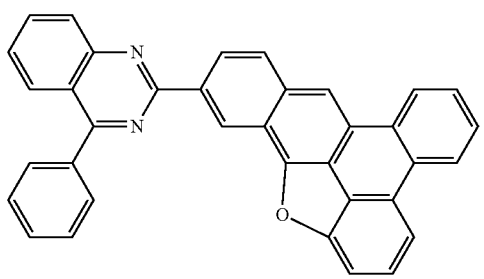
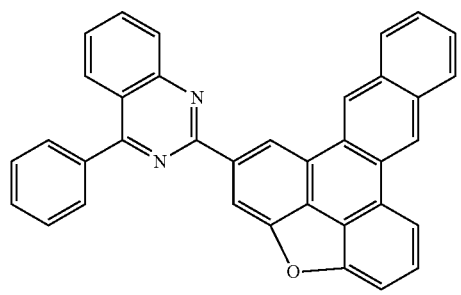
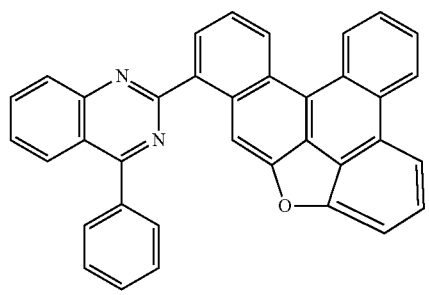
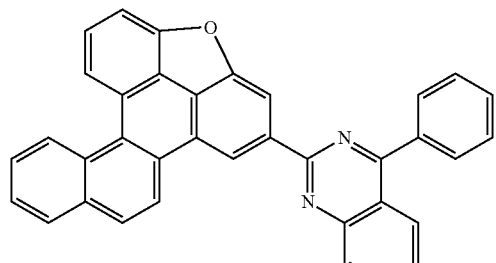
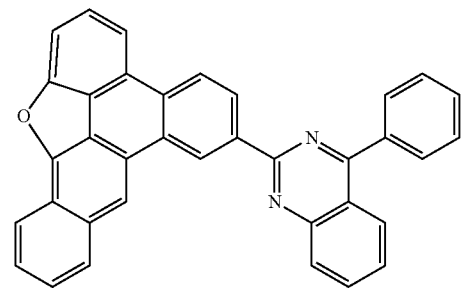
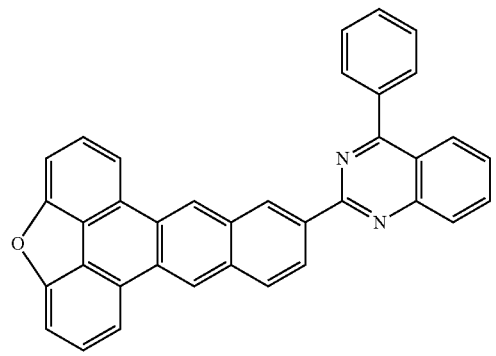
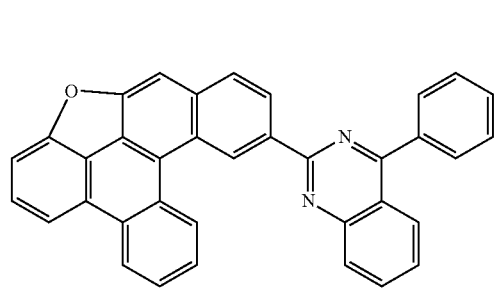

-continued
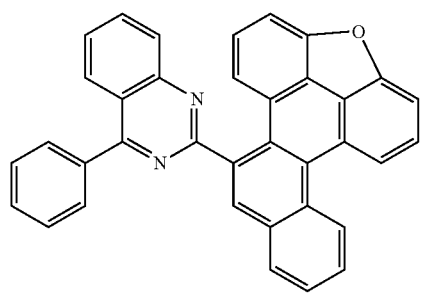
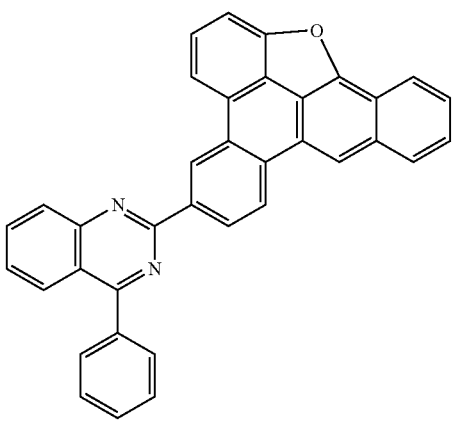
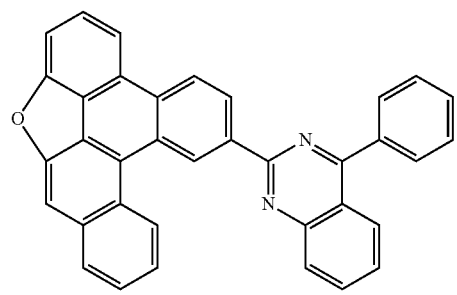
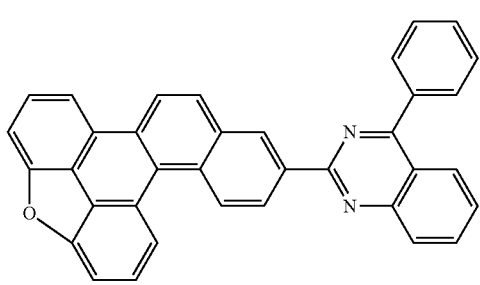
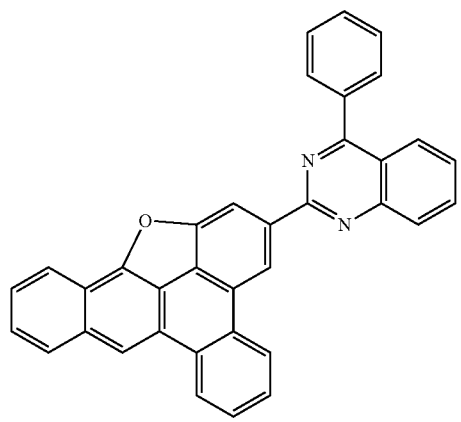
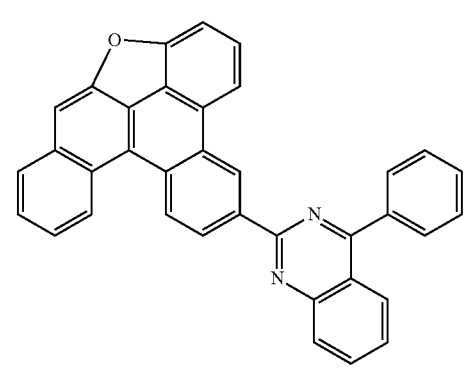
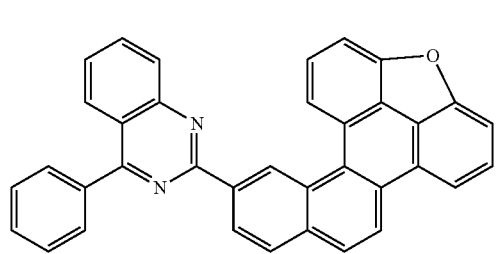
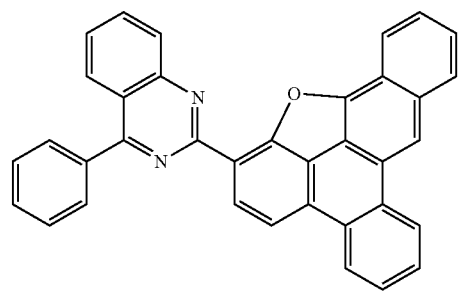

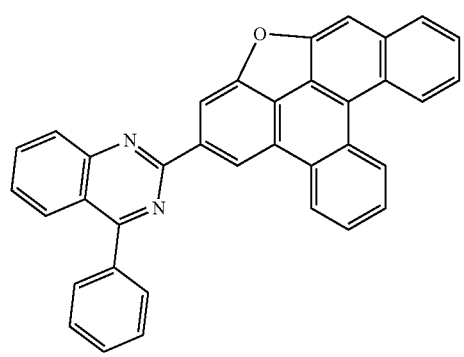
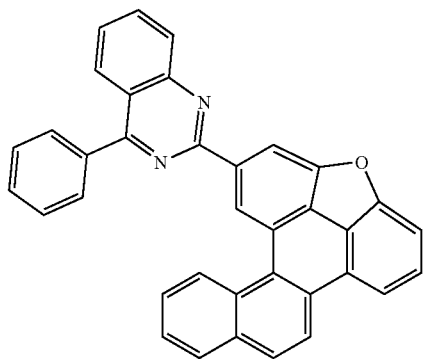
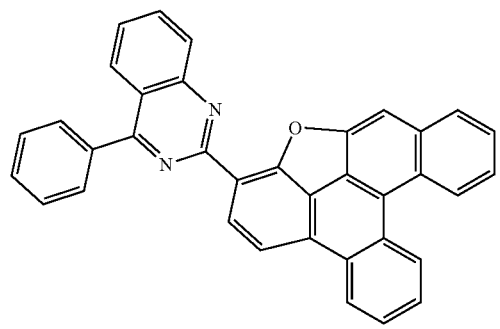
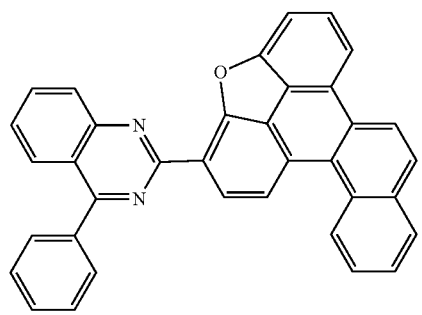
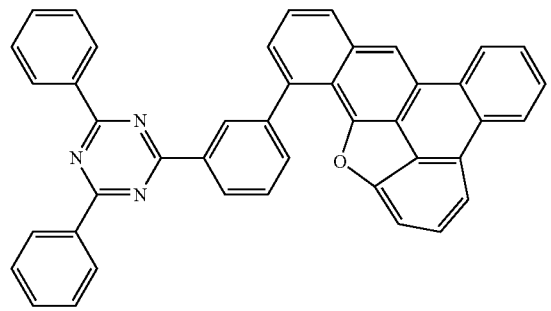
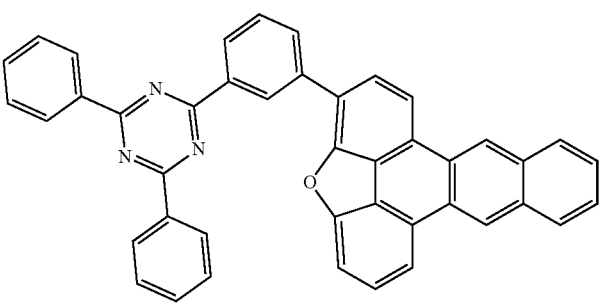
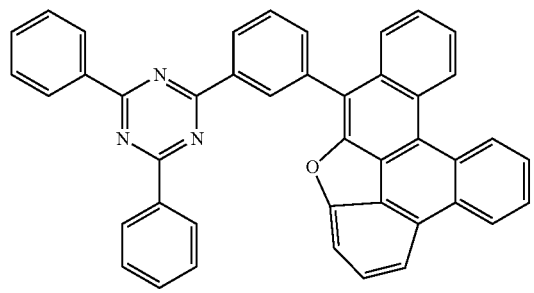
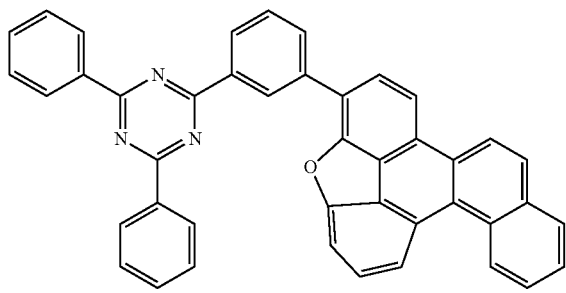
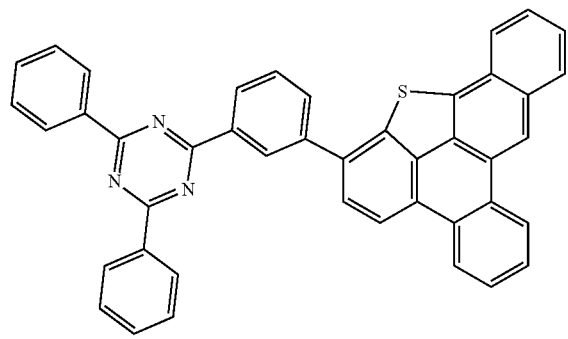
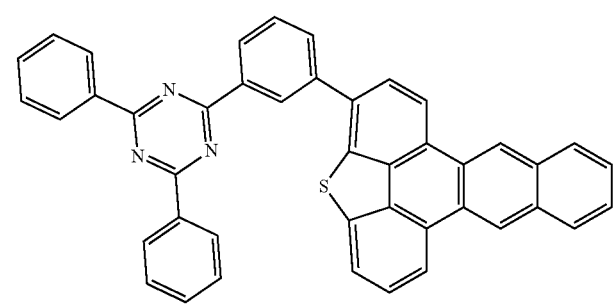

101 102
-continued
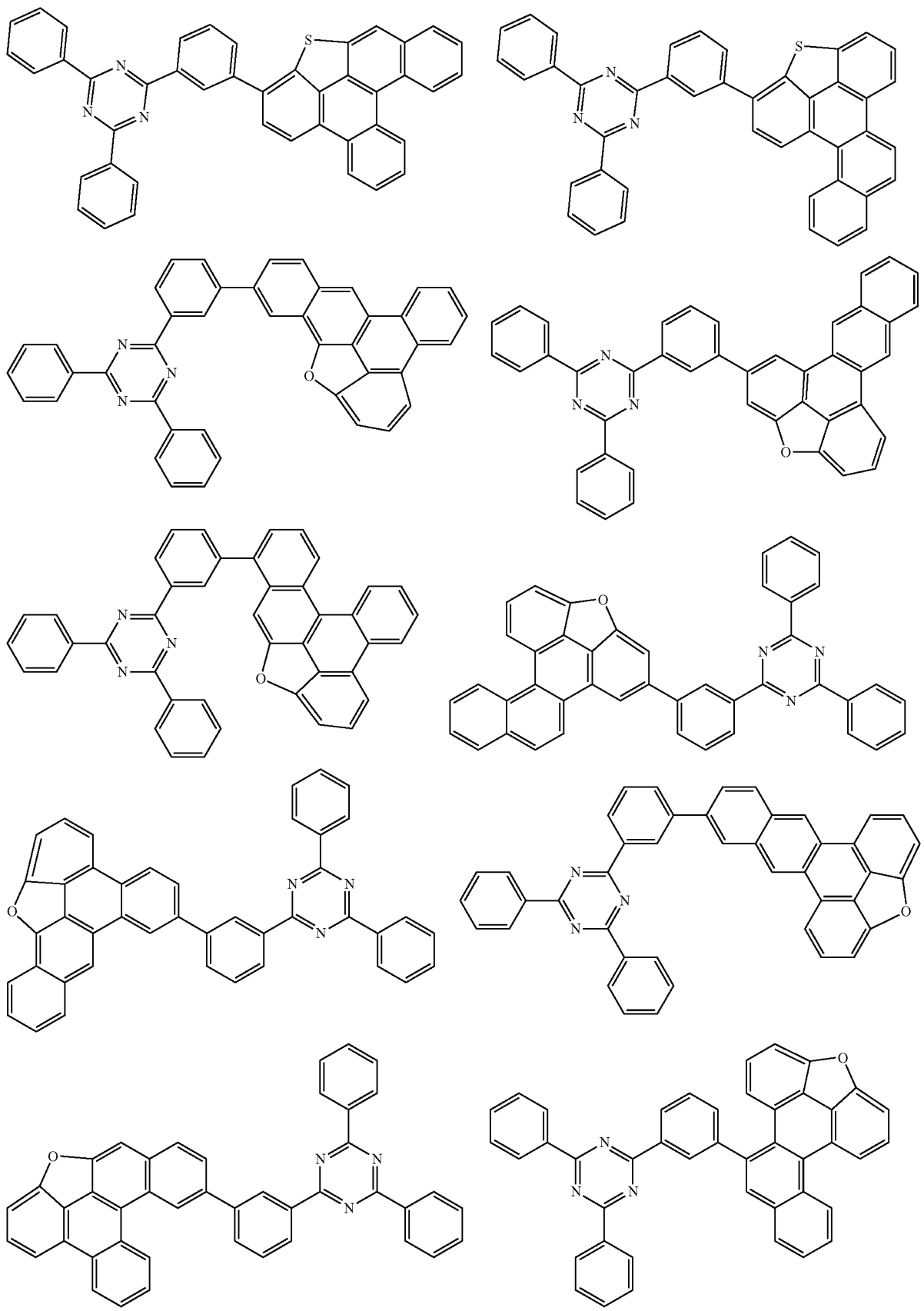

103
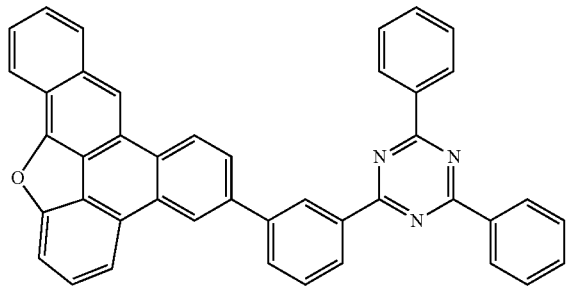
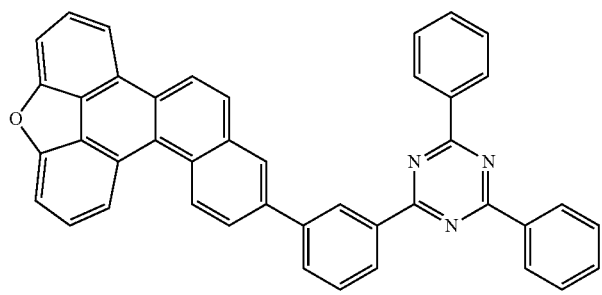
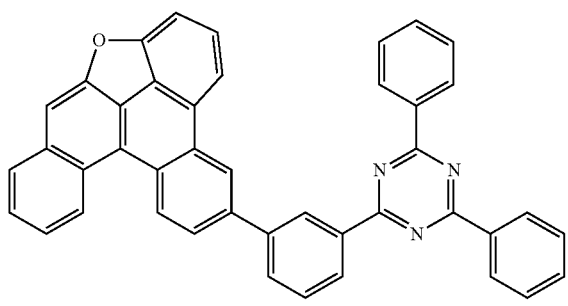
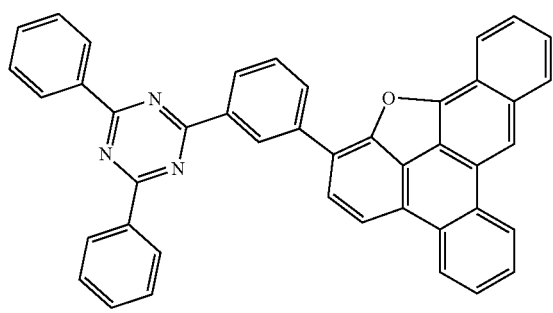
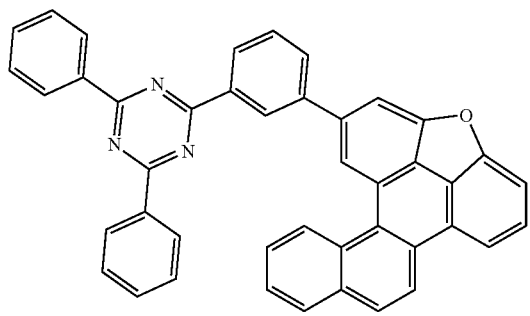
104
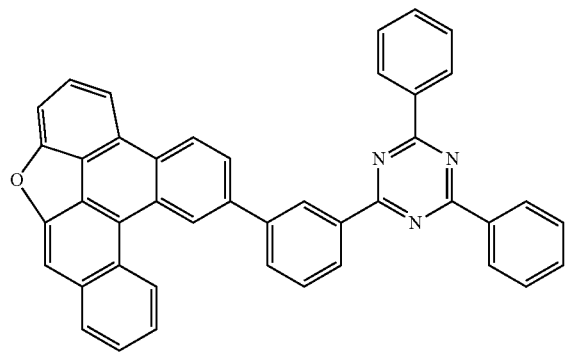
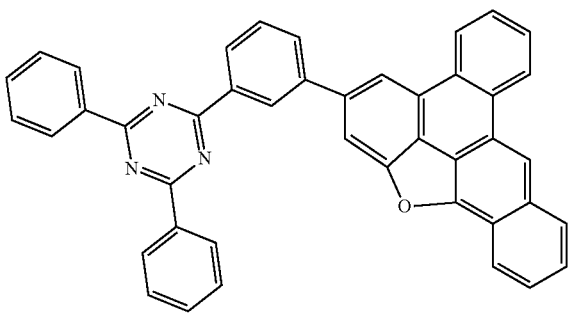
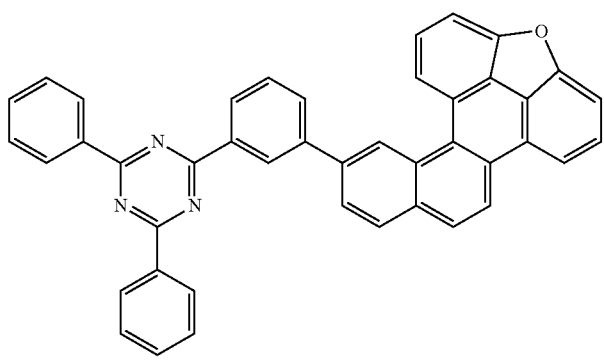
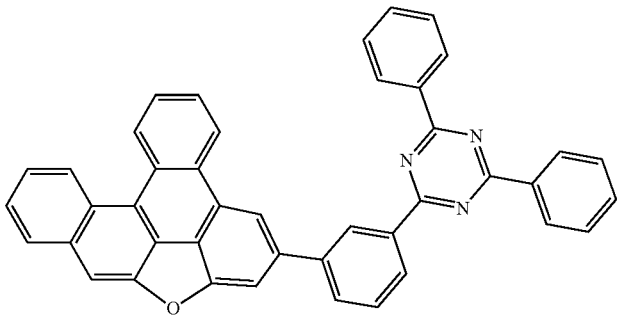
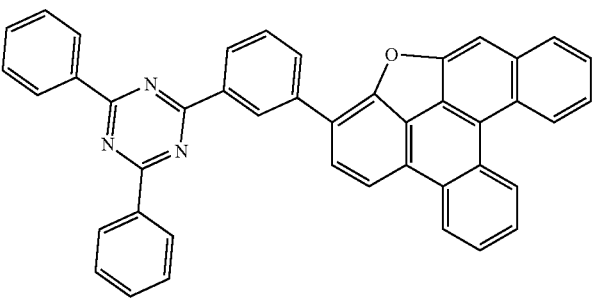

-continued
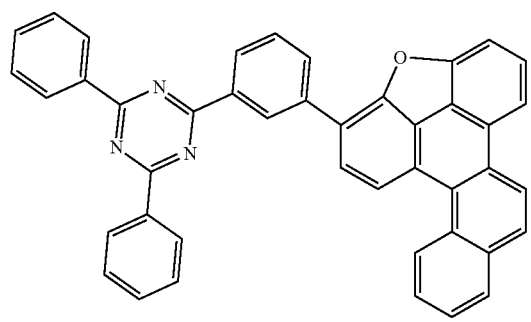
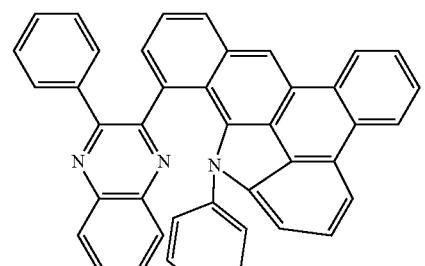
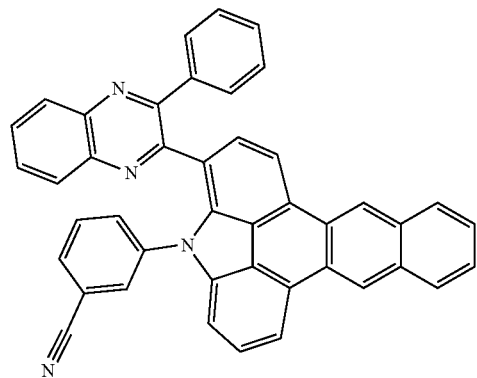
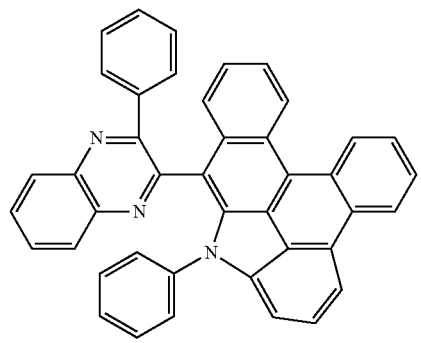
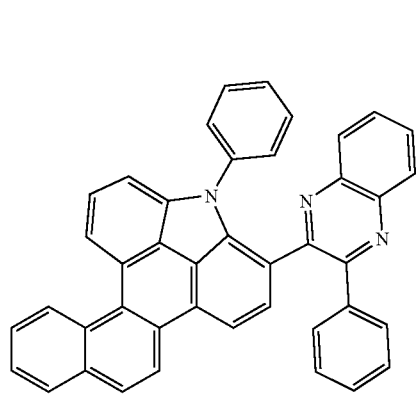
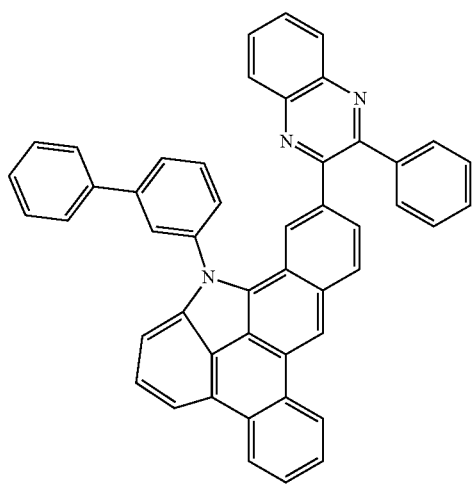
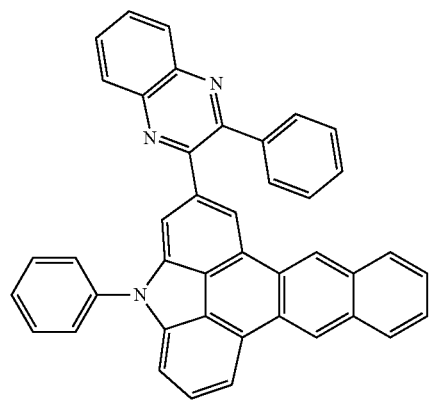
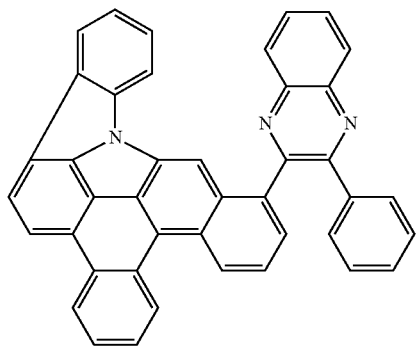

-continued
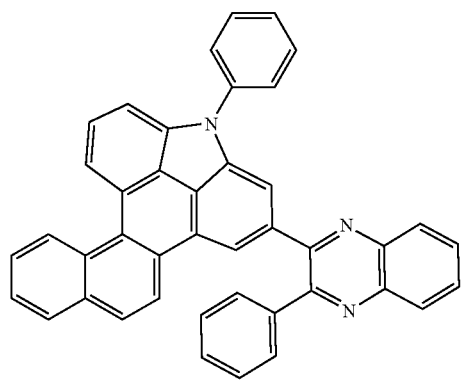 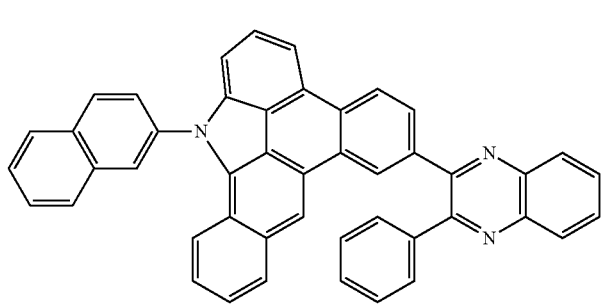
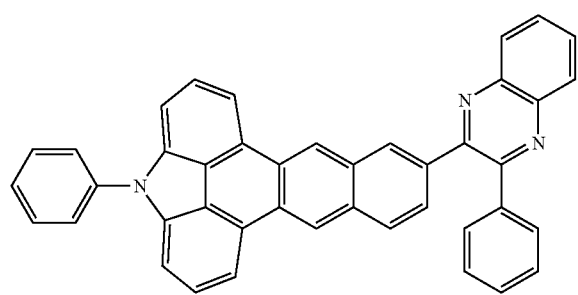 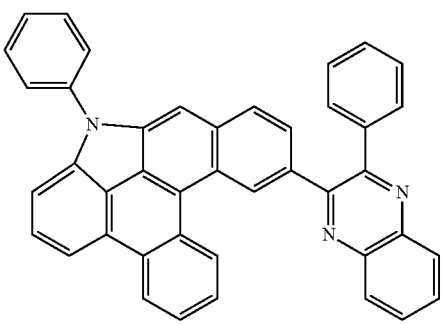
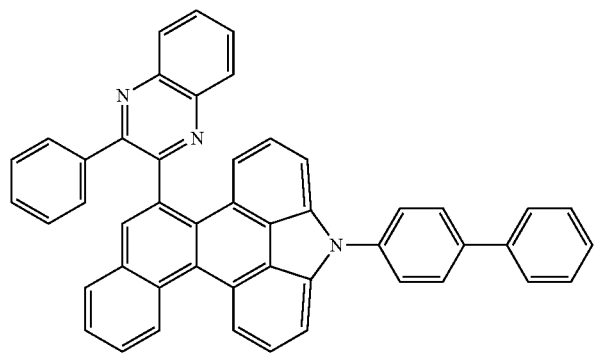 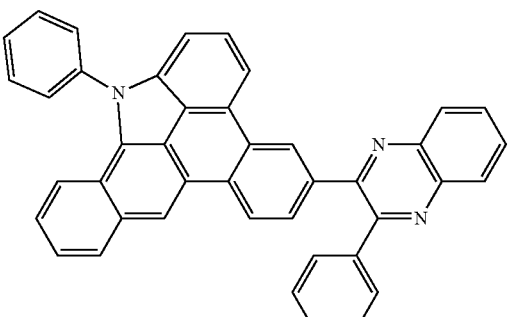
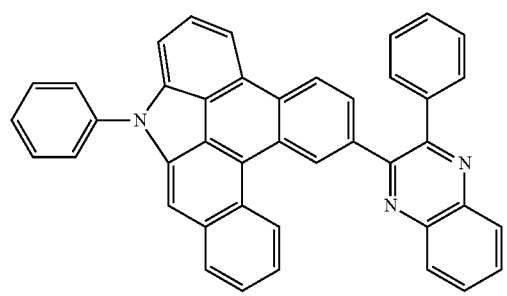 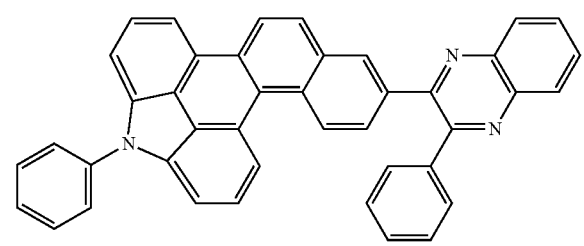
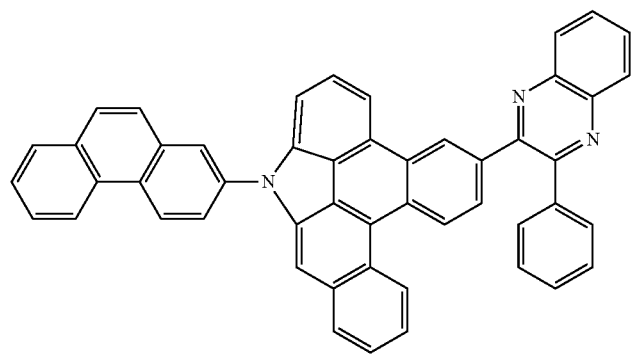

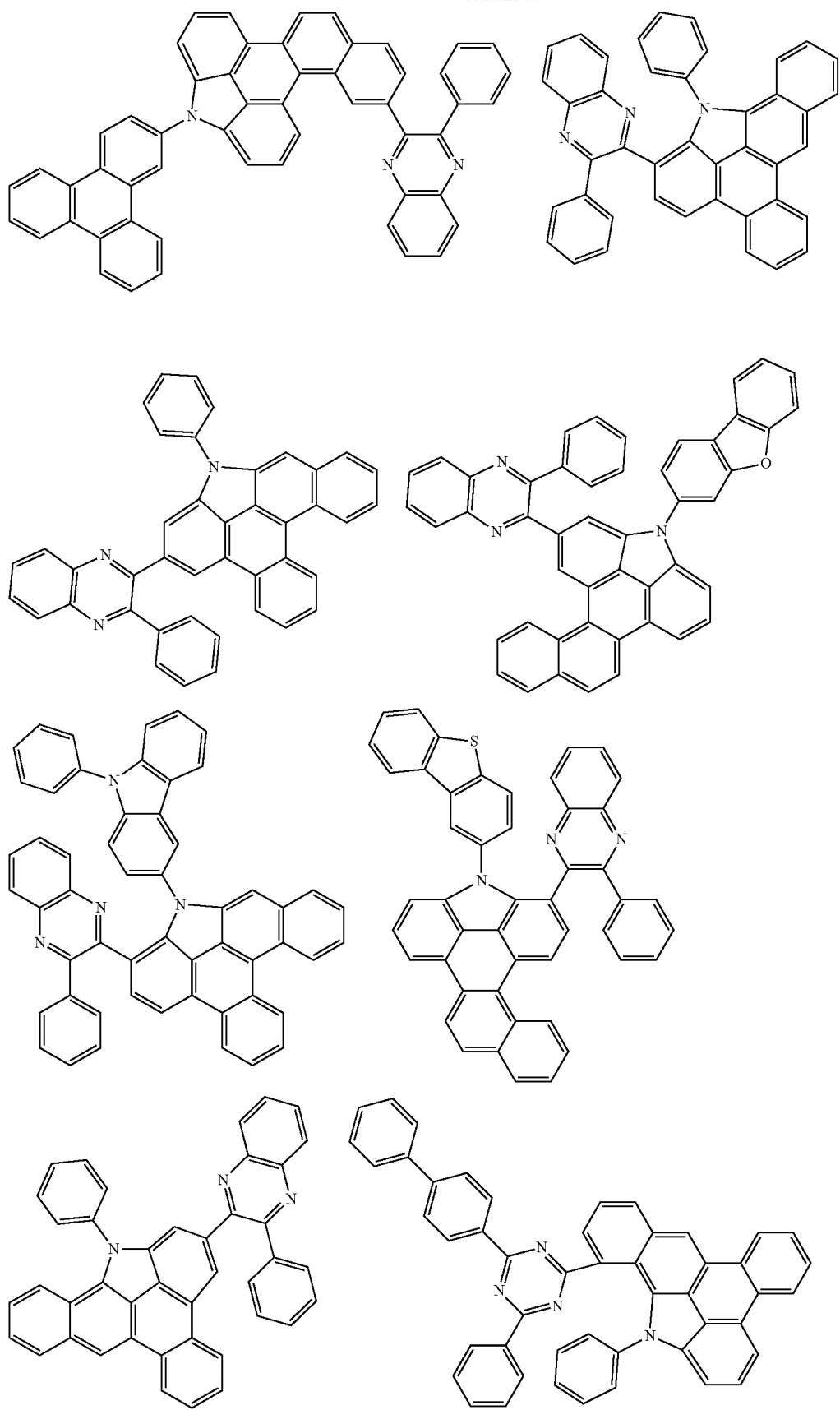

111
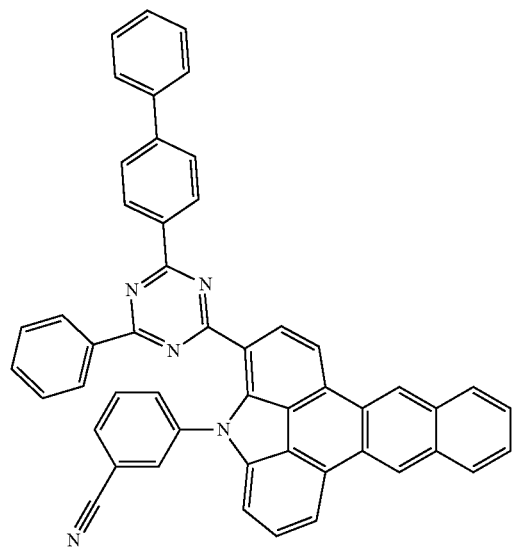
112
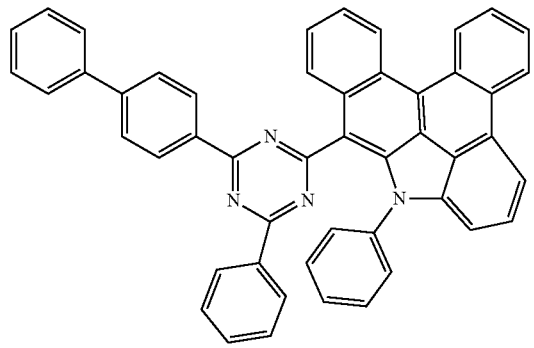
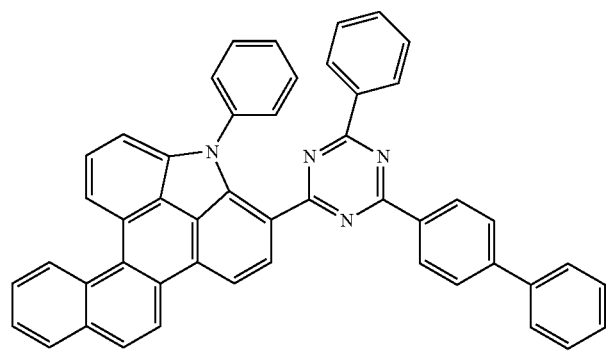
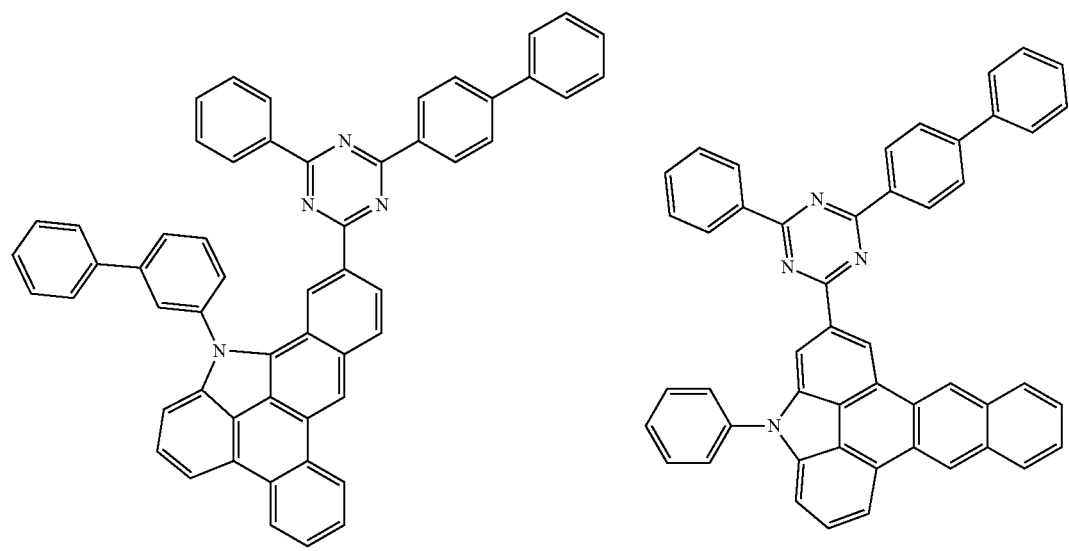

-continued
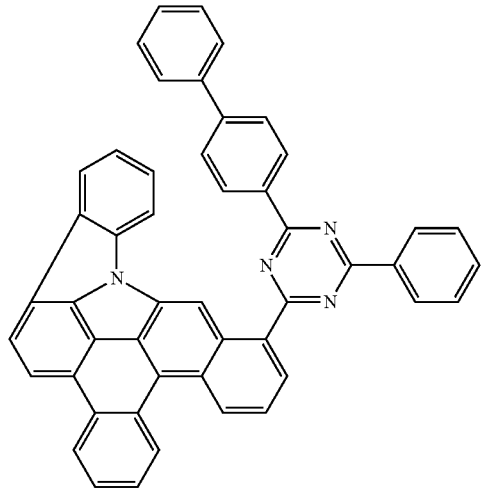
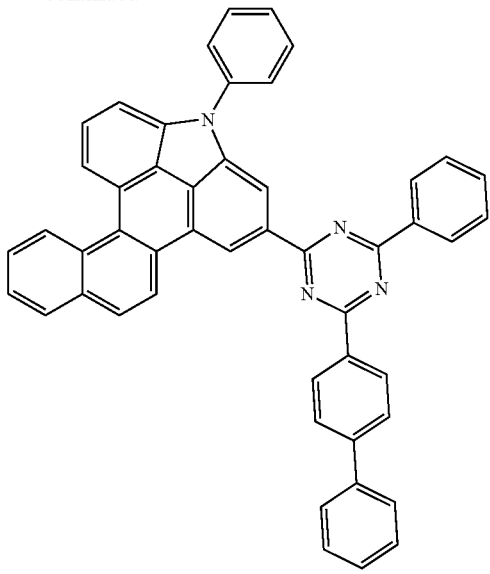
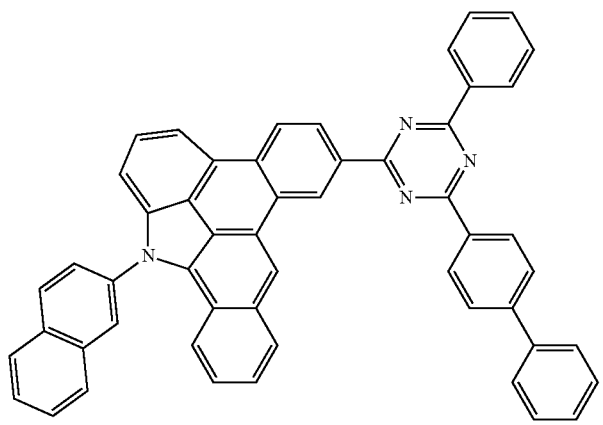
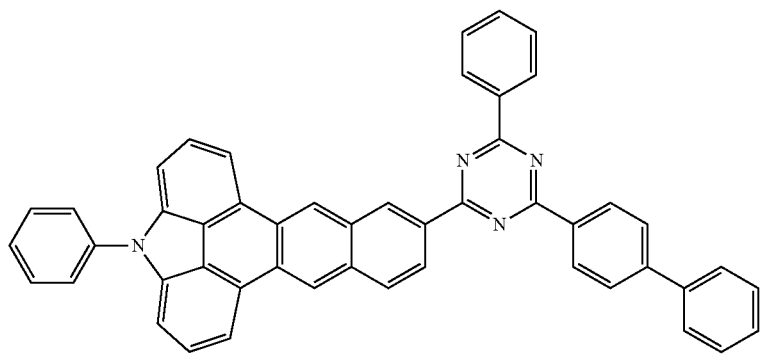

115 116
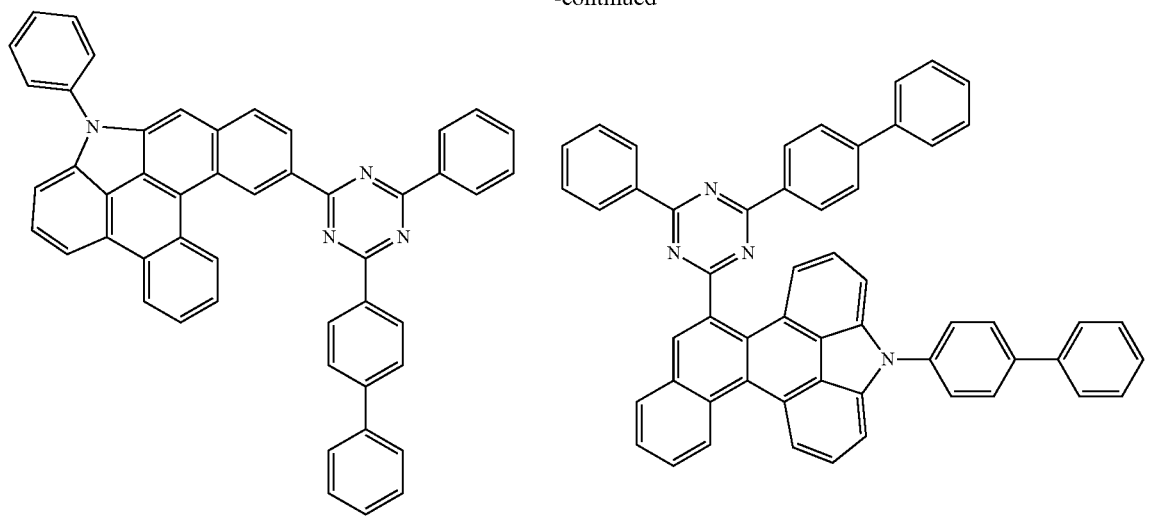
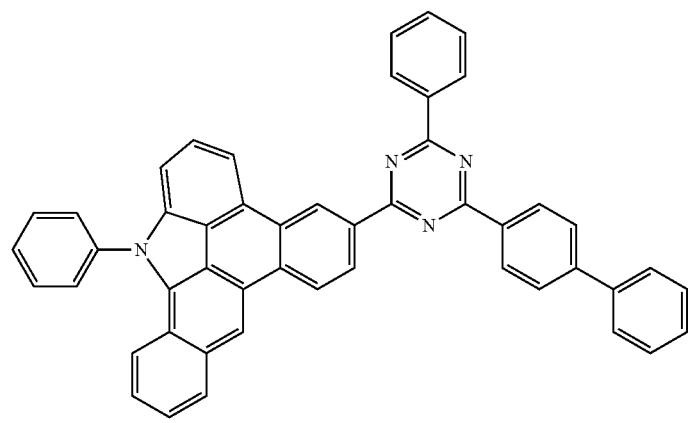
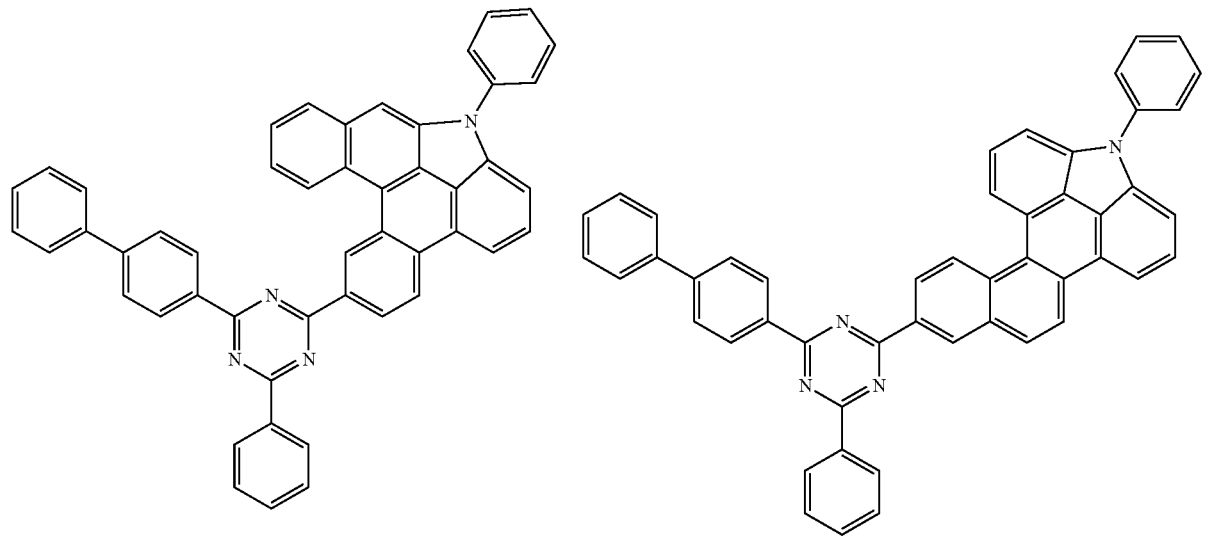

-continued
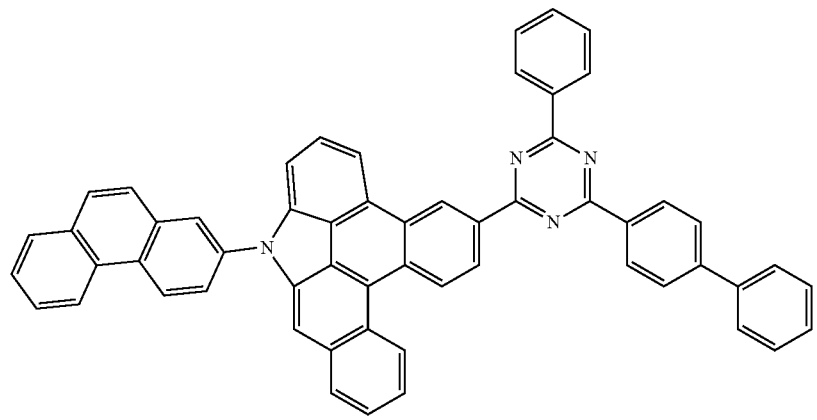
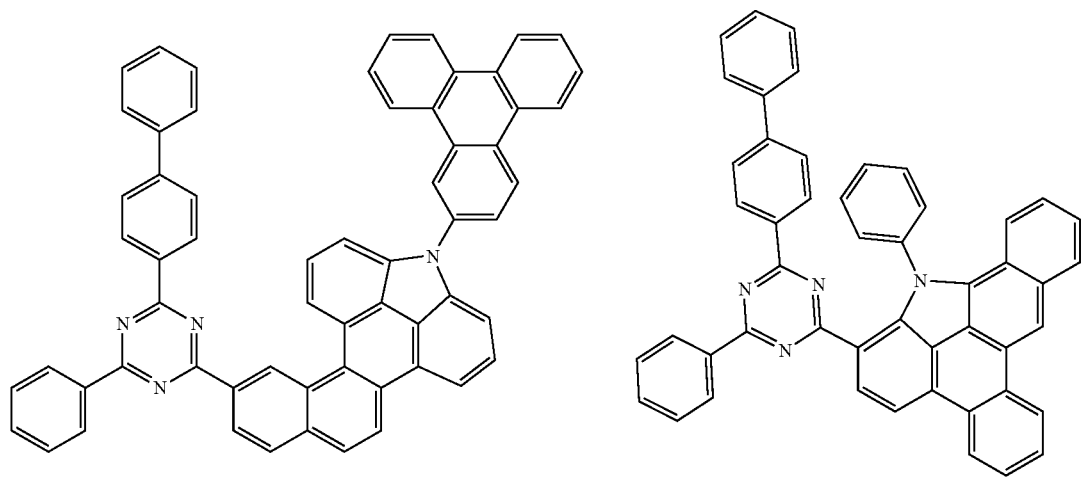
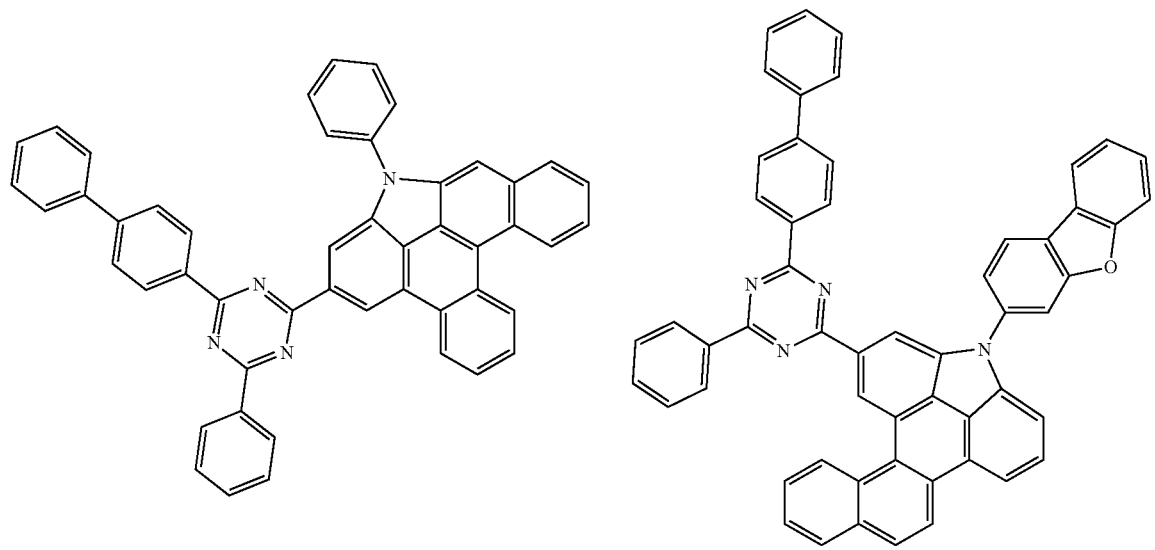

119 120
-continued
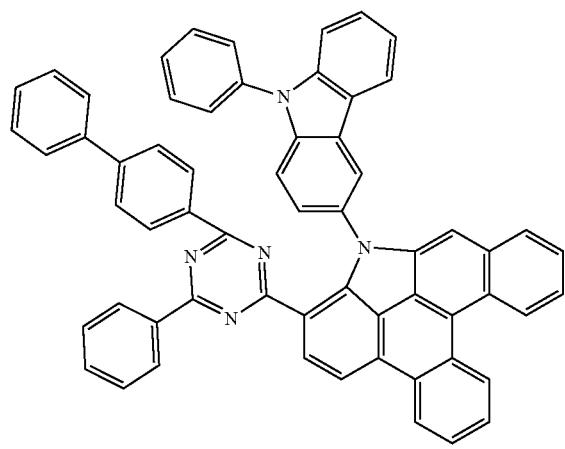
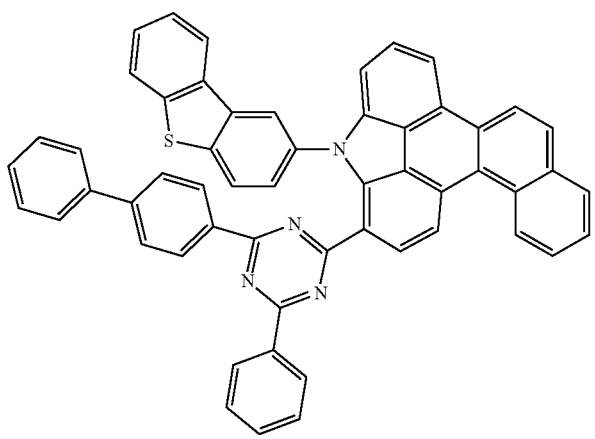
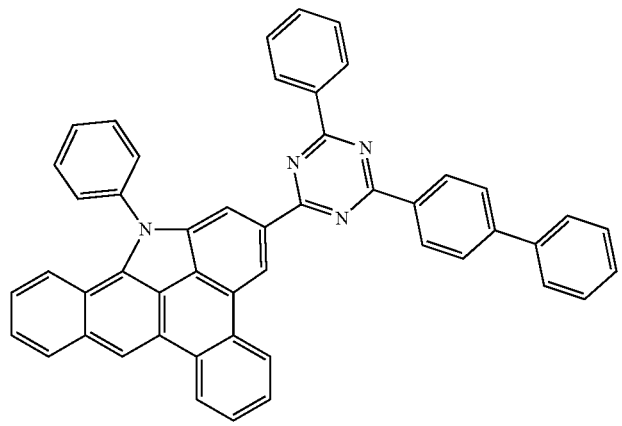
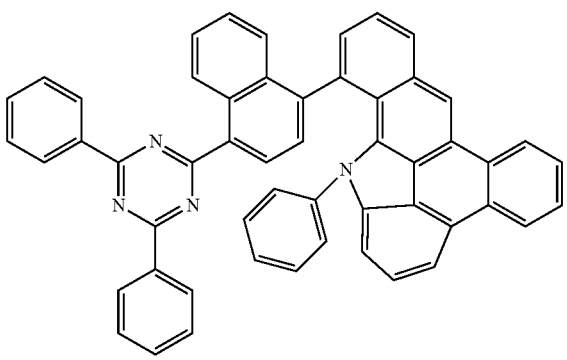
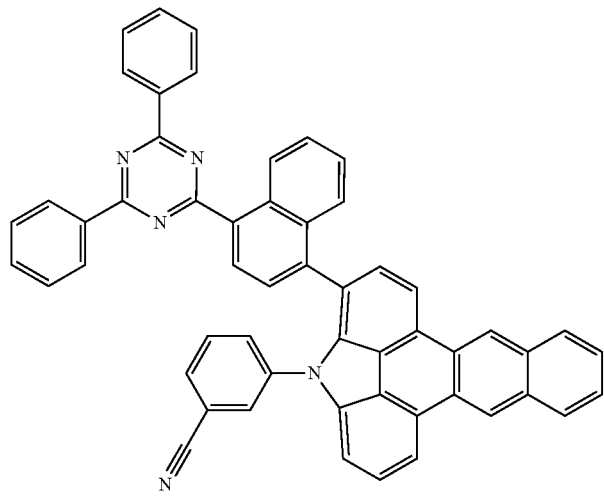
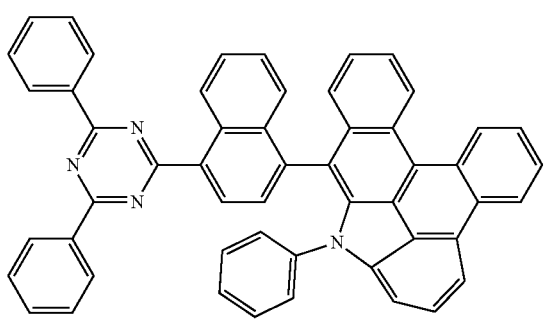

121 122
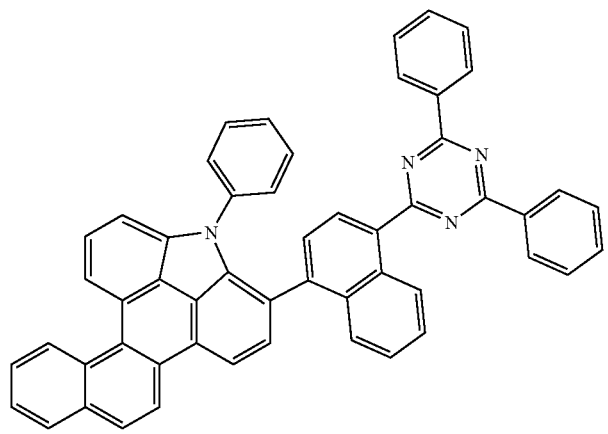
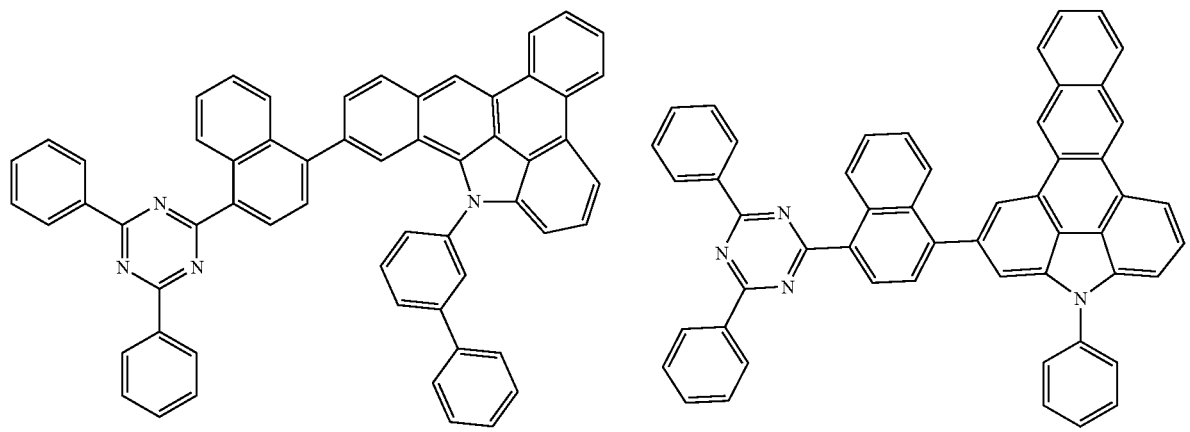
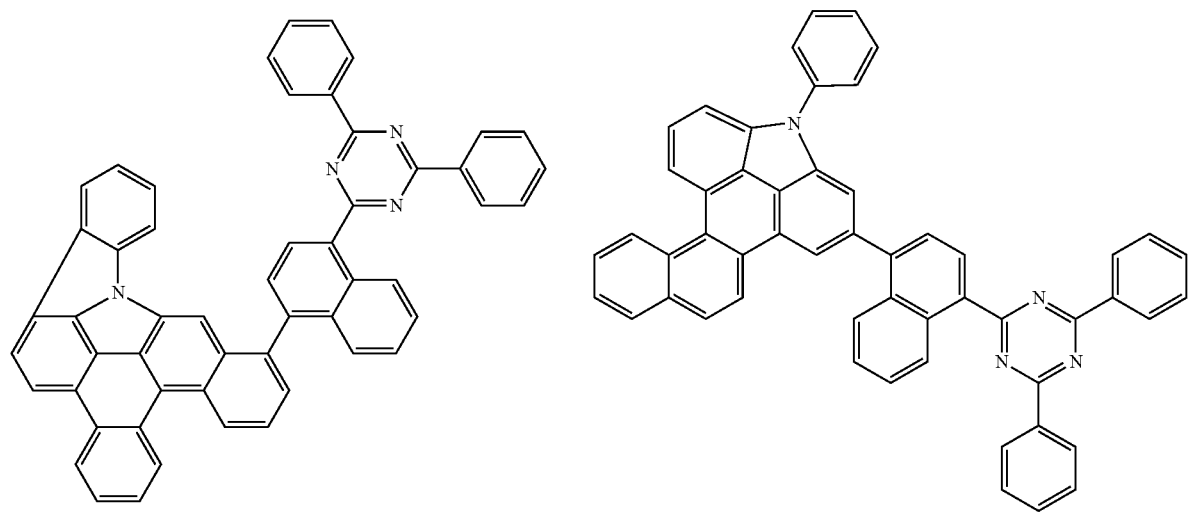

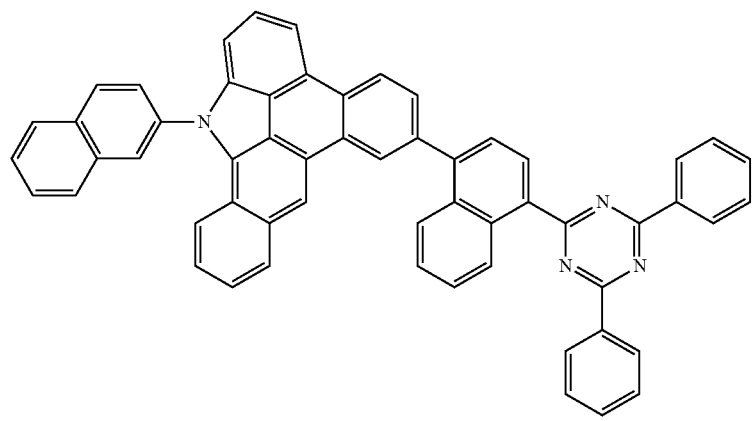
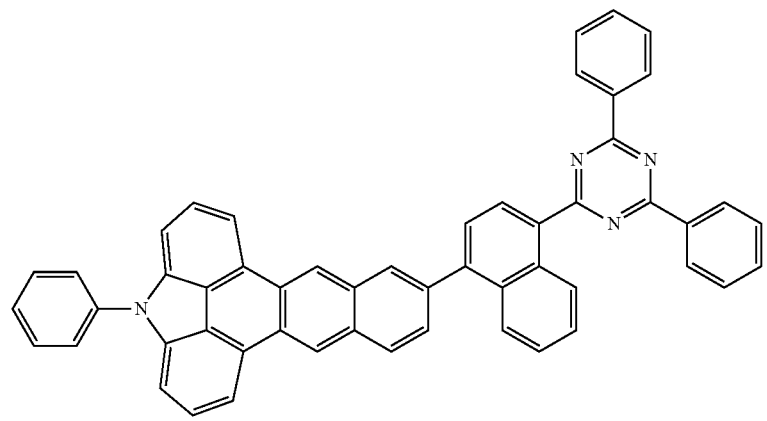
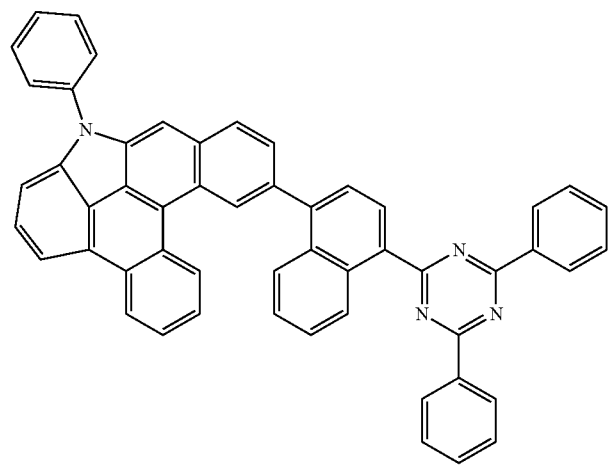

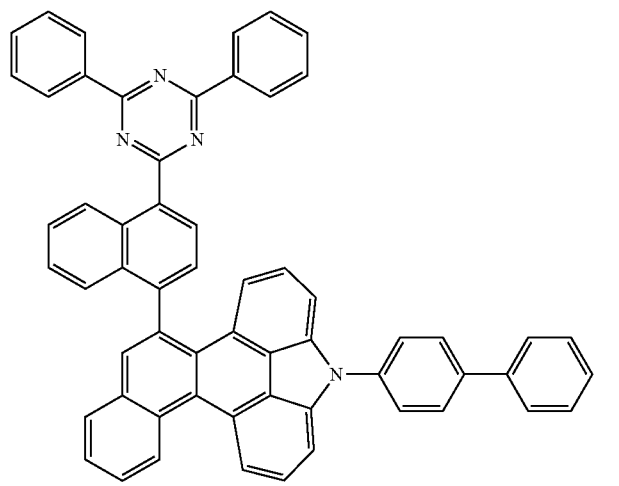
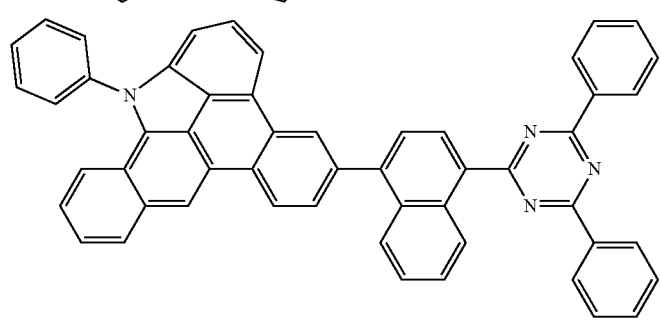
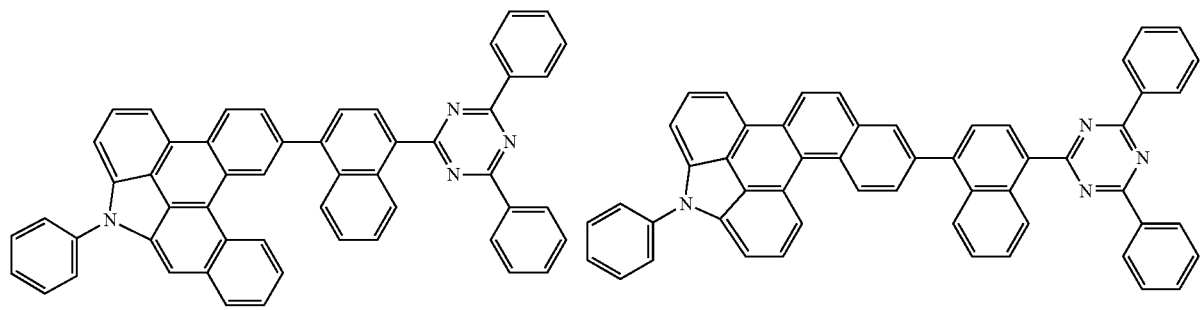
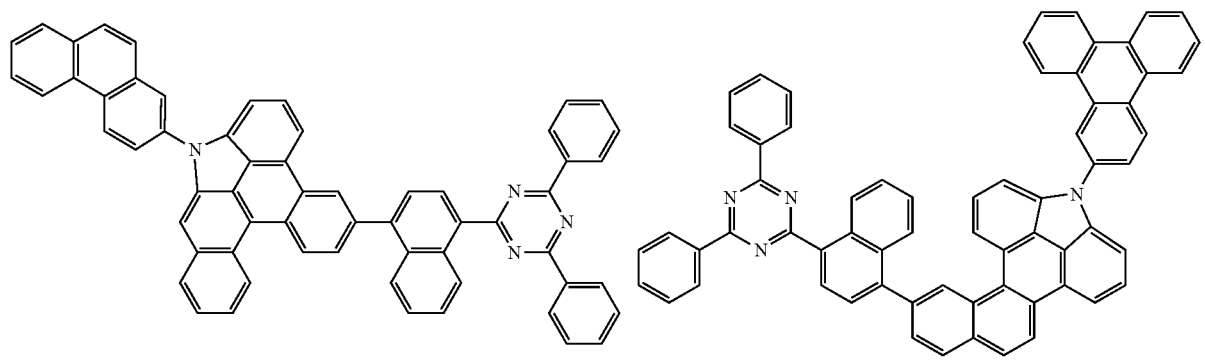

-continued
| 127 | 128 |
|---|---|
| 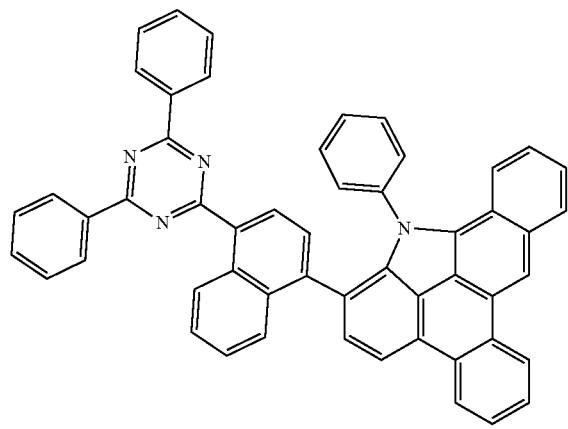 | 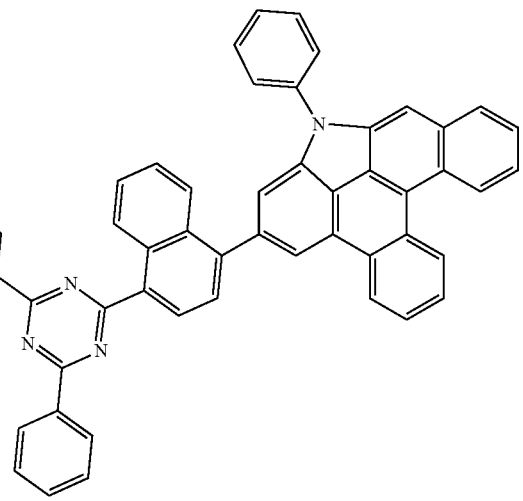 |
| 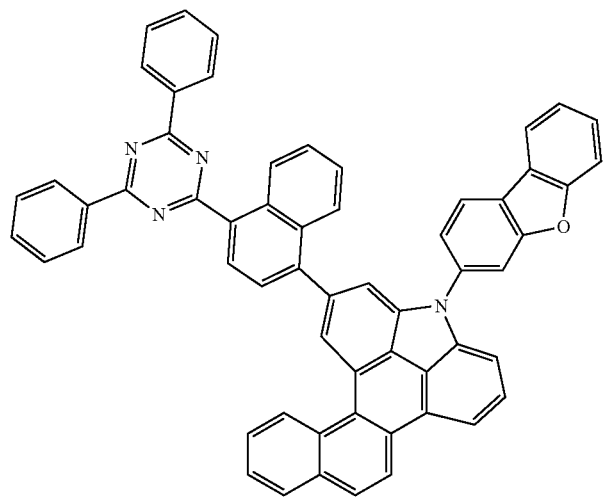 | 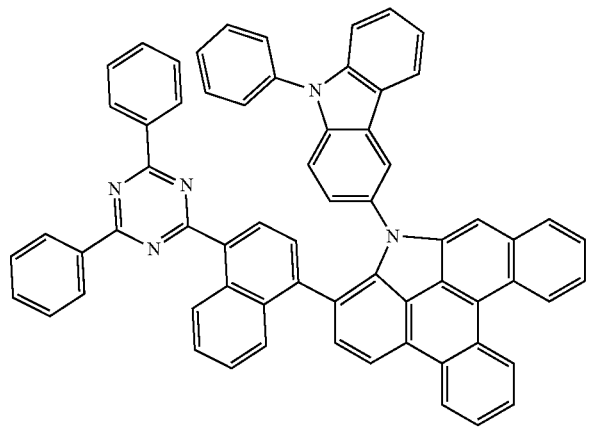 |
| 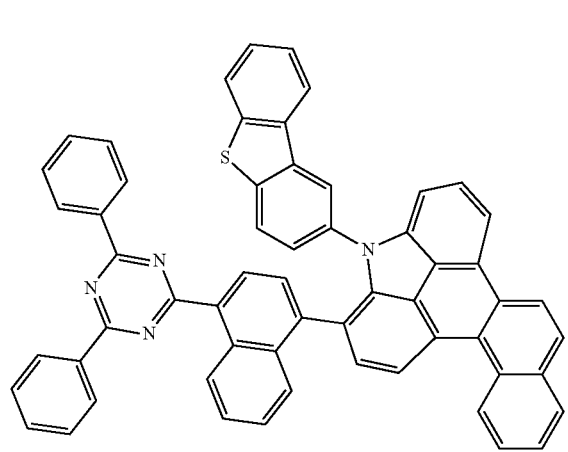 | 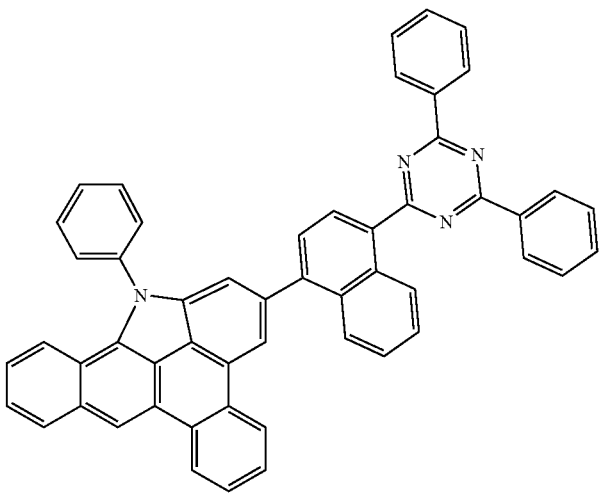 |

-continued
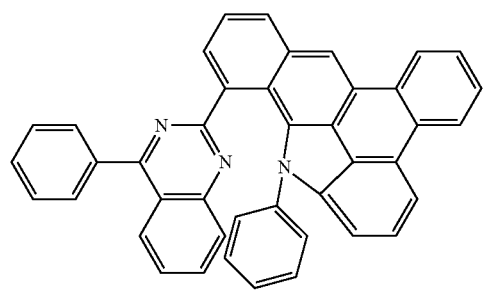
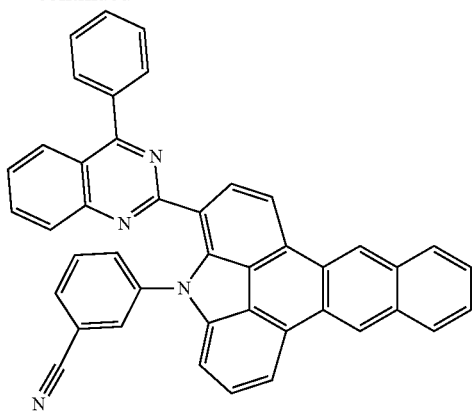
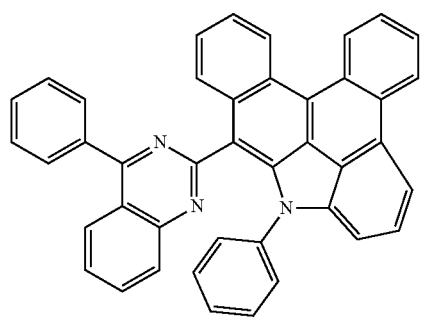
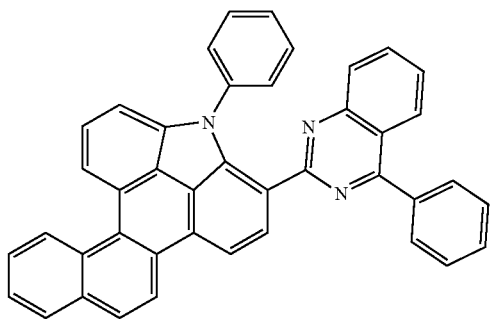
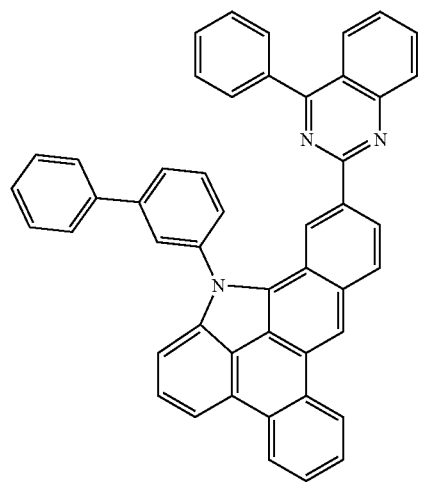
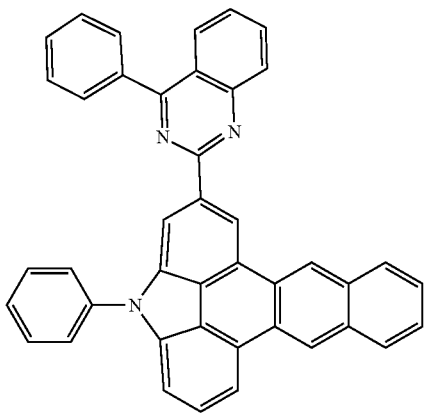
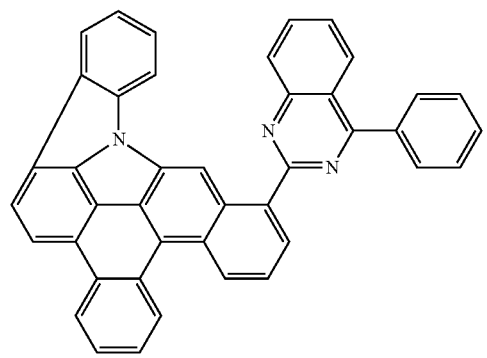
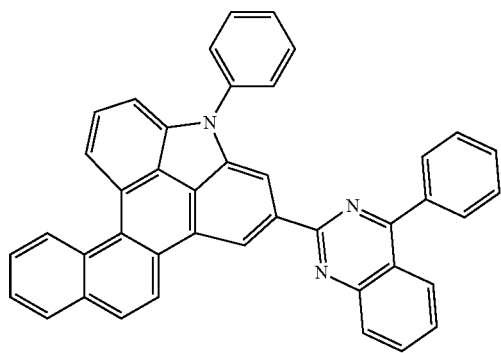

131 132
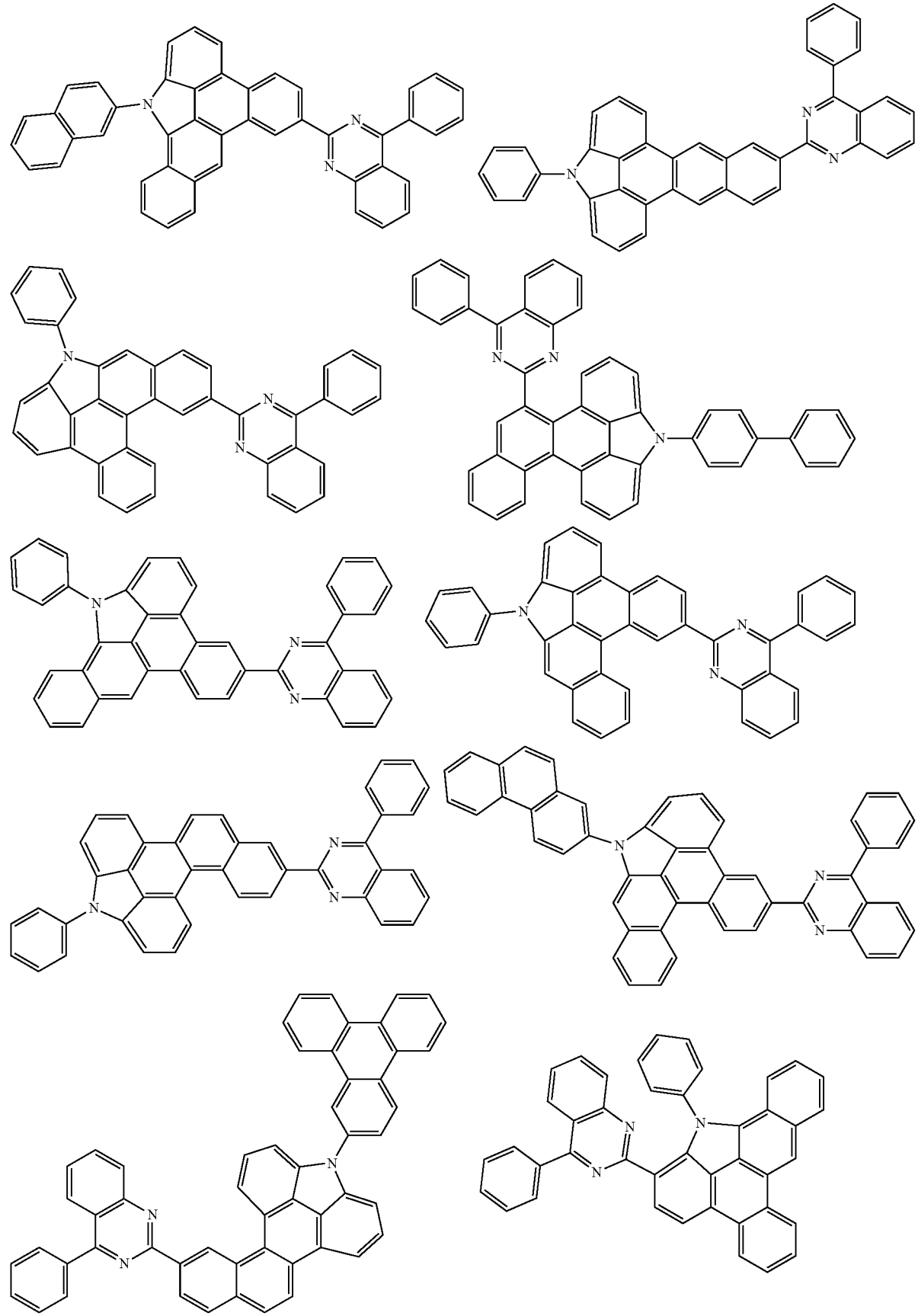
-continued

-continued
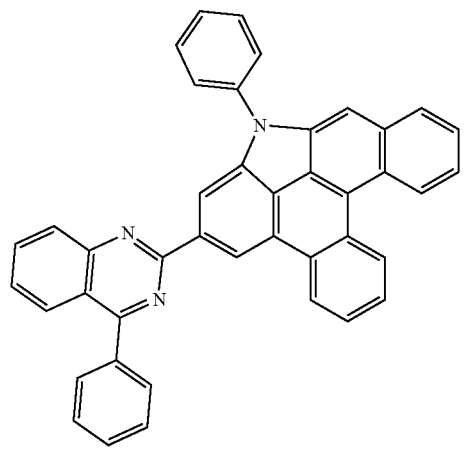
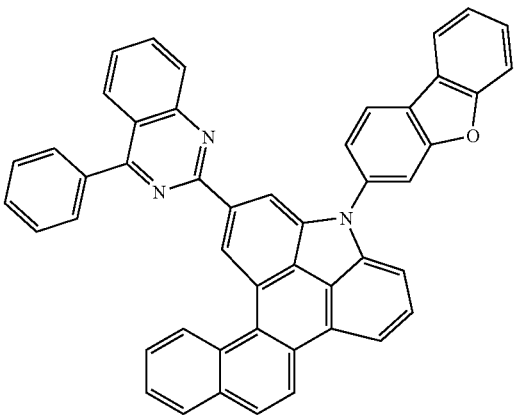
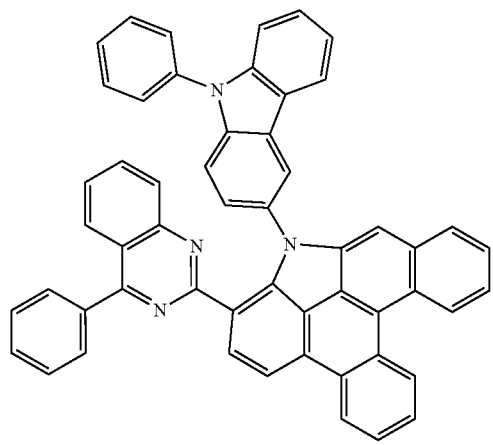
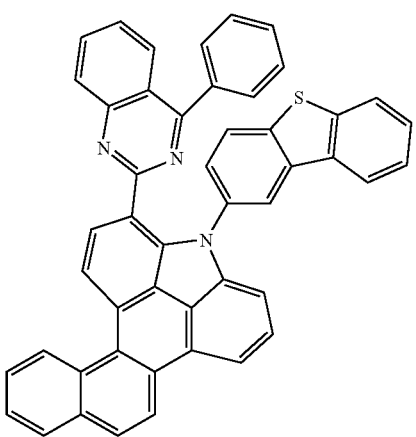
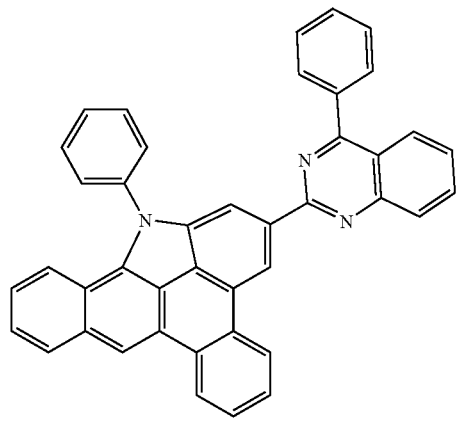
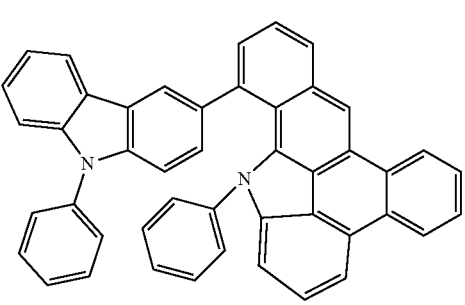
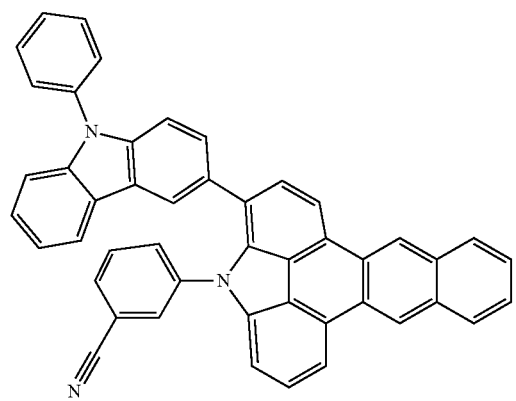
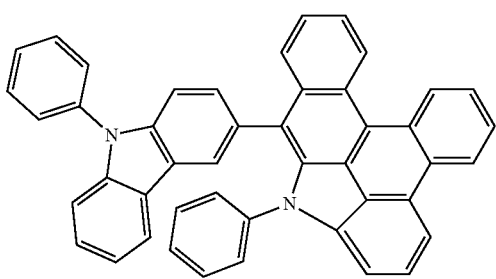

-continued
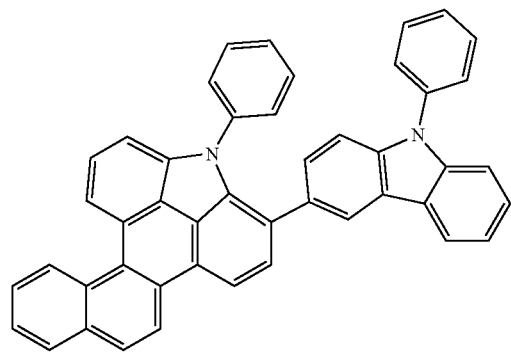
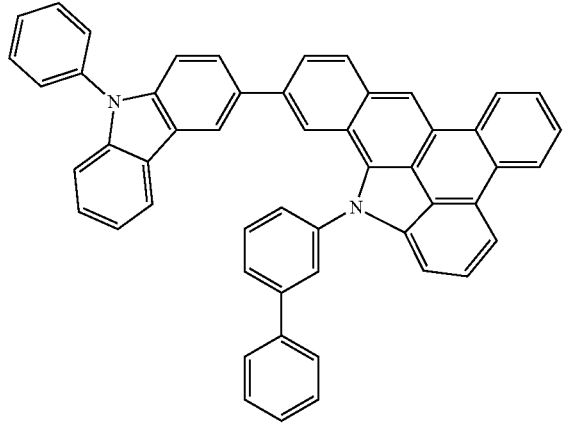
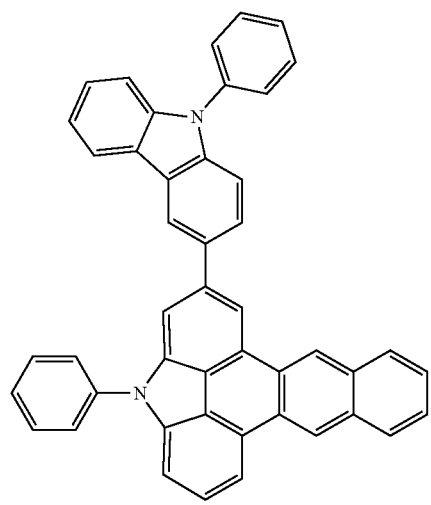
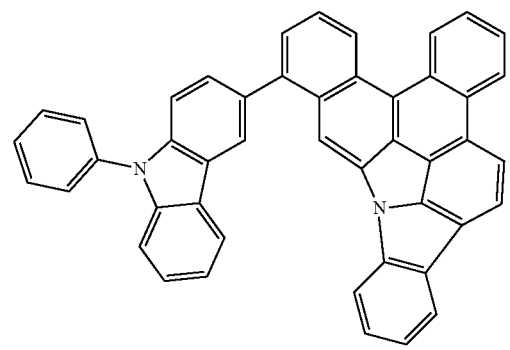
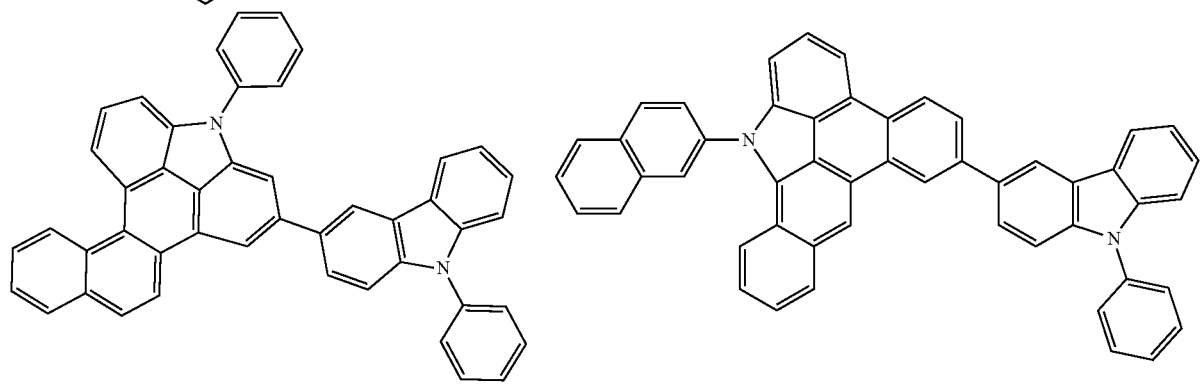
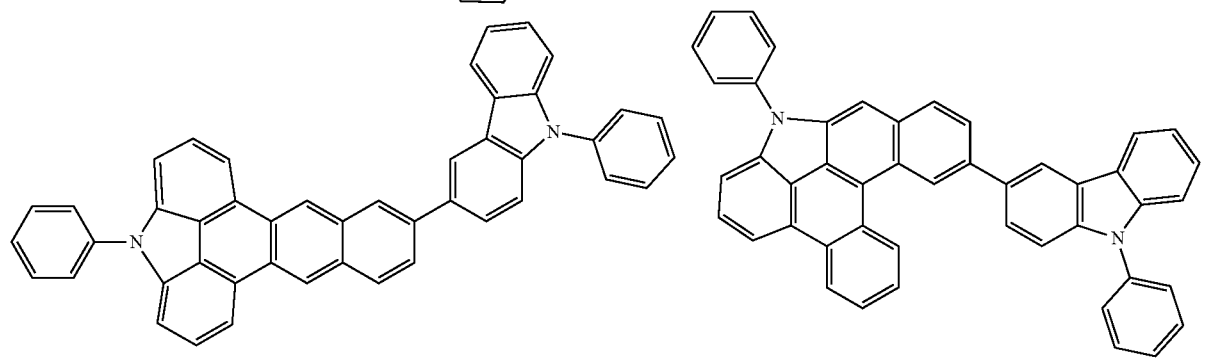

-continued
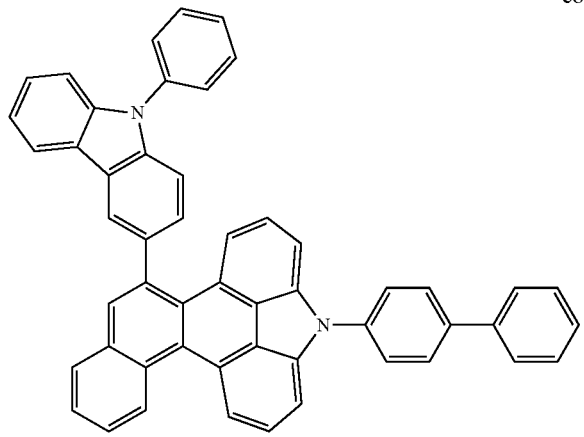
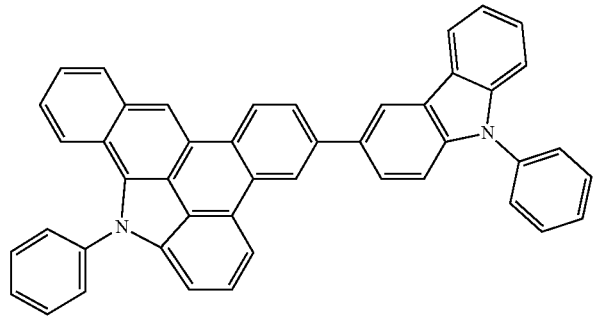
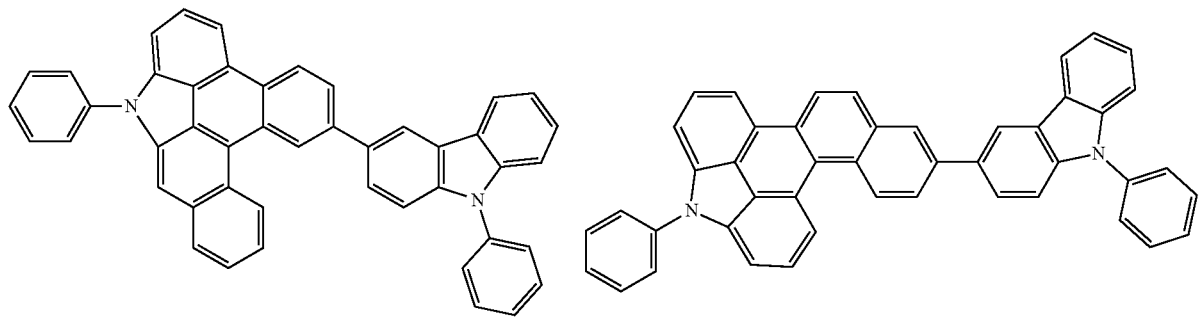
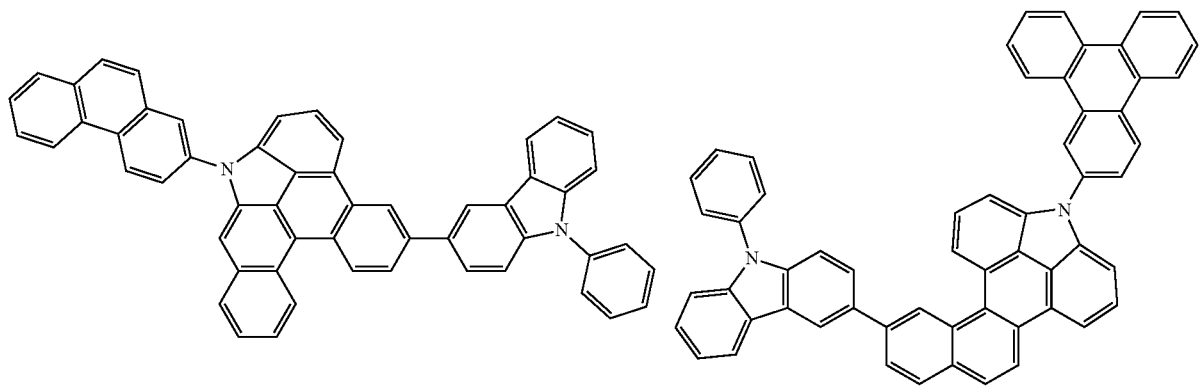
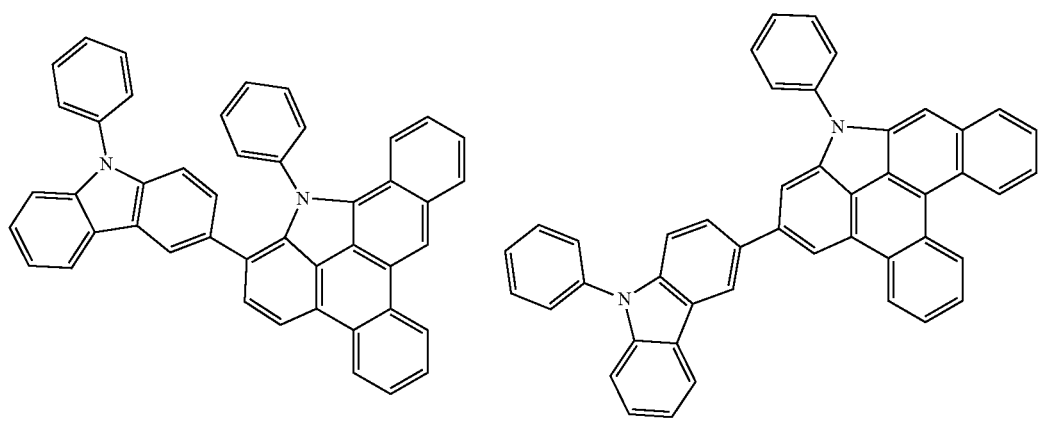

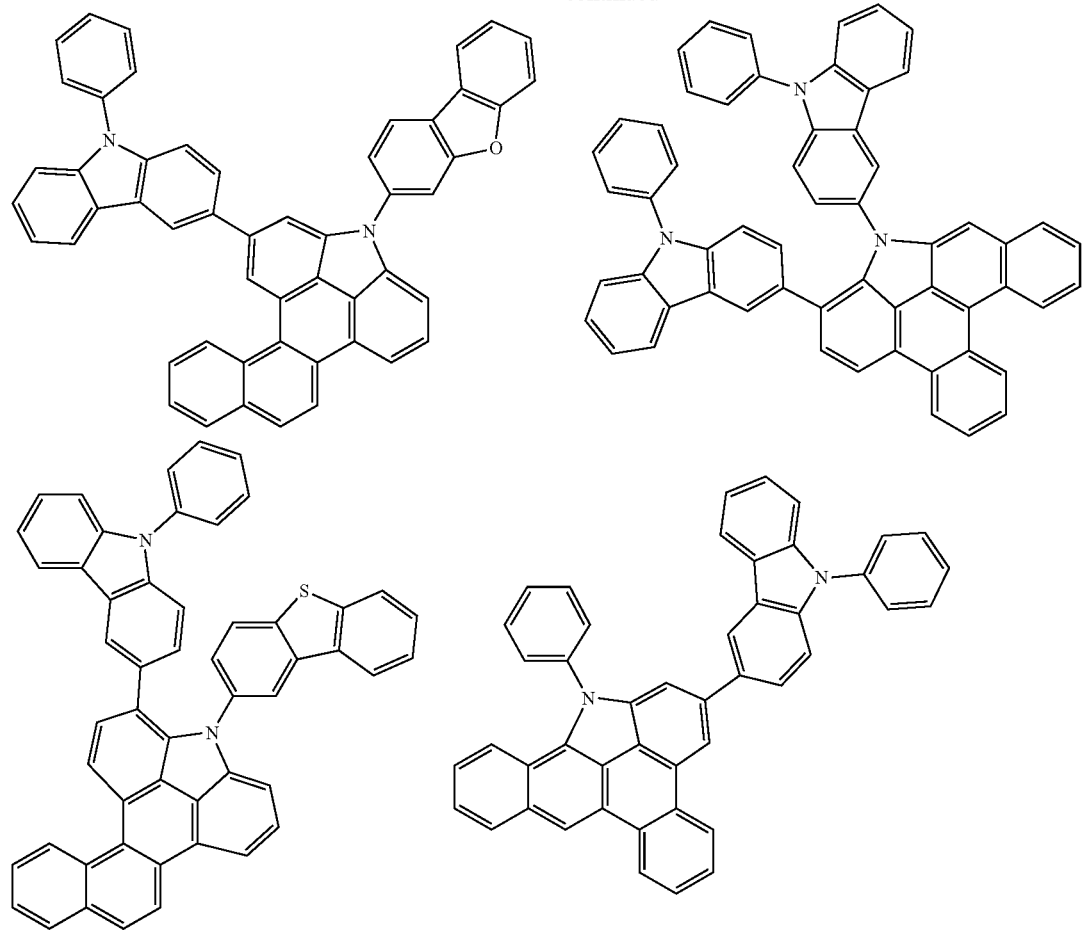
The base structure of the compounds of the invention can be prepared by the routes outlined in schemes 1, 2 and 3. Schemes 1 and 2 show the synthesis of the compounds in which Y is NAr[1], whereas Y in scheme 3 is O.
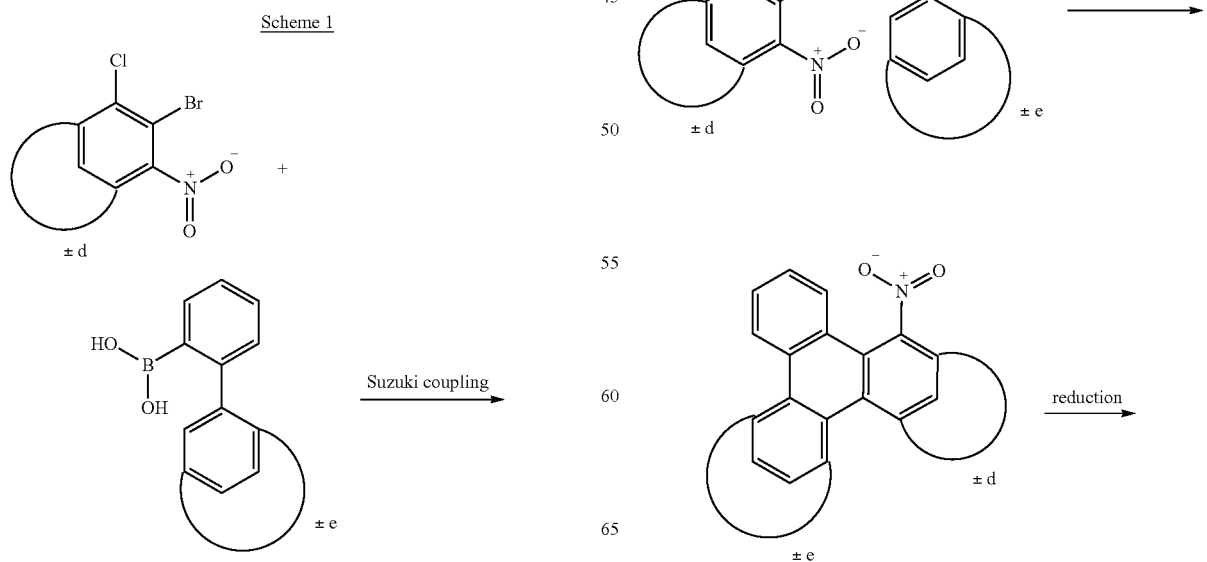

141
-continued
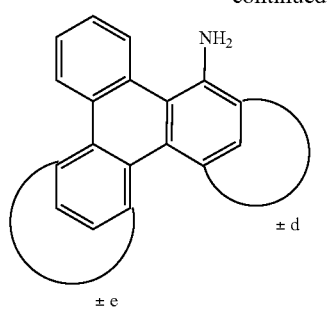
±d
±e
Oxidative ring closure →
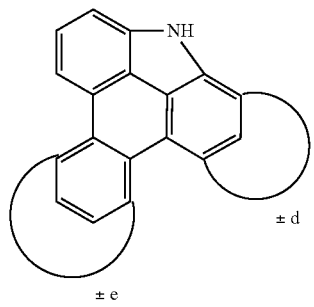
±d
±e
Br/Cl-L-Ar
Buchwald coupling →
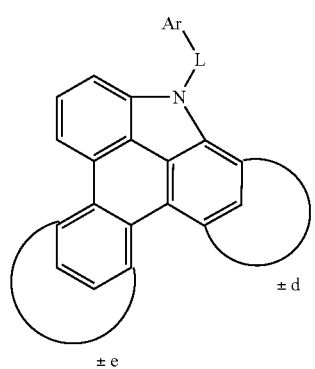
±d
±e
Scheme 2
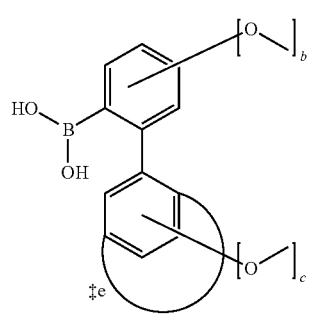
‡d
+
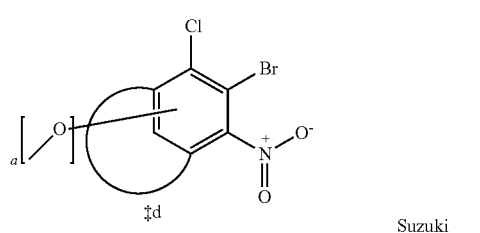
‡e
Suzuki coupling →
142
-continued
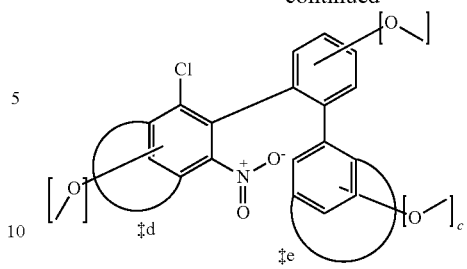
‡d
‡e
Intramolecular Heck reaction →
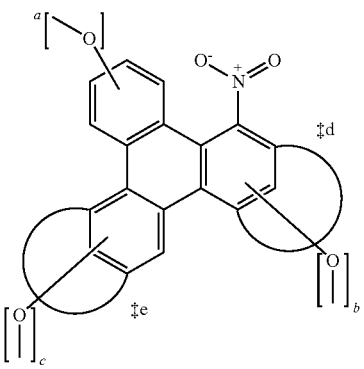
‡d
‡e
Reduction →
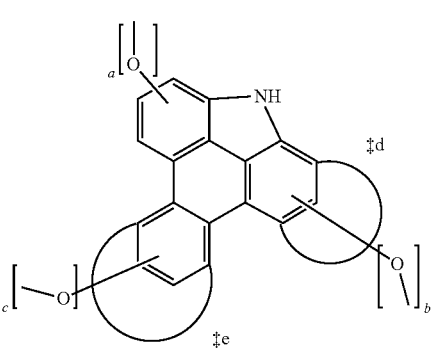
‡d
‡e
Br/Cl-L-Ar
Buchwald coupling →
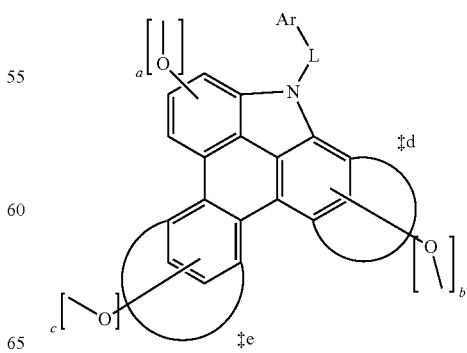
‡d
‡e
De-methylation, $BBr_3$ →

143
-continued
144
-continued
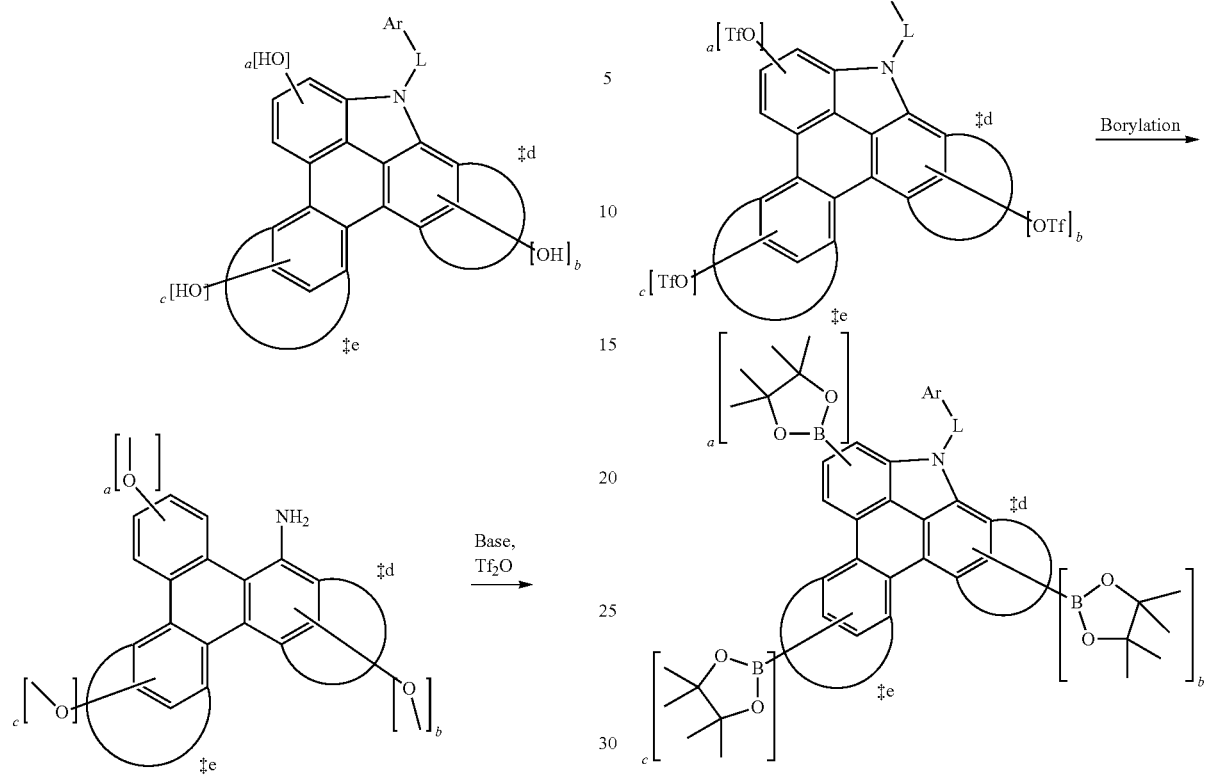
Scheme 3
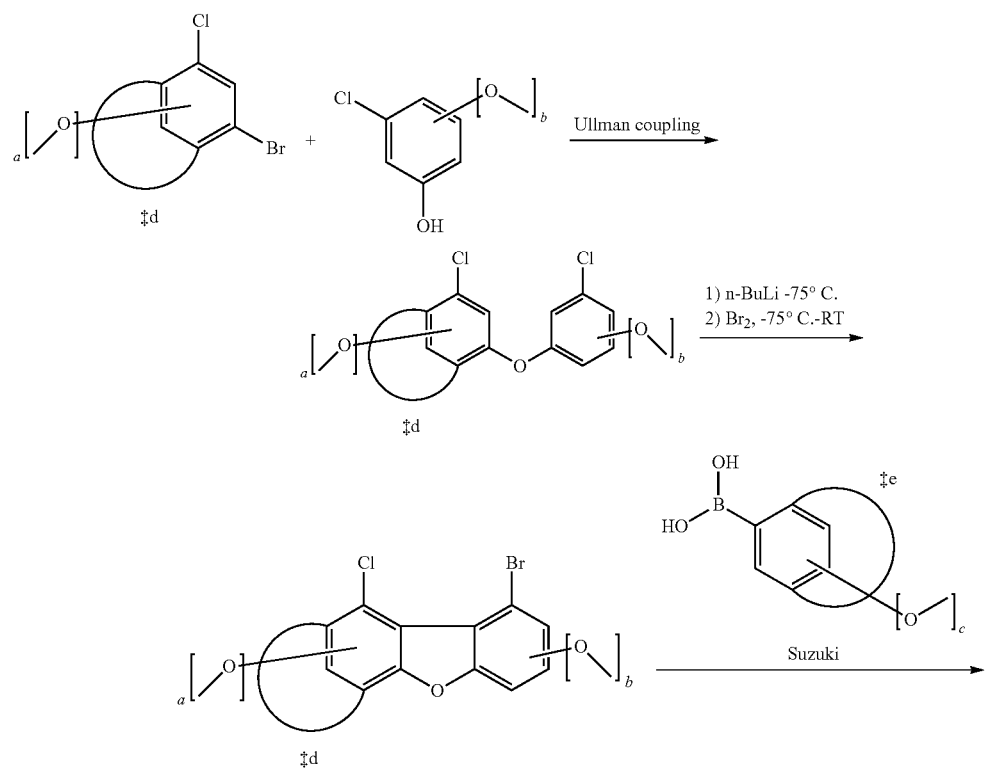

-continued
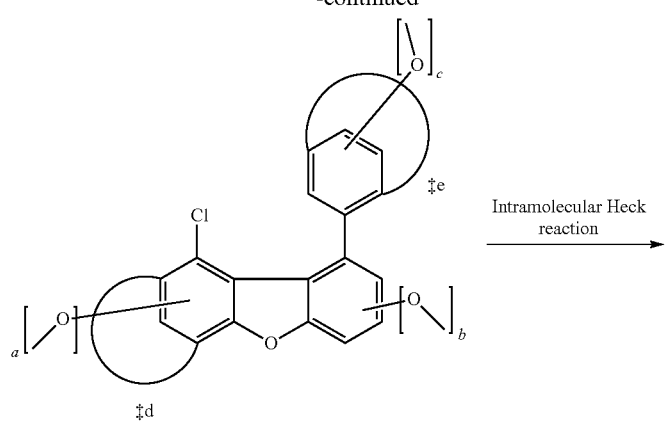
Intramolecular Heck reaction →
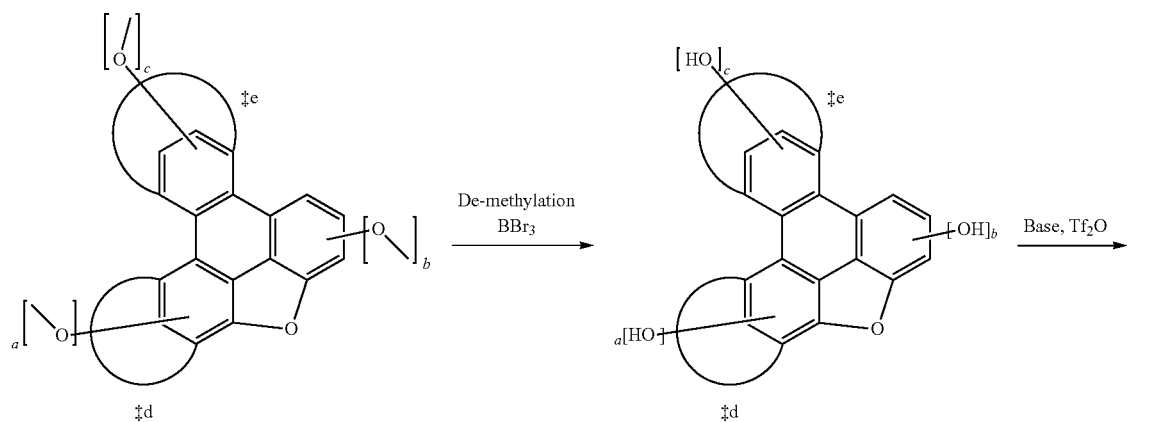
De-methylation BBr$_3$ → Base, Tf$_2$O →
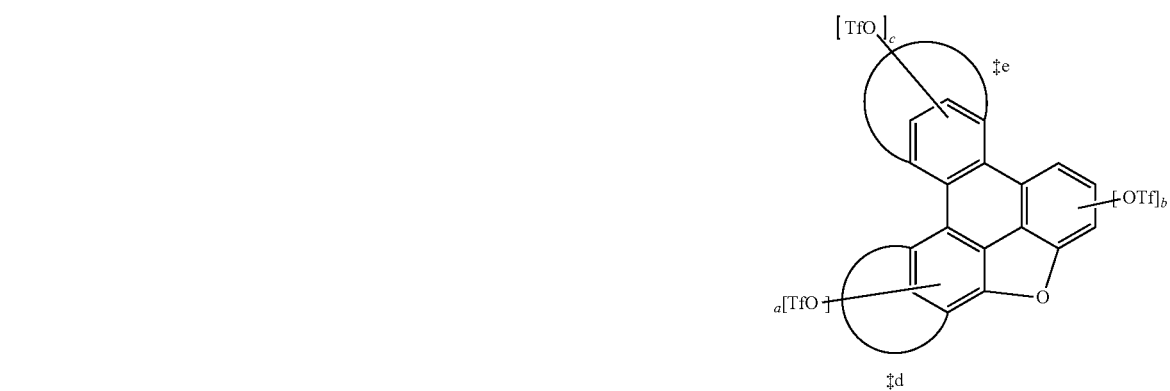
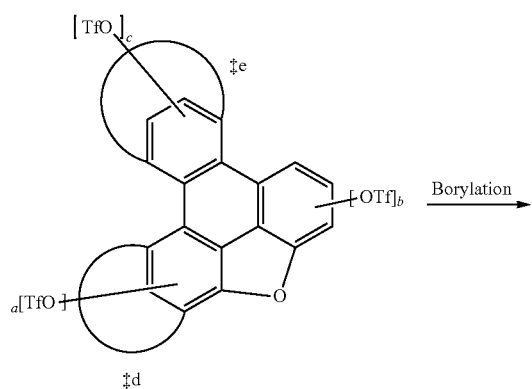
Borylation →

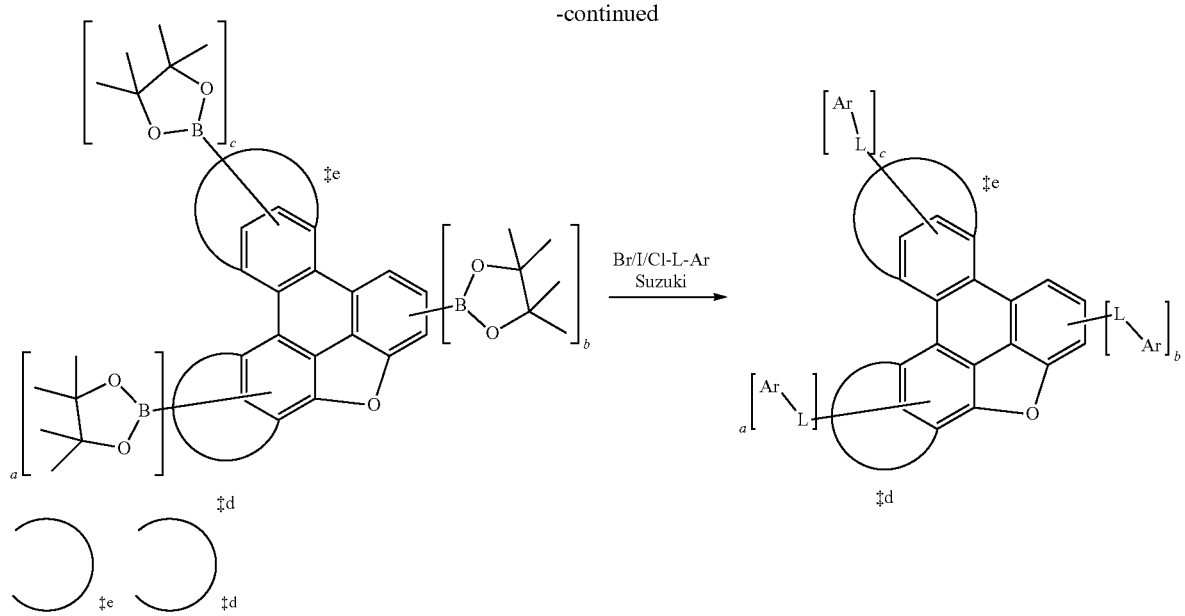

represent fused phenyl rings at varios positions: d = 0 or 1, e = 0 or 1; d + e = 1
a,b,c = 0 or 1

The compounds of the invention can be prepared by synthesis steps known to those skilled in the art, for example bromination, Suzuki coupling, Ullmann coupling, Hartwig-Buchwald coupling, etc. In schemes 1, 2 and 3, L represents a divalent aromatic or heteroaromatic ring system, and Ar an aromatic or heteroaromatic ring system.

For the processing of the compounds of the invention from a liquid phase, for example by spin-coating or by printing methods, formulations of the compounds of the invention are required. These formulations may, for example, be solutions, dispersions or emulsions. For this purpose, it may be preferable to use mixtures of two or more solvents. Suitable and preferred solvents are, for example, toluene, anisole, o-, m- or p-xylene, methyl benzoate, mesitylene, tetralin, veratrole, THF, methyl-THF, THP, chlorobenzene, dioxane, phenoxytoluene, especially 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane, 2-methylbiphenyl, 3-methylbiphenyl, 1-methylnaphthalene, 1-ethylnaphthalene, ethyl octanoate, diethyl sebacate, octyl octanoate, heptylbenzene, menthyl isovalerate, cyclohexyl hexanoate or mixtures of these solvents.

The present invention therefore further provides a formulation comprising at least one compound of the invention and at least one further compound. The further compound may, for example, be a solvent, especially one of the abovementioned solvents or a mixture of these solvents. The further compound may alternatively be at least one further organic or inorganic compound which is likewise used in the electronic device, for example an emitting compound and/or a further matrix material. Suitable emitting compounds and further matrix materials are listed at the back in connection with the organic electroluminescent device. This further compound may also be polymeric.

The compounds of the invention are suitable for use in an electronic device, especially in an organic electroluminescent device.

The present invention therefore further provides for the use of a compound of the invention in an electronic device, especially in an organic electroluminescent device.

The present invention still further provides an electronic device comprising at least one compound of the invention.

An electronic device in the context of the present invention is a device comprising at least one layer comprising at least one organic compound. This component may also comprise inorganic materials or else layers formed entirely from inorganic materials.

The electronic device is preferably selected from the group consisting of organic electroluminescent devices (OLEDs), organic integrated circuits (O-ICs), organic field-effect transistors (O-FETs), organic thin-film transistors (O-TFTs), organic light-emitting transistors (O-LETs), organic solar cells (O-SCs), dye-sensitized organic solar cells (DSSCs), organic optical detectors, organic photoreceptors, organic field-quench devices (O-FQDs), light-emitting electrochemical cells (LECs), organic laser diodes (O-lasers) and organic plasmon emitting devices, but preferably organic electroluminescent devices (OLEDs), more preferably phosphorescent OLEDs.

The organic electroluminescent device comprises cathode, anode and at least one emitting layer. Apart from these layers, it may also comprise further layers, for example in each case one or more hole injection layers, hole transport layers, hole blocker layers, electron transport layers, electron injection layers, exciton blocker layers, electron blocker layers and/or charge generation layers. It is likewise possible for interlayers having an exciton-blocking function, for example, to be introduced between two emitting layers. However, it should be pointed out that not necessarily every one of these layers need be present. In this case, it is possible for the organic electroluminescent device to contain an emitting layer, or for it to contain a plurality of emitting layers. If a plurality of emission layers are present, these preferably have several emission maxima between 380 nm and 750 mm overall, such that the overall result is white emission; in other words, various emitting compounds which may fluoresce or phosphoresce are used in the emitting layers. Especially preferred are systems having three emitting layers, where the three layers show blue, green and orange or red emission. The organic electroluminescent device of the invention may also be a tandem OLED, especially for white-emitting OLEDs.

The compound of the invention according to the above-detailed embodiments may be used in different layers, according to the exact structure. Preference is given to an organic electroluminescent device comprising a compound of formula (1) or the above-recited preferred embodiments in an emitting layer as matrix material for phosphorescent emitters or for emitters that exhibit TADF (thermally activated delayed fluorescence), especially for phosphorescent emitters. In this case, the organic electroluminescent device may contain an emitting layer, or it may contain a plurality of emitting layers, where at least one emitting layer contains at least one compound of the invention as matrix material. In addition, the compound of the invention can also be used in an electron transport layer and/or in a hole blocker layer and/or in a hole transport layer and/or in an exciton blocker layer.

When the compound of the invention is used as matrix material for a phosphorescent compound in an emitting layer, it is preferably used in combination with one or more phosphorescent materials (triplet emitters). Phosphorescence in the context of this invention is understood to mean luminescence from an excited state having higher spin multiplicity, i.e. a spin state>1, especially from an excited triplet state. In the context of this application, all luminescent complexes with transition metals or lanthanides, especially all iridium, platinum and copper complexes, shall be regarded as phosphorescent compounds.

The mixture of the compound of the invention and the emitting compound contains between 99% and 1% by volume, preferably between 98% and 10% by volume, more preferably between 97% and 60% by volume and especially between 95% and 80% by volume of the compound of the invention, based on the overall mixture of emitter and matrix material.

Correspondingly, the mixture contains between 1% and 99% by volume, preferably between 2% and 90% by volume, more preferably between 3% and 40% by volume and especially between 5% and 20% by volume of the emitter, based on the overall mixture of emitter and matrix material.

A further preferred embodiment of the present invention is the use of the compound of the invention as matrix material for a phosphorescent emitter in combination with a further matrix material. Suitable matrix materials which can be used in combination with the inventive compounds are aromatic ketones, aromatic phosphine oxides or aromatic sulfoxides or sulfones, for example according to WO 2004/013080, WO 2004/093207, WO 2006/005627 or WO 2010/006680, triarylamines, carbazole derivatives, e.g. CBP (N,N-biscarbazolylbiphenyl) or WO 2005/039246, US 2005/0069729, JP 2004/288381, EP 1205527, WO 2008/086851 or WO 2013/041176, indolocarbazole derivatives, for example according to WO 2007/063754 or WO 2008/056746, indenocarbazole derivatives, for example according to WO 2010/136109, WO 2011/000455, WO 2013/041176 or WO 2013/056776, azacarbazole derivatives, for example according to EP 1617710, EP 1617711, EP 1731584, JP 2005/347160, bipolar matrix materials, for example according to WO 2007/137725, silanes, for example according to WO 2005/111172, azaboroles or boronic esters, for example according to WO 2006/117052, triazine derivatives, for example according to WO 2007/063754, WO 2008/056746, WO 2010/015306, WO 2011/057706, WO 2011/060859 or WO 2011/060877, zinc complexes, for example according to EP 652273 or WO 2009/062578, diazasilole or tetraazasilole derivatives, for example according to WO 2010/054729, diazaphosphole derivatives, for example according to WO 2010/054730, bridged carbazole derivatives, for example according to WO 2011/042107, WO 2011/060867, WO 2011/088877 and WO 2012/143080, triphenylene derivatives, for example according to WO 2012/048781, or dibenzofuran derivatives, for example according to WO 2015/169412, WO 2016/015810, WO 2016/023608, WO 2017/148564 or WO 2017/148565. It is likewise possible for a further phosphorescent emitter having shorter-wavelength emission than the actual emitter to be present as co-host in the mixture, or a compound not involved in charge transport to a significant extent, if at all, as described, for example, in WO 2010/108579.

In a preferred embodiment of the invention, the materials are used in combination with a further matrix material. Preferred co-matrix materials, especially when the compound of the invention is substituted by an electron-deficient heteroaromatic ring system, are selected from the group of the biscarbazoles, the bridged carbazoles, the triarylamines, the dibenzofuranyl-carbazole derivatives or dibenzofuranyl-amine derivatives and the carbazoleamines.

Preferred biscarbazoles are the structures of the following formulae (9) and (10):

Formula (9)

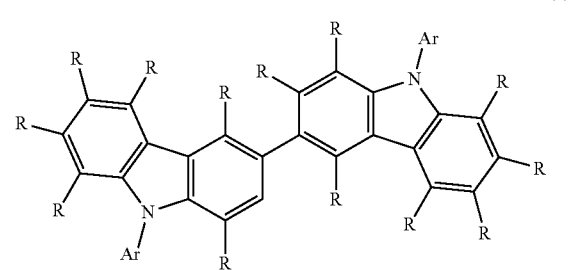

Formula (10)

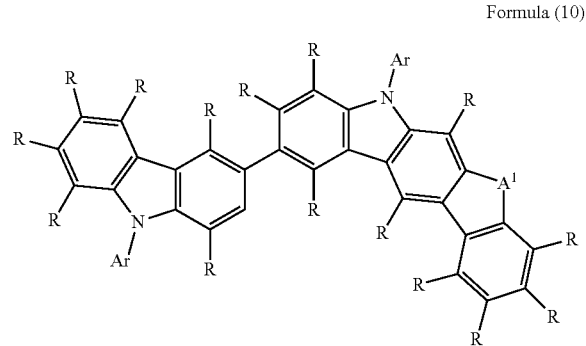

where Ar, R and $A^1$ are as follows:

$A^1$ is the same or different at each instance and is $NAr^2$, O, S or $C(R)_2$;

Ar is the same or different at each instance and is an aromatic or heteroaromatic ring system which has 5 to 60 aromatic ring atoms and may be substituted in each case by one or more R radicals;

R is the same or different at each instance and is H, D, F, Cl, Br, I, $B(OR^1)_2$, CHO, $C(=O)R^1$, $CR^1=C(R^1)_2$, CN, $C(=O)OR^1$, $C(=O)N(R^1)_2$, $Si(R^1)_3$, $N(R^1)_2$, $NO_2$, $P(=O)(R^1)_2$, $OSO_2R^1$, $OR^1$, $S(=O)R^1$, $S(=O)_2R^1$, $SR^1$, a straight-chain alkylalkyl group having 1 to 20 carbon atoms or an alkenyl or alkynyl group having 2 to 20 carbon atoms or a branched or cyclic alkyl group having 3 to 20 carbon atoms, where the alkyl, alkenyl or alkynyl group may be substituted in each case by one or more $R^1$ radicals, where one or more nonadjacent $CH_2$ groups may be replaced by $-R^1C=CR^1-$, $-C\equiv C-$, $Si(R^1)_2$, C=O, C=S, $C=NR^1$, $-C(=O)O-$, $-C(=O)NR^1-$, $NR^1$, $P(=O)(R^1)$, $-O-$, $-S-$, SO or $SO_2$, or an aromatic or heteroaromatic ring system which has 5 to 60 aromatic ring atoms, preferably 5 to 40 aromatic ring atoms, and may be substituted in each case by one or more $R^1$ radicals, where two or more R radicals may be joined to one another and may form a ring;

In a preferred embodiment of the invention, $A^1$ is $CR_2$.

Ar in the case of the formulae (9) and (10) is preferably an aromatic or heteroaromatic ring system, preferably the same or different at each instance and selected from the groups of the following formulae Ar-1 to Ar-82:

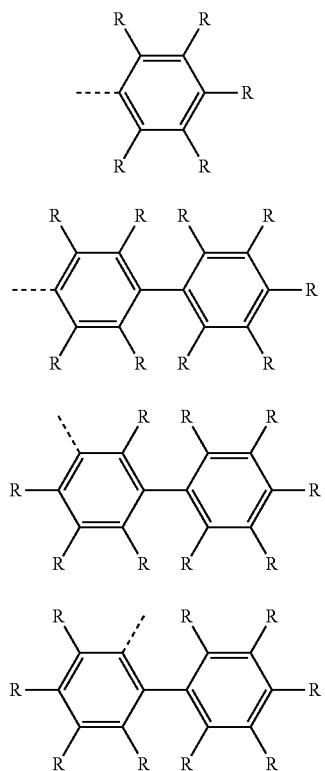

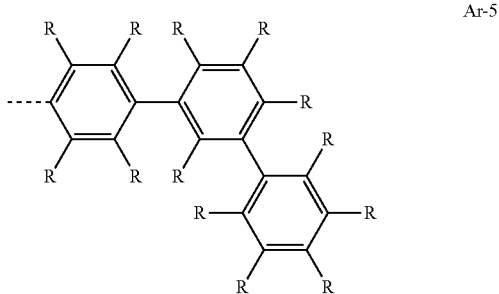

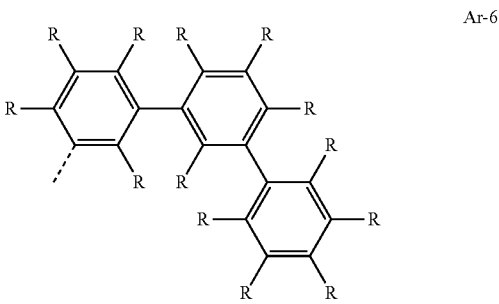

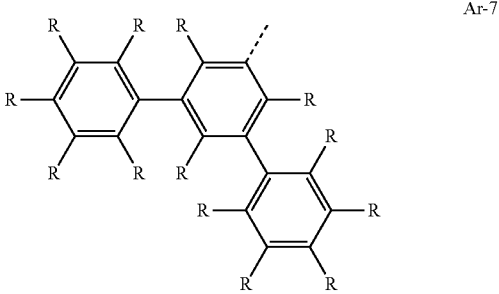

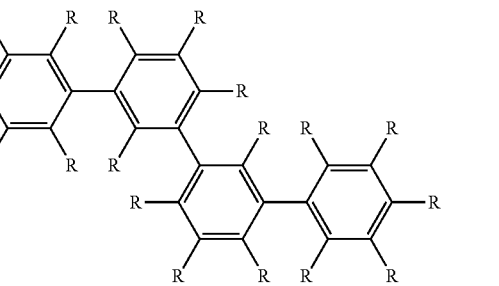

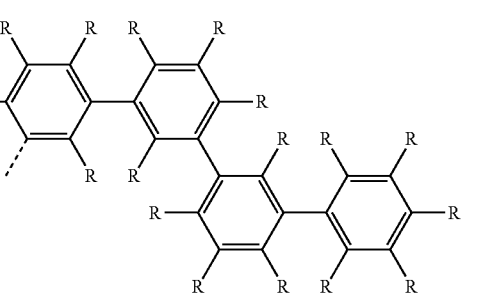

Ar-10
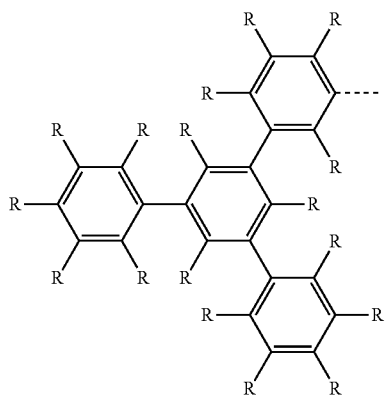
Ar-11
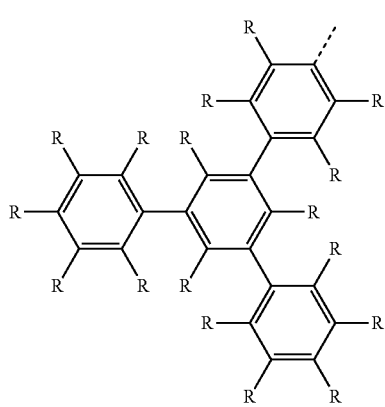
Ar-12
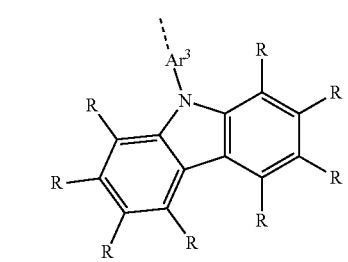
Ar-13
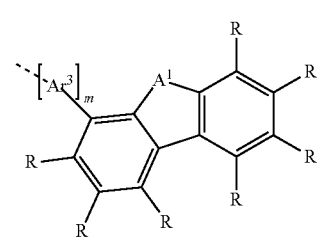
Ar-14
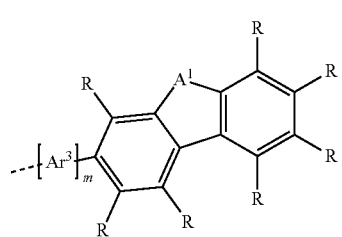
Ar-15
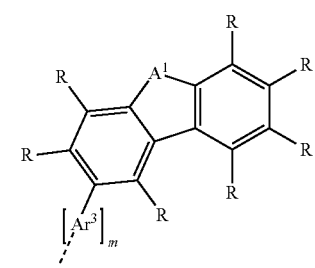
Ar-16
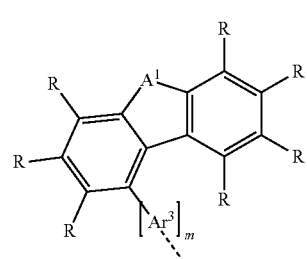
Ar-17
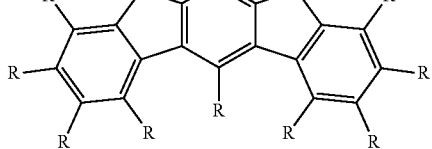
Ar-18
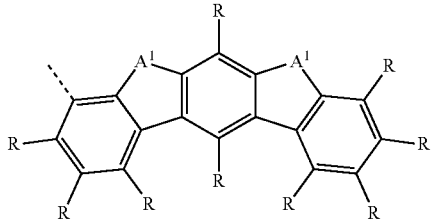
Ar-19
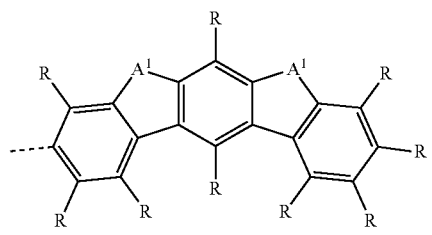
Ar-20
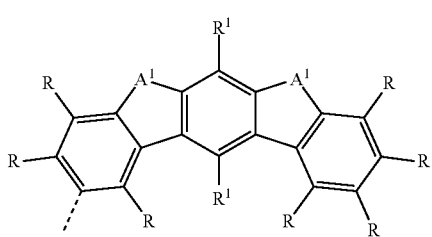

Ar-21
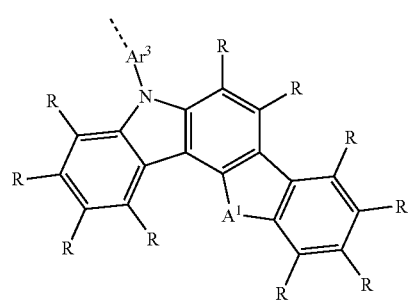
Ar-22
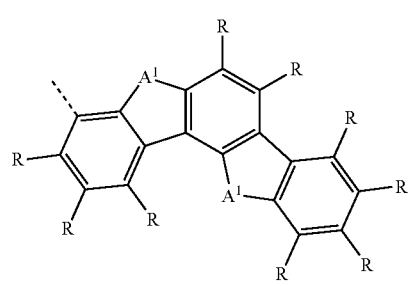
Ar-23
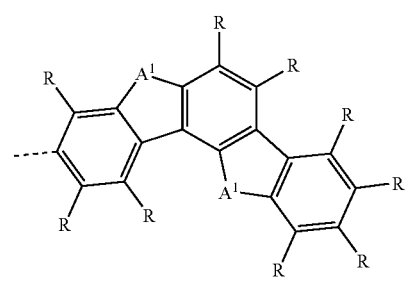
Ar-24
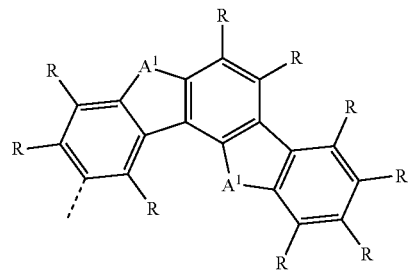
Ar-25
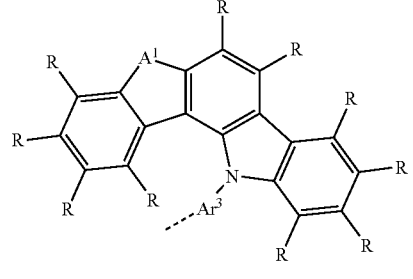
Ar-26
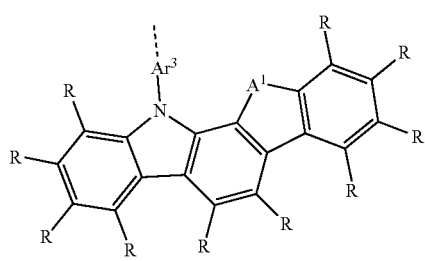
Ar-27
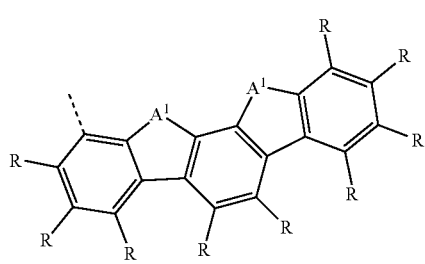
Ar-28
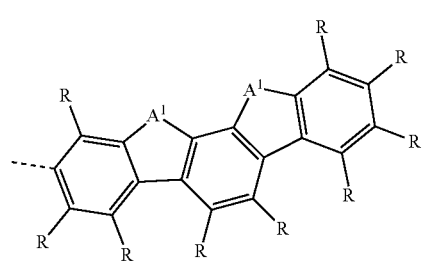
Ar-29
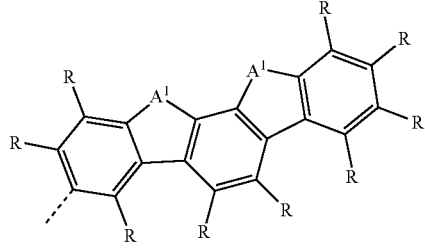
Ar-30
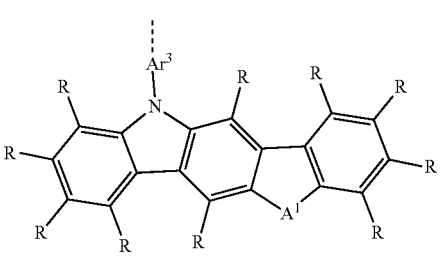
Ar-31
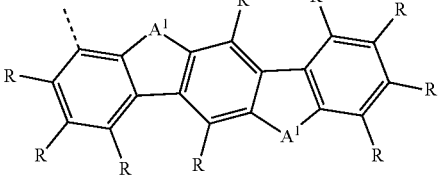

Ar-32 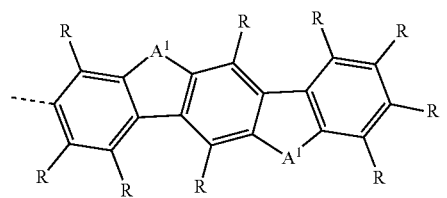
Ar-33 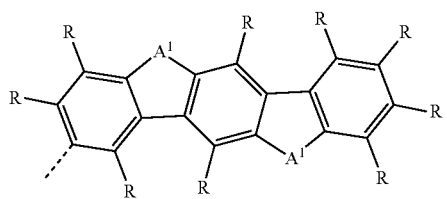
Ar-34 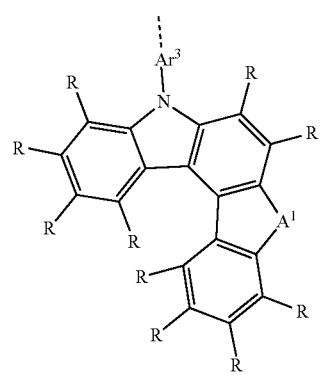
Ar-35 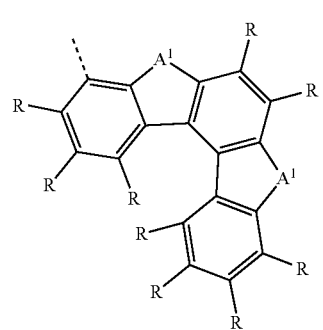
Ar-36 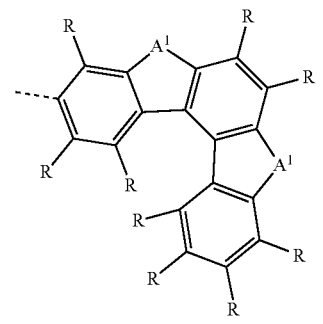
Ar-37 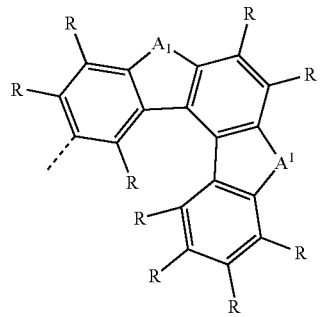
Ar-38 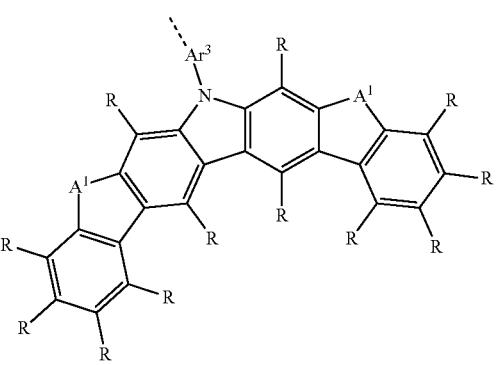
Ar-39 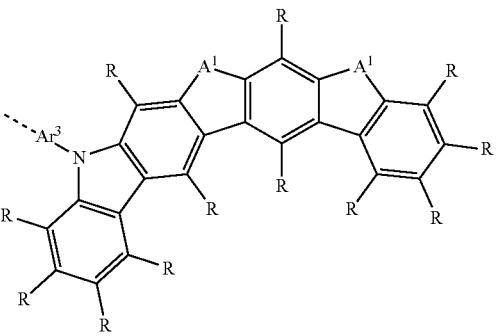
Ar-40 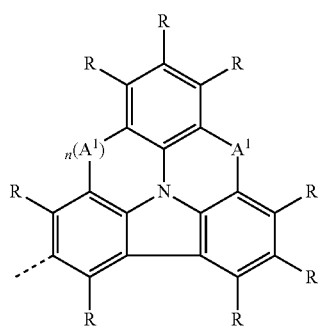

-continued
Ar-41
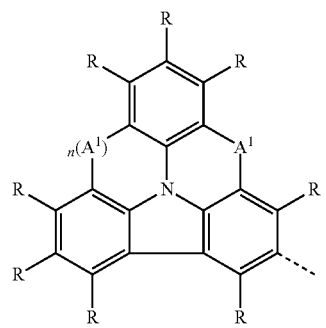
Ar-42
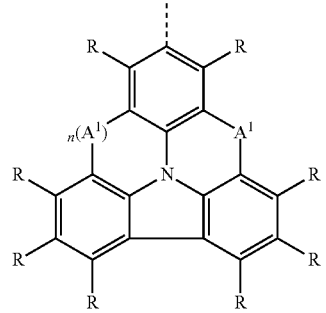
Ar-43
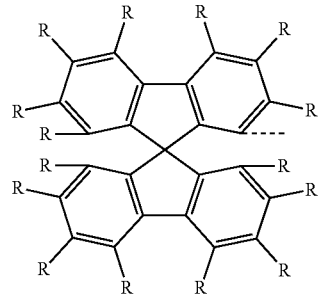
Ar-44
Ar-45
-continued
Ar-46
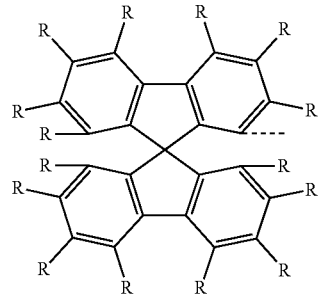
Ar-47
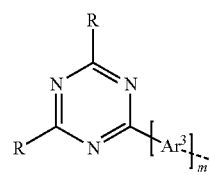
Ar-48
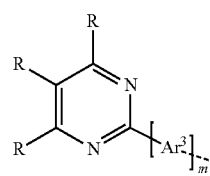
Ar-49
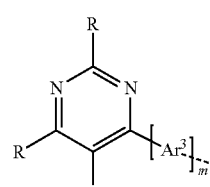
Ar-50
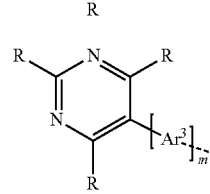
Ar-51
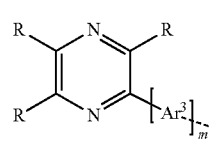
Ar-52
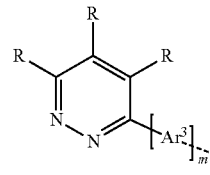
Ar-53
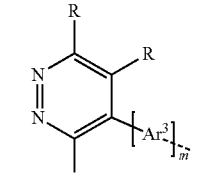

-continued
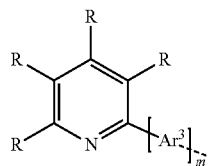
Ar-54
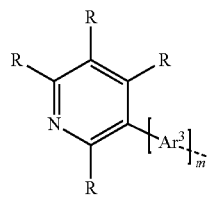
Ar-55
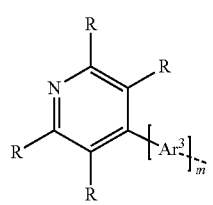
Ar-56
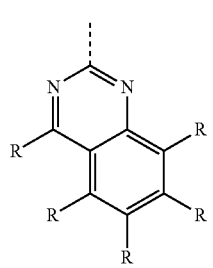
Ar-57
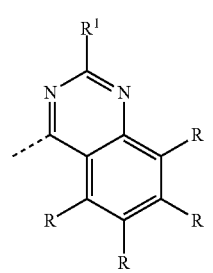
Ar-58
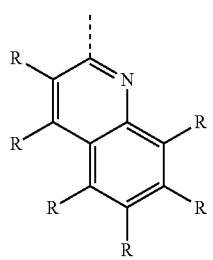
Ar-59
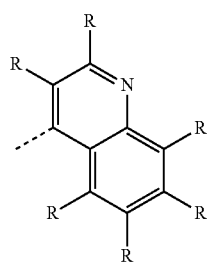
Ar-60
-continued
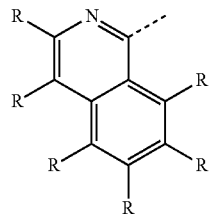
Ar-61
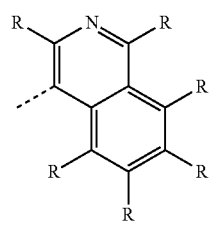
Ar-62
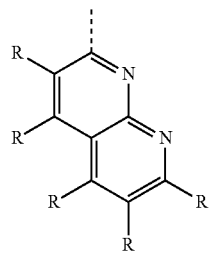
Ar-63
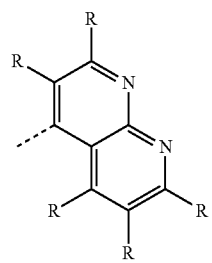
Ar-64
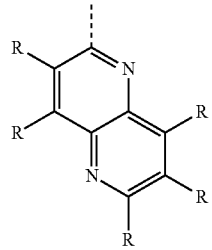
Ar-65
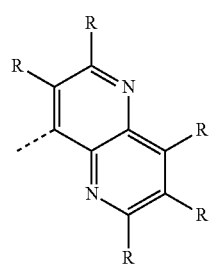
Ar-66

-continued
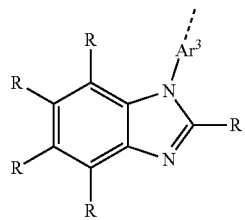
Ar-67
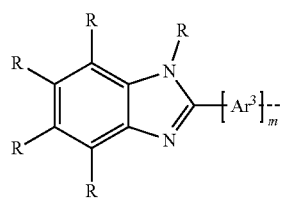
Ar-68
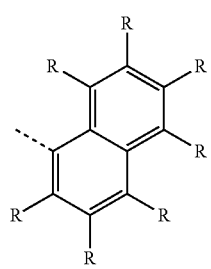
Ar-69
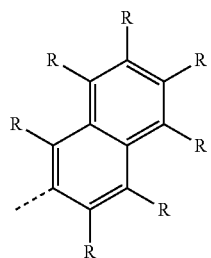
Ar-70
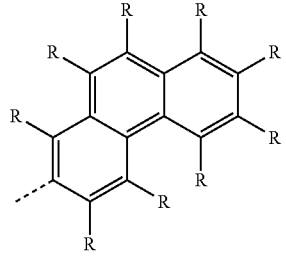
Ar-71
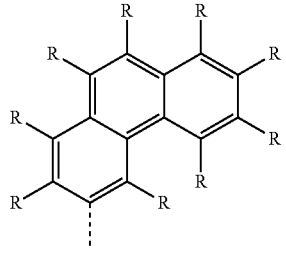
Ar-72
-continued
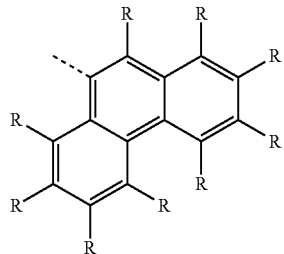
Ar-73
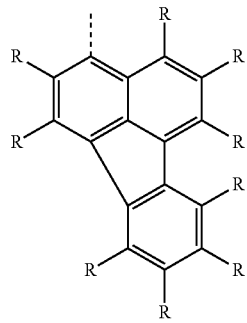
Ar-74
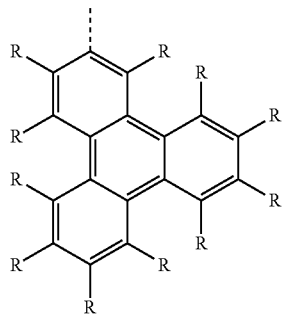
Ar-75
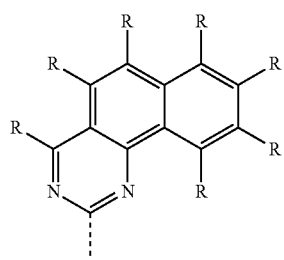
Ar-76
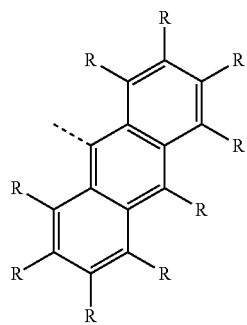
Ar-77

-continued

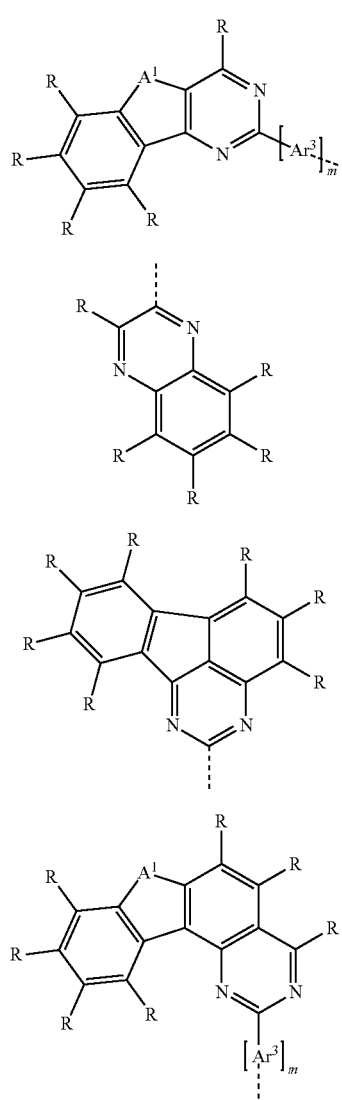

Ar-78

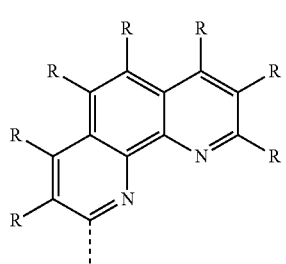

Ar-79

Ar-80

Ar-81

Ar-82 where the dotted line represents the bond to the base skeleton, and in addition:

Ar³ is the same or different at each instance and is a bivalent aromatic or heteroaromatic ring system which has 6 to 18 aromatic ring atoms and may be substituted in each case by one or more R radicals;

Ar² is an aromatic or heteroaromatic ring system which has 5 to 40 aromatic ring atoms and may be substituted by one or more R radicals;

A¹ is the same or different at each instance and is NAr², O, S or C(R)₂;

n is 0 or 1, where n=0 means that no A¹ group is bonded at this position and R radicals are bonded to the corresponding carbon atoms in its place;

m is 0 or 1, where m=0 means that the Ar³ group is absent and that the corresponding aromatic or heteroaromatic group is bonded directly to the nitrogen atom.

Preferred embodiments of the compounds of the formulae (9) and (10) are the compounds of the following formulae (9a) and (10a):

Formula (9a)

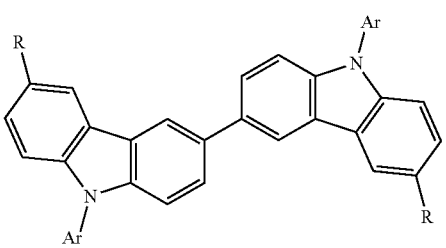

Formula (10a)

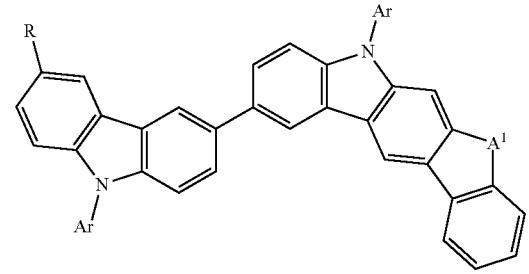

where the symbols used have the above-specified definitions according to formula (9) and formula (10).

Examples of suitable compounds of formulae (9) and (10) are the compounds depicted below:

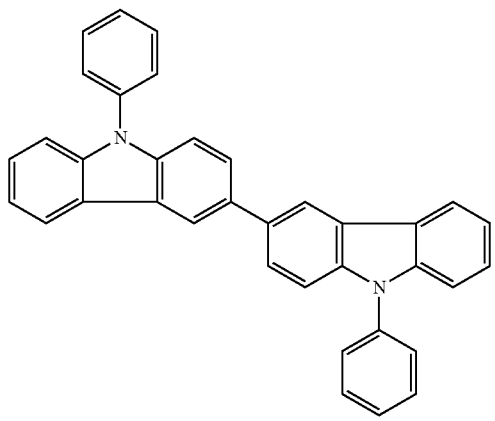

167
-continued
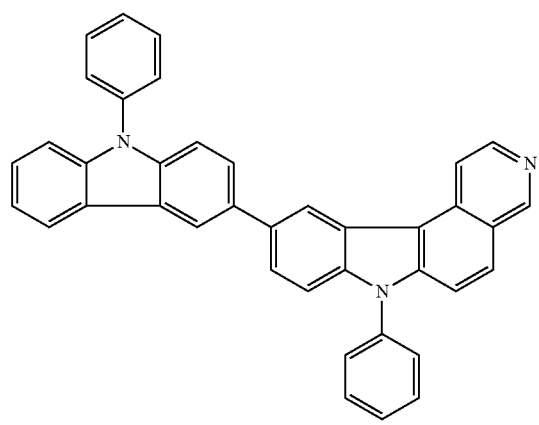
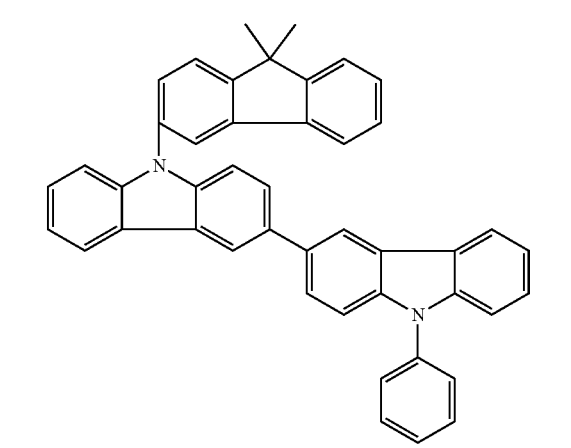
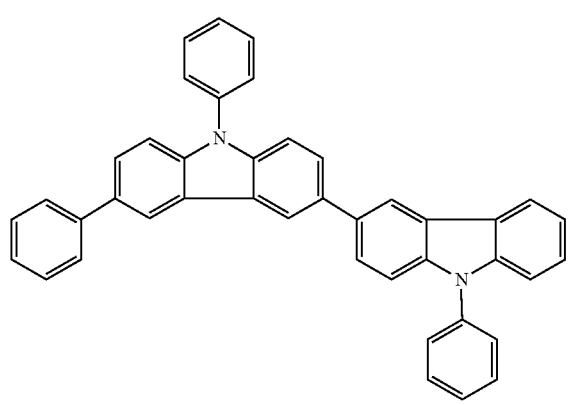
168
-continued
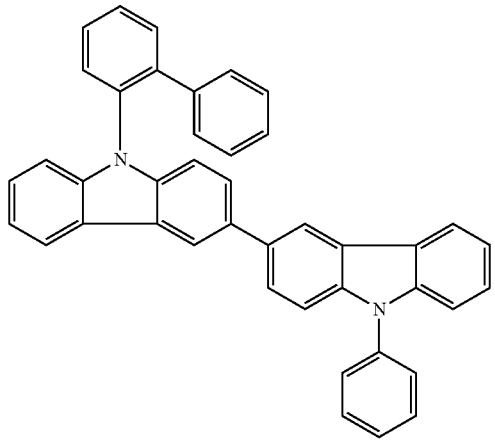
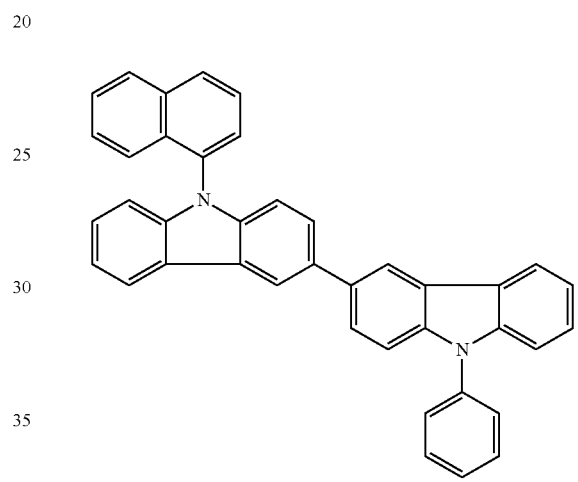
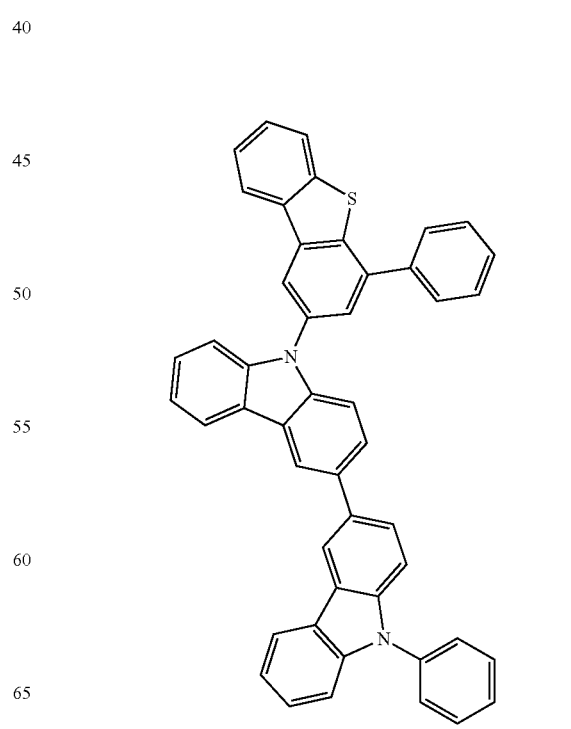

169
-continued
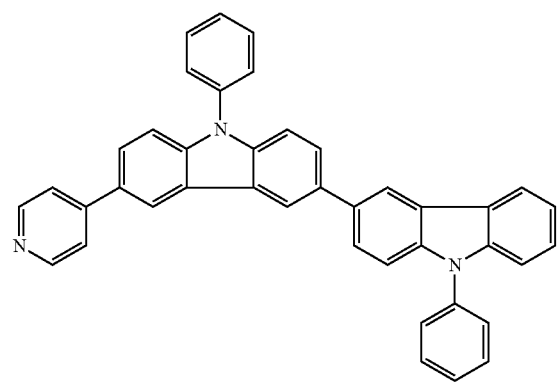
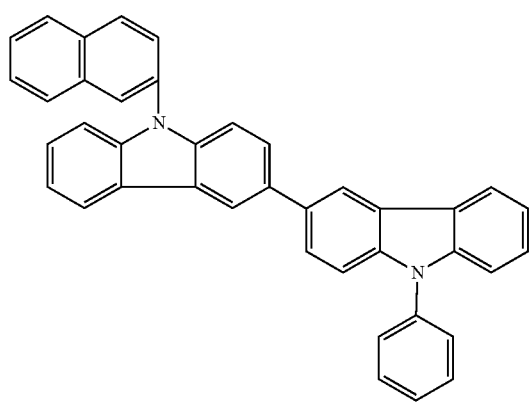
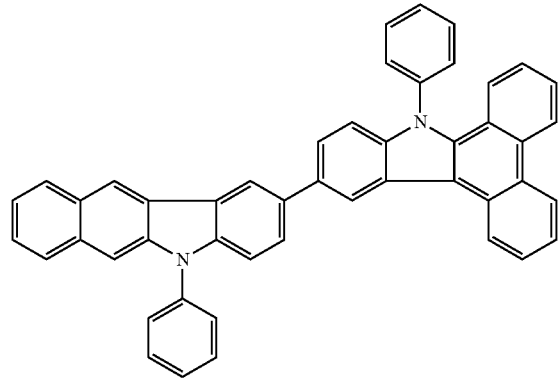
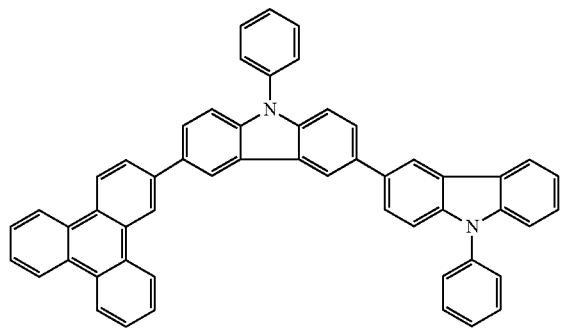
170
-continued
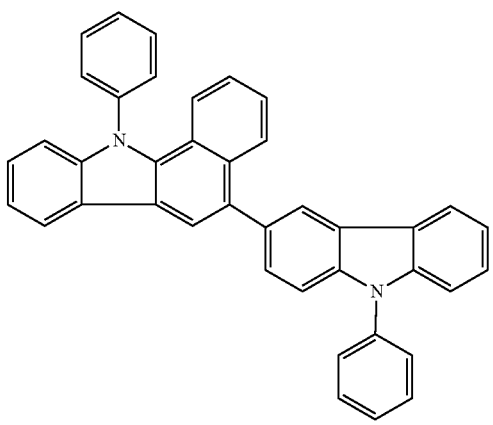
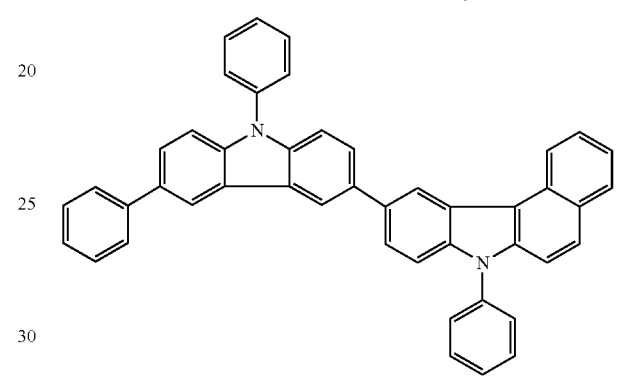
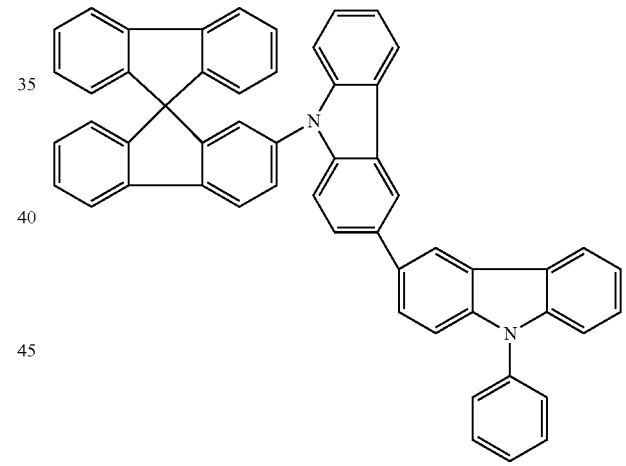
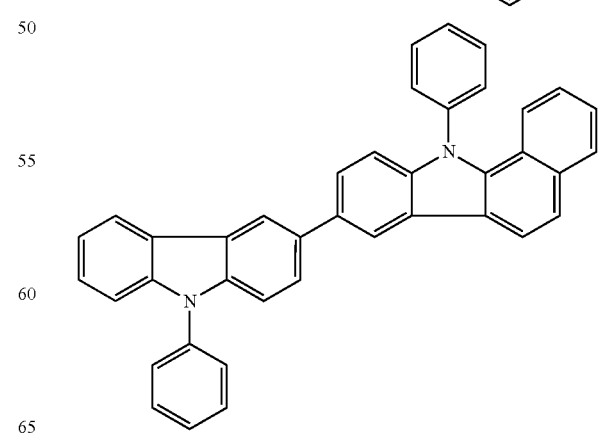

-continued
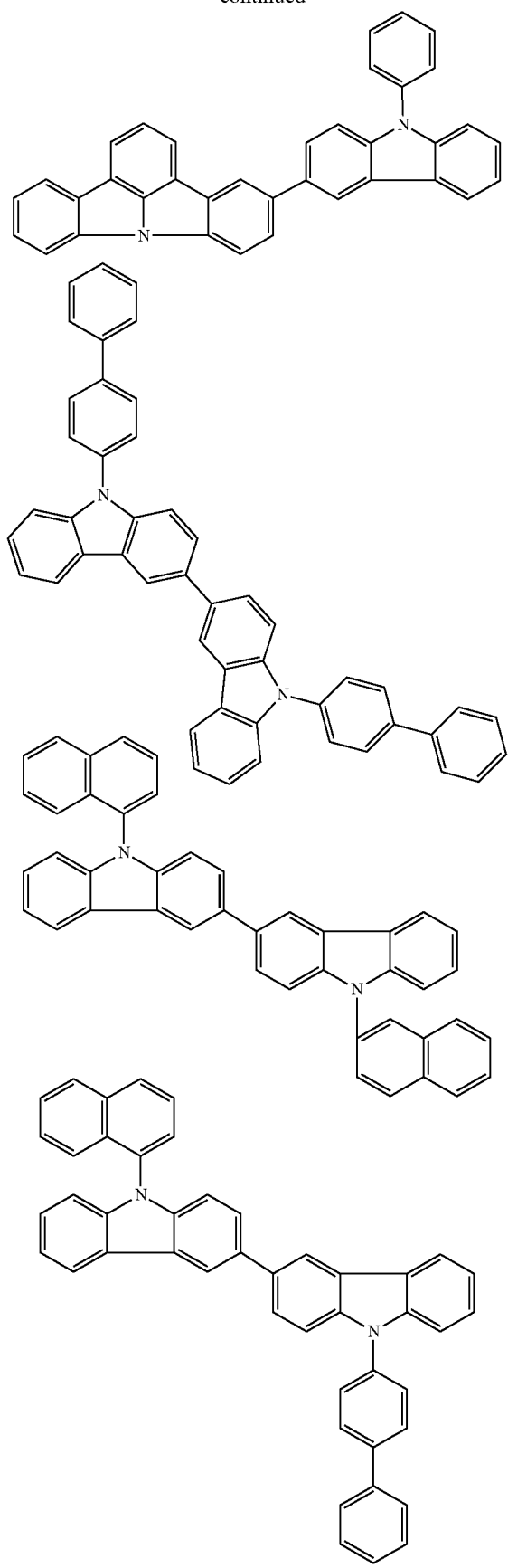
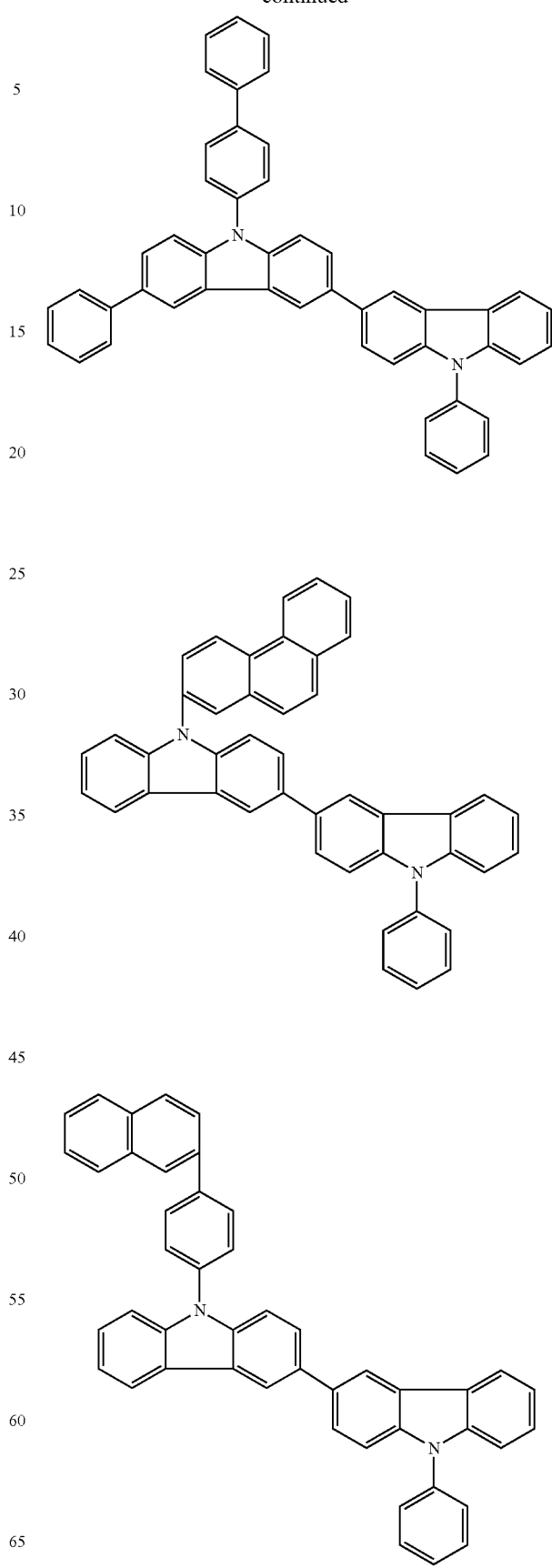

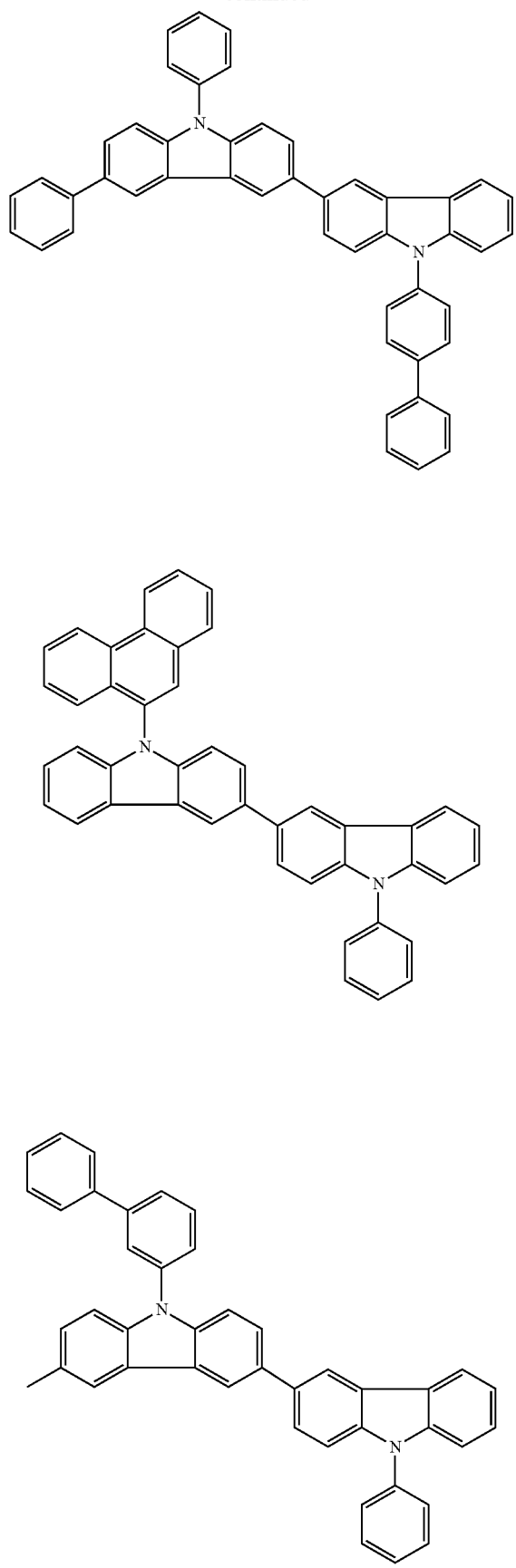
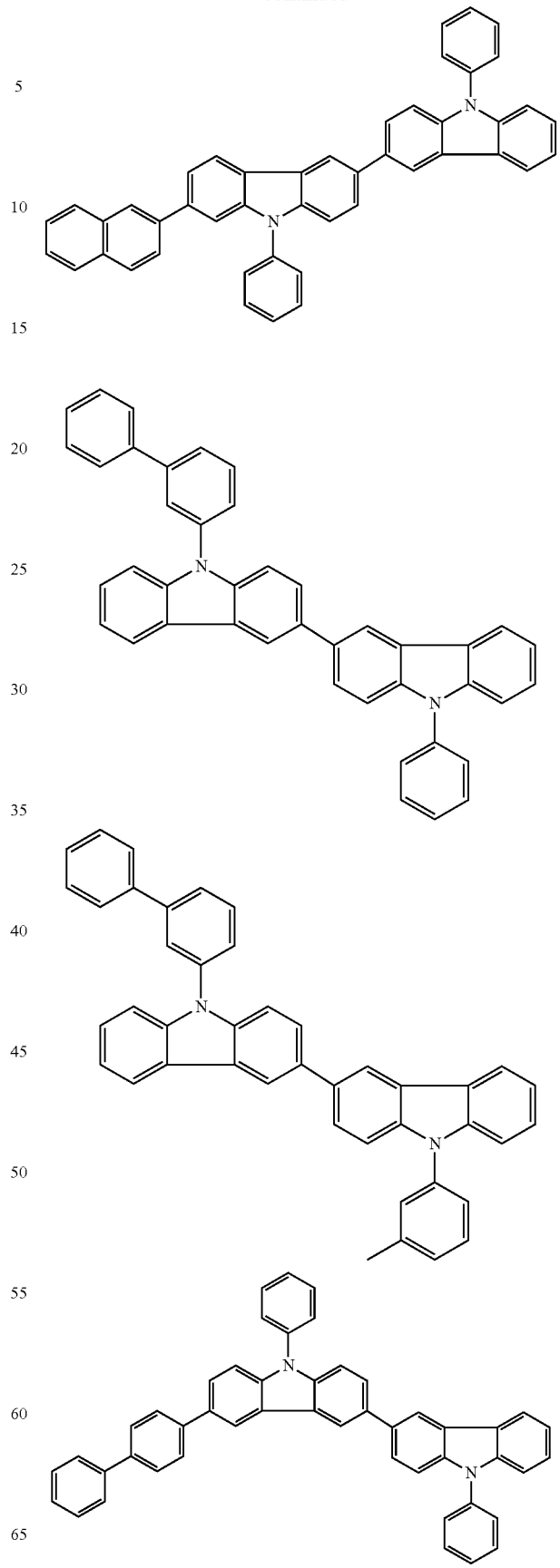

175
-continued
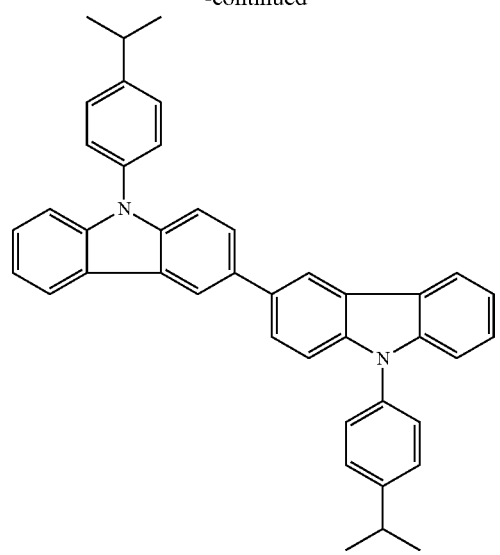
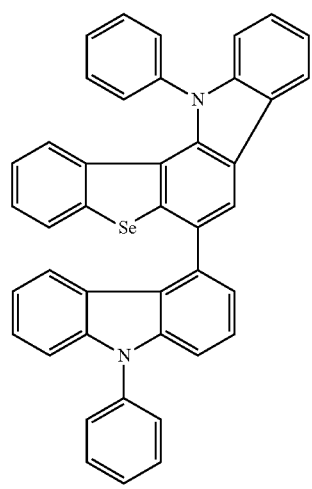
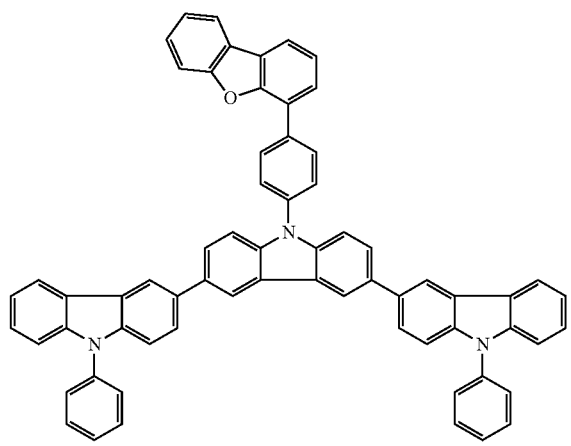
176
-continued
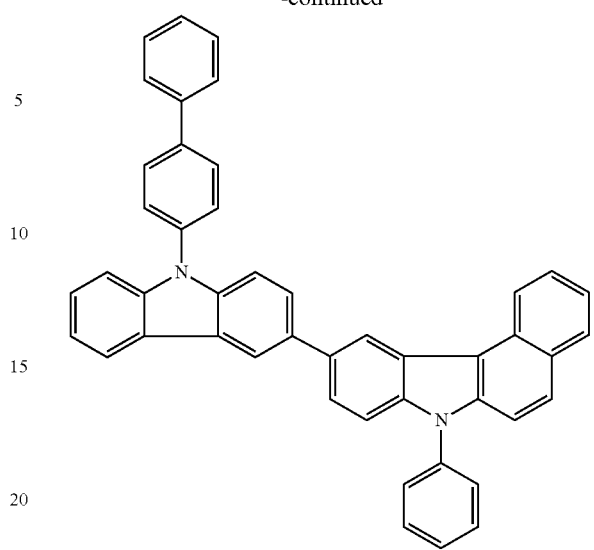
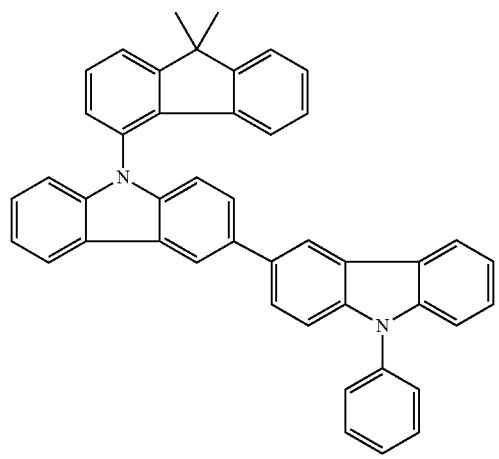
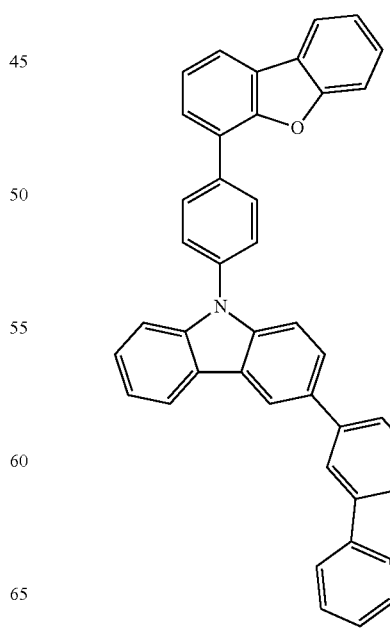

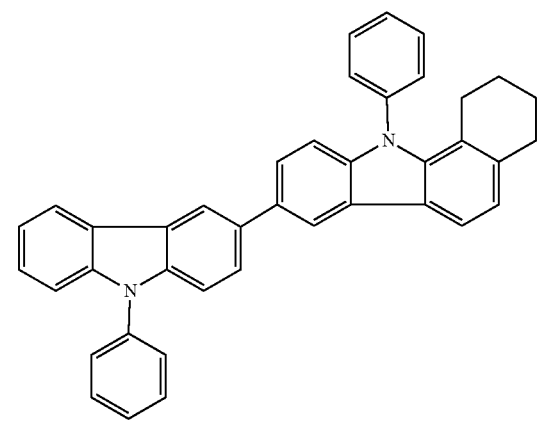
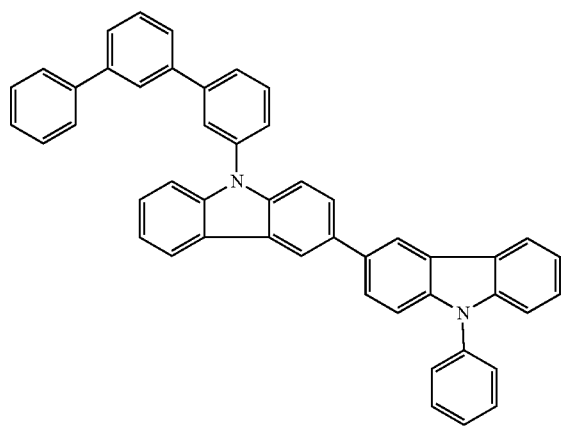
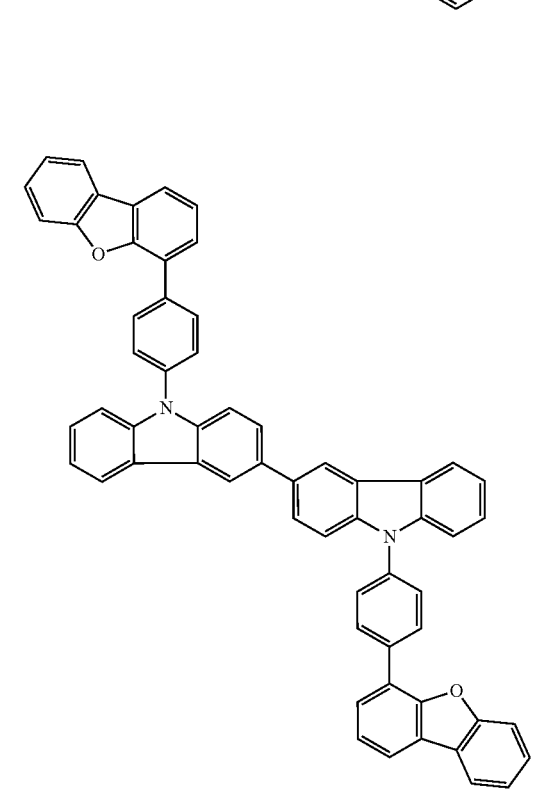
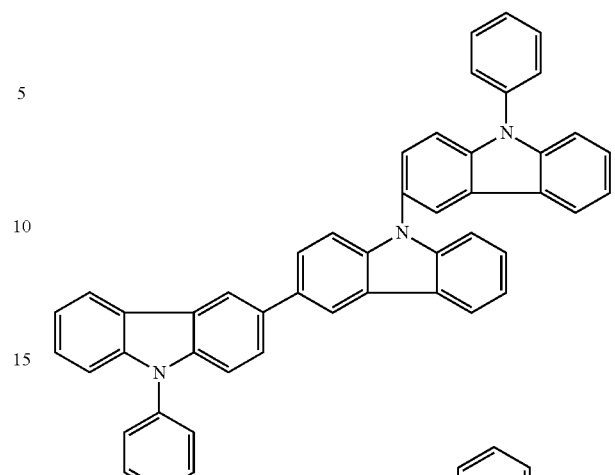
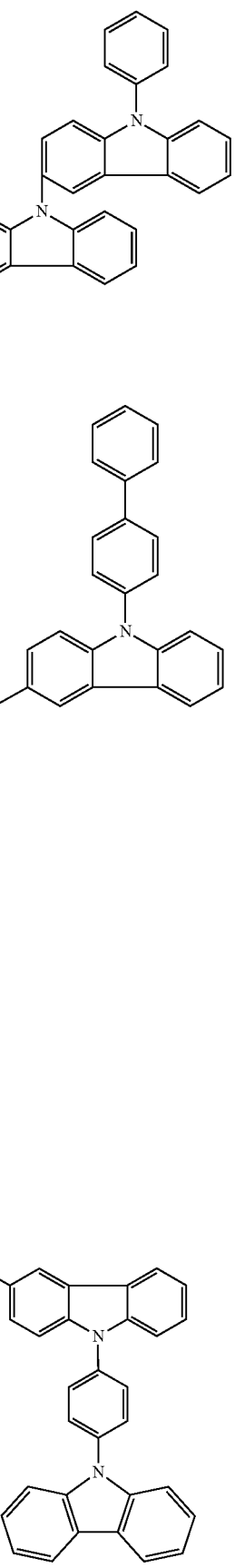

179
-continued
180
-continued
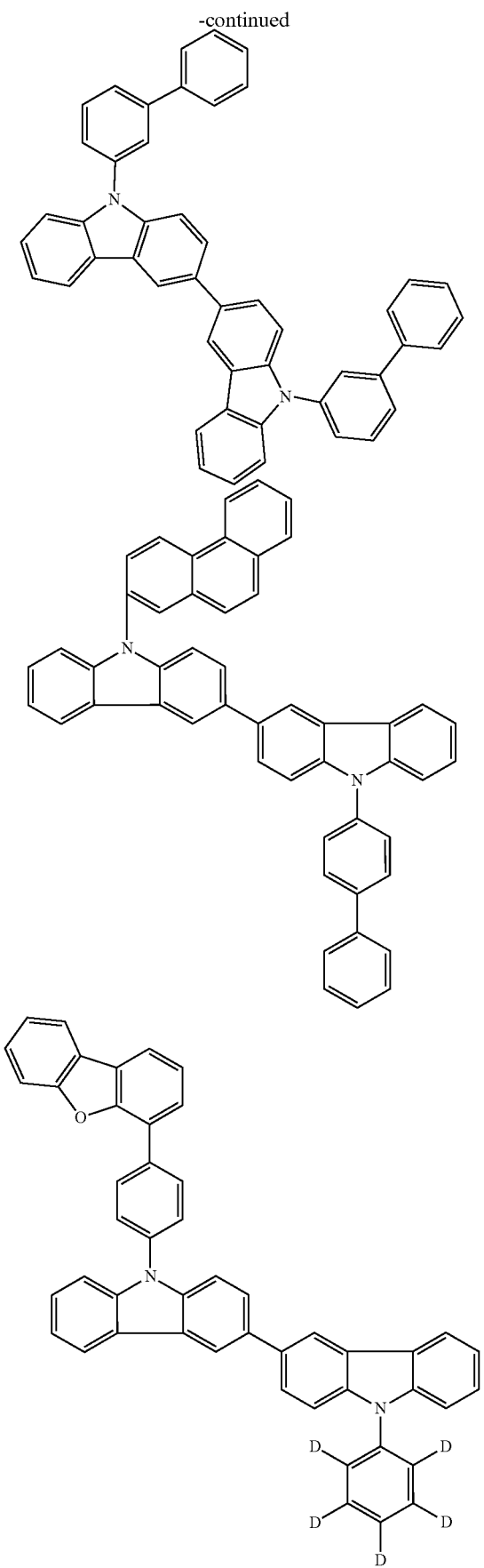
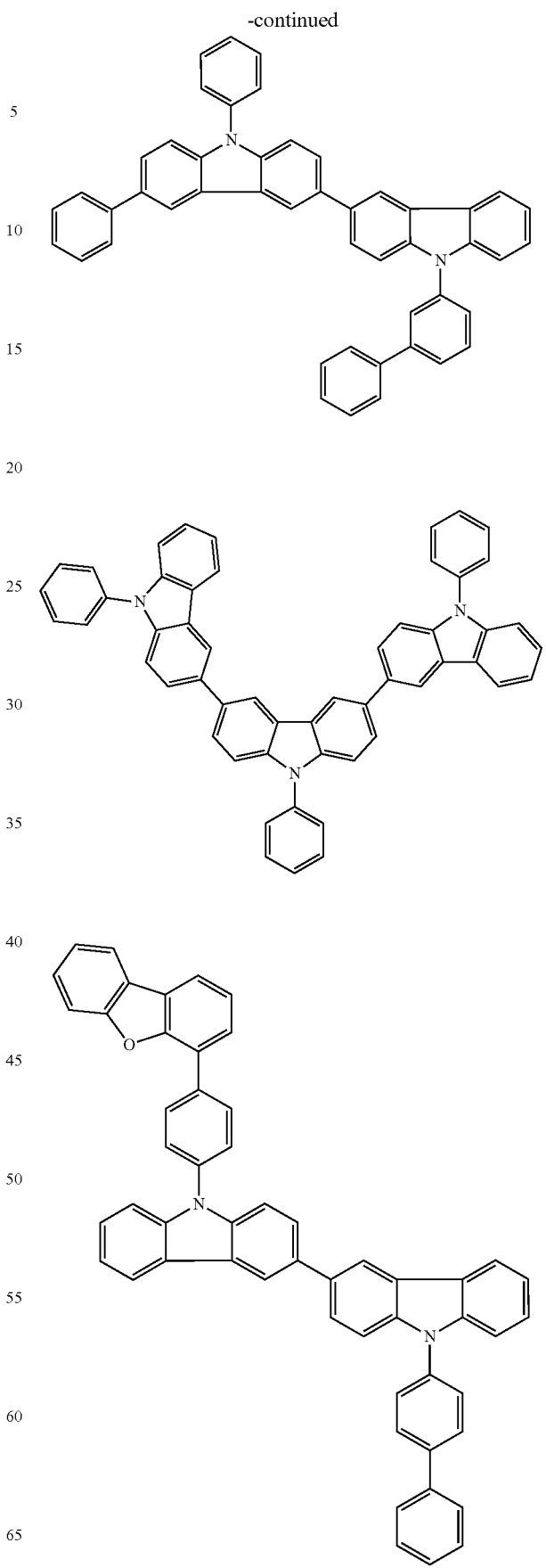

181
-continued
182
-continued
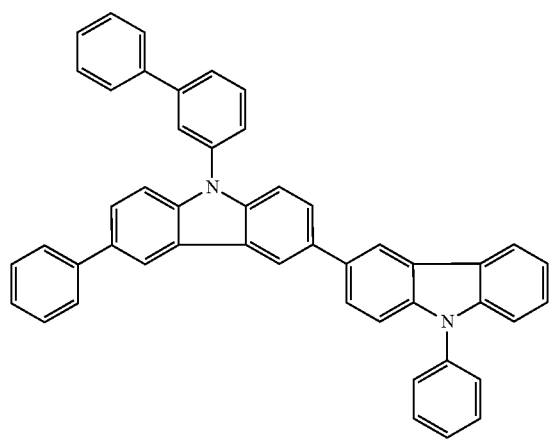
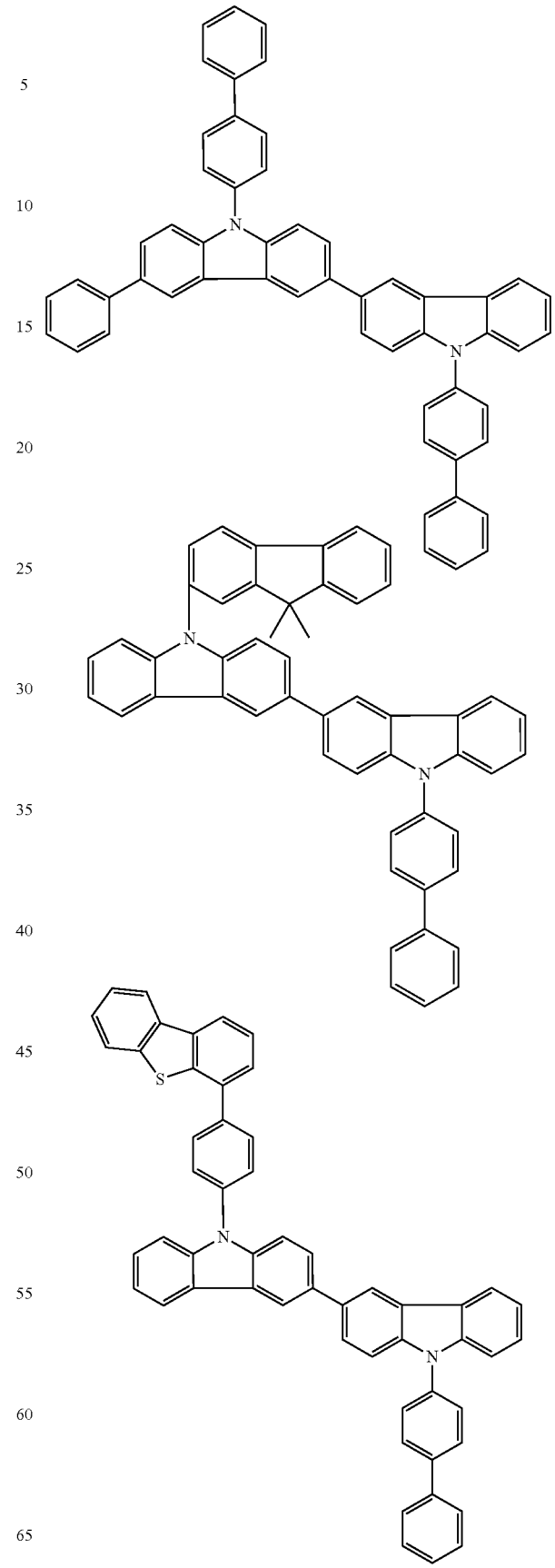

183
184
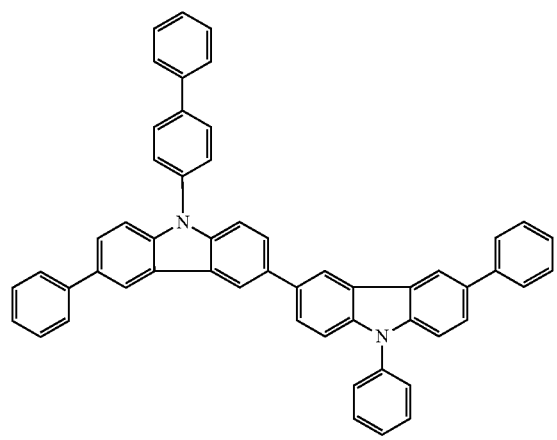
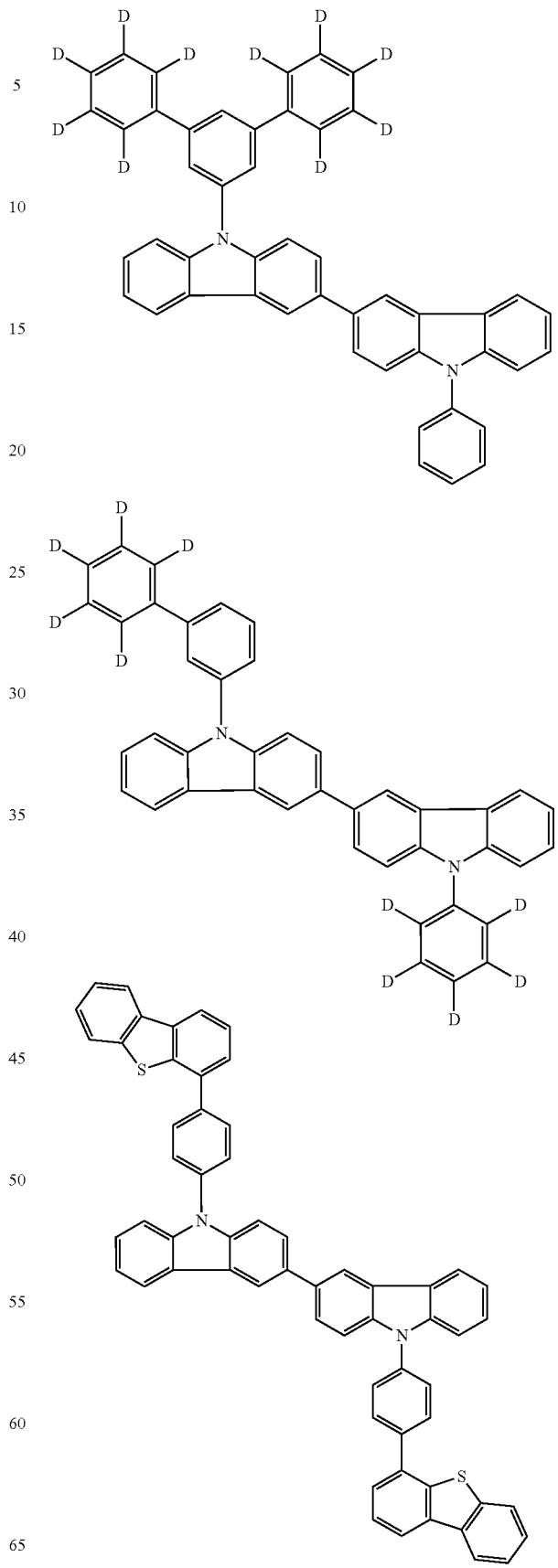

185
-continued
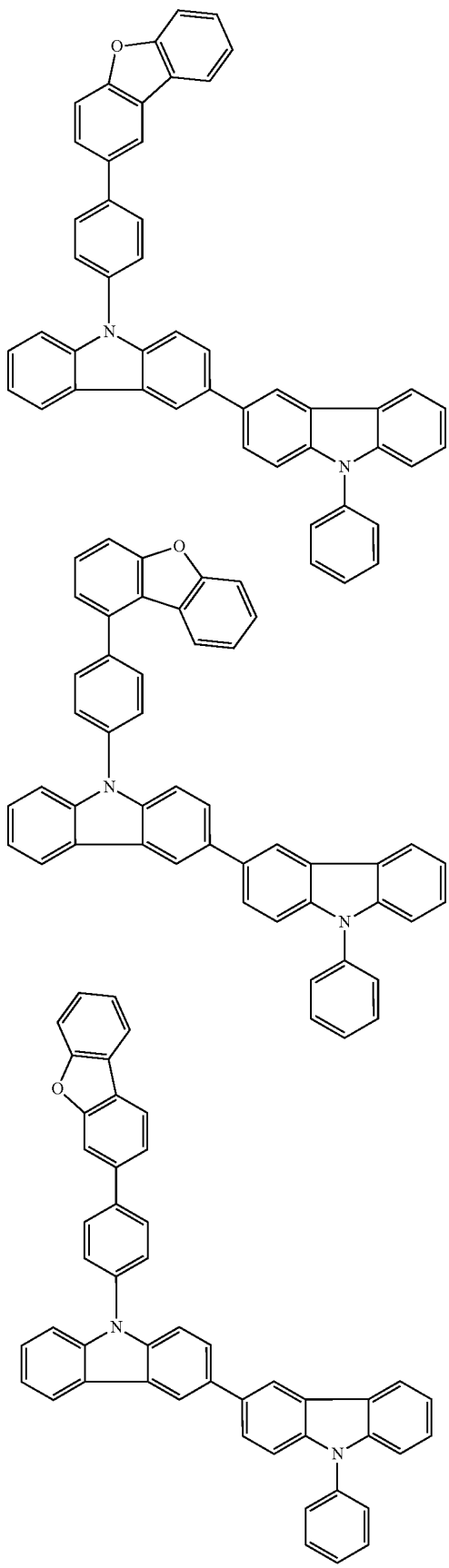
186
-continued
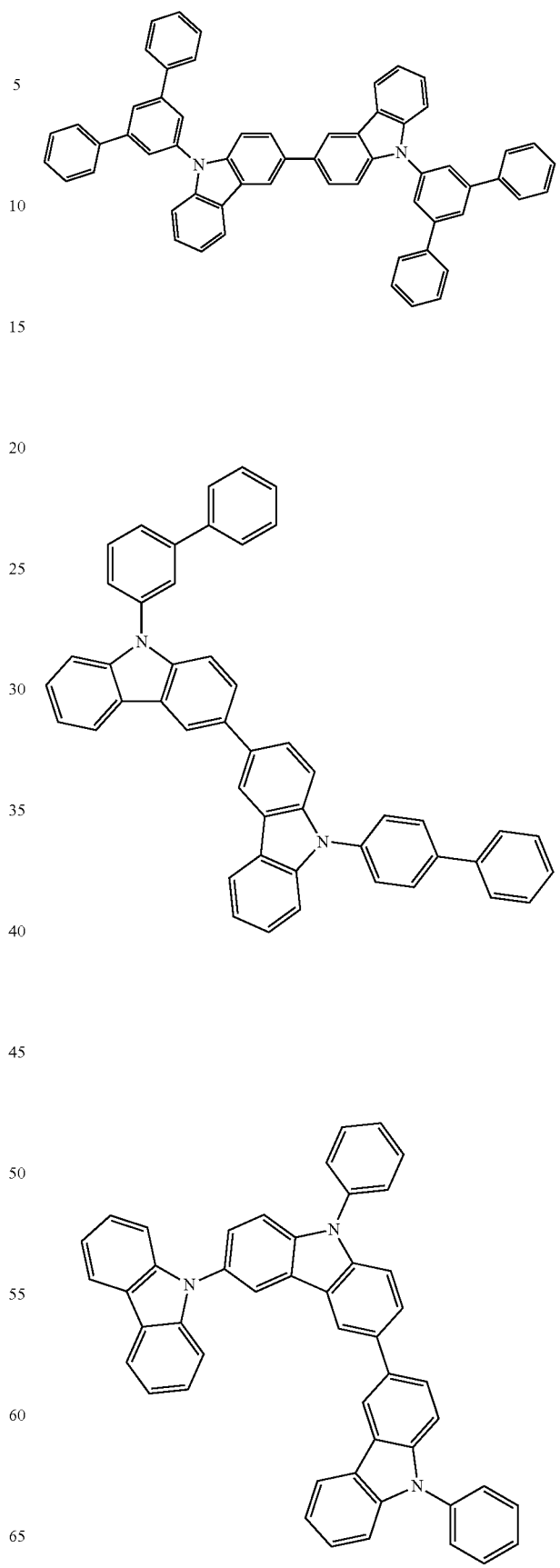

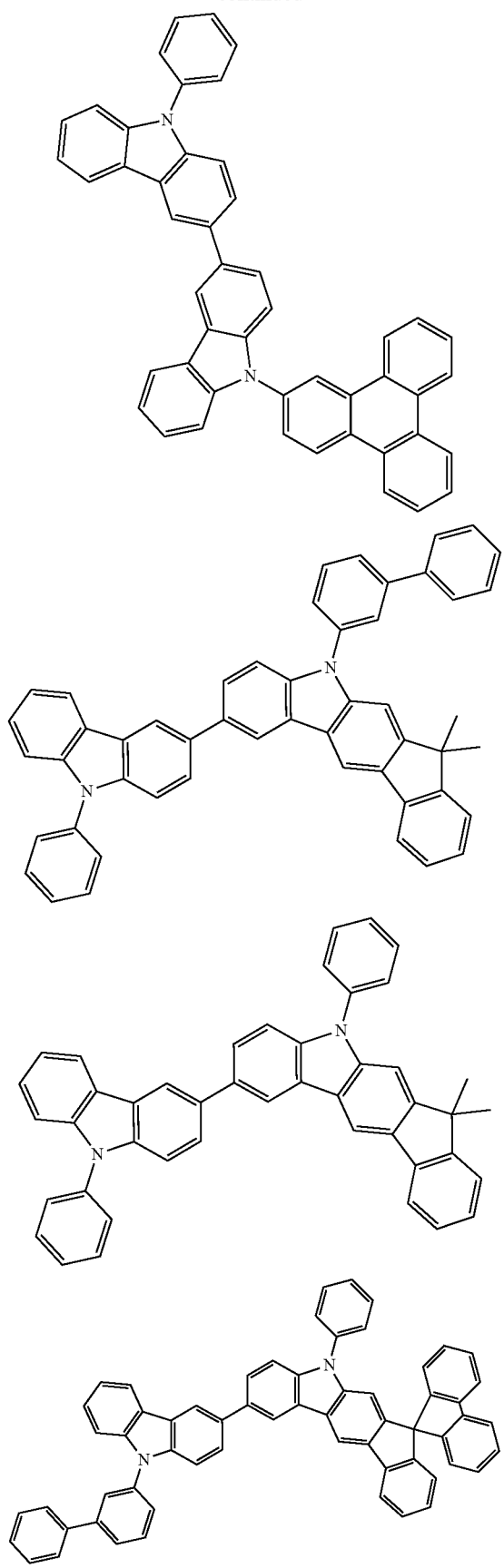
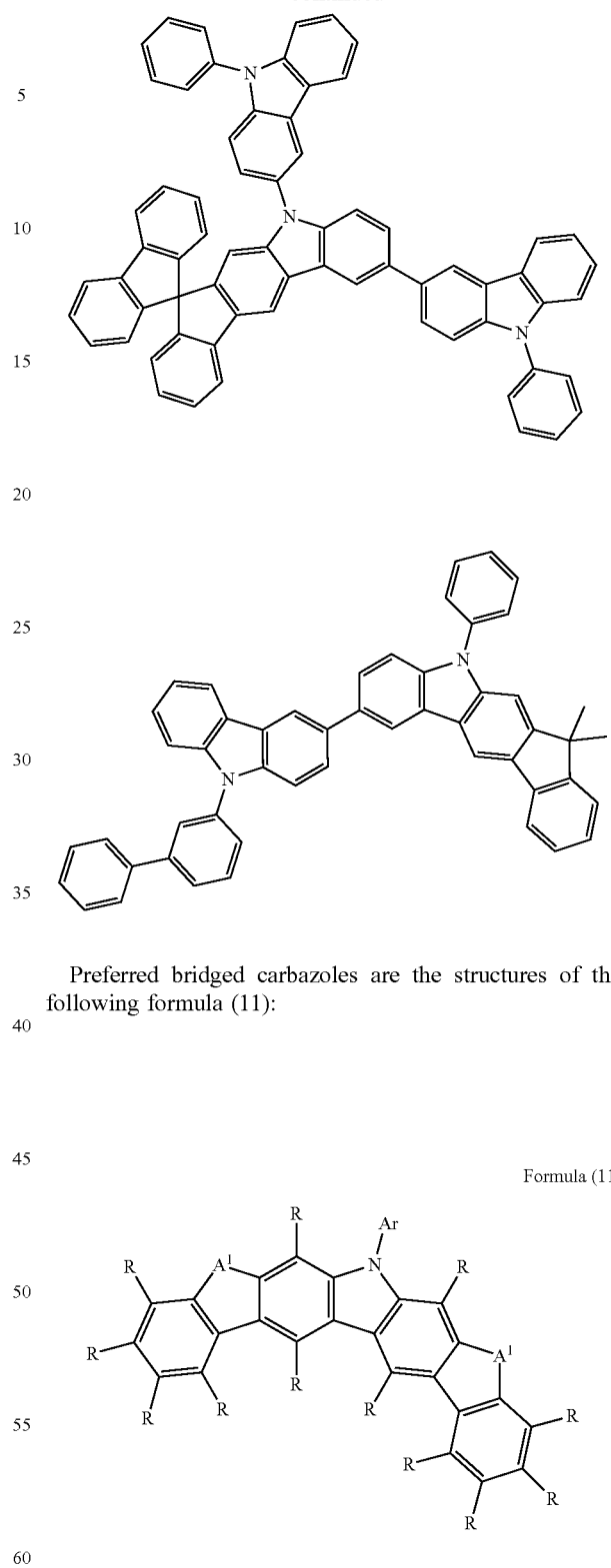

Preferred bridged carbazoles are the structures of the following formula (11):

Formula (11)

where $A_1$ and R have the above-specified definitions according to the formulae (9) and (10), and $A^1$ is preferably the same or different at each instance and is selected from the group consisting of NAr and $CR_2$.

Preferred dibenzofuran derivatives are the compounds of the following formula (12):

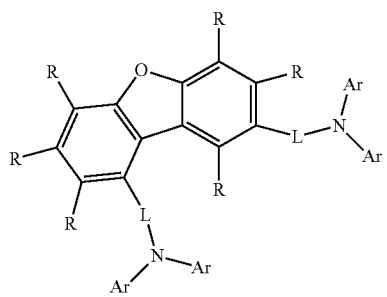

Formula (12)

where the oxygen may also be replaced by sulfur so as to form a dibenzothiophene, L is a single bond or an aromatic or heteroaromatic ring system which has 5 to 30 aromatic ring atoms and may also be substituted by one or more R radicals, and R and Ar have the definitions given above. It is also possible here for the two Ar groups that bind to the same nitrogen atom, or for one Ar group and one L group that bind to the same nitrogen atom, to be bonded to one another, for example to give a carbazole.

Examples of suitable dibenzofuran derivatives are the compounds depicted below.

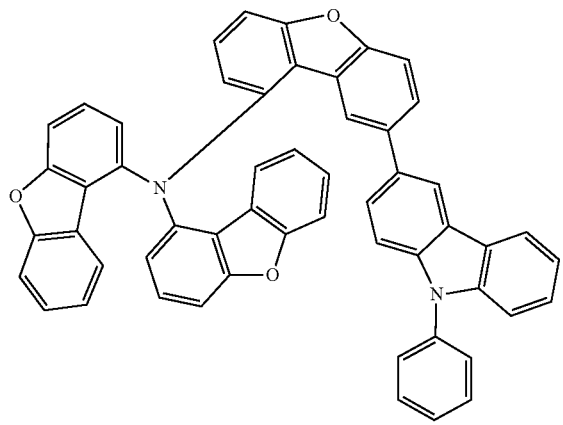

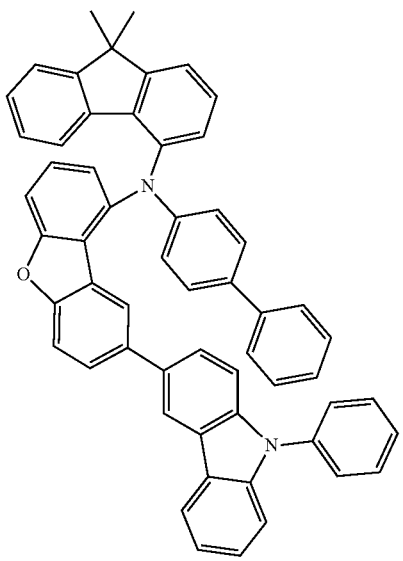

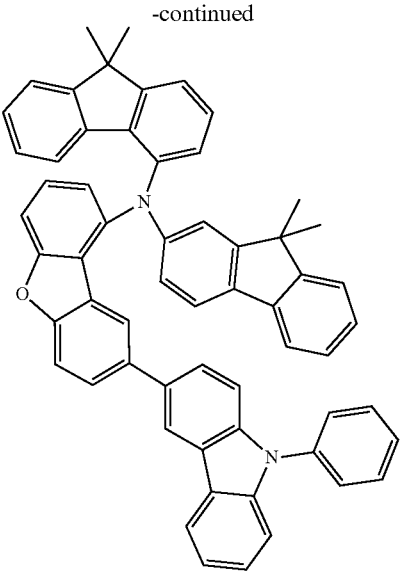

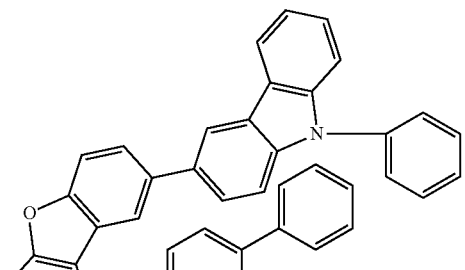

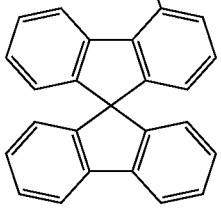

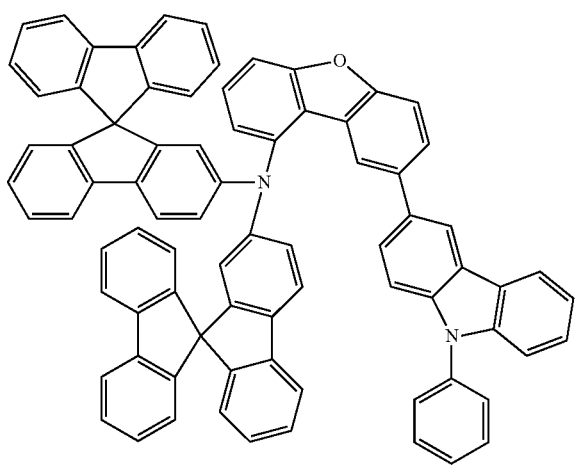

191
-continued
192
-continued
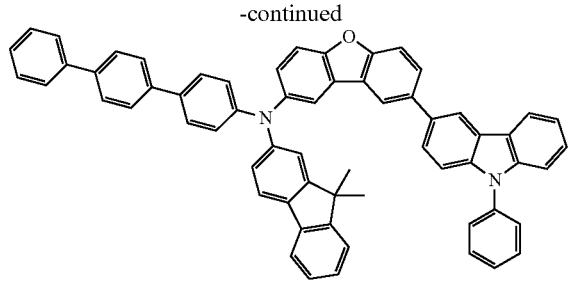
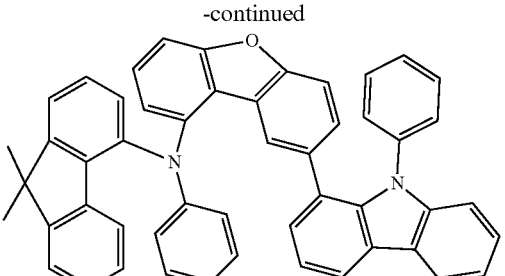
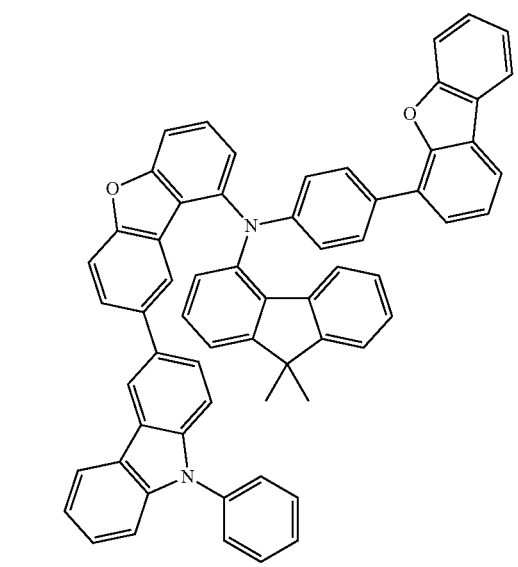
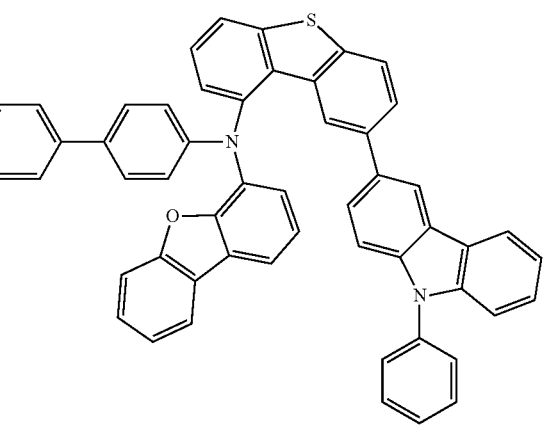
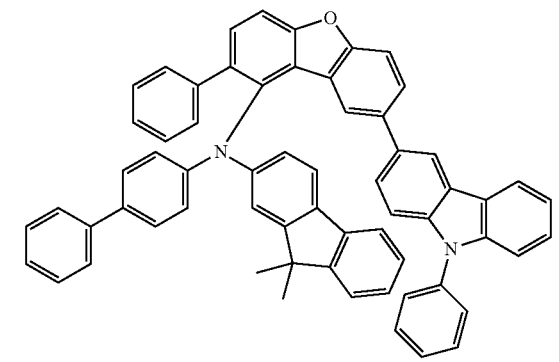
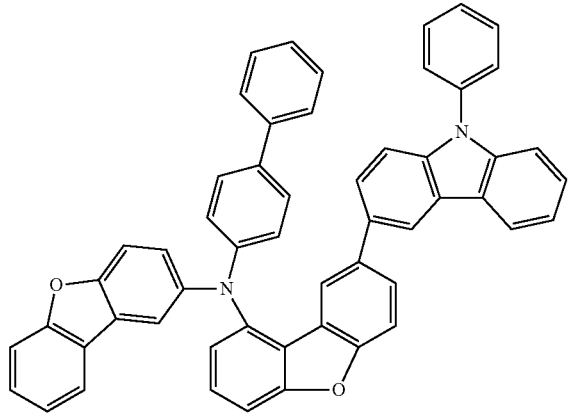
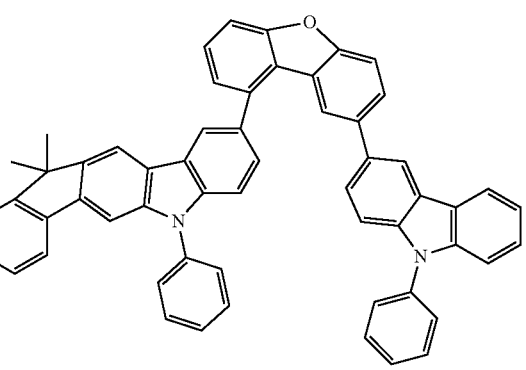

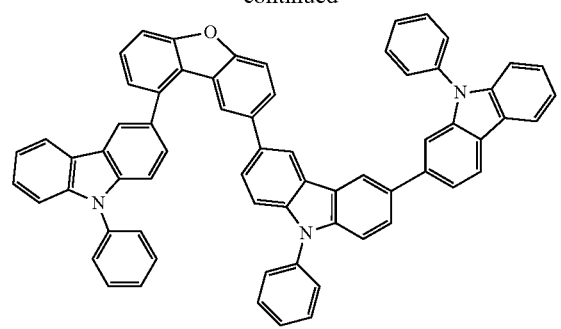
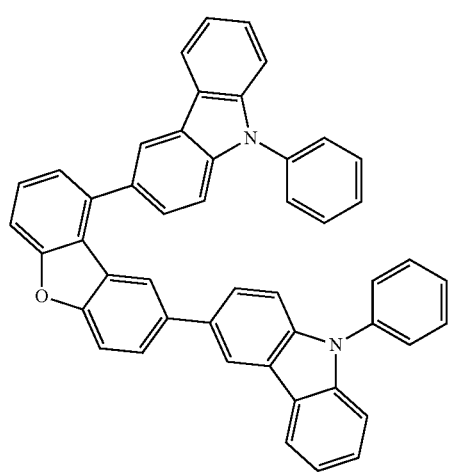
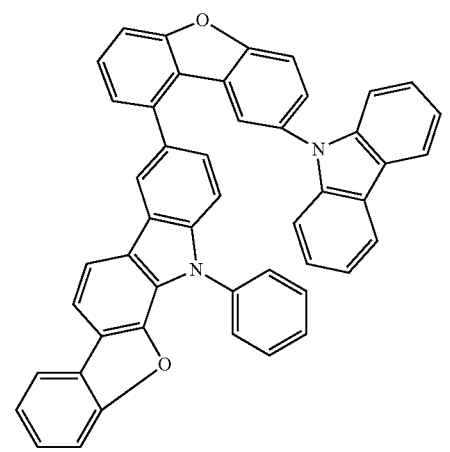
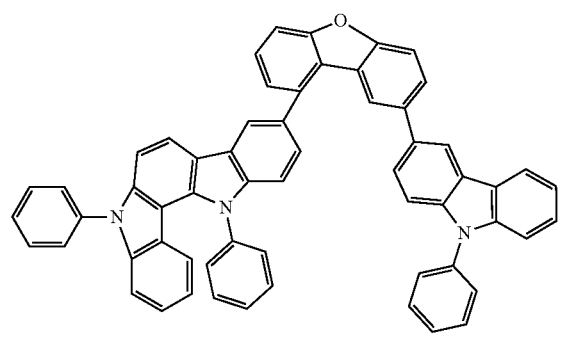
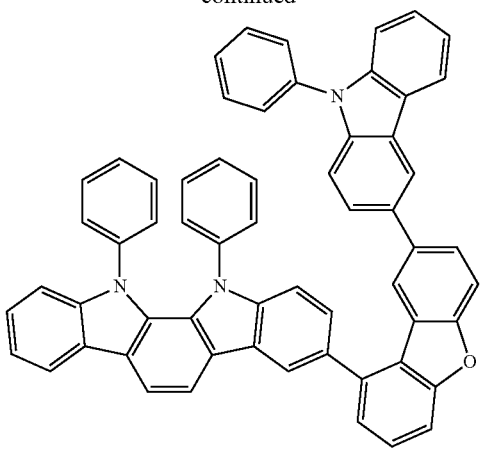
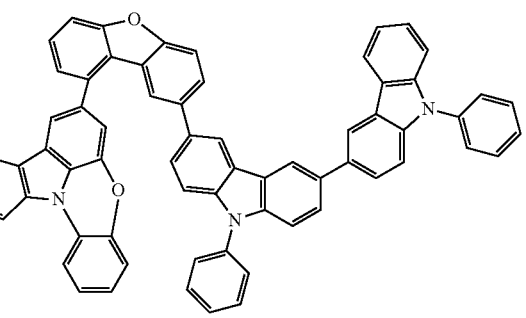
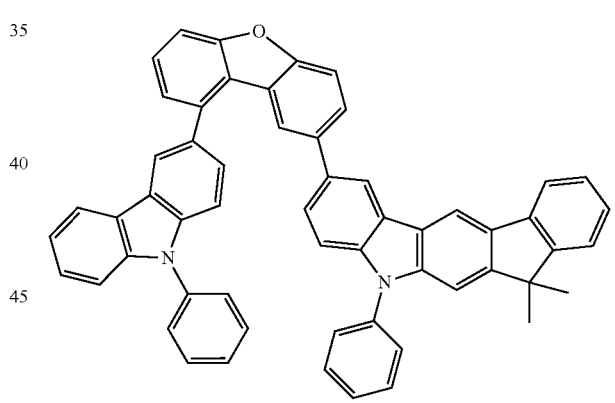
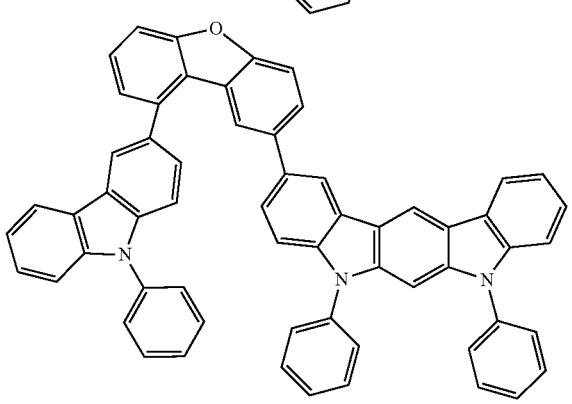
Preferred carbazoleamines are the structures of the following formulae (13), (14) and (15):

Formula (13)
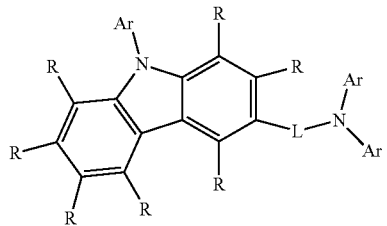
Formula (14)
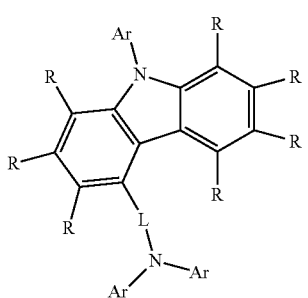
Formula (15)
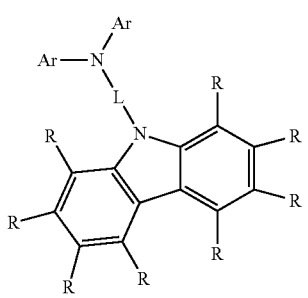
where L is an aromatic or heteroaromatic ring system which has 5 to 30 aromatic ring atoms and may be substituted by one or more R radicals, and R and Ar have the above-specified definitions according to the formulae (9) and (10).
Examples of suitable carbazoleamine derivatives are the compounds depicted below.
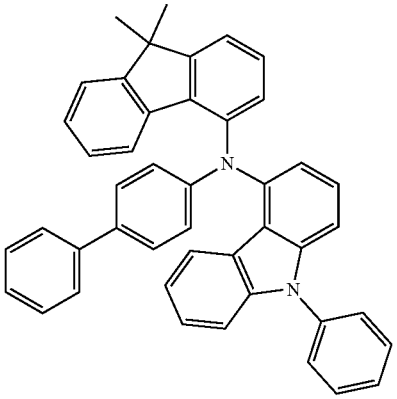
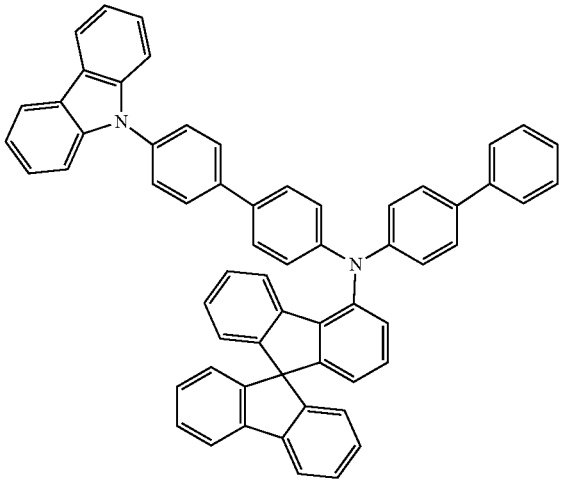
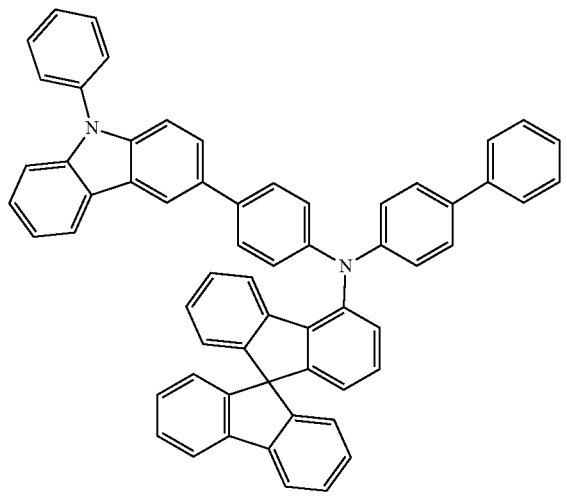
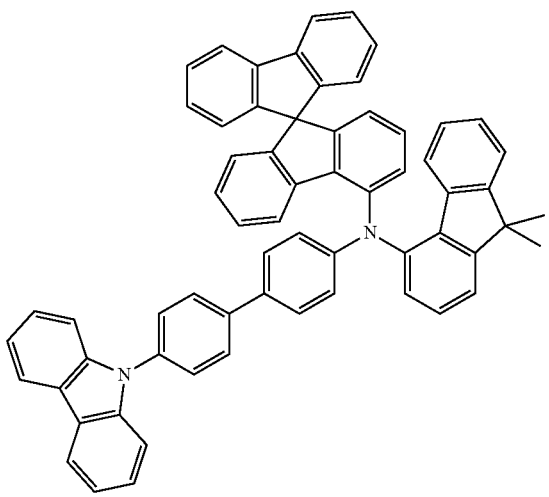

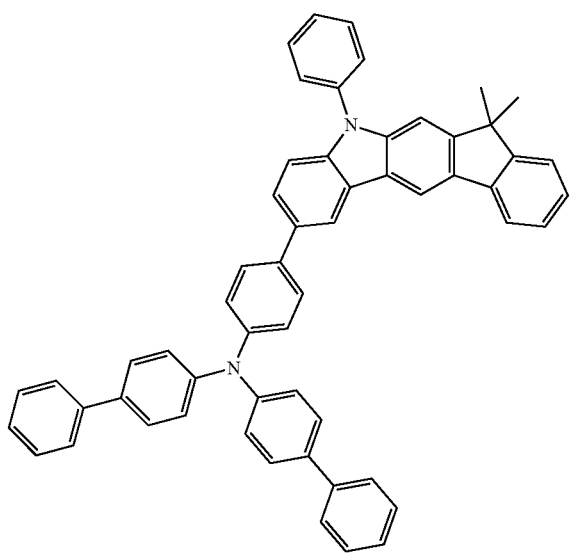
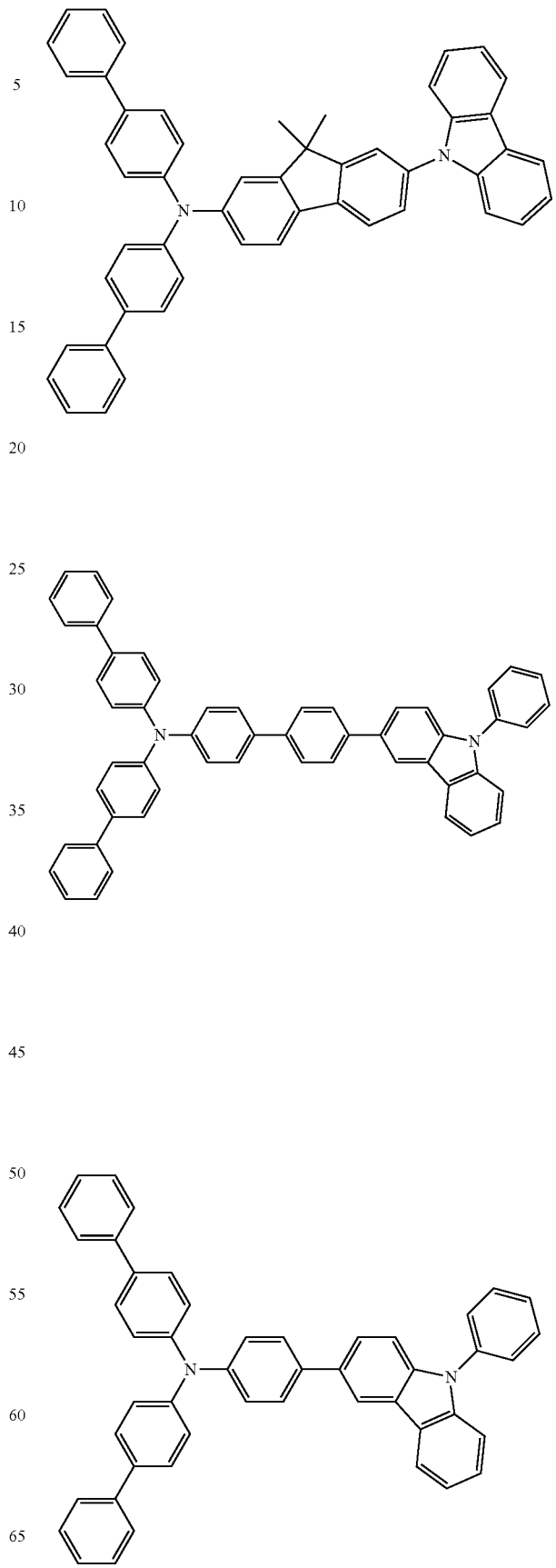

199
-continued
200
-continued
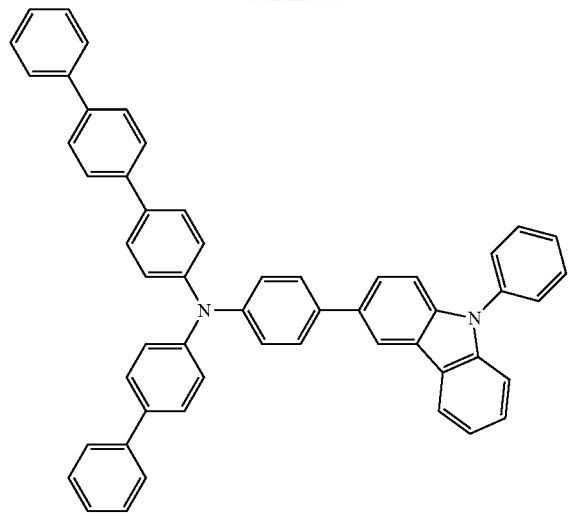
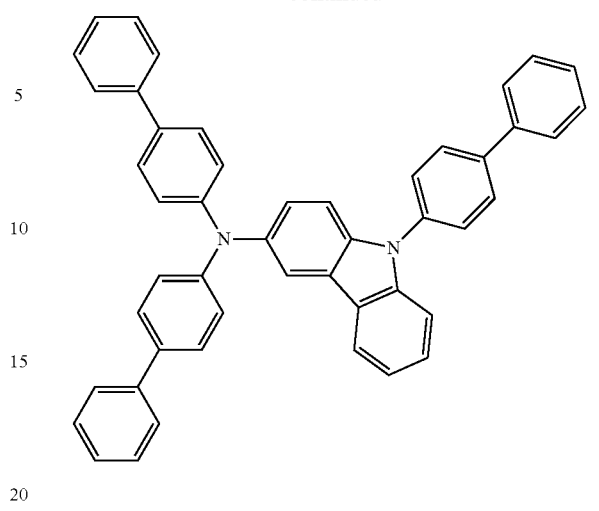
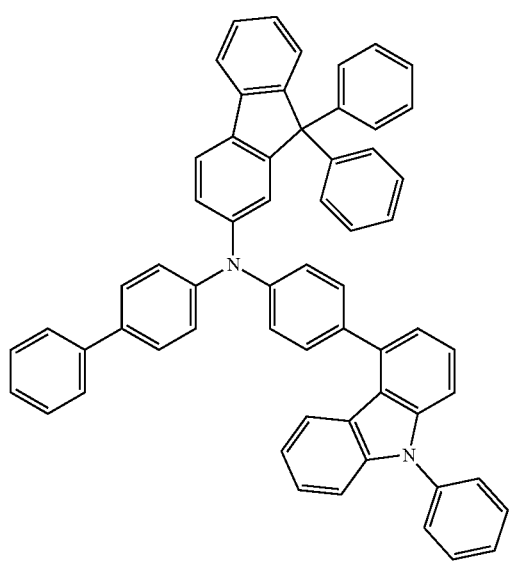
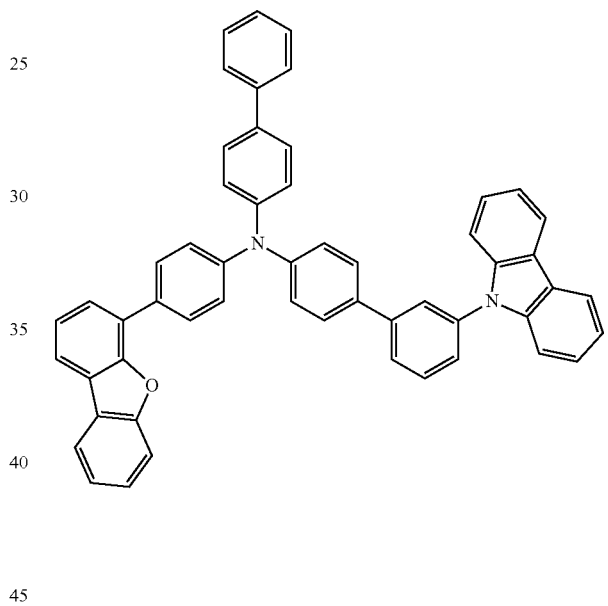
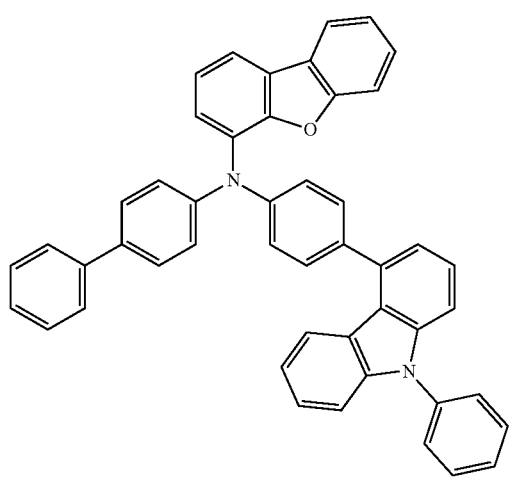
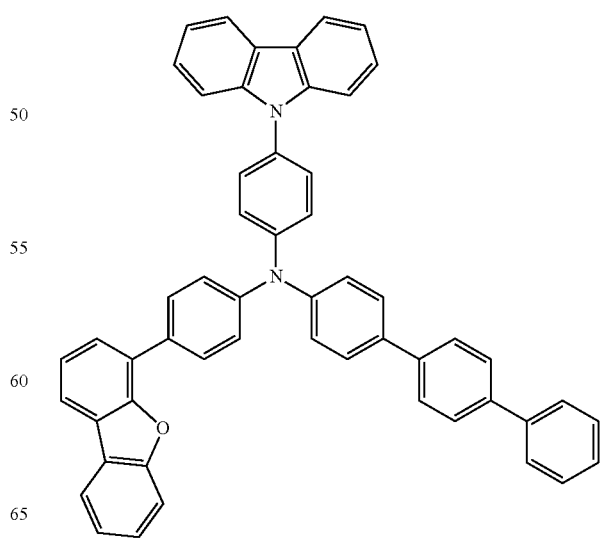

201
-continued
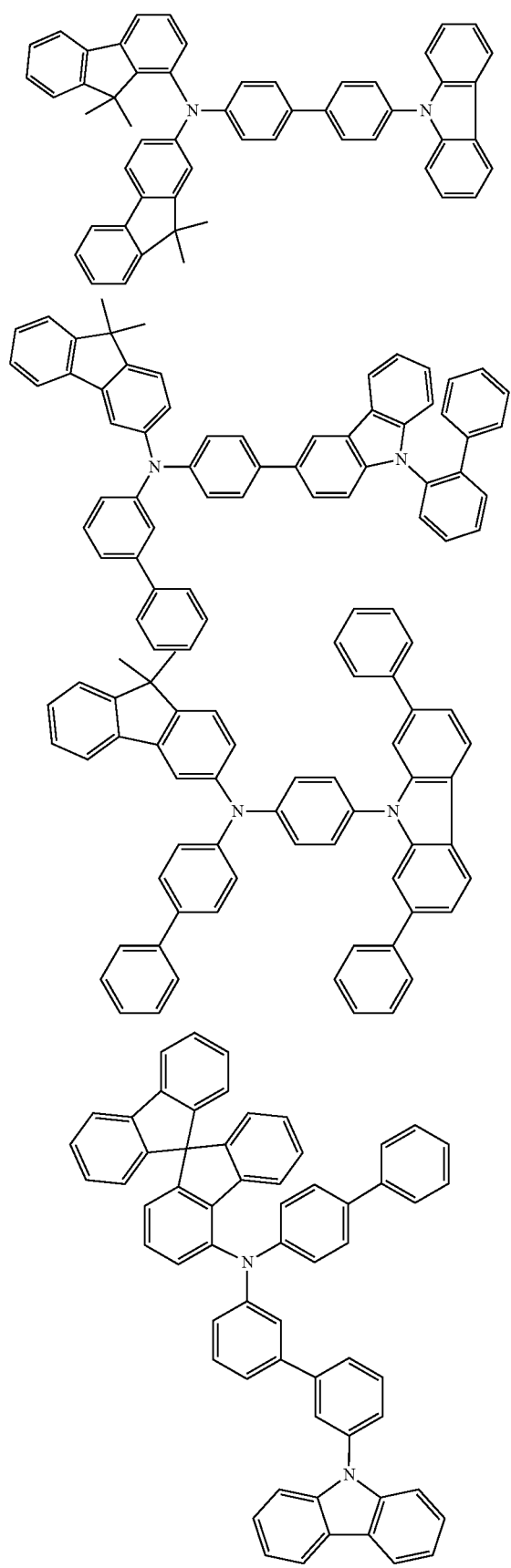
202
-continued
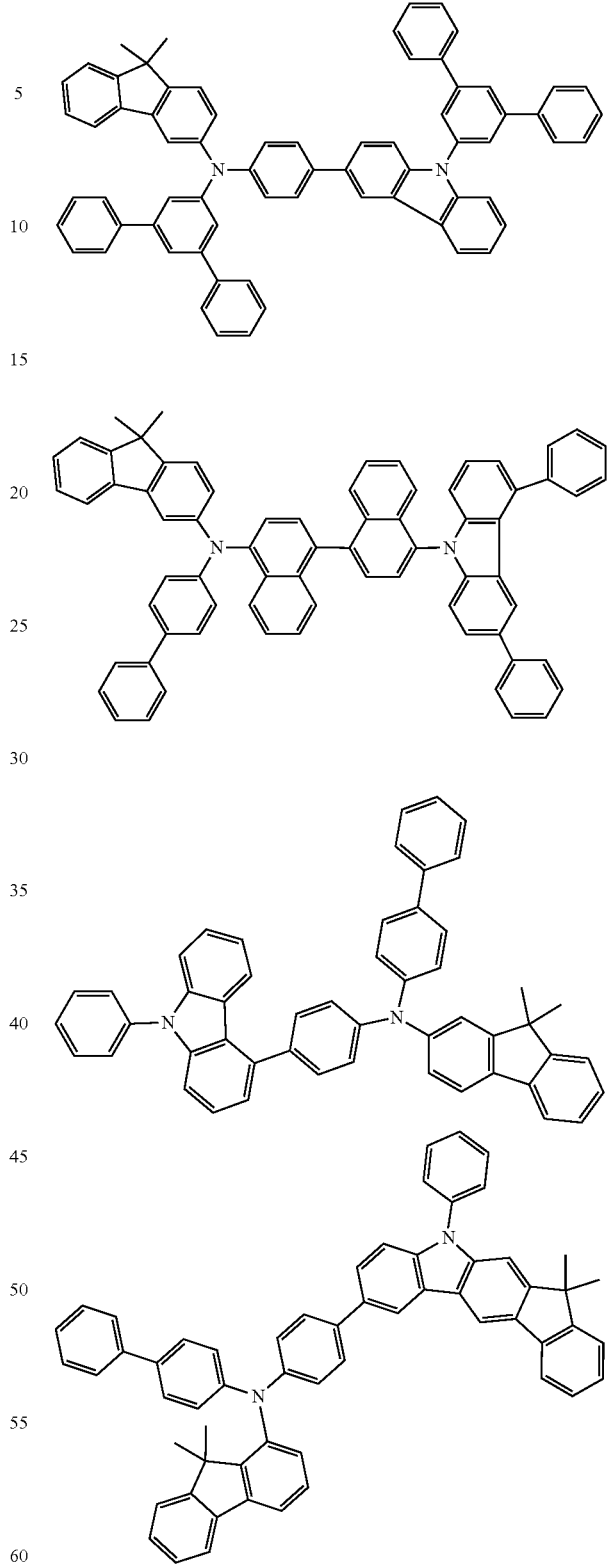
Further particularly preferred co-matrix materials, especially hole-transporting co-hosts, especially when the compound of the invention is substituted by an electron-deficient heteroaromatic ring system, are shown in the following table:

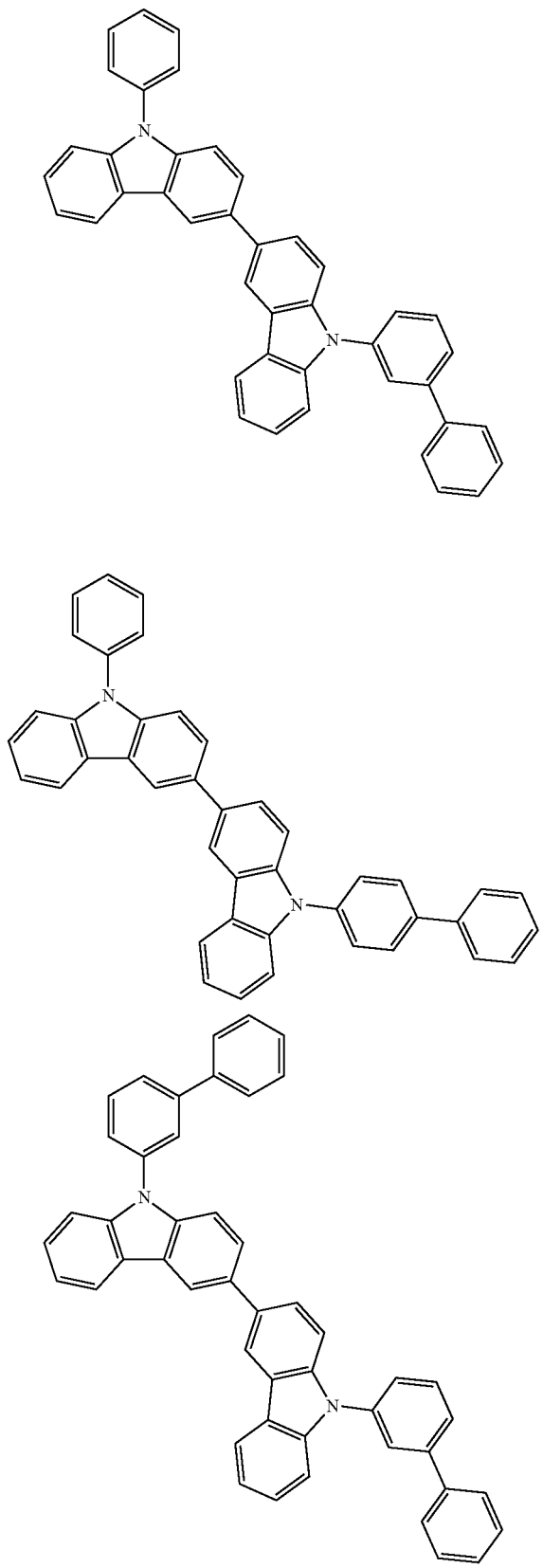
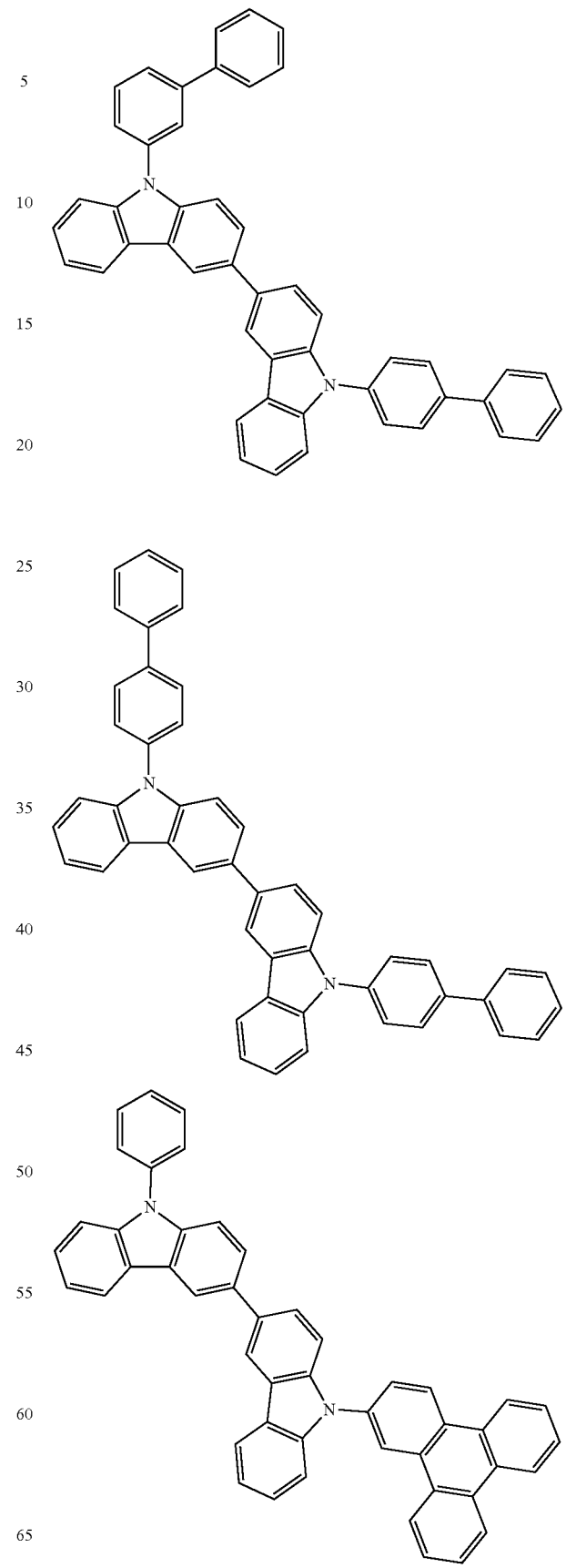

205
-continued
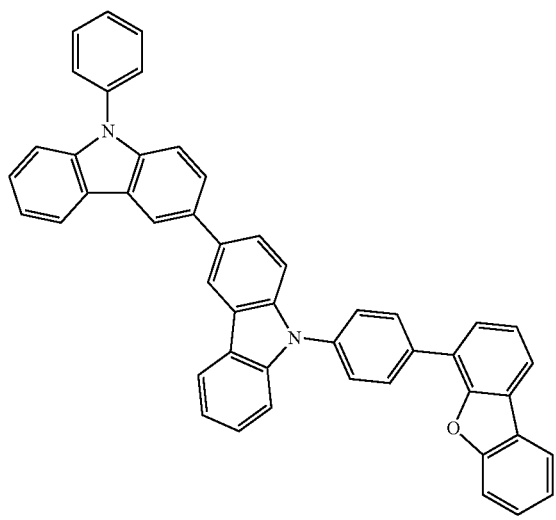
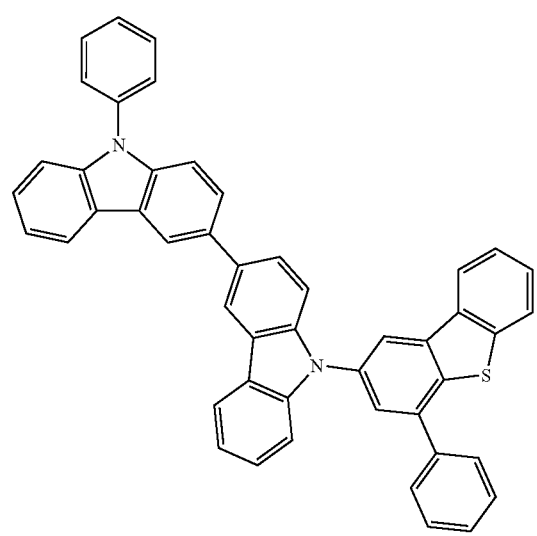
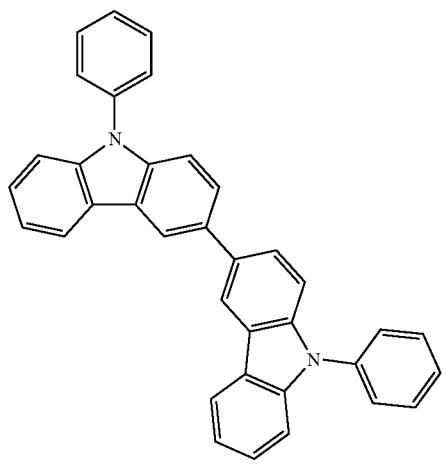
206
-continued
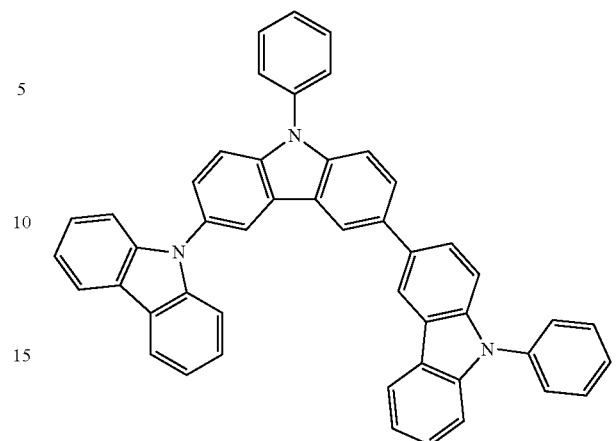
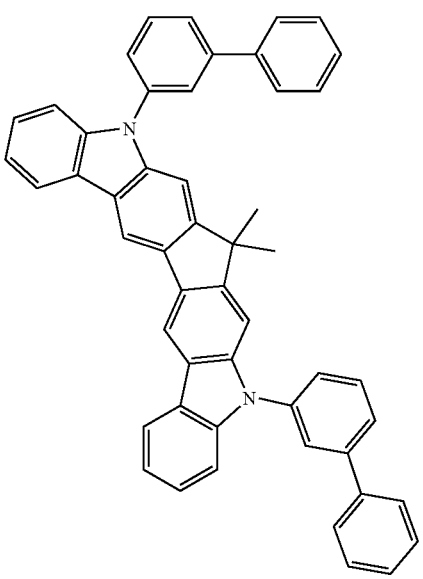

207
-continued
208
-continued
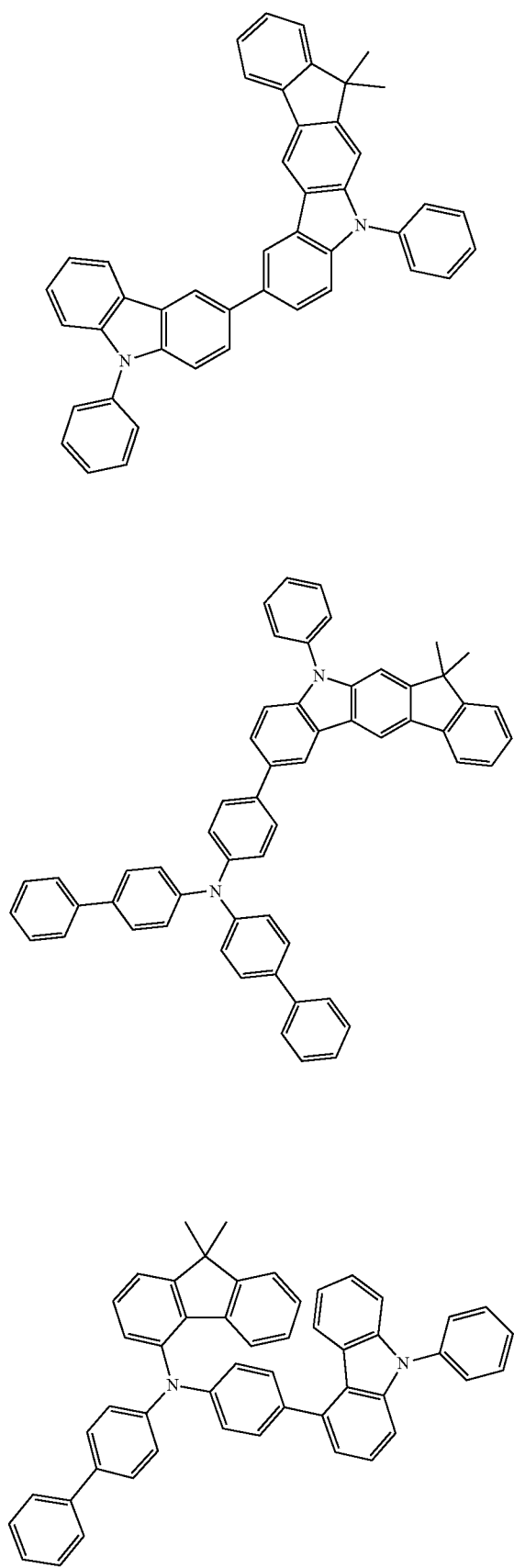
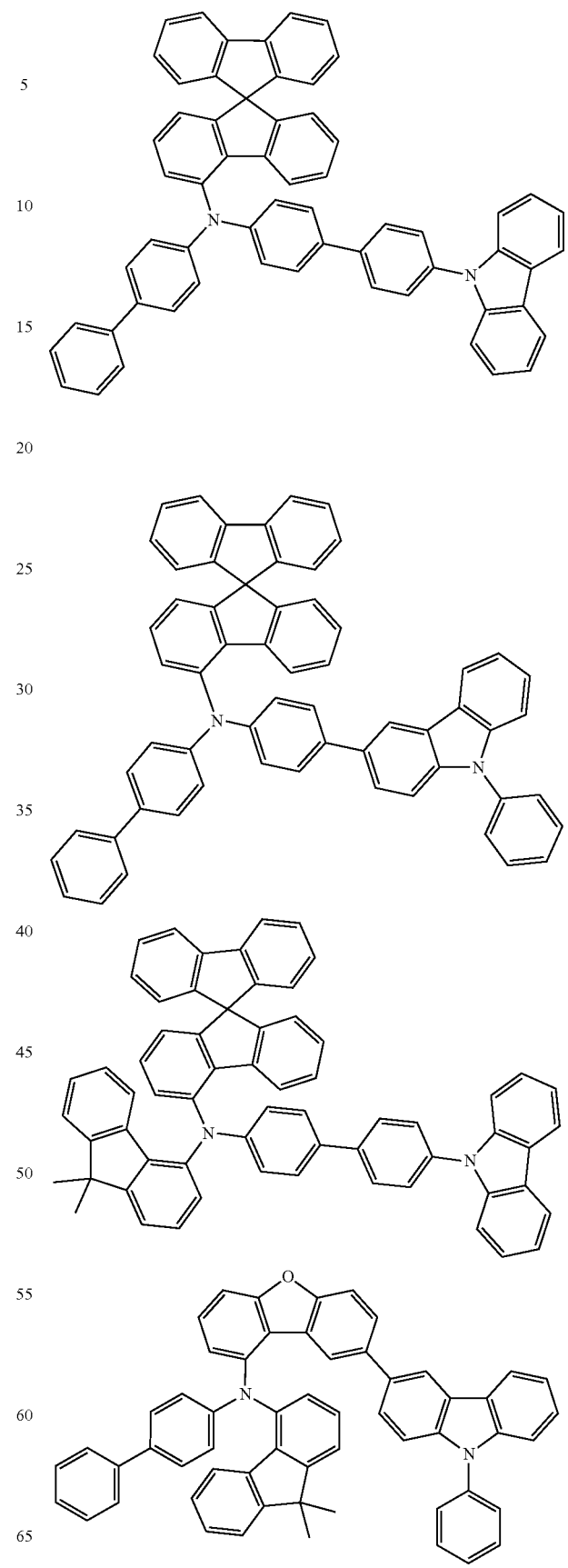

-continued
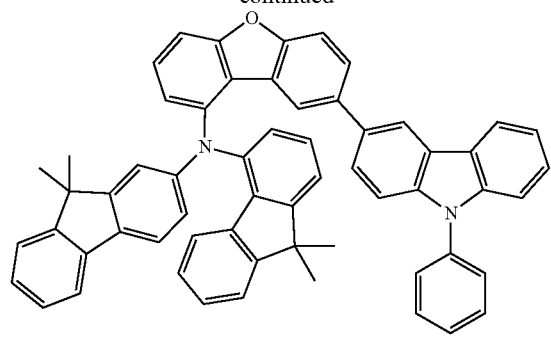
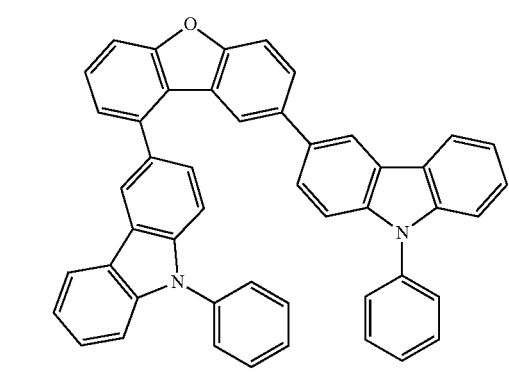
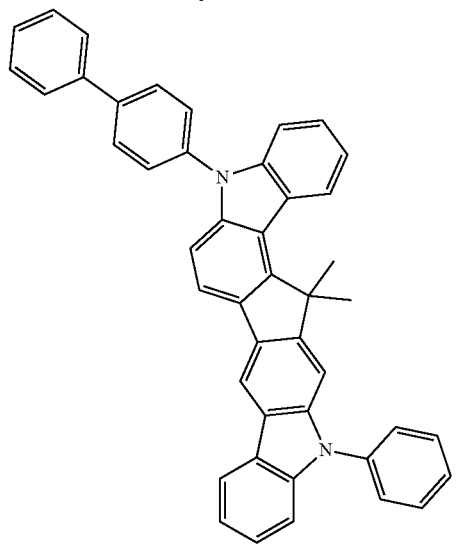
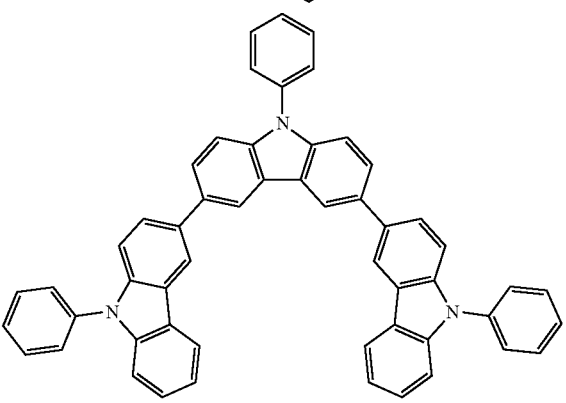
-continued
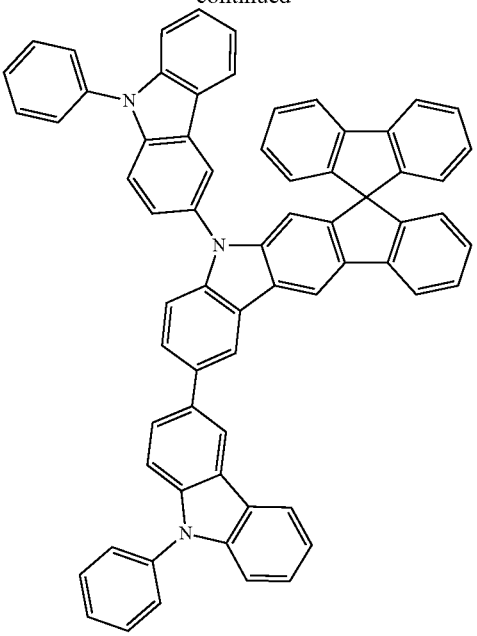
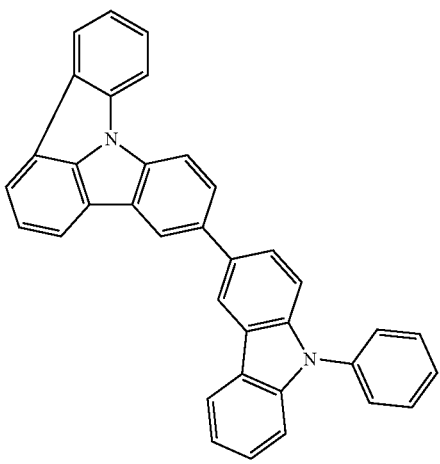
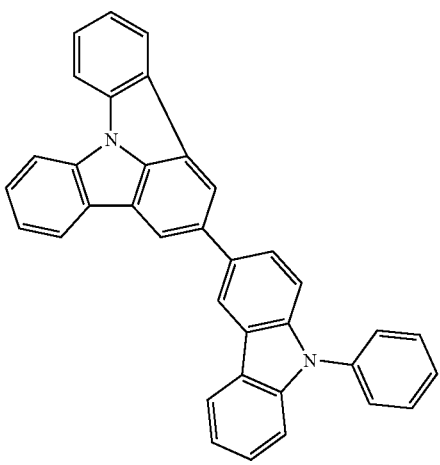

211
-continued
212
-continued
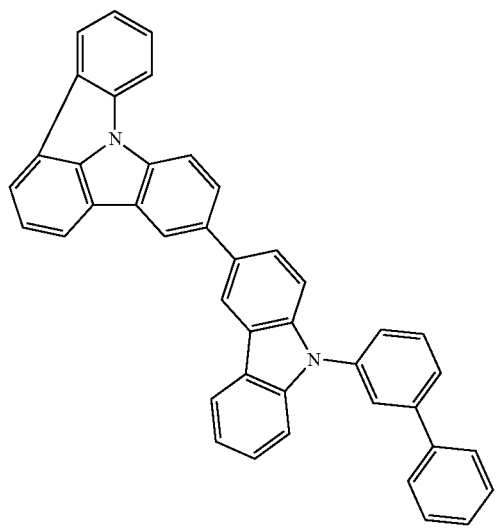
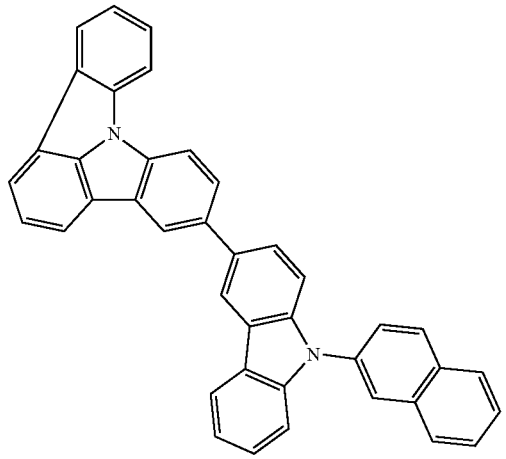 [SMILES: c1ccc2cc(-n3c4ccccc4c4cc(-c5ccc6c(c5)c5cccc7c8ccccc8n6c75)ccc43)ccc2c1]
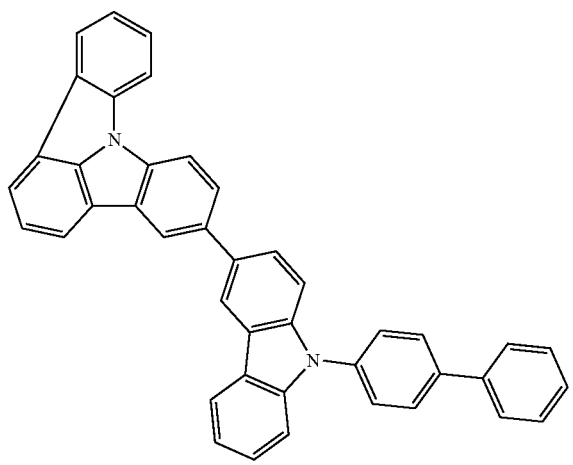
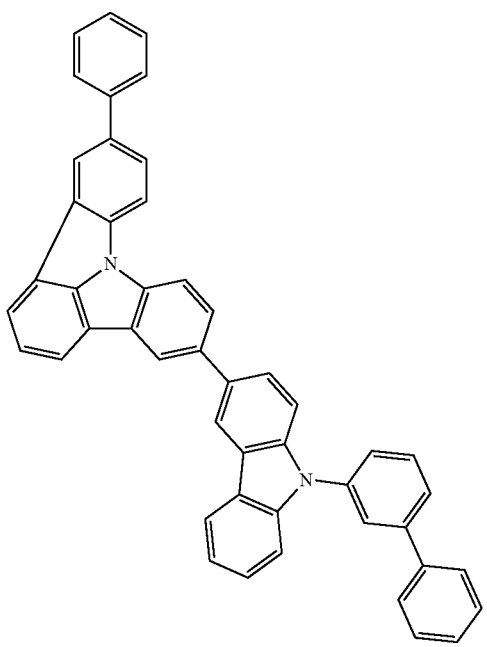
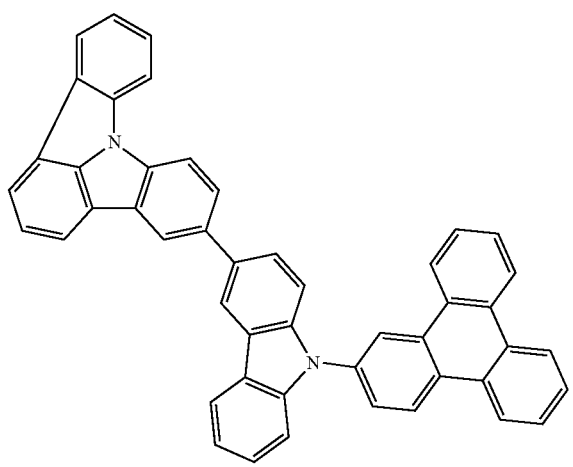
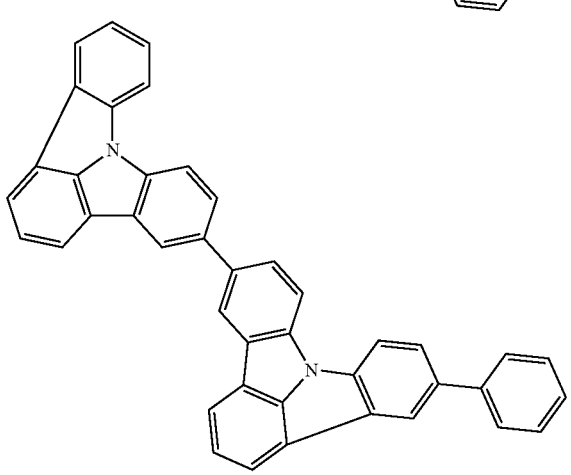

213
-continued
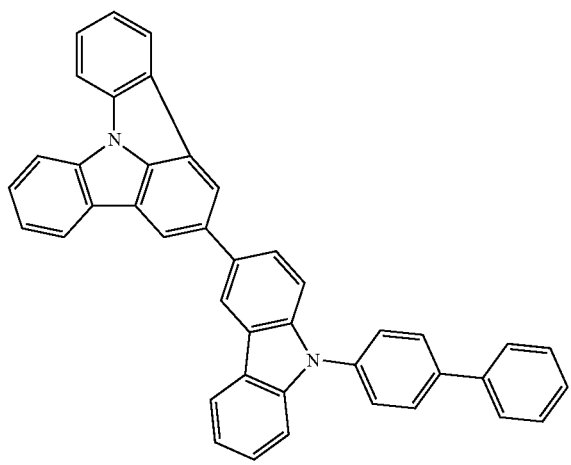
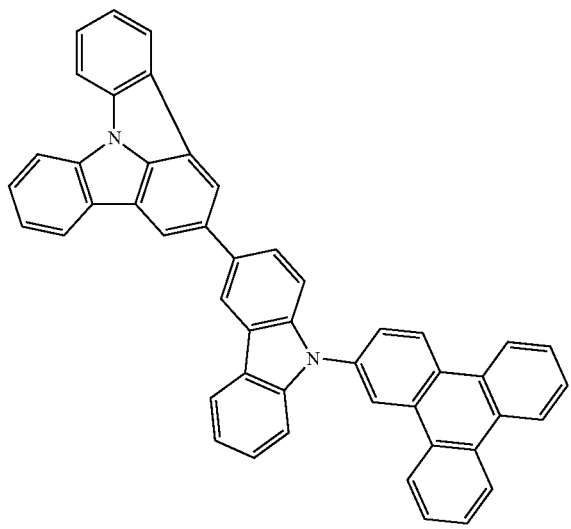
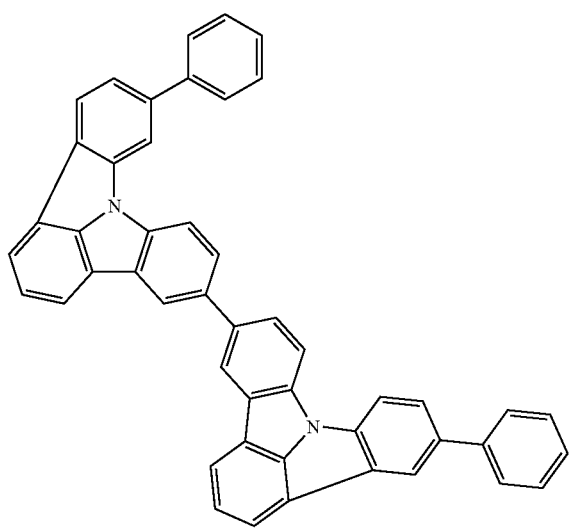
214
-continued
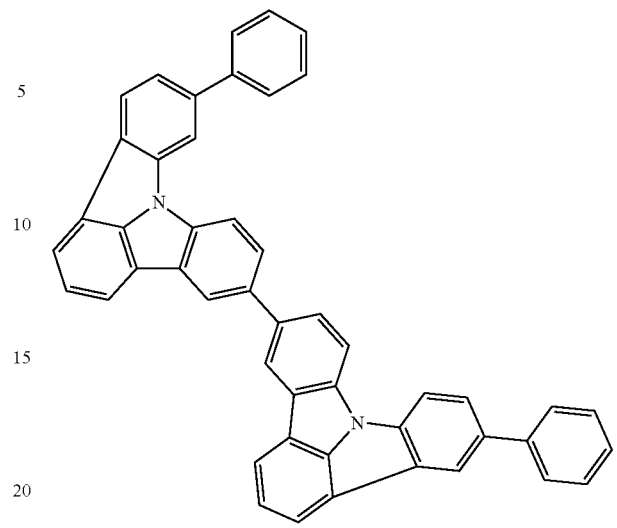
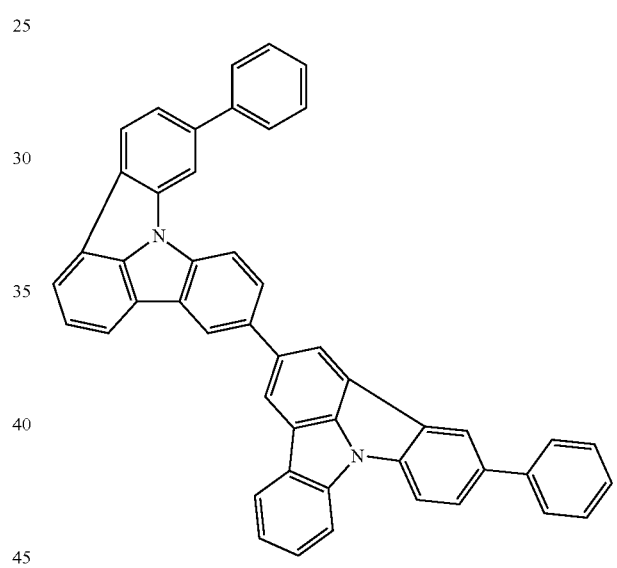
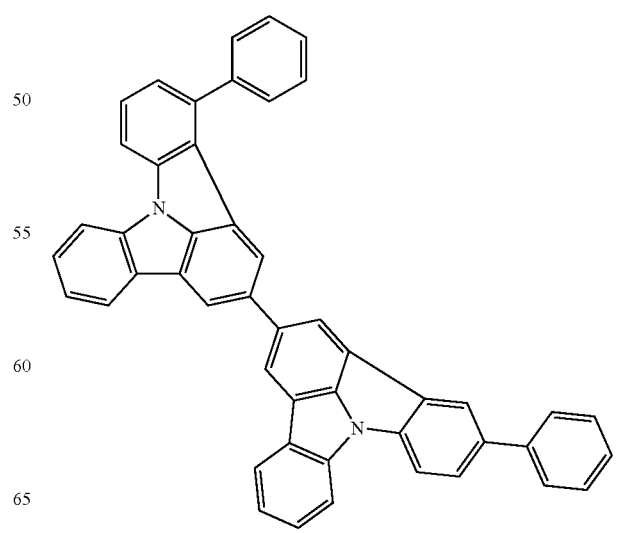

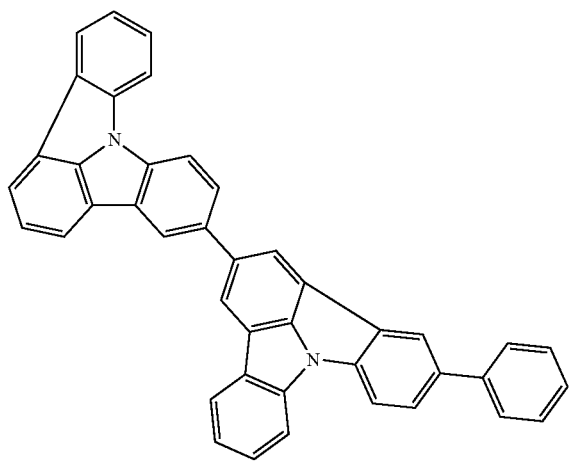
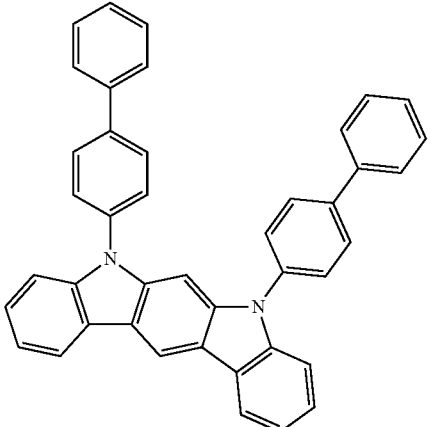
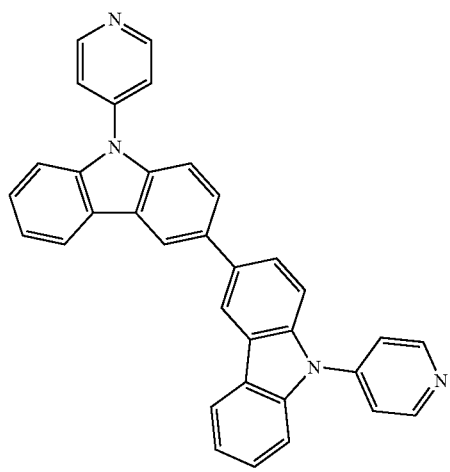
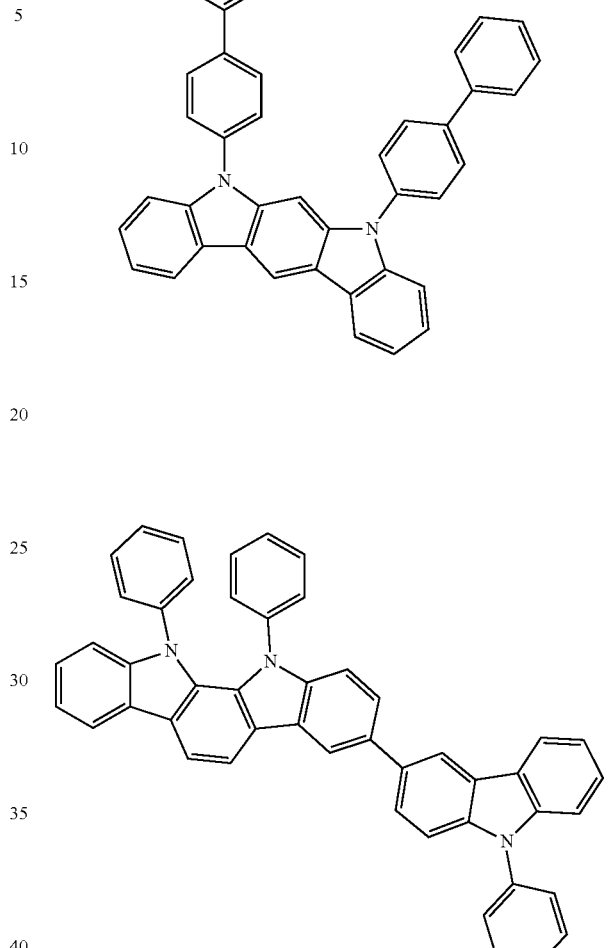
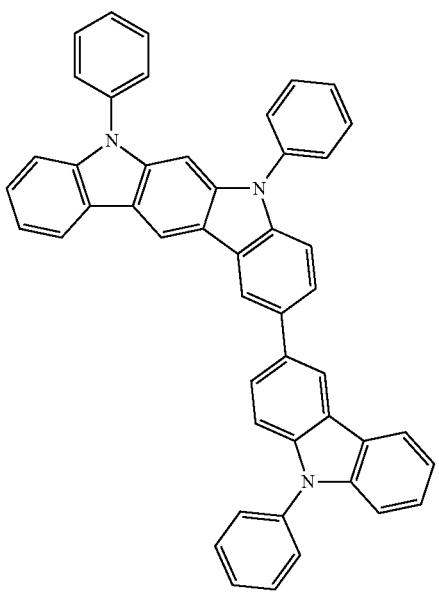
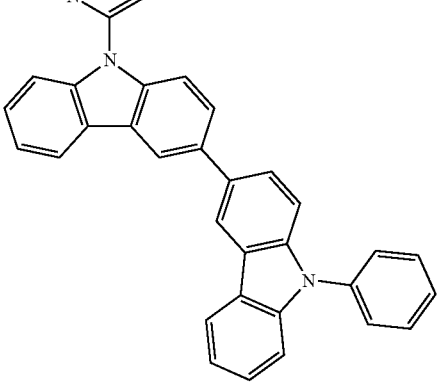

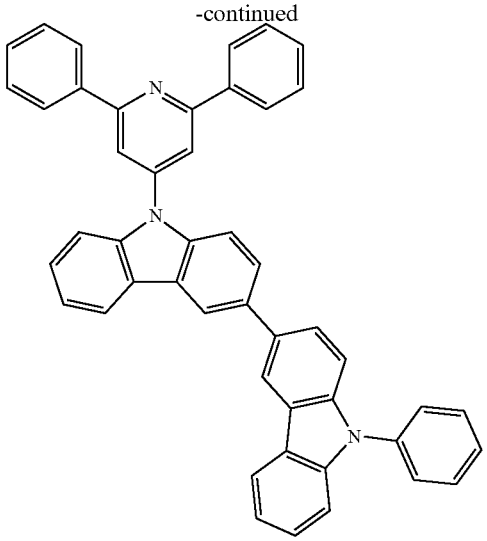


Formula (18)

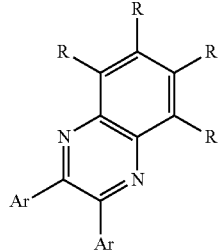

Formula (19)

Preferred co-matrix materials, especially when the compound of the invention is substituted by an electron-rich heteroaromatic ring system, for example a carbazole group, are also selected from the group consisting of triazine derivatives, pyrimidine derivatives and quinazoline derivatives. Preferred triazine, quinazoline or pyrimidine derivatives that can be used as a mixture together with the compounds of the invention are the compounds of the following formulae (16), (17), (18) and (19):

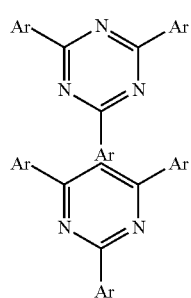

Formula (16)

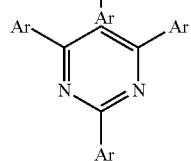

Formula (17)

where Ar and R have the above-specified definitions according to the formulae (9) and (10).

Particular preference is given to the triazine derivatives of the formula (16) and the quinoxaline derivatives of the formula (19), especially the triazine derivatives of the formula (16).

In a preferred embodiment of the invention, Ar in the formulae (16), (17), (18) and (19) is the same or different at each instance and is an aromatic or heteroaromatic ring system which has 6 to 30 aromatic ring atoms, especially 6 to 24 aromatic ring atoms, and may be substituted by one or more R radicals. Suitable aromatic or heteroaromatic ring systems Ar here are the same as set out above as embodiments for Ar, especially the structures Ar-1 to Ar-82.

Examples of suitable triazine and pyrimidine compounds that may be used as matrix materials together with the compounds of the invention are the compounds depicted in the following table:

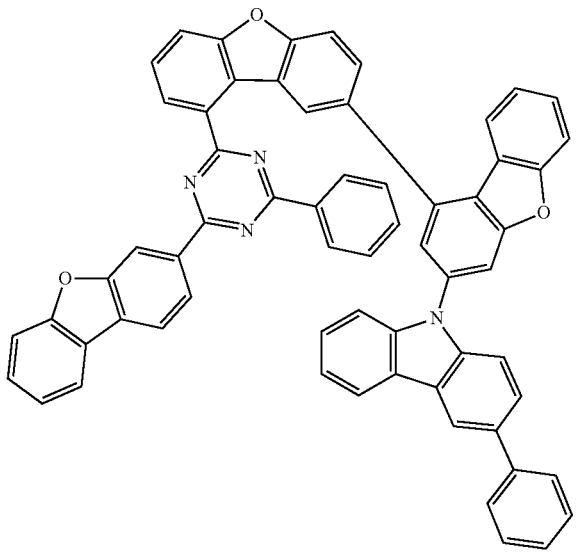

-continued
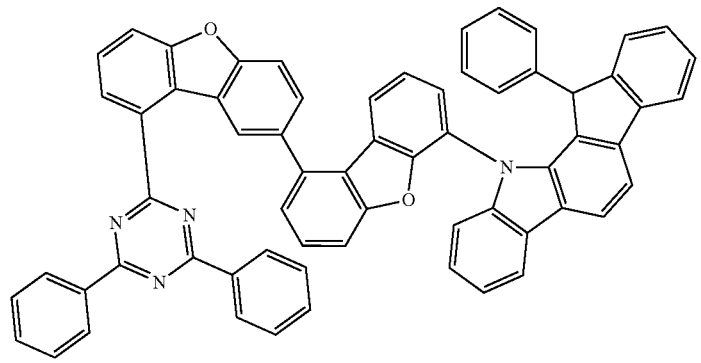
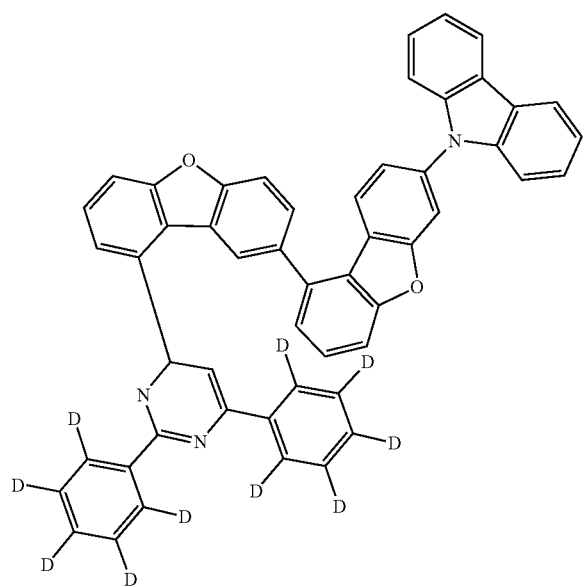
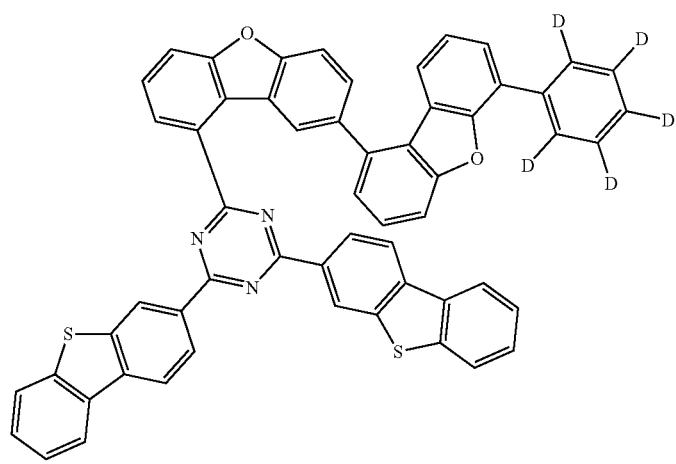

221
222
-continued
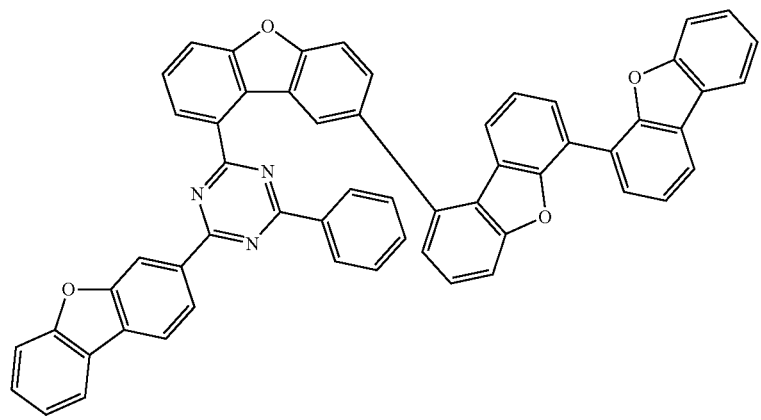
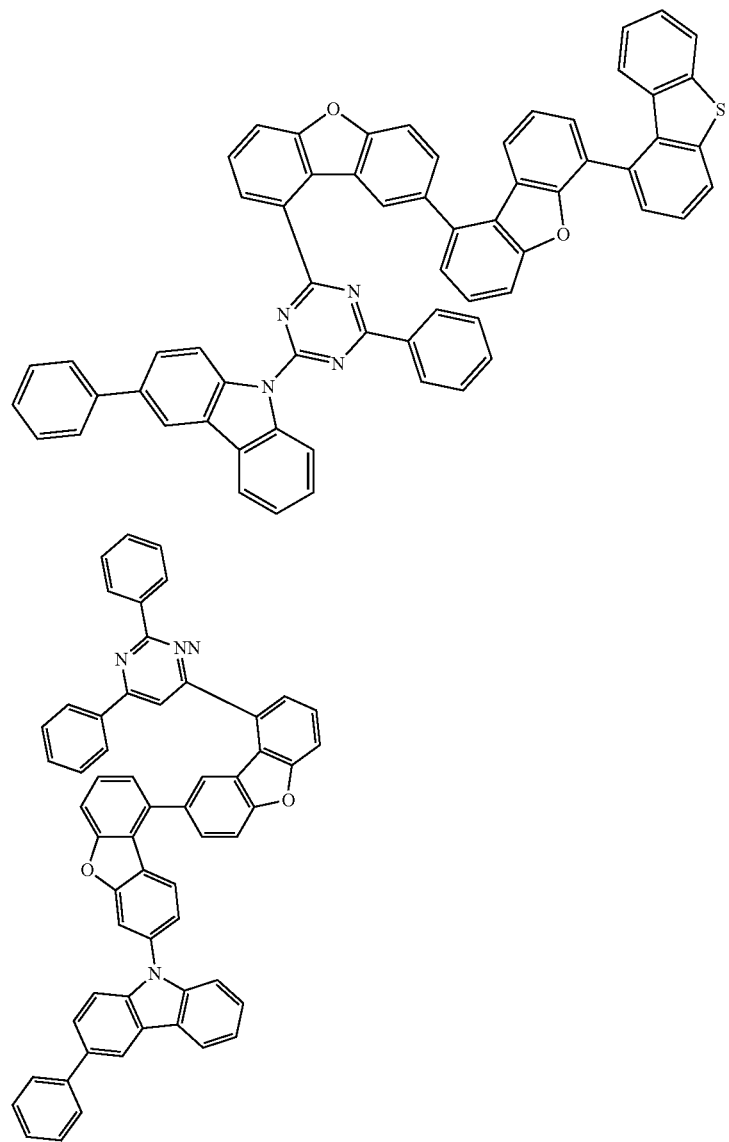

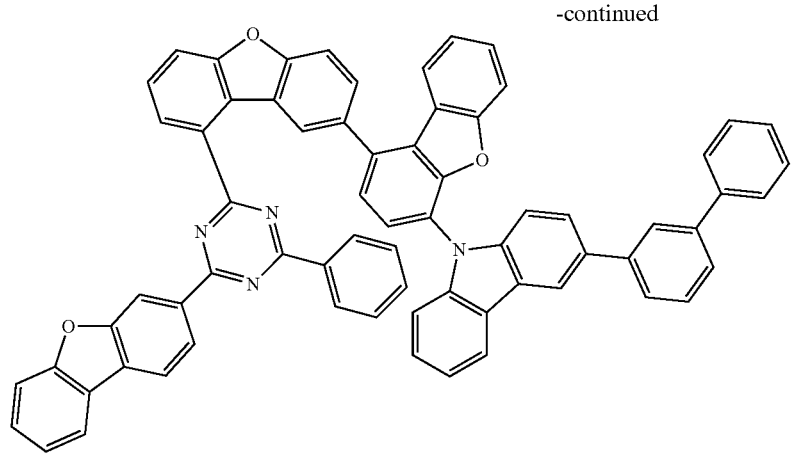
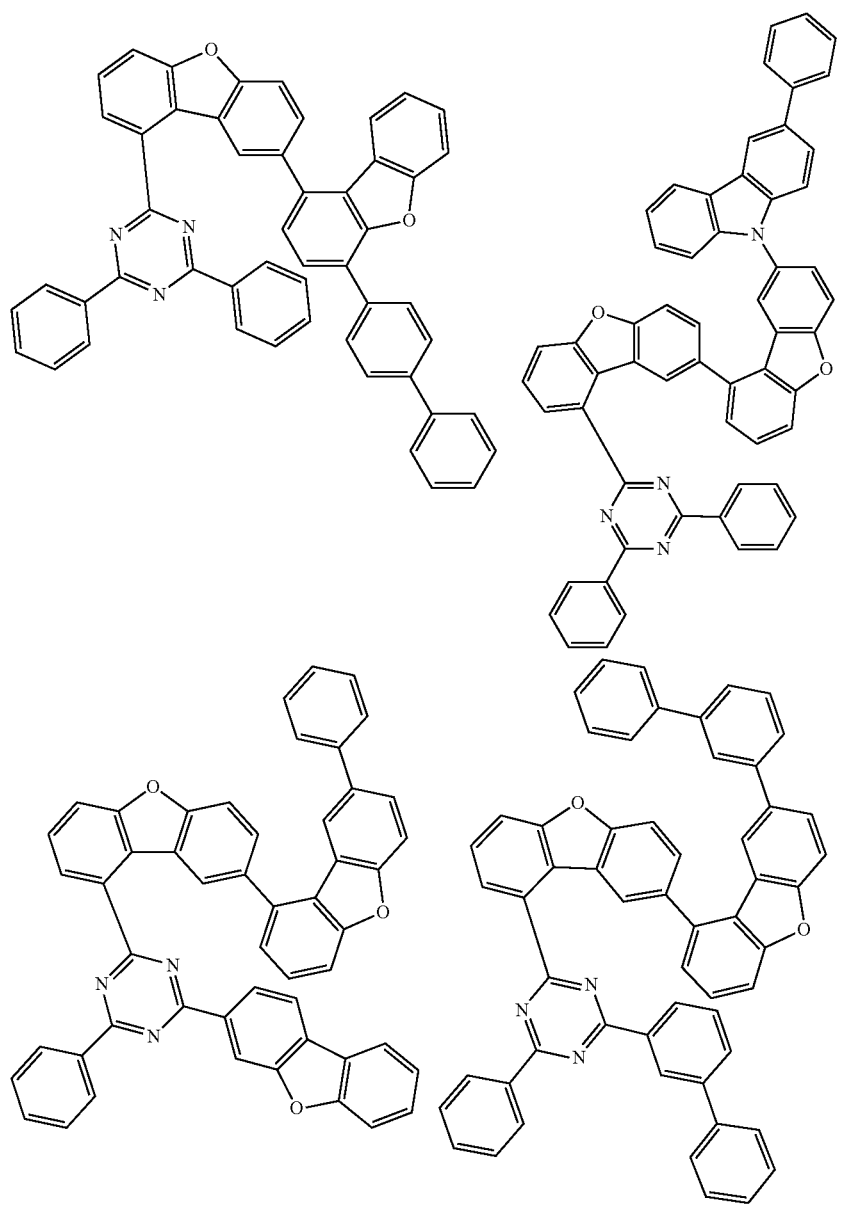

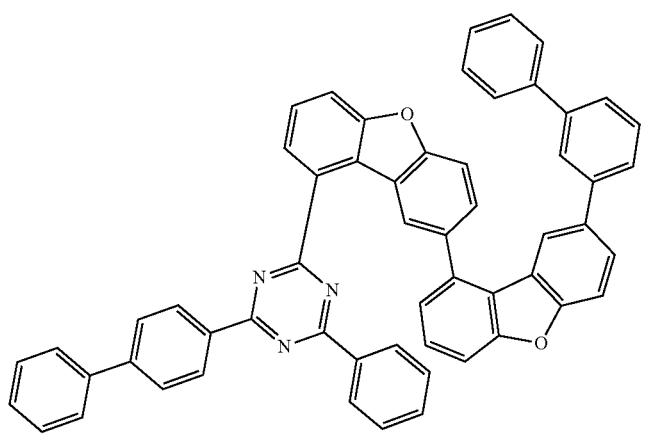
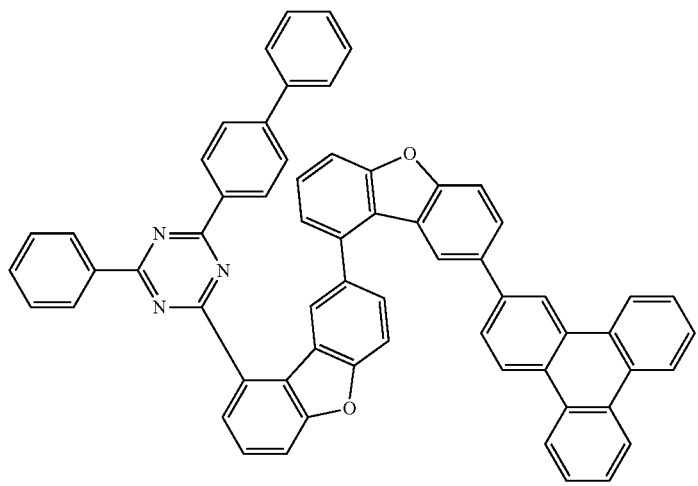
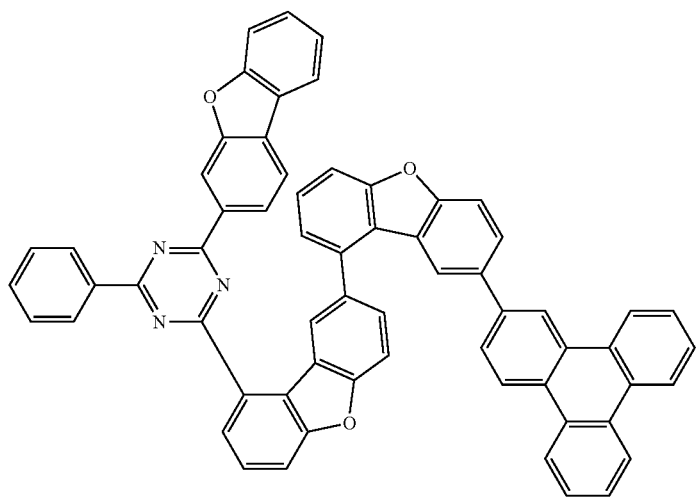

-continued
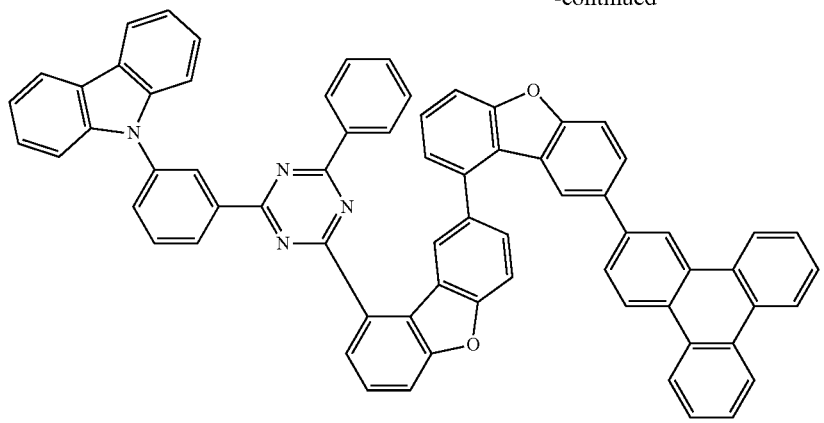
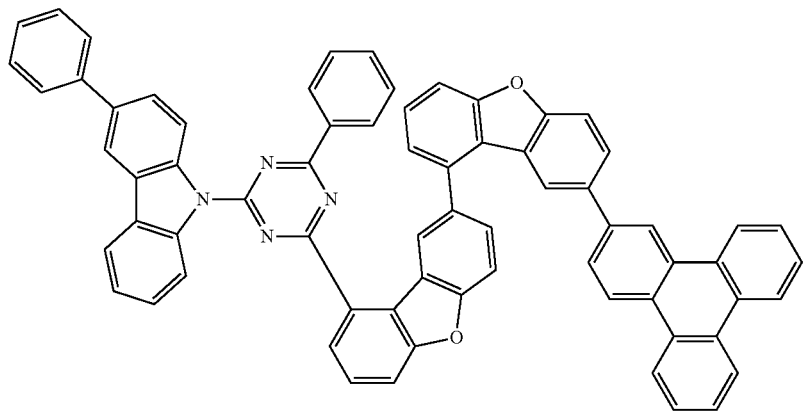
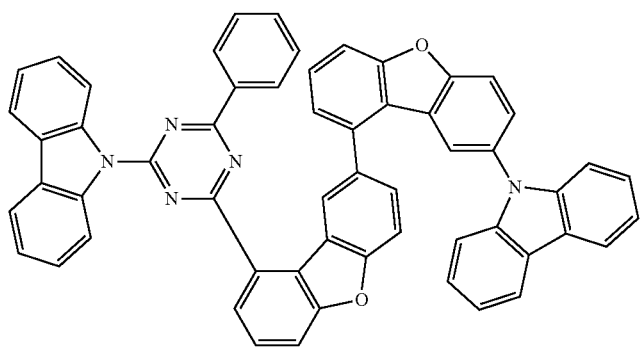
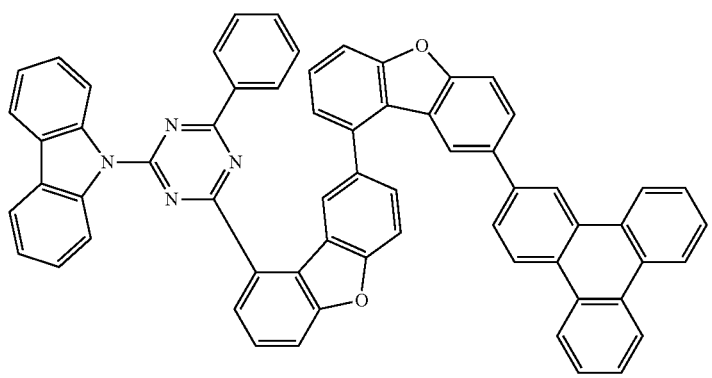

-continued
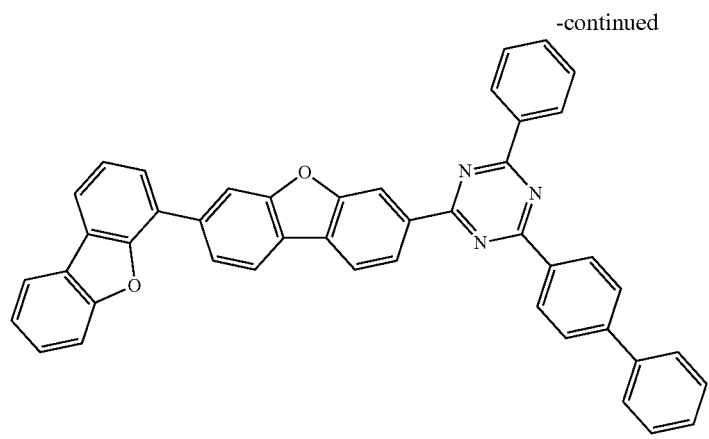
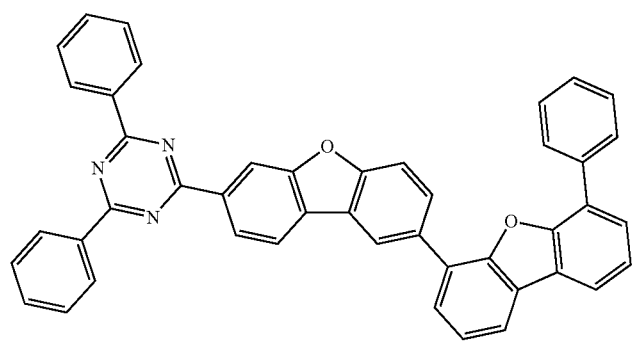
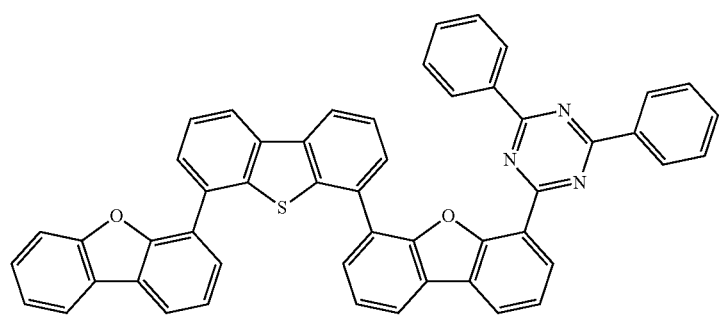
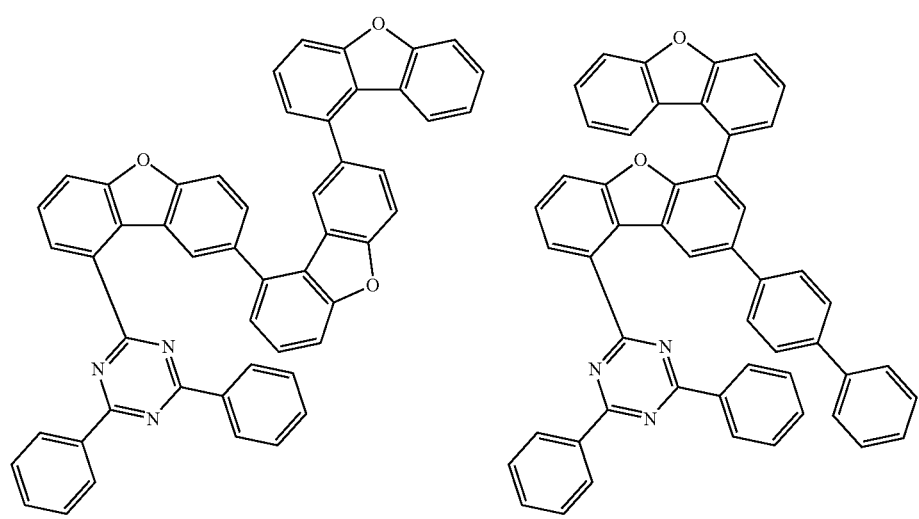

231 232
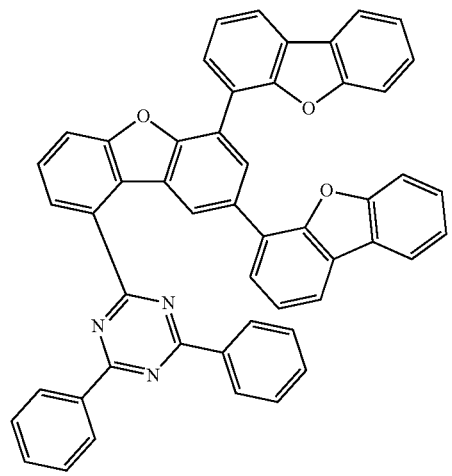
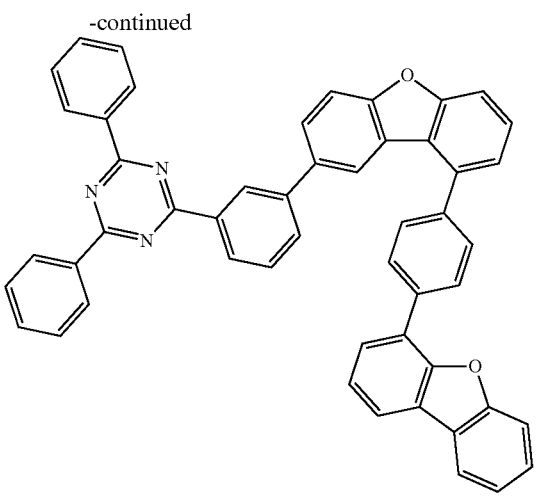
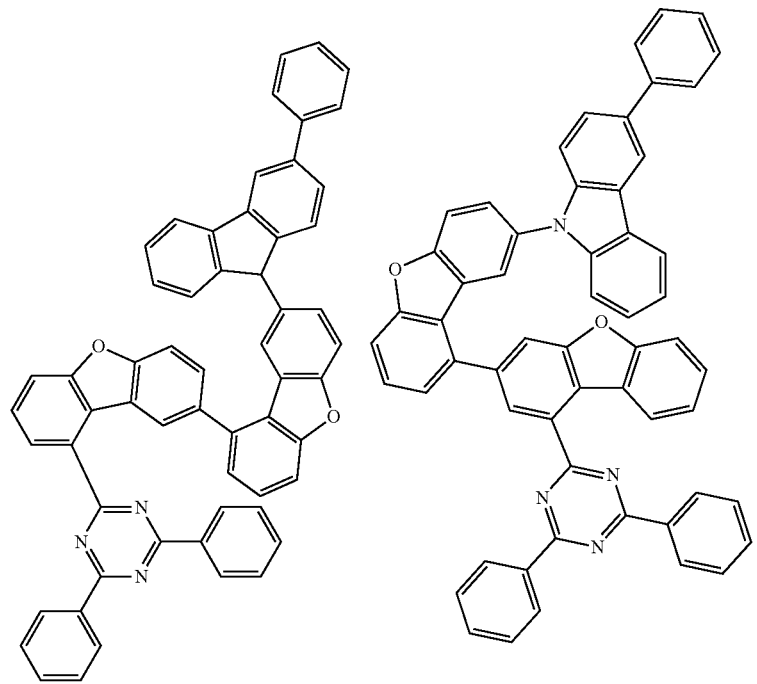

233 234
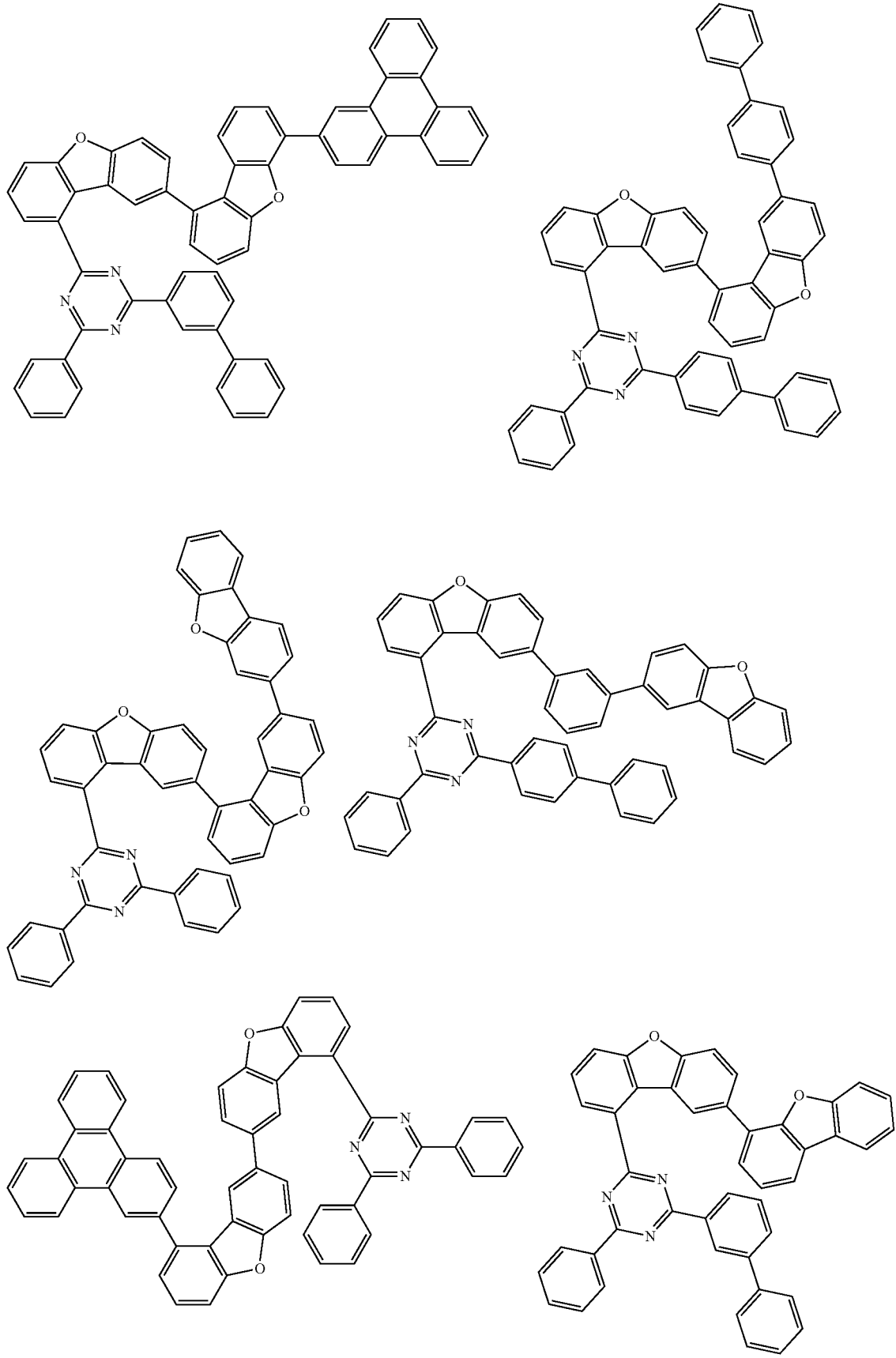
-continued

-continued
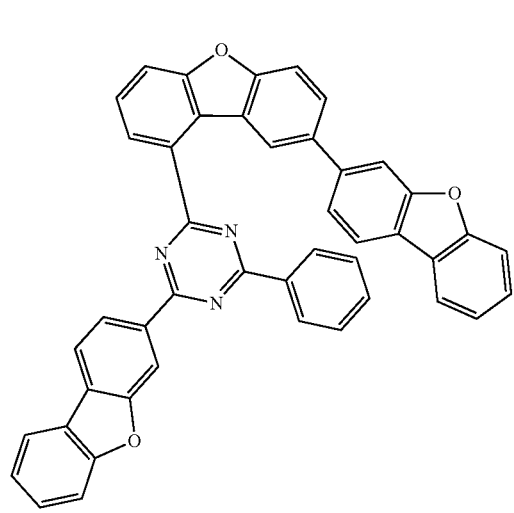
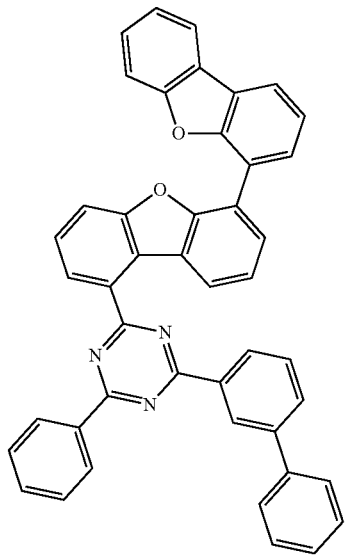
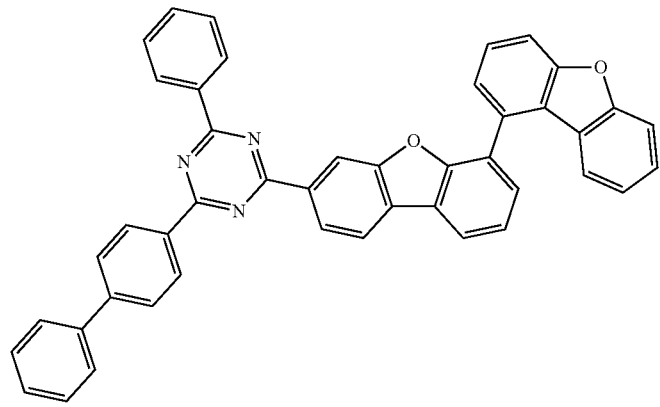
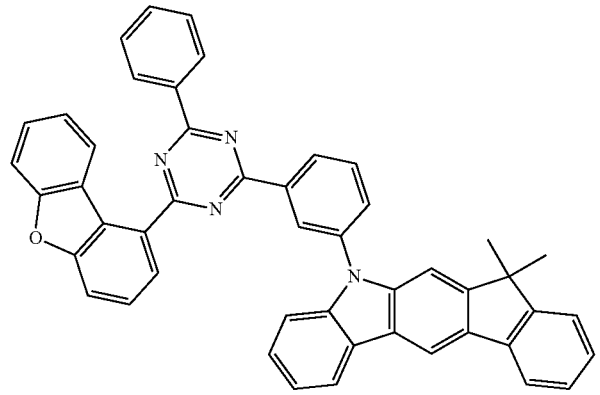
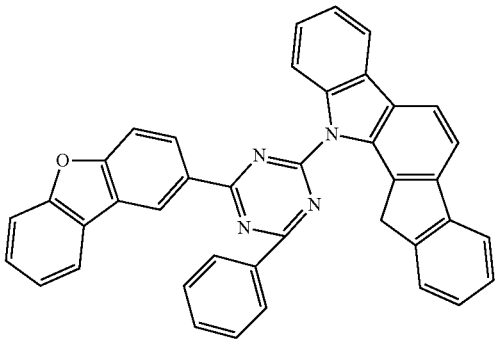
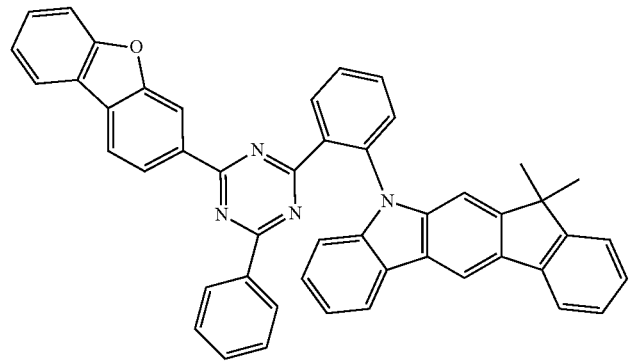

237 238
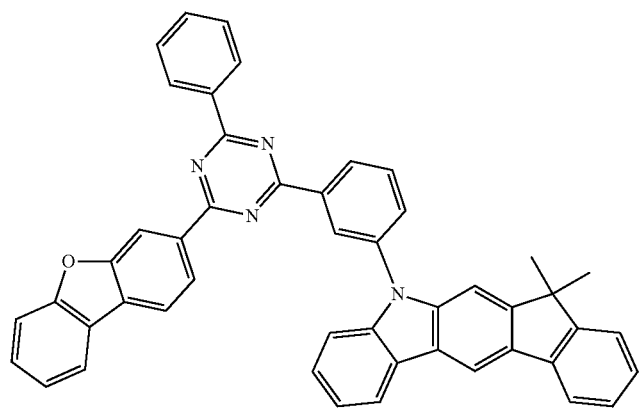
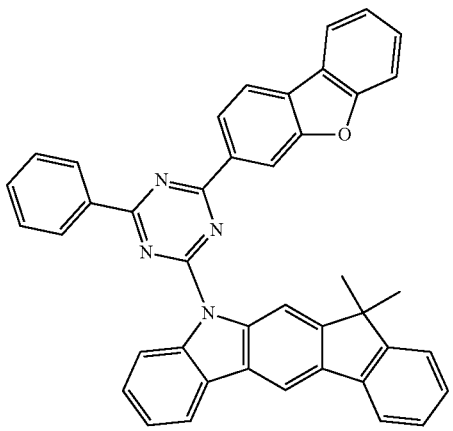
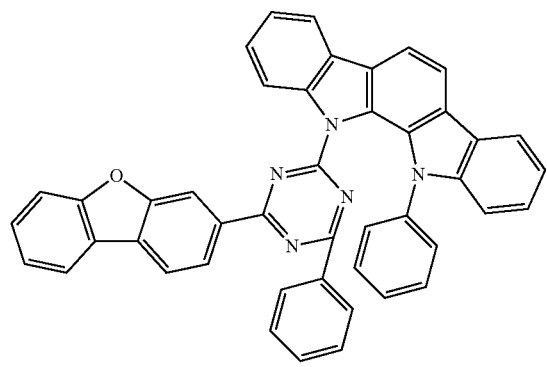
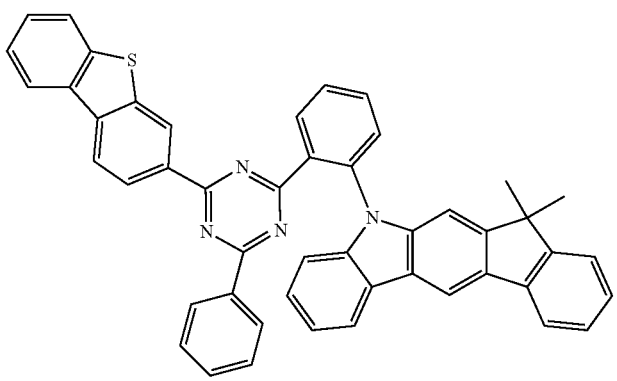
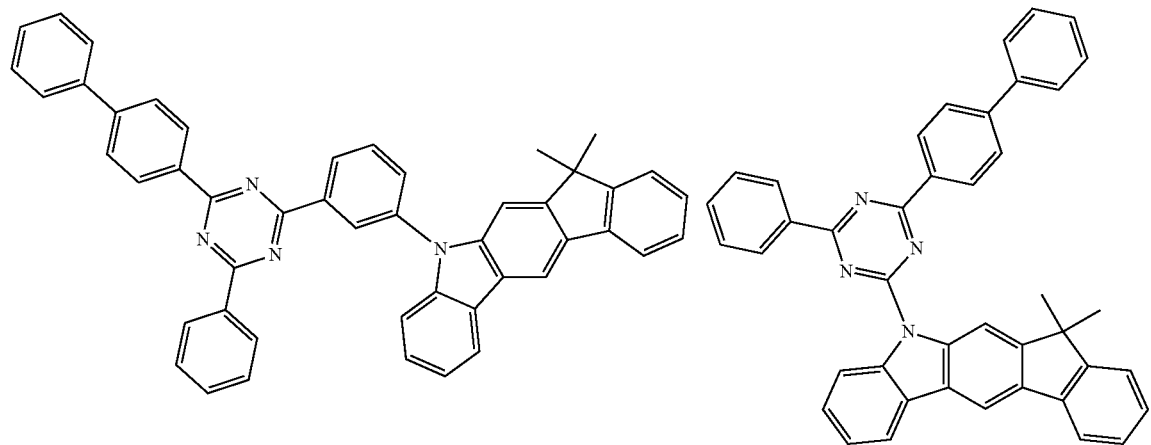

-continued
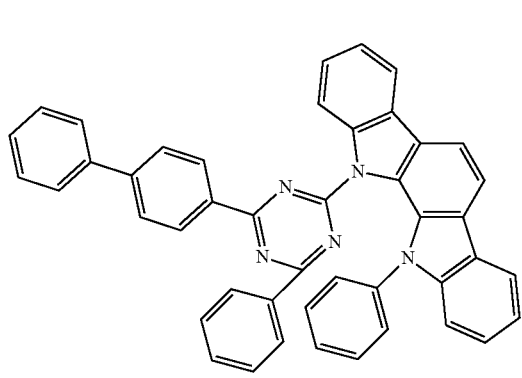
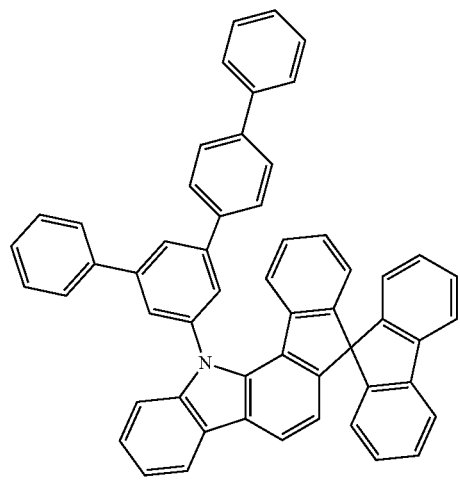
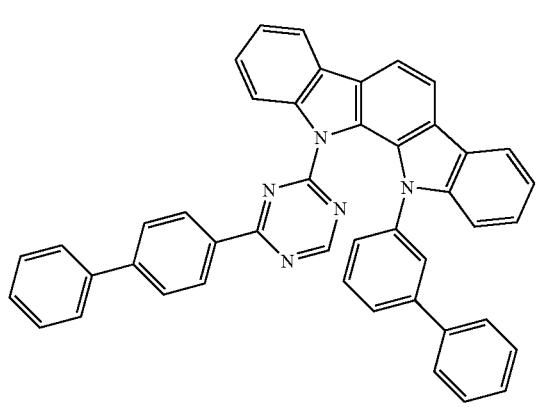
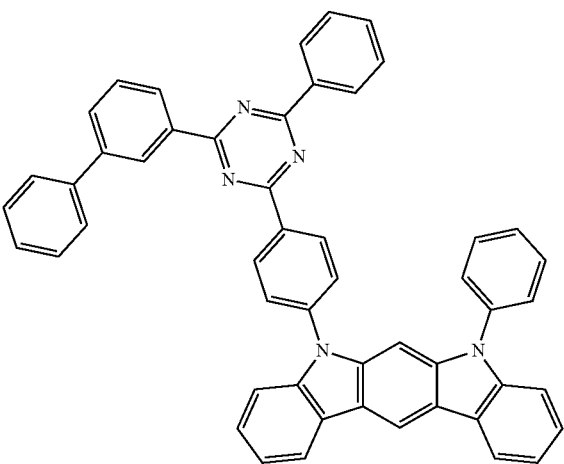
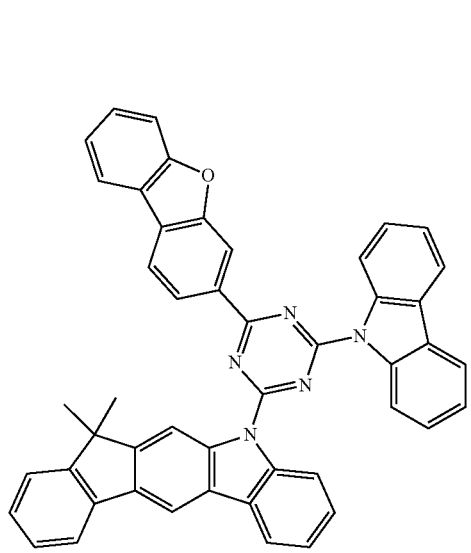
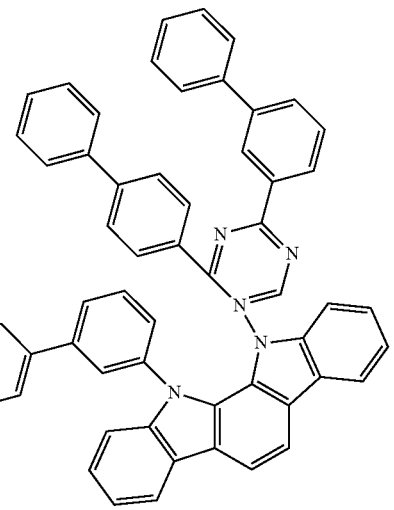

-continued
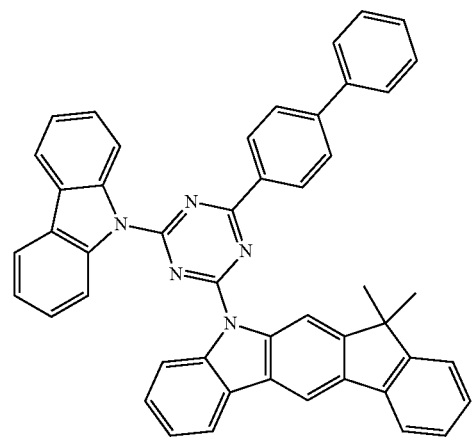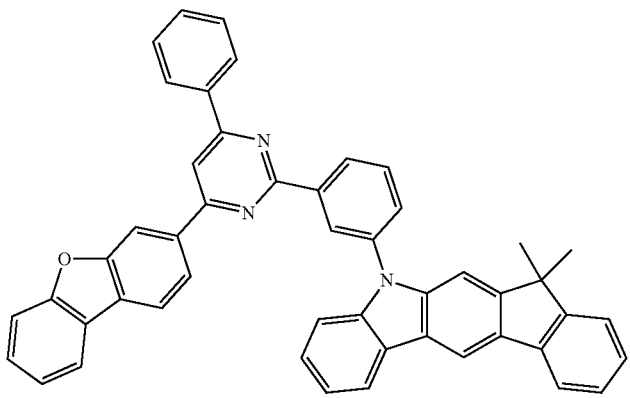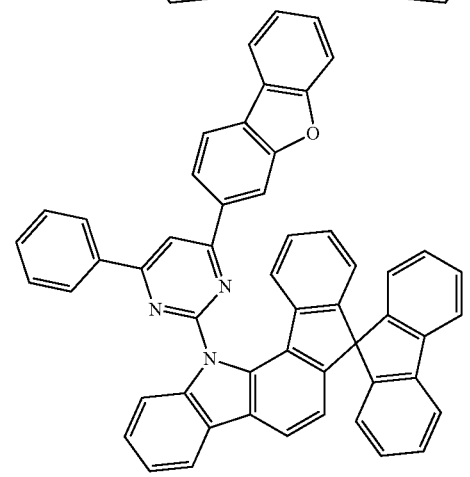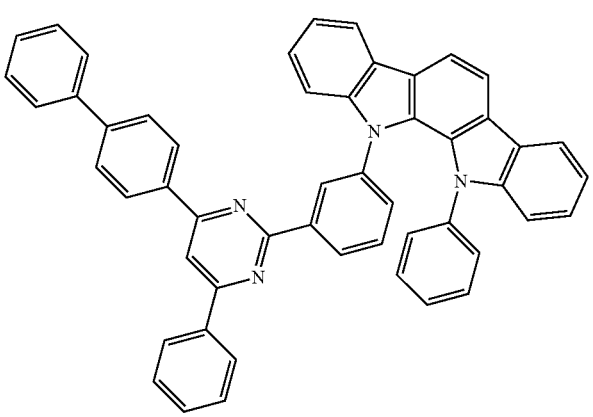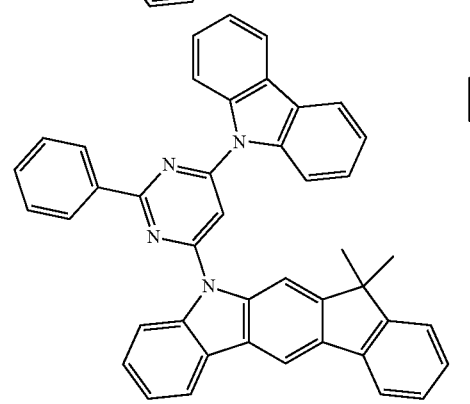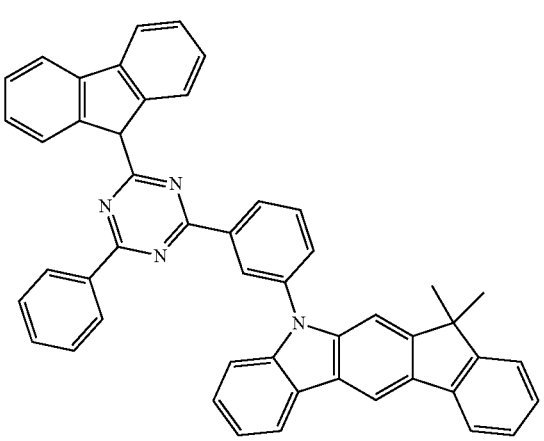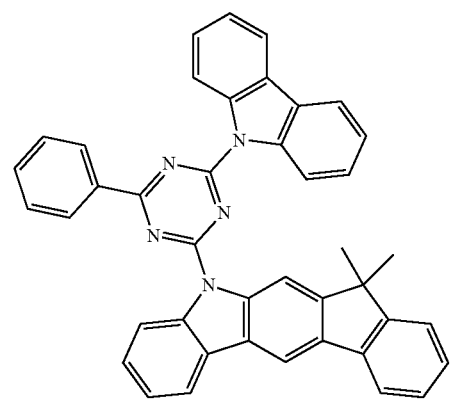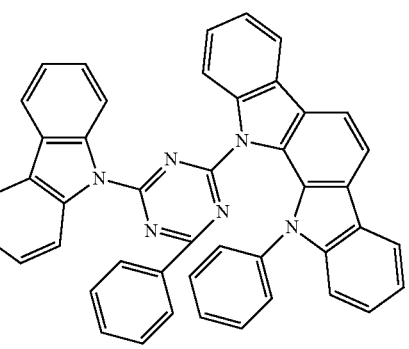

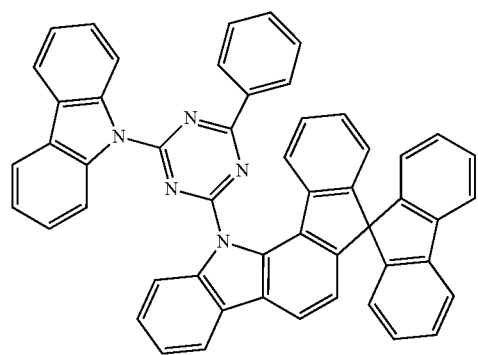
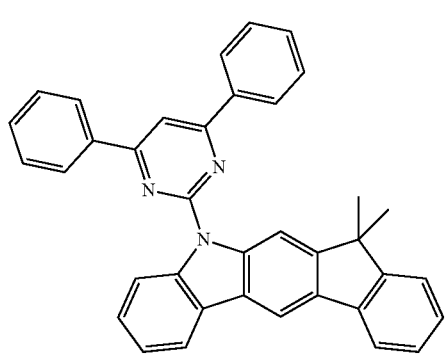
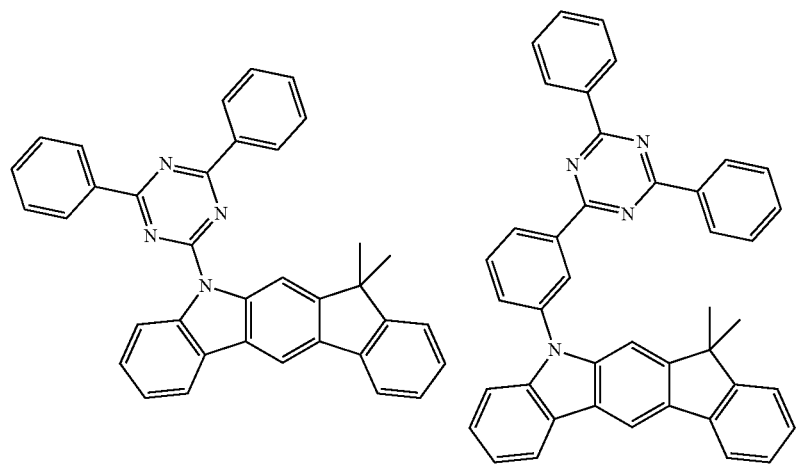
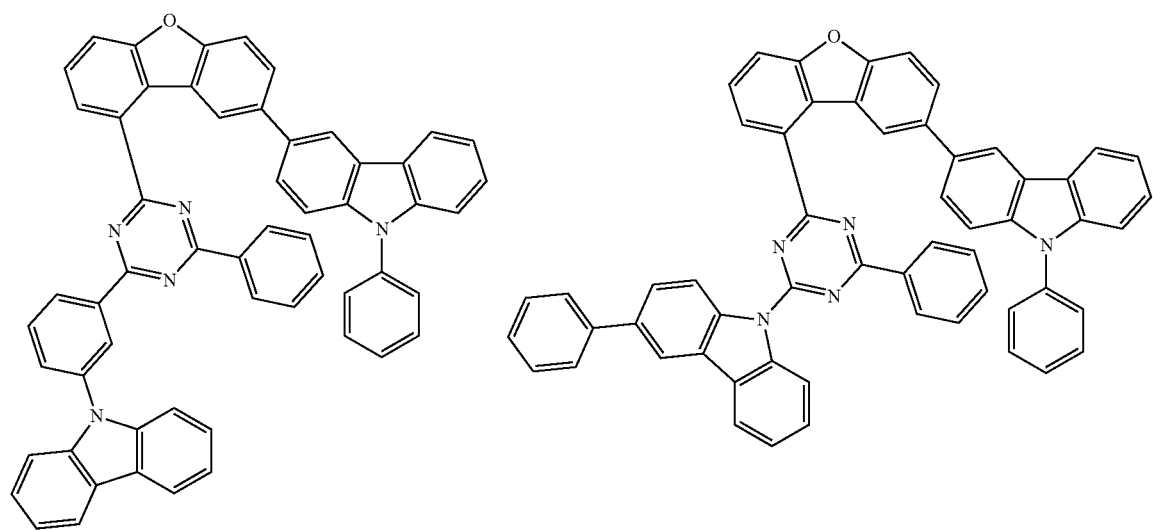

245
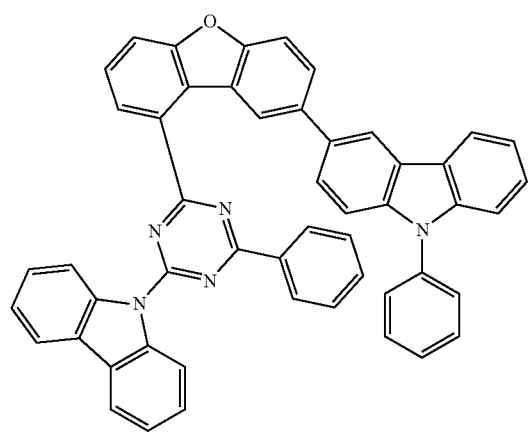
246
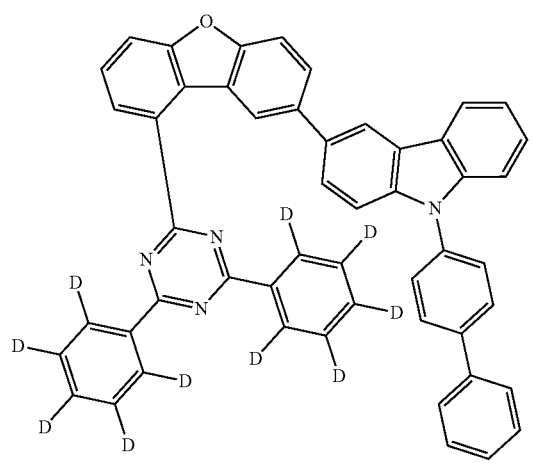
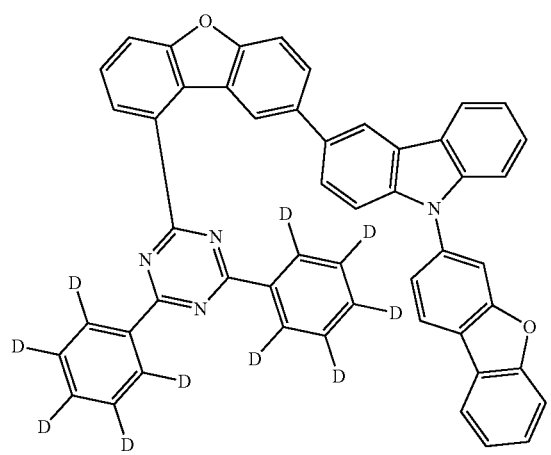
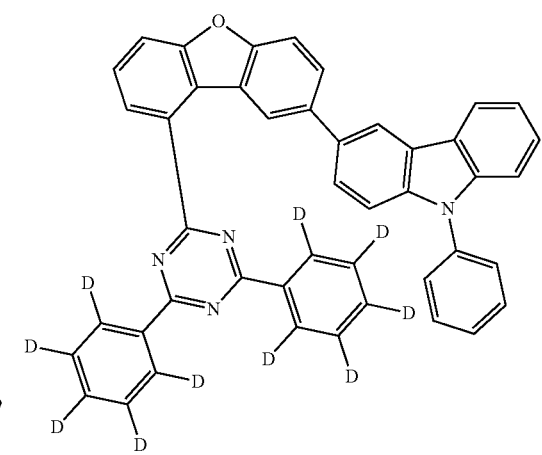
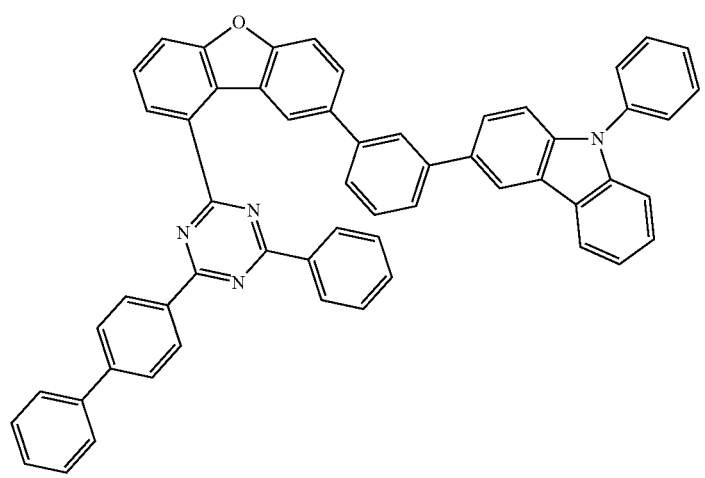

-continued
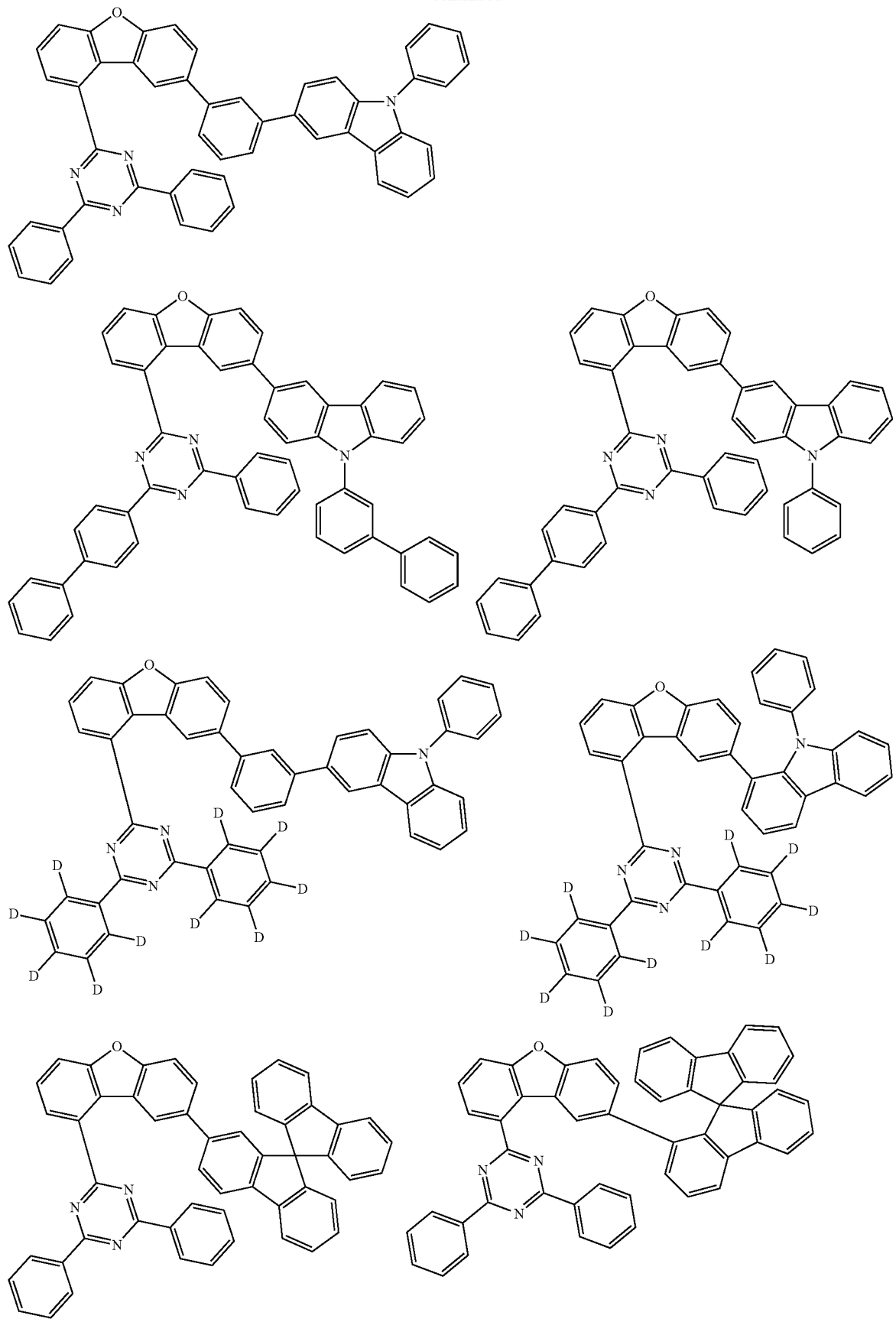

-continued
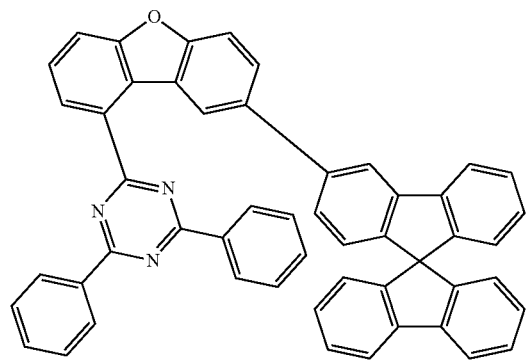
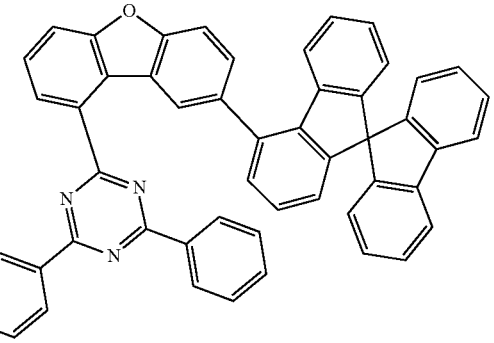
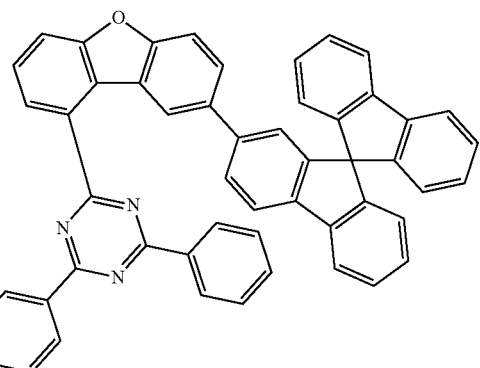
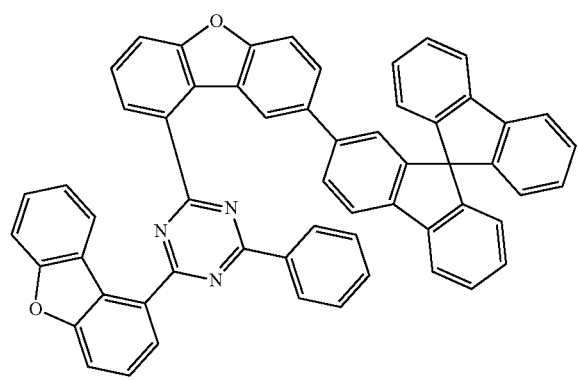
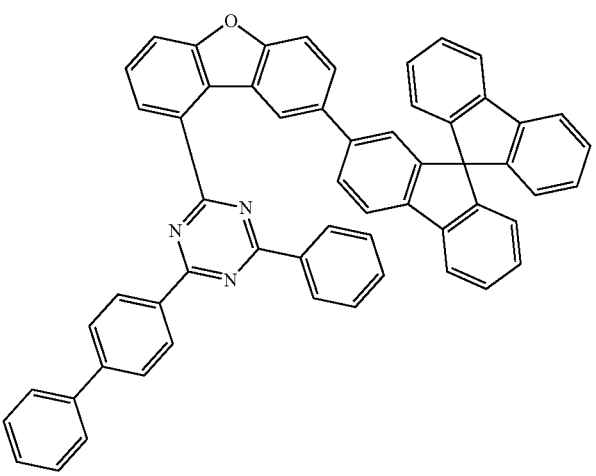
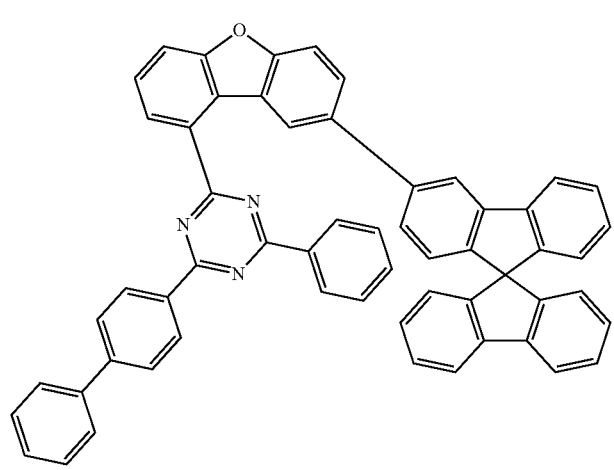

-continued
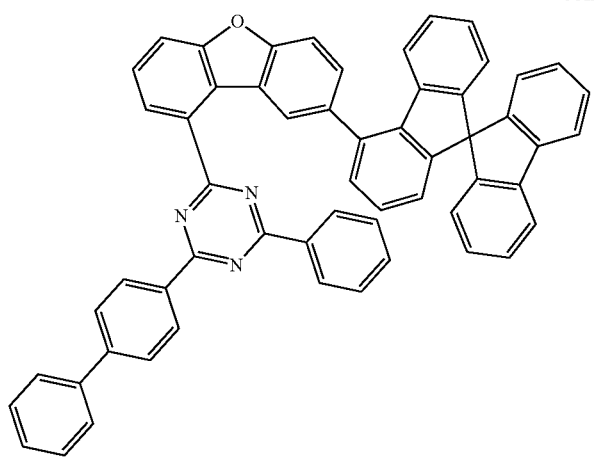
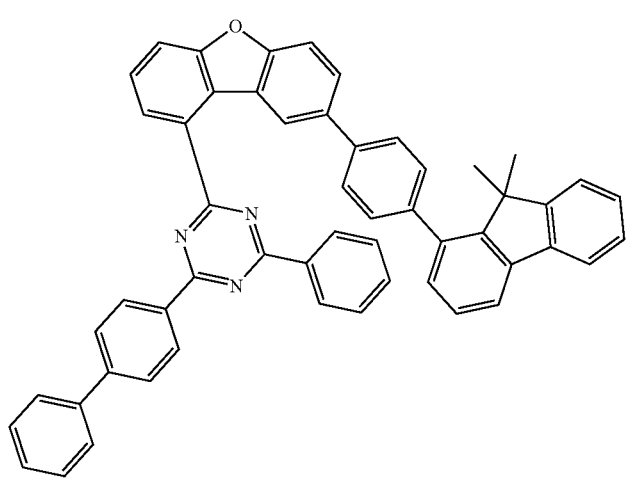
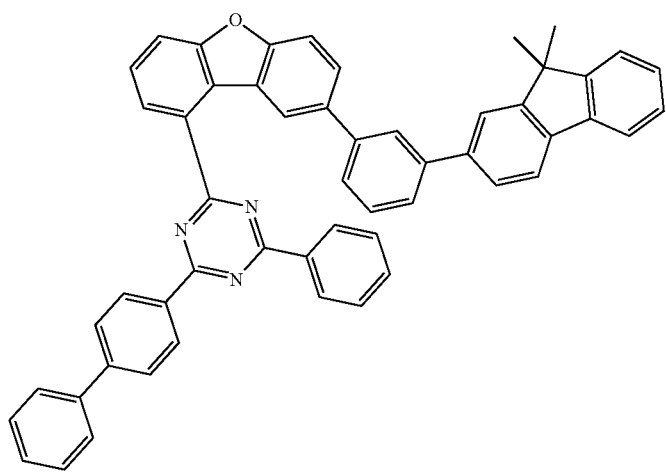

253 254
-continued
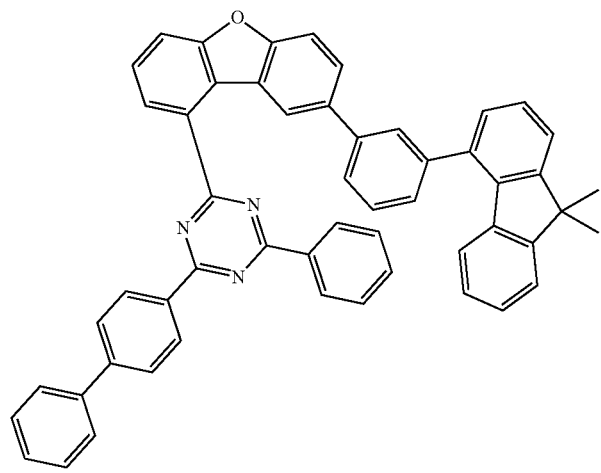
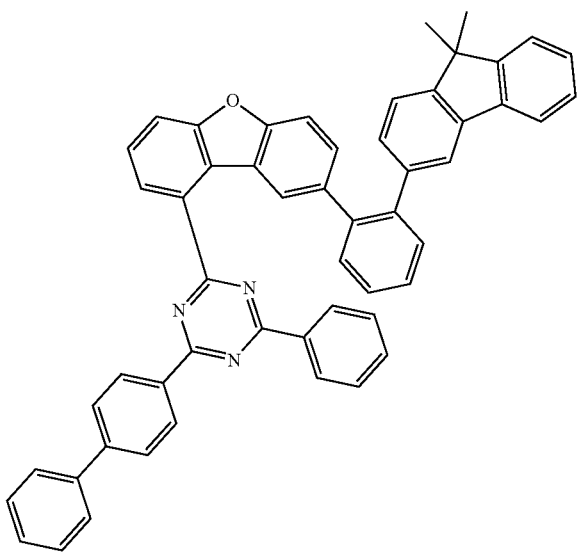
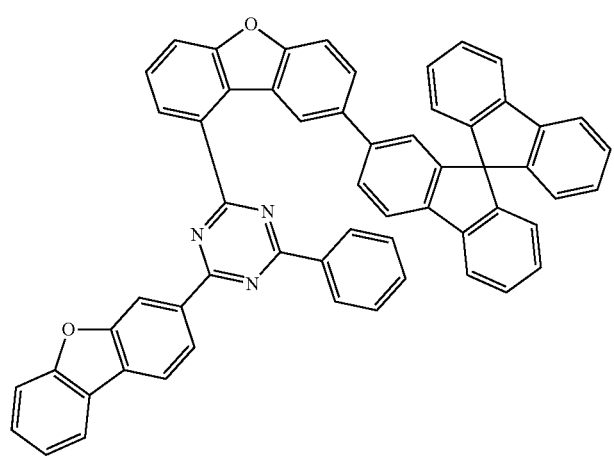
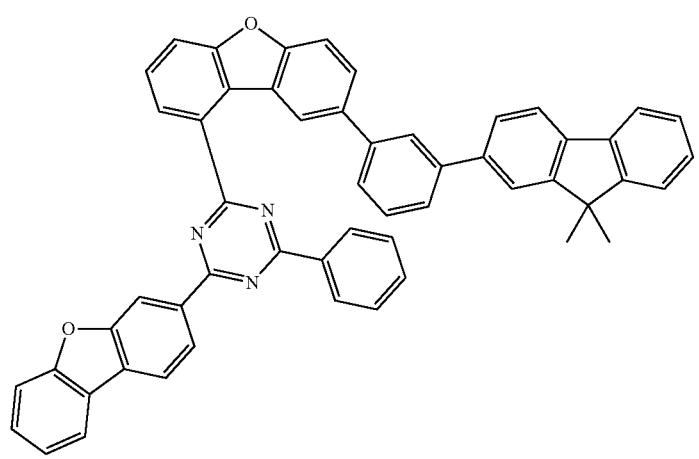

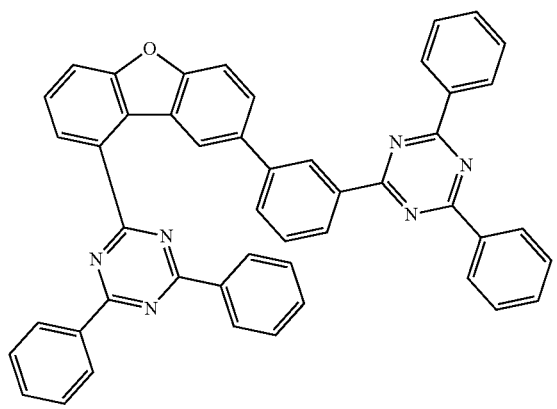
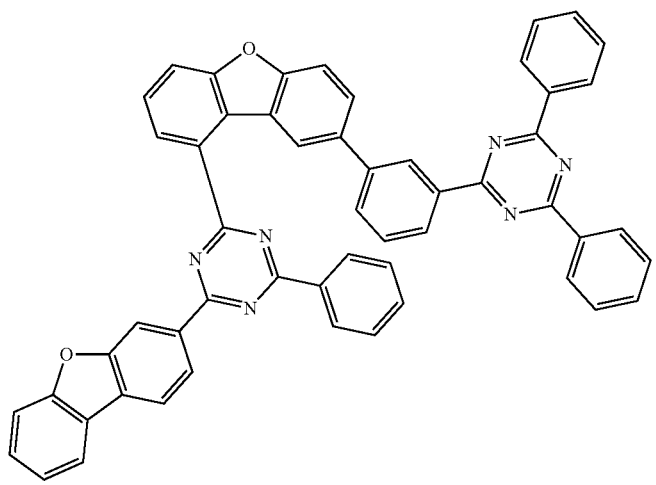
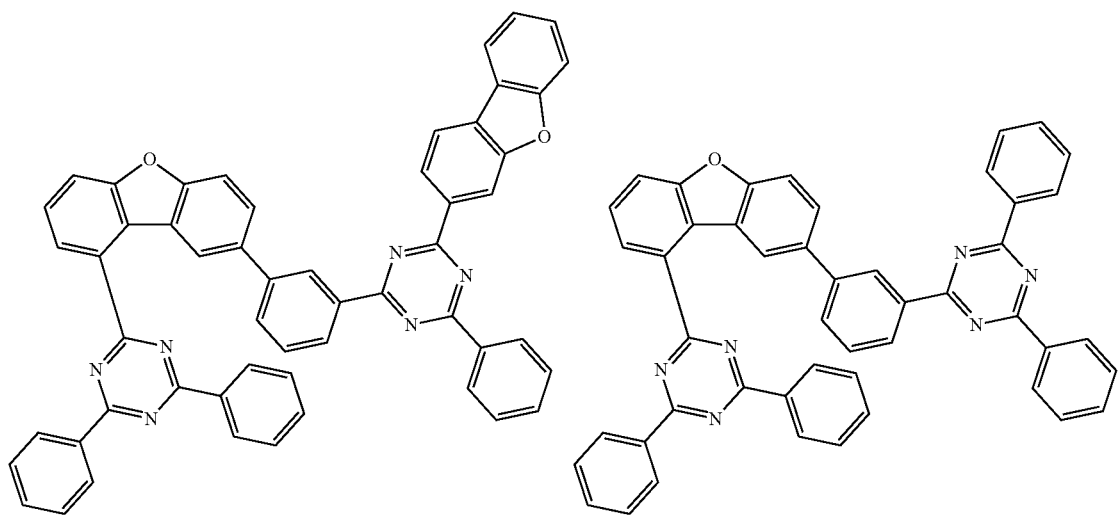

-continued
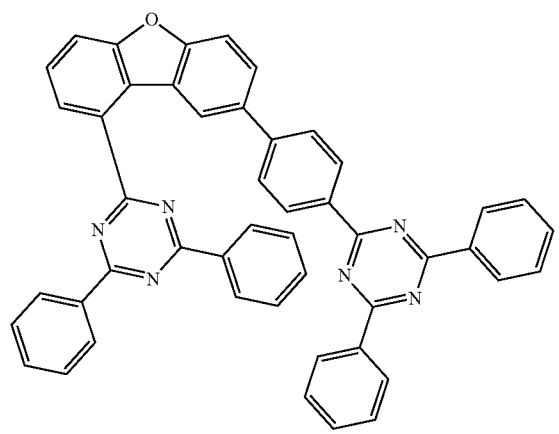
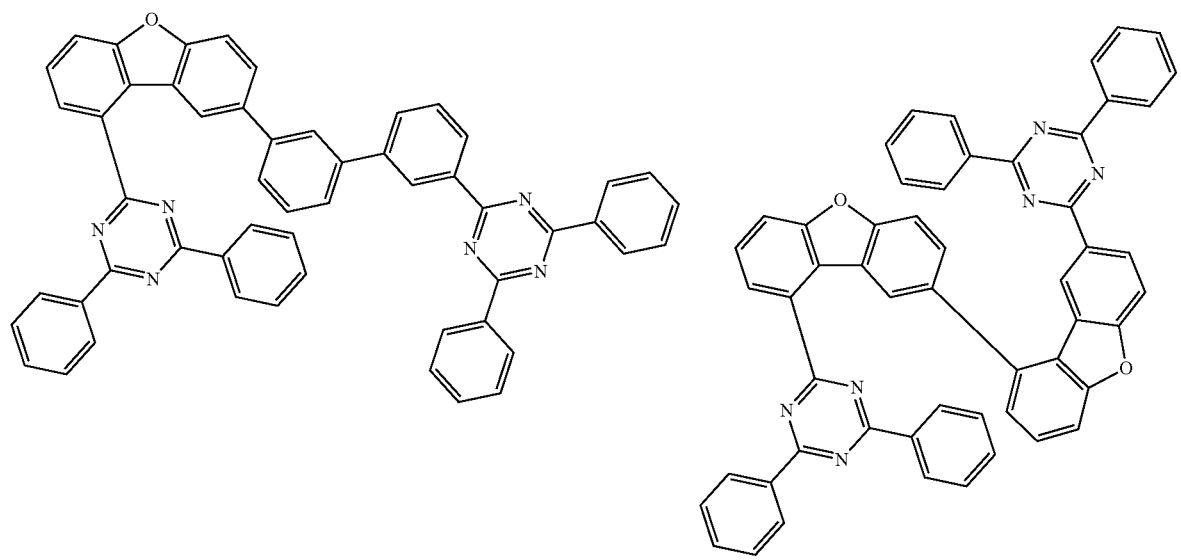
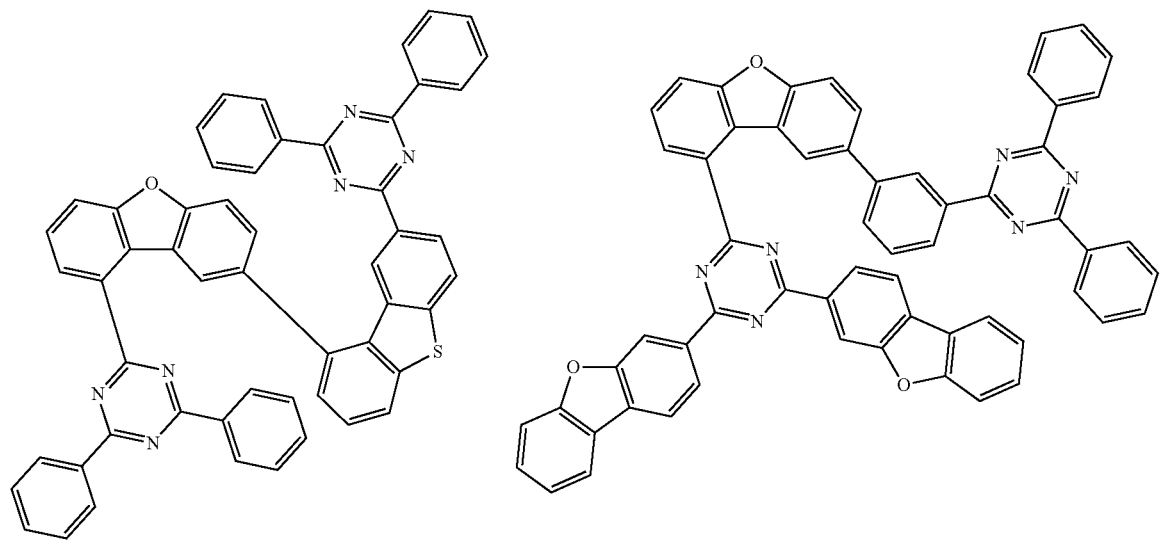

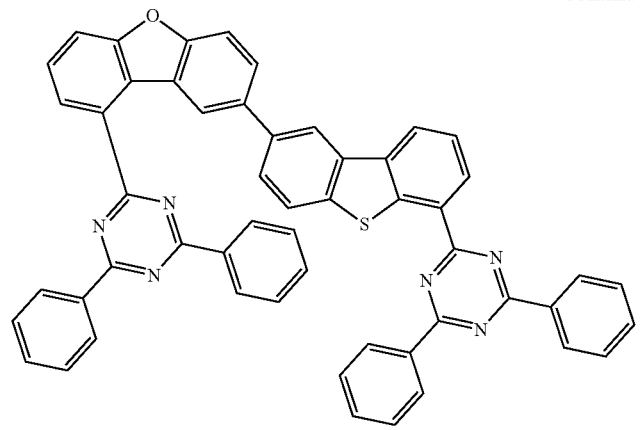
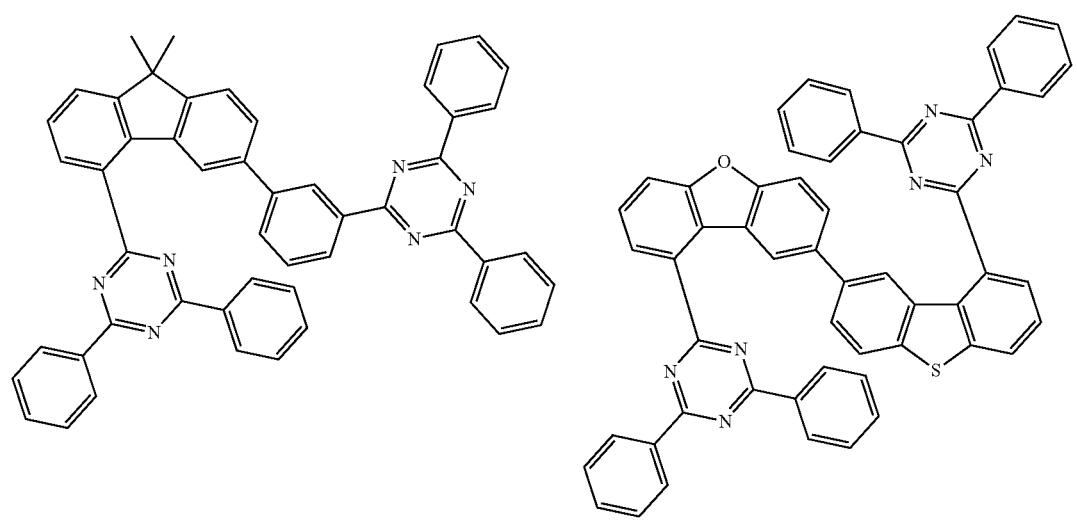
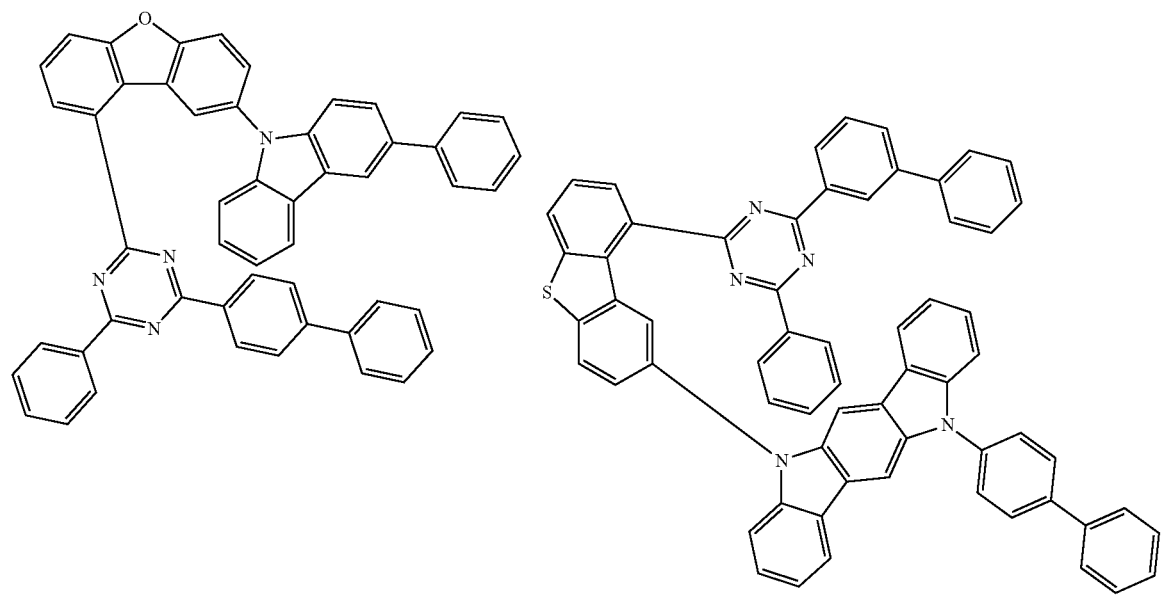

-continued
261
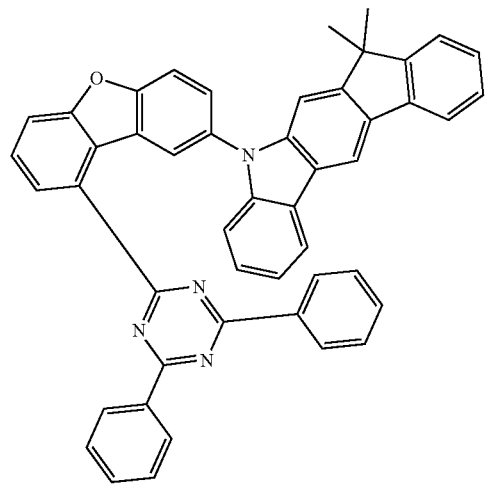
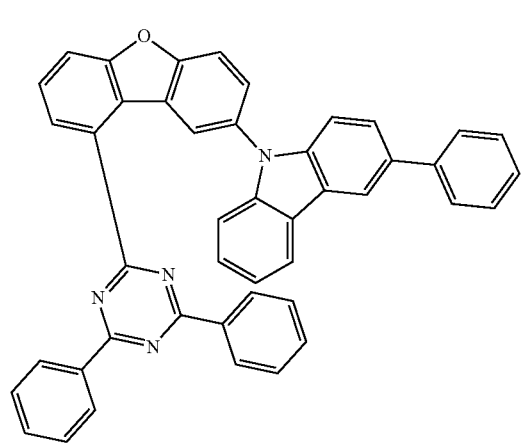
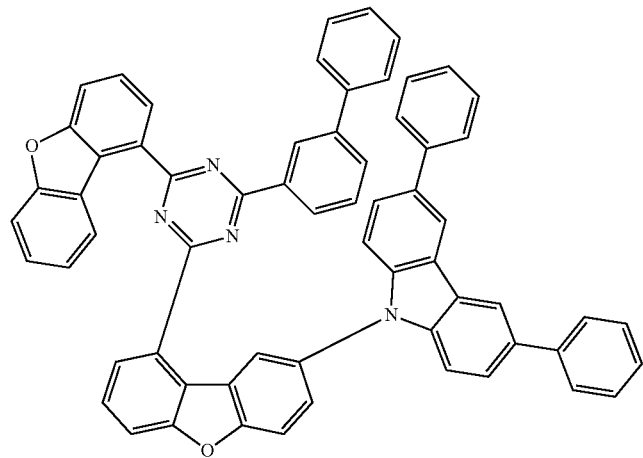
262
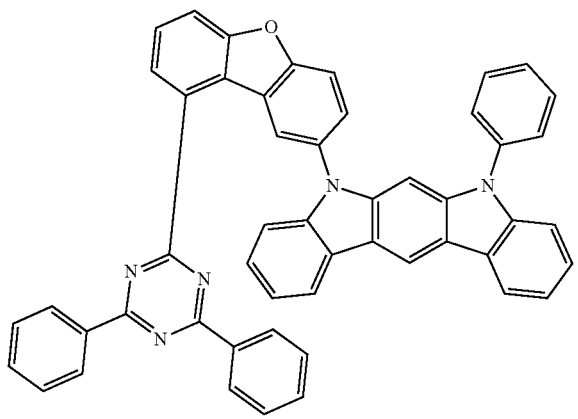
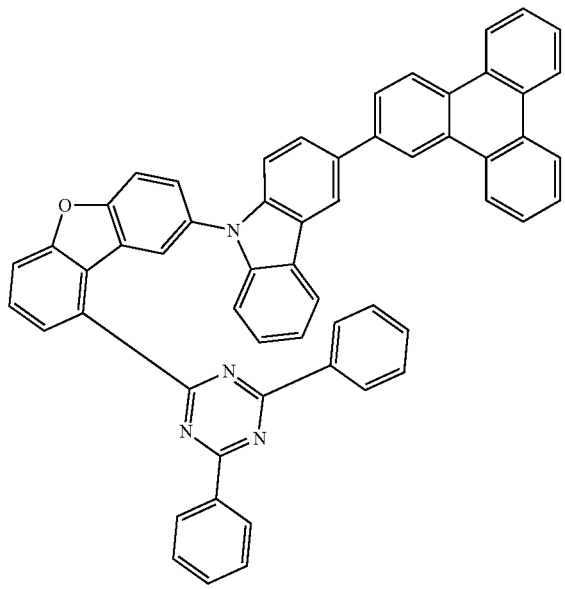
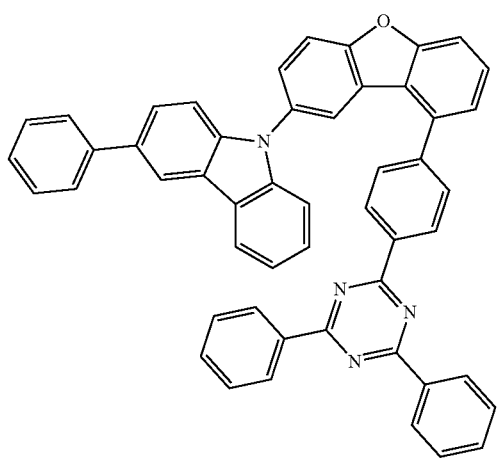

-continued
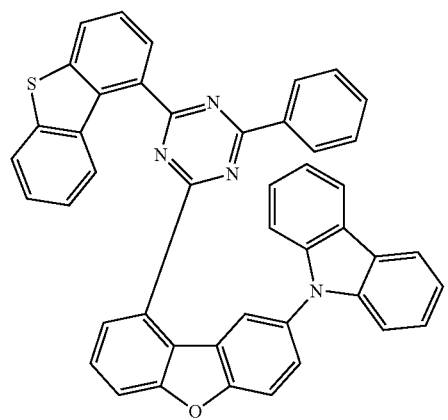
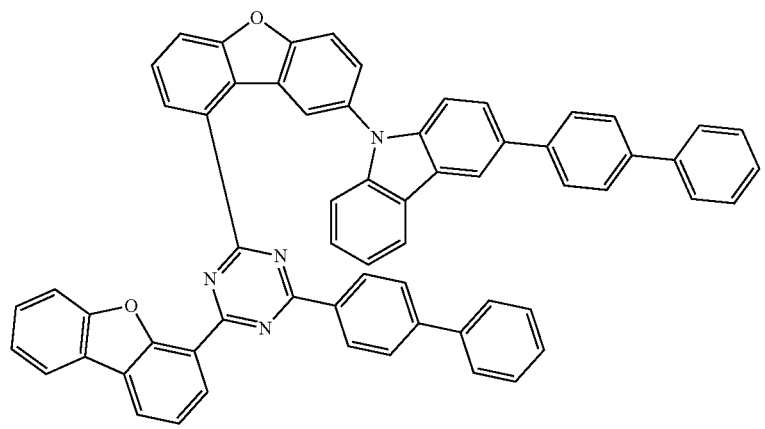
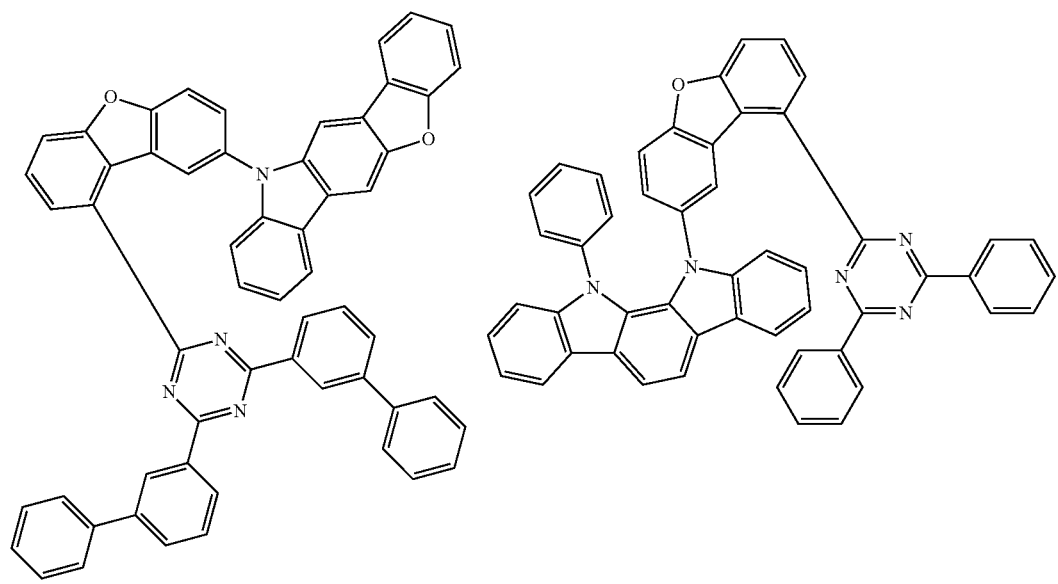

-continued
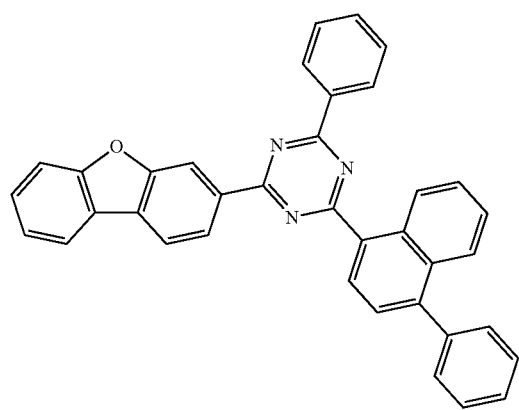
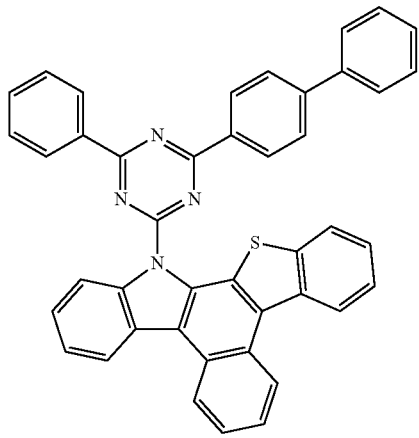
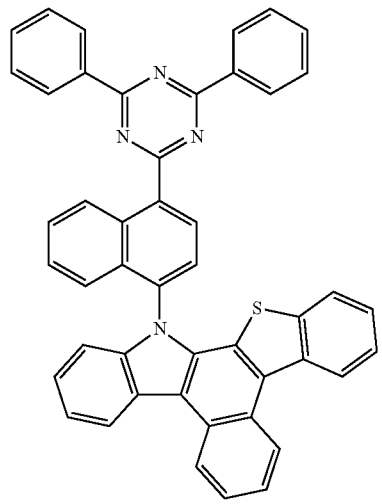
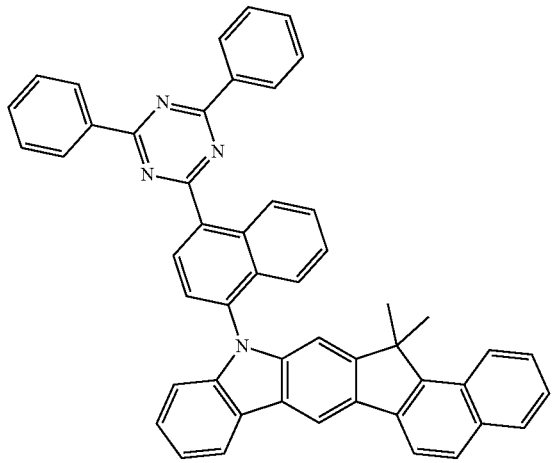
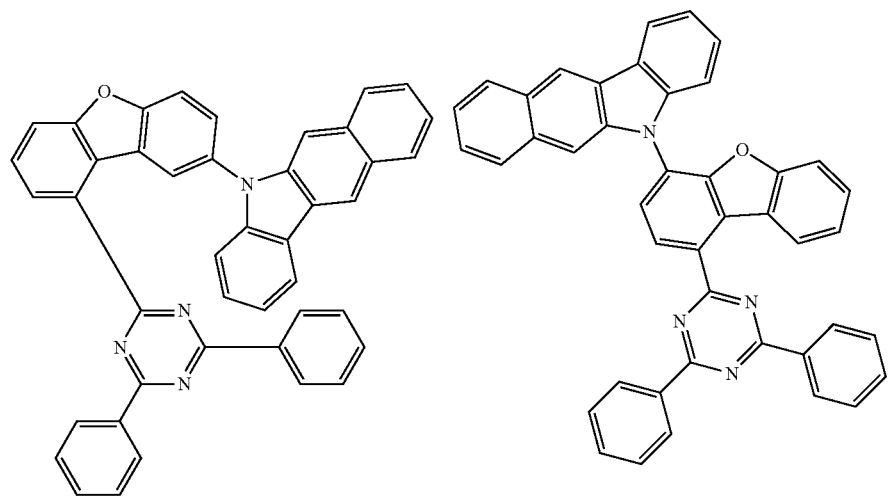

Examples of suitable quinazoline and quinoxaline compounds are the compounds depicted in the following table:
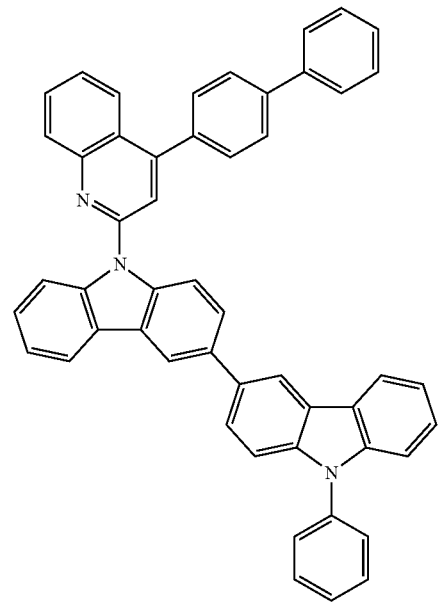
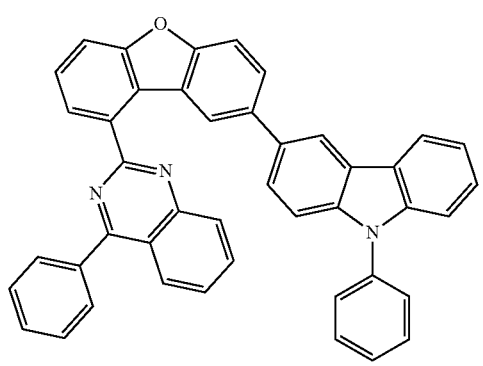
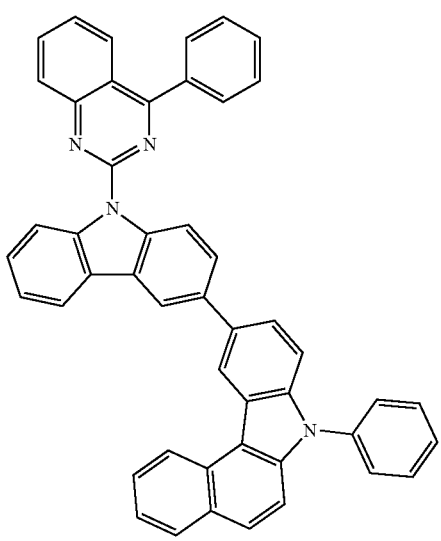
-continued
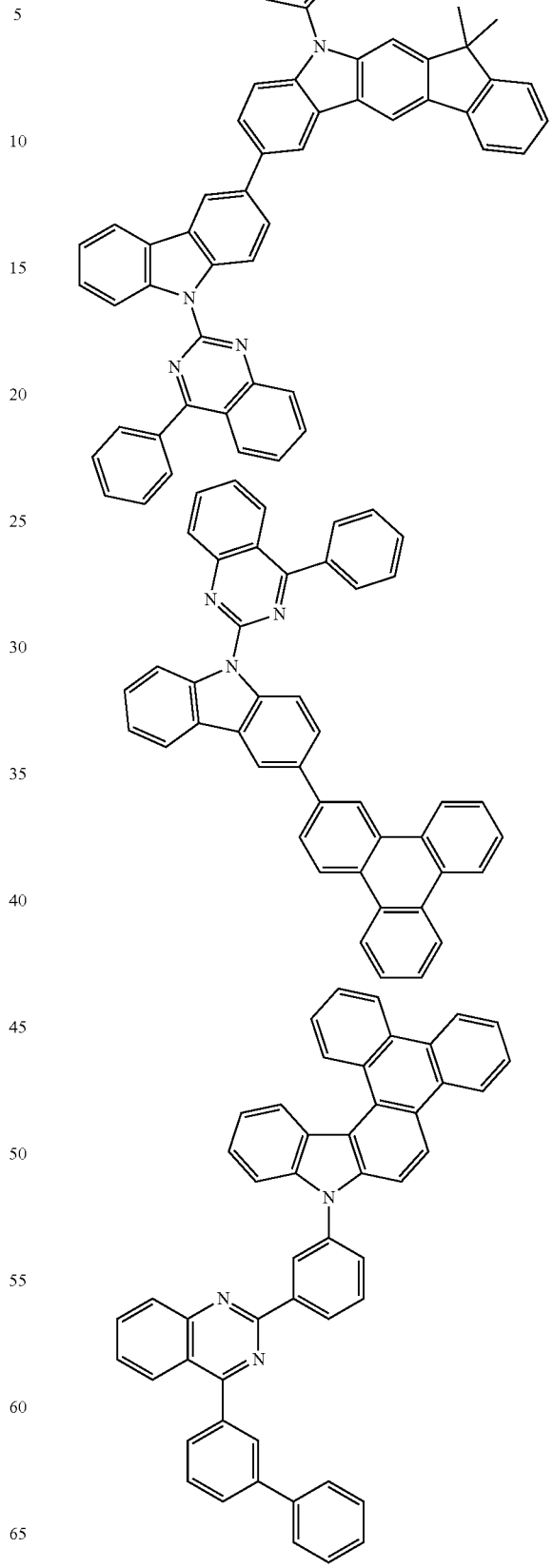

269
-continued

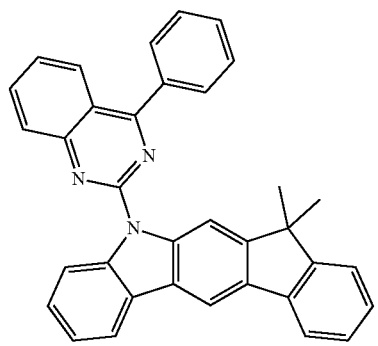

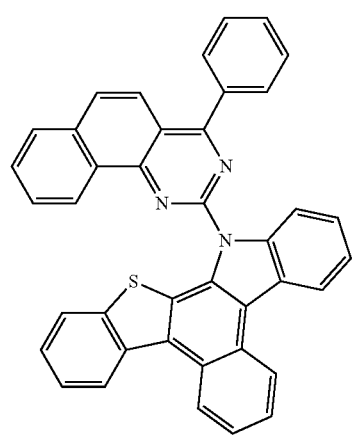

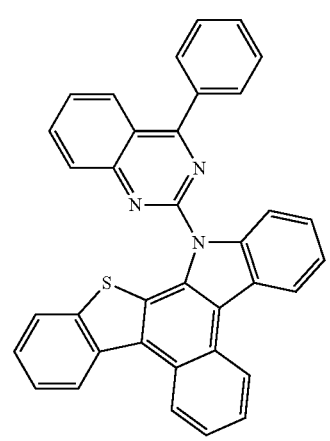

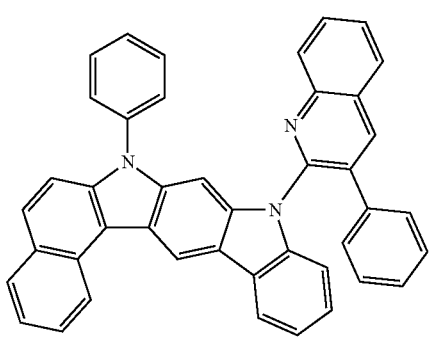

270
-continued

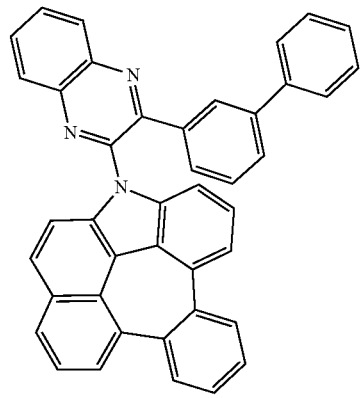

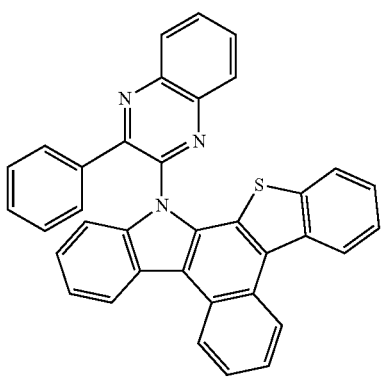

Suitable phosphorescent compounds (=triplet emitters) are especially compounds which, when suitably excited, emit light, preferably in the visible region, and also contain at least one atom of atomic number greater than 20, preferably greater than 38 and less than 84, more preferably greater than 56 and less than 80, especially a metal having this atomic number. Preferred phosphorescence emitters used are compounds containing copper, molybdenum, tungsten, rhenium, ruthenium, osmium, rhodium, iridium, palladium, platinum, silver, gold or europium, especially compounds containing iridium or platinum.

Examples of the emitters described above can be found in applications WO 00/70655, WO 2001/41512, WO 2002/02714, WO 2002/15645, EP 1191613, EP 1191612, EP 1191614, WO 05/033244, WO 05/019373, US 2005/0258742, WO 2009/146770, WO 2010/015307, WO 2010/031485, WO 2010/054731, WO 2010/054728, WO 2010/086089, WO 2010/099852, WO 2010/102709, WO 2011/032626, WO 2011/066898, WO 2011/157339, WO 2012/007086, WO 2014/008982, WO 2014/023377, WO 2014/094961, WO 2014/094960, WO 2015/036074, WO 2015/104045, WO 2015/117718, WO 2016/015815, WO 2016/124304, WO 2017/032439, WO 2018/011186, WO 2018/041769, WO 2019/020538, WO 2018/178001, WO 2019/115423 and WO 2019/158453. In general, all phosphorescent complexes as used for phosphorescent OLEDs according to the prior art and as known to those skilled in the art in the field of organic electroluminescence are suitable, and the person skilled in the art will be able to use further phosphorescent complexes without exercising inventive skill.

Examples of phosphorescent dopants are adduced below.
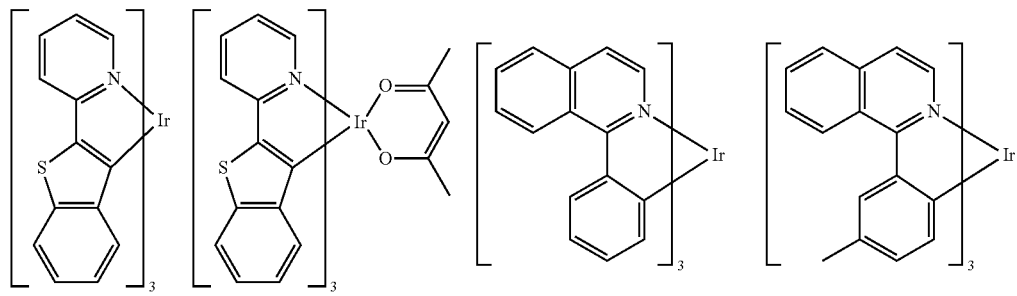
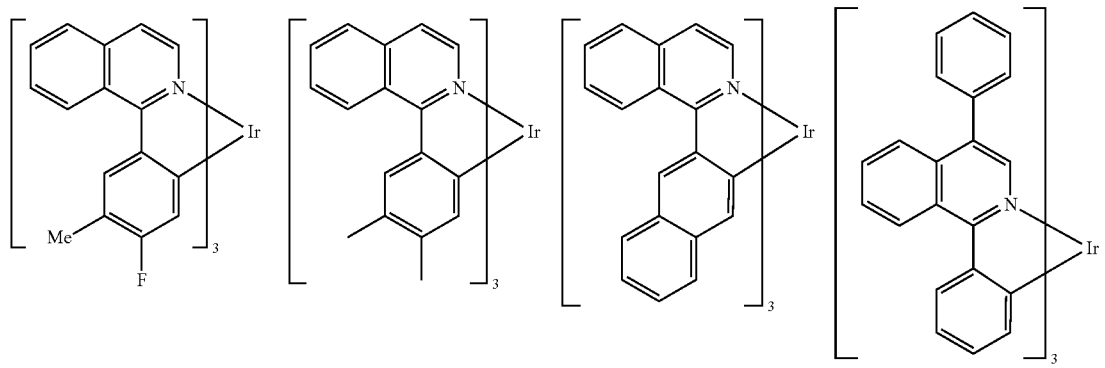
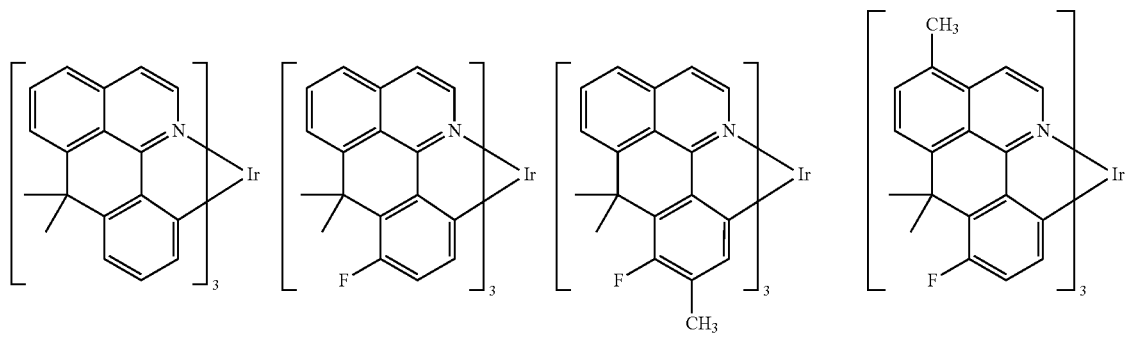
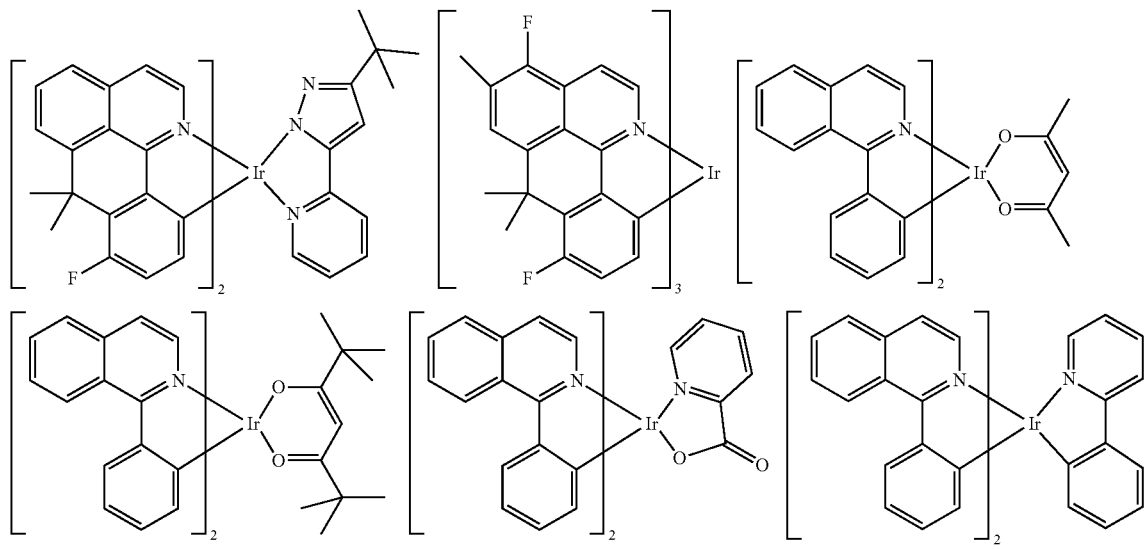

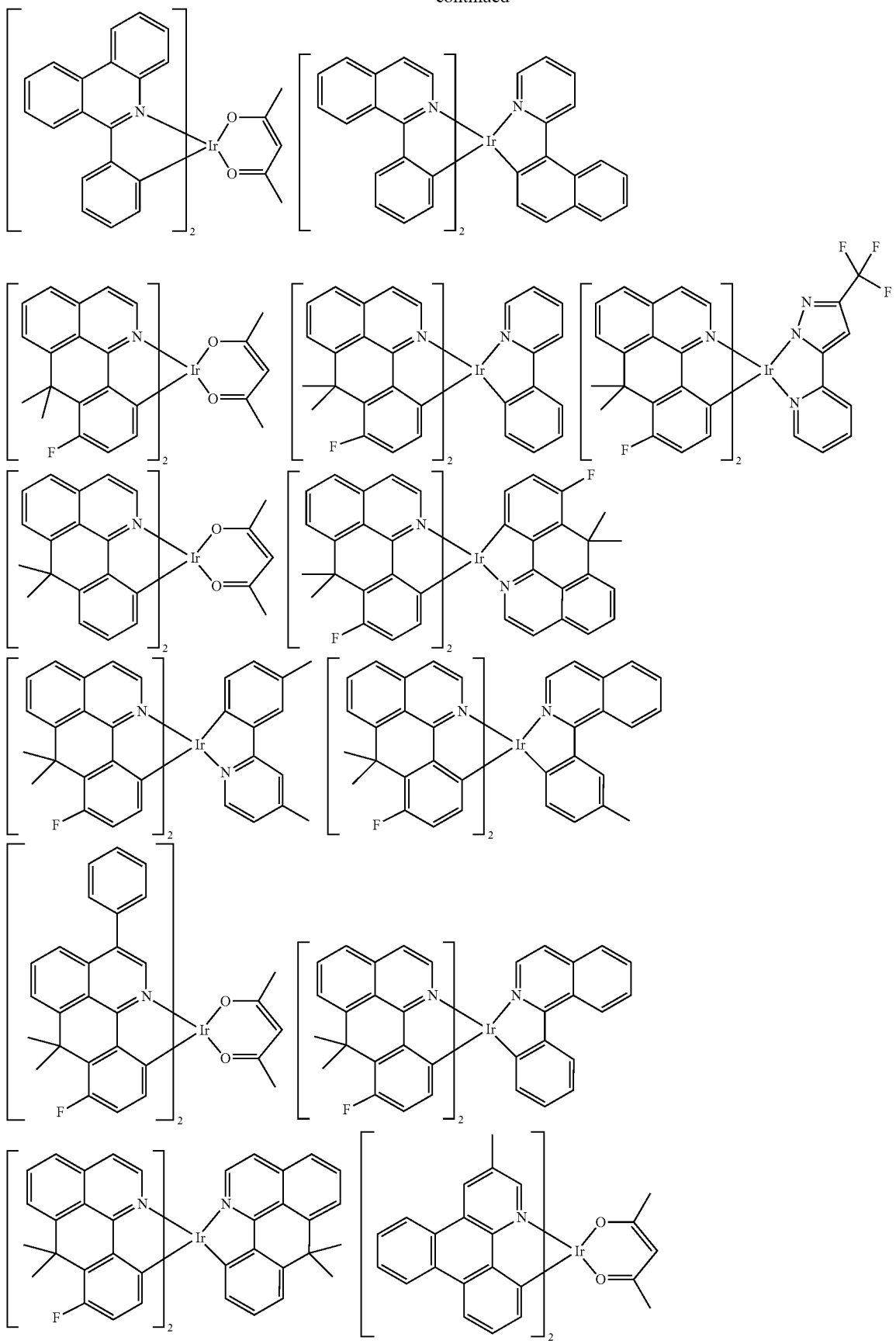

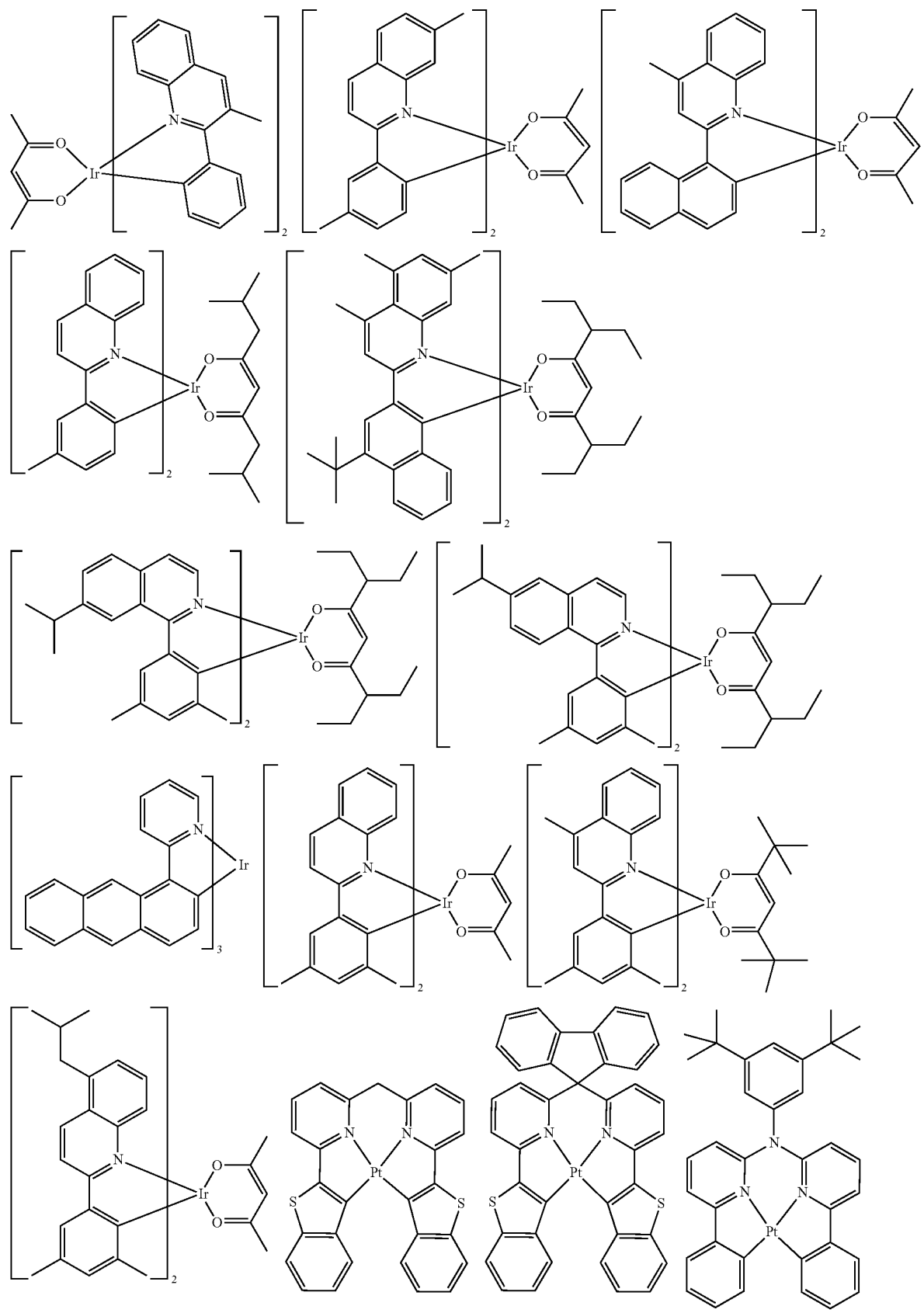

-continued
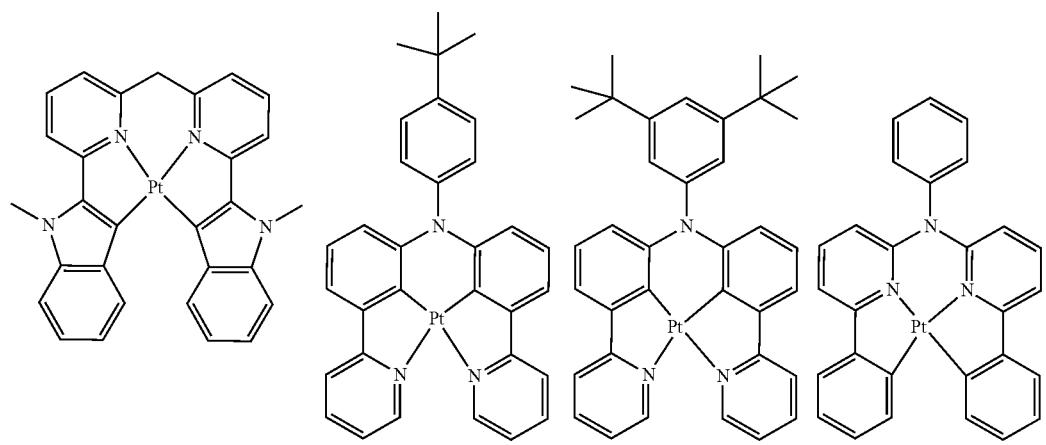
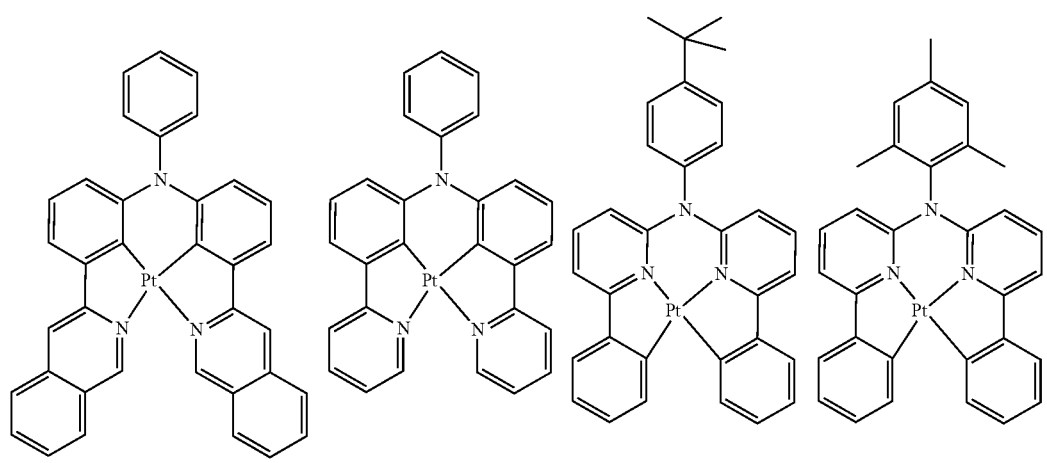
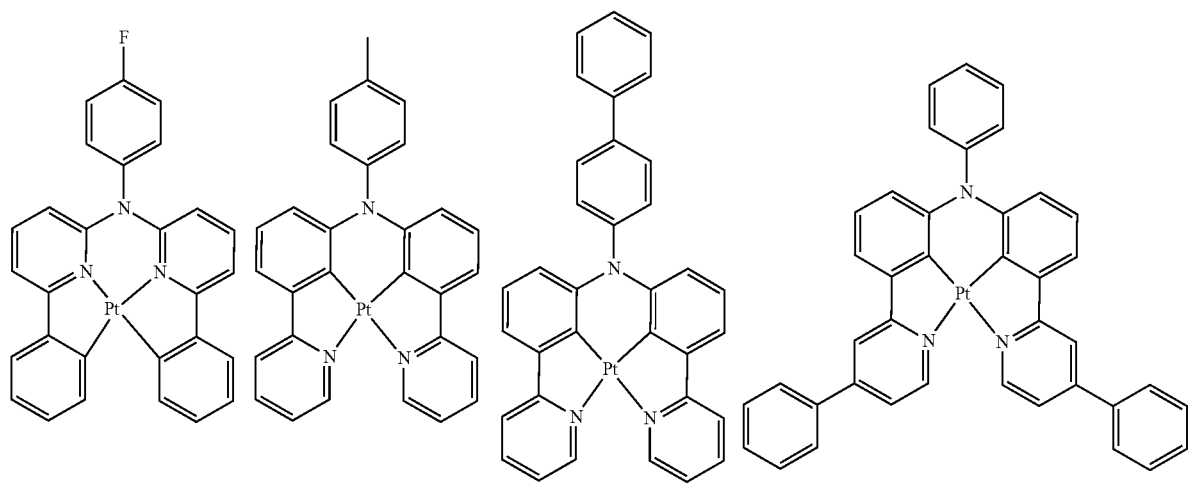

-continued
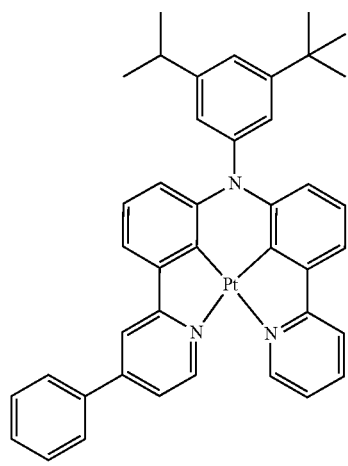
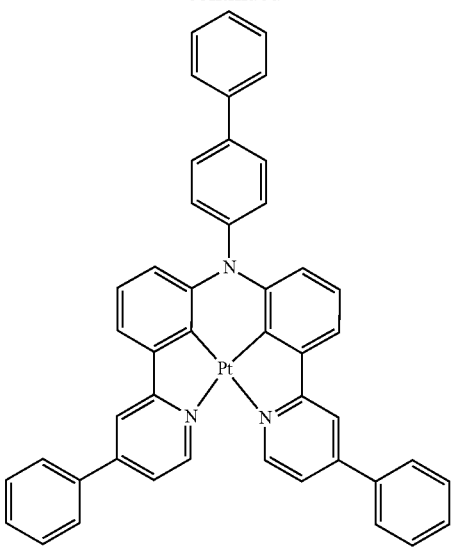
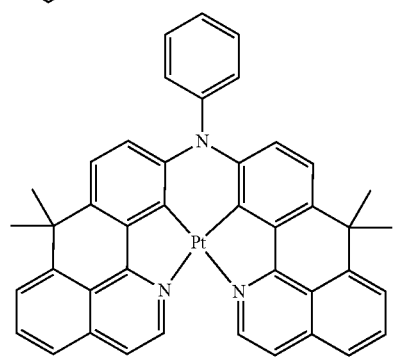
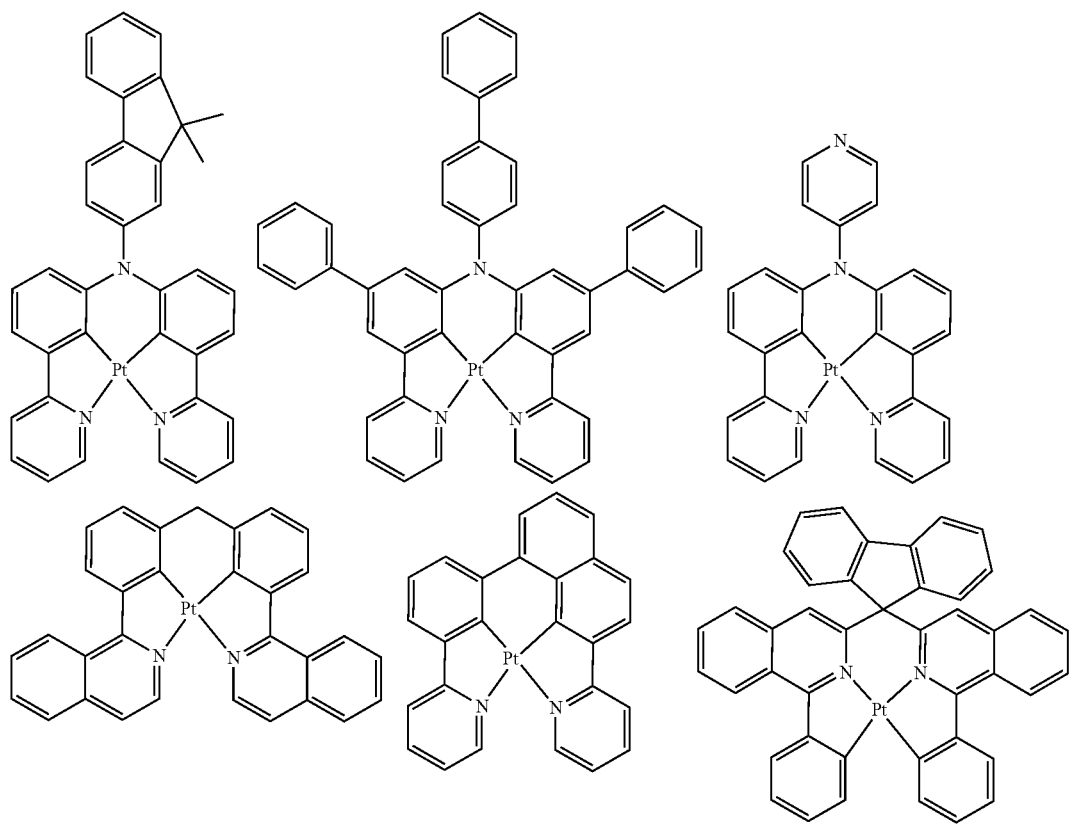

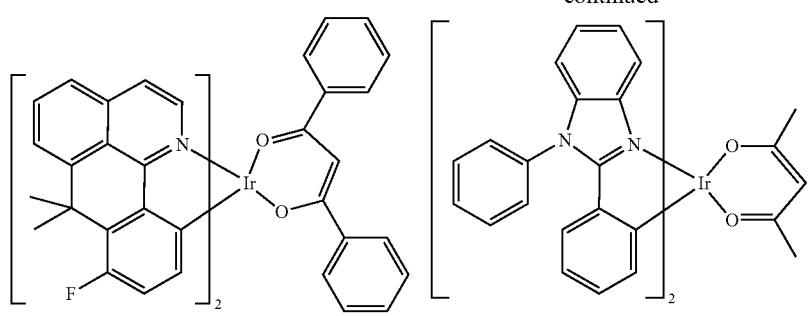
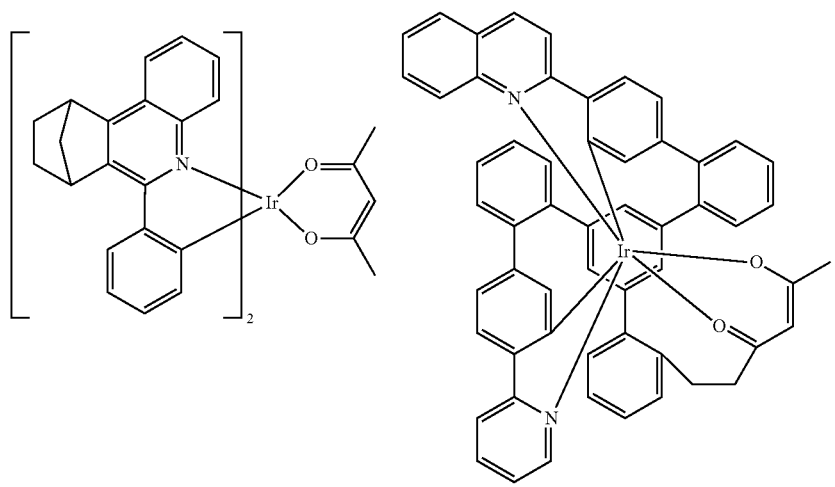
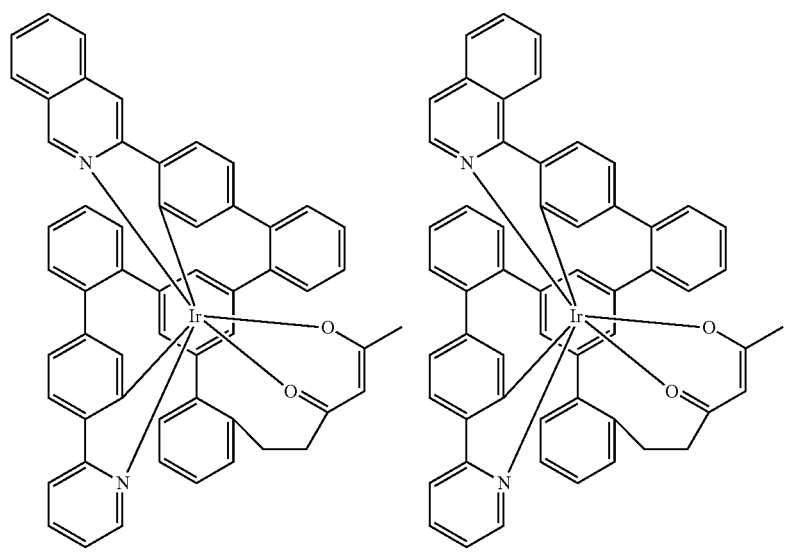

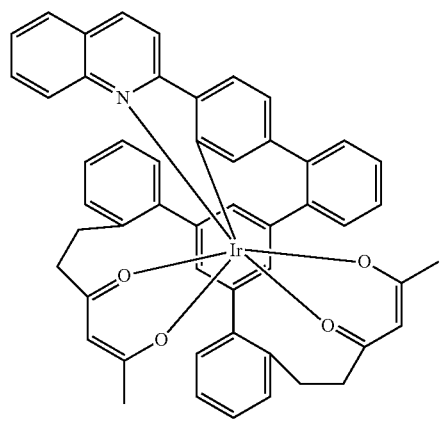
-continued
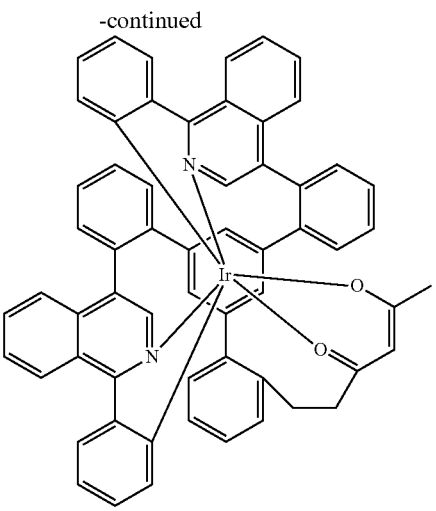
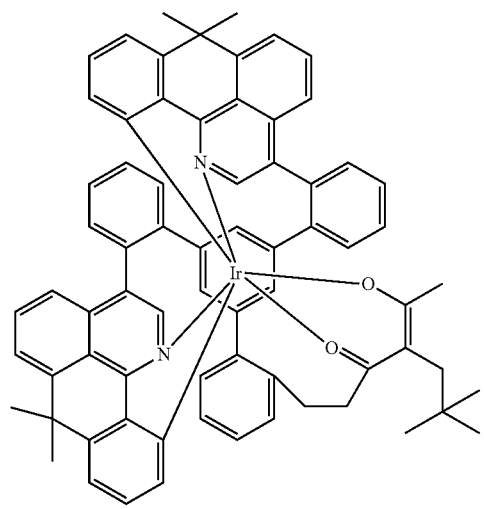
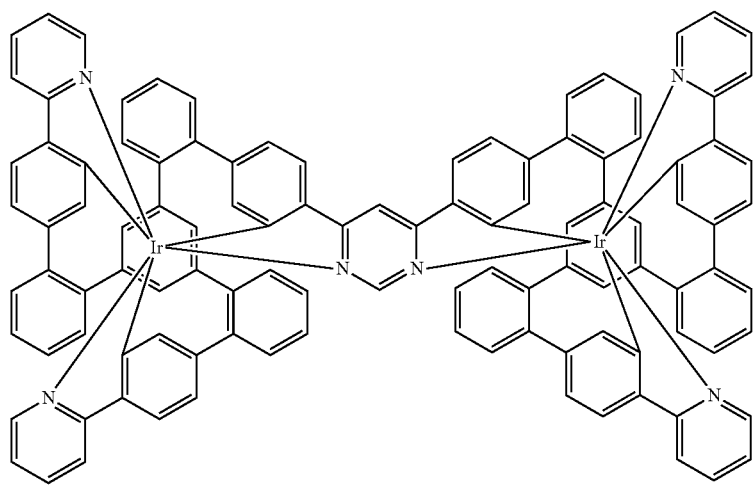

-continued
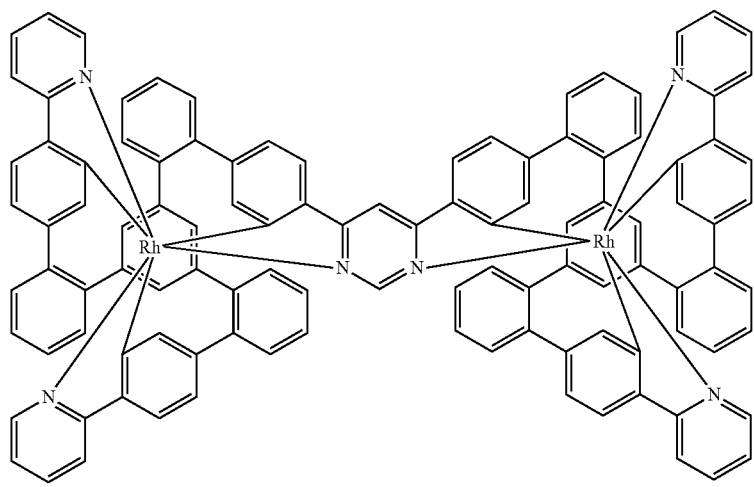
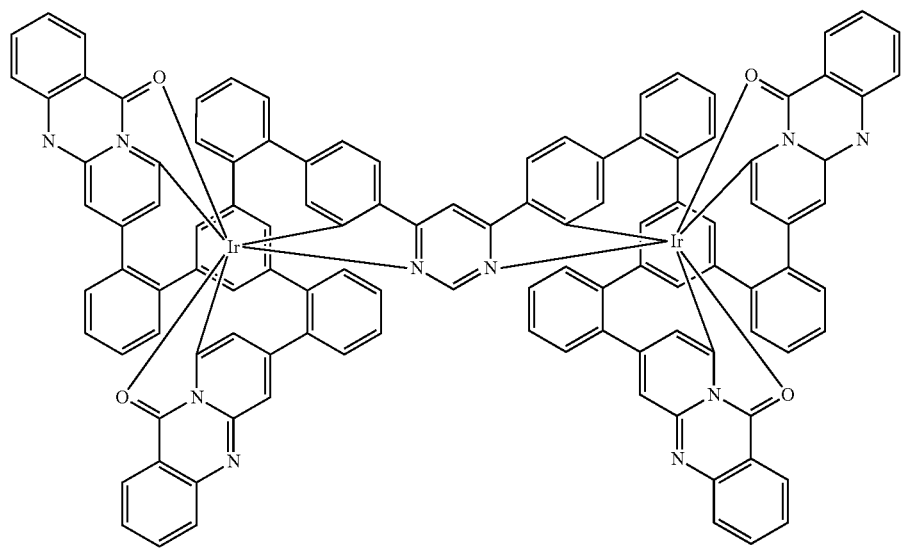
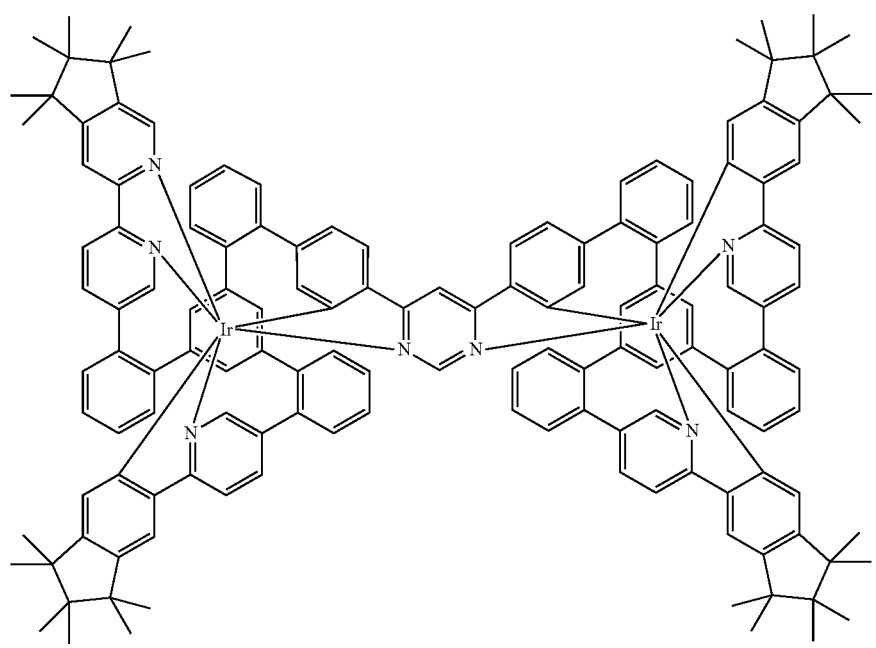

-continued

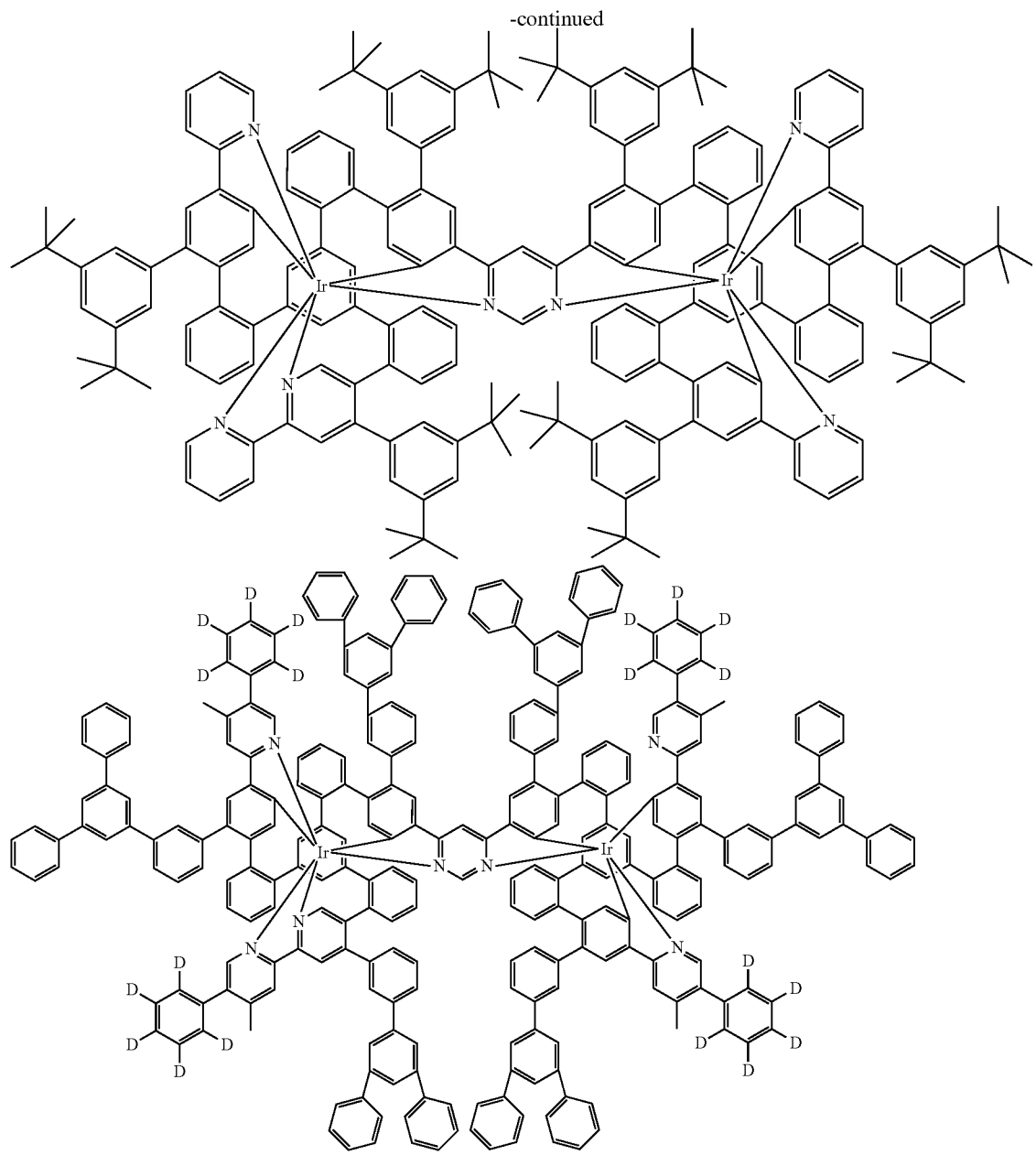

In the further layers of the organic electroluminescent device of the invention, it is possible to use any materials as typically used according to the prior art. The person skilled in the art will therefore be able, without exercising inventive skill, to use any materials known for organic electroluminescent devices in combination with the inventive compounds of formula (1) or the above-recited preferred embodiments.

Additionally preferred is an organic electroluminescent device, characterized in that one or more layers are coated by a sublimation process. In this case, the materials are applied by vapor deposition in vacuum sublimation systems at an initial pressure of less than $10^{-5}$ mbar, preferably less than $10^{-6}$ mbar. However, it is also possible that the initial pressure is even lower, for example less than $10^{-7}$ mbar.

Preference is likewise given to an organic electroluminescent device, characterized in that one or more layers are coated by the OVPD (organic vapor phase deposition) method or with the aid of a carrier gas sublimation. In this case, the materials are applied at a pressure between $10^{-5}$ mbar and 1 bar. A special case of this method is the OVJP (organic vapor jet printing) method, in which the materials are applied directly by a nozzle and thus structured.

Preference is additionally given to an organic electroluminescent device, characterized in that one or more layers are produced from solution, for example by spin-coating, or by any printing method, for example screen printing, flexographic printing, offset printing, LITI (light-induced thermal imaging, thermal transfer printing), inkjet printing or nozzle printing. For this purpose, soluble compounds are needed, which are obtained, for example, through suitable substitution.

In addition, hybrid methods are possible, in which, for example, one or more layers are applied from solution and one or more further layers are applied by vapor deposition.

Those skilled in the art are generally aware of these methods and are able to apply them without exercising inventive skill to organic electroluminescent devices comprising the compounds of the invention.

The compounds of the invention and the organic electroluminescent devices of the invention are notable for one or more of the following surprising properties:

1. The compounds of the invention, used as matrix material for phosphorescent emitters, lead to long lifetimes.
2. The compounds of the invention lead to high efficiencies, especially to a high EQE. This is especially true when the compounds are used as matrix material for a phosphorescent emitter.
3. The compounds of the invention lead to low operating voltages. This is especially true when the compounds are used as matrix material for a phosphorescent emitter.

The invention is illustrated in detail by the examples which follow, without any intention of restricting it thereby. The person skilled in the art will be able to use the information given to execute the invention over the entire scope disclosed and to prepare further compounds of the invention without exercising inventive skill and to use them in electronic devices or to employ the process of the invention.

EXAMPLES

The syntheses which follow, unless stated otherwise, are conducted under a protective gas atmosphere in dried solvents. The solvents and reagents can be purchased, for example, from Sigma-ALDRICH or ABCR. The respective figures in square brackets or the numbers quoted for individual compounds relate to the CAS numbers of the compounds known from the literature.

Preparation of the Synthons:

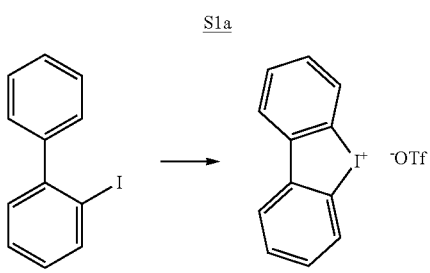 [SMILES: Ic1ccccc1-c1ccccc1 ; c1ccc2c(c1)[I+]c1ccccc1-2 ; "-OTf"]
S1a

Trifluoromethanesulfonic acid (73 g, 482 mmol) is added dropwise to a solution of 2-iodo-1,1'-biphenyl (45 g, 160 mmol) and 3-chlorobenzoic acid (55.5 g, 241 mmol) in DCM (700 mL) at 0° C. over a period of 30 min. Subsequently, the reaction is allowed to warm up to room temperature and left to stir for one hour, and the reaction mixture is then concentrated. MTBE (300 mL) is added to the residue, and the mixture is stirred at room temperature for 1 h. The solids are filtered off and washed with MTBE (3×50 mL) and dried in a vacuum drying cabinet. Yield: 56.4 g (131 mmol, 82%), 96% by NMR.

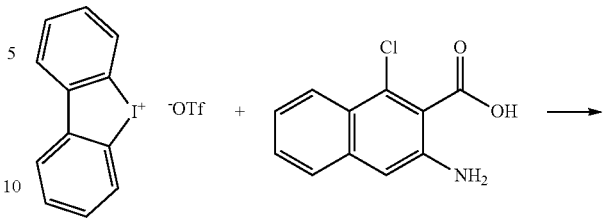
S2a

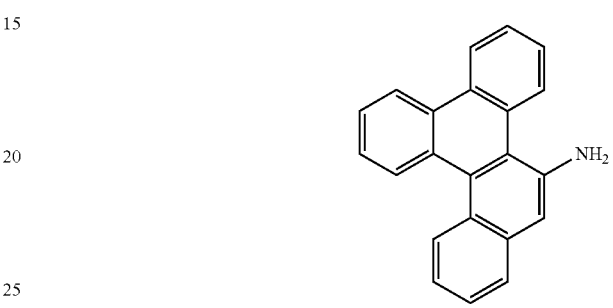

An initial charge under an inert atmosphere in a closed 1 L flask is formed by 3-amino-1-chloro-2-naphthalenecarboxylic acid (11.59 g. 52.3 mmol) [CAS-1823470-44-5], S1a (56.4 g, 131 mmol), $K_2CO_3$, (16.00 g, 115.9 mmol) and NMP (350 mL). Subsequently, $Pd(OAc)_2$ (350 mg, 1.66 mmol) is added and the reaction mixture is stirred at 145° C. for 17 h. After cooling, the reaction is worked up by extraction with ethyl acetate and water. The combined organic phases are washed 3× with water (200 mL each time) and 2× with sat. NaCl solution (100 mL each time) and dried over $Na_2SO_4$, and the solvent was removed by rotary evaporation on a rotary evaporator. The crude product is purified further by column chromatography. Yield: 3.8 g (13 mmol, 25%), 95% purity by $^1H$ NMR.

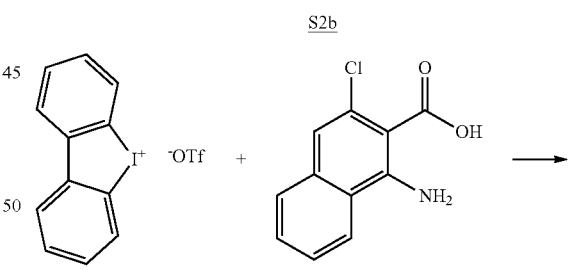
S2b

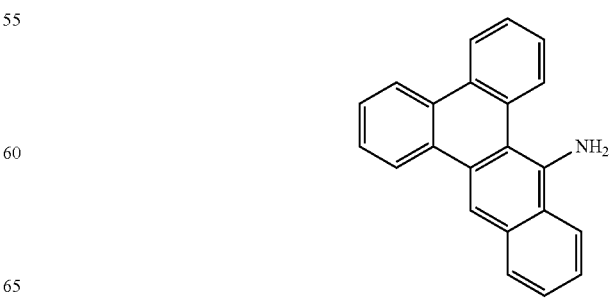

Compound S2b can be prepared analogously to the procedure described for synthon S2a proceeding from 1-amino-3-chloronaphthalene-2-carboxylic acid and S1a. Yield: 21%

S3a

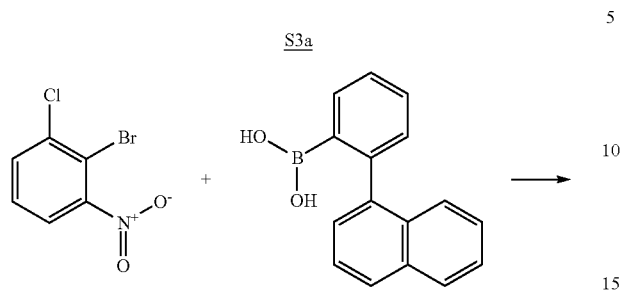

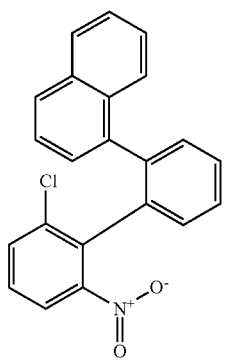

An initial charge under an inert atmosphere was formed by 2-bromo-1-chloro-3-nitrobenzene (23.6 g, 100 mmol) [CAS-19128-48-4], B-[2-(1-naphthyl)phenyl]boronic acid (24.8 g, 100 mmol) [CAS-500904-93-8] and sodium carbonate (21.2 g, 200 mmol) in toluene (700 mL) and water (150 mL). Subsequently, tetrakis(triphenylphosphine)palladium(0) (2.32 g, 2.00 mmol) is added and the reaction mixture is stirred under reflux for 16 h. After cooling, the reaction mixture is filtered with suction through a frit packed with toluene and Celite and then worked up by extraction with toluene and water. The organic phase is washed with water (200 mL) and sat. NaCl solution (100 mL) and dried over Na$_2$SO$_4$, and the solvent is drawn off on a rotary evaporator. The crude product is recrystallized from ethanol. Yield: 21.6 g (60 mmol, 60%), 96% purity by $^1$H NMR.

S3b

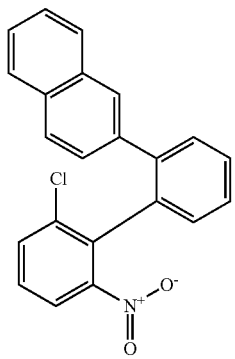

Compound S3b can be prepared analogously to the procedure described for synthon S3a. Rather than B-[2-(1-naphthyl)phenyl]boronic acid, B-[2-(2-naphthyl)phenyl]boronic acid is used. Yield: 55%

S3c

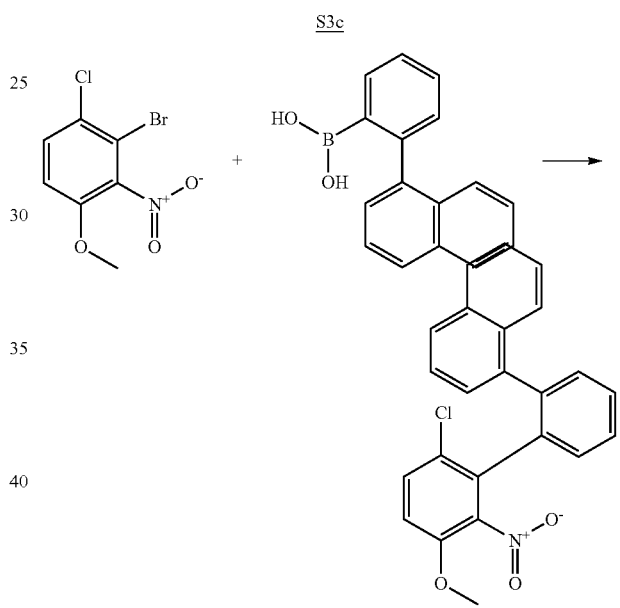

Compound S3c can be prepared analogously to the procedure described for synthon S3a proceeding from 2-bromo-3-chloro-6-methoxynitrobenzene [1698810-56-8] and B-[2-(1-naphthyl)phenyl]boronic acid. Yield: 46%

S4a

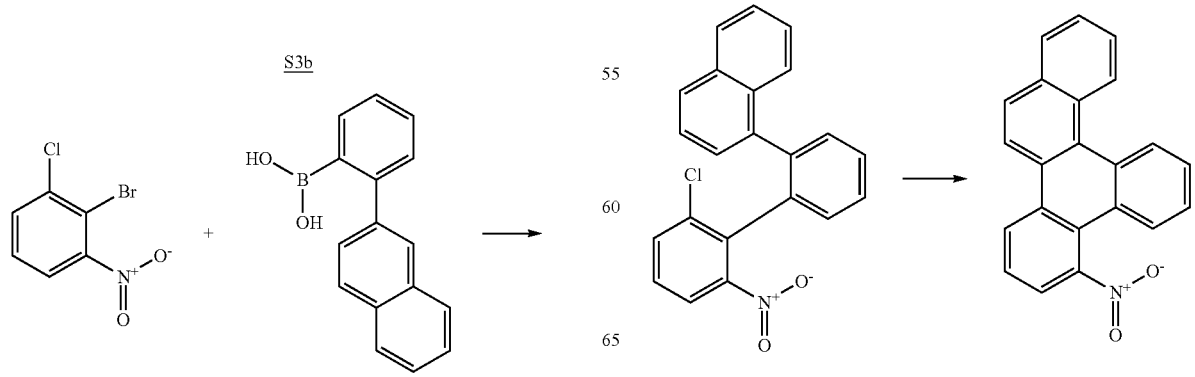

An initial charge under an inert atmosphere is formed by S3a (21.6 g, 60 mmol) and potassium carbonate (41.5 g, 300 mmol) in dimethylacetamide (400 mL). Subsequently, palladium acetate (674 mg, 3.00 mmol) and 1,3-bis(2,6-diisopropylphenyl)-3H-imidazol-1-ium chloride (2.55 g, 6.00 mmol) [CAS-250285-32-6] are added and the reaction mixture is stirred at 145° C. for 24 h. After cooling, the DMAc is largely removed by rotary evaporation, and the mixture is worked up by extraction with toluene (600 mL) and water. The aqueous phase is extracted 2× with toluene (250 mL each time). Subsequently, the combined organic phases are washed 2× with water (300 mL each time) and sat. NaCl solution (150 mL) and dried over $Na_2SO_4$, and the filtrate is concentrated by rotary evaporation. 400 mL of n-heptane is added to the crude product and the mixture is stirred at room temperature for 30 min. Subsequently, the solids are filtered off with suction, washed with n-heptane and dried in a vacuum drying cabinet. Yield: 10.1 g (31.2 mmol, 52%), 95% purity by $^1$H NMR.

Compound S4c can be prepared analogously to the procedure described for synthon S4a proceeding from S3c. Yield: 49%

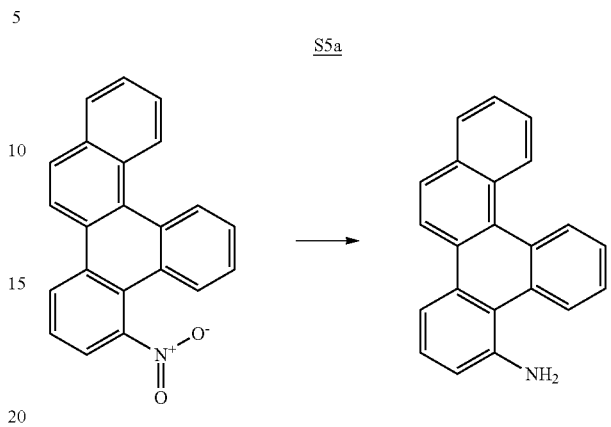

S4a (14.4 g, 44.4 mmol) in 150 mL of ethanol is hydrogenated over 1 g of palladium/charcoal at hydrogen pressure 3 bar over the course of 36 h. The reaction mixture is filtered 2× through a Celite bed. The filtrate is concentrated by rotary evaporation, and the solids obtained are recrystallized from toluene.

Yield: 10.7 g (36.6 mmol, 82%), 97% purity by $^1$H NMR.

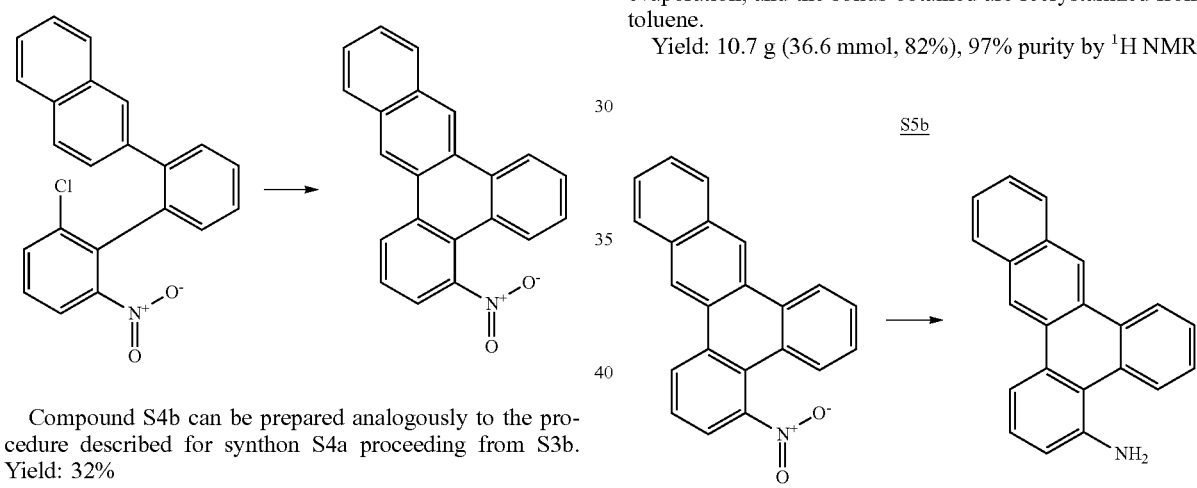

Compound S4b can be prepared analogously to the procedure described for synthon S4a proceeding from S3b. Yield: 32%

Compound S5b can be prepared analogously to the procedure described for synthon S5a proceeding from S4b. Yield: 87%

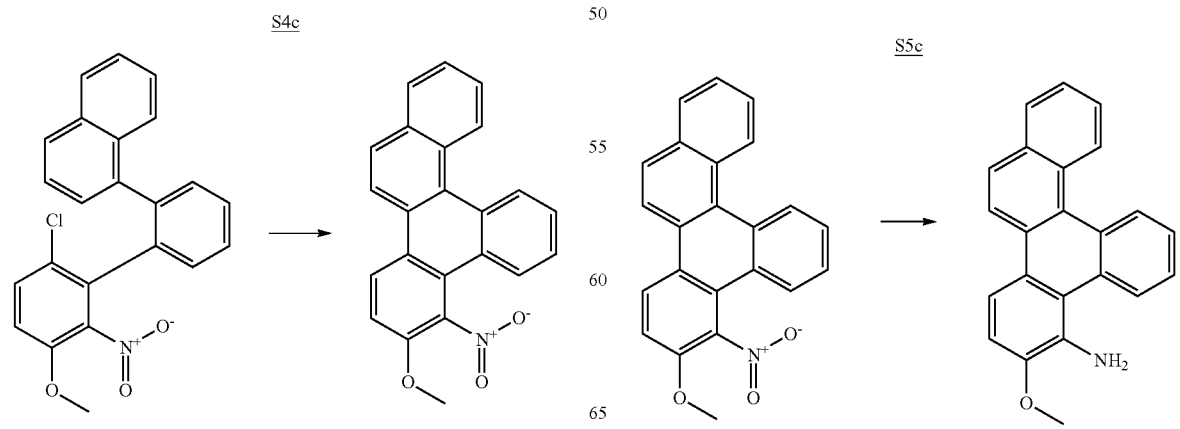

Compound S5c can be prepared analogously to the procedure described for synthon S5a proceeding from S4c. Yield: 62%

S6a

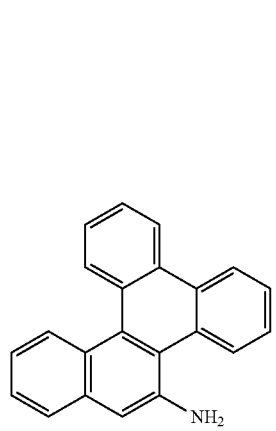

An initial charge in a flask is formed by S2a (3.8 g, 13.0 mmol), pivalic acid (2.66 g, 26.0 mmol), Cu(OAc)$_2$ [CAS-142-71-2](485 mg, 2.67 mmol), [Cp*IrCl$_2$]$_2$ [CAS-12354-84-6](426 mg, 0.53 mmol) and NMP (100 mL). Air is passed through the reaction mixture with a needle, and the reaction is stirred at 120° C. for 50 min. After cooling, the NMP is distilled off and the residue is purified further via column chromatography. Yield: 3.1 g (10.5 mmol, 81%), 98% purity by $^1$H NMR.

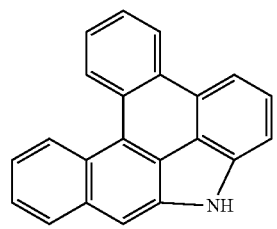

S6b

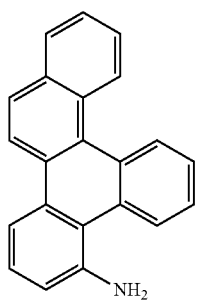

Analogously to S6a, compound S6b can be prepared proceeding from S5a. Yield: 72%

S6c

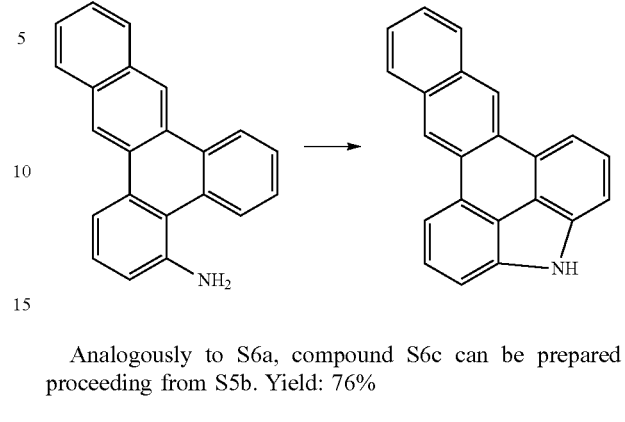

Analogously to S6a, compound S6c can be prepared proceeding from S5b. Yield: 76%

S6d

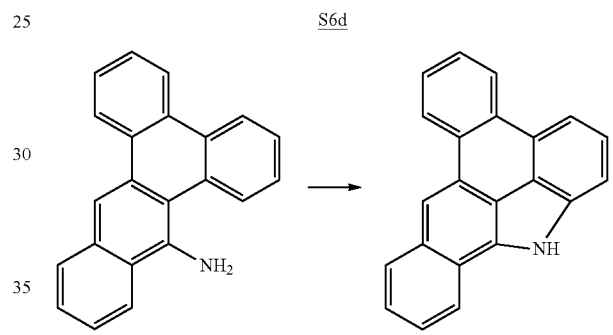

Analogously to S6a, compound S6d can be prepared proceeding from S2b. Yield: 44%

S6e

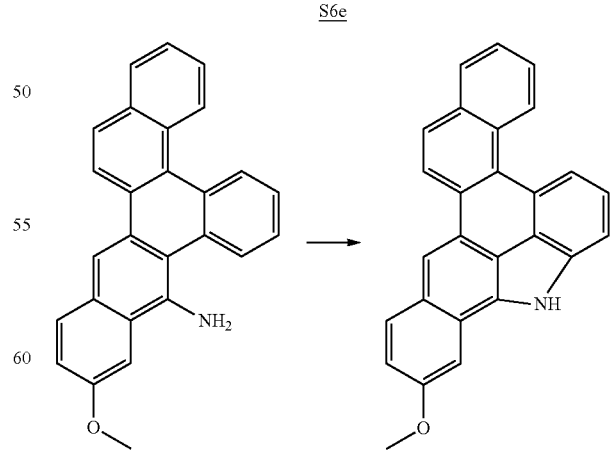

Analogously to S6a, compound S6e can be prepared proceeding from S5c. Yield 36%

S7a

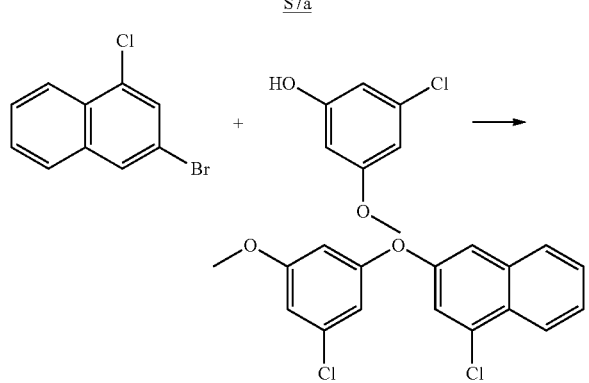

An initial charge under an inert atmosphere is formed by DMSO (100 mL), $K_3PO_4$ (106.15 g, 500 mmol), pyridine-2-carboxylic acid (3.06 g, 24.87 mmol) and CuI (2.37 g, 12.44 mmol). Subsequently, 3-chloro-5-methoxyphenol (45.57 g, 300 mmol) [65262-96-6] and 3-bromo-1-chloronaphthalene (60.38 g, 250 mmol) [325956-47-6] are gradually added successively, and the reaction mixture is heated at 85° C. for 16 h. After cooling, the reaction mixture is worked up by extraction with aqueous ammonia solution and methyl tert-butyl ether. The organic phase is washed 5 times with water and twice with sat. NaCl solution, the combined phases are dried over $Na_2SO_4$, and the solvent is drawn off on a rotary evaporator. The crude product is purified further via fractional distillation.

Yield: 64.64 g (202 mmol), 81% purity, 95% by $^1$H NMR.

The following compounds can be prepared analogously: Purification can be effected not only by distillation but also using column chromatography, or recrystallization can be effected using other standard solvents such as ethanol, butanol, acetone, ethyl acetate, acetonitrile, toluene, xylene, dichloromethane, methanol, tetrahydrofuran, n-butyl acetate, 1,4-dioxane, dimethyl sulfoxide, N,N-dimethylformamide, N,N-dimethylacetamide, N-methylpyrrolidone etc.

S8a

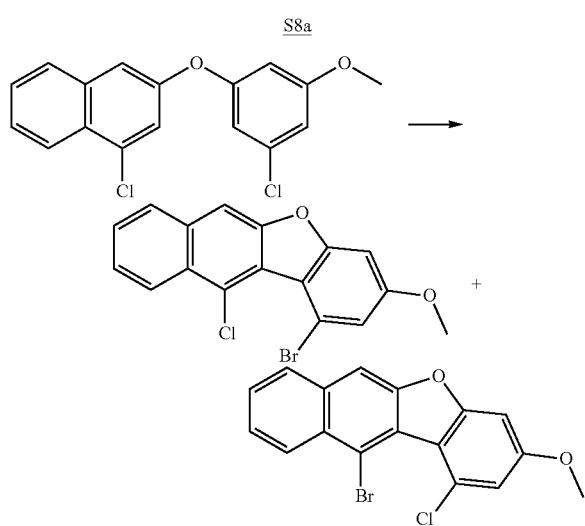

An initial charge of S7a (159.6 g, 500 mmol) in THF (750 mL) under an inert atmosphere is cooled down to −75° C. Subsequently, n-butyllithium (2.5 mol/L in hexane, 400 mL, 1.00 mmol) is slowly added dropwise in such a way that the internal temperature does not exceed −65° C. The mixture is left to stir at −75° C. for a further 4 h, and then bromine (28.0 mL, 546.5 mmol) is added dropwise in such a way that the internal temperature does not exceed −65° C. After the addition has ended, the mixture is stirred at −75° C. for 1 h, then allowed to warm up gradually to 10° C. within 1 h and stirred at 10° C. for 1 h. This is followed by cooling to 0° C. and cautious quenching of the mixture with sat. $Na_2SO_3$ solution (250 mL). The mixture is worked up by extraction with toluene and water, the combined organic phases are washed 3 times with water and once with sat. NaCl solution and dried over $Na_2SO_4$, and the solvent is removed on a rotary evaporator. The crude product is extracted by stirring 3 times with 2-propanol under reflux. The product is converted further as an isomer mixture. Yield: 133.8 g (370 mmol, 74%), purity 95% by $^1H$ NMR.

The following compounds can be prepared analogously: Purification can be effected not only by extractive stirring but also by distillation, or column chromatography or recrystallization can be effected using other standard solvents such as ethanol, butanol, acetone, ethyl acetate, acetonitrile, toluene, xylene, dichloromethane, methanol, tetrahydrofuran, n-butyl acetate, 1,4-dioxane, dimethyl sulfoxide, N,N-dimethylformamide, N,N-dimethylacetamide, N-methylpyrrolidone etc.

-continued

| Reactant 1 | Product | Yield |
|---|---|---|
| | | 86% |
| | 8d | |
| | | 71% |
| | 8e | |
| | | 79% |
| | 8f | |

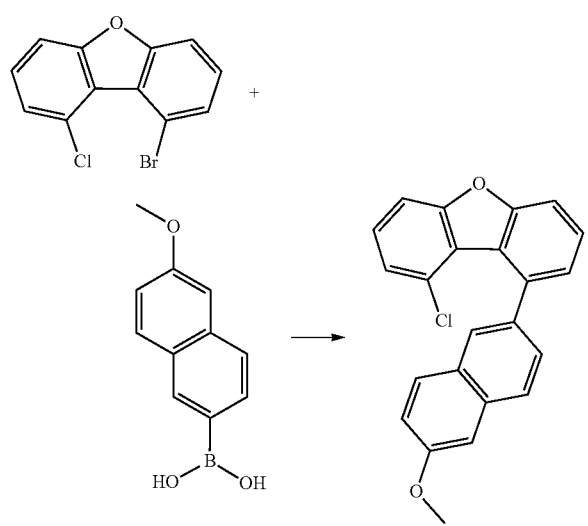

An initial charge of S8d (139.0 mmol), B-(6-methoxy-2-naphthyl)boronic acid (31.21 g, 154.5 mmol) [156641-984] and $K_2CO_3$ (38.84 g, 281.0 mmol) in THF (720 mL) and water (180 mL) is inertized for 30 min. Subsequently, tetrakis(triphenylphosphine)palladium [14221-01-3](1.78 mg, 1.54 mmol) is added and the reaction mixture is stirred under reflux for 16 h. The mixture is worked up by extraction with toluene and water, the combined organic phases are washed with water and sat. NaCl solution and dried over $Na_2SO_4$, and the solvent is drawn off on a rotary evaporator. The crude product is recrystallized from ethyl acetate. Yield: 35.8 g (100 mmol, 72%), 97% by $^1H$ NMR.

The following compounds can be prepared analogously: Purification can be effected by column chromatography, or recrystallization can be effected using other standard solvents such as ethanol, butanol, acetone, ethyl acetate, acetonitrile, toluene, xylene, dichloromethane, methanol, tetrahydrofuran, n-butyl acetate, 1,4-dioxane, dimethyl sulfoxide, N,N-dimethylformamide, N,N-dimethylacetamide, N-methylpyrrolidone etc.

| Reactant 1 | Reactant 2 | Product | Yield |
|---|---|---|---|
| 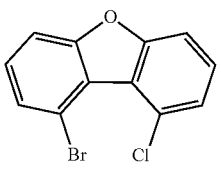<br>8d | 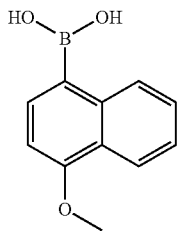<br>219834-95-4 | 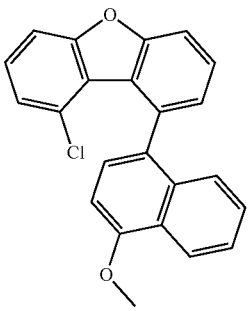 [SMILES: COc1ccc(-c2cccc3oc4cccc(Cl)c4c23)c2ccccc12]<br>S9b | 56% |
| 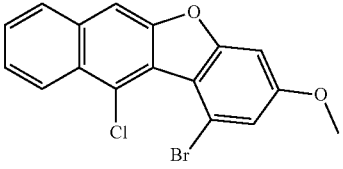 [SMILES: COc1cc(Br)c2c(c1)oc1cc3ccccc3c(Cl)c12]<br>+<br>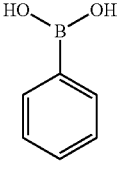<br>8a | 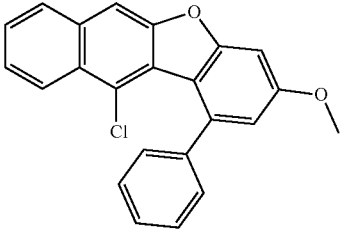 [SMILES: COc1cc(-c2ccccc2)c2c(c1)oc1cc3ccccc3c(Cl)c12]<br>98-80-6 | 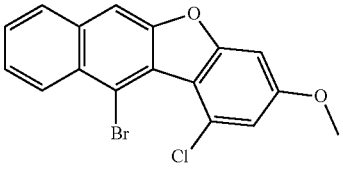 [SMILES: COc1cc(Cl)c2c(c1)oc1cc3ccccc3c(Br)c12]<br>+<br>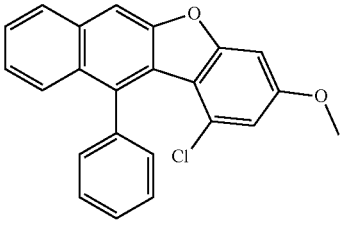 [SMILES: COc1cc(Cl)c2c(c1)oc1cc3ccccc3c(-c3ccccc3)c12]<br>S9c | 65% |
| 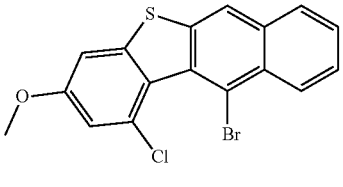 [SMILES: COc1cc(Cl)c2c(c1)sc1cc3ccccc3c(Br)c12]<br>+<br>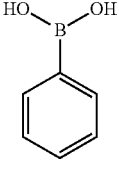<br>8b | 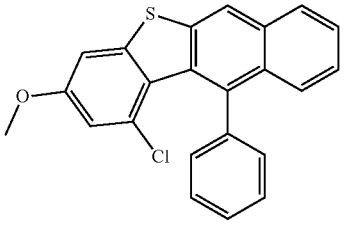 [SMILES: COc1cc(Cl)c2c(c1)sc1cc3ccccc3c(-c3ccccc3)c12]<br>98-80-6 | 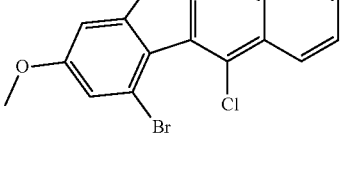<br>+<br>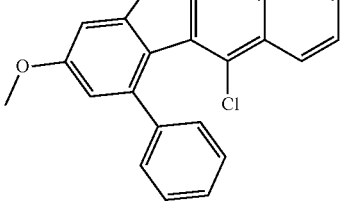<br>S9d | 51% |

-continued
| Reactant 1 | Reactant 2 | Product | Yield |
|---|---|---|---|
| 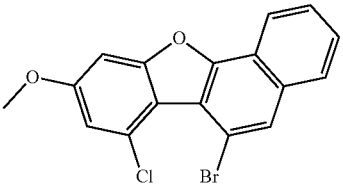 [SMILES: COc1cc(Cl)c2c(c1)oc1c3ccccc3cc(Br)c12]<br>+<br>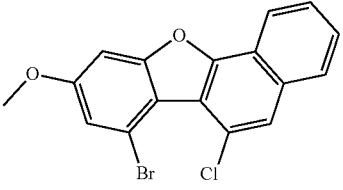<br>8c | 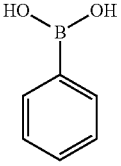<br>98-80-6 | 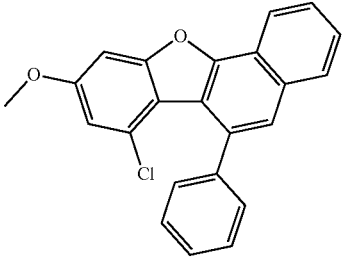 [SMILES: COc1cc(Cl)c2c(c1)oc1c3ccccc3cc(-c3ccccc3)c12]<br>+<br>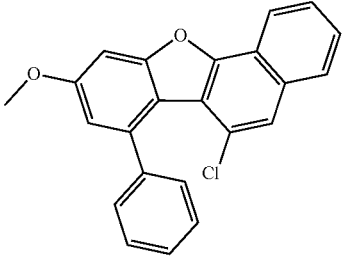 [SMILES: COc1cc(-c2ccccc2)c2c(c1)oc1c3ccccc3cc(Cl)c12]<br>S9e | 78% |
| 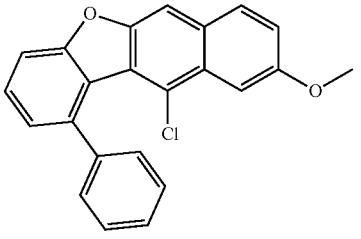<br>+<br><br>8e | 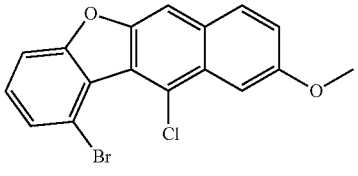<br>98-80-6 | 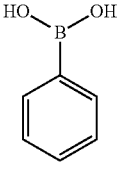<br>+<br>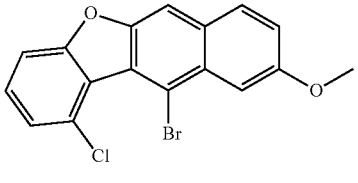<br>S9f | 48% |
| 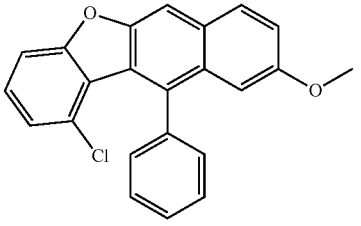 [SMILES: COc1ccc2cc3oc4cccc(Cl)c4c3c(-c3ccccc3)c2c1]<br>8f | 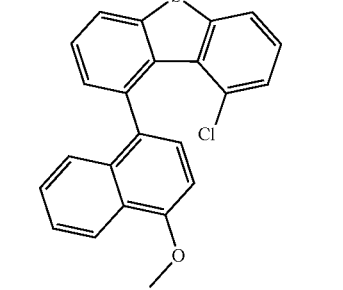<br>219834-95-4 | 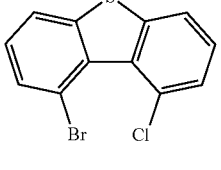<br>S9g | 55% |

-continued

| Reactant 1 | Reactant 2 | Product | Yield |
|---|---|---|---|
| 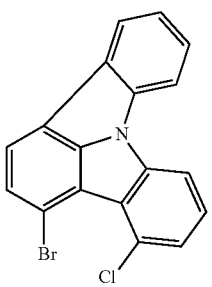 [SMILES: Clc1cccc2c1c1c(Br)ccc3c4ccccc4n2c31]<br>CAS-2136632-67-0 | 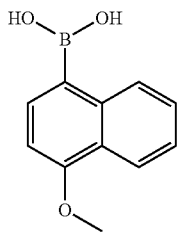<br>219834-95-4 | 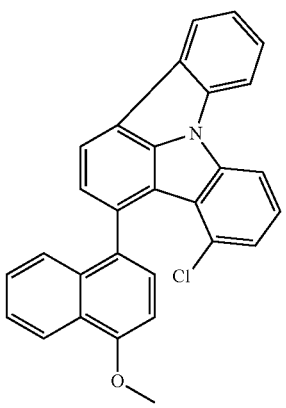 [SMILES: COc1ccc(-c2ccc3c4ccccc4n4c5cccc(Cl)c5c2c34)c2ccccc12]<br>S9h | 52% |
| 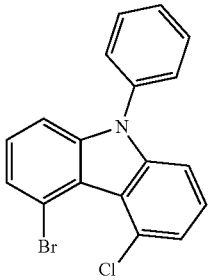 [SMILES: Clc1cccc2c1c1c(Br)cccc1n2-c1ccccc1] | 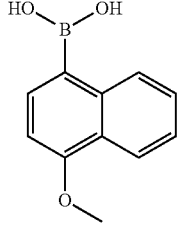<br>219834-95-4 | 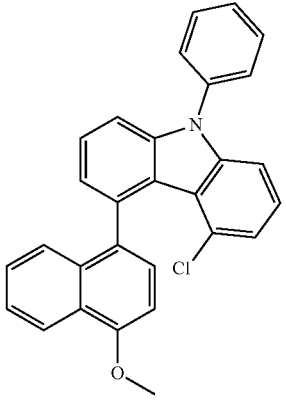 [SMILES: COc1ccc(-c2cccc3c2c2c(Cl)cccc2n3-c2ccccc2)c2ccccc12]<br>S9i | 58% |

S10a

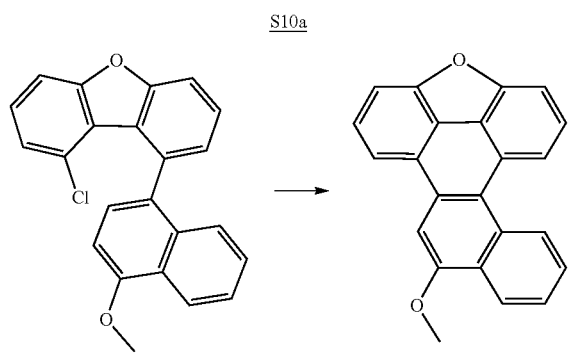 [SMILES: COc1ccc(-c2cccc3oc4cccc(Cl)c4c23)c2ccccc12 ; COc1cc2c3cccc4oc5cccc(c2c2ccccc12)c5c43]

To an initial charge of S9b (35.08 g, 100 mmol) and K₂CO₃ (41.37 g, 299.3 mmol) under an inert atmosphere is added DMAc (500 mL), and the mixture is inertized for 30 min. Subsequently, Pd(OAc)₂ (447 mg, 1.99 mmol) and 1,3-bis (2,6-diisopropylphenyl)-3H-imidazol-1-ium chloride (1.69 g, 3.98 mmol) are added, and the reaction mixture is stirred at 155° C. for 16 h. After cooling, the mixture is poured into ethanol/water (1:1, 800 mL) and stirred for a further 30 min. The precipitated solids are filtered off with suction and washed 5 times with water and 3 times with ethanol. The crude product is extracted by stirring with 2-propanol under reflux.

Yield: 26.4 g (82 mmol, 82%), 97% by 1H NMR.

The following compounds can be prepared analogously: Purification can be effected by column chromatography, or recrystallization can be effected using other standard solvents such as ethanol, butanol, acetone, ethyl acetate, acetonitrile, toluene, xylene, dichloromethane, methanol, tetrahydrofuran, n-butyl acetate, 1,4-dioxane, dimethyl sulfoxide, N,N-dimethylformamide, N,N-dimethylacetamide, N-methylpyrrolidone etc.

| Reactant 1 | Product | Yield |
|---|---|---|
| 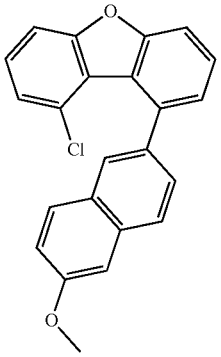 [SMILES: COc1ccc2cc(-c3cccc4oc5cccc(Cl)c5c34)ccc2c1] S9a | 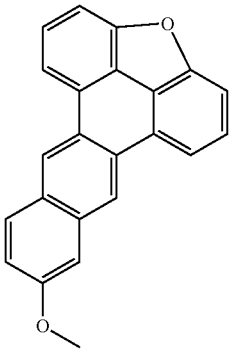 [SMILES: COc1ccc2cc3c(cc2c1)c1cccc2oc4cccc3c4c21] S10b | 73% |
| 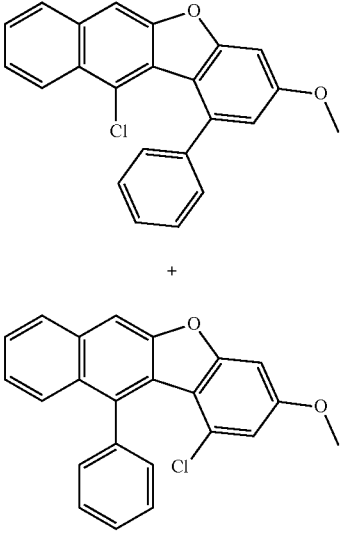 + 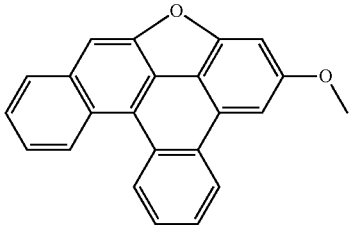 [SMILES: COc1cc2oc3cc4ccccc4c4c5ccccc5c(c1)c2c34] S9c | 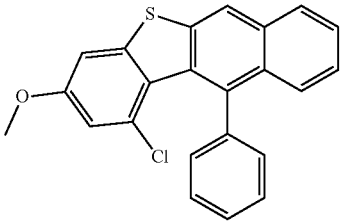 [SMILES: COc1cc(Cl)c2c(c1)sc1cc3ccccc3c(-c3ccccc3)c12] S10c | 78% |
| 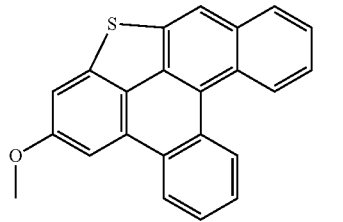 [SMILES: COc1cc2sc3cc4ccccc4c4c5ccccc5c(c1)c2c34] + 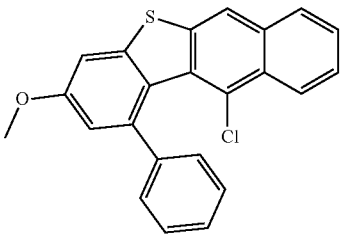 [SMILES: COc1cc(-c2ccccc2)c2c(c1)sc1cc3ccccc3c(Cl)c12] S9d |  S10d | 81% |

-continued

| Reactant 1 | Product | Yield |
|---|---|---|
| S9e + S9e (isomer) | S10e | 85% |
| S9f + S9f (isomer) | S10f | 68% |
| S9g | S10g | 65% |

| Reactant 1 | Product | Yield |
|---|---|---|
| S9h | S10h | 38% |
| S9i | S10i | 49% |

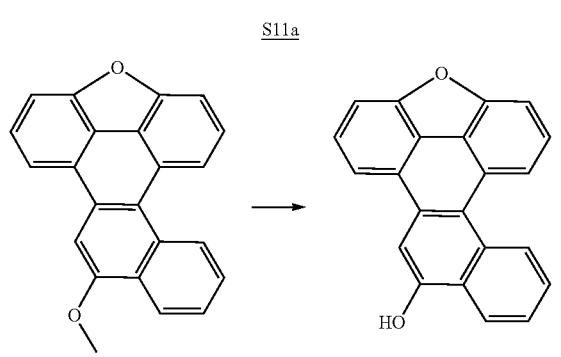 [SMILES: COc1cc2c3cccc4oc5cccc(c2c2ccccc12)c5c43 ; Oc1cc2c3cccc4oc5cccc(c2c2ccccc12)c5c43]

S11a

An initial charge of S10a (32.21 g, 100 mmol) in dichloromethane (650 mL) is cooled in an ice bath to 0° C. Subsequently, BBr₃ (6.0 mL, 63.2 mmol) is cautiously added dropwise. After the addition has ended, the mixture is allowed to warm up to room temperature. On completion of conversion, the mixture is cooled again to 0° C. and quenched cautiously with MeOH (200 mL). The solvent is drawn off on a rotary evaporator. Subsequently, each of 3 additions of 300 ml of MeOH to the mixture is followed by removal thereof on a rotary evaporator. Another 200 mL of MeOH is added, and the solids are filtered off with suction. The crude product is dried and used as such in the next stage. Yield 19.4 g (63 mmol, 63%).

The following compounds can be prepared analogously: Purification can be effected by column chromatography, or recrystallization can be effected using other standard solvents such as ethanol, butanol, acetone, ethyl acetate, acetonitrile, toluene, xylene, dichloromethane, methanol, tetrahydrofuran, n-butyl acetate, 1,4-dioxane, dimethyl sulfoxide, N,N-dimethylformamide, N,N-dimethylacetamide, N-methylpyrrolidone etc.

| Reactant 1 | Product | Yield |
|---|---|---|
| S10b | S11b | 70% |
| S10c | S11c | 72% |
| S10d | S11d | 75% |
| S10e | S11e | 66% |
| S10f | S11f | 62% |

| Reactant 1 | Product | Yield |
|---|---|---|
| 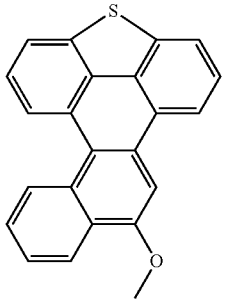 [SMILES: COc1cc2c3cccc4sc5cccc(c2c2ccccc12)c5c43] S10g | 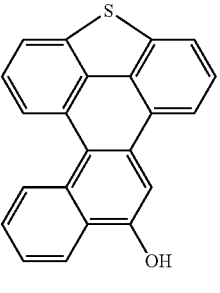 [SMILES: Oc1cc2c3cccc4sc5cccc(c2c2ccccc12)c5c43] S11g | 56% |
| 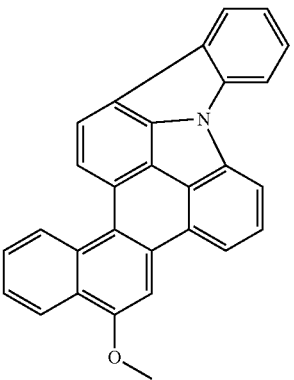 [SMILES: COc1cc2c3cccc4c3c3c(ccc5c6ccccc6n4c53)c2c2ccccc12] S10h | 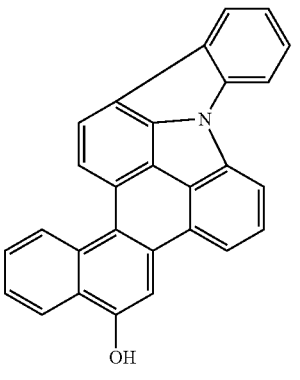 [SMILES: Oc1cc2c3cccc4c3c3c(ccc5c6ccccc6n4c53)c2c2ccccc12] S11h | 55% |
| 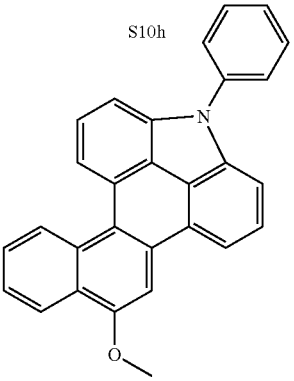 [SMILES: COc1cc2c3cccc4c3c3c(cccc3n4-c3ccccc3)c2c2ccccc12] S10i | 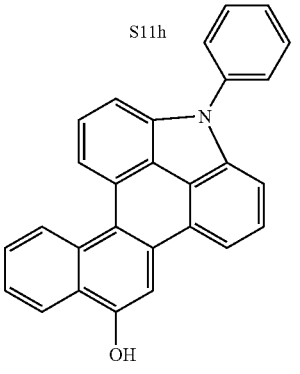 [SMILES: Oc1cc2c3cccc4c3c3c(cccc3n4-c3ccccc3)c2c2ccccc12] S11i | 49% |
| 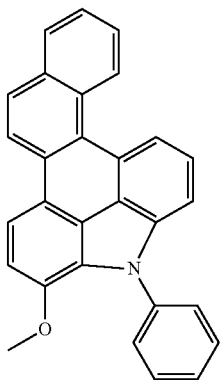 [SMILES: COc1ccc2c3ccc4ccccc4c3c3cccc4c3c2c1n4-c1ccccc1] S14a | 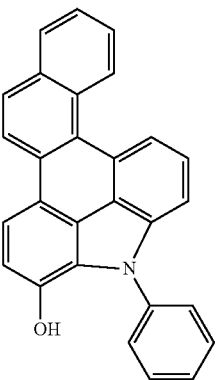 [SMILES: Oc1ccc2c3ccc4ccccc4c3c3cccc4c3c2c1n4-c1ccccc1] S11j | 51% |

S12a

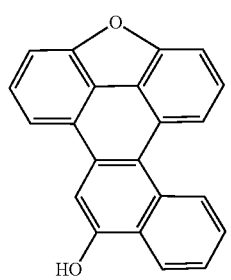
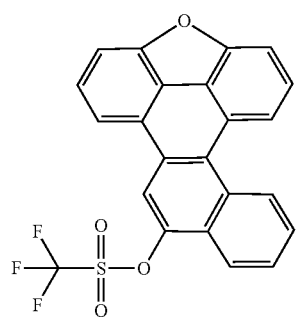

An initial charge of S11a (13.95 g, 45.3 mmol) and triethylamine (18.8 mL, 135.9 mmol) in dichloromethane (650 mL) is cooled to 0° C. in an ice bath. Subsequently, trifluoromethanesulfonic anhydride (9.9 mL, 58.9 mmol) is slowly added dropwise. After the addition has ended, the mixture is allowed to warm up to room temperature. On completion of conversion, the mixture is subjected to extractive workup with dichloromethane and water, the combined organic phases are dried over $Na_2SO_4$, and the solvent is removed on a rotary evaporator. The residue is taken up in 400 mL of cyclohexane, and the mixture is stirred at room temperature for 30 min. The solids are filtered off with suction and dried in a vacuum drying cabinet. Yield 14.95 g (34.0 mmol, 75%) The following compounds can be prepared analogously: Purification can be effected by column chromatography, or recrystallization can be effected using other standard solvents such as ethanol, butanol, acetone, ethyl acetate, acetonitrile, toluene, xylene, dichloromethane, methanol, tetrahydrofuran, n-butyl acetate, 1,4-dioxane, dimethyl sulfoxide, N,N-dimethylformamide, N,N-dimethylacetamide, N-methylpyrrolidone etc.

| Reactant 1 | Product | Yield |
|---|---|---|
| 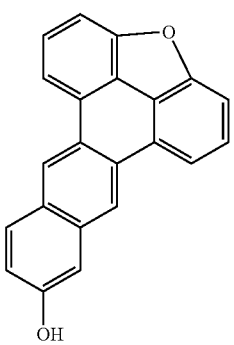 [SMILES: Oc1ccc2cc3c(cc2c1)c1cccc2oc4cccc3c4c21]<br>S11b | 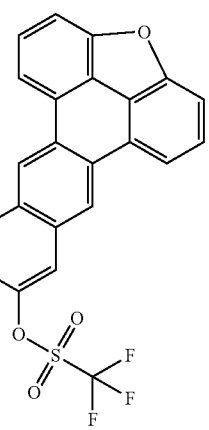<br>S12b | 70% |
| 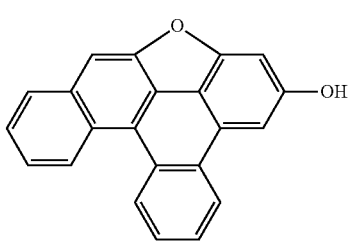<br>S11c | 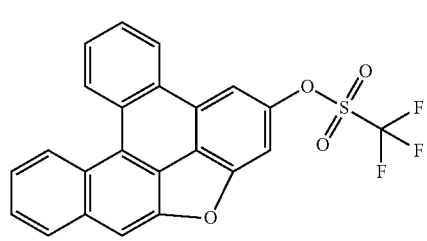 [SMILES: O=S(=O)(Oc1cc2oc3cc4ccccc4c4c5ccccc5c(c1)c2c34)C(F)(F)F]<br>S12c | 72% |

-continued

| Reactant 1 | Product | Yield |
|---|---|---|
| S11d | S12d | 75% |
| S11e | S12e | 66% |
| S11f | S12f | 62% |
| S11g | S12g | 56% |

-continued

| Reactant 1 | Product | Yield |
|---|---|---|
| S11h | S12h | 47% |
| S11i | S12i | 43% |
| S11j | S12j | 31% |

S13a

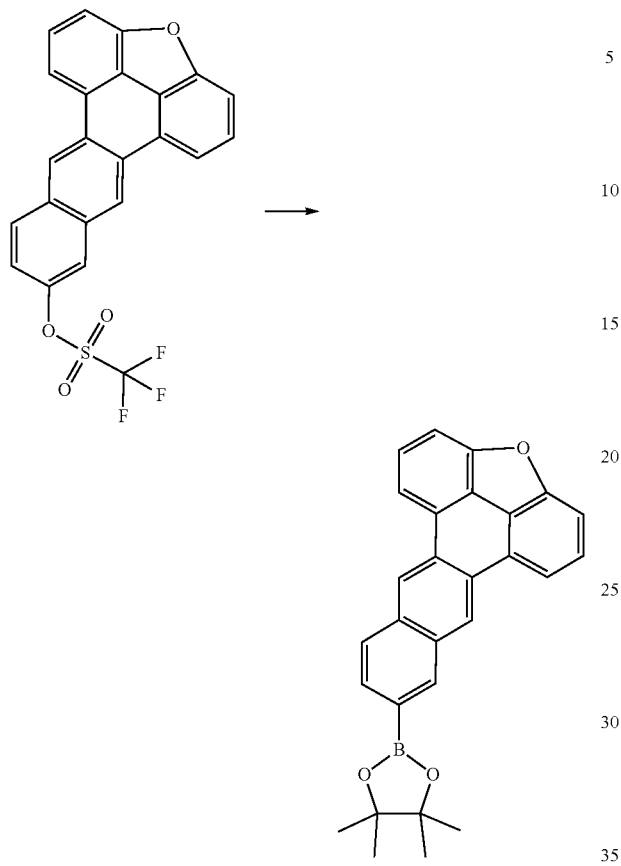

An initial charge of S12b (13.28 g, 30.2 mmol), bis(pinacolato)diboron (9.40 g, 36.3 mmol) and KOAc (8.90 g, 90.68 mmol) in 1,4-dioxane (250 ml) is inertized for 30 min. Then Pd(dppf)Cl$_2$ (740 mg, 0.91 mmol) is added, and the mixture 20 The following compounds can be prepared analogously: As an alternative, the catalyst system used may also be Pd(PCy$_3$)$_2$C$_{12}$ or Pd$_2$(dba)$_3$ with S-Phos (1:3). Purification can be effected not only by column chromatography but also by hot extraction, or recrystallization or hot extraction using other standard solvents such as ethanol, butanol, acetone, ethyl acetate, acetonitrile, toluene, xylene, dichloromethane, methanol, tetrahydrofuran, n-butyl acetate, 1,4-dioxane, or recrystallization using high boilers such as dimethyl sulfoxide, N,N-dimethylformamide, N,N-dimethylacetamide, N-methylpyrrolidone, etc.

| Reactant 1 | Product | Yield |
|---|---|---|
|  |  | 48% |

| Reactant 1 | Product | Yield |
|---|---|---|
| 12a | S13b | 77% |
| S12c | S13c | 80% |
| S12d | S13d | 64% |
| S12e | S13e | 70% |
| S12f | S13f | |

-continued

| Reactant 1 | Product | Yield |
|---|---|---|
| S12g | S13g | 50% |
| S12i | S13i | 47% |
| S12j | S13j | 33% |

S14

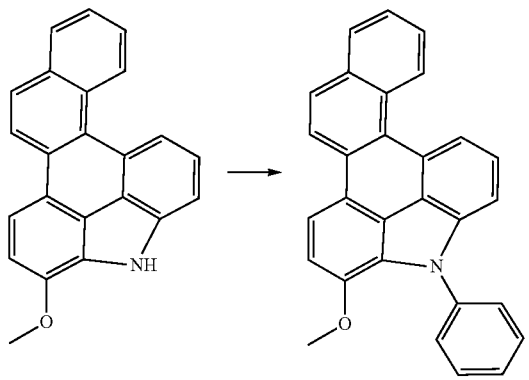

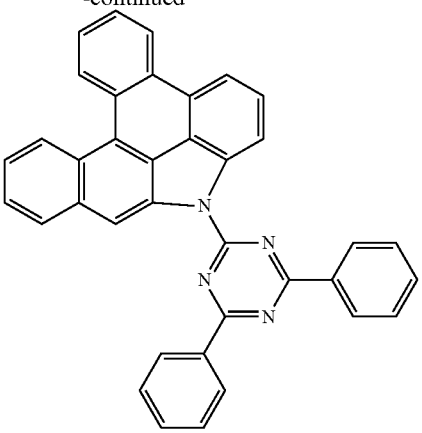

An initial charge is formed by S6e (32.1 g, 100 mmol), bromobenzene (17.3 g, 110 mmol) and sodium tert-butoxide (20.18 g, 210 mmol) in toluene (800 mL). Subsequently, XPhos Pd G3 [CAS-1445085-55-1](3.40 g, 4.6 mmol) is added and the reaction solution is heated to boiling for 24 h. The reaction solution is left to cool to room temperature. The reaction mixture is worked up by extraction with toluene and water. The combined organic phases are dried over Na$_2$SO$_4$, and the solvent is drawn off on a rotary evaporator. The crude product is recrystallized from n-butyl acetate. Yield: 18.0 g (87 mmol, 87%), purity 98% by $^1$H NMR.

Preparation of the Compounds of the Invention

Synthesis of P1a:

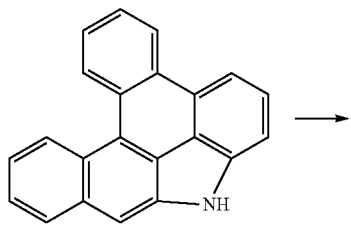

An initial charge is formed by S6a (8.30 g, 28.5 mmol), 2-chloro-4,6-diphenyl-1,3,5-triazine (8.40 g, 31.3 mmol) [CAS-3842-55-5] and sodium tert-butoxide (3.00 g, 31.3 mmol) in toluene (250 mL). Subsequently, XPhos Pd G3 [CAS-1445085-55-1](2.10 g, 2.8 mmol) is added and the reaction solution is heated to boiling for 72 h. The reaction solution is cooled down to room temperature and the solvent is removed by rotary evaporator. The crude product is purified via column chromatography (n-heptane/ethyl acetate), followed by recrystallization 4 times from n-butyl acetate and sublimation under high vacuum. Yield: 7.9 g (15.1 mmol, 53%); purity: >99.9% by HPLC.

The following compounds can be prepared analogously: Purification can be effected not only by column chromatography but also by hot extraction, or recrystallization or hot extraction using other standard solvents such as ethanol, butanol, acetone, ethyl acetate, acetonitrile, toluene, xylene, dichloromethane, methanol, tetrahydrofuran, n-butyl acetate, 1,4-dioxane, or recrystallization using high boilers such as dimethyl sulfoxide, N,N-dimethylformamide, N,N-dimethylacetamide, N-methylpyrrolidone, etc.

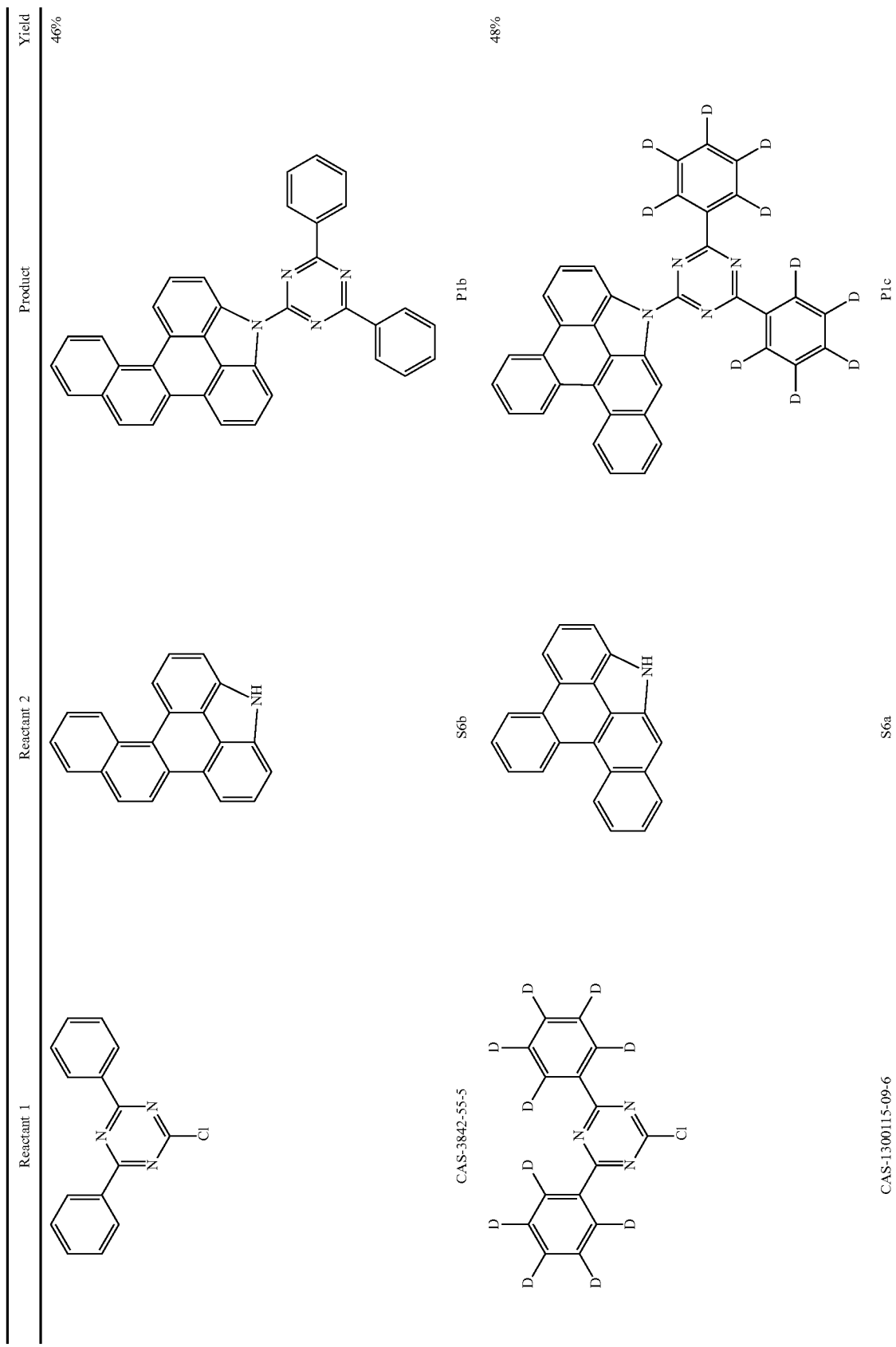

-continued
| Reactant 1 | Reactant 2 | Product | Yield |
|---|---|---|---|
| 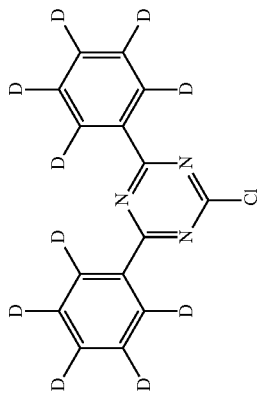<br>CAS-1300115-09-6 | 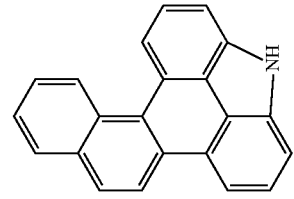 | 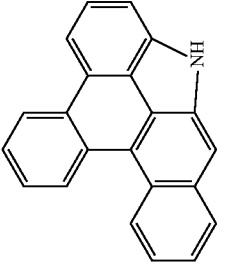<br>P1d | 53% |
| 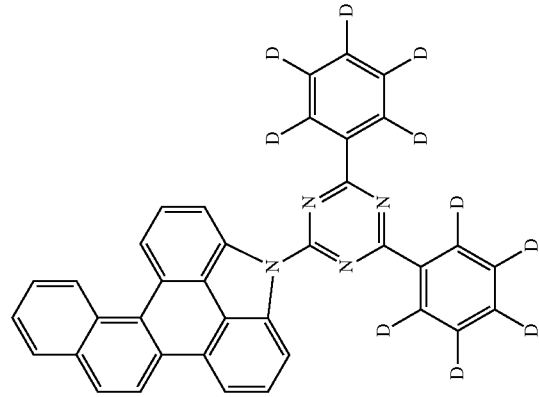<br>CAS-1472062-95-5 | 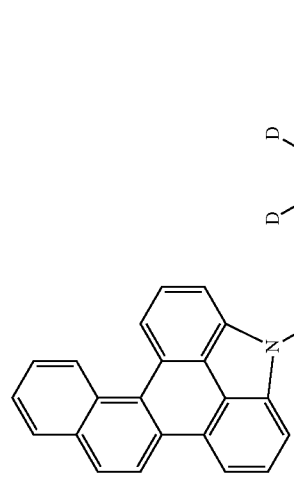 | 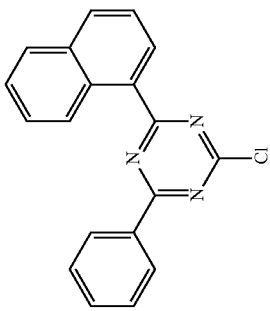<br>P1e | 45% |

-continued

| Reactant 1 | Reactant 2 | Product | Yield |
|---|---|---|---|
| CAS-1472062-95-5 | S6b | P1f | 41% |
| CAS-1621467-30-8 | S6a | P1g | 60% |

| Reactant 1 | Reactant 2 | Product | Yield |
|---|---|---|---|
| 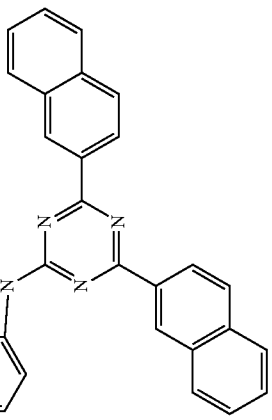<br>CAS-1621467-30-8 | 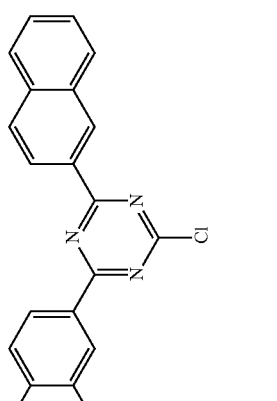<br>S6b | 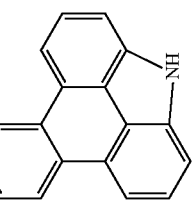<br>P1h | 58% |

| Reactant 1 | Reactant 2 | Product | Yield |
|---|---|---|---|
| 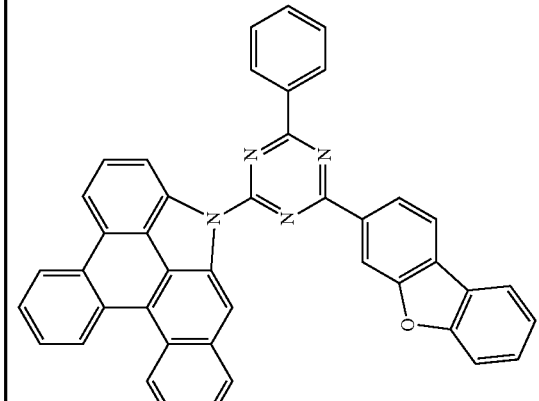<br>CAS-2142681-84-1 | 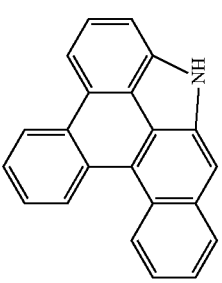<br>S6a | 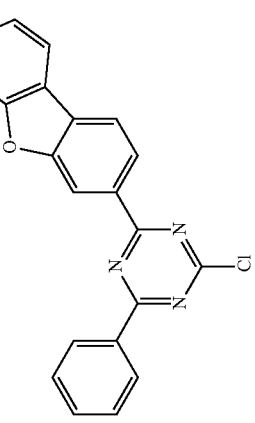<br>P1i | 44% |

| Reactant 1 | Reactant 2 | Product | Yield |
|---|---|---|---|
| CAS-2142681-84-1 | S6b | P1j | 38% |
| CAS-2074632-09-8 | S6a | P1k | 55% |

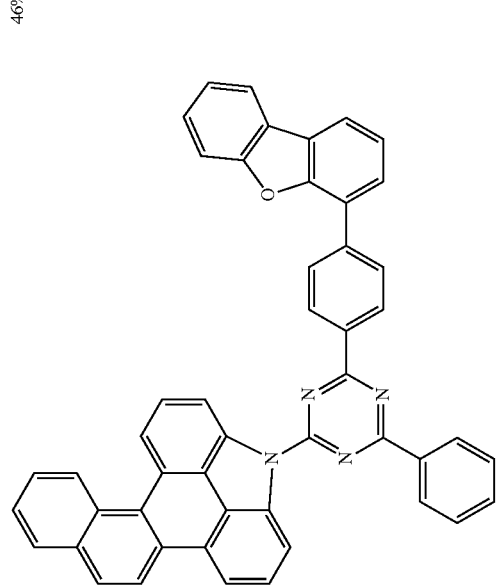

| Reactant 1 | Reactant 2 | Product | Yield |
|---|---|---|---|
| 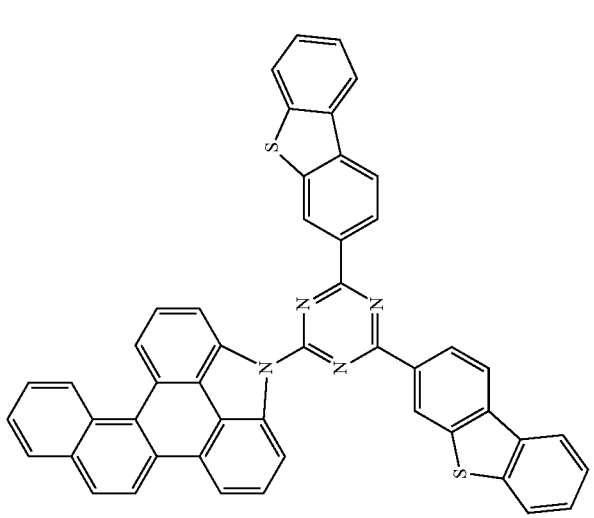<br>CAS-2172944-02-2 | 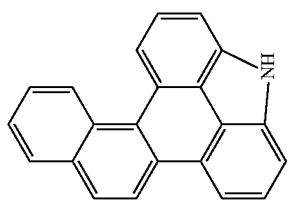<br>S6b | 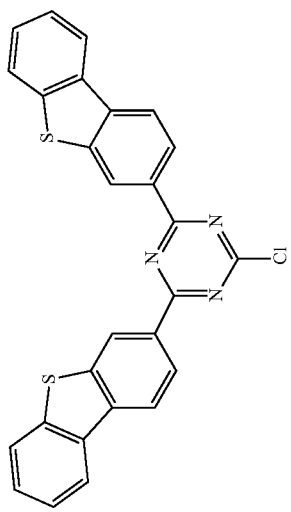<br>P1n | 59% |

-continued
| Reactant 1 | Reactant 2 | Product | Yield |
|---|---|---|---|
| 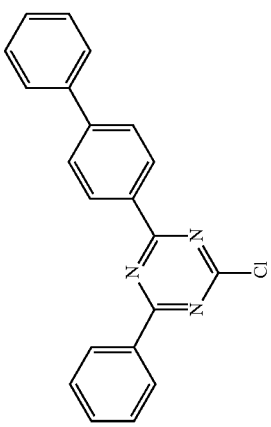 CAS-1472062-94-4 | 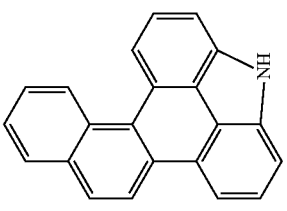 S6a | 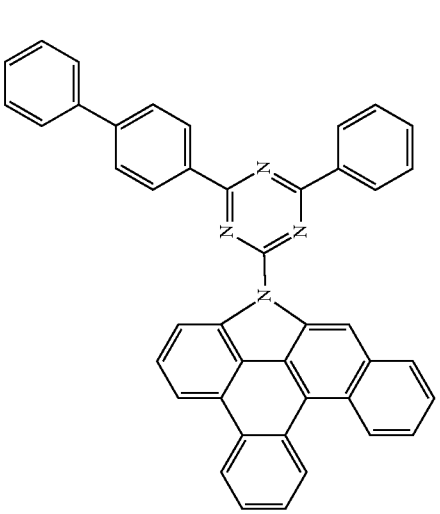 P1o | 51% |
| 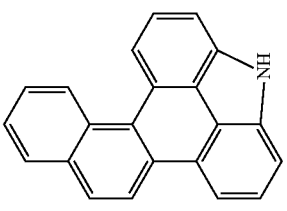 CAS-1472062-94-4 | 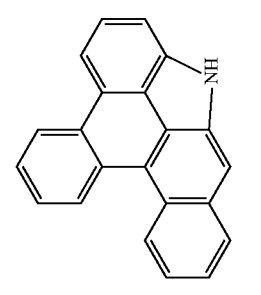 S6b | 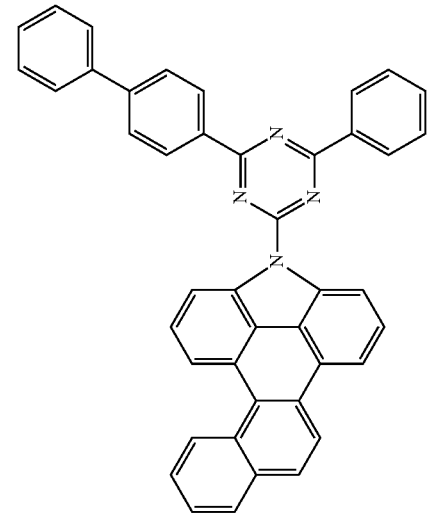 P1p | 47% |

| Reactant 1 | Reactant 2 | Product | Yield |
|---|---|---|---|
| CAS-2260688-83-1 | S6a | P1q | 49% |

| Reactant 1 | Reactant 2 | Product | Yield |
|---|---|---|---|
| <br>CAS-2260688-83-1 | 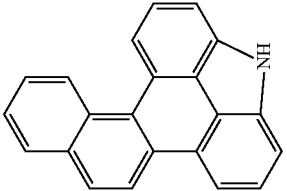<br>S6b | 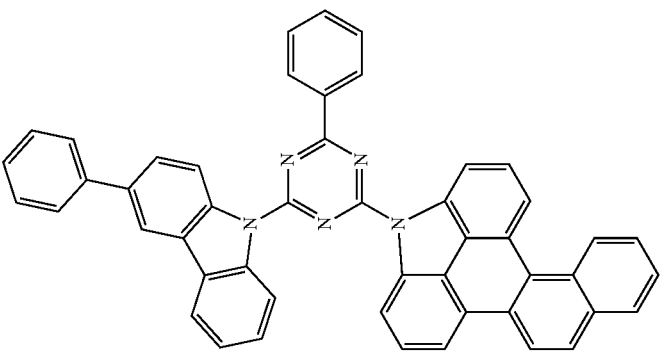<br>P1r | 50% |

-continued
| Reactant 1 | Reactant 2 | Product | Yield |
|---|---|---|---|
| CAS-2915-16-4 | S6a | P1s | 42% |
| CAS-2915-16-4 | S6b | P1t | 48% |
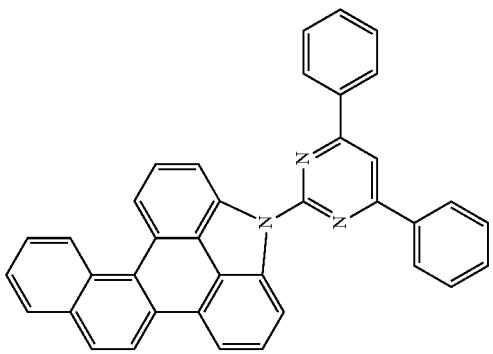

-continued
| Reactant 1 | Reactant 2 | Product | Yield |
|---|---|---|---|
| 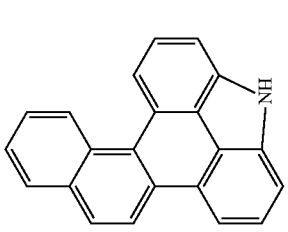 CAS-6484-25-9 | 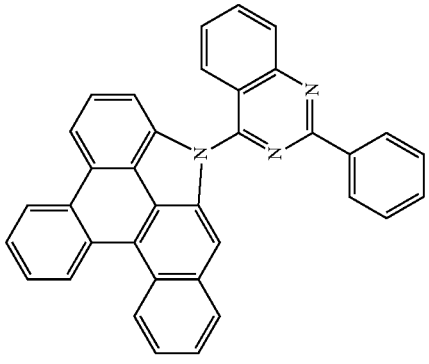 S6a | 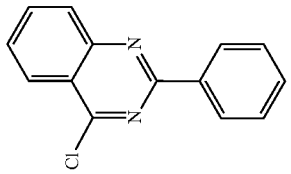 P1u | 34% |
| 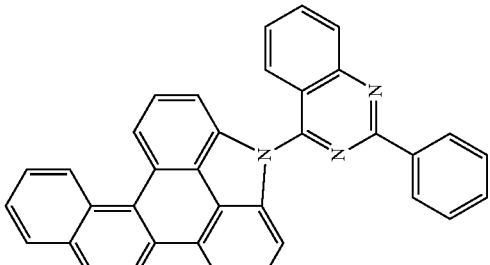 CAS-6484-25-9 | 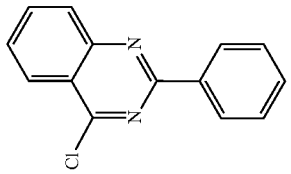 S6b | 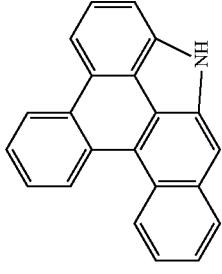 P1v | 31% |

| Reactant 1 | Reactant 2 | Product | Yield |
|---|---|---|---|
| CAS-147062-94-4 | S6c | P1w | 50% |
| CAS-147062-94-4 | S6d | P1x | 15% |

-continued
| Reactant 1 | Reactant 2 | Product | Yield |
|---|---|---|---|
| 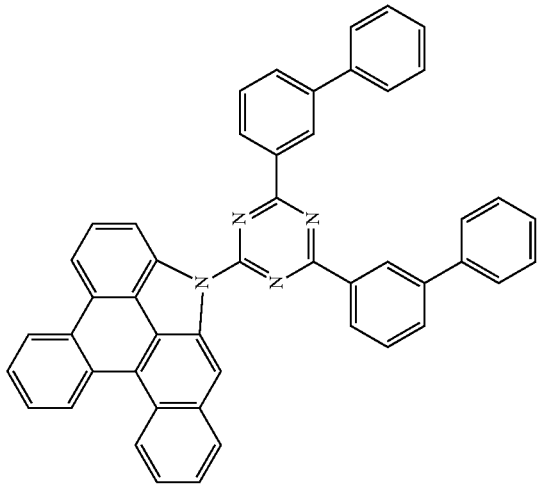 CAS-1205748-61-3 | 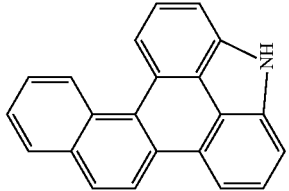 S6b | 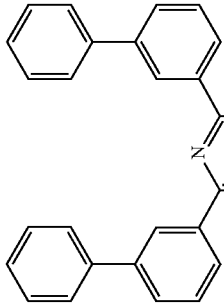 P1y | 40% |

| Reactant 1 | Reactant 2 | Product | Yield |
|---|---|---|---|
| 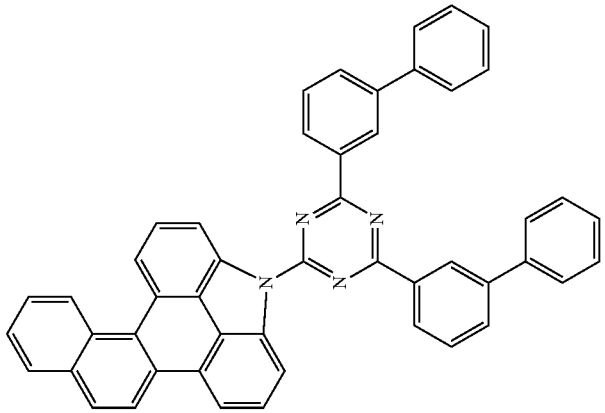<br>CAS-1205748-61-3 | 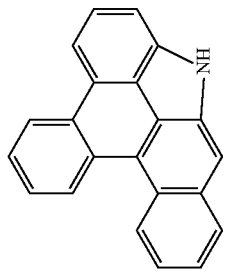<br>S6a | 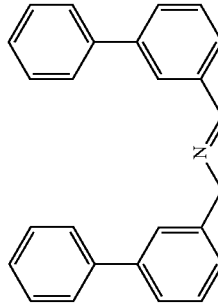<br>P1z | 35% |

| Reactant 1 | Reactant 2 | Product | Yield |
|---|---|---|---|
| 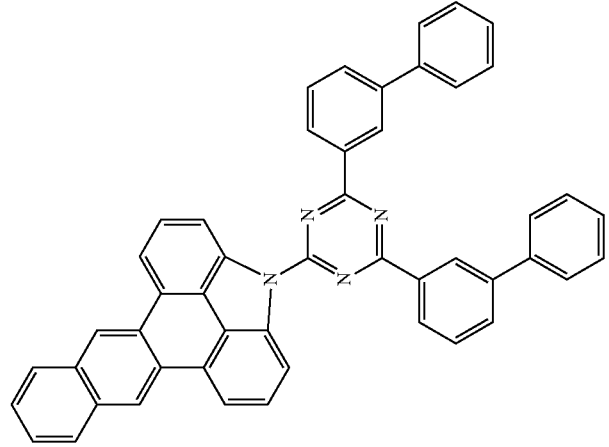<br>CAS-1205748-61-3 | 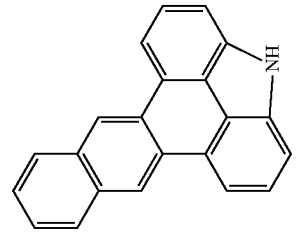<br>S6c | 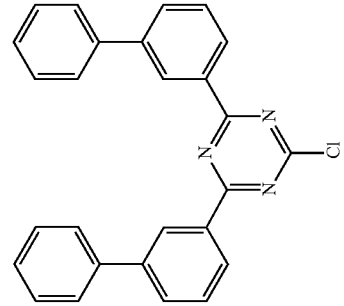<br>P1za | 42% |

-continued

| Reactant 1 | Reactant 2 | Product | Yield |
|---|---|---|---|
| CAS-1205748-61-3 | S6d | P1zb | 21% |

P2a

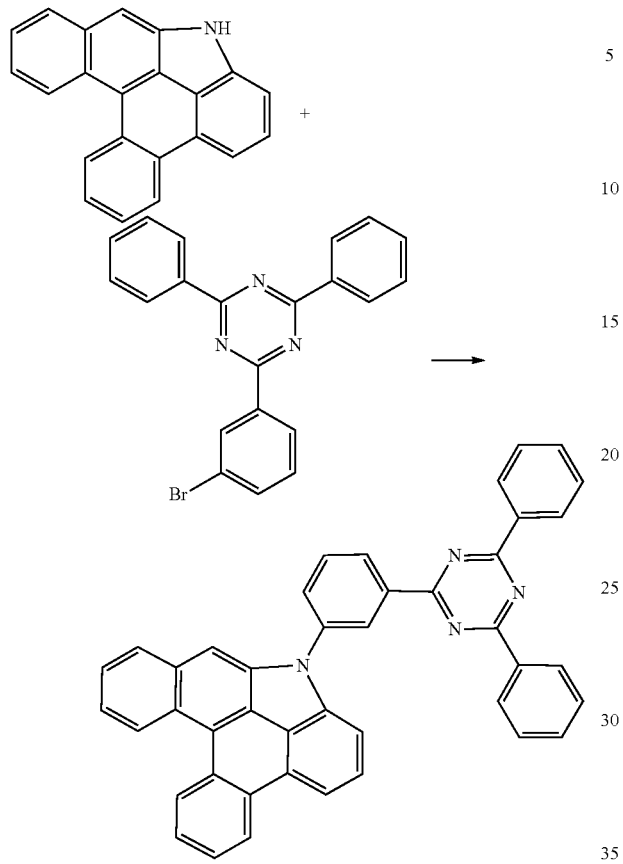

An initial charge is formed by S6a (17.92 g, 61.5 mmol), 2-(3-bromophenyl)-4,6-diphenyl-1,3,5-triazine [CAS-864377-31-1](25.2 g, 65.0 mmol) and sodium tert-butoxide (13.4 g, 139.1 mmol) in o-xylene (550 mL). Subsequently, XPhos Pd G3 (1.70 g, 2.3 mmol) is added and the reaction solution is heated to boiling for 24 h. The reaction solution is left to cool to room temperature, and the precipitated solids are filtered off with suction and washed 3× with ethanol (150 mL each time). The crude product is subjected to basic hot extraction three times with toluene over aluminum oxide, then recrystallized 2× from 1,4-dioxane and finally sublimed under high vacuum. Yield: 18.0 g (30.1 mmol, 49%); purity: >99.9% by HPLC.

The following compounds can be prepared analogously: The catalyst system used may also be $Pd_2(dba)_3$ or $Pd(OAc)_2$ together with X-Phos or S-Phos. Purification can be effected using column chromatography, hot extraction or recrystallization. Recrystallization or hot extraction can be effected using standard solvents such as ethanol, butanol, acetone, ethyl acetate, acetonitrile, toluene, xylene, dichloromethane, methanol, tetrahydrofuran, n-butyl acetate, 1,4-dioxane, or recrystallization using high boilers such as dimethyl sulfoxide, N,N-dimethylformamide, N,N-dimethylacetamide, N-methylpyrrolidone, etc.

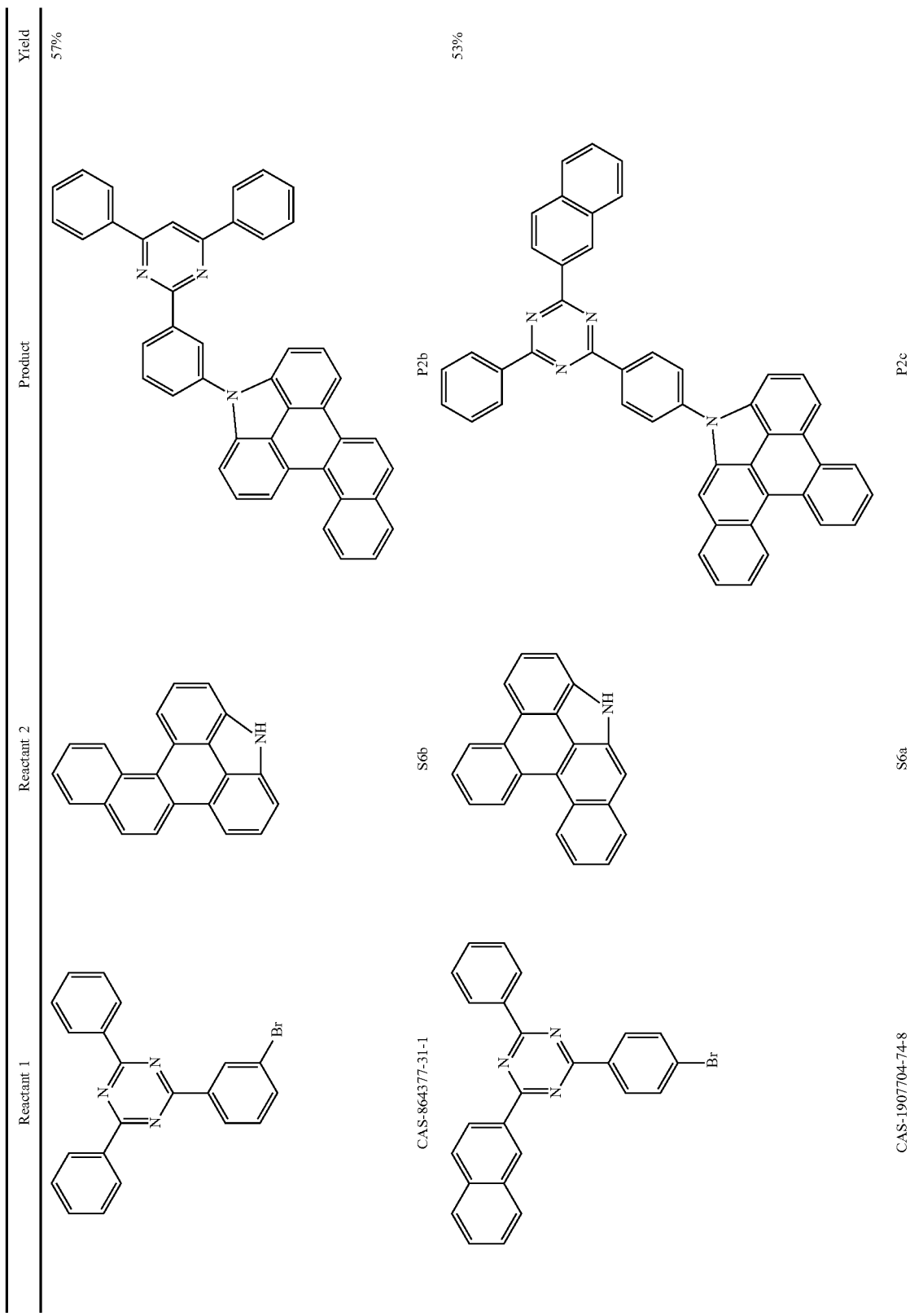

-continued
| Reactant 1 | Reactant 2 | Product | Yield |
|---|---|---|---|
| 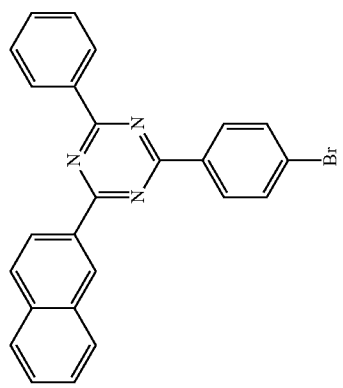<br>CAS-1907704-74-8 | 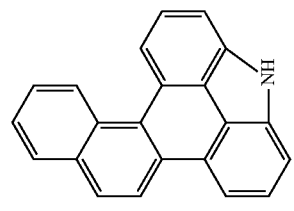<br>S6b | 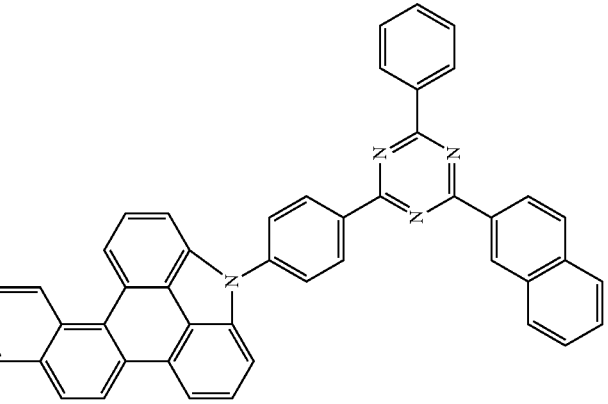<br>P2d | 53% |

| Reactant 1 | Reactant 2 | Product | Yield |
|---|---|---|---|
| CAS-1613700-80-3 | S6a | P2e | 56% |

-continued

| Reactant 1 | Reactant 2 | Product | Yield |
|---|---|---|---|
| CAS-1613700-80-3 | S6b | P2f | 43% |
| CAS-864377-22-0 | S6a | P2g | 58% |

-continued
| Reactant 1 | Reactant 2 | Product | Yield |
|---|---|---|---|
| 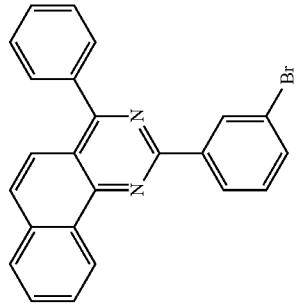<br>CAS-864377-22-0 | 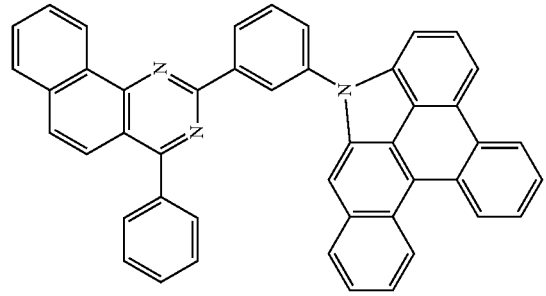<br>S6b | 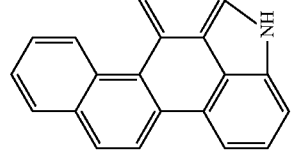<br>P2h | 58% |
| 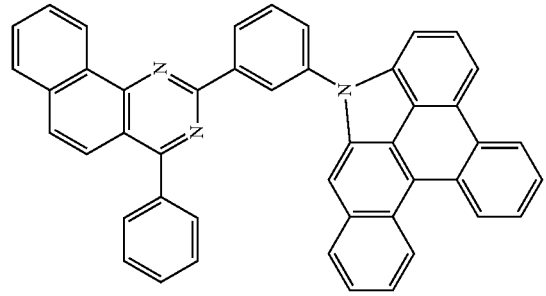<br>CAS-1646861-13-3 | 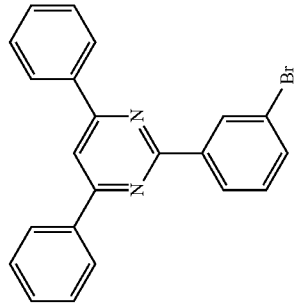<br>S6a | 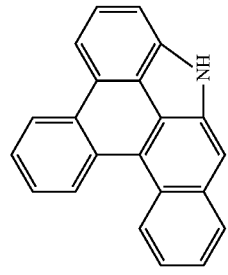<br>P2i | 66% |

-continued

| Reactant 1 | Reactant 2 | Product | Yield |
|---|---|---|---|
| CAS-1646861-13-3 | S6b | P2j | 61% |

| Reactant 1 | Reactant 2 | Product | Yield |
|---|---|---|---|
| 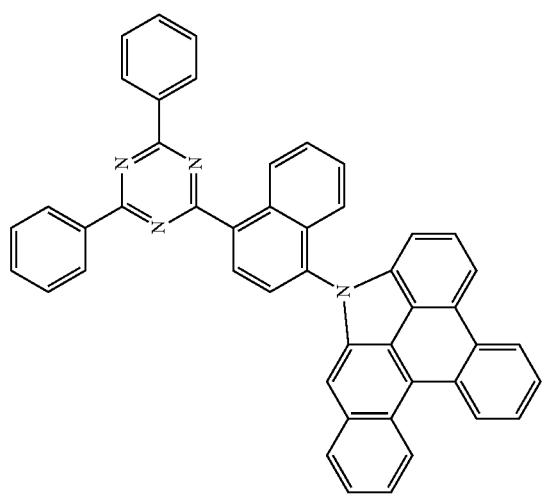<br>CAS-1800220-86-7 | 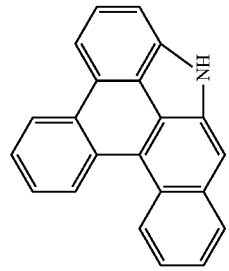<br>S6a | 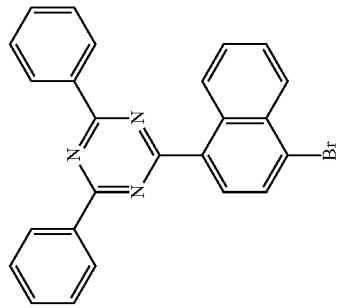<br>P2k | 40% |

| Reactant 1 | Reactant 2 | Product | Yield |
|---|---|---|---|
|  CAS-1800220-86-7 | 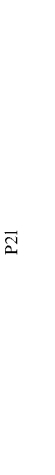 S6b | 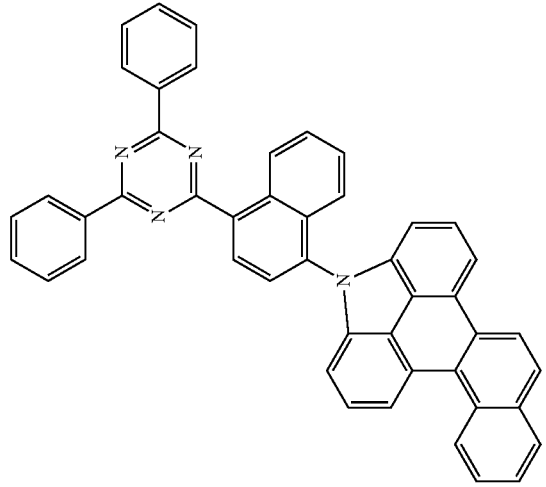 P21 | 35% |

| Reactant 1 | Reactant 2 | Product | Yield |
|---|---|---|---|
| CAS-2379260-79-2 | S6a | P21 | 46% |

| Reactant 1 | Reactant 2 | Product | Yield |
|---|---|---|---|
| 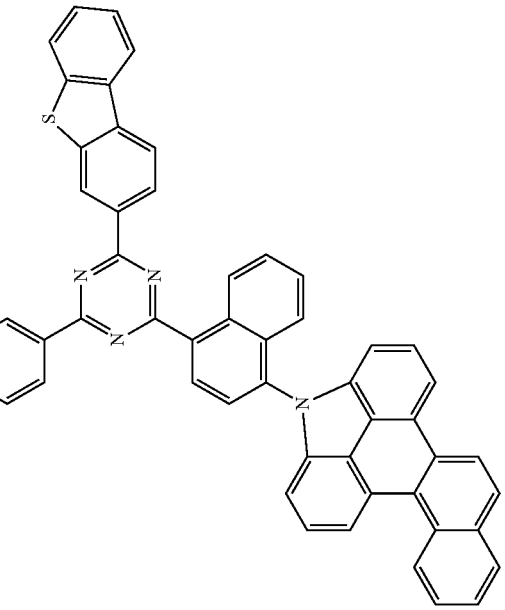 CAS-2379260-79-2 | 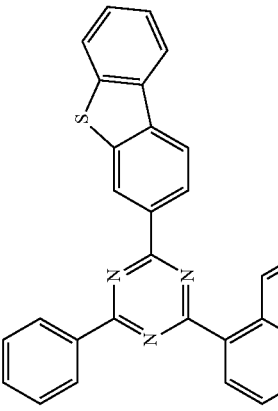 S6b | 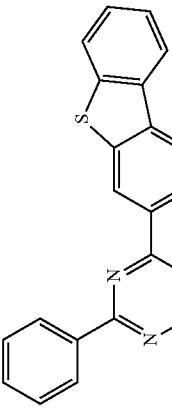 P2m | 50% |

-continued
| Reactant 1 | Reactant 2 | Product | Yield |
|---|---|---|---|
| 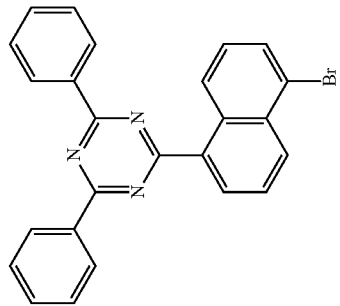<br>CAS-2377798-39-3 | 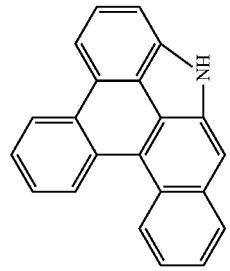<br>S6a | 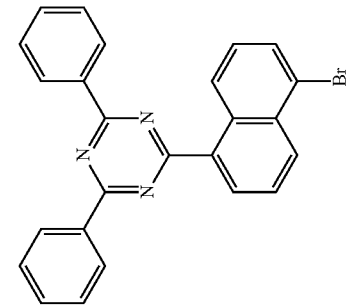<br>P2n | 59% |
| 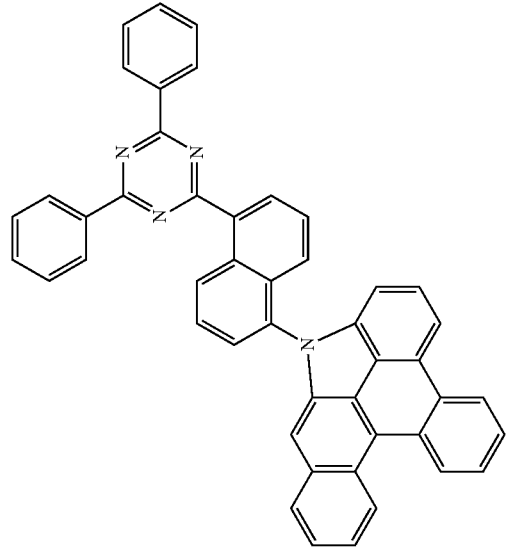<br>CAS-2377798-39-3 | 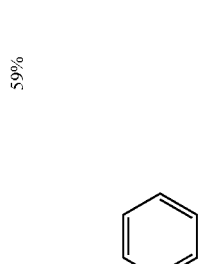<br>S6b | 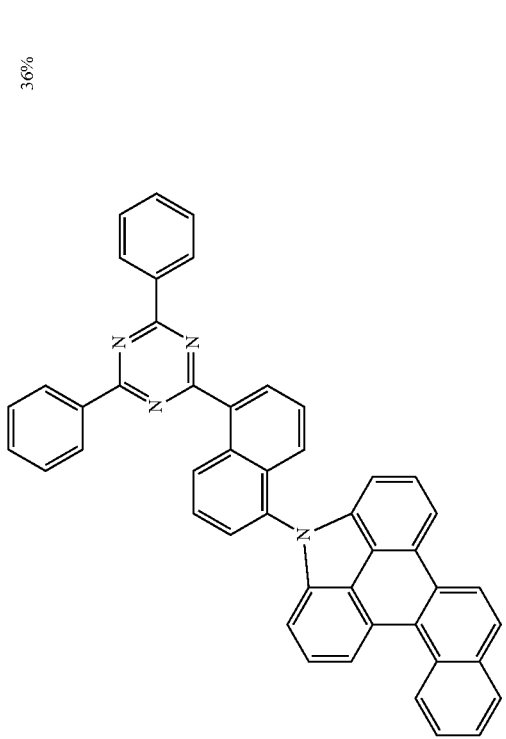<br>P2o | 36% |

| Reactant 1 | Reactant 2 | Product | Yield |
|---|---|---|---|
| 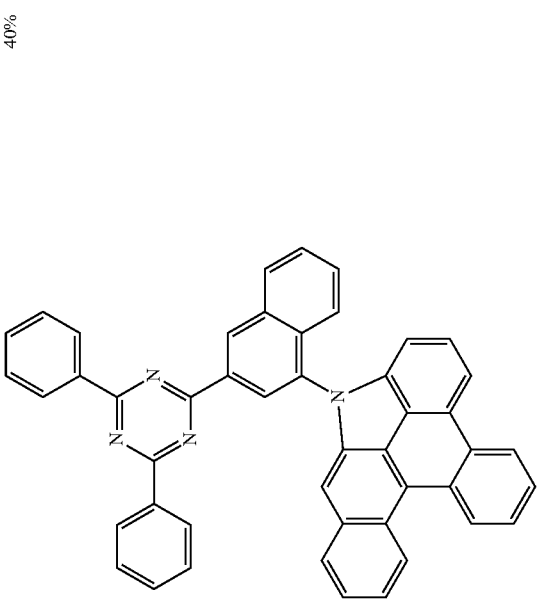 CAS-1869142-07-3 | 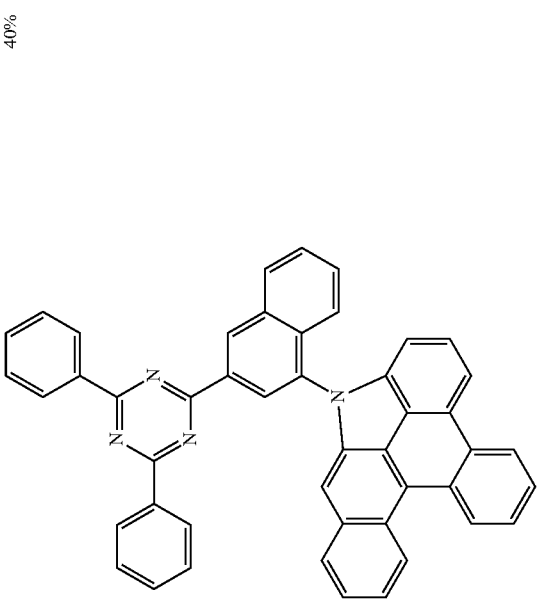 S6a | 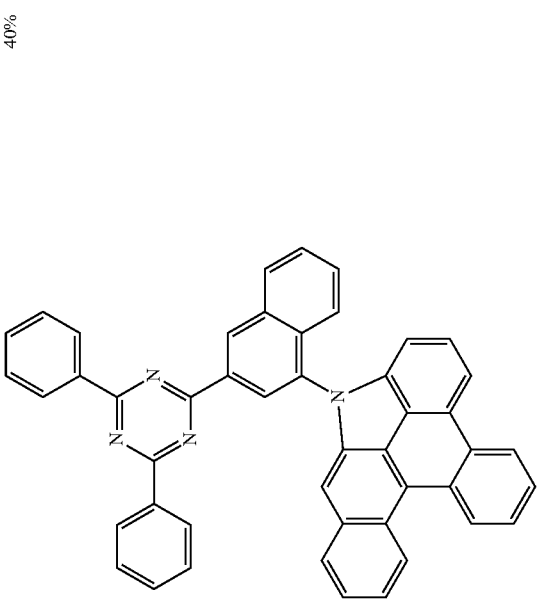 P2p | 40% |

| Reactant 1 | Reactant 2 | Product | Yield |
|---|---|---|---|
| CAS-1869142-07-3 | S6b | P2q | 41% |

| Reactant 1 | Reactant 2 | Product | Yield |
|---|---|---|---|
| 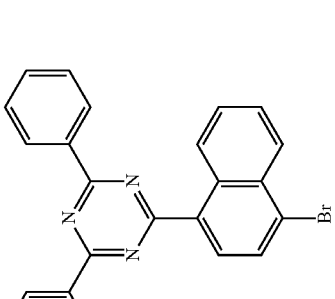 CAS-1800220-86-7 | 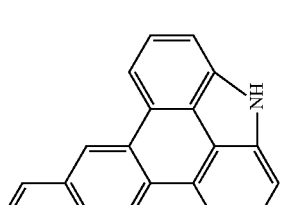 S6c | 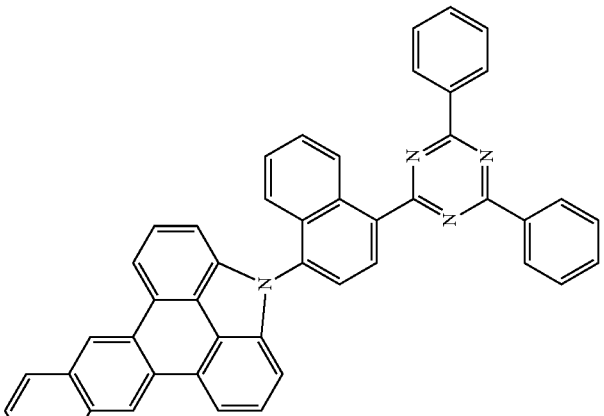 P2r | 40% |

| Reactant 1 | Reactant 2 | Product | Yield |
|---|---|---|---|
| CAS-1800220-86-7 | S6d | P2s | 17% |
| CAS-2102445-25-8 | S6b | P2t | 34% |

| Reactant 1 | Reactant 2 | Product | Yield |
|---|---|---|---|
| 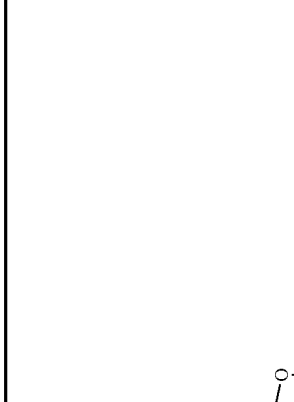<br>CAS-2408705-82-6 | 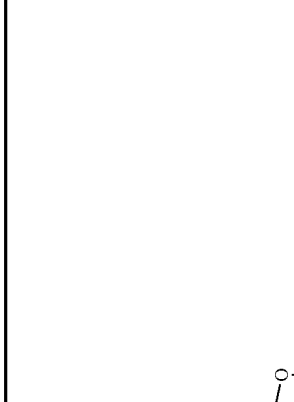<br>S6a | 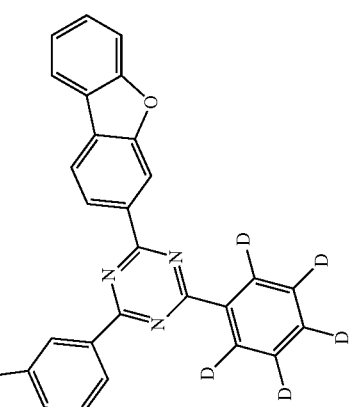<br>P2u | 38% |

| Reactant 1 | Reactant 2 | Product | Yield |
|---|---|---|---|
| 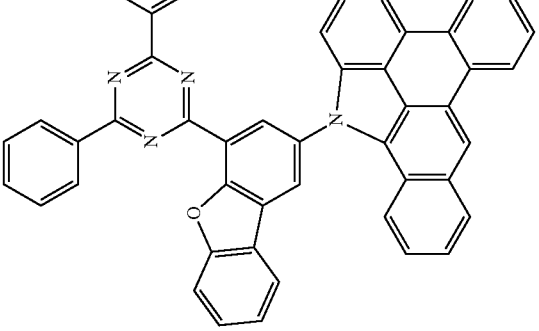 CAS-2375066-17-2 | 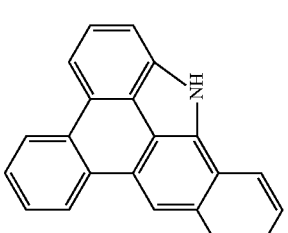 S6d | 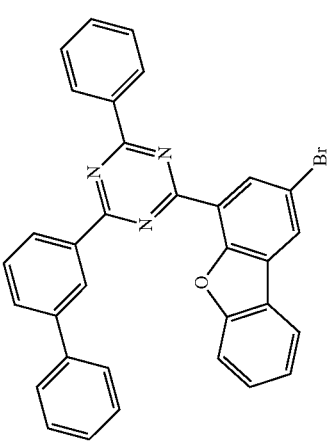 P2v | 36% |

-continued

| Reactant 1 | Reactant 2 | Product | Yield |
|---|---|---|---|
| CAS-2399473-96-0 | | P2w | 37% |
| CAS-128223310-63-3 | S6c | P2x | 44% |
|  | S6b |  |  |

| Reactant 1 | Reactant 2 | Product | Yield |
|---|---|---|---|
| CAS-185112-61-2 | S6b | P2y | 48% |
| PhBr | S6a | P2z | 61% |

-continued
| Reactant 1 | Reactant 2 | Product | Yield |
|---|---|---|---|
| 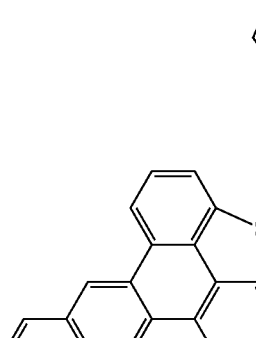 CAS-26608-06-0 | 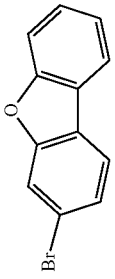 S6d | 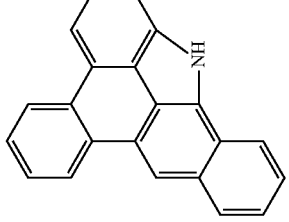 P2za | 58% |
| 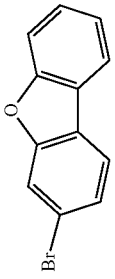 CAS-2399464-48-1 | 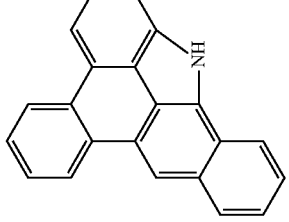 S6c | 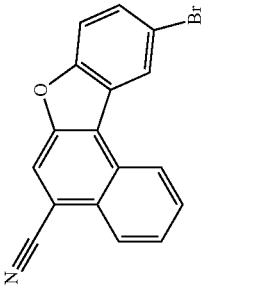 P2zb | 34% |

| Reactant 1 | Reactant 2 | Product | Yield |
|---|---|---|---|
| 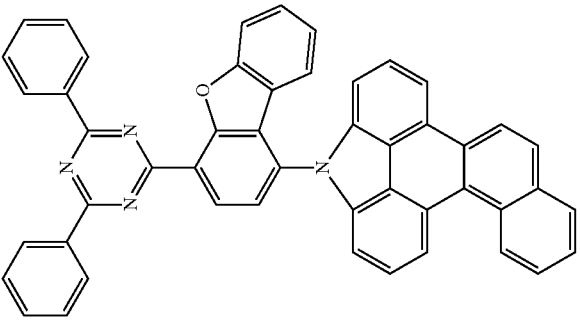 CAS-2183475-67-2 | 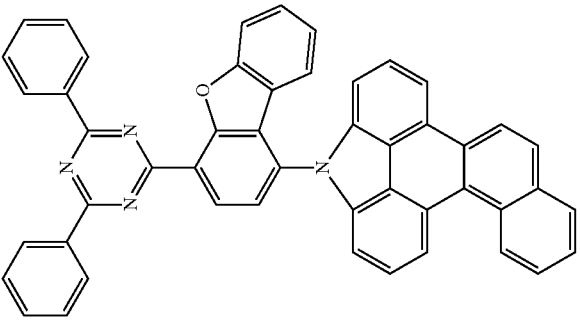 S6b | 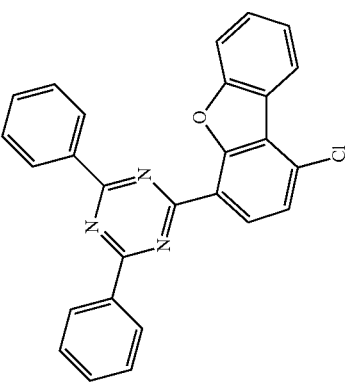 P2zc | 30% |

-continued
| Reactant 1 | Reactant 2 | Product | Yield |
|---|---|---|---|
| 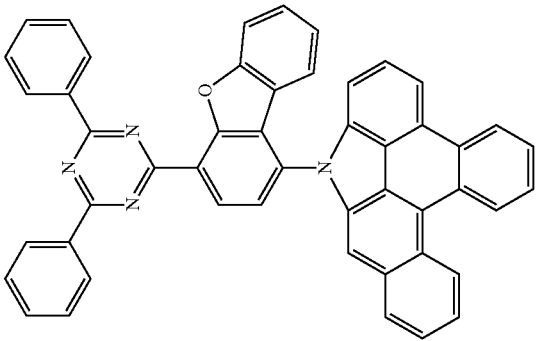 CAS-2183475-67-2 | 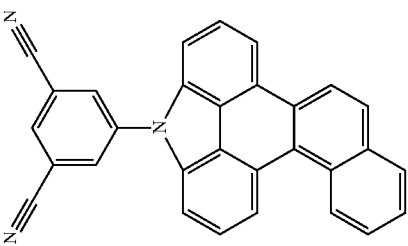 S6a | 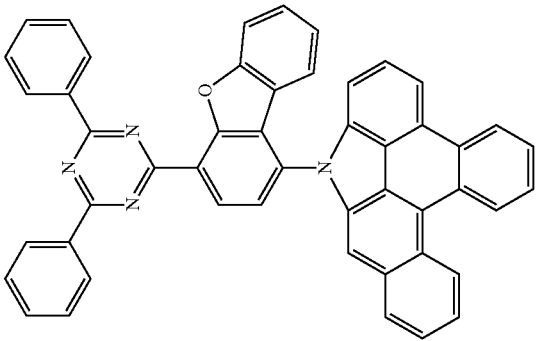 P2zd | 38% |
| 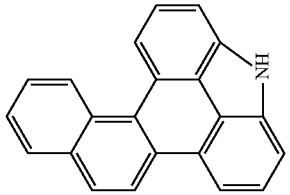 CAS-160892-07-9 | 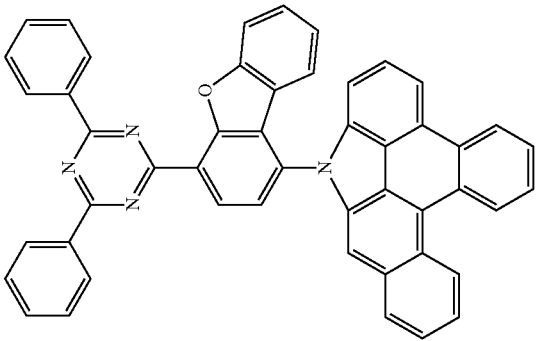 S6b | 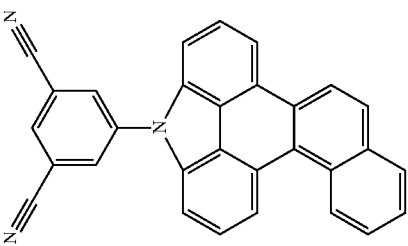 P2ze | 56% |

-continued
| Reactant 1 | Reactant 2 | Product | Yield |
|---|---|---|---|
| 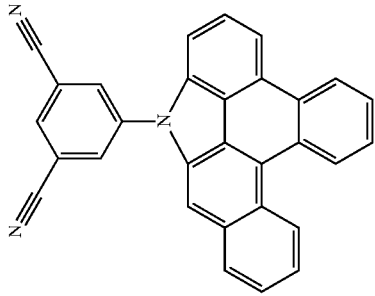<br>CAS-160892-07-9 | 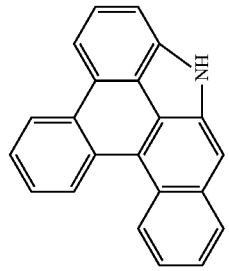<br>S6a | 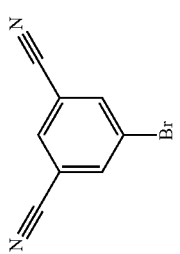<br>P2zf | 51% |

P3a

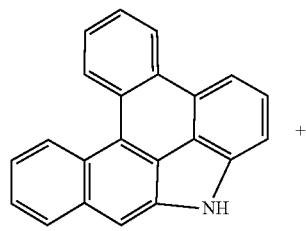

+

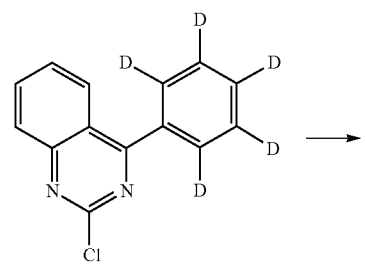

→

-continued

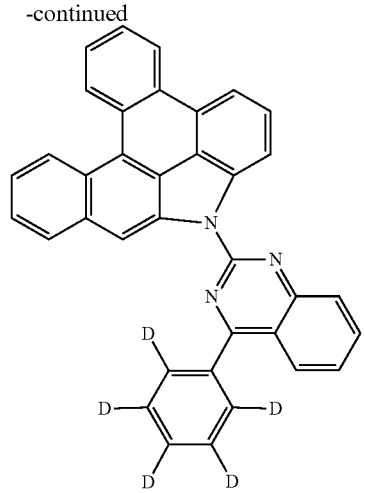

To an initial charge of S6a (17.48 g, 60.0 mmol) in DMSO (400 mL) is added sodium tert-butoxide (6.34 g, 66.0 mmol), and the mixture is stirred at room temperature for 30 min. Subsequently, 2-chloro-4-d5-phenylquinazoline (16.25 g, 66.0 mmol) [CAS-1614244-83-5] is added and the reaction is stirred at room temperature for 24 h. Subsequently, the solvent is removed under reduced pressure and the residue is extracted by stirring with 1500 mL hot ethanol. The crude product is subjected to basic hot extraction three times with o-xylene over aluminum oxide, then recrystallized 2× from DMF and finally sublimed under high vacuum. Yield: 16.52 g (33.0 mmol, 55%); purity: >99.9% by HPLC.

The following compounds can be prepared analogously: Purification can be effected using column chromatography, hot extraction or recrystallization. Recrystallization or hot extraction can be effected using standard solvents such as ethanol, butanol, acetone, ethyl acetate, acetonitrile, toluene, xylene, dichloromethane, methanol, tetrahydrofuran, n-butyl acetate, 1,4-dioxane, or recrystallization using high boilers such as dimethyl sulfoxide, N,N-dimethylformamide, N,N-dimethylacetamide, N-methylpyrrolidone, etc.

| Reactant 1 | Reactant 2 | Product | Yield |
|---|---|---|---|
| CAS-1614244-83-5 | S6b | P3b | 46% |

-continued
| Reactant 1 | Reactant 2 | Product | Yield |
|---|---|---|---|
| 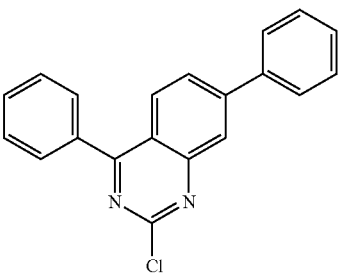 [SMILES: Clc1nc(-c2ccccc2)c2ccc(-c3ccccc3)cc2n1]<br>CAS-1709578-41-5 | 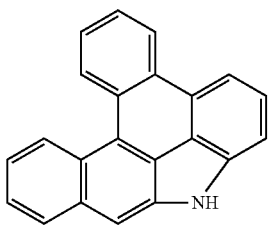 [SMILES: c1ccc2c(c1)cc1[nH]c3cccc4c5ccccc5c2c1c34]<br>S6a | 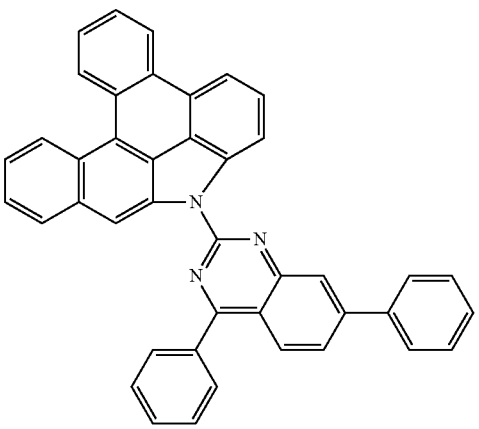 [SMILES: c1ccc(-c2ccc3c(-c4ccccc4)nc(-n4c5cccc6c7ccccc7c7c8ccccc8cc4c7c65)nc3c2)cc1]<br>P3c | 50% |
| 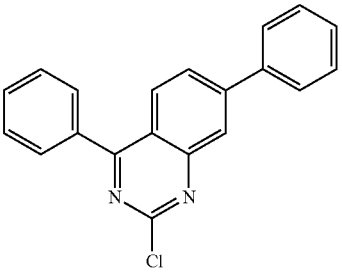 [SMILES: Clc1nc(-c2ccccc2)c2ccc(-c3ccccc3)cc2n1]<br>CAS-1709578-41-5 | 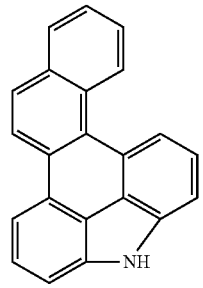 [SMILES: c1ccc2c(c1)ccc1c3cccc4[nH]c5cccc(c21)c5c43]<br>S6b | 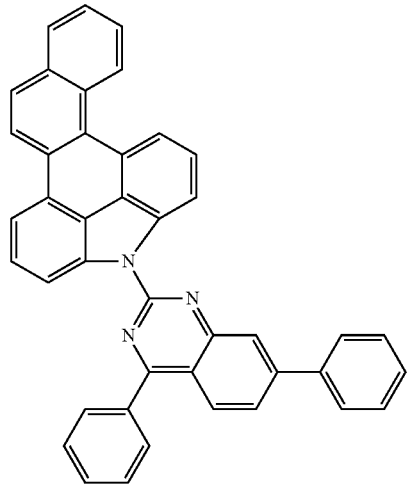 [SMILES: c1ccc(-c2ccc3c(-c4ccccc4)nc(-n4c5cccc6c7ccc8ccccc8c7c7cccc4c7c65)nc3c2)cc1]<br>P3d | 54% |
| 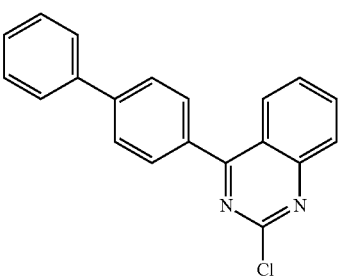 [SMILES: Clc1nc(-c2ccc(-c3ccccc3)cc2)c2ccccc2n1]<br>CAS-1262866-93-2 | 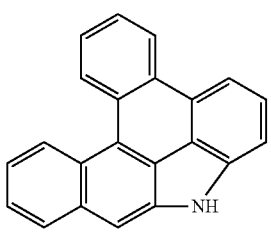 [SMILES: c1ccc2c(c1)cc1[nH]c3cccc4c5ccccc5c2c1c34]<br>S6a | 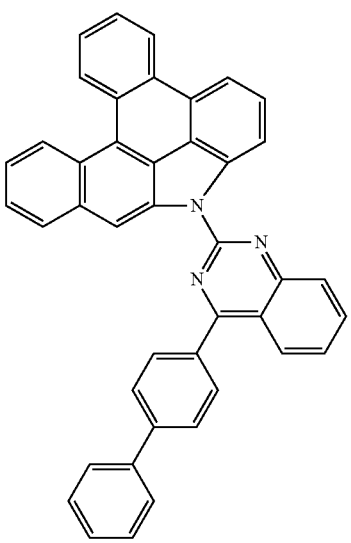 [SMILES: c1ccc(-c2ccc(-c3nc(-n4c5cccc6c7ccccc7c7c8ccccc8cc4c7c65)nc4ccccc34)cc2)cc1]<br>P3e | 55% |

-continued
| Reactant 1 | Reactant 2 | Product | Yield |
|---|---|---|---|
| 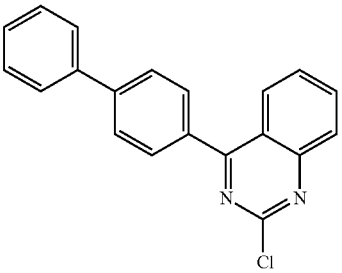 [SMILES: Clc1nc(-c2ccc(-c3ccccc3)cc2)c2ccccc2n1]<br>CAS-1262866-93-2 | 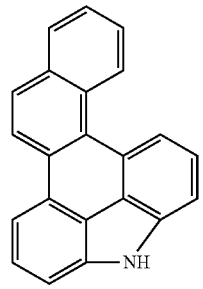 [SMILES: c1ccc2c(c1)ccc1c3cccc4[nH]c5cccc(c21)c5c43]<br>S6b | 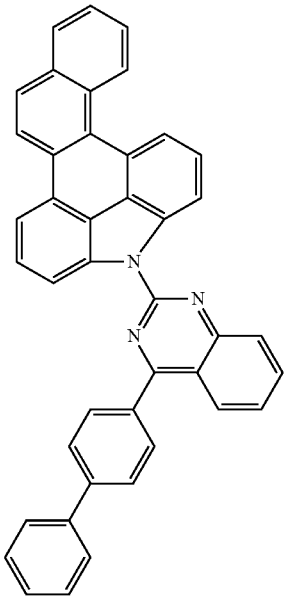 [SMILES: c1ccc(-c2ccc(-c3nc(-n4c5cccc6c7ccc8ccccc8c7c7cccc4c7c65)nc4ccccc34)cc2)cc1]<br>P3f | 48% |
| 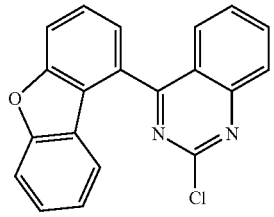<br>CAS-2075660-93-2 | 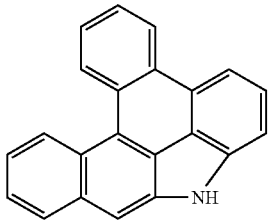 [SMILES: c1ccc2c(c1)cc1[nH]c3cccc4c5ccccc5c2c1c34]<br>S6a | 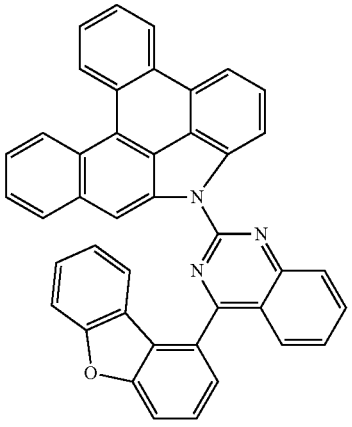 [SMILES: c1ccc2c(c1)cc1c3c2c2ccccc2c2cccc(c23)n1-c1nc(-c2cccc3oc4ccccc4c23)c2ccccc2n1]<br>P3g | 34% |
| 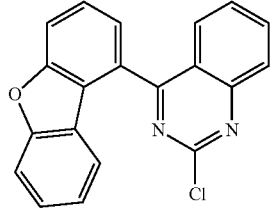 [SMILES: Clc1nc(-c2cccc3oc4ccccc4c23)c2ccccc2n1]<br>CAS-2075660-93-2 | 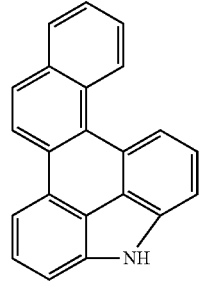 [SMILES: c1ccc2c(c1)ccc1c3cccc4[nH]c5cccc(c21)c5c43]<br>S6b | 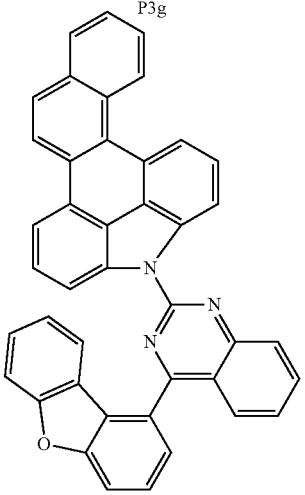<br>P3h | 41% |

-continued
| Reactant 1 | Reactant 2 | Product | Yield |
|---|---|---|---|
| 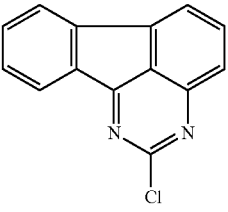 [SMILES: Clc1nc2c3c(cccc3n1)-c1ccccc1-2]<br>CAS-666854-39-3 | 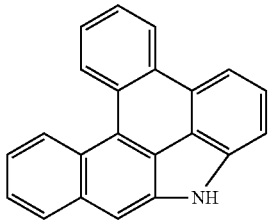 [SMILES: c1ccc2c(c1)cc1[nH]c3cccc4c5ccccc5c2c1c34]<br>S6a | 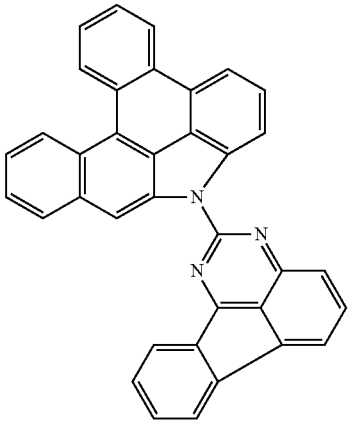 [SMILES: c1ccc2c(c1)-c1cccc3nc(-n4c5cccc6c7ccccc7c7c8ccccc8cc4c7c65)nc-2c13]<br>P3i | 57% |
| 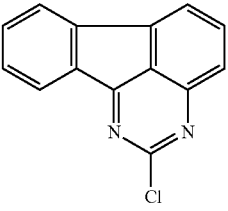 [SMILES: Clc1nc2c3c(cccc3n1)-c1ccccc1-2]<br>CAS-666854-39-3 | 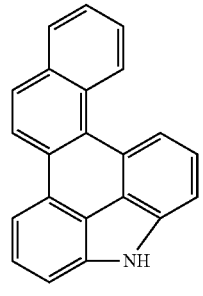<br>S6b | 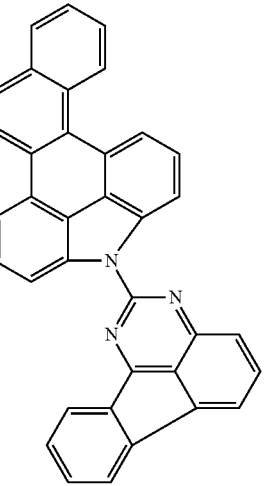<br>P3j | 50% |
| 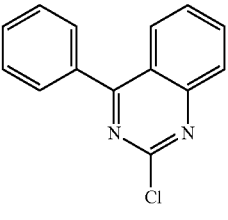 [SMILES: Clc1nc(-c2ccccc2)c2ccccc2n1]<br>CAS-29874-83-7 | 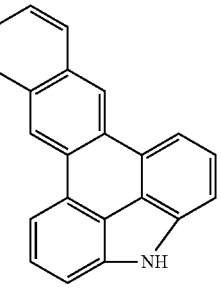<br>S6c | 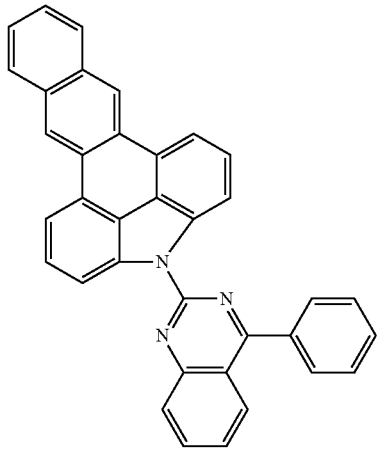 [SMILES: c1ccc(-c2nc(-n3c4cccc5c6cc7ccccc7cc6c6cccc3c6c54)nc3ccccc23)cc1]<br>P3k | 43% |

| Reactant 1 | Reactant 2 | Product | Yield |
|---|---|---|---|
| 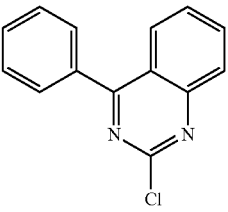 [SMILES: Clc1nc(-c2ccccc2)c2ccccc2n1]<br>CAS-29874-83-7 | 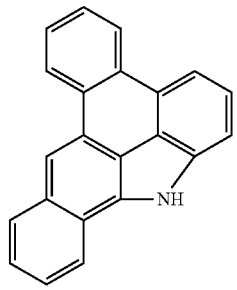 [SMILES: c1ccc2c(c1)cc1c3ccccc3c3cccc4[nH]c2c1c43]<br>S6d | 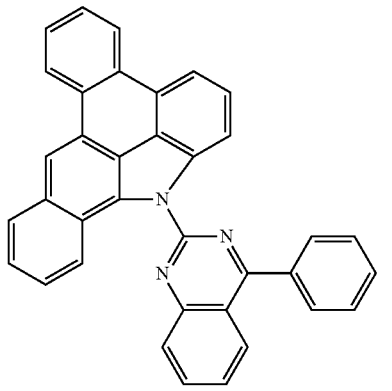 [SMILES: c1ccc(-c2nc(-n3c4cccc5c6ccccc6c6cc7ccccc7c3c6c54)nc3ccccc23)cc1]<br>P31 | 24% |

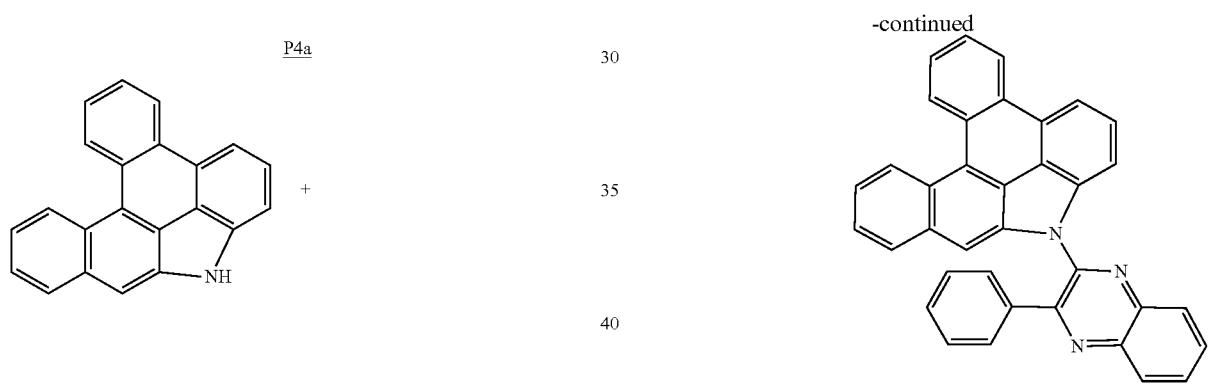

To an initial charge of S6a (17.48 g, 60.0 mmol) and 2-chloro-3-phenylquinoxaline (20.0 g, 60.0 mmol) [CAS-7065-92-1] in DMF (350 mL) is added potassium phosphate (38.20 g, 180.0 mmol), and the mixture is stirred under reflux for 24 h. After cooling, the solvent is removed under reduced pressure, and the residue obtained is suspended in 250 mL of ethanol and 250 mL of water. The solids are filtered off and washed with ethanol (5×150 mL). The crude product is subjected to basic hot extraction twice with toluene and twice with n-butyl acetate over aluminium oxide, and then sublimed under high vacuum.

Yield: 13.96 g (28.2 mmol, 47%); purity: >99.9% by HPLC.

The following compounds can be prepared analogously: Purification can be effected using column chromatography, hot extraction or recrystallization. Recrystallization or hot extraction can be effected using standard solvents such as ethanol, butanol, acetone, ethyl acetate, acetonitrile, toluene, xylene, dichloromethane, methanol, tetrahydrofuran, n-butyl acetate, 1,4-dioxane, or recrystallization using high boilers such as dimethyl sulfoxide, N,N-dimethylformamide, N,N-dimethylacetamide, N-methylpyrrolidone, etc.

| Reactant 1 | Reactant 2 | Product | Yield |
|---|---|---|---|
| 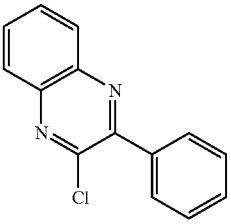 [SMILES: Clc1nc2ccccc2nc1-c1ccccc1]<br>CAS-7065-92-1 | 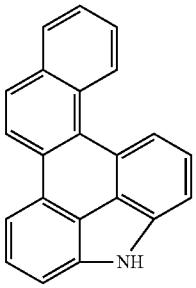 [SMILES: c1ccc2c(c1)ccc1c3cccc4[nH]c5cccc(c21)c5c43]<br>S6b | 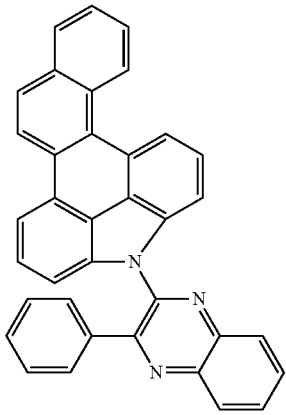 [SMILES: c1ccc(-c2nc3ccccc3nc2-n2c3cccc4c5ccc6ccccc6c5c5cccc2c5c43)cc1]<br>P4b | 50% |
| 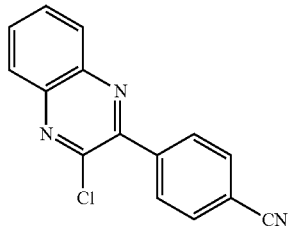 [SMILES: N#Cc1ccc(-c2nc3ccccc3nc2Cl)cc1]<br>CAS-2305856-66-8 | 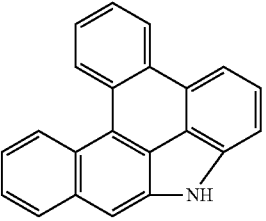 [SMILES: c1ccc2c(c1)cc1[nH]c3cccc4c5ccccc5c2c1c34]<br>S6a | 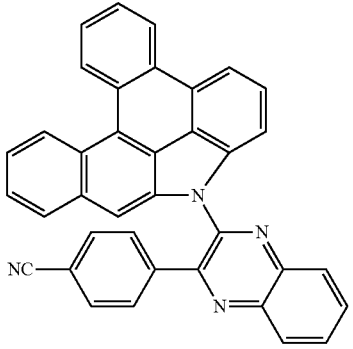 [SMILES: N#Cc1ccc(-c2nc3ccccc3nc2-n2c3cccc4c5ccccc5c5c6ccccc6cc2c5c43)cc1]<br>P4c | 51% |
| 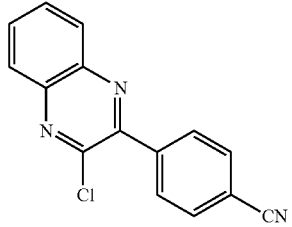 [SMILES: N#Cc1ccc(-c2nc3ccccc3nc2Cl)cc1]<br>CAS-2305856-66-8 | 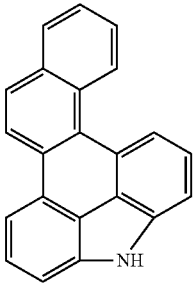 [SMILES: c1ccc2c(c1)ccc1c3cccc4[nH]c5cccc(c21)c5c43]<br>S6b | 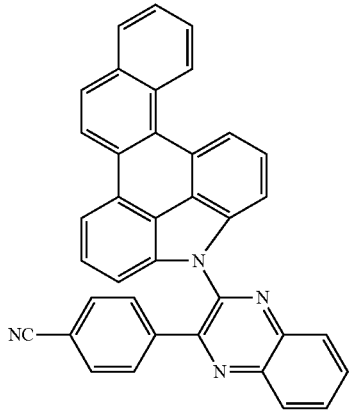 [SMILES: N#Cc1ccc(-c2nc3ccccc3nc2-n2c3cccc4c5ccc6ccccc6c5c5cccc2c5c43)cc1]<br>P4d | 45% |

-continued
| Reactant 1 | Reactant 2 | Product | Yield |
|---|---|---|---|
| 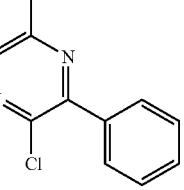<br>CAS-.2376527-28-3 | 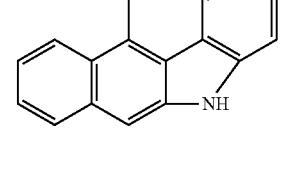<br>S6a | 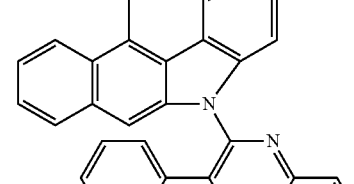<br>P4e | 50% |
| 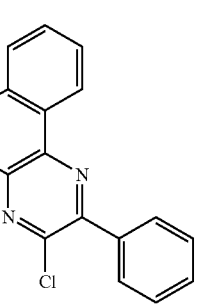<br>CAS-.2376527-28-3 | 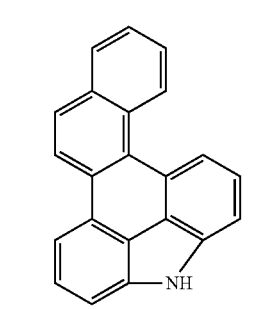 [SMILES: c1ccc2c(c1)ccc1c3cccc4[nH]c5cccc(c21)c5c43]<br>S6b | 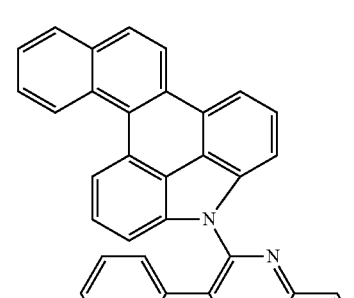<br>P4f | 50% |
| 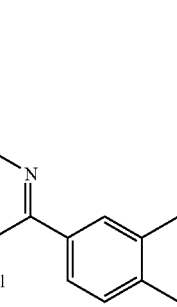<br>CAS-955938-18-8 | 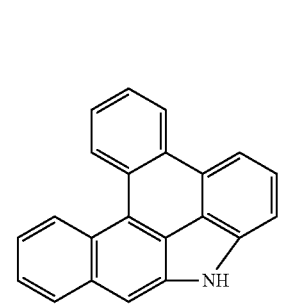 [SMILES: c1ccc2c(c1)cc1[nH]c3cccc4c5ccccc5c2c1c34]<br>S6a | 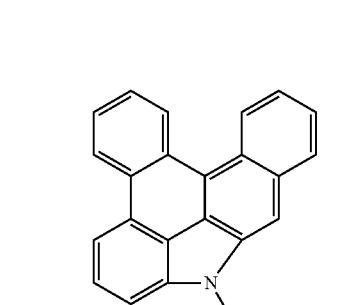<br>P4g | 32% |

| Reactant 1 | Reactant 2 | Product | Yield |
|---|---|---|---|
| 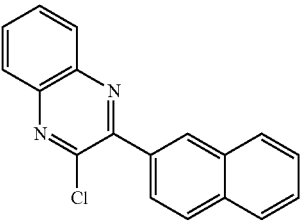 [SMILES: Clc1nc2ccccc2nc1-c1ccc2ccccc2c1] CAS-955938-18-8 | 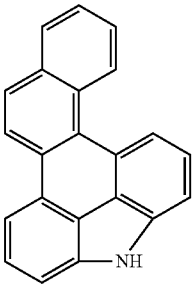 [SMILES: c1ccc2c(c1)ccc1c3cccc4[nH]c5cccc(c21)c5c43] S6b | 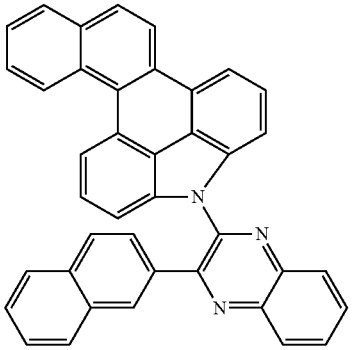 [SMILES: c1ccc2cc(-c3nc4ccccc4nc3-n3c4cccc5c6ccc7ccccc7c6c6cccc3c6c54)ccc2c1] P4h | 30% |
| 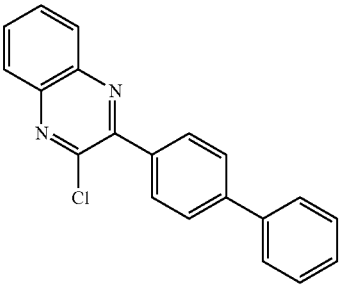 [SMILES: Clc1nc2ccccc2nc1-c1ccc(-c2ccccc2)cc1] CAS-2176462-89-6 | 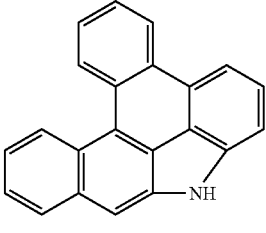 [SMILES: c1ccc2c(c1)cc1[nH]c3cccc4c5ccccc5c2c1c34] S6a | 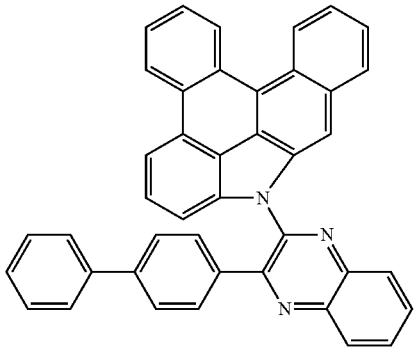 [SMILES: c1ccc(-c2ccc(-c3nc4ccccc4nc3-n3c4cccc5c6ccccc6c6c7ccccc7cc3c6c54)cc2)cc1] P4i | 38% |
| 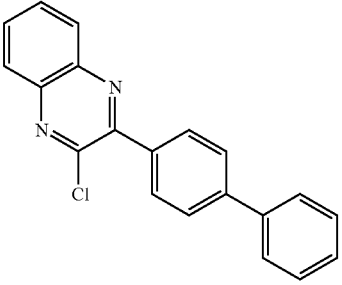 [SMILES: Clc1nc2ccccc2nc1-c1ccc(-c2ccccc2)cc1] CAS-2176462-89-6 | 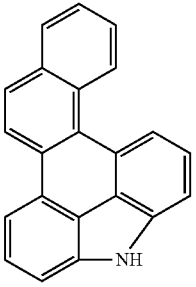 [SMILES: c1ccc2c(c1)ccc1c3cccc4[nH]c5cccc(c21)c5c43] S6b | 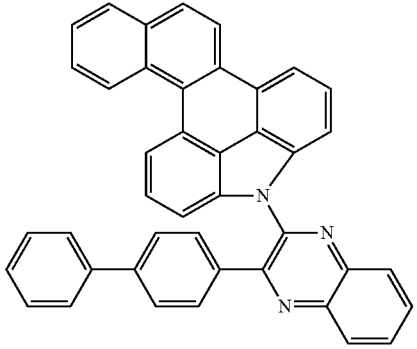 [SMILES: c1ccc(-c2ccc(-c3nc4ccccc4nc3-n3c4cccc5c6ccc7ccccc7c6c6cccc3c6c54)cc2)cc1] P4j | 40% |

-continued
| Reactant 1 | Reactant 2 | Product | Yield |
|---|---|---|---|
| 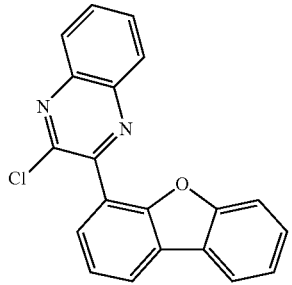 [SMILES: Clc1nc2ccccc2nc1-c1cccc2c1oc1ccccc12]<br>CAS-2245928-02-1 | 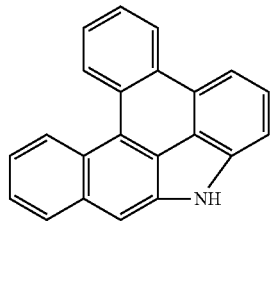 [SMILES: c1ccc2c(c1)cc1[nH]c3cccc4c5ccccc5c2c1c34]<br>S6a | 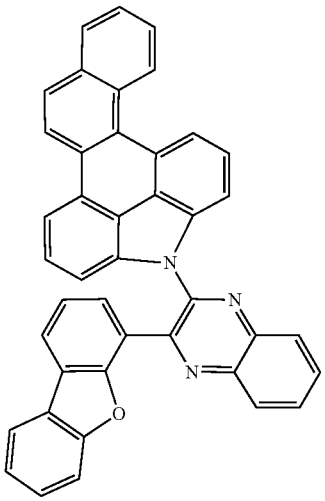 [SMILES: c1ccc2c(c1)ccc1c3cccc4c3c3c(cccc3n4-c3nc4ccccc4nc3-c3cccc4c3oc3ccccc34)c21]<br>P4k | 34% |
| 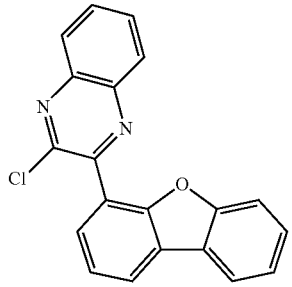 [SMILES: Clc1nc2ccccc2nc1-c1cccc2c1oc1ccccc12]<br>CAS-2245928-02-1 | 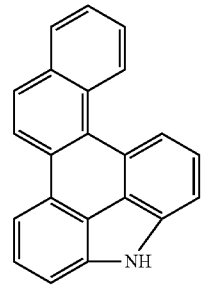 [SMILES: c1ccc2c(c1)ccc1c3cccc4[nH]c5cccc(c21)c5c43]<br>S6b | 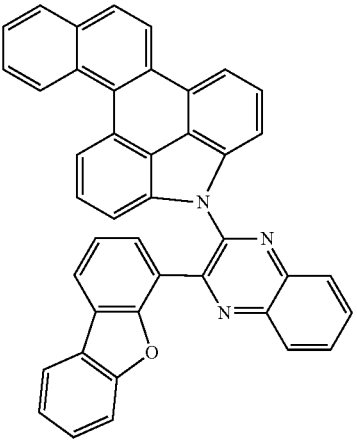 [SMILES: c1ccc2c(c1)ccc1c3cccc4c3c3c(cccc3n4-c3nc4ccccc4nc3-c3cccc4c3oc3ccccc34)c21]<br>P4l | 40% |
| 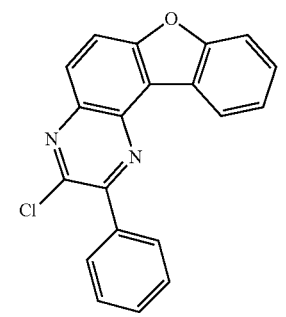 [SMILES: Clc1nc2ccc3oc4ccccc4c3c2nc1-c1ccccc1]<br>CAS-2376527-27-2 | 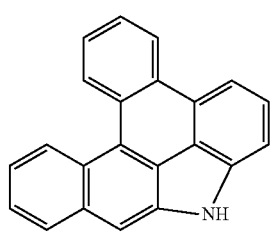 [SMILES: c1ccc2c(c1)cc1[nH]c3cccc4c5ccccc5c2c1c34]<br>S6a | 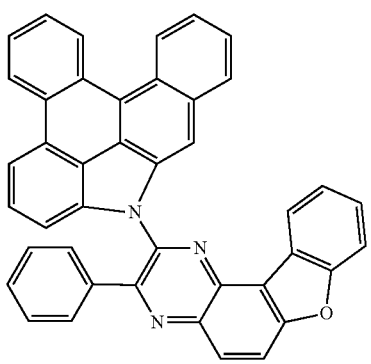 [SMILES: c1ccc(-c2nc3ccc4oc5ccccc5c4c3nc2-n2c3cccc4c5ccccc5c5c6ccccc6cc2c5c43)cc1]<br>P4m | 44% |

-continued
| Reactant 1 | Reactant 2 | Product | Yield |
|---|---|---|---|
| 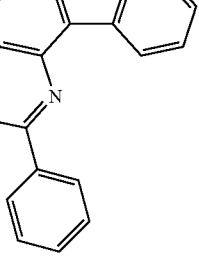<br>CAS-2376527-27-2 | 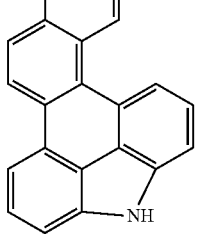<br>S6b | 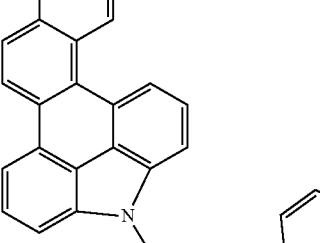<br>P4n | 32% |
| 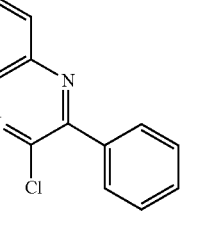<br>CAS-7065-92-1 | 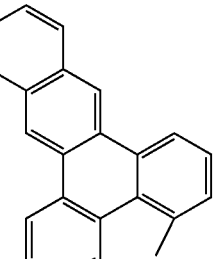<br>S6c | 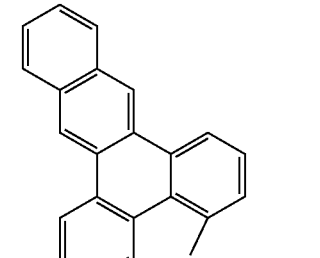<br>P4o | 36% |
P5a An initial charge of S13a (33.3 mmol) of 2-[1,1'-biphenyl]-4-yl-4-(3-bromophenyl)-6-phenyl-1,3,5-triazine (35.0 mmol) [CAS-1955546-91-4] and $K_3PO_4$ (14.14 g, 66.6 mmol) in toluene/dioxane/water (200 mL/200 mL/100 mL) is inertized for 30 min. Subsequently, triphenylphosphine (175 mg, 0.67 mmol) and $Pd_2(dba)_3$ (305 mg, 0.33 mmol) are added successively, and the mixture is stirred under reflux for 16 h. The mixture is worked up by extraction with toluene and water.

The combined organic phases are dried over $Na_2SO_4$, and the solvent is drawn off on a rotary evaporator. The crude product is subjected to hot extraction three times with toluene/heptane 1:1, then recrystallized twice from n-butyl acetate and finally sublimed under high vacuum. Yield: 10.6 g (15.7 mmol, 47%); purity: >99.9% by HPLC The following compounds can be prepared analogously: The catalyst system used may also be S-Phos or X-Phos or $P(o-tol)_3$ with $Pd_2(dba)_3$ or $Pd(OAc)_2$. Purification can be effected using column chromatography, hot extraction or recrystallization. Recrystallization or hot extraction can be effected using standard solvents such as ethanol, butanol, acetone, ethyl acetate, acetonitrile, toluene, xylene, dichloromethane, methanol, tetrahydrofuran, n-butyl acetate, 1,4-dioxane, or recrystallization using high boilers such as dimethyl sulfoxide, N,N-dimethylformamide, N,N-dimethylacetamide, N-methylpyrrolidone, etc.

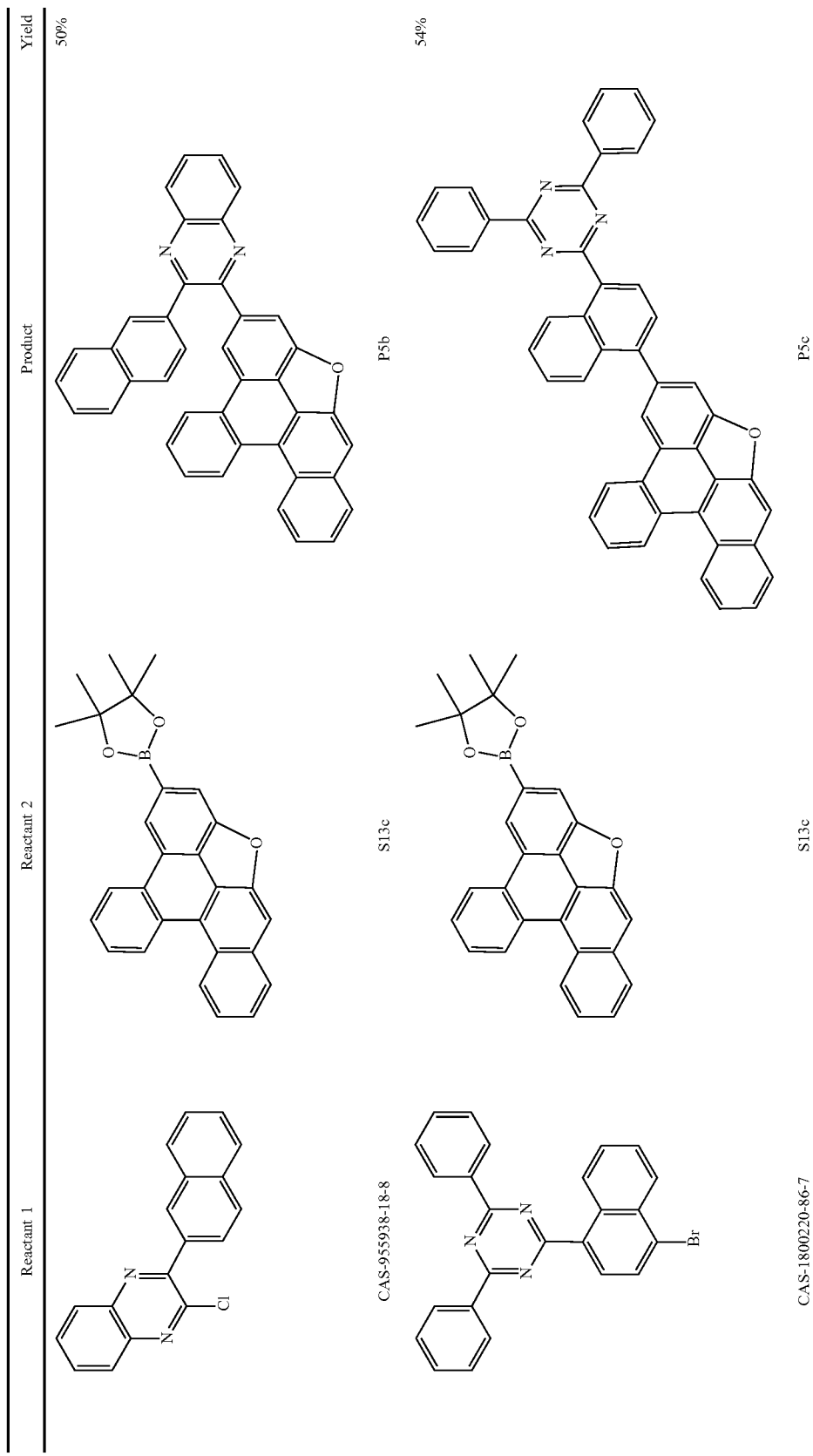

| Reactant 1 | Reactant 2 | Product | Yield |
|---|---|---|---|
| CAS-2142681-84- | S13d | P5d | 48% |
| CAS-2260688-83-1 | S13e | P5e | 56% |

| Reactant 1 | Reactant 2 | Product | Yield |
|---|---|---|---|
| CAS-6484-25-9 | S13f | P5f | 36% |
| CAS-1646861-13-3 | S13g | P5g | 25% |

| Reactant 1 | Reactant 2 | Product | Yield |
|---|---|---|---|
| 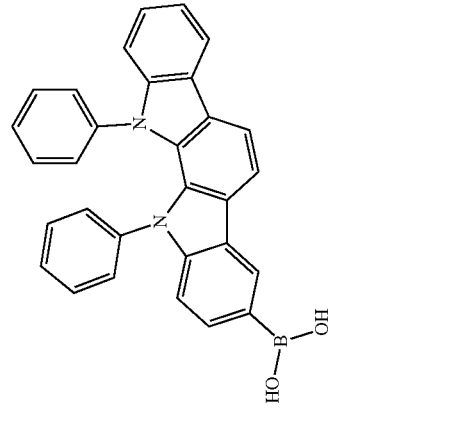 S12h | 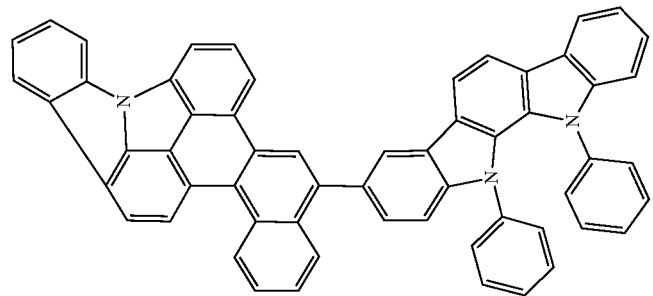 CAS-1373359-67-1 | 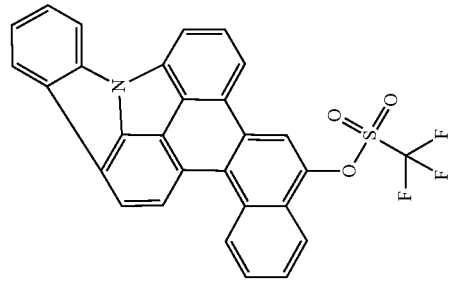 P5h | 27% |

| Reactant 1 | Reactant 2 | Product | Yield |
|---|---|---|---|
| 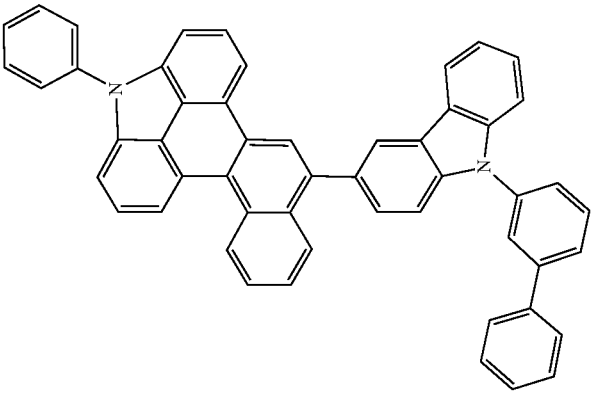 CAS-1428551-28-3 | 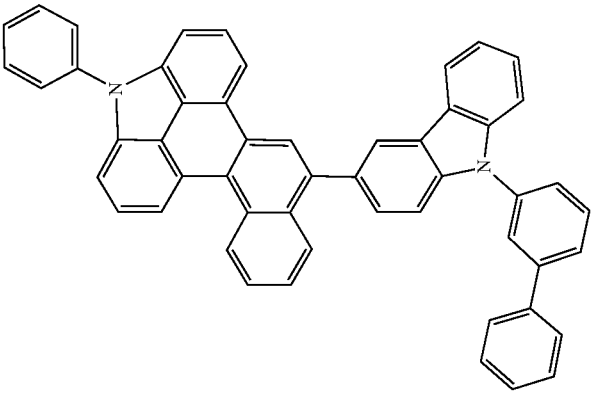 S12i | 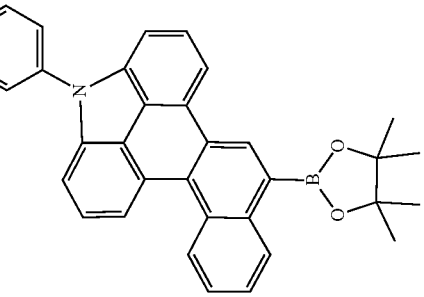 P5i | 36% |

| Reactant 1 | Reactant 2 | Product | Yield |
|---|---|---|---|
| 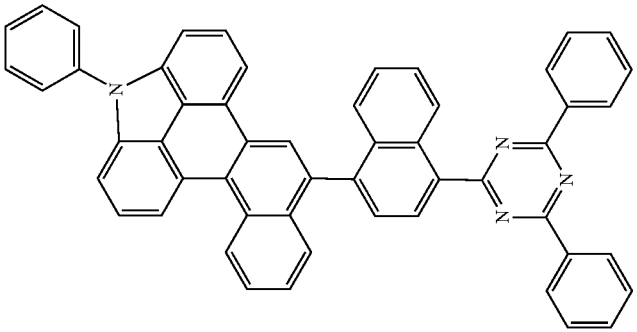 CAS-1800220-86-7 | 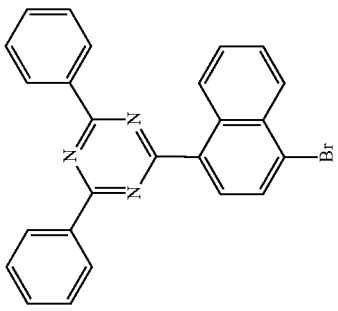 S12i | 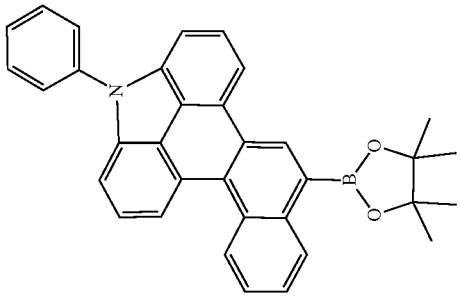 P5j | 25% |

| Reactant 1 | Reactant 2 | Product | Yield |
|---|---|---|---|
| CAS-2176462-89-6 | S13j | P5k | 18% |

| Reactant 1 | Reactant 2 | Product | Yield |
|---|---|---|---|
| 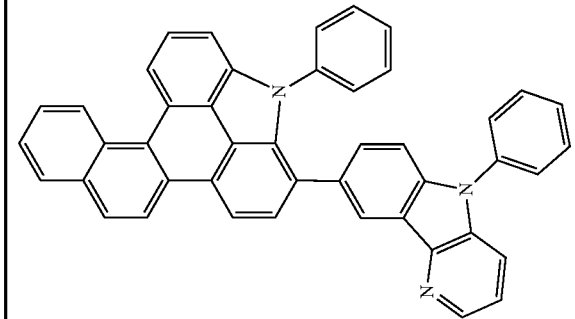 CAS-1449401-87-9 | 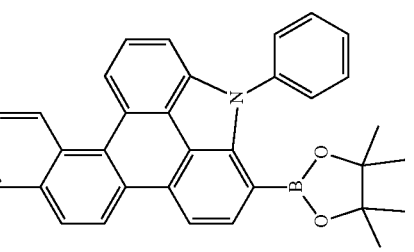 S13j | 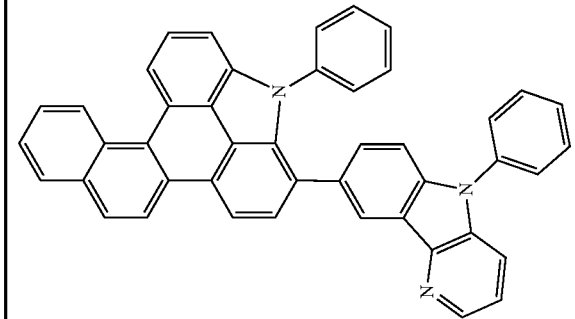 P51 | 36% |

-continued
| Reactant 1 | Reactant 2 | Product | Yield |
|---|---|---|---|
| 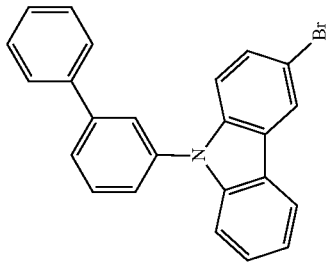 CAS-1428551-28-3 | 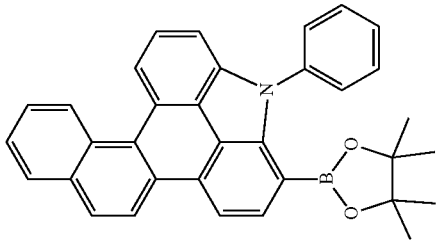 S13j | 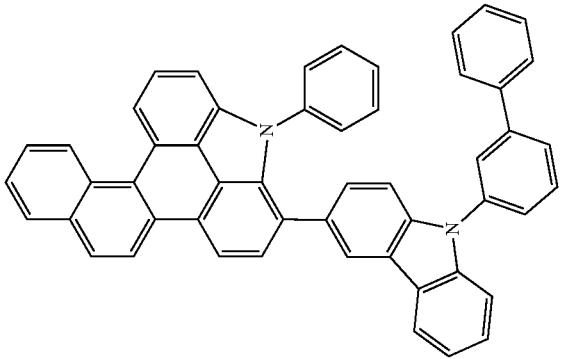 P5m | 37% |
| 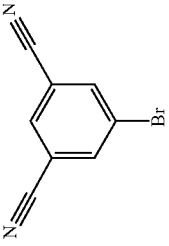 CAS-160892-07-9 | 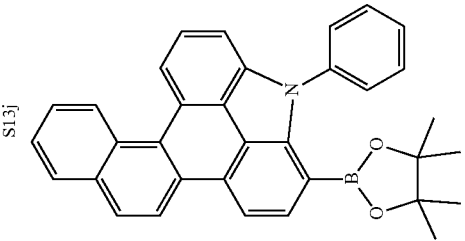 S13j | 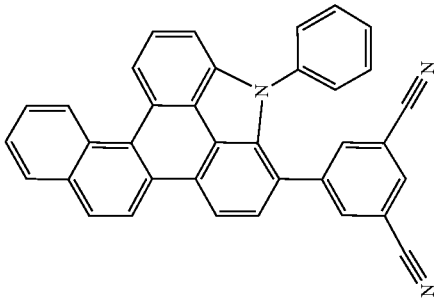 P5n | 49% |

-continued
| Reactant 1 | Reactant 2 | Product | Yield |
|---|---|---|---|
| 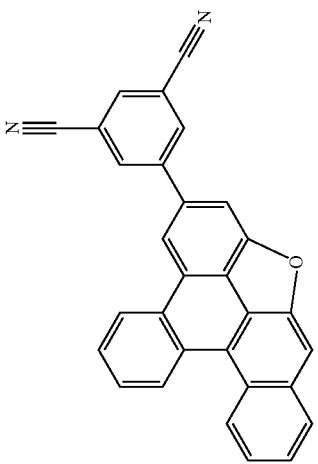<br>CAS-955959-84-9 | 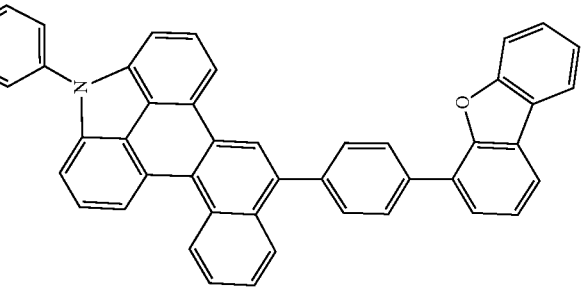<br>S12i | 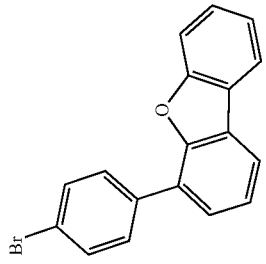<br>P5o | 45% |
| 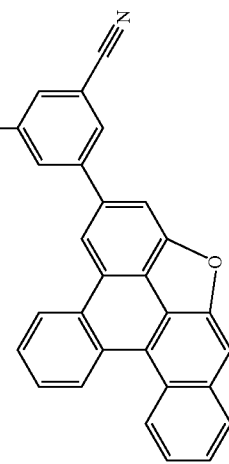<br>CAS-160892-07-9 | 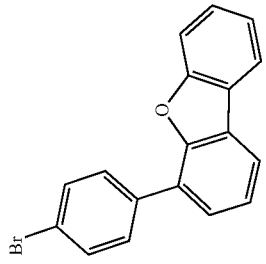<br>S13c | 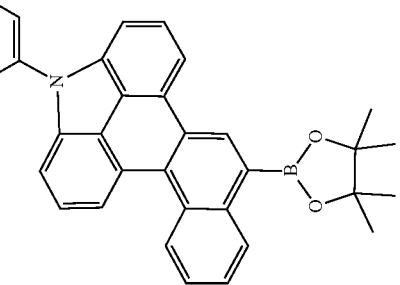<br>P5p | 60% |

-continued
| Reactant 1 | Reactant 2 | Product | Yield |
|---|---|---|---|
| 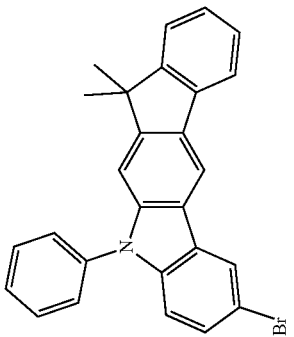<br>CAS-1257220-44-2 | 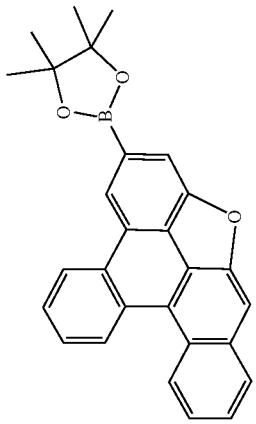 | 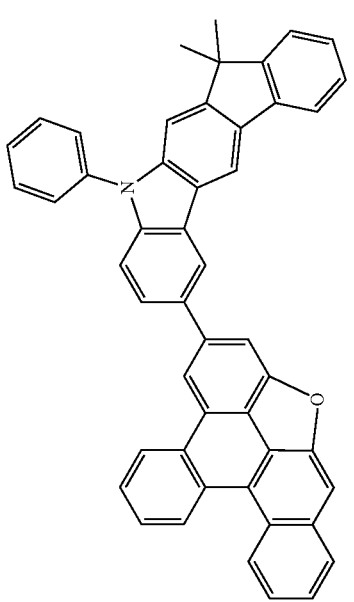<br>P5q | 48% |
| 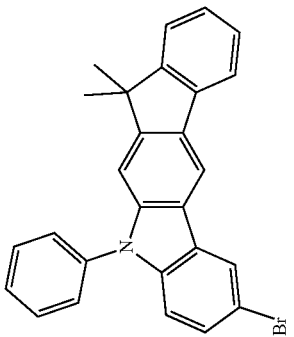<br>CAS-1614244-83-5 | 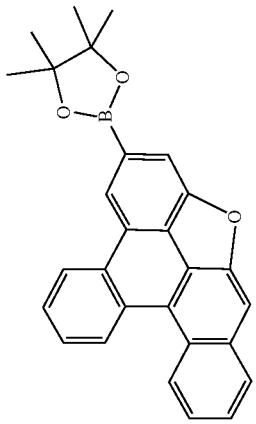<br>S13c | 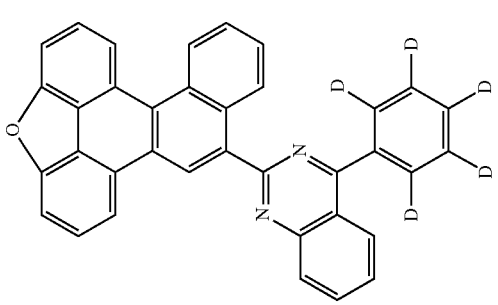<br>P5r | 32% |

Production of the OLEDs

Pretreatment for Examples V1 to E5h: Glass plates coated with structured ITO (indium tin oxide) of thickness 50 nm are treated prior to coating, first with an oxygen plasma, followed by an argon plasma. These plasma-treated glass plates form the substrates to which the OLEDs are applied.

The OLEDs basically have the following layer structure: substrate/hole injection layer (HIL)/hole transport layer (HTL)/electron blocker layer (EBL)/emission layer (EML)/ optional hole blocker layer (HBL)/electron transport layer (ETL)/optional electron injection layer (EIL) and finally a cathode. The cathode is formed by an aluminum layer of thickness 100 nm. The exact structure of the OLEDs can be found in table 1. The materials required for production of the OLEDs are shown in table 3. The data of the OLEDs are listed in table 2.

All materials are applied by thermal vapor deposition in a vacuum chamber. In this case, the emission layer always consists of at least one matrix material (host material) and an emitting dopant (emitter) which is added to the matrix material(s) in a particular proportion by volume by co-evaporation. Details given in such a form as P1a:IC2:TER1 (57%:40%:3%) mean here that the material P1a is present in the layer in a proportion by volume of 57%, IC2 in a proportion by volume of 40% and TER1 in a proportion by volume of 3%. Analogously, the electron transport layer may also consist of a mixture of two materials.

The OLEDs are characterized in a standard manner. For this purpose, the electroluminescence spectra, the external quantum efficiency (EQE, measured in %) as a function of the luminance, calculated from current-voltage-luminance characteristics assuming Lambertian radiation characteristics, and the lifetime are determined. Electroluminescence spectra are determined at a luminance of 1000 cd/m$^2$, and these are used to calculate the CIE 1931 x and y color coordinates. The parameter U1000 in table 3 refers to the voltage which is required for a luminance of 1000 cd/m$^2$. EQE1000 denotes the external quantum efficiency which is attained at 1000 cd/m$^2$. The lifetime LT is defined as the time after which the luminance drops from the starting luminance to a certain proportion L1 in the course of operation with constant current density $j_0$. A figure of L1=95% in table 3 means that the lifetime reported in the LT column corresponds to the time after which the luminance falls to 95% of its starting value.

Use of Mixtures of the Invention in the Emission Layer of Phosphorescent OLEDs

The inventive materials are used in examples E1a-E1n, E2a-E2j, E3a-E3f, E4a-E4e and E5a-E5h as matrix material in the emission layer of red-phosphorescing OLEDs. By comparison with the prior art (V1 to V5), it is possible to achieve a distinct improvement in lifetime with otherwise comparable parameters.

TABLE 1

Structure of the OLEDs

| Ex. | HIL thickness | HTL thickness | EBL thickness | EML thickness | HBL thicknes | ETL thickness | EIL thickness |
|---|---|---|---|---|---|---|---|
| V1 | SpMA1:PD1 (95%:5%) 20 nm | SpMA1 110 nm | SpMA2 10 nm | SdT1:IC2:TER1 (57%:40%:3%) 35 nm | ST2 10 nm | ST2:LiQ (50%:50%) 30 nm | LiQ 1 nm |
| E1a | SpMA1:PD1 (95%:5%) 20 nm | SpMA1 110 nm | SpMA2 10 nm | P1a:IC2:TER1 (57%:40%:3%) 35 nm | ST2 10 nm | ST2:LiQ (50%:50%) 30 nm | LiQ 1 nm |
| E1b | SpMA1:PD1 (95%:5%) 20 nm | SpMA1 110 nm | SpMA2 10 nm | P1h:IC2:TER1 (57%:40%:3%) 35 nm | ST2 10 nm | ST2:LiQ (50%:50%) 30 nm | LiQ 1 nm |
| E1c | SpMA1:PD1 (95%:5%) 20 nm | SpMA1 110 nm | SpMA2 10 nm | P1o:IC2:TER1 (57%:40%:3%) 35 nm | ST2 10 nm | ST2:LiQ (50%:50%) 30 nm | LiQ 1 nm |
| E1d | SpMA1:PD1 (95%:5%) 20 nm | SpMA1 110 nm | SpMA2 10 nm | P1za:IC2:TER1 (57%:40%:3%) 35 nm | ST2 10 nm | ST2:LiQ (50%:50%) 30 nm | LiQ 1 nm |
| E1e | SpMA1:PD1 (95%:5%) 20 nm | SpMA1 110 nm | SpMA2 10 nm | P2c:IC2:TER1 (57%:40%:3%) 35 nm | ST2 10 nm | ST2:LiQ (50%:50%) 30 nm | LiQ 1 nm |
| E1f | SpMA1:PD1 (95%:5%) 20 nm | SpMA1 110 nm | SpMA2 10 nm | P2l:IC2:TER1 (57%:40%:3%) 35 nm | ST2 10 nm | ST2:LiQ (50%:50%) 30 nm | LiQ 1 nm |
| E1g | SpMA1:PD1 (95%:5%) 20 nm | SpMA1 110 nm | SpMA2 10 nm | P2r:IC2:TER1 (57%:40%:3%) 35 nm | ST2 10 nm | ST2:LiQ (50%:50%) 30 nm | LiQ 1 nm |
| E1h | SpMA1:PD1 (95%:5%) 20 nm | SpMA1 110 nm | SpMA2 10 nm | P2u:IC2:TER1 (57%:40%:3%) 35 nm | ST2 10 nm | ST2:LiQ (50%:50%) 30 nm | LiQ 1 nm |
| E1i | SpMA1:PD1 (95%:5%) 20 nm | SpMA1 110 nm | SpMA2 10 nm | P2zc:IC2:TER1 (57%:40%:3%) 35 nm | ST2 10 nm | ST2:LiQ (50%:50%) 30 nm | LiQ 1 nm |
| E1j | SpMA1:PD1 (95%:5%) 20 nm | SpMA1 110 nm | SpMA2 10 nm | P3a:IC2:TER1 (57%:40%:3%) 35 nm | ST2 10 nm | ST2:LiQ (50%:50%) 30 nm | LiQ 1 nm |
| E1k | SpMA1:PD1 (95%:5%) 20 nm | SpMA1 110 nm | SpMA2 10 nm | P3j:IC2:TER1 (57%:40%:3%) 35 nm | ST2 10 nm | ST2:LiQ (50%:50%) 30 nm | LiQ 1 nm |
| E1l | SpMA1:PD1 (95%:5%) 20 nm | SpMA1 110 nm | SpMA2 10 nm | P4b:IC2:TER1 (57%:40%:3%) 35 nm | ST2 10 nm | ST2:LiQ (50%:50%) 30 nm | LiQ 1 nm |

TABLE 1-continued

| | | | | Structure of the OLEDs | | | |
|---|---|---|---|---|---|---|---|
| Ex. | HIL thickness | HTL thickness | EBL thickness | EML thickness | HBL thicknes | ETL thickness | EIL thickness |
| E1m | SpMA1:PD1 (95%:5%) 20 nm | SpMA1 110 nm | SpMA2 10 nm | P4c:IC2:TER1 (57%:40%:3%) 35 nm | ST2 10 nm | ST2:LiQ (50%:50%) 30 nm | LiQ 1 nm |
| E1n | SpMA1:PD1 (95%:5%) 20 nm | SpMA1 110 nm | SpMA2 10 nm | P5c:IC2:TER1 (57%:40%:3%) 35 nm | ST2 10 nm | ST2:LiQ (50%:50%) 30 nm | LiQ 1 nm |
| V2 | SpMA1:PD1 (95%:5%) 20 nm | SpMA1 110 nm | SpMA2 10 nm | SdT2:IC1:TER1 (57%:40%:3%) 35 nm | ST2 10 nm | ST2:LiQ (50%:50%) 30 nm | LiQ 1 nm |
| E2a | SpMA1:PD1 (95%:5%) 20 nm | SpMA1 110 nm | SpMA2 10 nm | P1s:IC1:TER1 (57%:40%:3%) 35 nm | ST2 10 nm | ST2:LiQ (50%:50%) 30 nm | LiQ 1 nm |
| E2b | SpMA1:PD1 (95%:5%) 20 nm | SpMA1 110 nm | SpMA2 10 nm | P1v:IC1:TER1 (57%:40%:3%) 35 nm | ST2 10 nm | ST2:LiQ (50%:50%) 30 nm | LiQ 1 nm |
| E2c | SpMA1:PD1 (95%:5%) 20 nm | SpMA1 110 nm | SpMA2 10 nm | P1x:IC1:TER1 (57%:40%:3%) 35 nm | ST2 10 nm | ST2:LiQ (50%:50%) 30 nm | LiQ 1 nm |
| E2d | SpMA1:PD1 (95%:5%) 20 nm | SpMA1 110 nm | SpMA2 10 nm | P2g:IC1:TER1 (57%:40%:3%) 35 nm | ST2 10 nm | ST2:LiQ (50%:50%) 30 nm | LiQ 1 nm |
| E2e | SpMA1:PD1 (95%:5%) 20 nm | SpMA1 110 nm | SpMA2 10 nm | P2j:IC1:TER1 (57%:40%:3%) 35 nm | ST2 10 nm | ST2:LiQ (50%:50%) 30 nm | LiQ 1 nm |
| E2f | SpMA1:PD1 (95%:5%) 20 nm | SpMA1 110 nm | SpMA2 10 nm | P3f:IC1:TER1 (57%:40%:3%) 35 nm | ST2 10 nm | ST2:LiQ (50%:50%) 30 nm | LiQ 1 nm |
| E2g | SpMA1:PD1 (95%:5%) 20 nm | SpMA1 110 nm | SpMA2 10 nm | P4l:IC1:TER1 (57%:40%:3%) 35 nm | ST2 10 nm | ST2:LiQ (50%:50%) 30 nm | LiQ 1 nm |
| E2h | SpMA1:PD1 (95%:5%) 20 nm | SpMA1 110 nm | SpMA2 10 nm | P4m:IC1:TER1 (57%:40%:3%) 35 nm | ST2 10 nm | ST2:LiQ (50%:50%) 30 nm | LiQ 1 nm |
| E2i | SpMA1:PD1 (95%:5%) 20 nm | SpMA1 110 nm | SpMA2 10 nm | P4o:IC1:TER1 (57%:40%:3%) 35 nm | ST2 10 nm | ST2:LiQ (50%:50%) 30 nm | LiQ 1 nm |
| E2j | SpMA1:PD1 (95%:5%) 20 nm | SpMA1 110 nm | SpMA2 10 nm | P5f:IC1:TER1 (57%:40%:3%) 35 nm | ST2 10 nm | ST2:LiQ (50%:50%) 30 nm | LiQ 1 nm |
| V3 | SpMA1:PD1 (95%:5%) 20 nm | SpMA1 110 nm | SpMA2 10 nm | SdT3:IC3:TER1 (57%:40%:3%) 35 nm | ST2 10 nm | ST2:LiQ (50%:50%) 30 nm | LiQ 1 nm |
| E3a | SpMA1:PD1 (95%:5%) 20 nm | SpMA1 110 nm | SpMA2 10 nm | P3b:IC3:TER1 (57%:40%:3%) 35 nm | ST2 10 nm | ST2:LiQ (50%:50%) 30 nm | LiQ 1 nm |
| E3b | SpMA1:PD1 (95%:5%) 20 nm | SpMA1 110 nm | SpMA2 10 nm | P3g:IC3:TER1 (57%:40%:3%) 35 nm | ST2 10 nm | ST2:LiQ (50%:50%) 30 nm | LiQ 1 nm |
| E3c | SpMA1:PD1 (95%:5%) 20 nm | SpMA1 110 nm | SpMA2 10 nm | P4a:IC3:TER1 (57%:40%:3%) 35 nm | ST2 10 nm | ST2:LiQ (50%:50%) 30 nm | LiQ 1 nm |
| E3d | SpMA1:PD1 (95%:5%) 20 nm | SpMA1 110 nm | SpMA2 10 nm | P4d:IC3:TER1 (57%:40%:3%) 35 nm | ST2 10 nm | ST2:LiQ (50%:50%) 30 nm | LiQ 1 nm |
| E3e | SpMA1:PD1 (95%:5%) 20 nm | SpMA1 110 nm | SpMA2 10 nm | P2s:IC3:TER1 (57%:40%:3%) 35 nm | ST2 10 nm | ST2:LiQ (50%:50%) 30 nm | LiQ 1 nm |
| E3f | SpMA1:PD1 (95%:5%) 20 nm | SpMA1 110 nm | SpMA2 10 nm | P2v:IC3:TER1 (57%:40%:3%) 35 nm | ST2 10 nm | ST2:LiQ (50%:50%) 30 nm | LiQ 1 nm |
| V4 | SpMA1:PD1 (95%:5%) 20 nm | SpMA1 110 nm | SpMA2 10 nm | IC4:SdT4:TER1 (47%:50%:3%) 35 nm | ST2 10 nm | ST2:LiQ (50%:50%) 30 nm | LiQ 1 nm |
| E4a | SpMA1:PD1 (95%:5%) 20 nm | SpMA1 110 nm | SpMA2 10 nm | IC4:P2y:TER1 (47%:50%:3%) 35 nm | ST2 10 nm | ST2:LiQ (50%:50%) 30 nm | LiQ 1 nm |
| E4b | SpMA1:PD1 (95%:5%) 20 nm | SpMA1 110 nm | SpMA2 10 nm | IC4:P5h:TER1 (57%:40%:3%) 35 nm | ST2 10 nm | ST2:LiQ (50%:50%) 30 nm | LiQ 1 nm |
| E4c | SpMA1:PD1 (95%:5%) 20 nm | SpMA1 110 nm | SpMA2 10 nm | IC4:P5i:TER1 (57%:40%:3%) 35 nm | ST2 10 nm | ST2:LiQ (50%:50%) 30 nm | LiQ 1 nm |
| E4d | SpMA1:PD1 (95%:5%) 20 nm | SpMA1 110 nm | SpMA2 10 nm | IC4:P5l:TER1 (47%:50%:3%) 35 nm | ST2 10 nm | ST2:LiQ (50%:50%) 30 nm | LiQ 1 nm |

TABLE 1-continued

Structure of the OLEDs

| Ex. | HIL thickness | HTL thickness | EBL thickness | EML thickness | HBL thicknes | ETL thickness | EIL thickness |
|---|---|---|---|---|---|---|---|
| E4e | SpMA1:PD1 (95%:5%) 20 nm | SpMA1 110 nm | SpMA2 10 nm | IC4:P5q:TER1 (47%:50%:3%) 35 nm | ST2 10 nm | ST2:LiQ (50%:50%) 30 nm | LiQ 1 nm |
| V5 | SpMA1:PD1 (95%:5%) 20 nm | SpMA1 110 nm | SpMA2 10 nm | SdT5:IC2:TER1 (57%:40%:3%) 35 nm | ST2 10 nm | ST2:LiQ (50%:50%) 30 nm | LiQ 1 nm |
| E5a | SpMA1:PD1 (95%:5%) 20 nm | SpMA1 110 nm | SpMA2 10 nm | P5a:IC2:TER1 (57%:40%:3%) 35 nm | ST2 10 nm | ST2:LiQ (50%:50%) 30 nm | LiQ 1 nm |
| E5b | SpMA1:PD1 (95%:5%) 20 nm | SpMA1 110 nm | SpMA2 10 nm | P5c:IC2:TER1 (57%:40%:3%) 35 nm | ST2 10 nm | ST2:LiQ (50%:50%) 30 nm | LiQ 1 nm |
| E5c | SpMA1:PD1 (95%:5%) 20 nm | SpMA1 110 nm | SpMA2 10 nm | P5d:IC2:TER1 (57%:40%:3%) 35 nm | ST2 10 nm | ST2:LiQ (50%:50%) 30 nm | LiQ 1 nm |
| E5d | SpMA1:PD1 (95%:5%) 20 nm | SpMA1 110 nm | SpMA2 10 nm | P5b:IC2:TER1 (57%:40%:3%) 35 nm | ST2 10 nm | ST2:LiQ (50%:50%) 30 nm | LiQ 1 nm |
| E5e | SpMA1:PD1 (95%:5%) 20 nm | SpMA1 110 nm | SpMA2 10 nm | P5e:IC2:TER1 (57%:40%:3%) 35 nm | ST2 10 nm | ST2:LiQ (50%:50%) 30 nm | LiQ 1 nm |
| E5f | SpMA1:PD1 (95%:5%) 20 nm | SpMA1 110 nm | SpMA2 10 nm | P5f:IC2:TER1 (57%:40%:3%) 35 nm | ST2 10 nm | ST2:LiQ (50%:50%) 30 nm | LiQ 1 nm |
| E5g | SpMA1:PD1 (95%:5%) 20 nm | SpMA1 110 nm | SpMA2 10 nm | P5g:IC2:TER1 (57%:40%:3%) 35 nm | ST2 10 nm | ST2:LiQ (50%:50%) 30 nm | LiQ 1 nm |
| E5h | SpMA1:PD1 (95%:5%) 20 nm | SpMA1 110 nm | SpMA2 10 nm | P5p:IC2:TER1 (57%:40%:3%) 35 nm | ST2 10 nm | ST2:LiQ (50%:50%) 30 nm | LiQ 1 nm |

TABLE 2

Data of the OLEDs

| Ex. | U1000 (V) | EQE 1000 (%) | CIE x/y at 1000 cd/m² | $j_0$ (mA/cm²) | L1 (%) | LT (h) |
|---|---|---|---|---|---|---|
| V1 | 3.4 | 25.3 | 0.66/0.33 | 60 | 95 | 34 |
| E1a | 3.3 | 25.9 | 0.67/0.33 | 60 | 95 | 95 |
| E1b | 3.2 | 25.2 | 0.66/0.33 | 60 | 95 | 82 |
| E1c | 3.3 | 25.6 | 0.67/0.33 | 60 | 95 | 111 |
| E1d | 3.4 | 25.0 | 0.66/0.33 | 60 | 95 | 64 |
| E1e | 3.3 | 24.7 | 0.66/0.33 | 60 | 95 | 82 |
| E1f | 3.2 | 25.6 | 0.66/0.33 | 60 | 95 | 147 |
| E1g | 3.4 | 24.4 | 0.67/0.33 | 60 | 95 | 122 |
| E1h | 3.3 | 26.0 | 0.66/0.33 | 60 | 95 | 126 |
| E1i | 3.2 | 26.2 | 0.66/0.33 | 60 | 95 | 154 |
| E1j | 3.7 | 25.2 | 0.66/0.33 | 60 | 95 | 225 |
| E1k | 3.7 | 24.6 | 0.66/0.33 | 60 | 95 | 185 |
| E1l | 3.4 | 25.7 | 0.67/0.33 | 60 | 95 | 132 |
| E1m | 3.3 | 24.3 | 0.67/0.33 | 60 | 95 | 110 |
| E1n | 3.2 | 26.2 | 0.67/0.33 | 60 | 95 | 59 |
| V2 | 3.4 | 25.9 | 0.66/0.33 | 60 | 95 | 19 |
| E2a | 3.3 | 25.6 | 0.66/0.33 | 60 | 95 | 53 |
| E2b | 3.4 | 25.2 | 0.66/0.33 | 60 | 95 | 40 |
| E2c | 3.2 | 25.8 | 0.66/0.33 | 60 | 95 | 62 |
| E2d | 3.4 | 24.7 | 0.67/0.33 | 60 | 95 | 34 |
| E2e | 3.6 | 23.9 | 0.67/0.33 | 60 | 95 | 78 |
| E2f | 3.8 | 25.0 | 0.66/0.33 | 60 | 95 | 236 |
| E2g | 3.3 | 26.0 | 0.66/0.33 | 60 | 95 | 117 |
| E2h | 3.4 | 25.7 | 0.66/0.33 | 60 | 95 | 103 |
| E2i | 3.6 | 24.5 | 0.67/0.33 | 60 | 95 | 90 |
| E2 | 3.9 | 24.8 | 0.67/0.33 | 60 | 95 | 33 |
| V3 | 3.8 | 24.9 | 0.66/0.33 | 60 | 95 | 67 |
| E3a | 3.8 | 25.4 | 0.67/0.33 | 60 | 95 | 201 |
| E3b | 3.7 | 24.5 | 0.66/0.33 | 60 | 95 | 132 |
| E3c | 3.4 | 25.8 | 0.66/0.33 | 60 | 95 | 115 |
| E3d | 3.4 | 24.7 | 0.67/0.33 | 60 | 95 | 102 |
| E3e | 3.6 | 26.0 | 0.66/0.33 | 60 | 95 | 167 |
| E3f | 3.3 | 26.0 | 0.66/0.33 | 60 | 95 | 126 |
| V4 | 3.9 | 24.2 | 0.66/0.33 | 60 | 95 | 36 |
| E4a | 3.7 | 24.4 | 0.66/0.33 | 60 | 95 | 52 |
| E4b | 3.4 | 25.0 | 0.67/0.33 | 60 | 95 | 82 |
| E4c | 3.5 | 25.2 | 0.66/0.33 | 60 | 95 | 91 |
| E4d | 3.4 | 24.7 | 0.66/0.33 | 60 | 95 | 65 |
| E4e | 3.8 | 24.0 | 0.66/0.33 | 60 | 95 | 57 |
| V5 | 3.7 | 24.1 | 0.66/0.33 | 60 | 95 | 12 |
| E5a | 3.4 | 25.0 | 0.66/0.33 | 60 | 95 | 34 |
| E5b | 3.5 | 25.1 | 0.67/0.33 | 60 | 95 | 62 |
| E5c | 3.6 | 24.7 | 0.67/0.33 | 60 | 95 | 45 |
| E5d | 3.3 | 24.4 | 0.66/0.33 | 60 | 95 | 84 |
| E5e | 3.5 | 24.0 | 0.66/0.33 | 60 | 95 | 39 |
| E5f | 3.7 | 24.3 | 0.66/0.33 | 60 | 95 | 49 |
| E5g | 3.8 | 23.9 | 0.66/0.33 | 60 | 95 | 146 |
| E5h | 3.9 | 24.1 | 0.67/0.33 | 60 | 95 | 32 |

TABLE 3
Structural formulae of the materials of the OLEDs used, if not already described before:
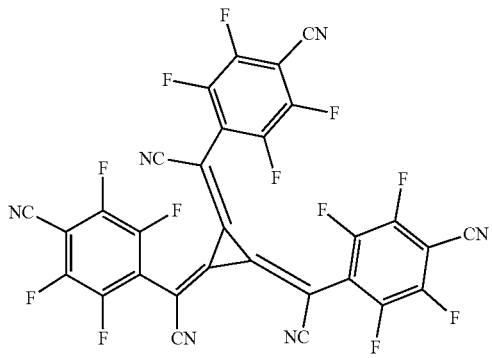
PD1 (CAS 1224447-88-4)
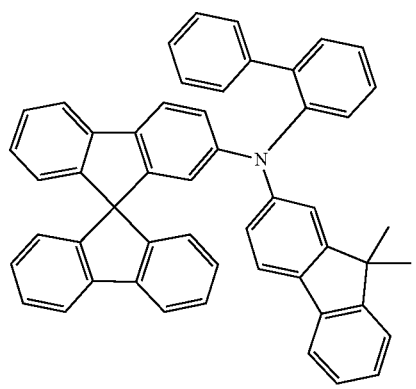
SpMA1
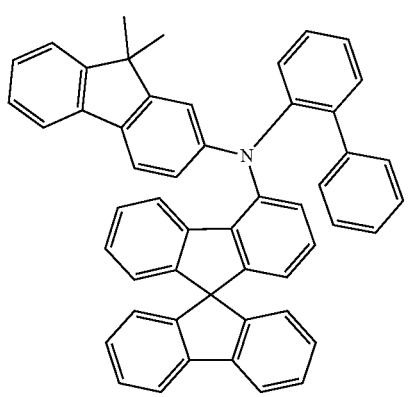
SpMA2
TABLE 3-continued
Structural formulae of the materials of the OLEDs used, if not already described before:
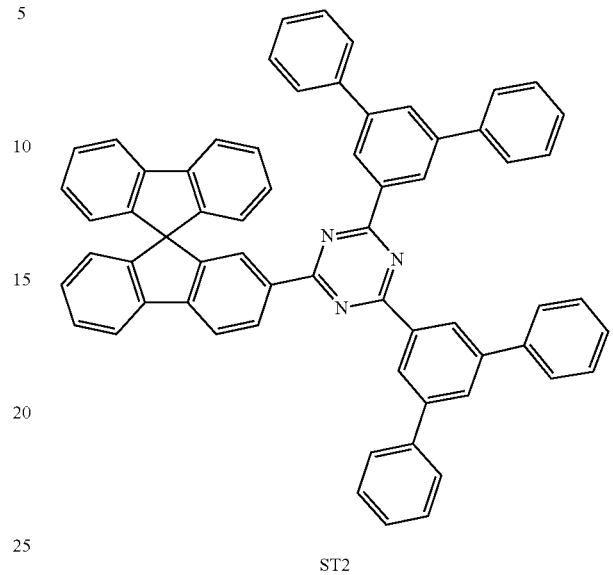
ST2
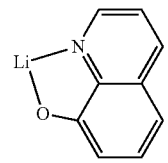
LiQ
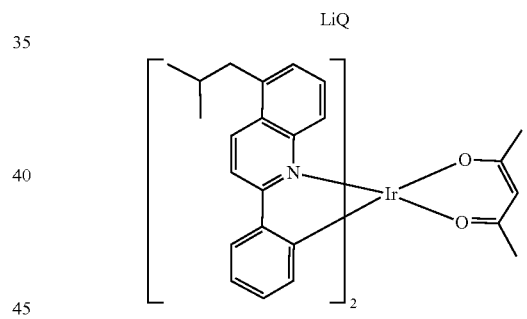
TER1
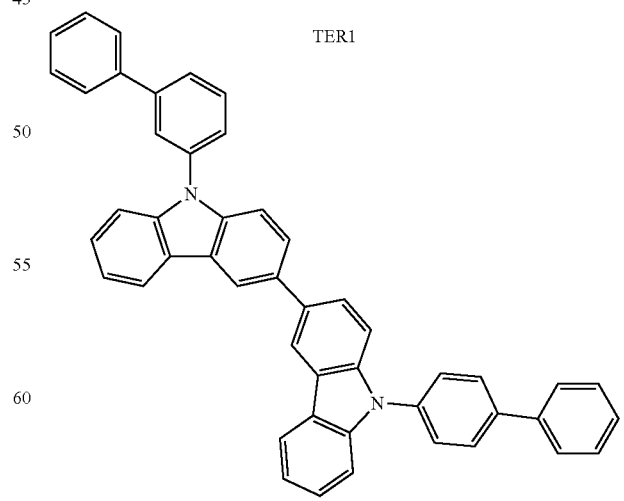
IC1

TABLE 3-continued
Structural formulae of the materials of the OLEDs used, if not already described before:
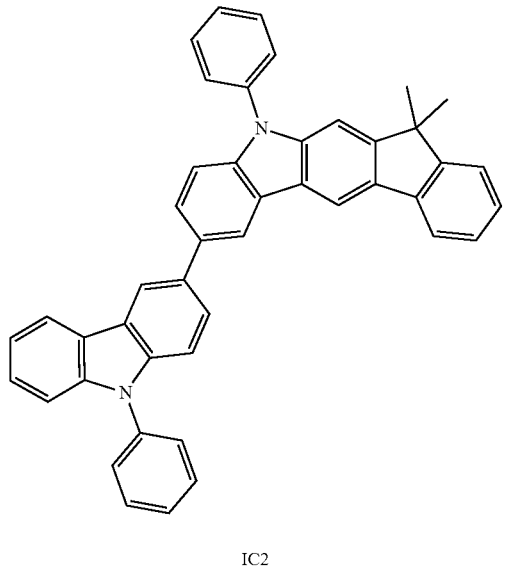
IC2
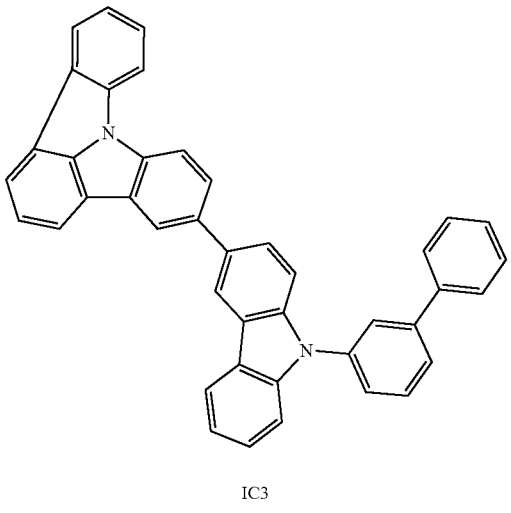
IC3
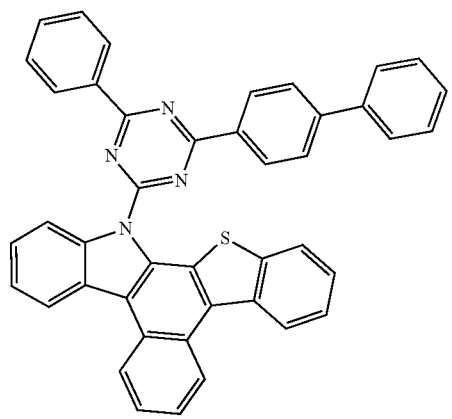
IC4
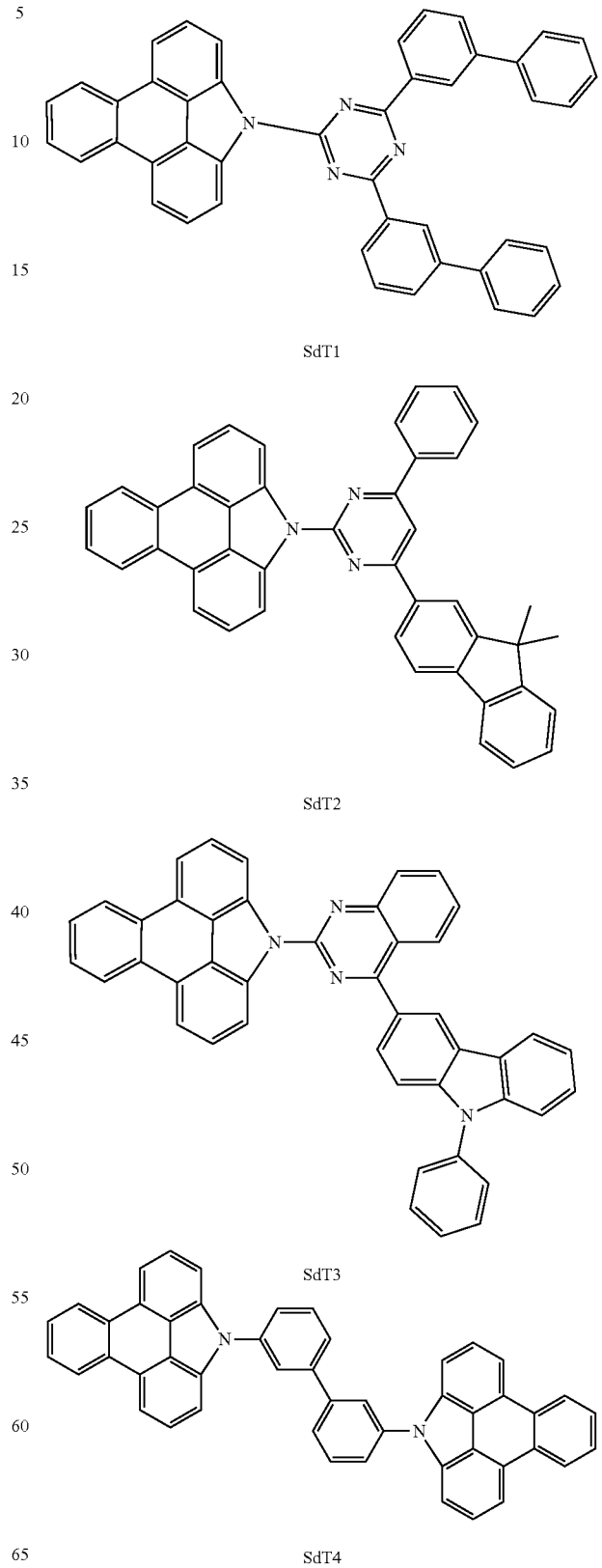
SdT1
SdT2
SdT3
SdT4

TABLE 3-continued

Structural formulae of the materials of the OLEDs used, if not already described before:

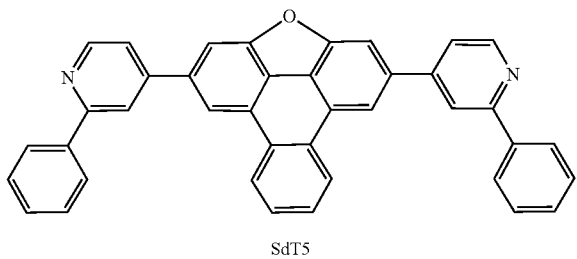

SdT5

The invention claimed is:
1. A compound of formula (1)

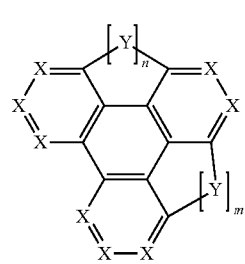

Formula (1)

comprising a structure of formula (2)

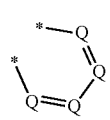

Formula (2)

wherein:
X is the same or different at each instance and is CR or N, with the proviso that not more than two X groups per cycle are N; and two adjacent X groups that are part of the same cycle are C, at which a group of the formula (2), via the bonds identified by *, form an aromatic or heteroaromatic ring system fused onto the cycle;
Q is the same or different at each instance and is $CR^1$ or N, with the proviso that at most two Q groups per ring are N;
Y is the same or different at each instance and is a BR, $C(R)_2$, C=O, $Si(R)_2$, NR, $NAr^1$, O, Se, SO, $SO_2$, PR or P(=O)R, where, in the case that m or n is 0, the carbon atoms that bind to Y are each X;
m and n are 0 or 1, where m+n is 1;
$Ar^1$ is an aromatic ring system which has 6 to 40 aromatic ring atoms and may be substituted by one or more $R^1$ radicals, or a heteroaromatic ring system which has 5 to 40 aromatic ring atoms and may be substituted by one or more $R^1$ radicals;
R is the same or different at each instance and is H, D, F, Cl, Br, I, $N(Ar^{2'})_2$, $N(R^1)_2$, $OAr^{2'}$, $SAr^{2'}$, $B(OR^1)_2$, CHO, C(=O)$R^1$, $CR^1$=C($R^1$)$_2$, CN, C(=O)O$R^1$, C(=O)N$R^1$, Si($R^1$)$_3$, $NO_2$, P(=O)($R^1$)$_2$, $OSO_2R^1$, $OR^1$, S(=O)$R^1$, S(=O)$_2R^1$, $SR^1$, a straight-chain alkyl group having 1 to 20 carbon atoms or an alkenyl or alkynyl group having 2 to 20 carbon atoms or a branched or cyclic alkyl group having 3 to 20 carbon atoms, where the alkyl, alkenyl or alkynyl group may be substituted in each case by one or more $R^1$ radicals, where one or more nonadjacent $CH_2$ groups may be replaced by —$R^1$C=C$R^1$—, —C≡C—, Si($R^1$)$_2$, $NR^1$, CON$R^1$, C=O, C=S, —C(=O)O—, P(=O)($R^1$), —O—, —S—, SO or $SO_2$, or an aromatic or heteroaromatic ring system which has 5 to 60 aromatic ring atoms, preferably 5 to 40 aromatic ring atoms, and may be substituted in each case by one or more $R^1$ radicals, where two or more R radicals bonded to the same cycle may together form an aliphatic, heteroaliphatic, aromatic or heteroaromatic ring system which may be substituted by one or more $R^1$ radicals;
$Ar^{2'}$ is the same or different at each instance and is an aromatic or heteroaromatic ring system which has 5 to 40 aromatic ring atoms and may be substituted by one or more R radicals;
$R^1$ is the same or different at each instance and is H, D, F, I, B(O$R^2$)$_2$, N($R^2$)$_2$, CHO, C(=O)$R^2$, $CR^2$=C($R^2$)$_2$, CN, C(=O)O$R^2$, Si($R^2$)$_3$, $NO_2$, P(=O)($R^2$)$_2$, $OSO_2R^2$, $SR^2$, $OR^2$, S(=O)$R^2$, S(=O)$_2R^2$, a straight-chain alkyl group having 1 to 20 carbon atoms or an alkenyl or alkynyl group having 2 to 20 carbon atoms or a branched or cyclic alkyl group having 3 to 20 carbon atoms, where the alkyl, alkenyl or alkynyl group may in each case be substituted by one or more $R^2$ radicals and where one or more $CH_2$ groups in the abovementioned groups may be replaced by —$R^2$C=C$R^2$—, —C≡C—, Si($R^2$)$_2$, C=O, C=S, —C(=O)O—, $NR^2$, CON$R^2$, P(=O)($R^2$), —O—, —S—, SO or $SO_2$, and where one or more hydrogen atoms in the abovementioned groups may be replaced by D, F, Cl, Br, I, CN or $NO_2$, or an aromatic or heteroaromatic ring system which has 5 to 30 aromatic ring atoms and may be substituted in each case by one or more $R^2$ radicals, where two or more $R^1$ radicals together may form an aliphatic, heteroaliphatic, aromatic or heteroaromatic ring system;
$R^2$ is the same or different at each instance and is H, D, F, CN or an aliphatic, aromatic or heteroaromatic organic radical having 1 to 20 carbon atoms, in which one or more hydrogen atoms may also be replaced by D or F; at the same time, two or more $R^2$ substituents may be joined to one another and may form a ring.

2. The compound as claimed in claim 1, selected from the compounds of the formulae (3) and (4)

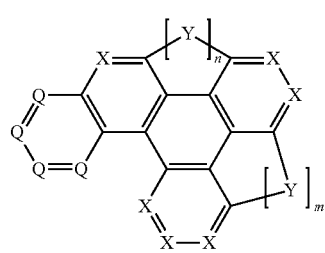

Formula (3)

Formula (4)

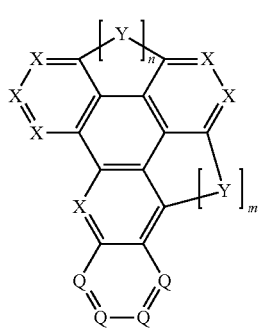

wherein:

X is the same or different at each instance and is CR or N, with the proviso that not more than two X groups per cycle are N; and two adjacent X groups that are part of the same cycle are C;

Q is the same or different at each instance and is $CR^1$ or N, with the proviso that at most two Q groups per ring are N.

3. The compound as claimed in claim 1, selected from the compounds of the formulae (5) to (8)

Formula (5)

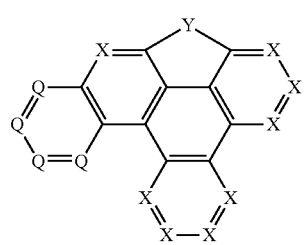

Formula (6)

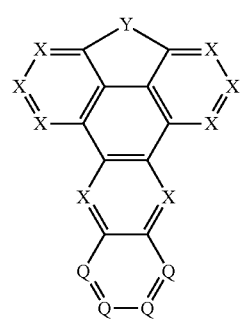

Formula (7)

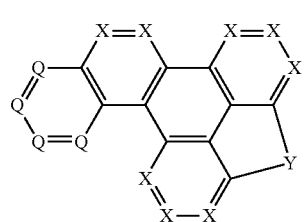

Formula (8)

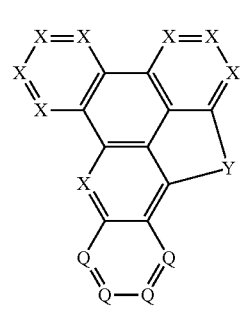

wherein:

X is the same or different at each instance and is CR or N, with the proviso that not more than two X groups per cycle are N; and two adjacent X groups that are part of the same cycle are C;

Q is the same or different at each instance and is $CR^1$ or N, with the proviso that at most two Q groups per ring are N.

4. The compound as claimed in claim 1, selected from the compounds of the formulae (5-1) to (8-1)

Formula (5-1)

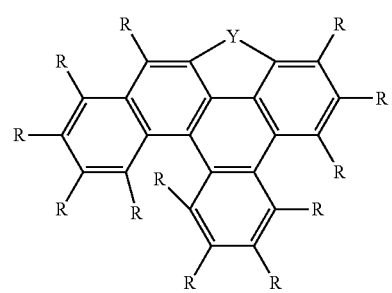

Formula (6-1)

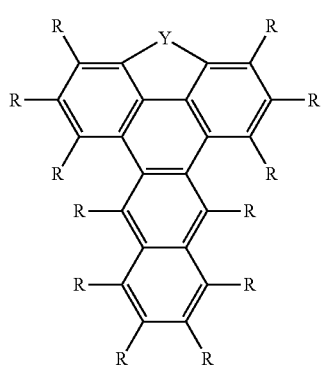

Formula (7-1)

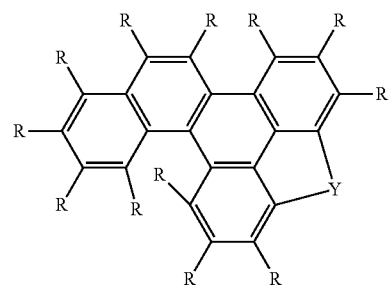

Formula (8-1)

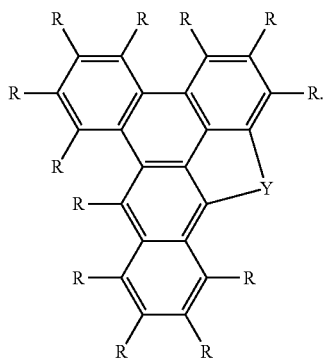

5. The compound as claimed in claim 1, wherein Y is NAr¹, O or S.

6. A formulation comprising at least one compound as claimed in claim 1 at least one further compound and/or at least one solvent.

7. A method comprising providing the compound as claimed in claim 1 incorporating the compound in an electronic device.

8. An electronic device comprising at least one compound as claimed in claim 1.

9. The electronic device as claimed in claim 8 is an organic electroluminescent device, wherein the compound is used in an emitting layer as matrix material for phosphorescent or fluorescent emitters or for emitters that exhibit TADF (thermally activated delayed fluorescence), or in an electron transport layer and/or in a hole blocker layer and/or in a hole transport layer and/or in an exciton blocker layer.

10. The compound as claimed in claim 1, selected from the compounds of the formulae (5-1-1) to (8-1-4):

Formula (5-1-1)

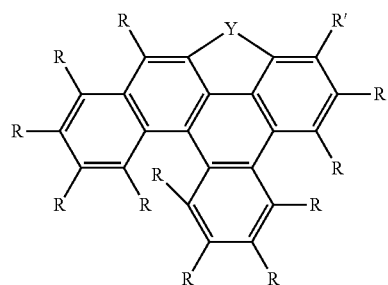

Formula (5-1-2)

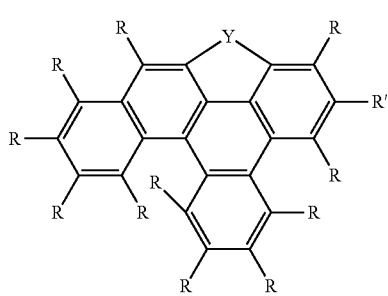

Formula (5-1-3)

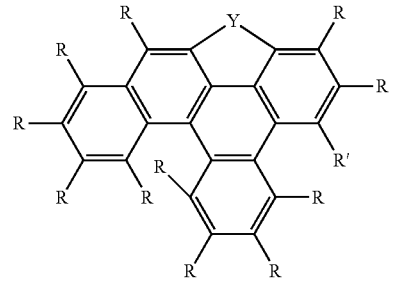

Formula (5-1-4)

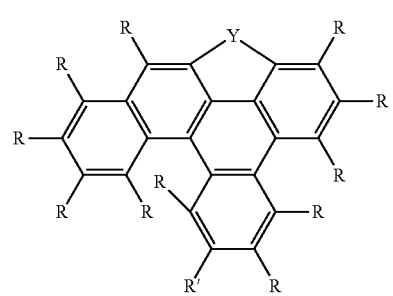

Formula (5-1-5)

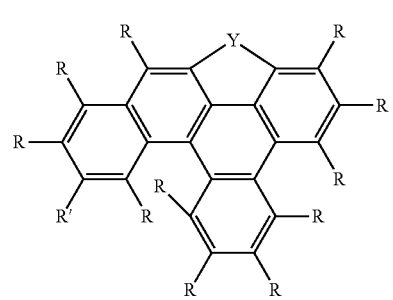

Formula (6-1-1)

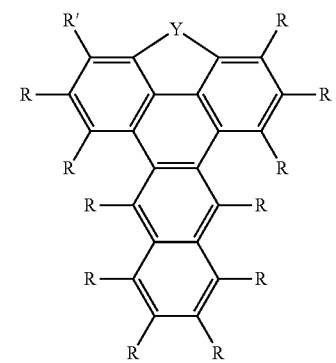

Formula (6-1-2)

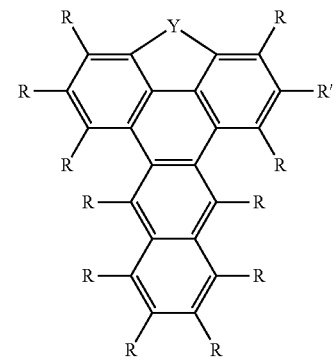

Formula (6-1-3)
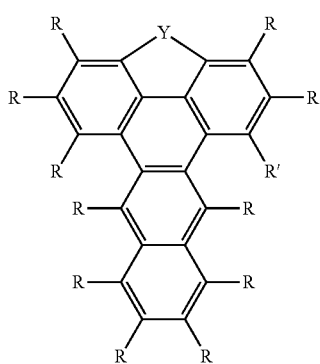
Formula (6-1-4)
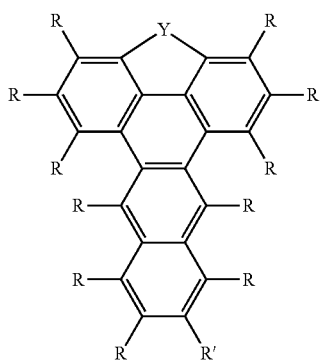
Formula (7-1-1)
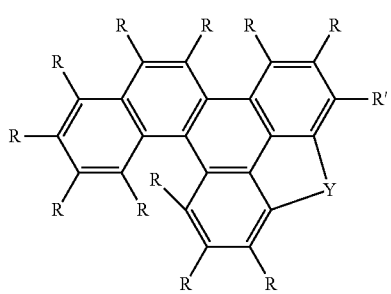
Formula (7-1-2)
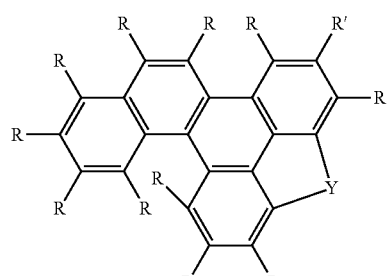
Formula (7-1-3)
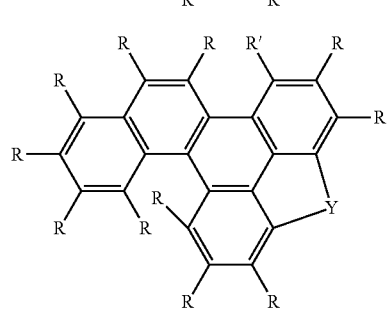
Formula (7-1-4)
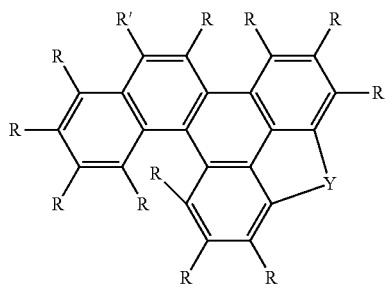
Formula (8-1-1)
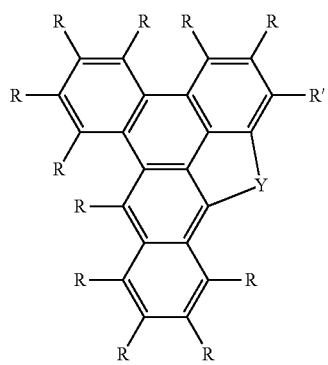
Formula (8-1-2)
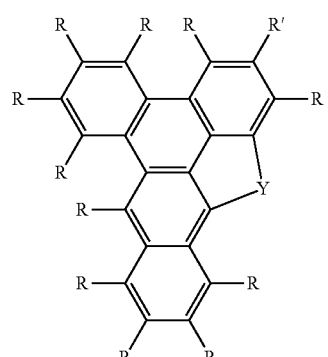
Formula (8-1-3)
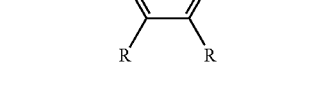

Formula (8-1-4)
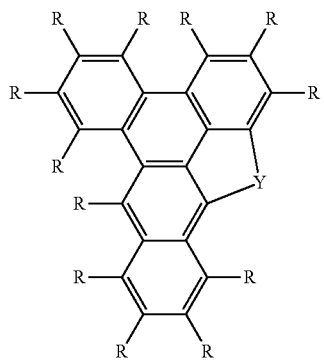
wherein
R' is the same or different at each instance or is an aromatic or heteroaromatic ring system which has 5 to 60 aromatic ring atoms, optionally substituted by one or more $R^1$ groups.
11. The compound as claimed in claim 1, wherein the compound is selected from
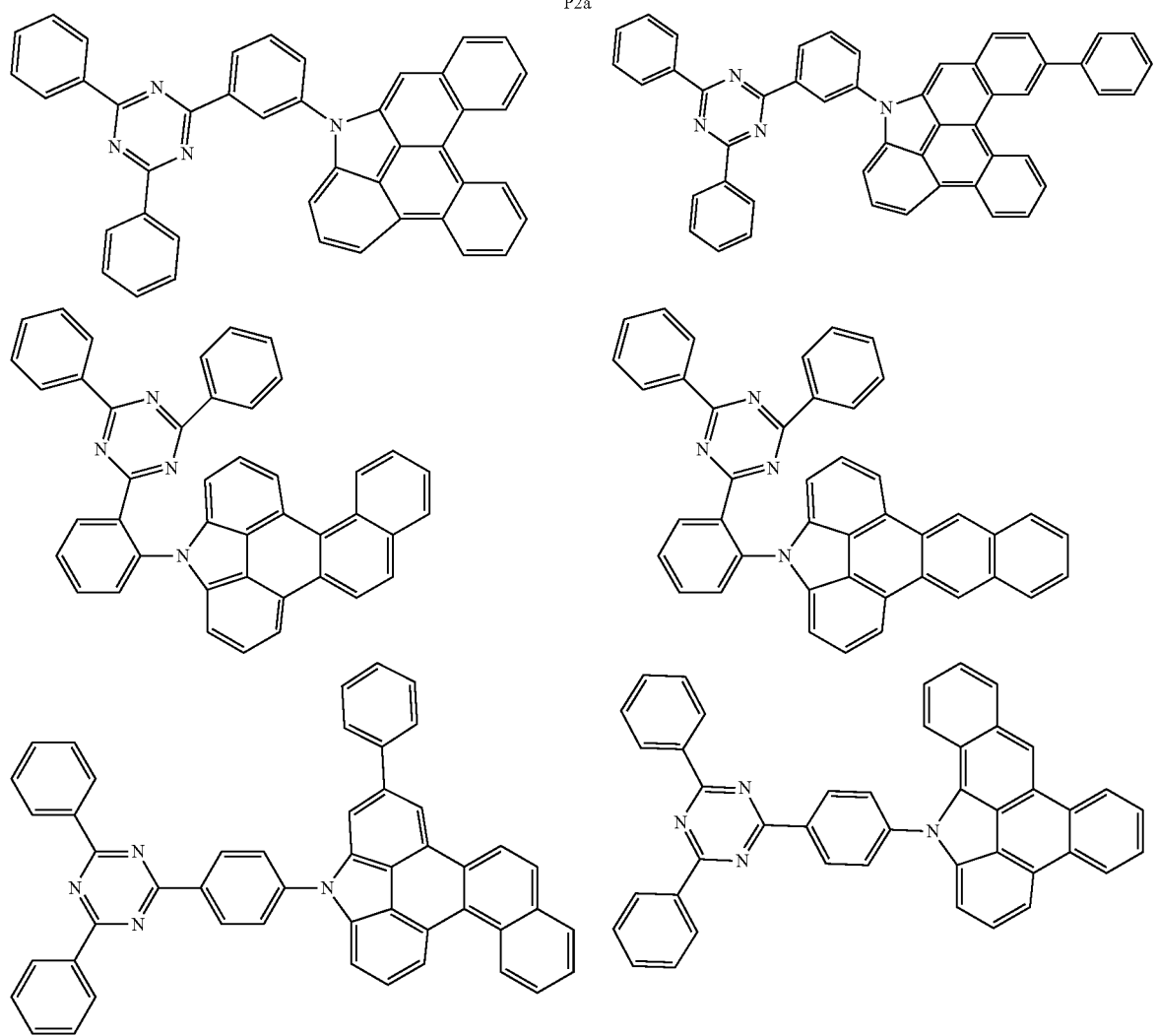
P2a 481 482
-continued
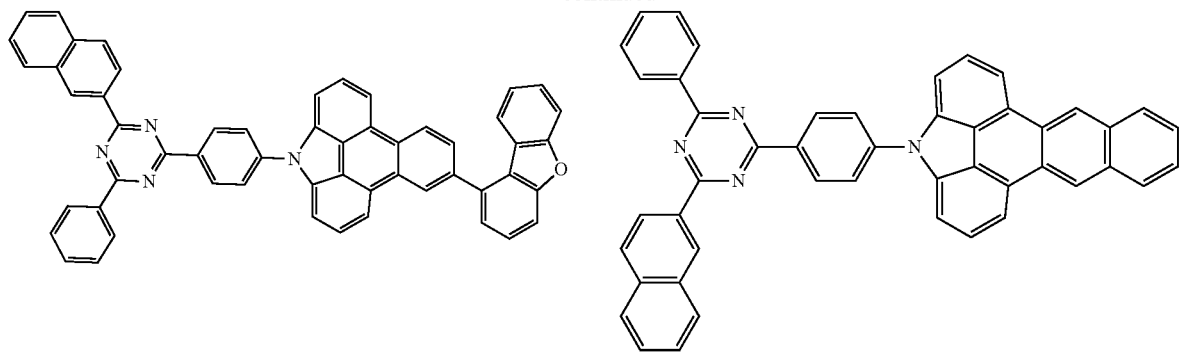
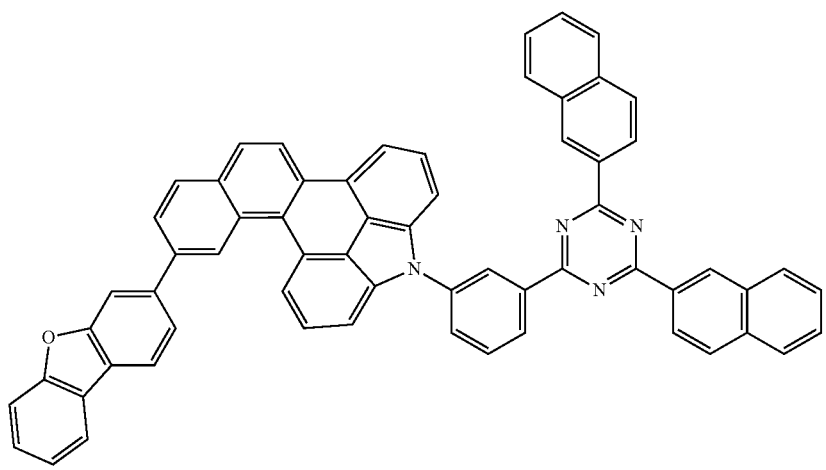
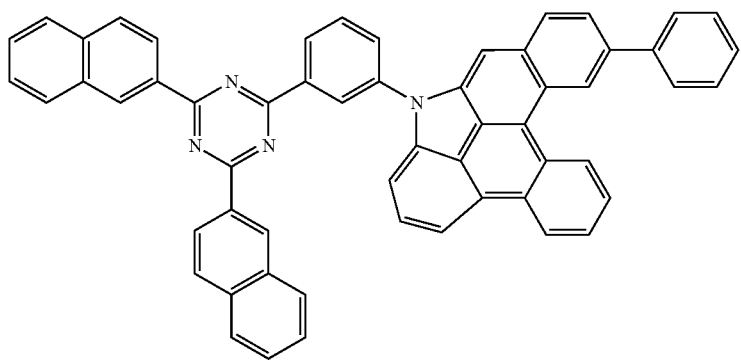
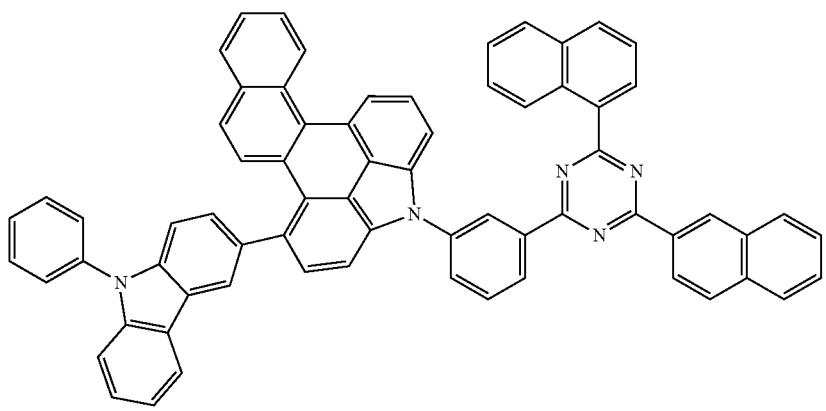

-continued
483
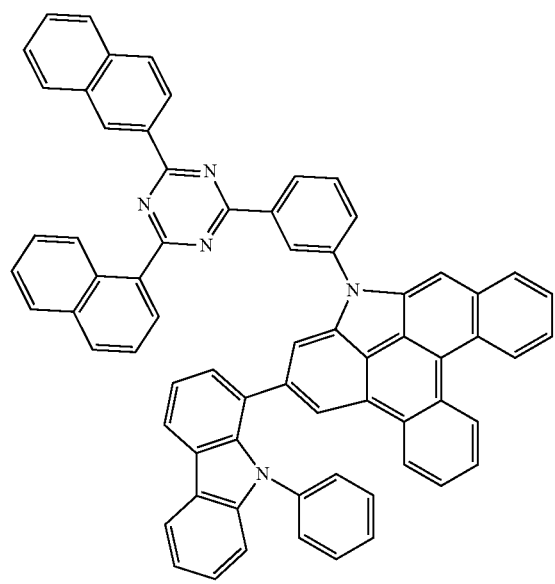
484
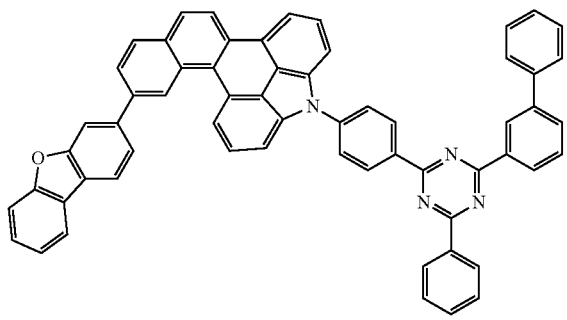
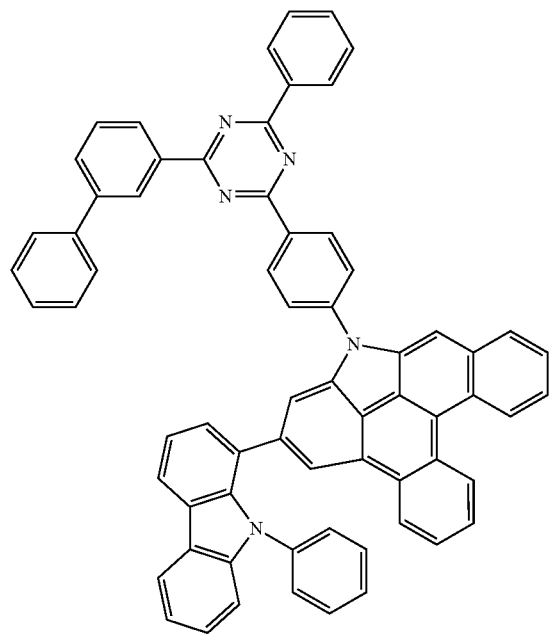
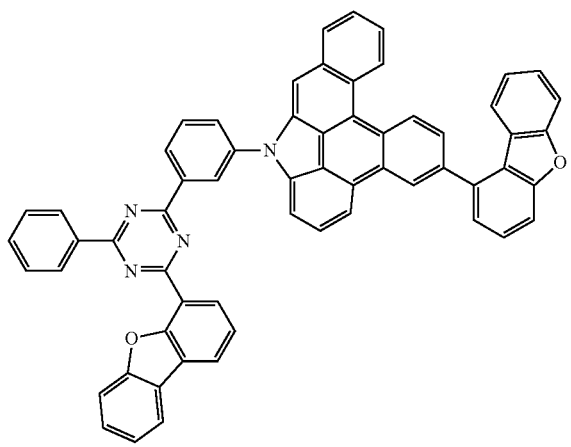
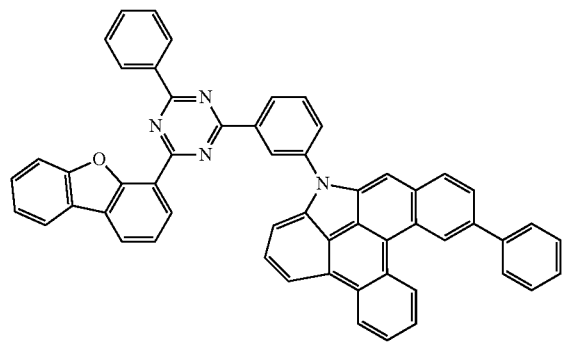
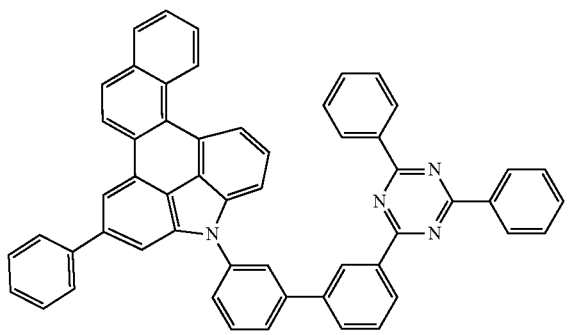

-continued
485
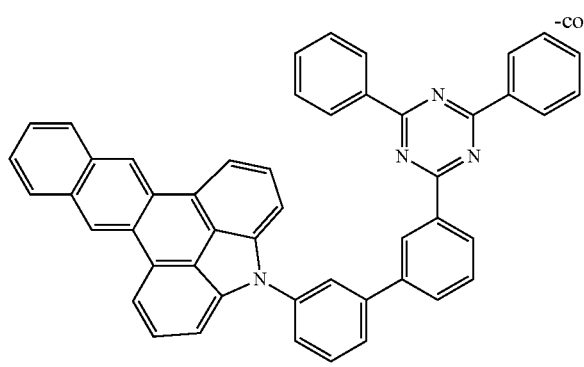
486
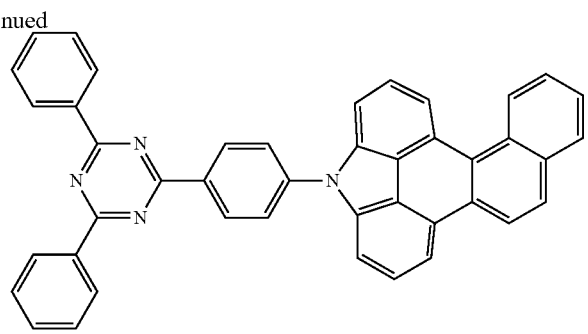
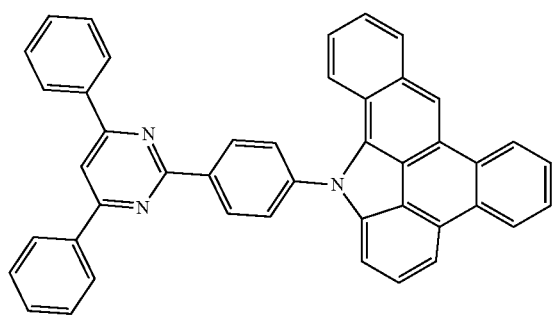
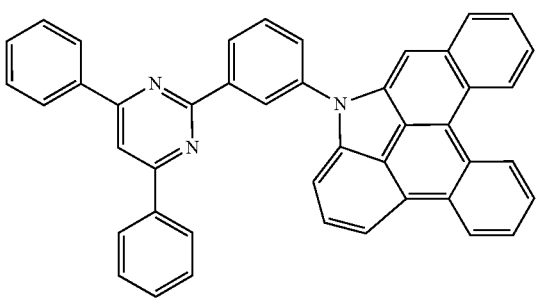
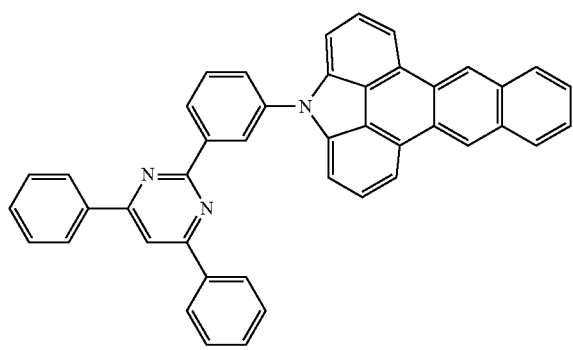
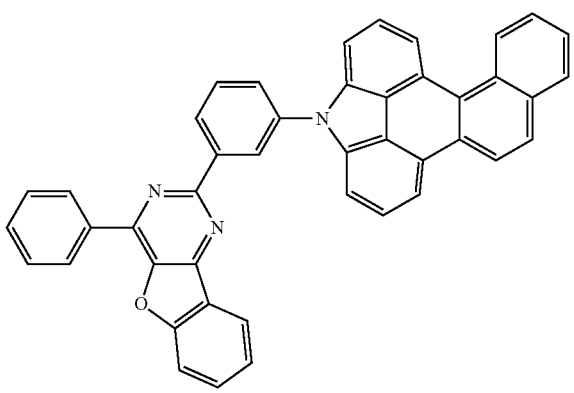
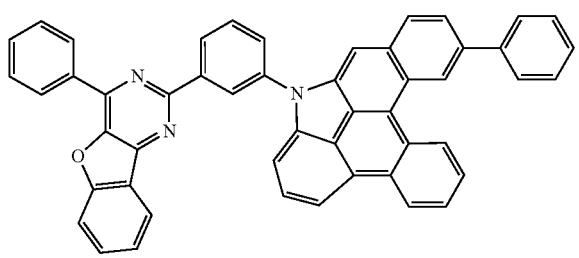
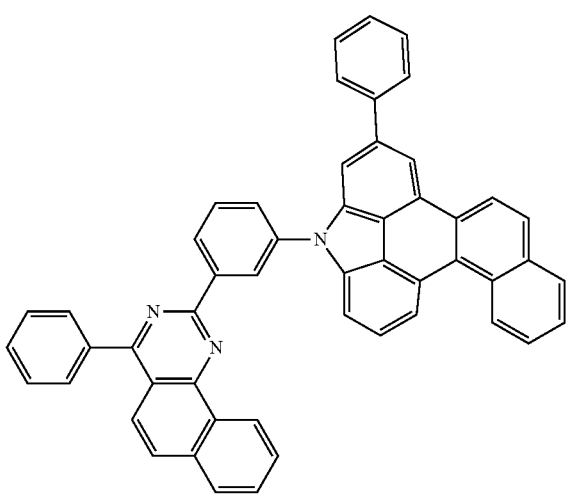

-continued
| 487 | 488 |
|---|---|
| 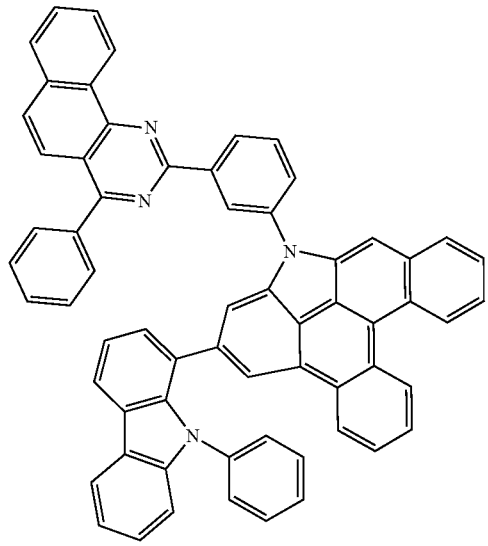 | 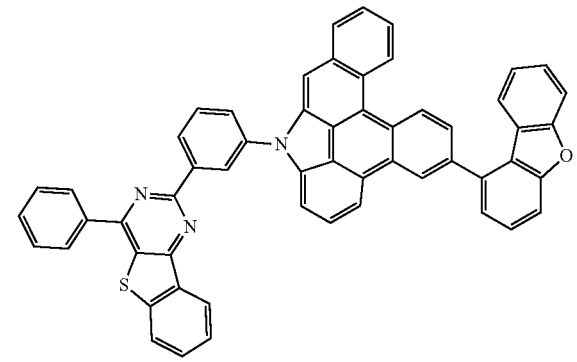 |
| 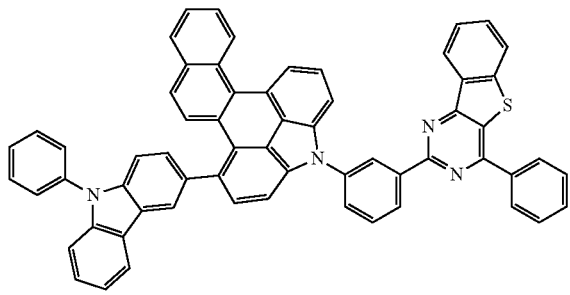 | 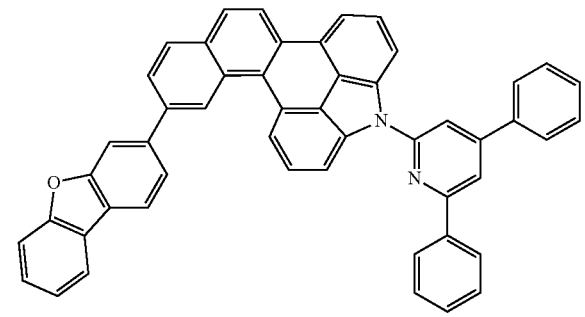 |
| | P4a |
| 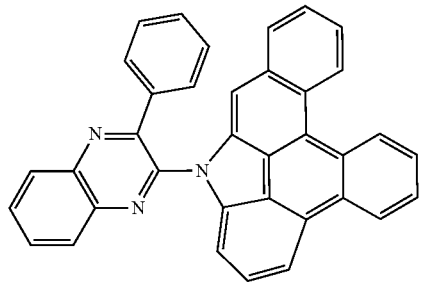 | 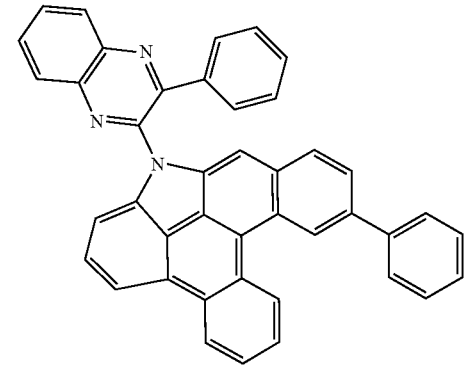 |
| 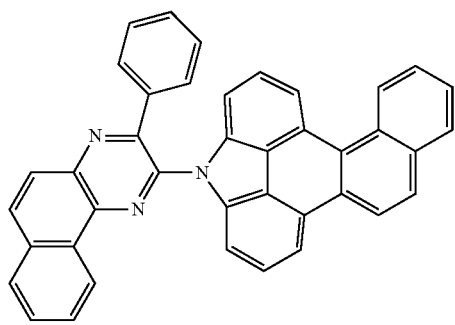 | 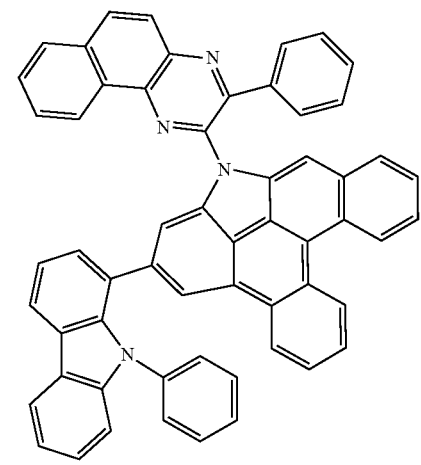 |

-continued
489 490
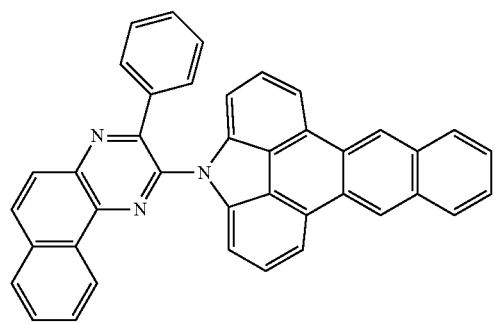 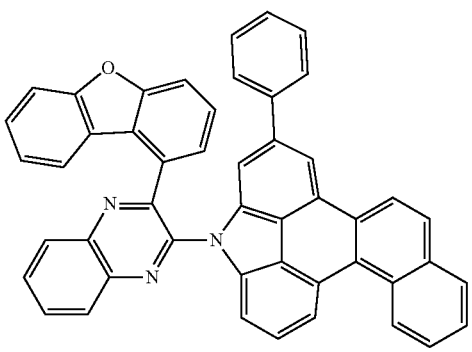
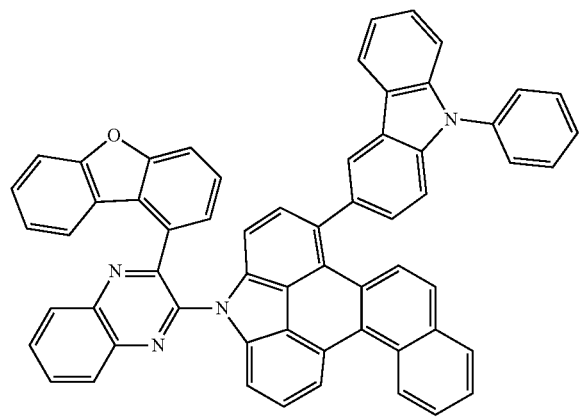 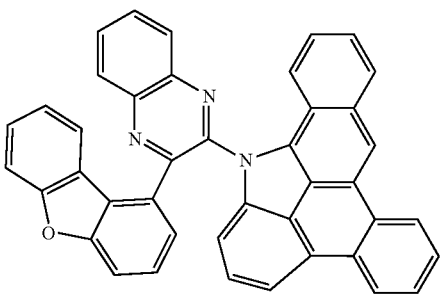
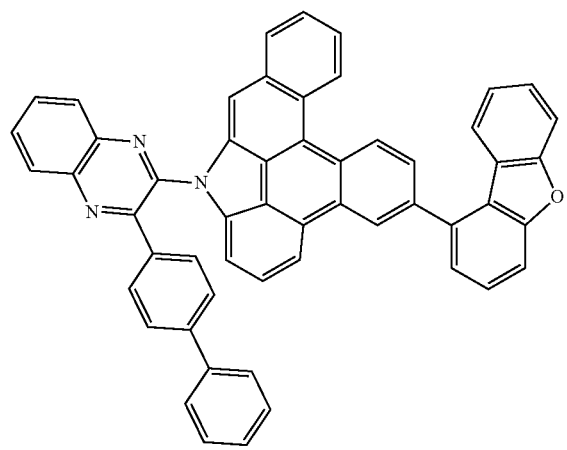 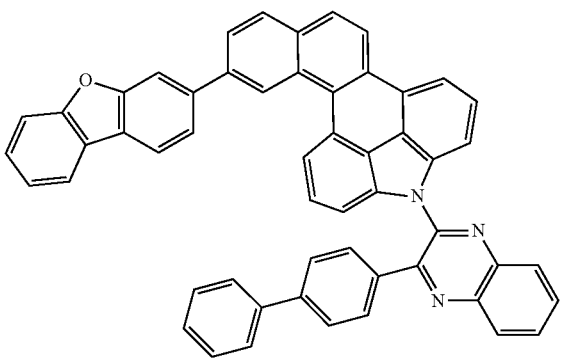
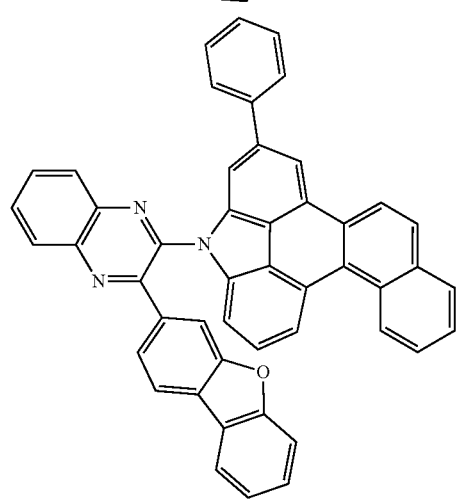 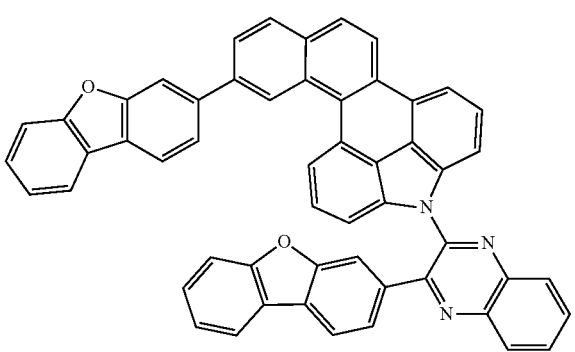

491
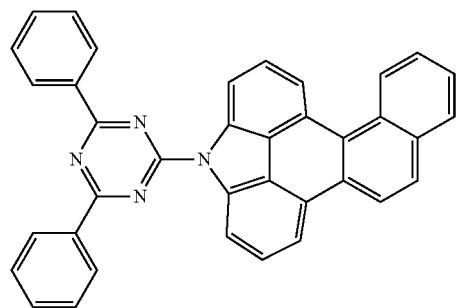
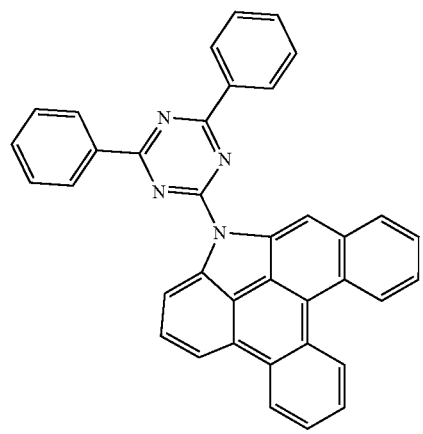
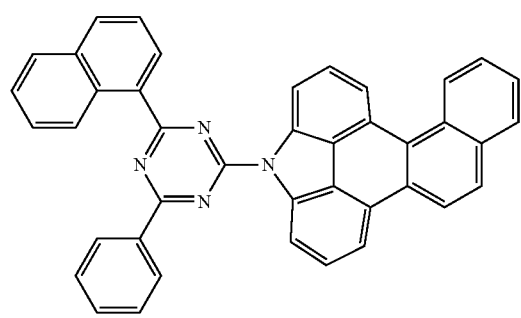
492
-continued
P1b
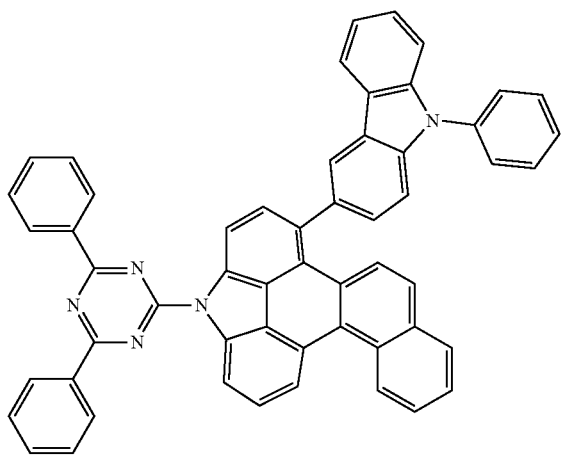
P1a
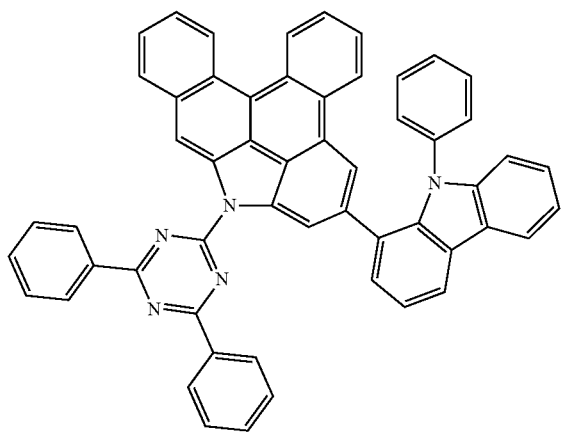
P1f
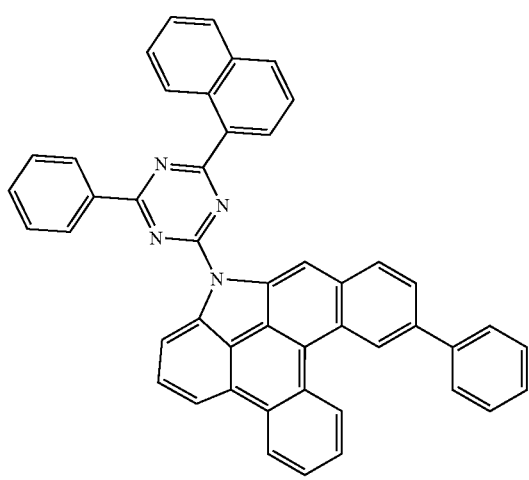

493
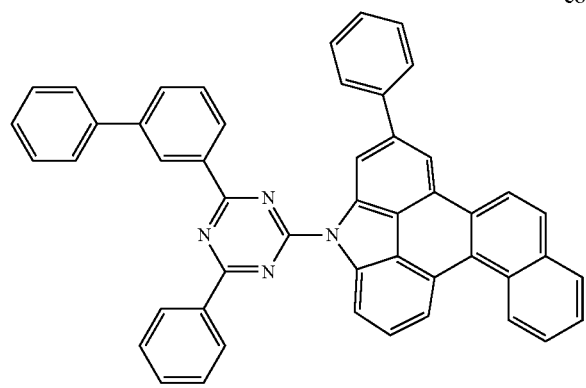
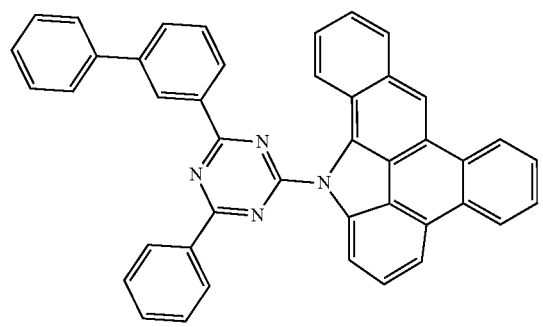
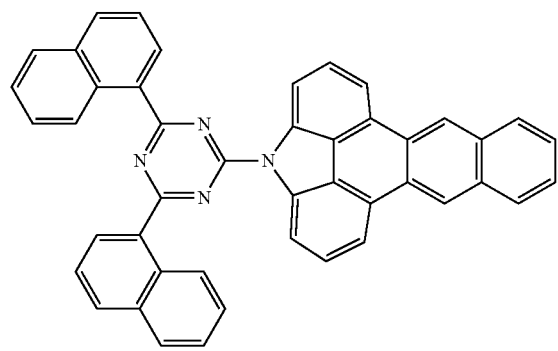
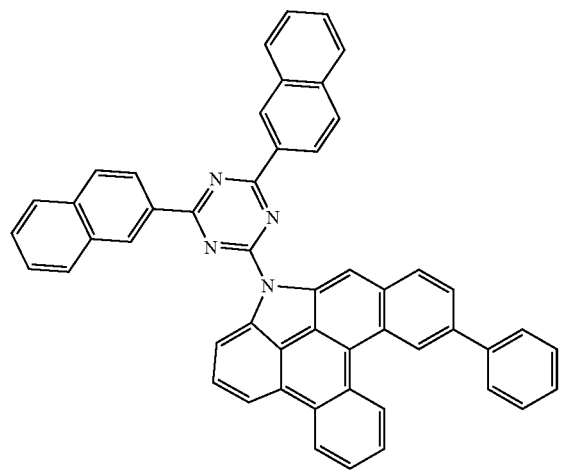
494
-continued
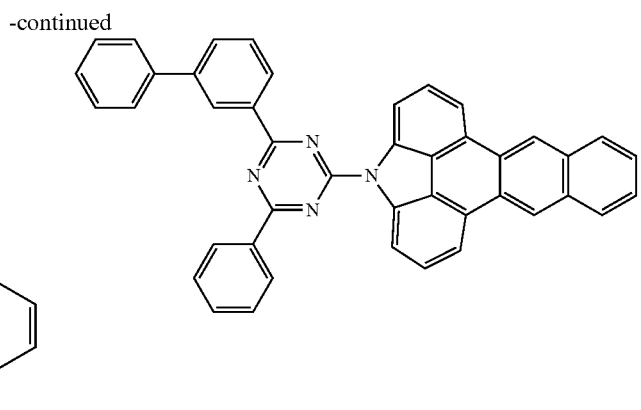
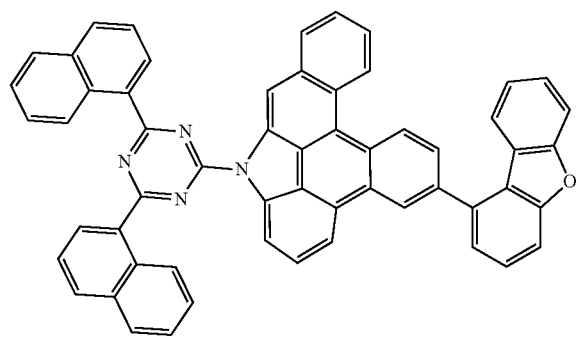
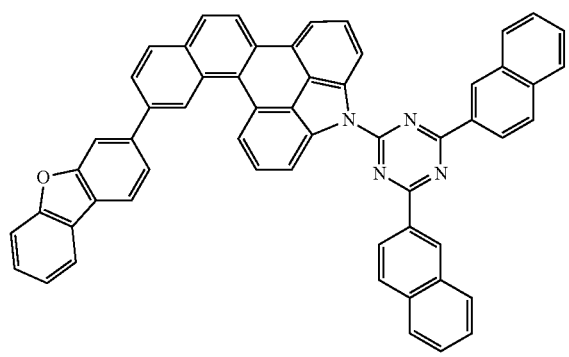
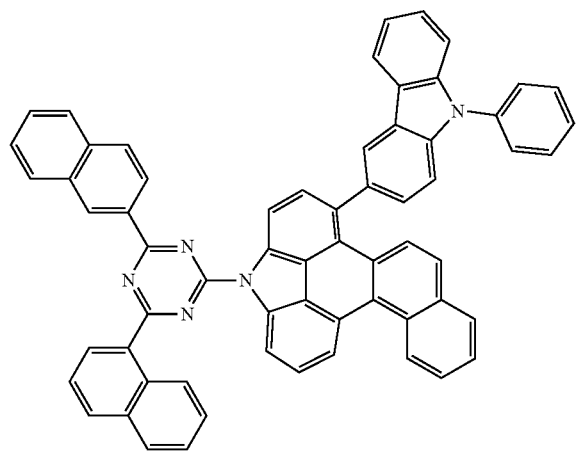

-continued
495 496
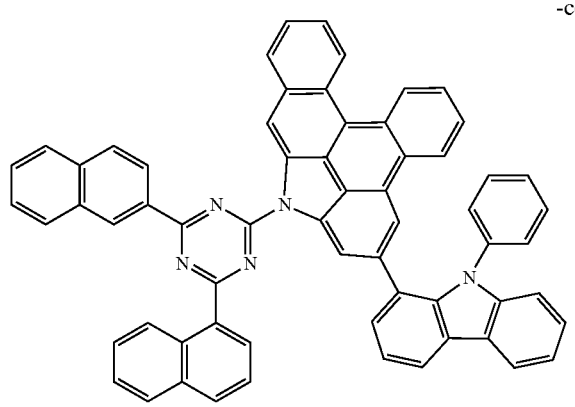
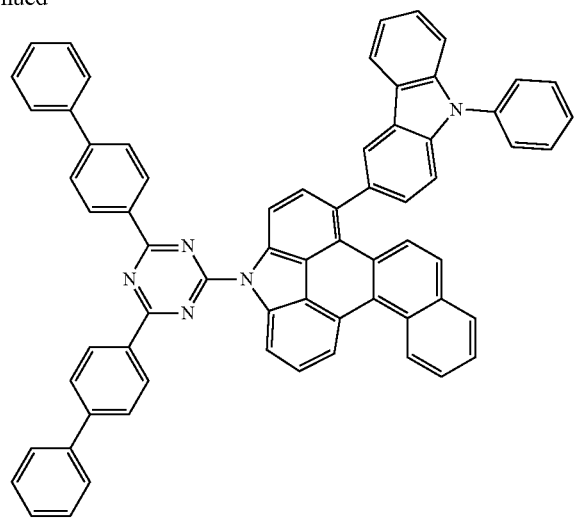
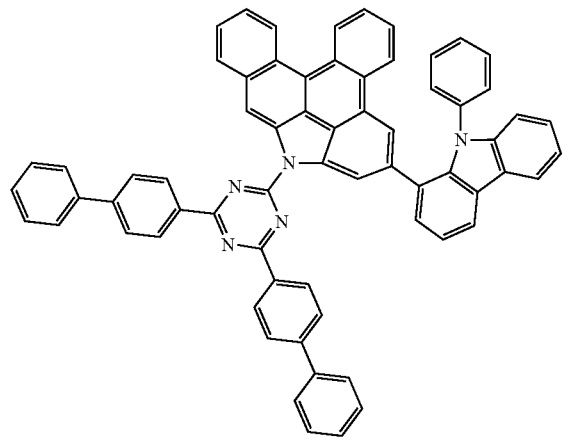
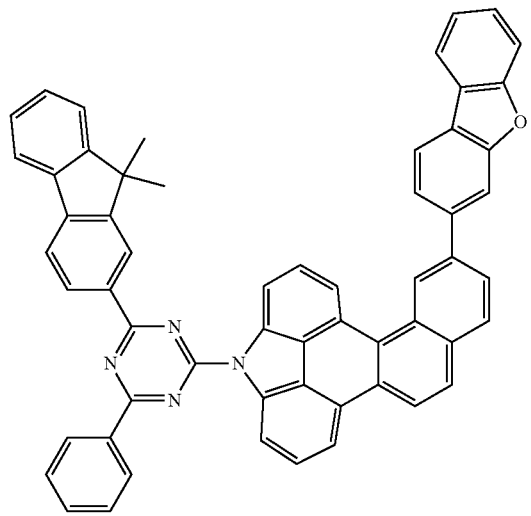
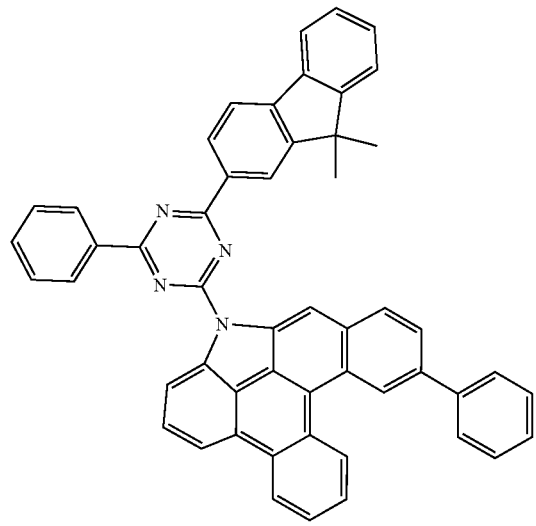
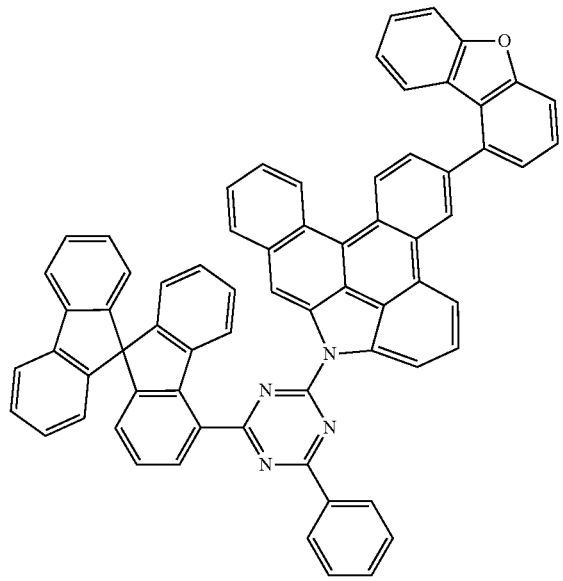

-continued
497
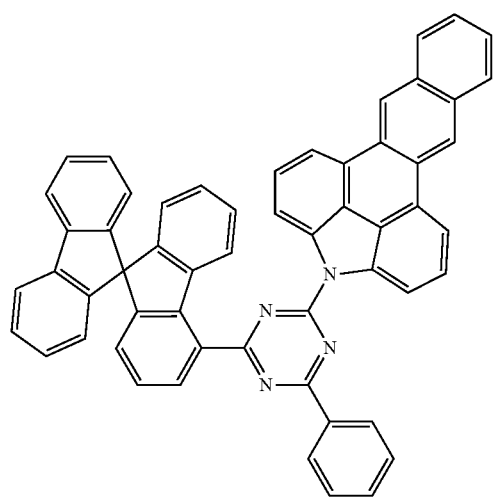
498
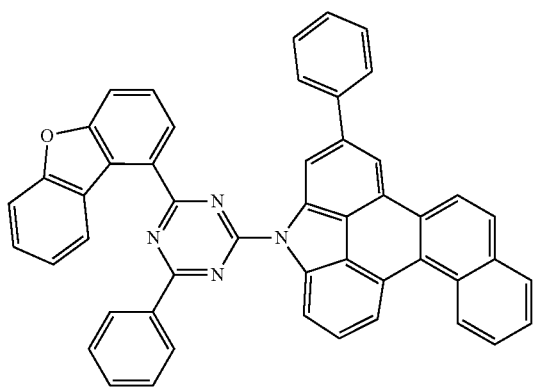
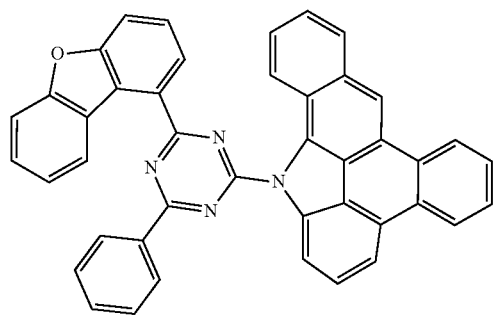
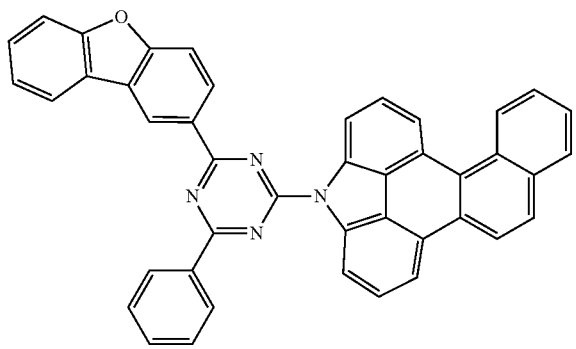
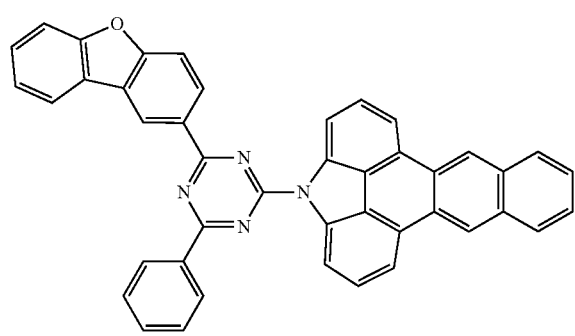
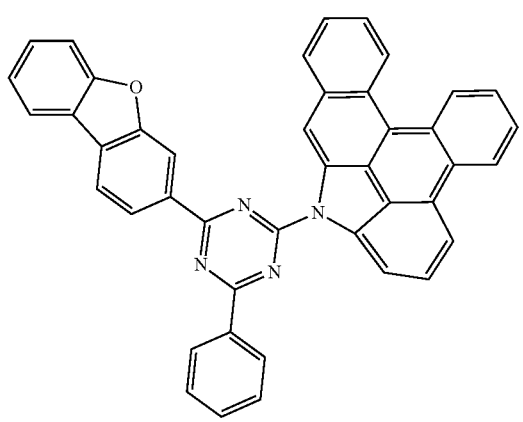
P1i -continued
499
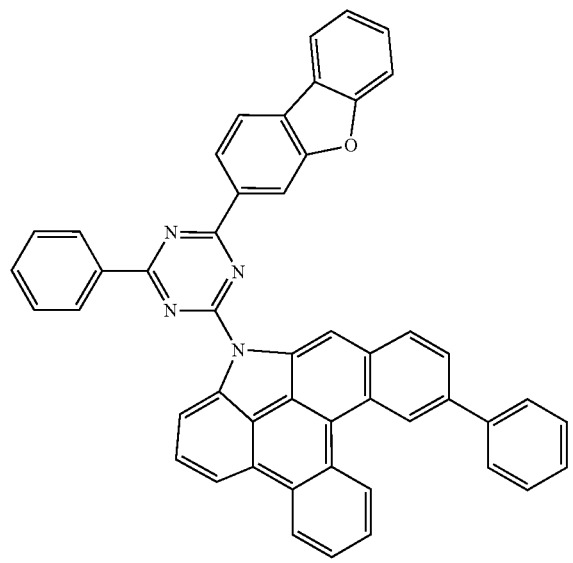
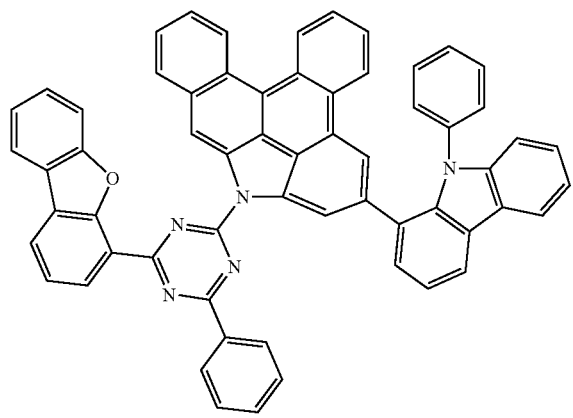
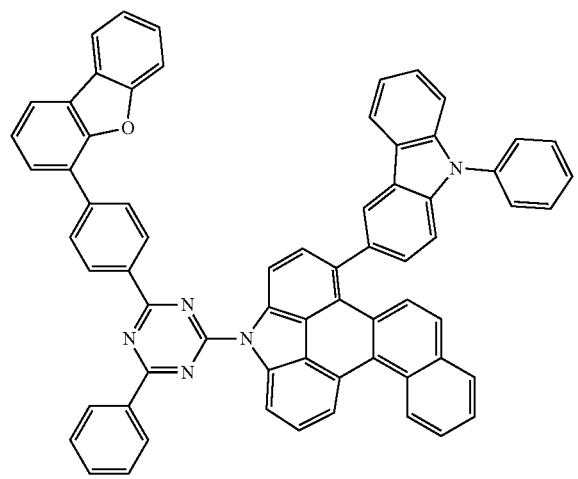
500
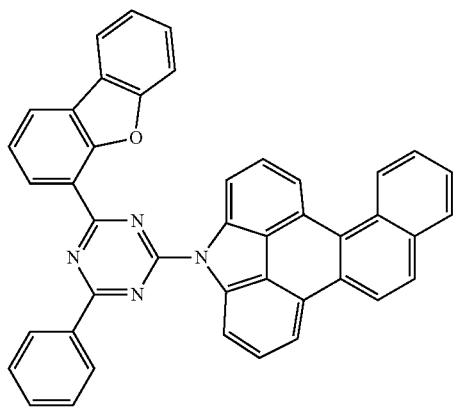
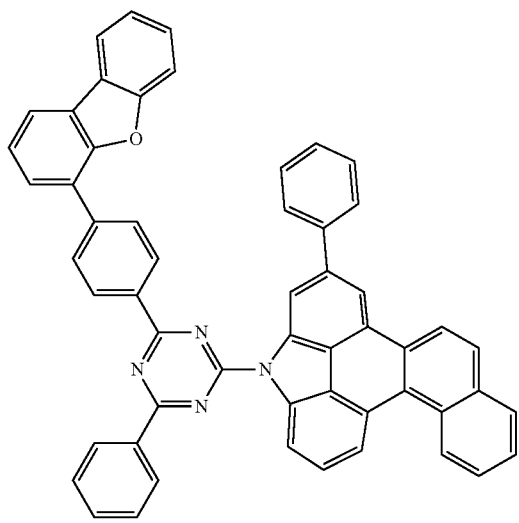
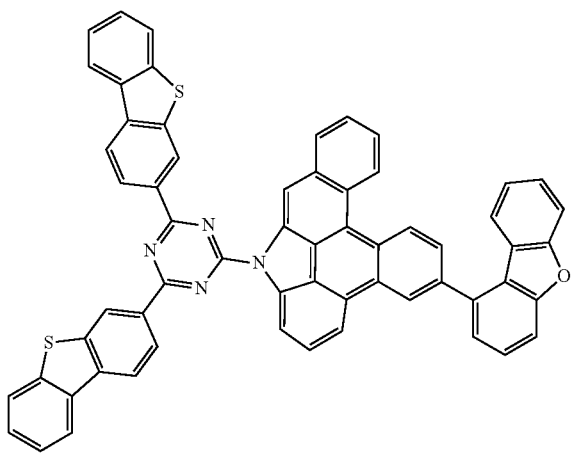

501
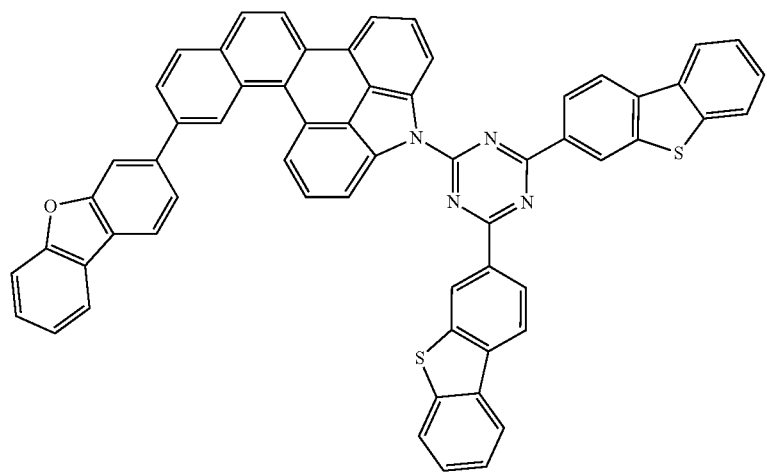
502
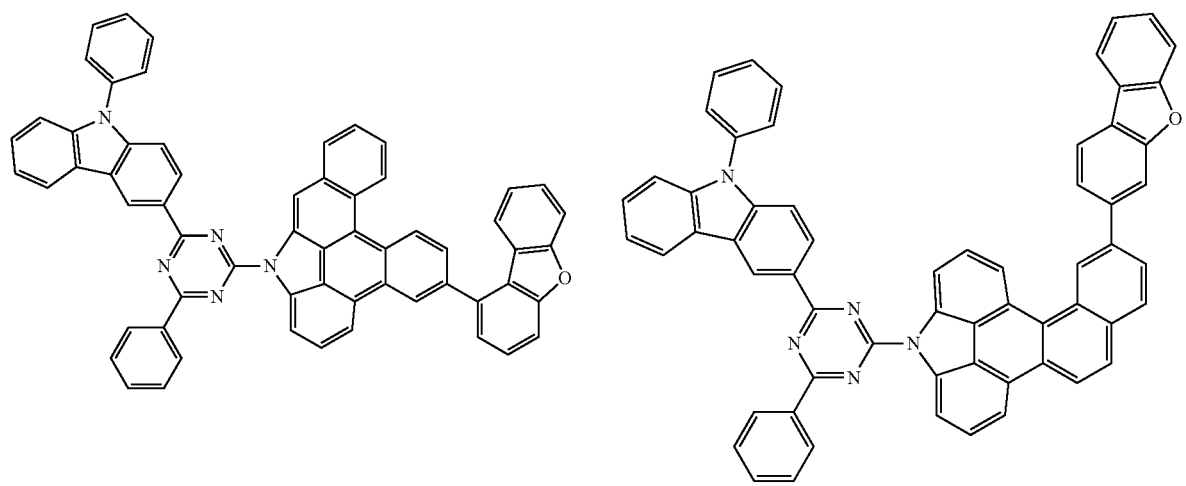
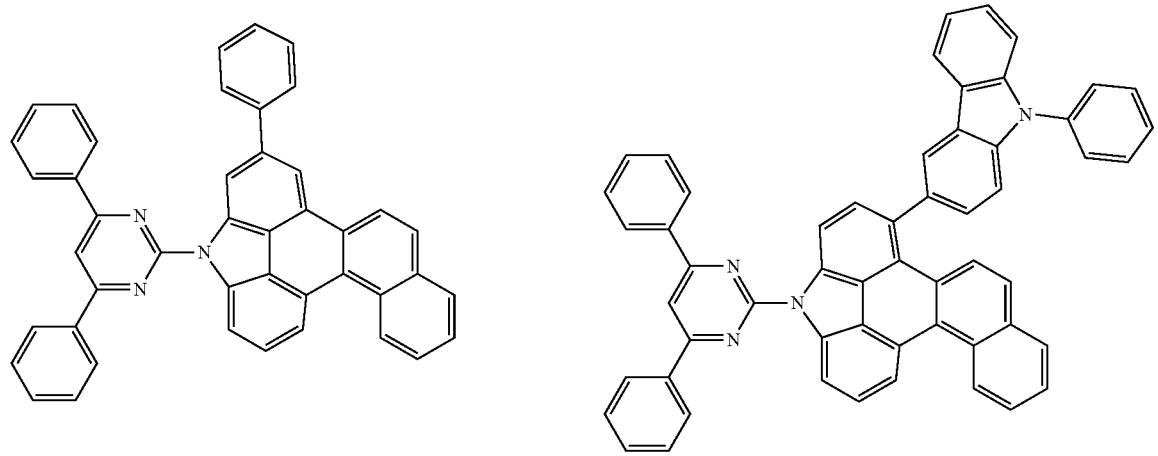

503 504
-continued
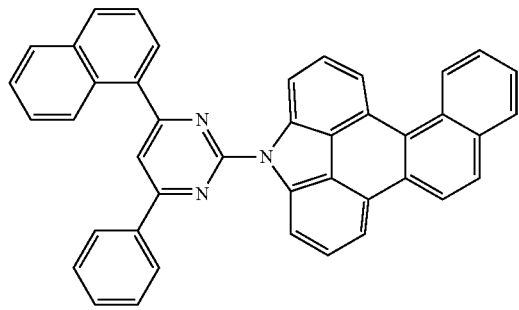
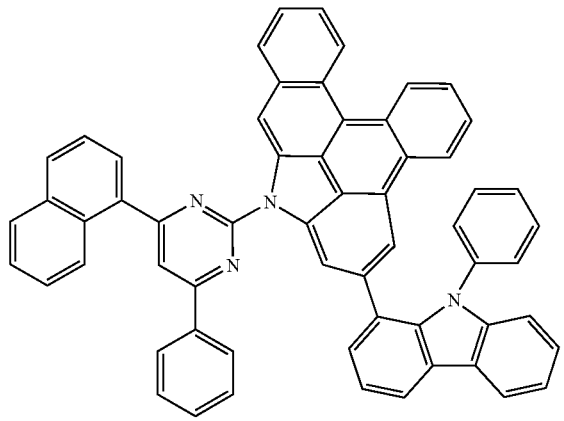
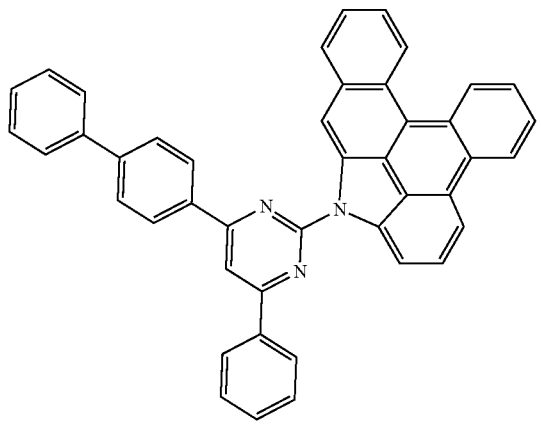
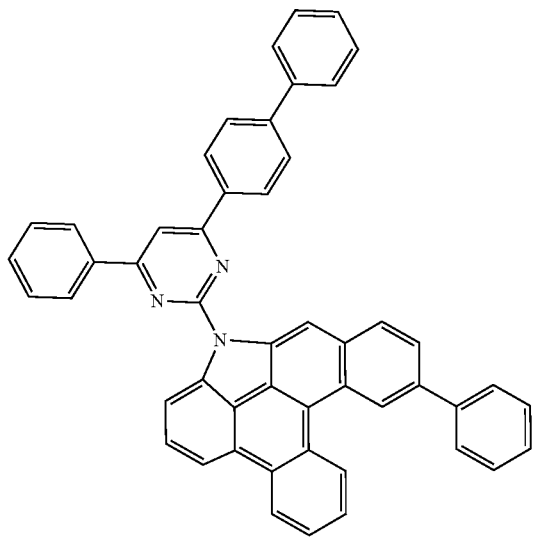
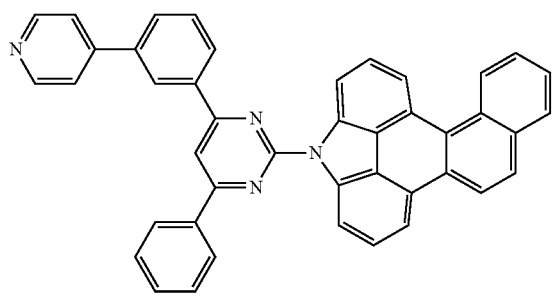
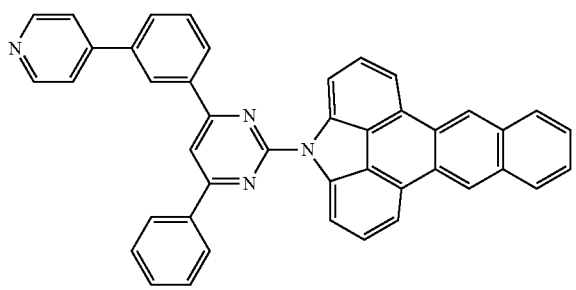
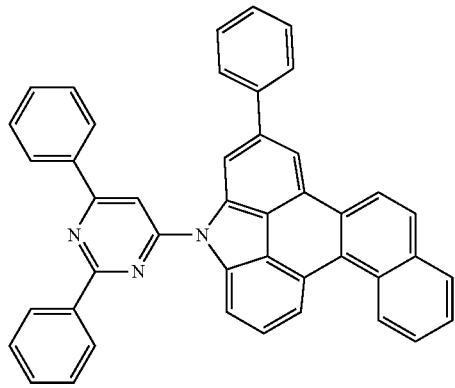
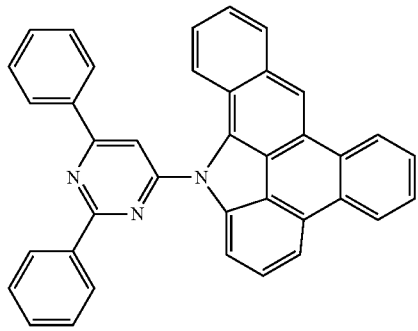

505
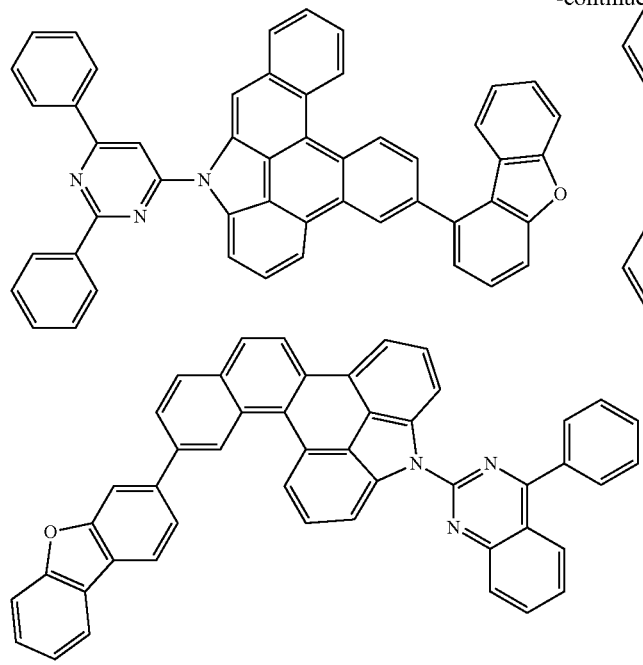
506
-continued
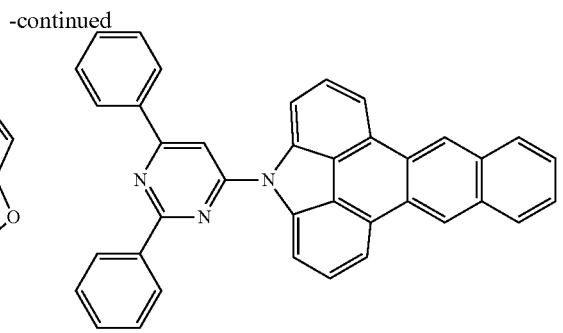
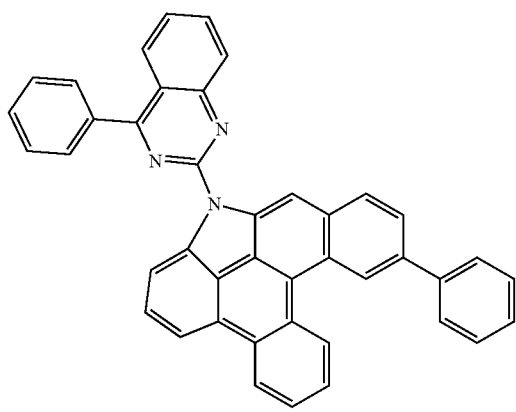
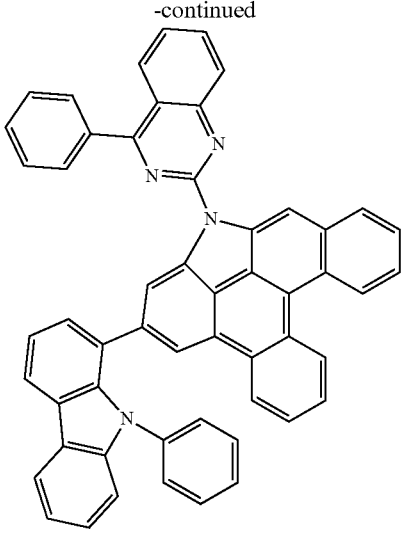
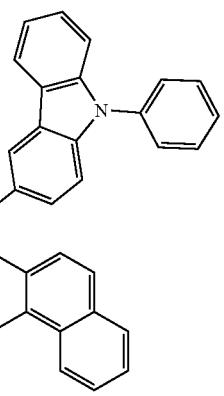

507 -continued
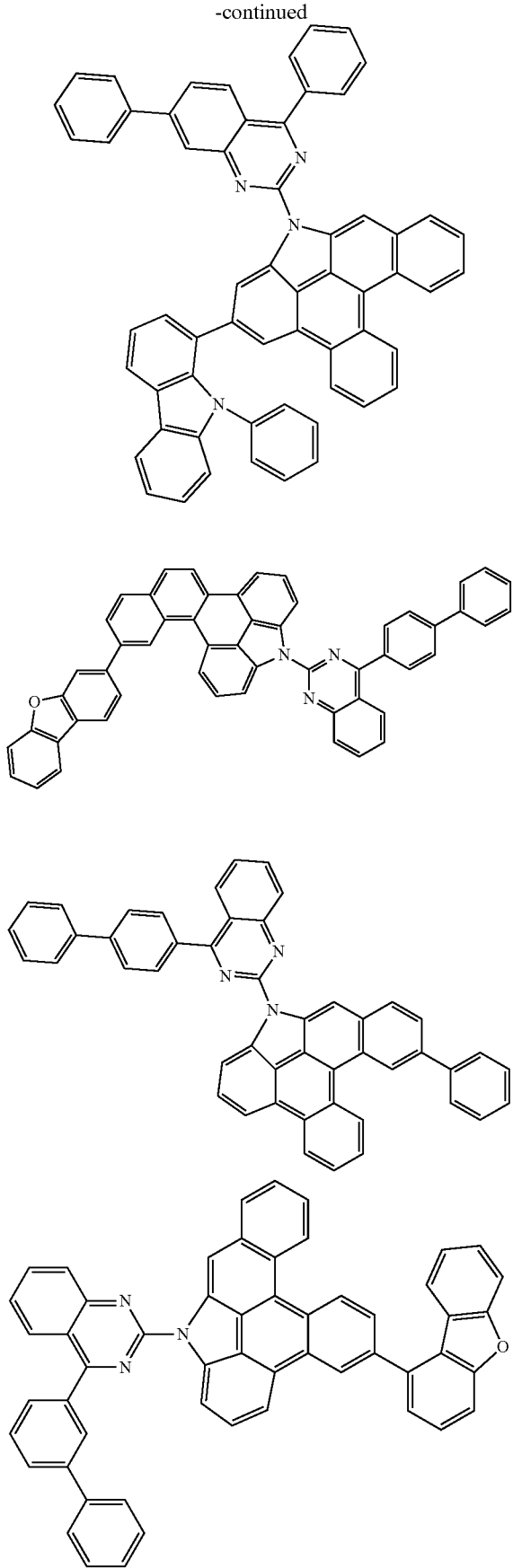
508 -continued
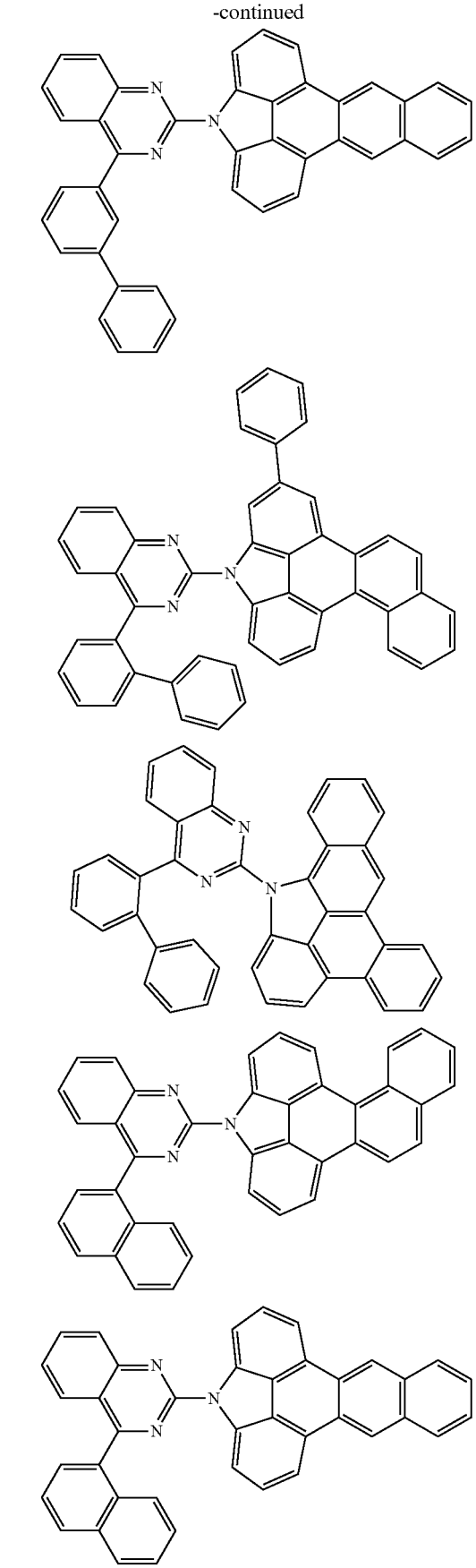

509
-continued
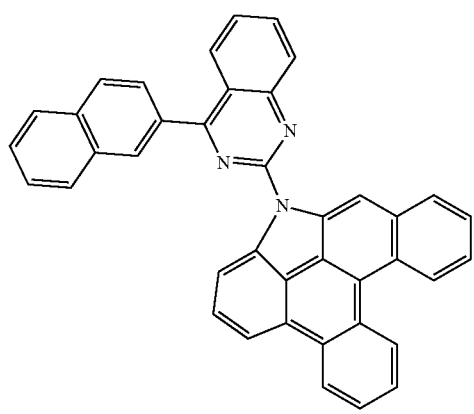
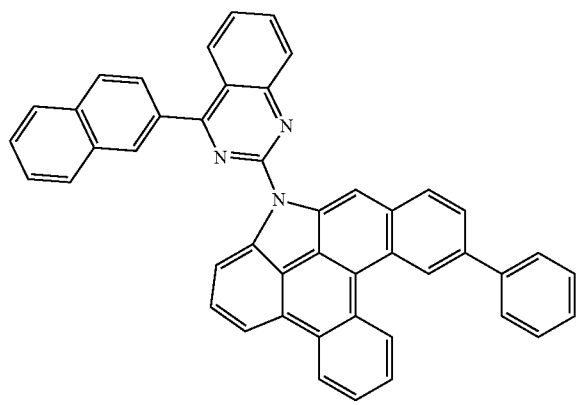
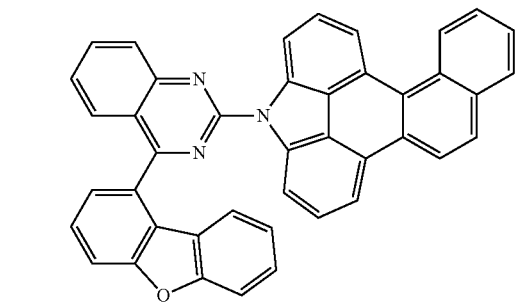
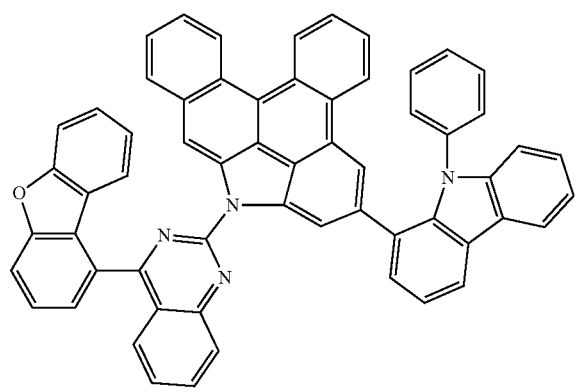
510
-continued
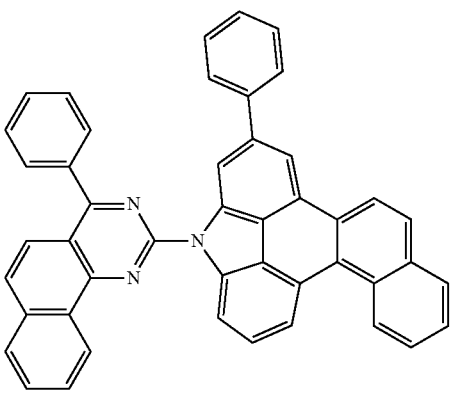
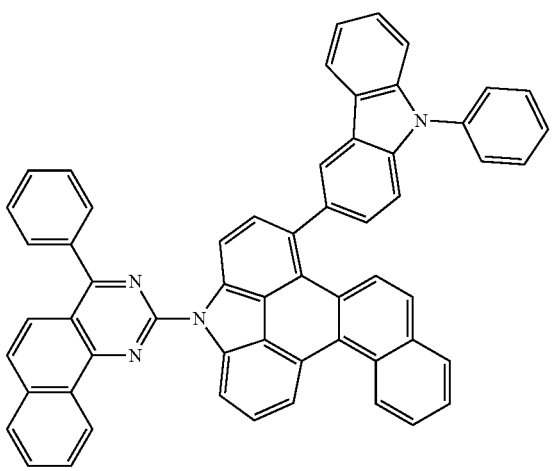
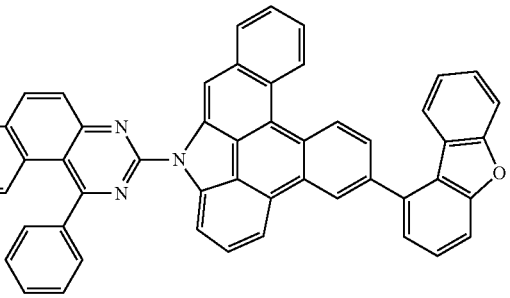
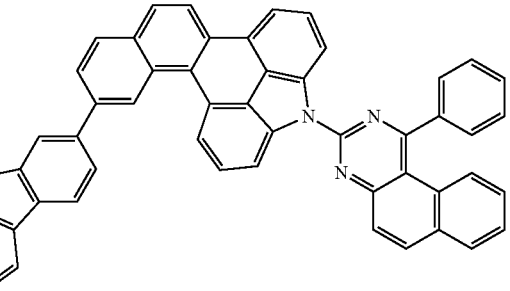

511
-continued
512
-continued
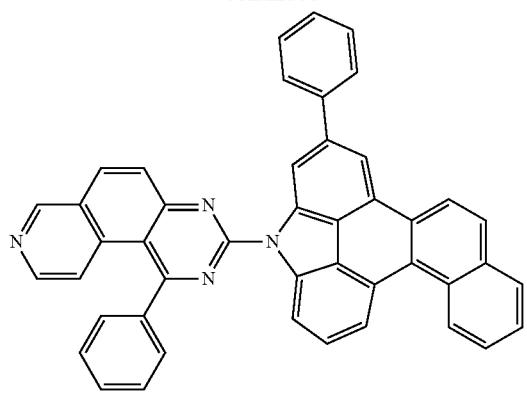
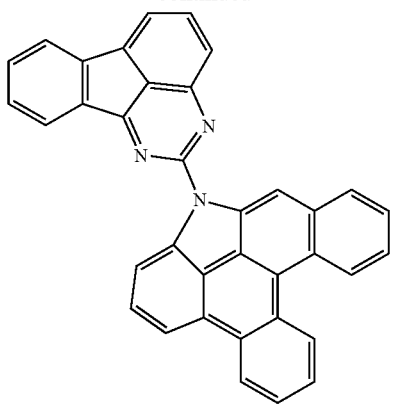
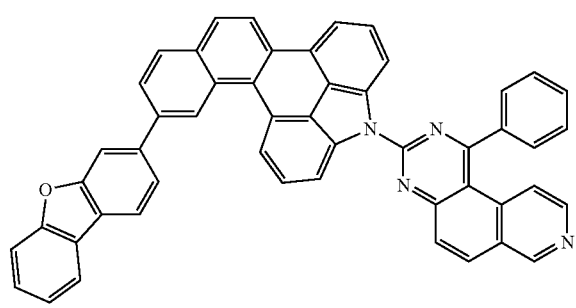
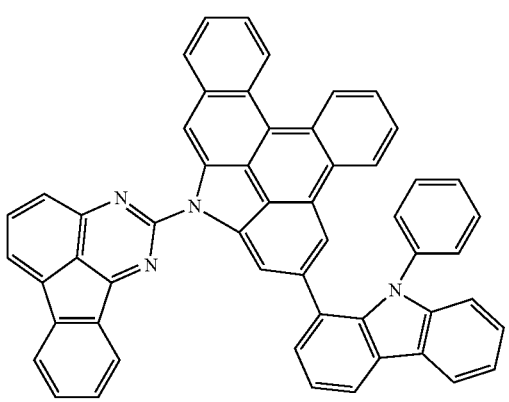
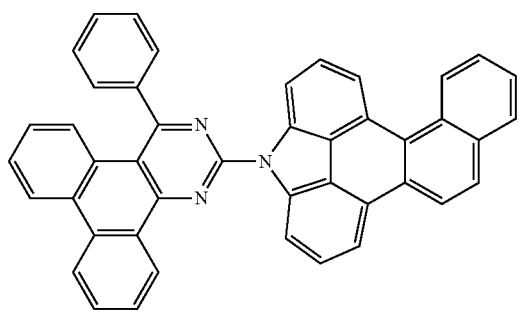
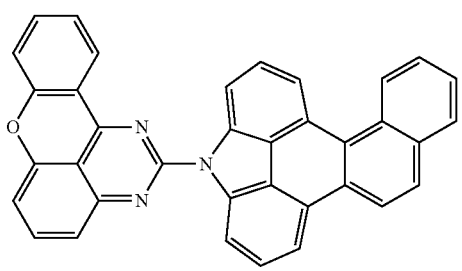
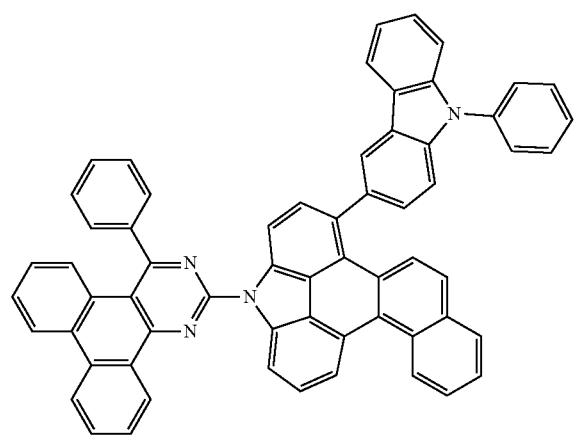
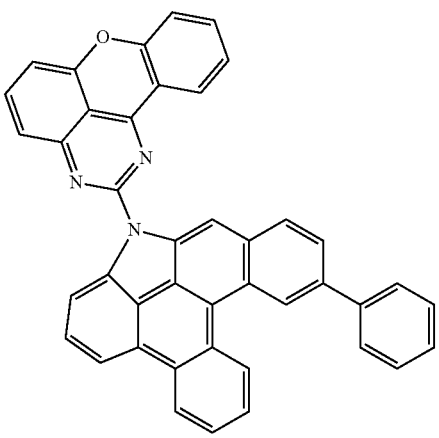

513
-continued
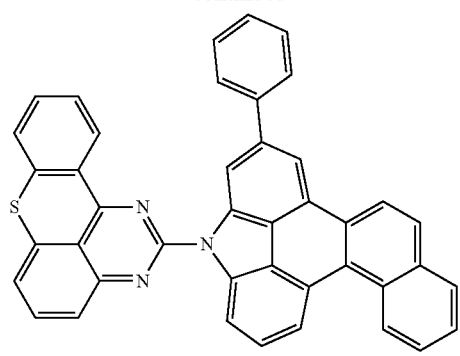
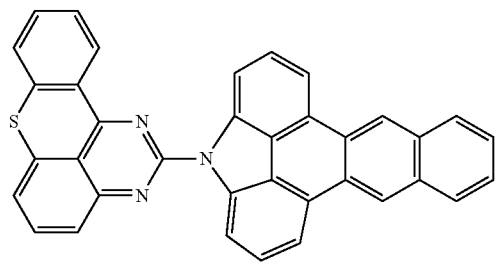
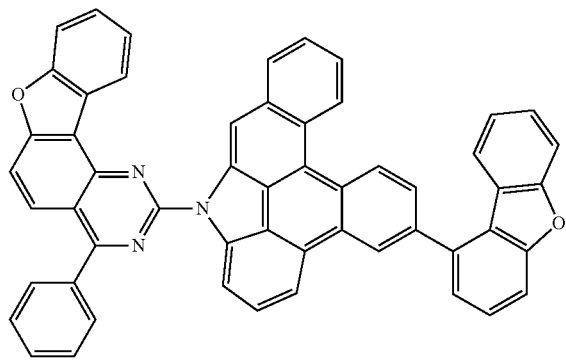
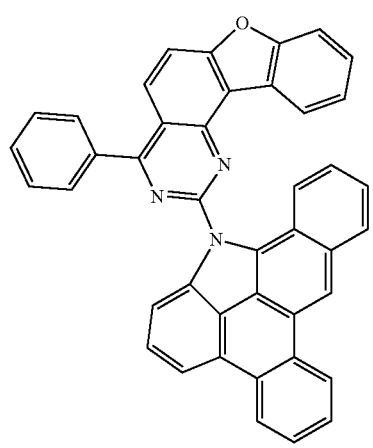
514
-continued
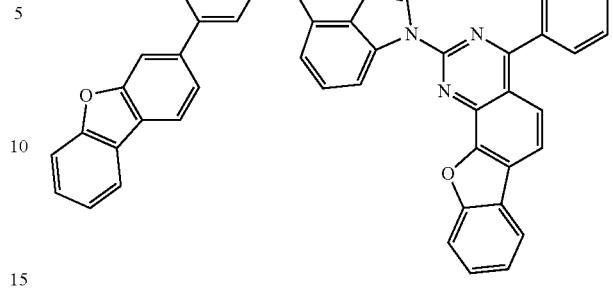
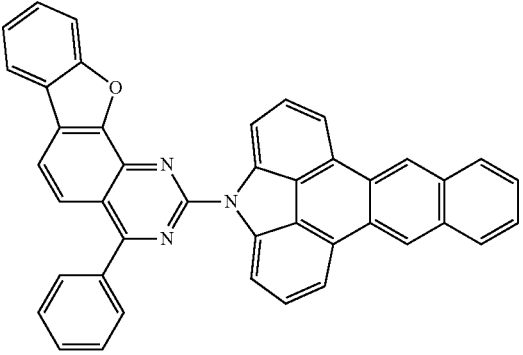
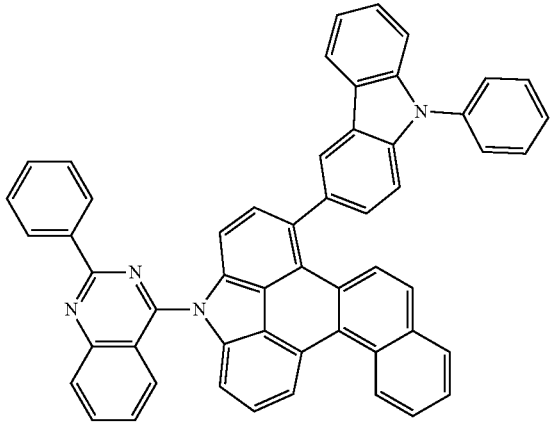
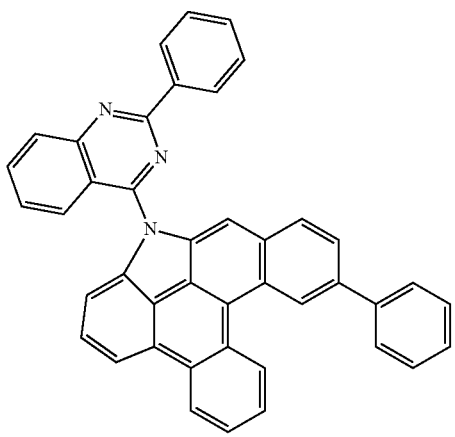

515
-continued
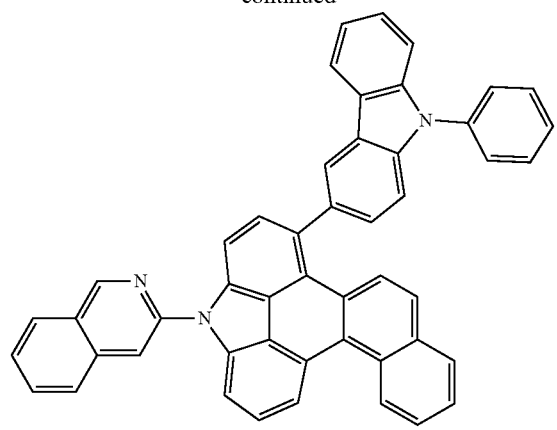
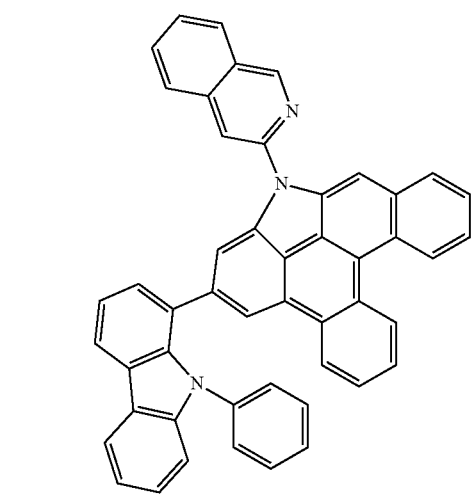
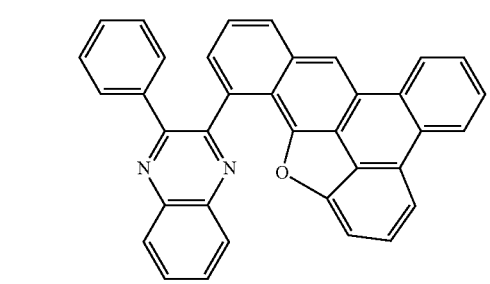
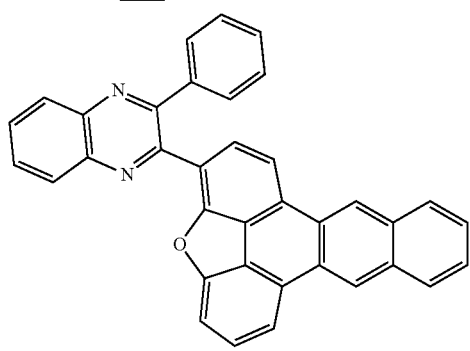
516
-continued
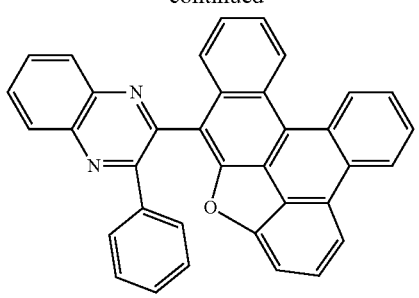
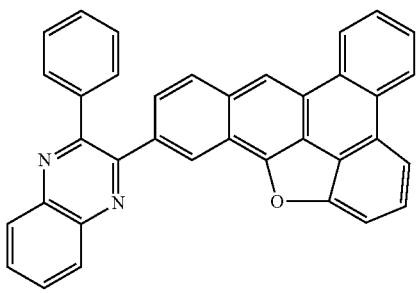
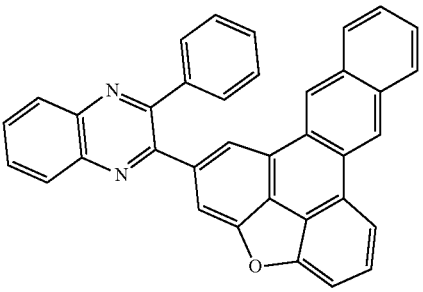
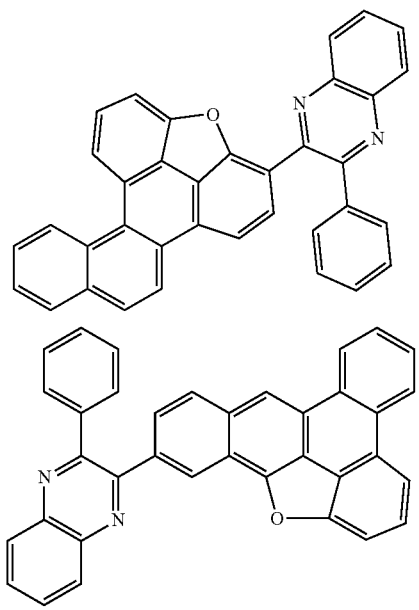
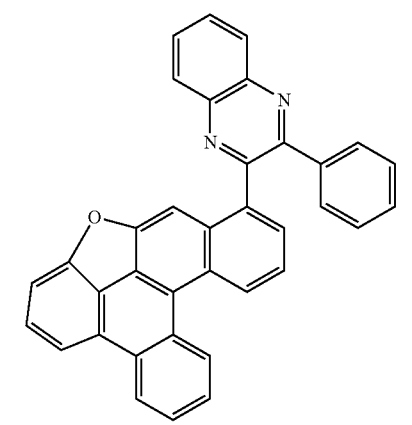

517
-continued
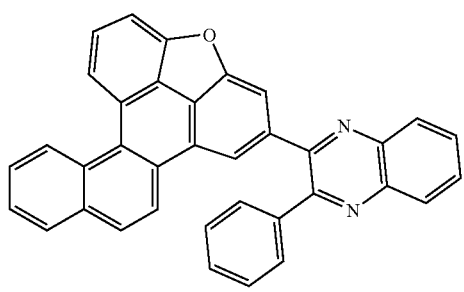
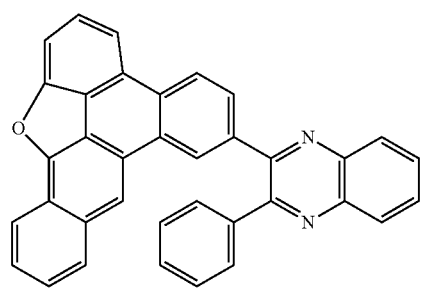
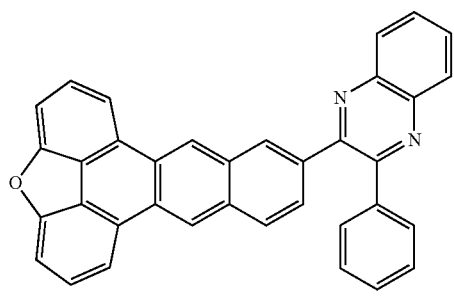
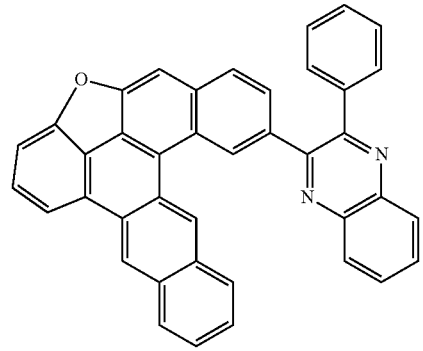
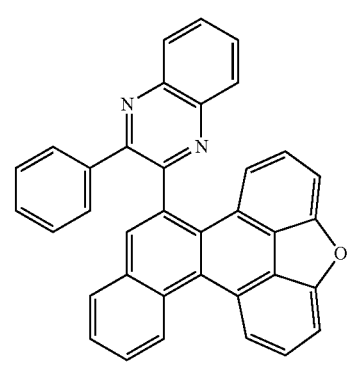
518
-continued
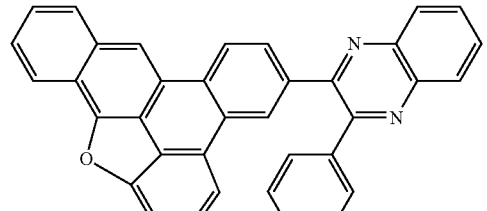
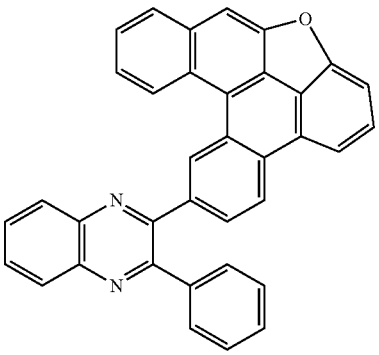
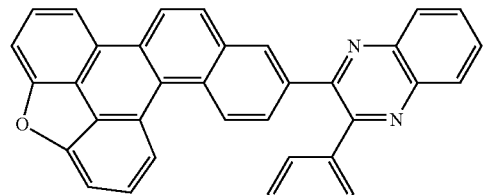
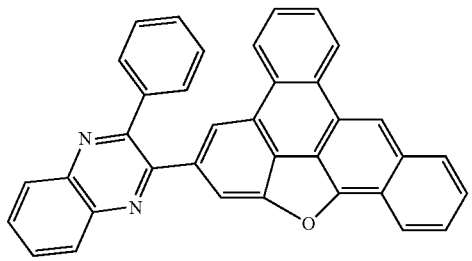
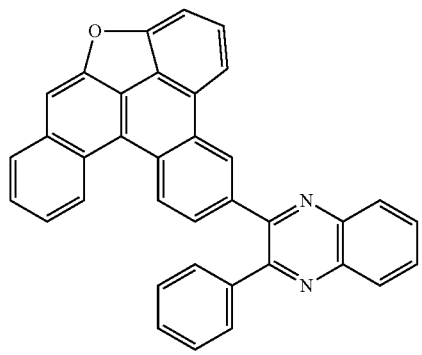
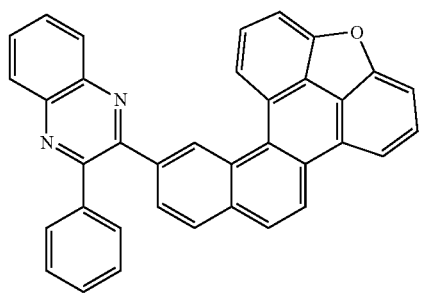

519
-continued
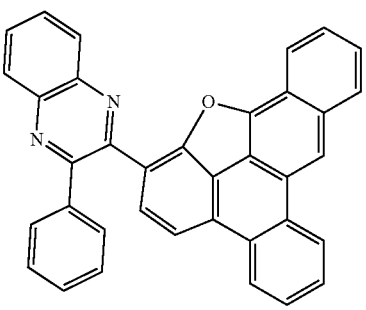
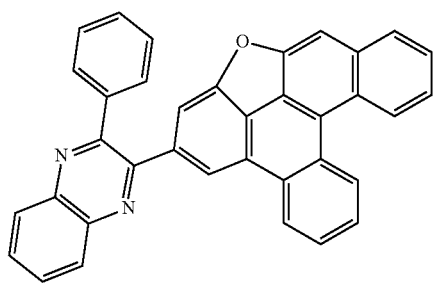
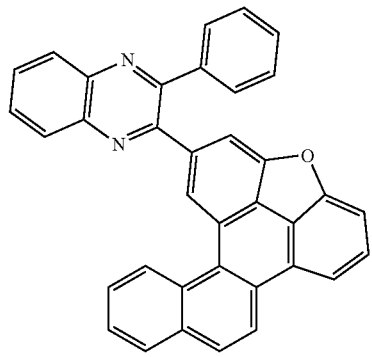
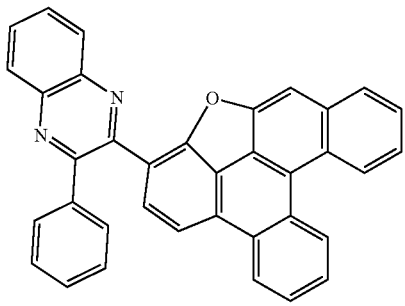
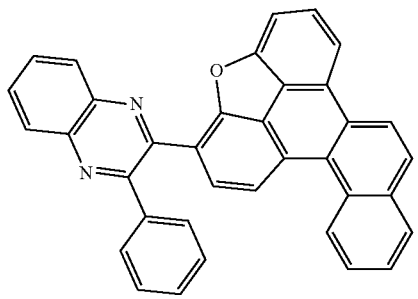
520
-continued
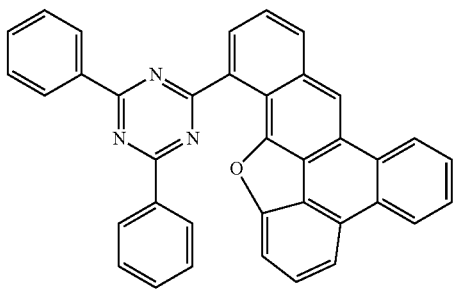
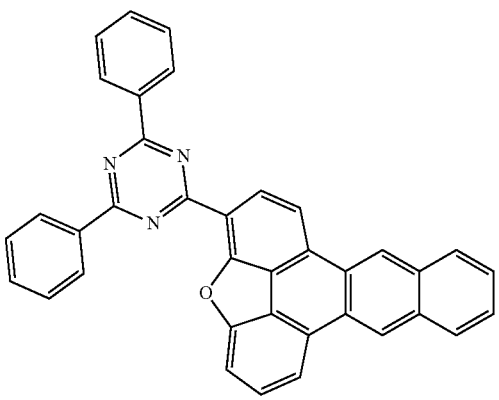
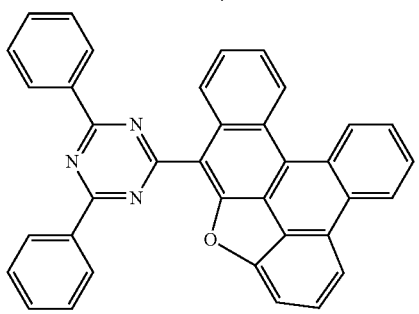
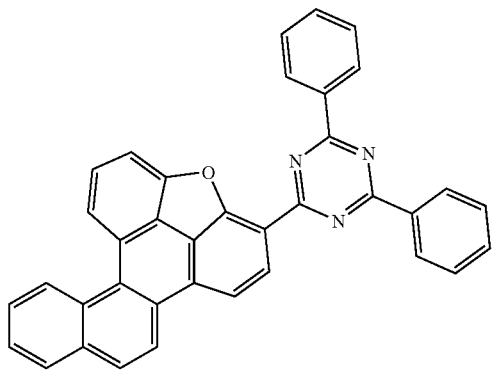
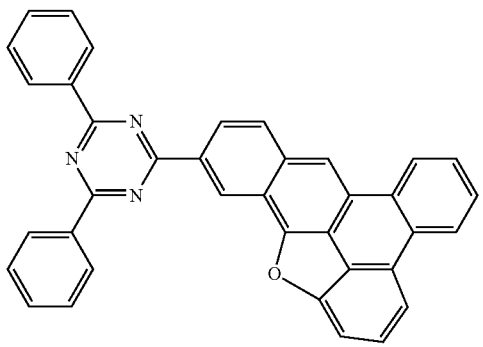

521
-continued
522
-continued
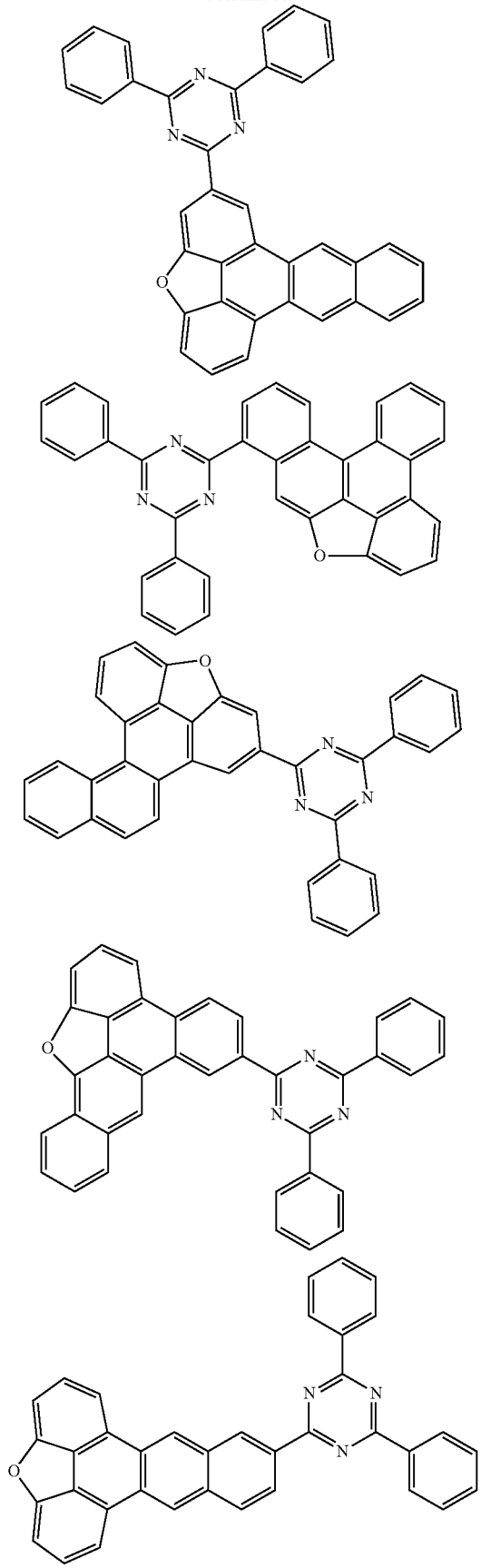
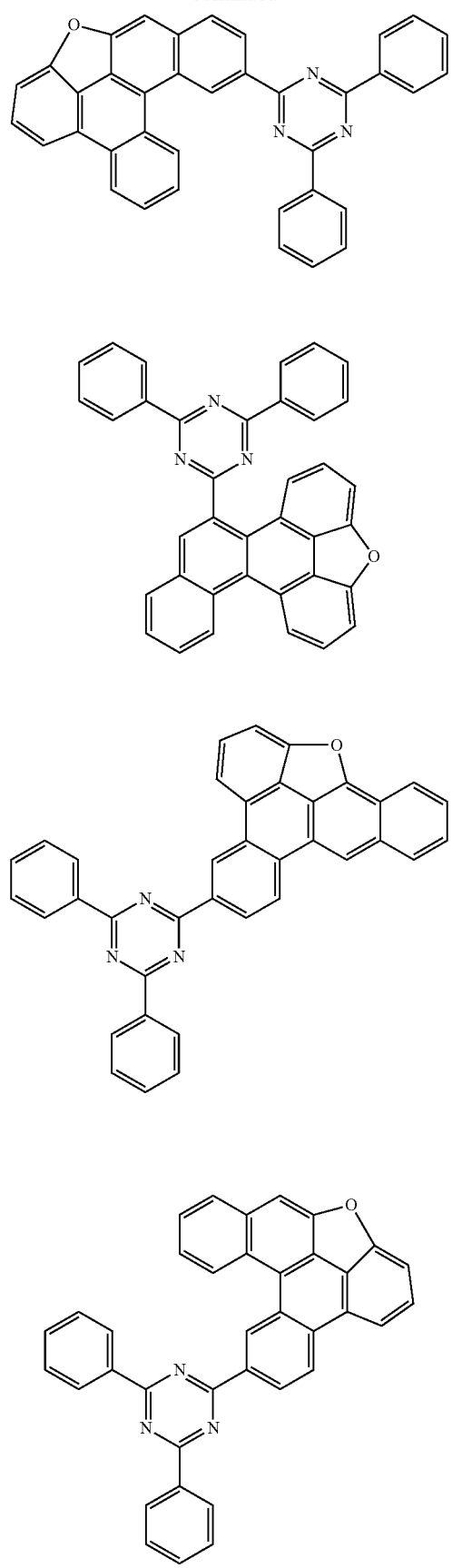

523
-continued
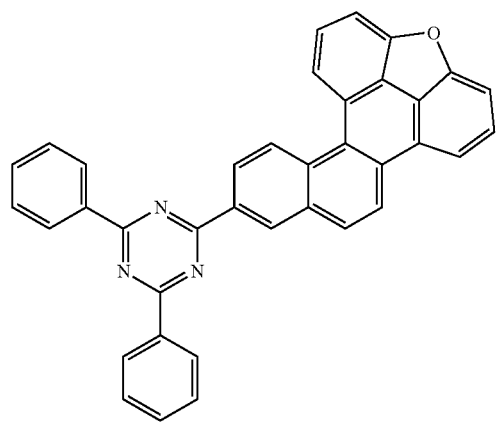
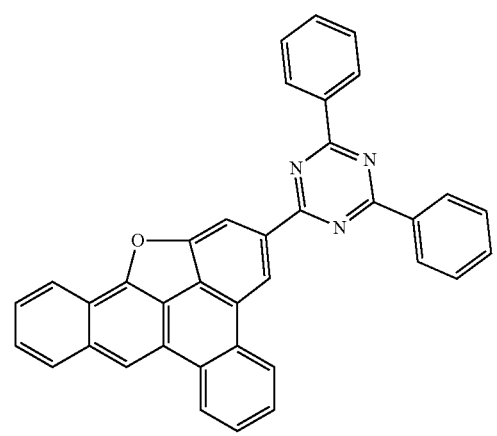
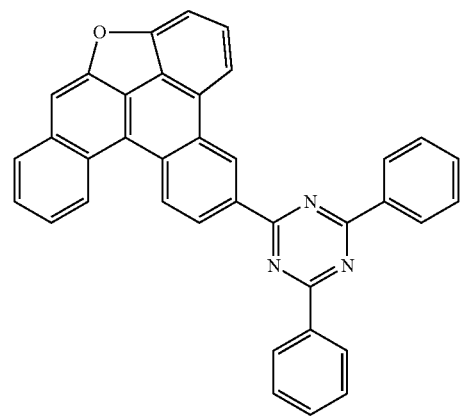
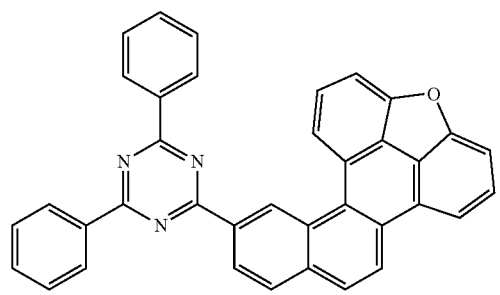
524
-continued
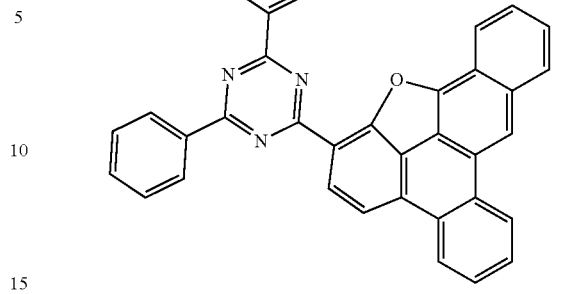
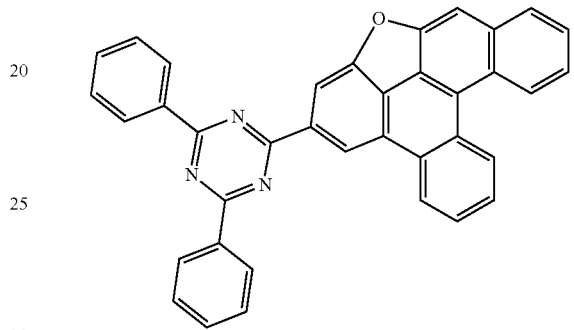
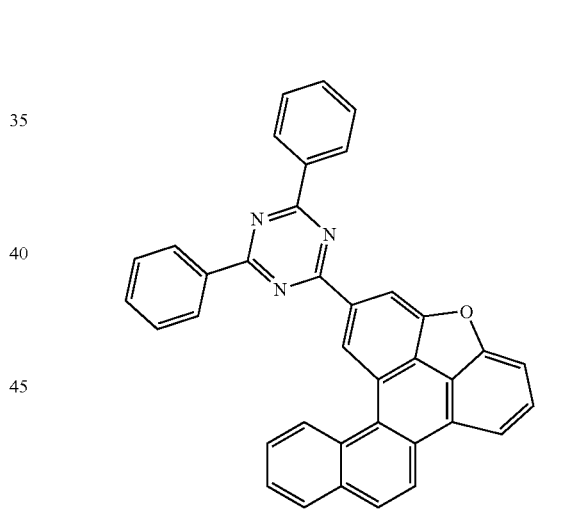
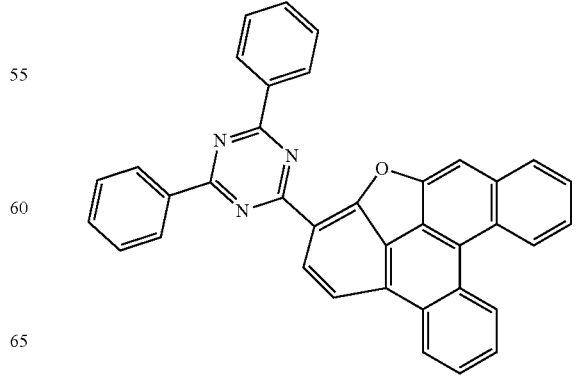

525
-continued
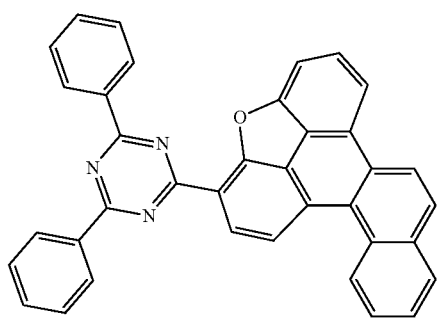
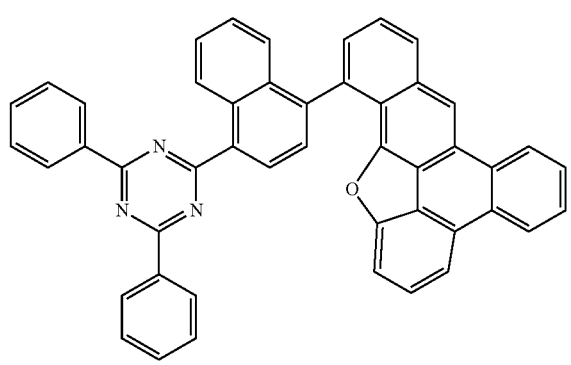
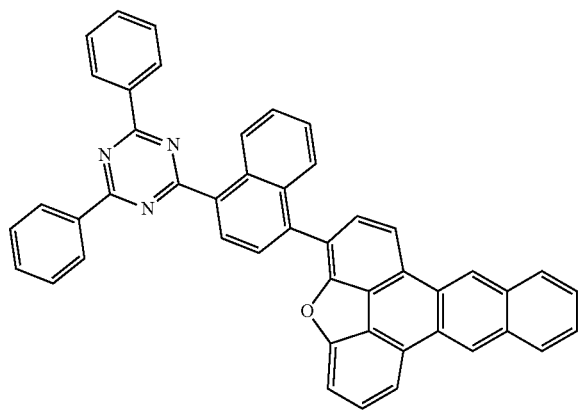
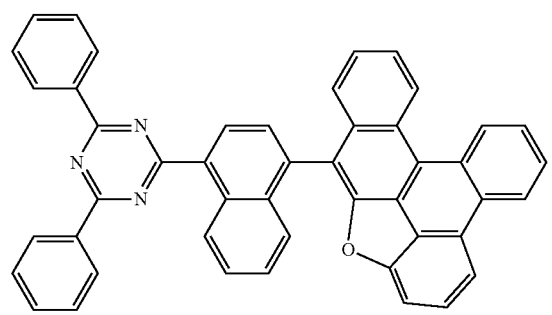
526
-continued
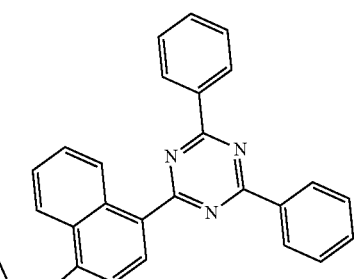
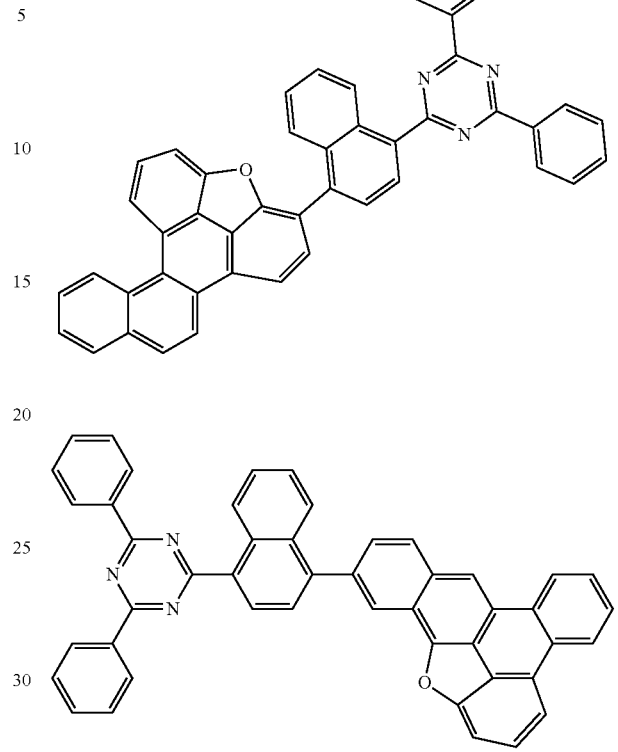
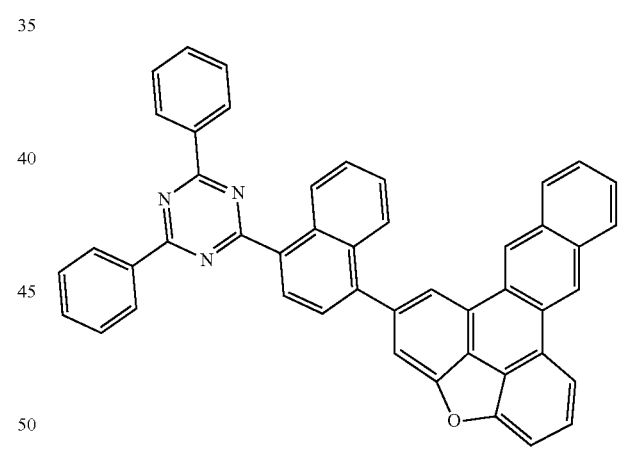
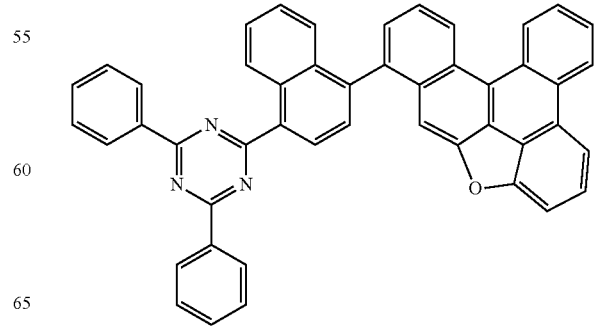

527
-continued
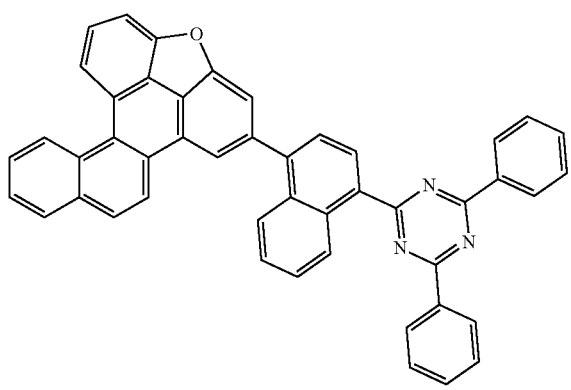
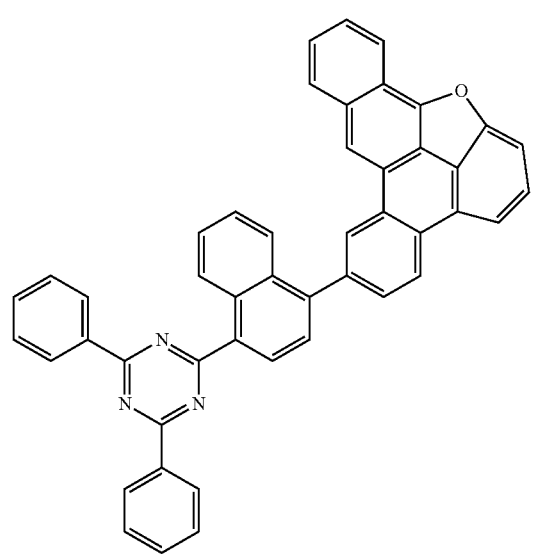
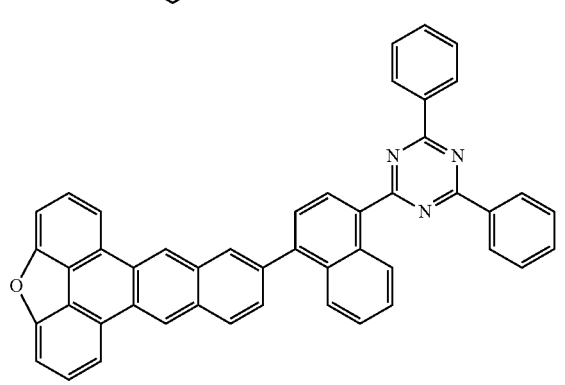
528
-continued
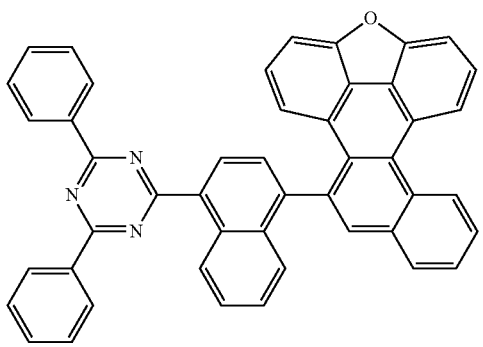
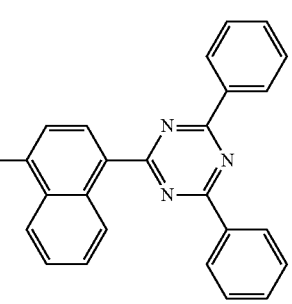
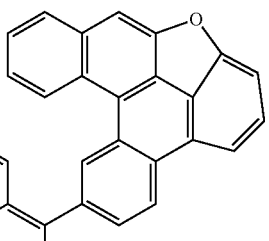
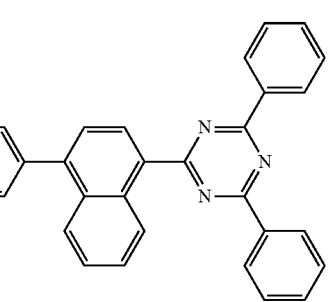

529
-continued
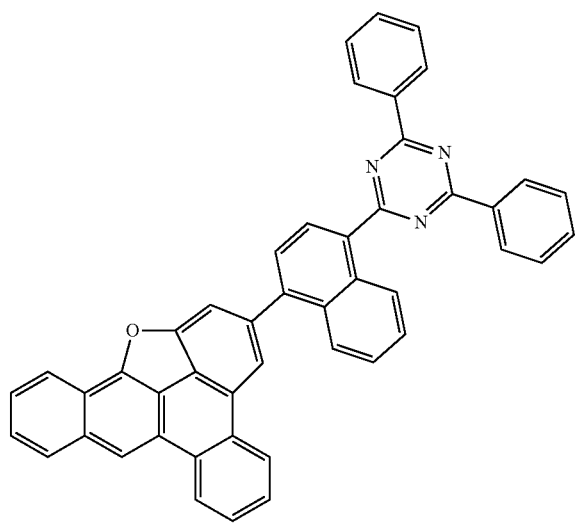
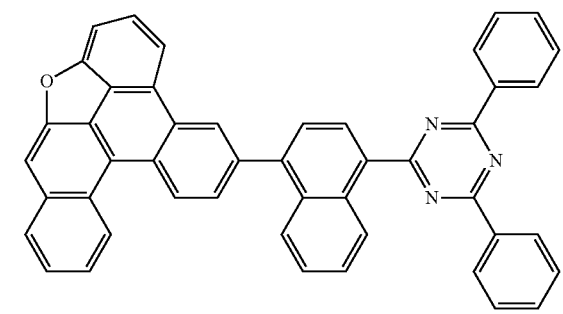
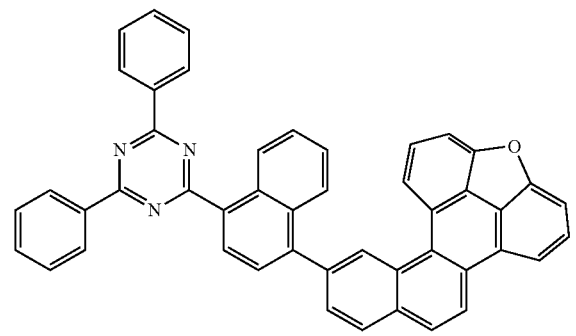
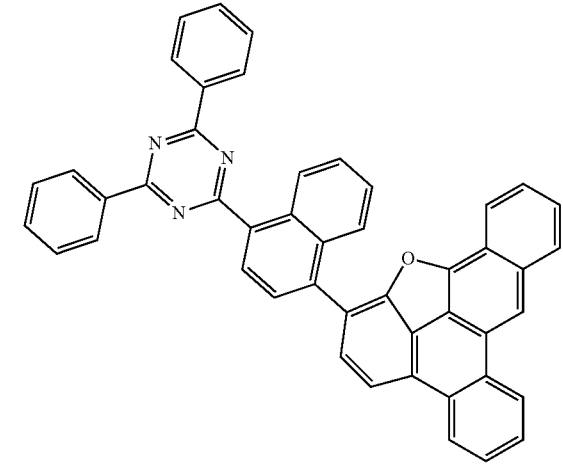
530
-continued
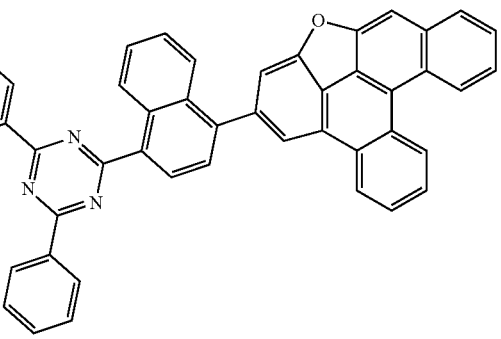
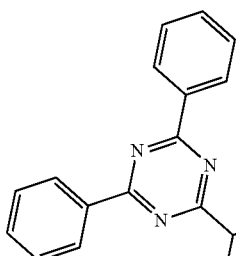
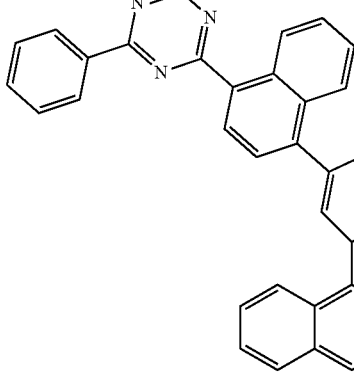
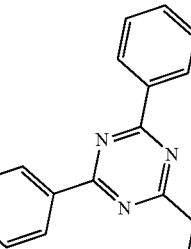
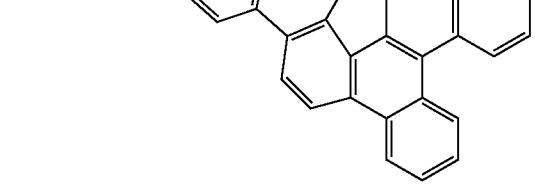
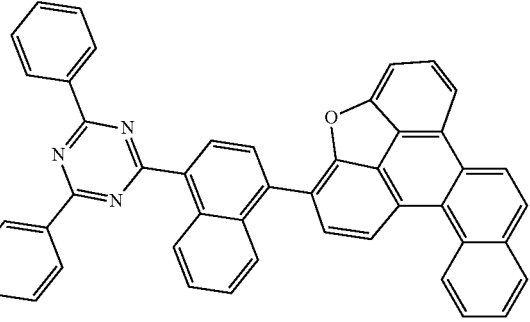

531
-continued
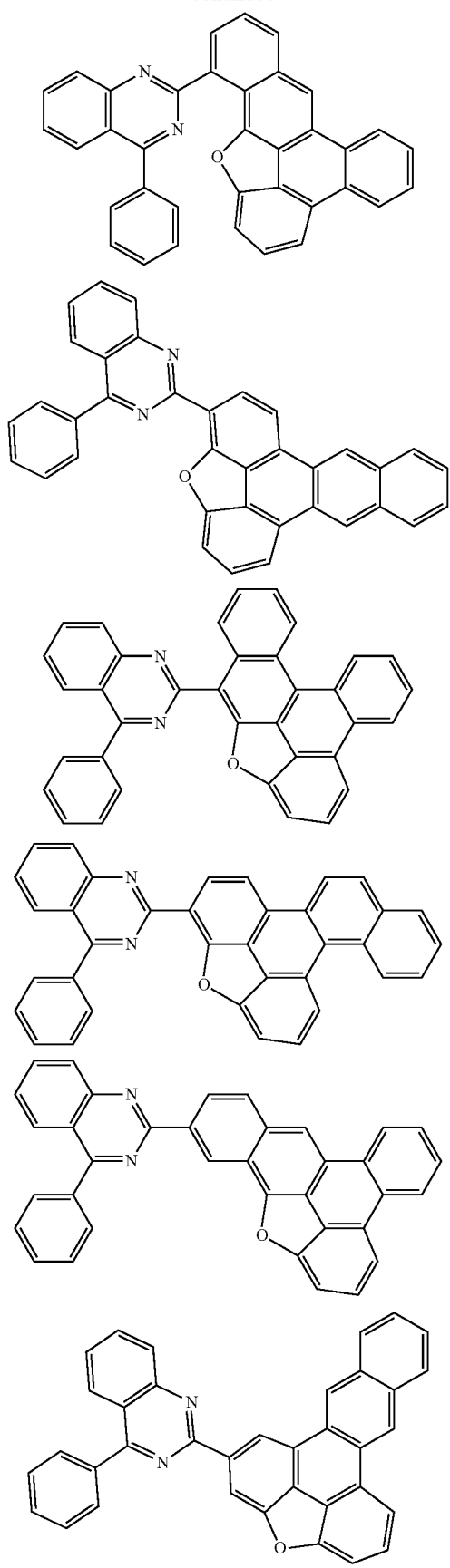
532
-continued
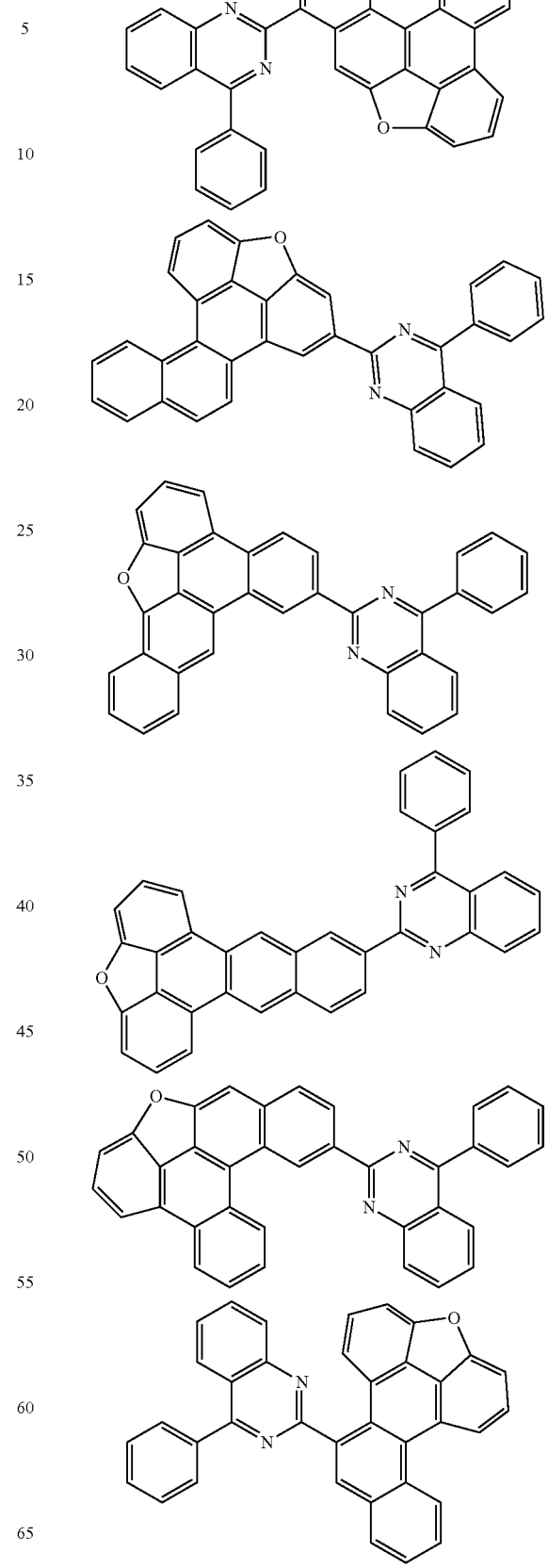

533
-continued
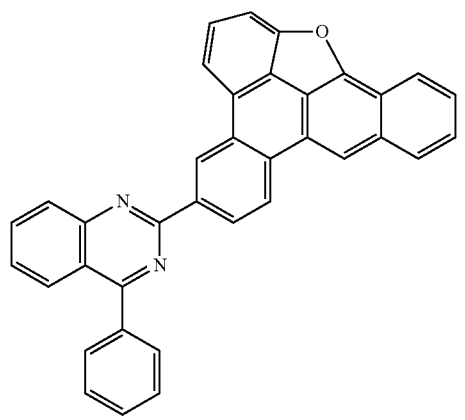
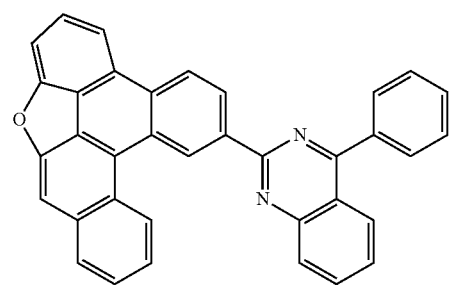
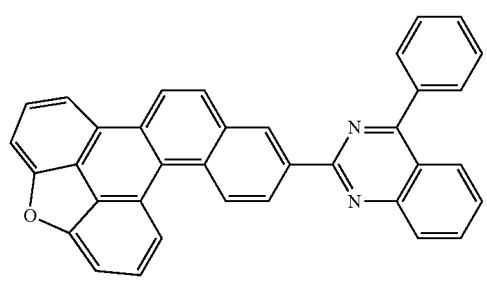
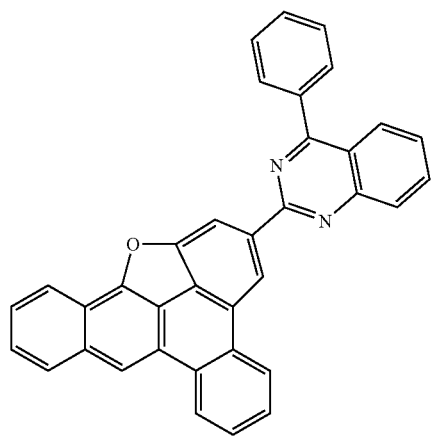
534
-continued
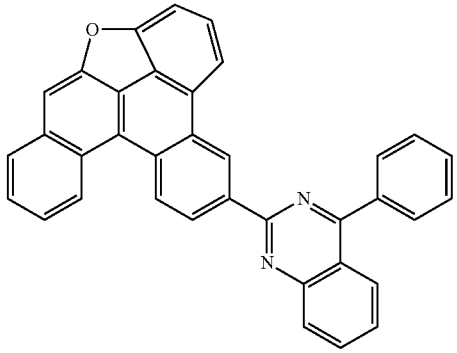
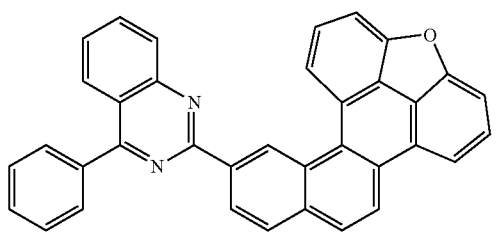
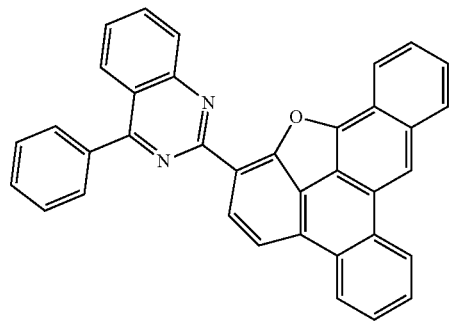
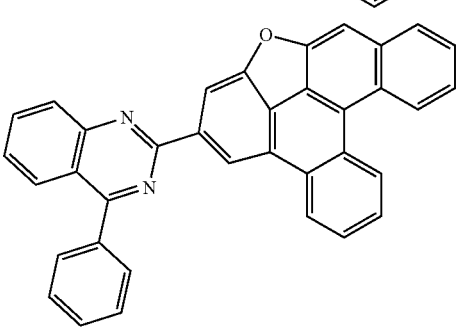
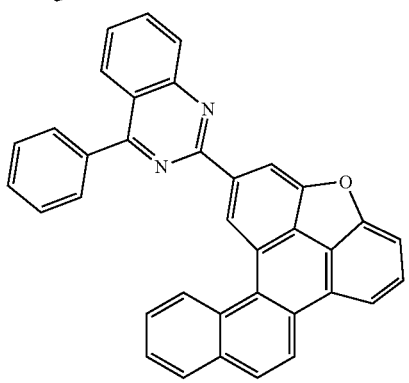

535
-continued
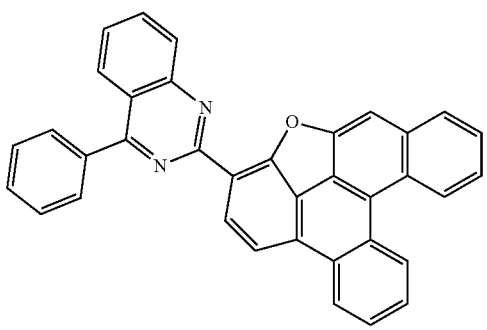
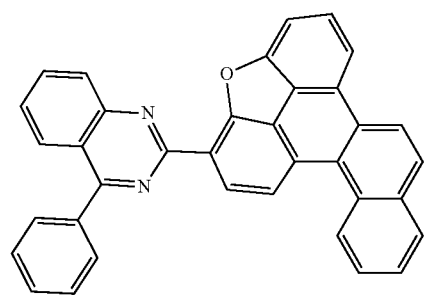
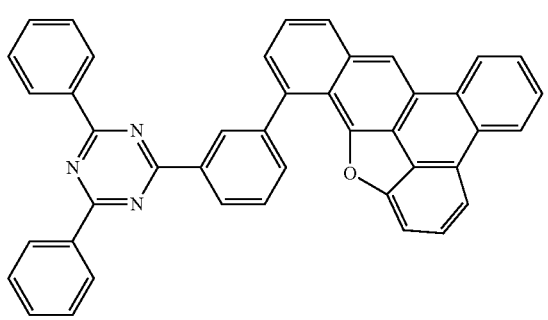
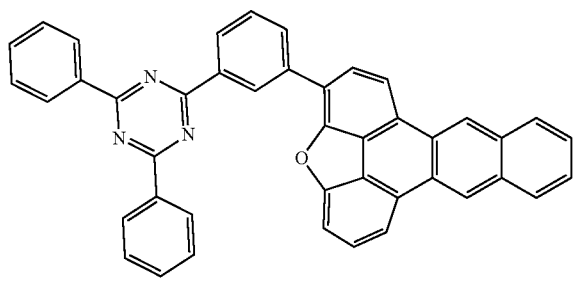
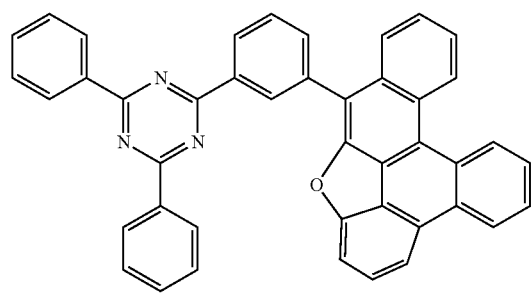
536
-continued
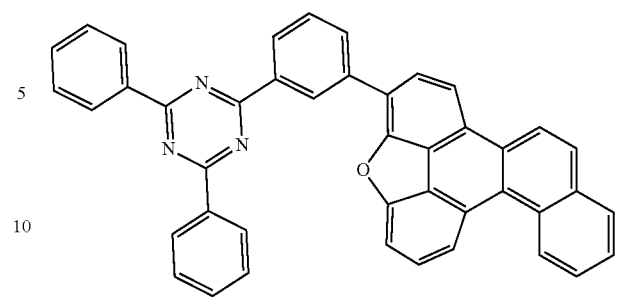
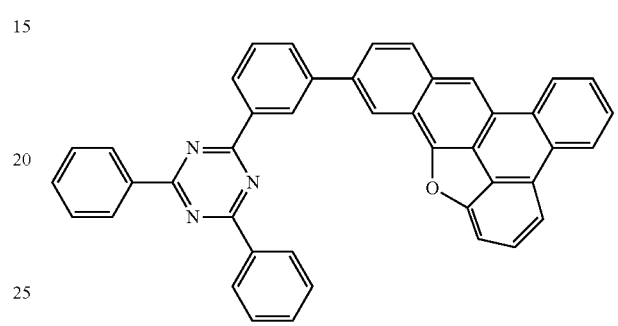
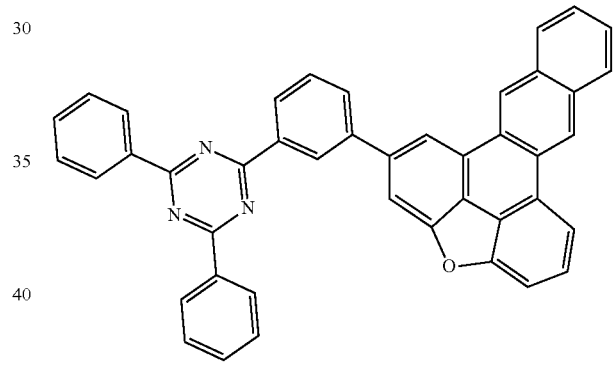
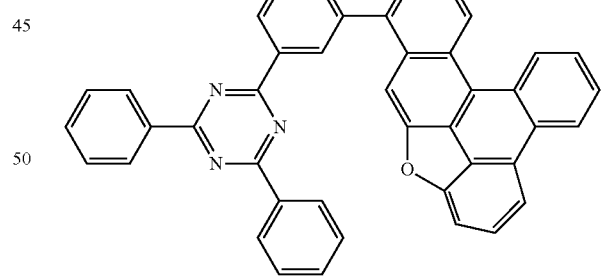
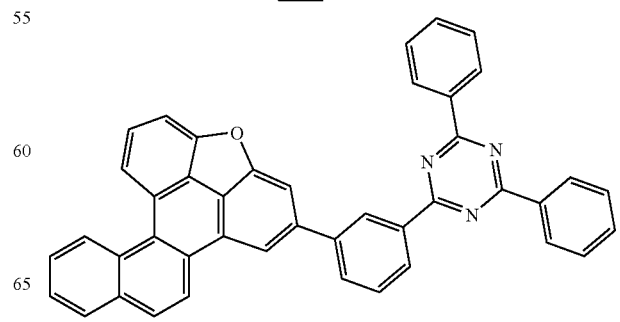

537
-continued
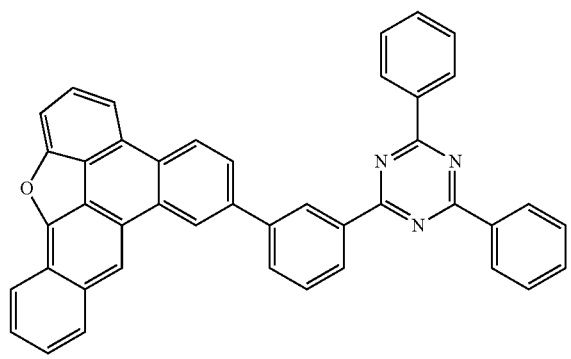
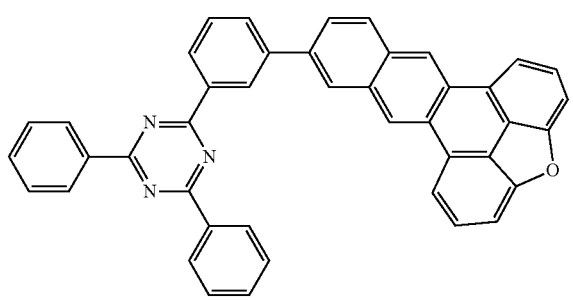
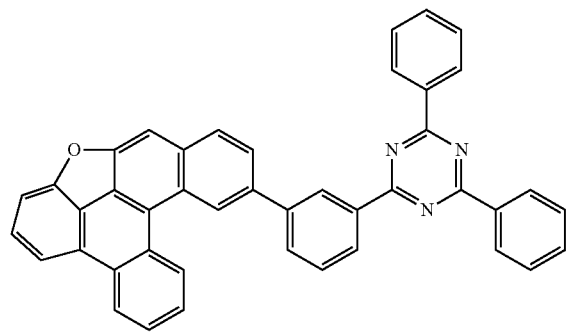
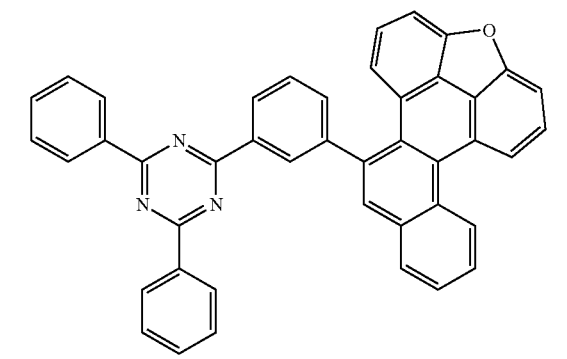
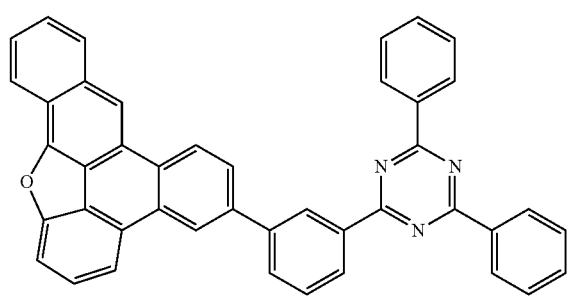
538
-continued
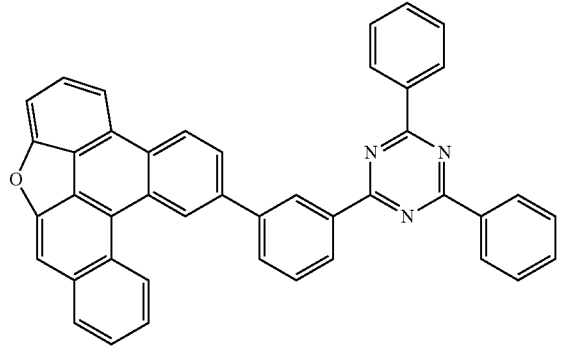
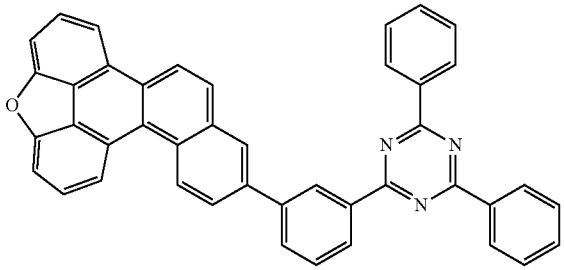
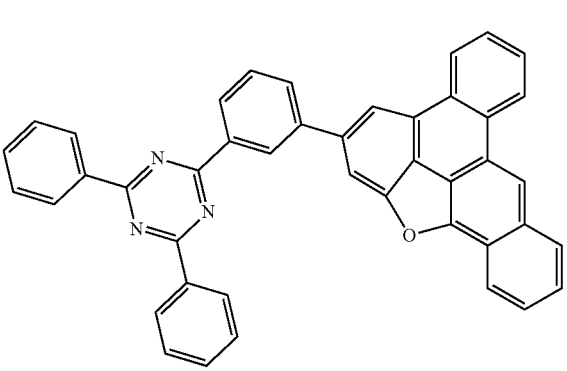
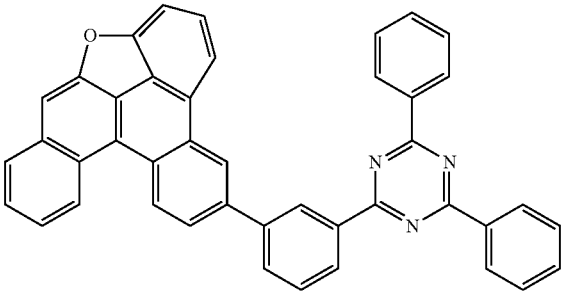
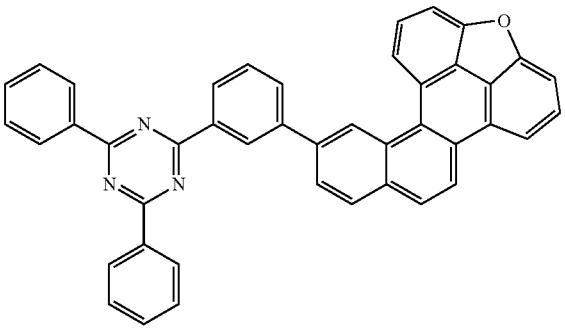

539
-continued
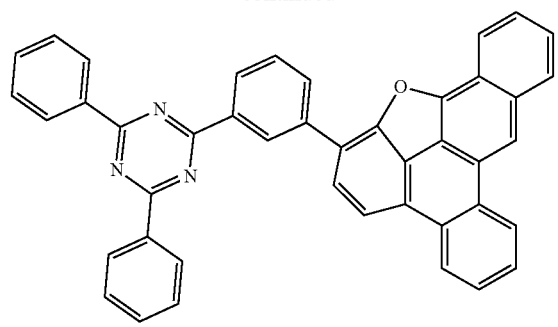
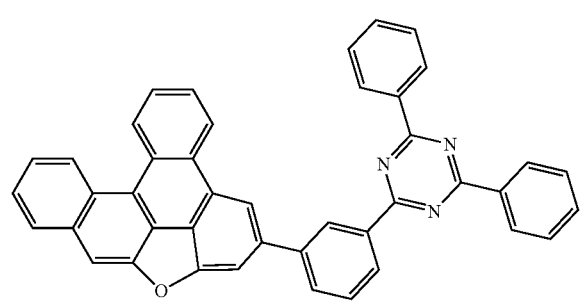
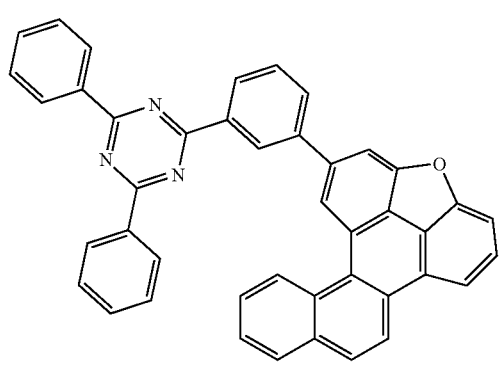
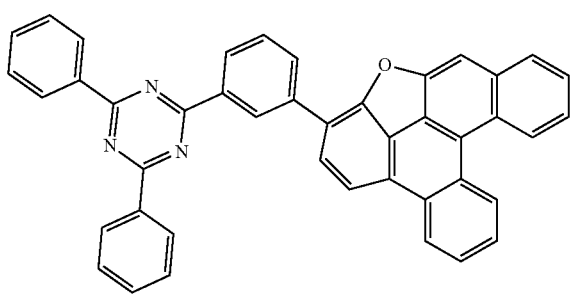
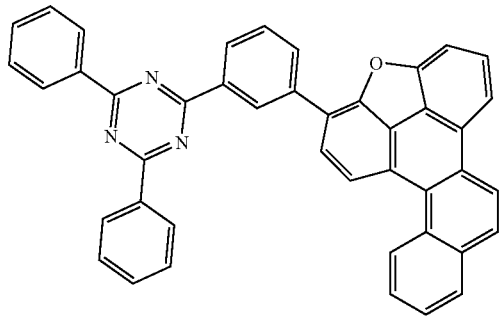
540
-continued
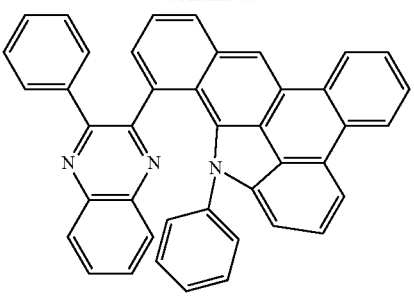
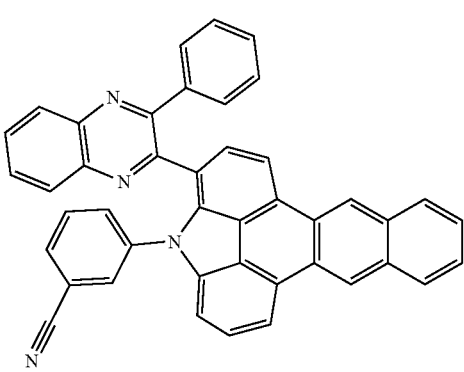
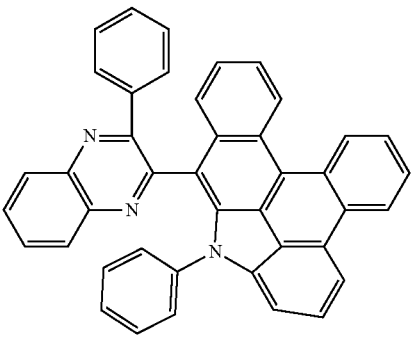
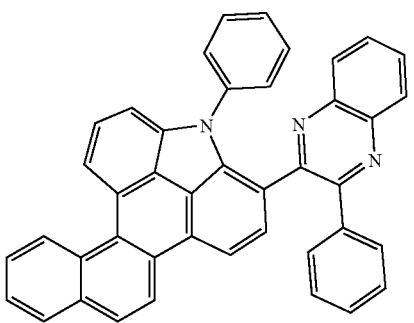

541
-continued
542
-continued
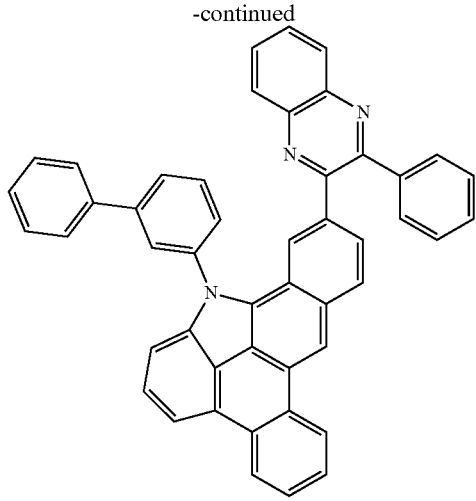
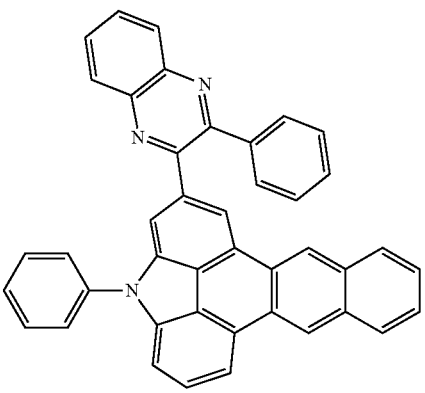
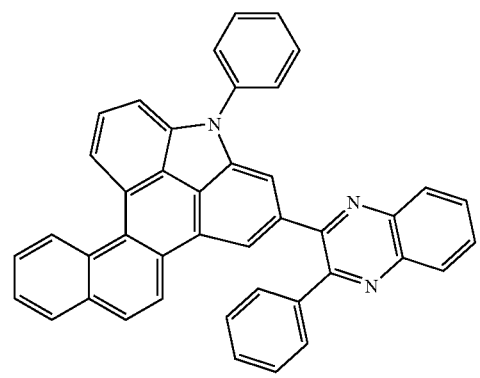
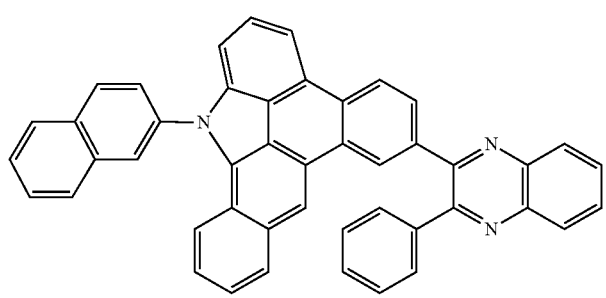
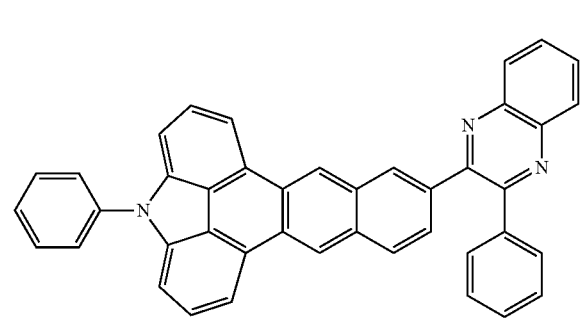
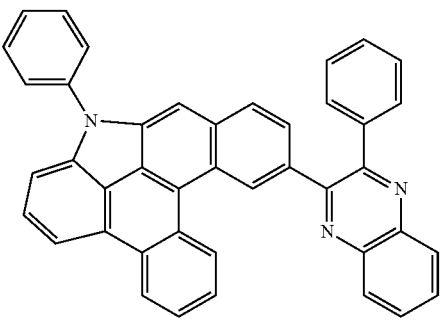
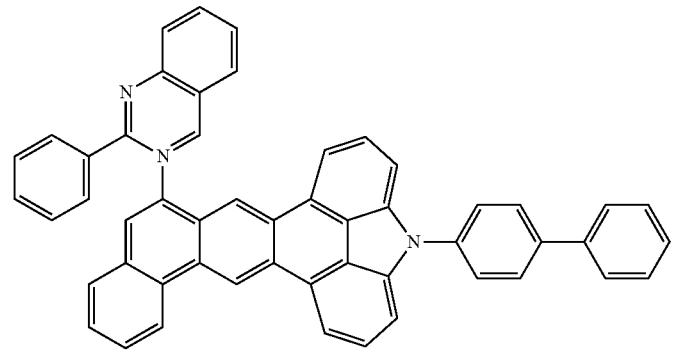
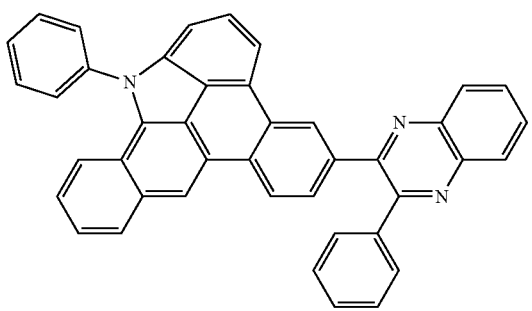

-continued
543 544
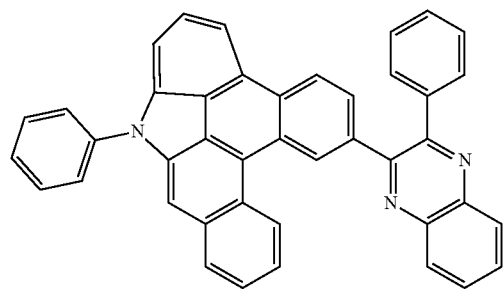
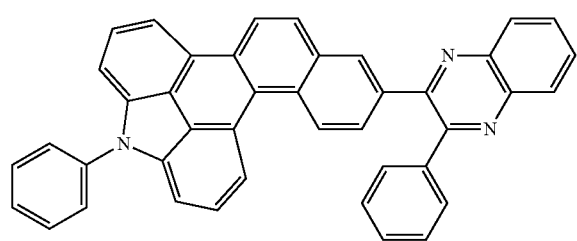
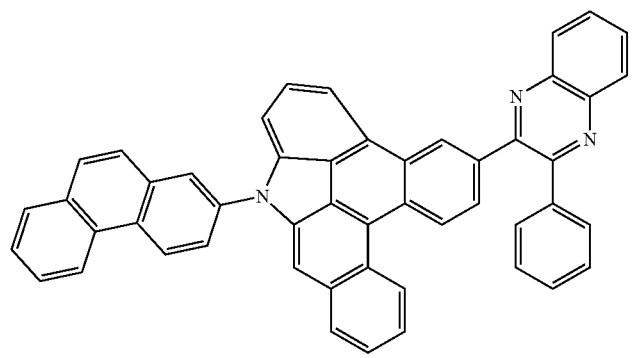
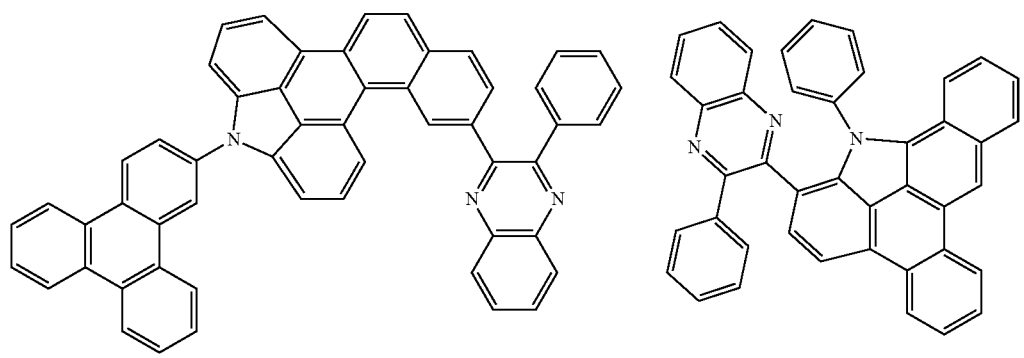
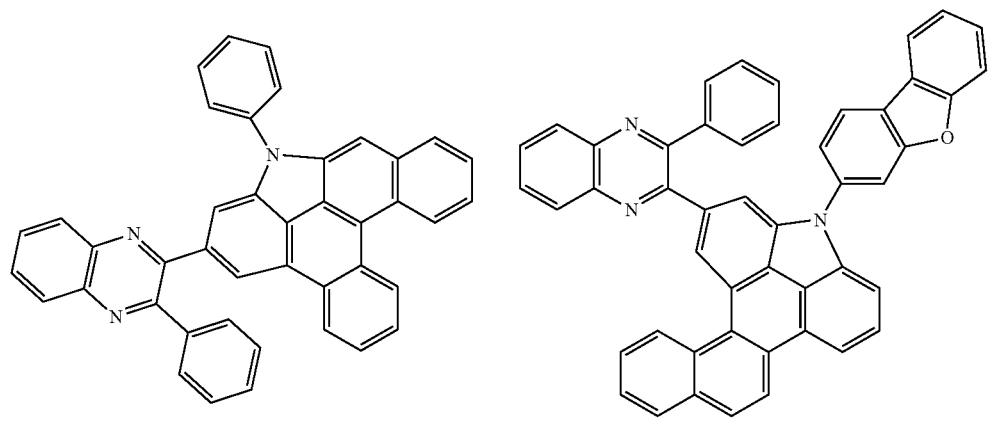

-continued
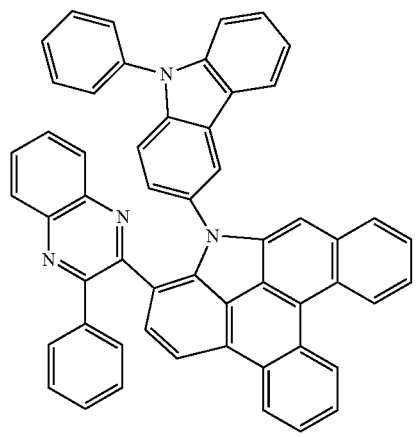
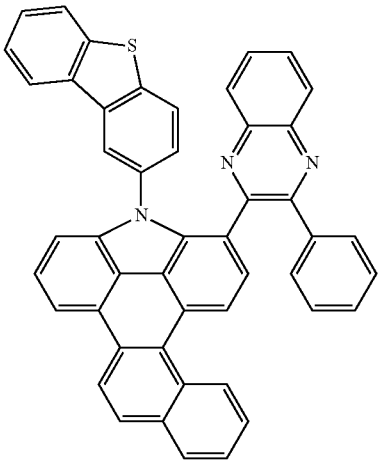
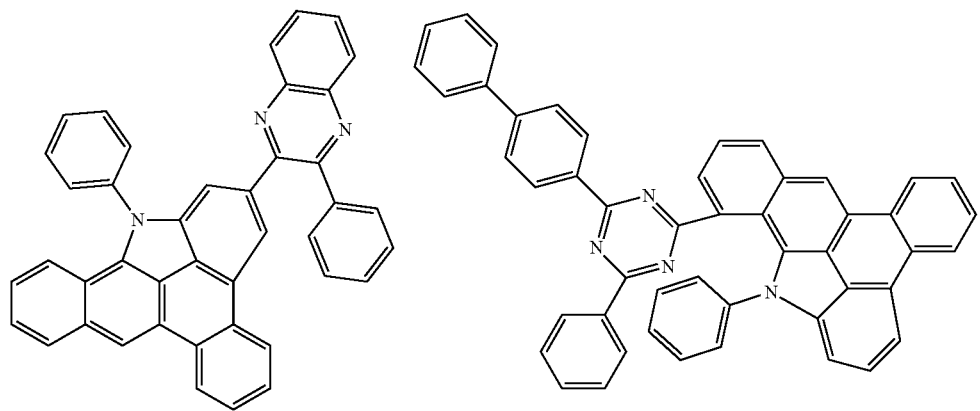
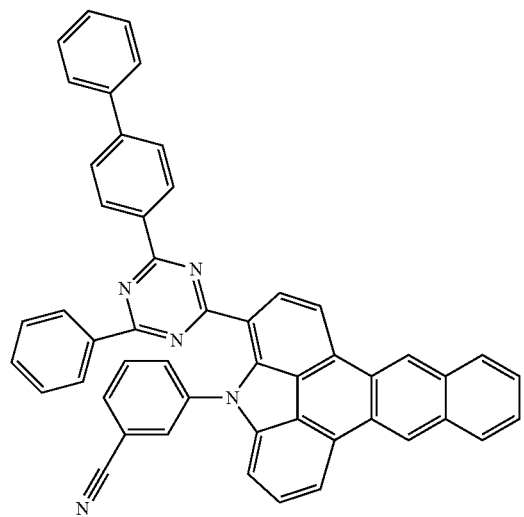
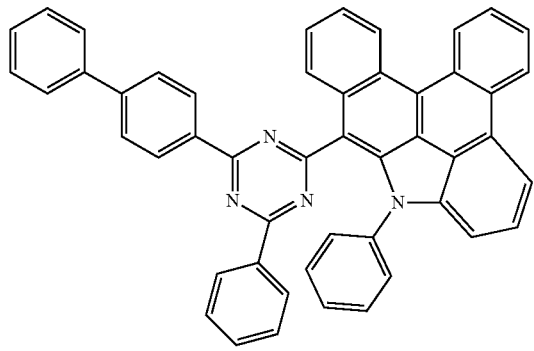

547 548
-continued
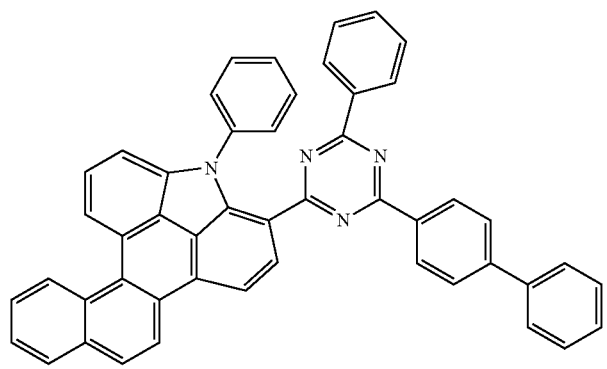
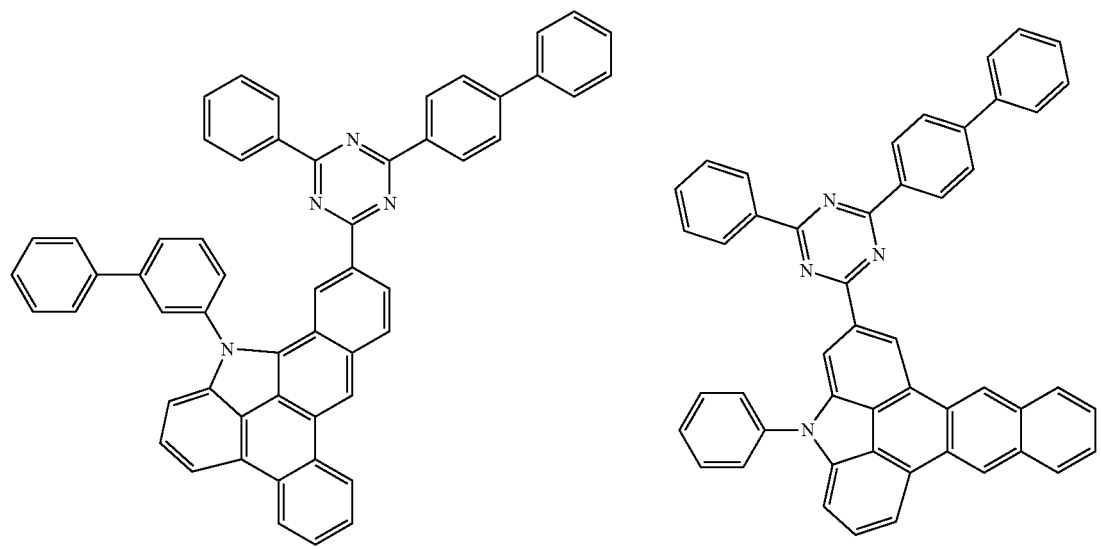
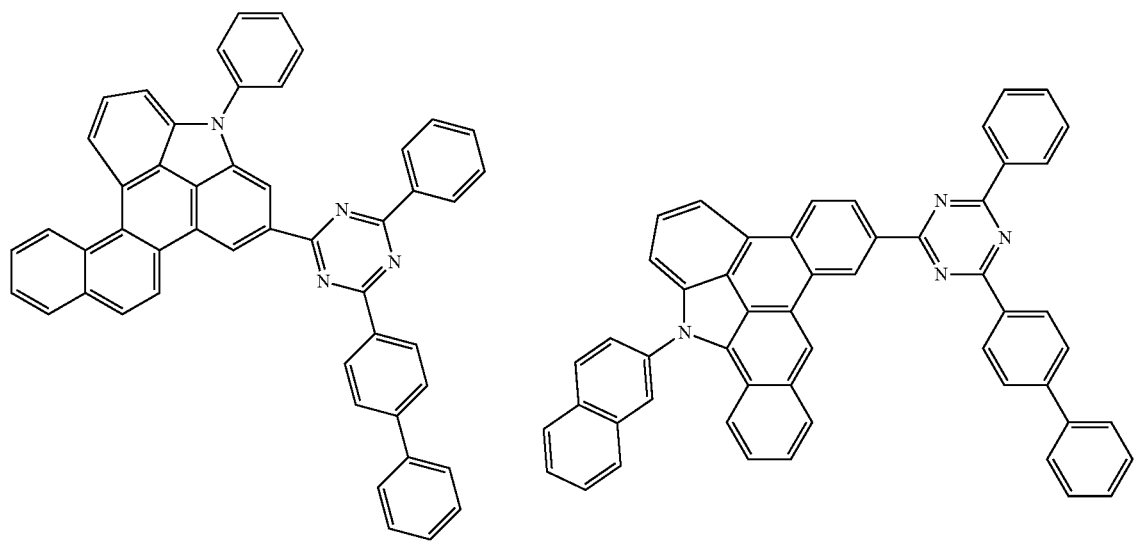

-continued
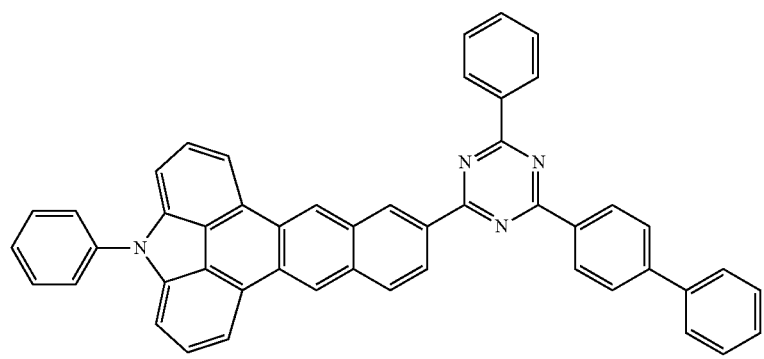
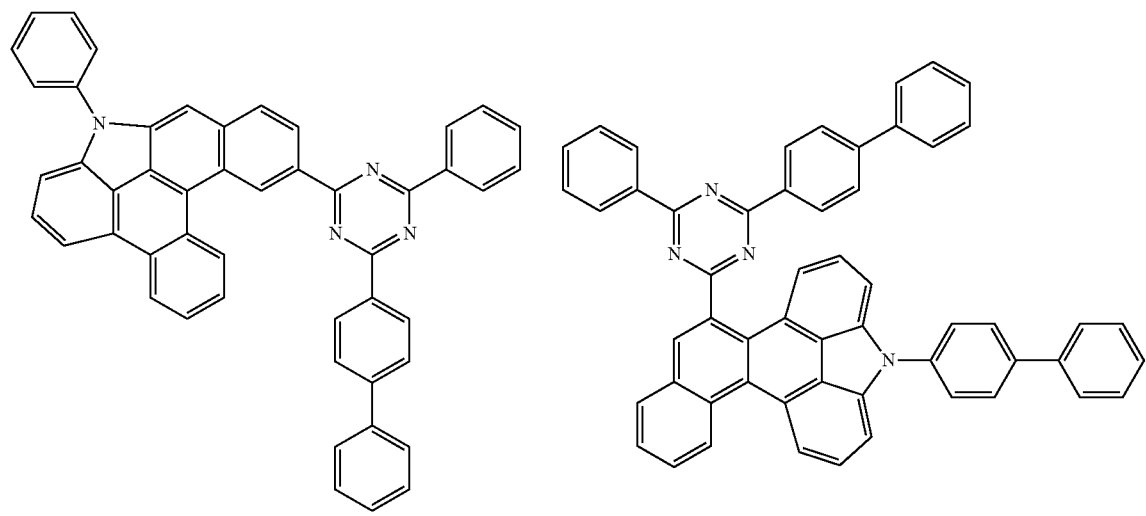
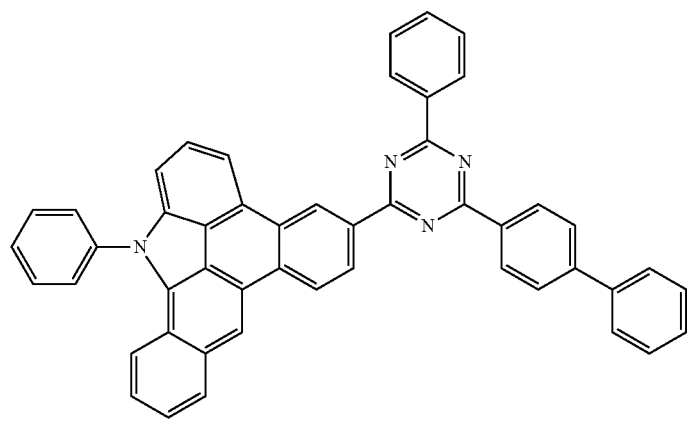

551 552
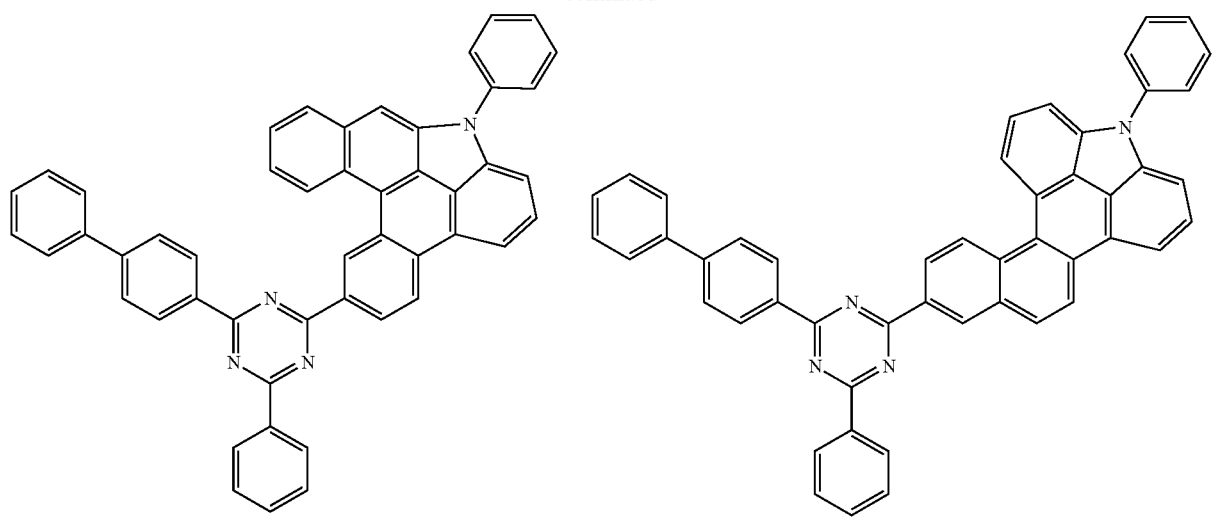
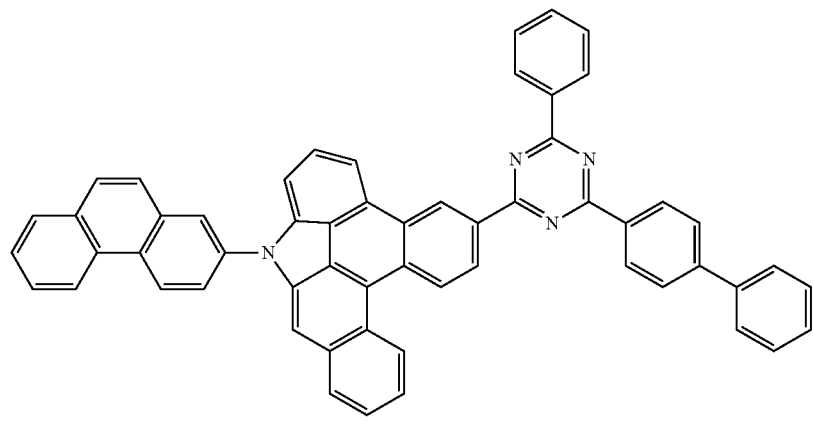
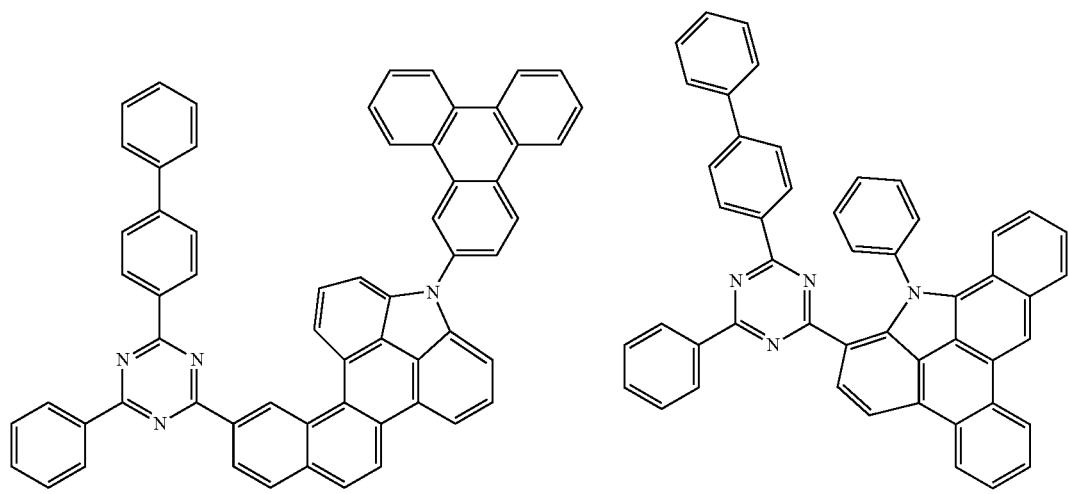

553
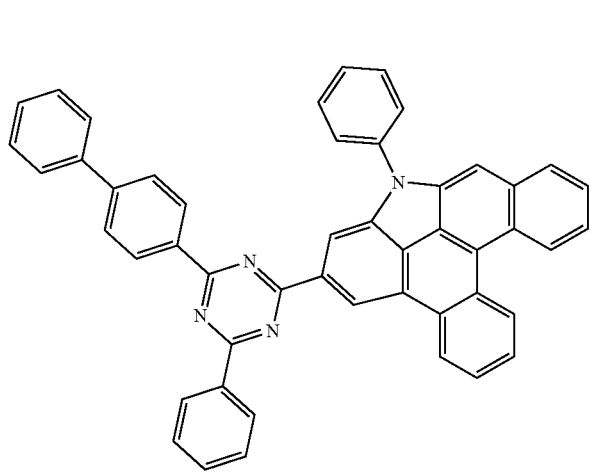
554
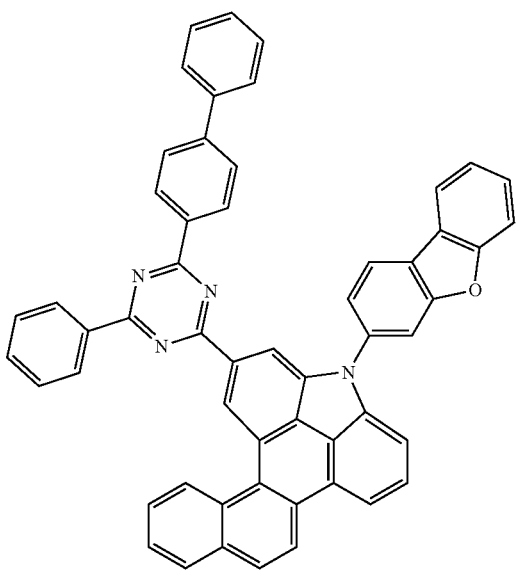
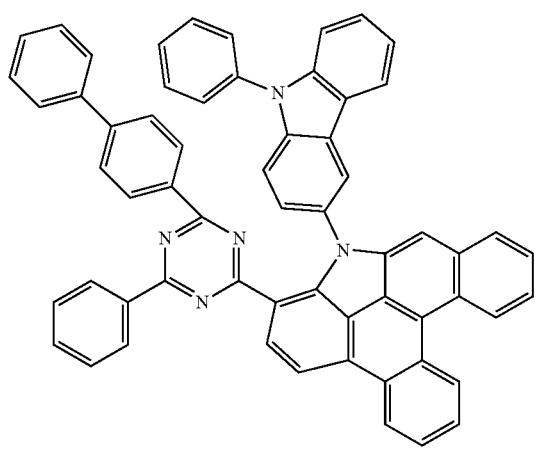
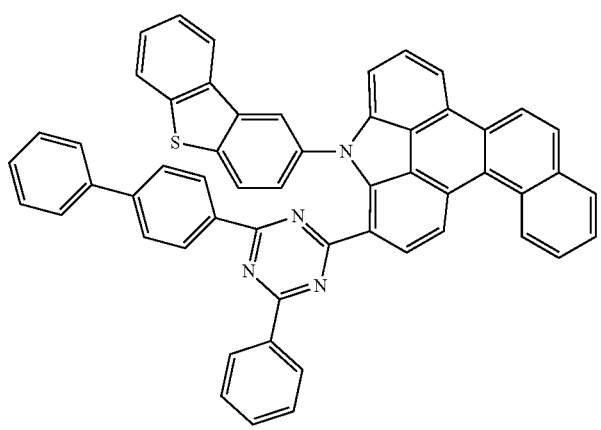
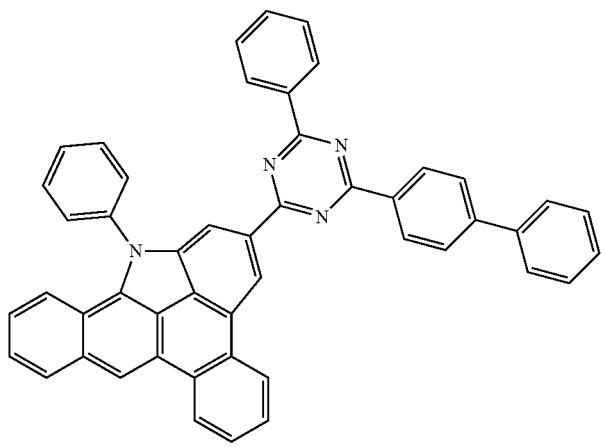
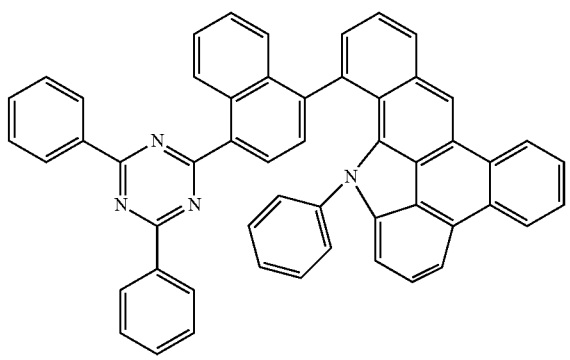

555 556
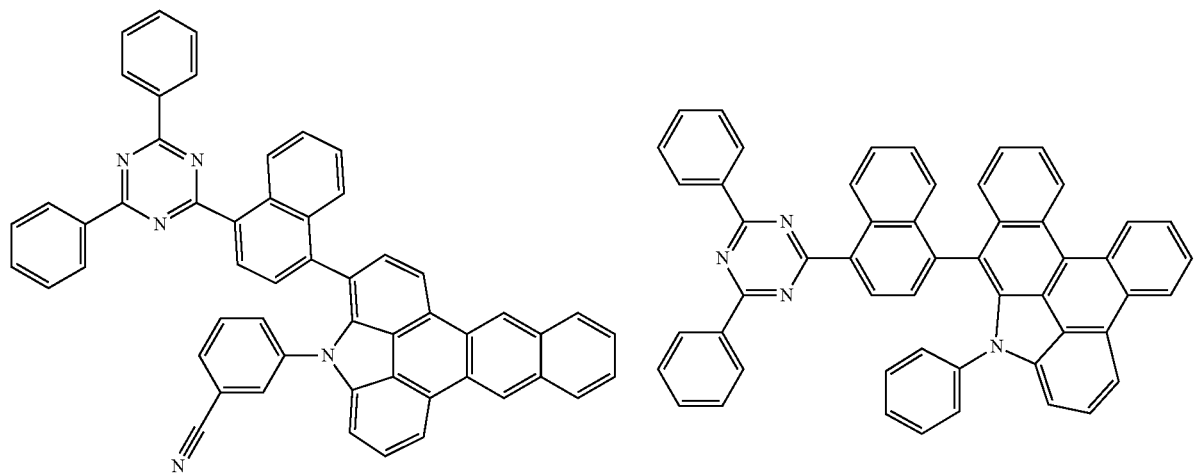
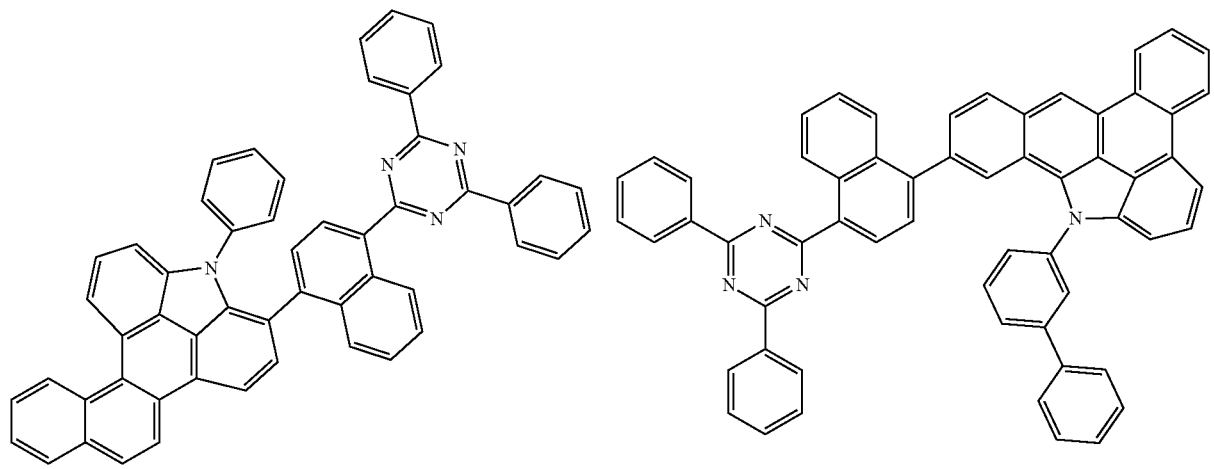
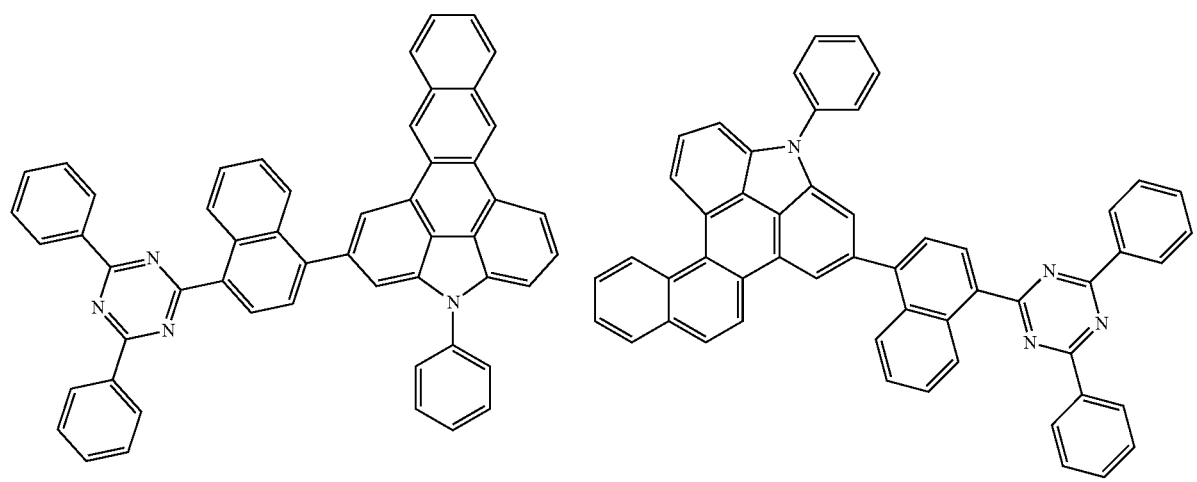

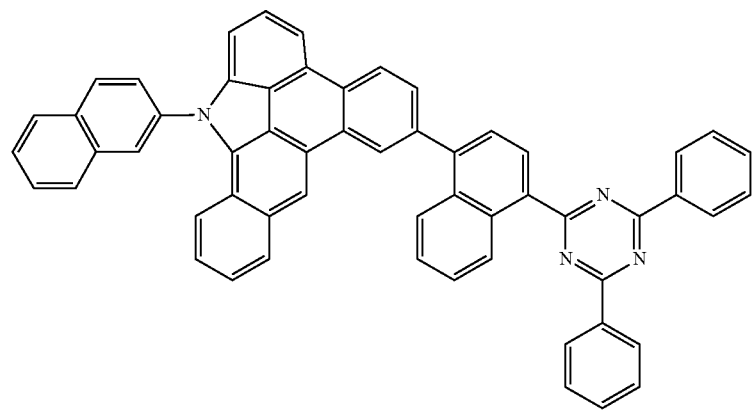
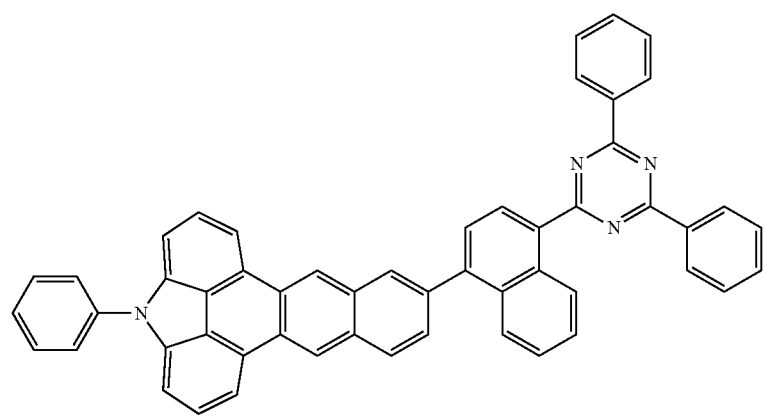
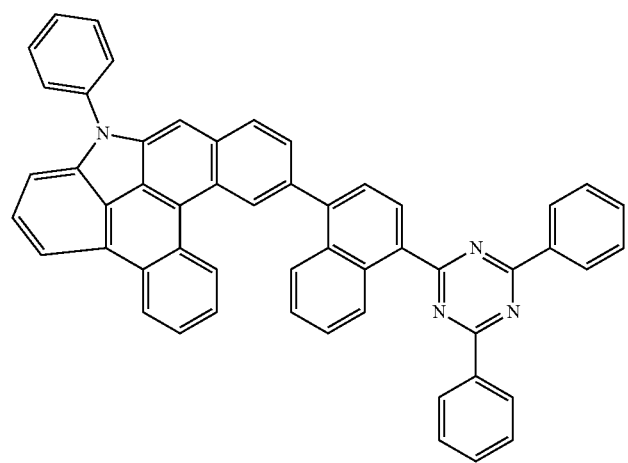

-continued
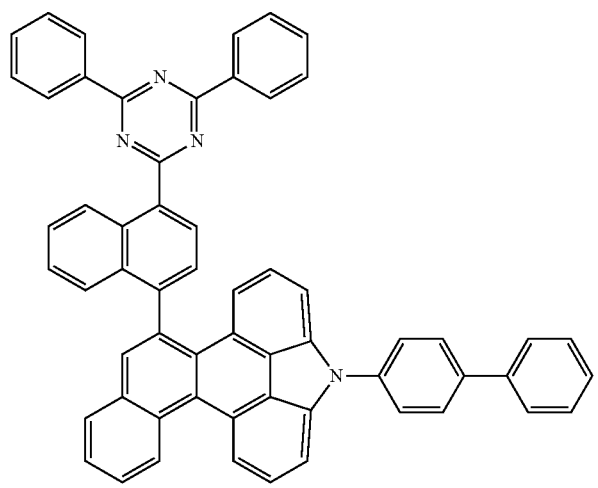
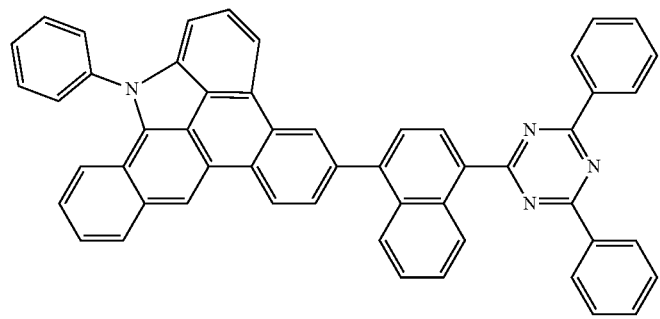
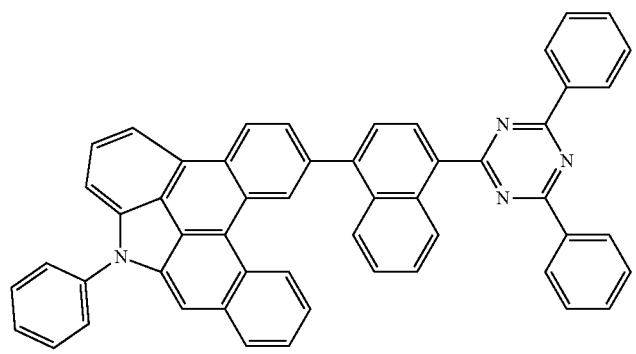
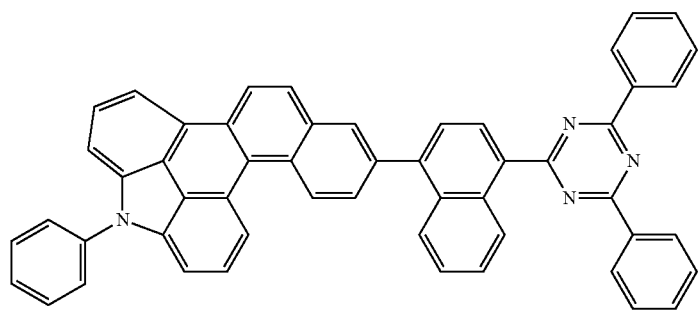

561
-continued
562
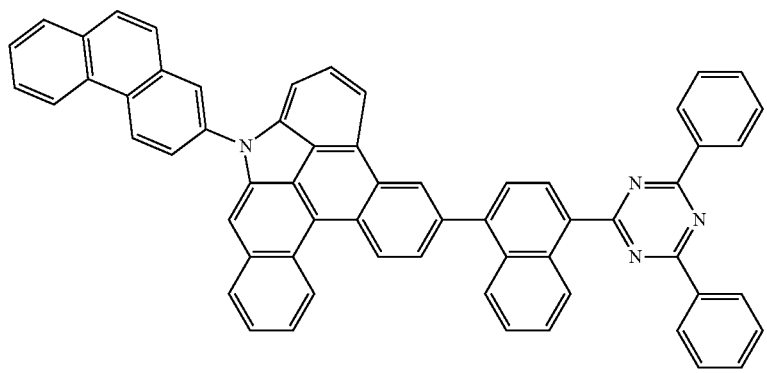
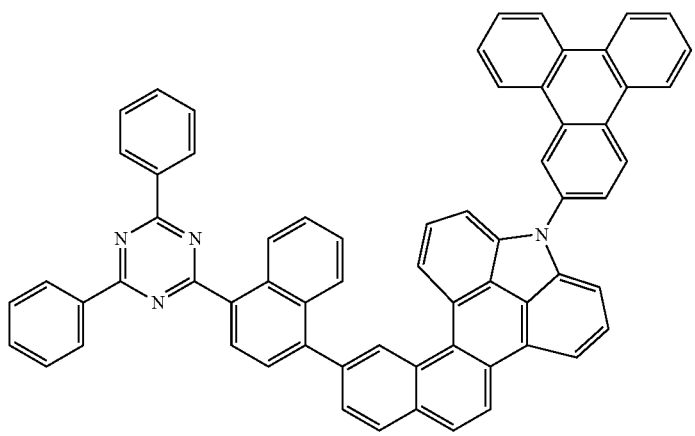
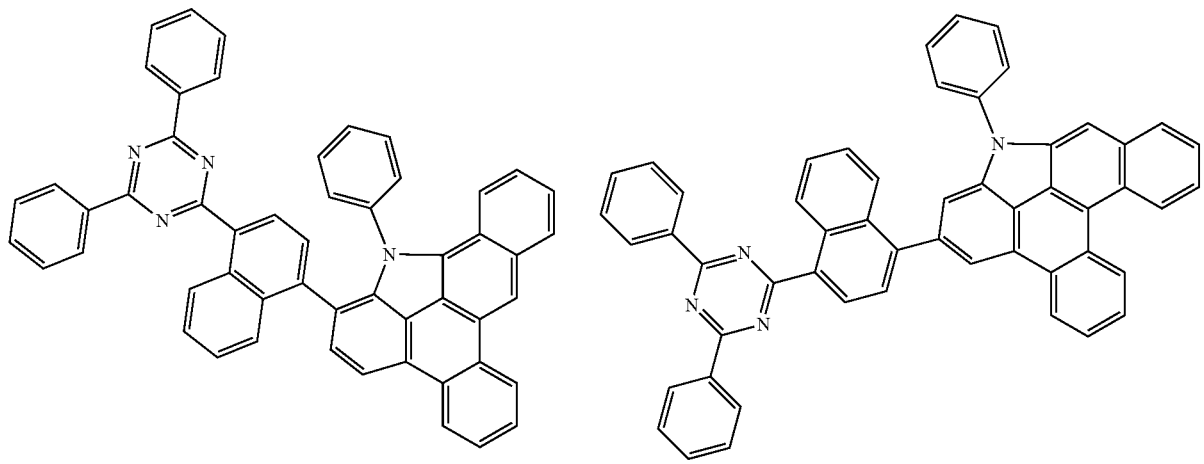

-continued
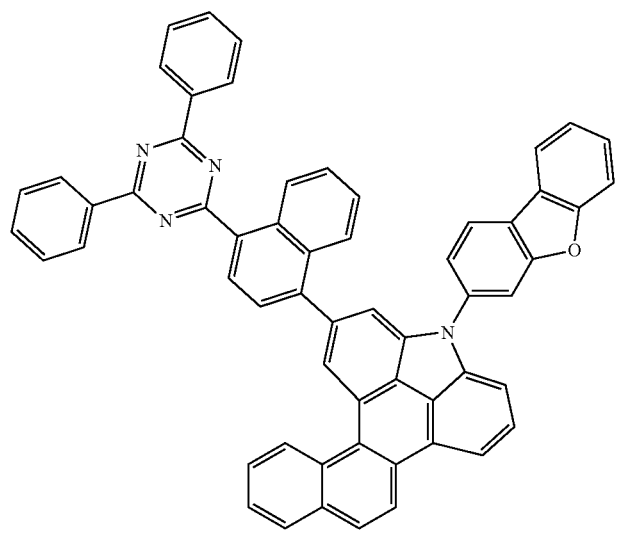
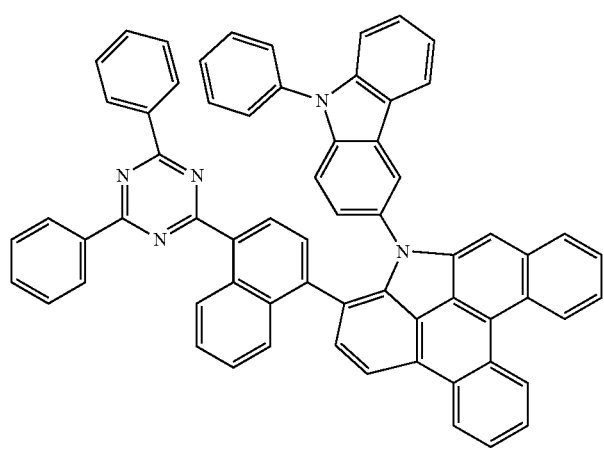
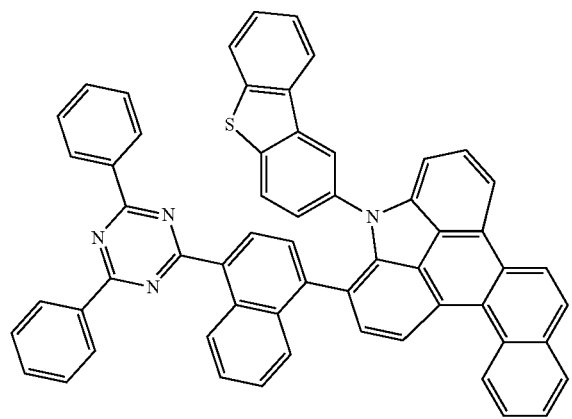
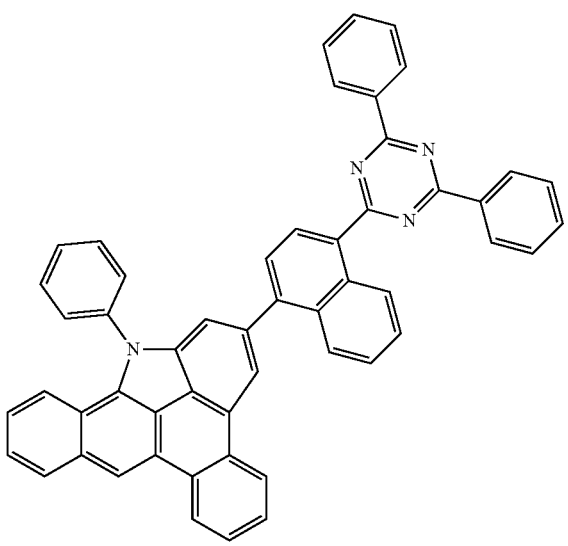

-continued
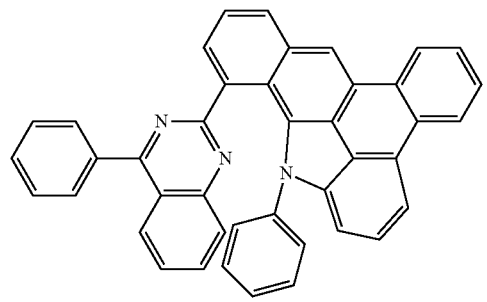
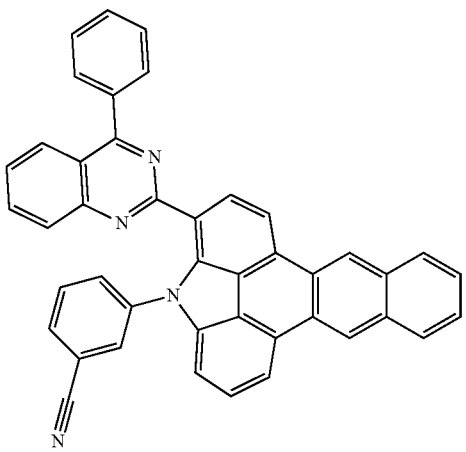
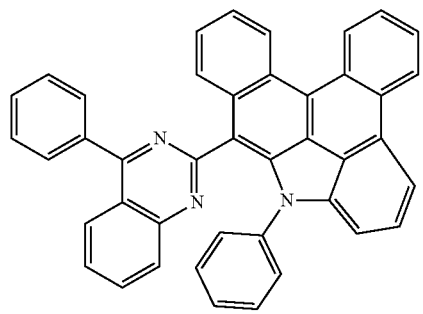
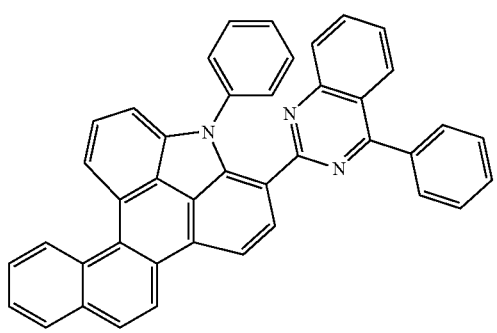
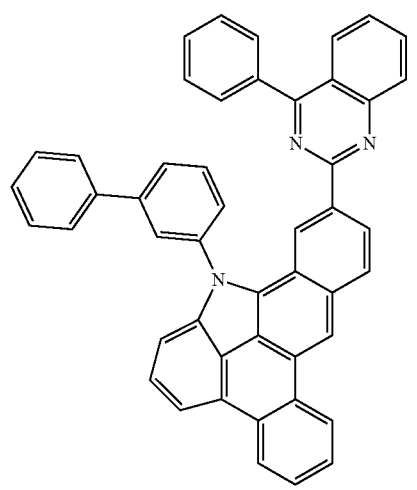
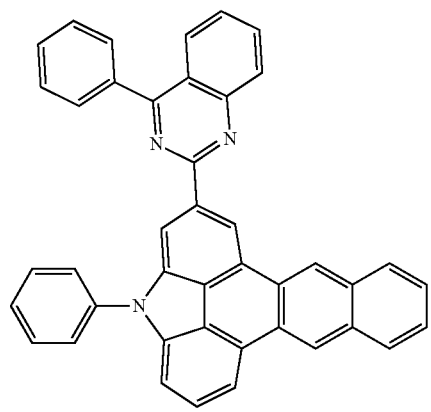
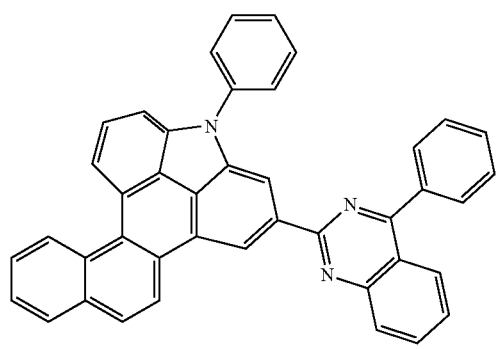
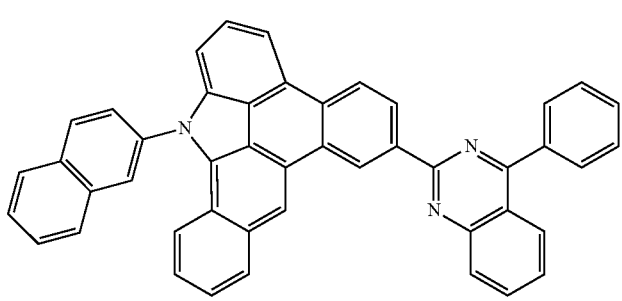

-continued
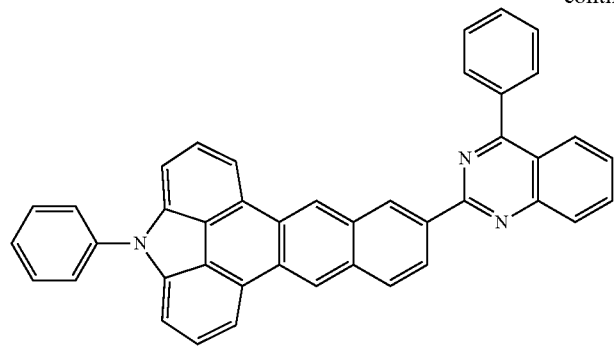
567
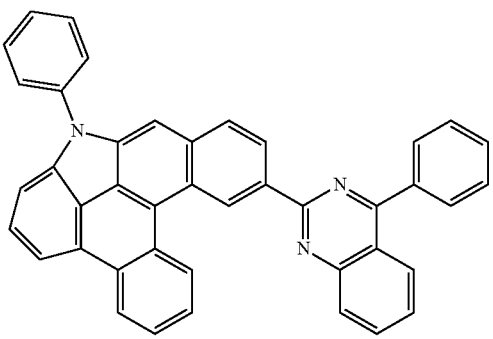
568
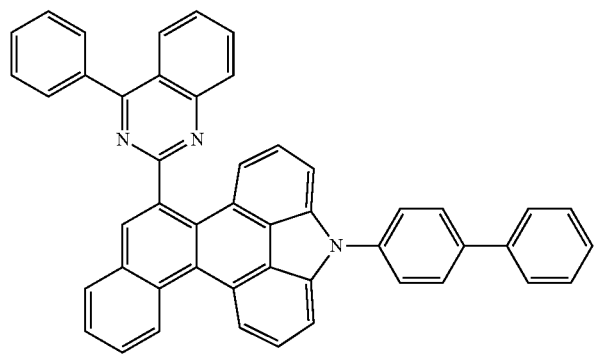
-continued
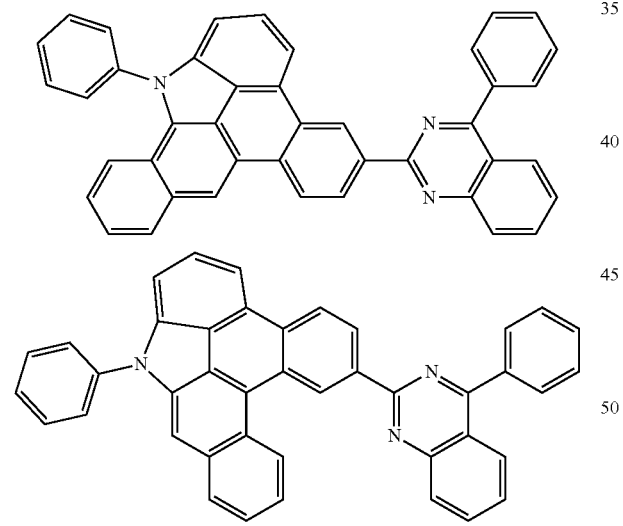
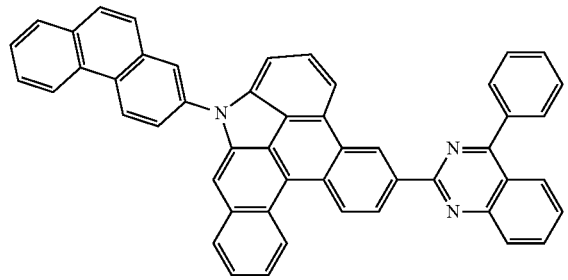
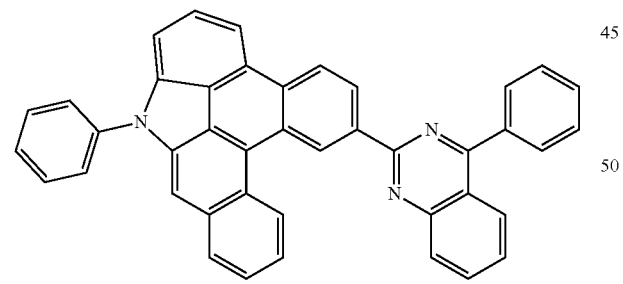
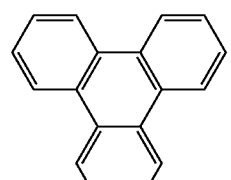
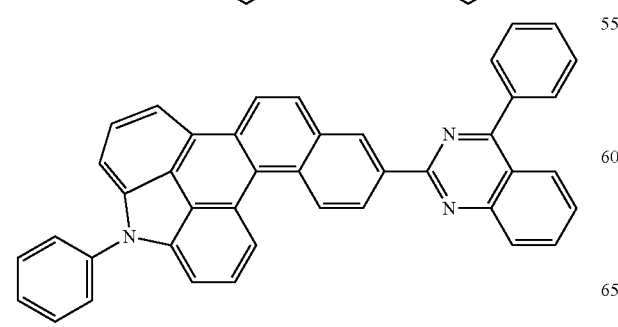
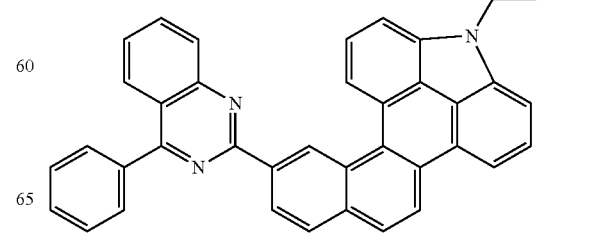

569
-continued
570
-continued
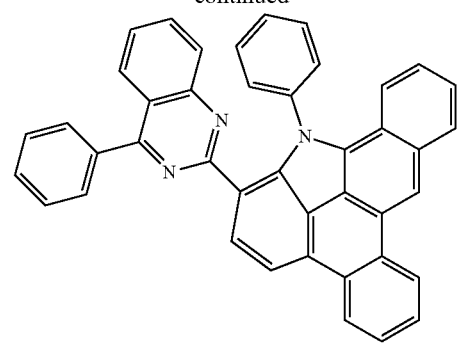
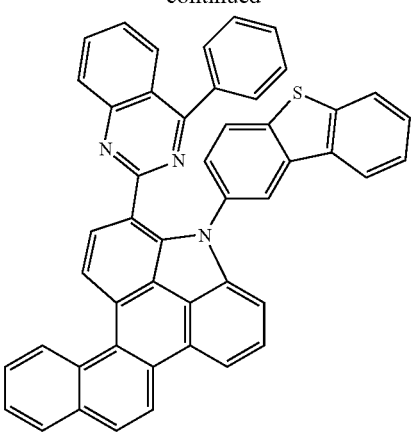
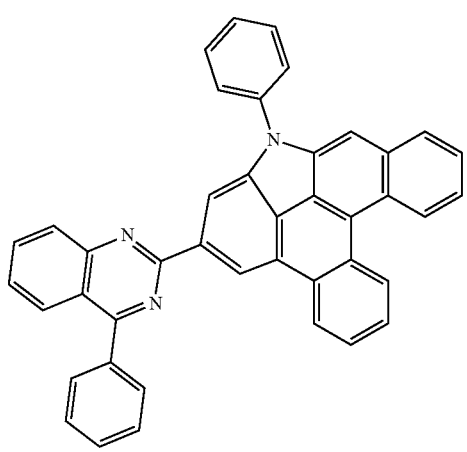
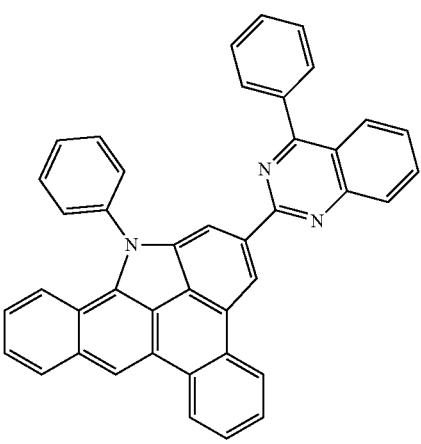
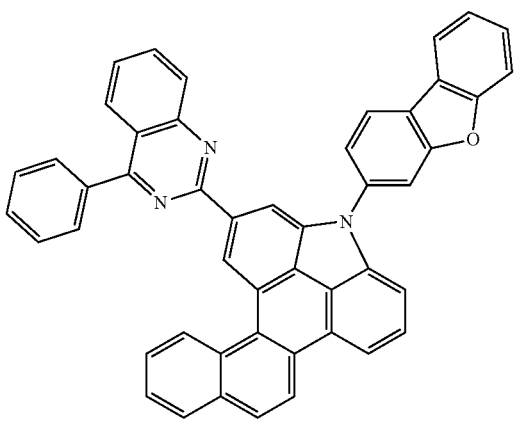
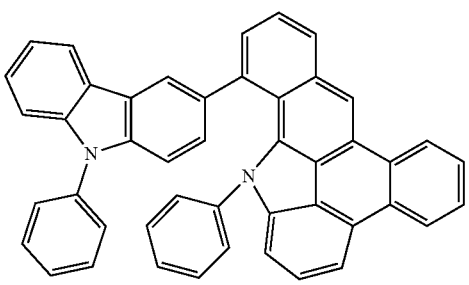
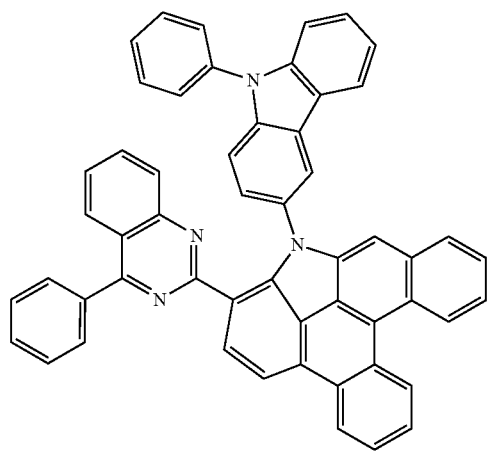
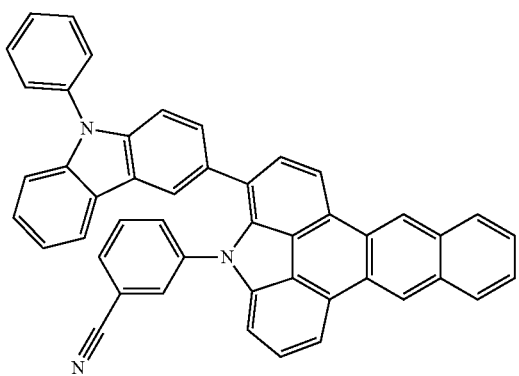

571
-continued
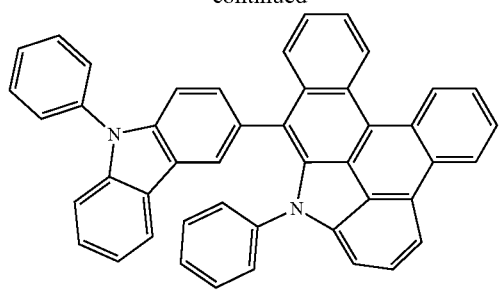
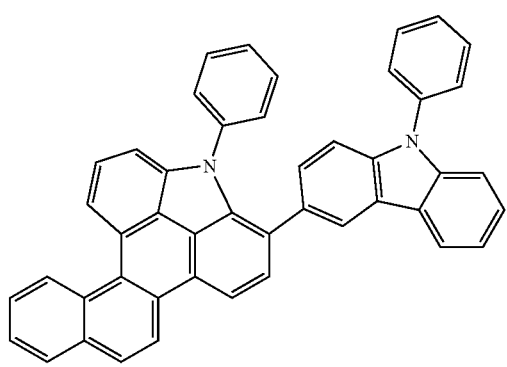
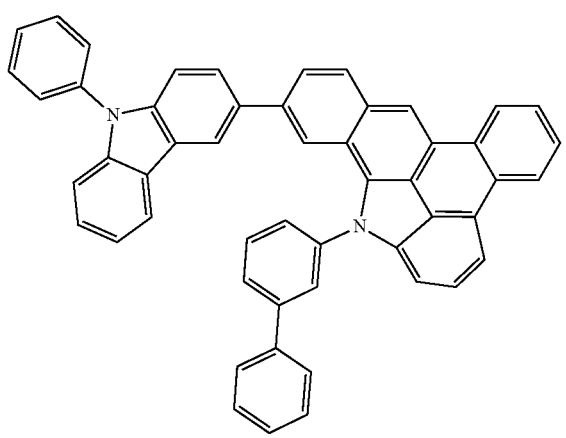
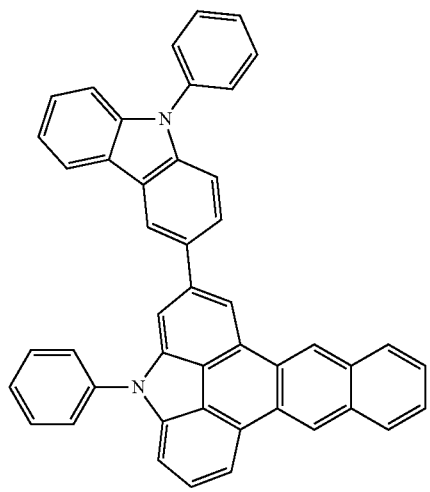
572
-continued
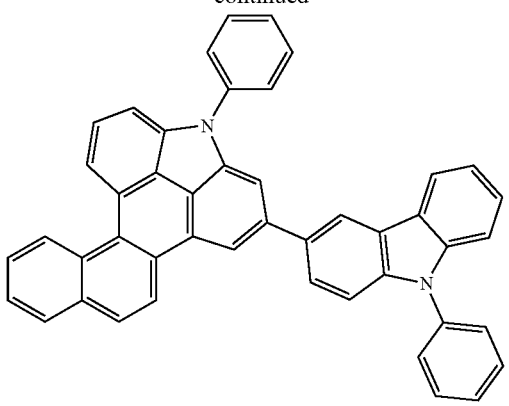
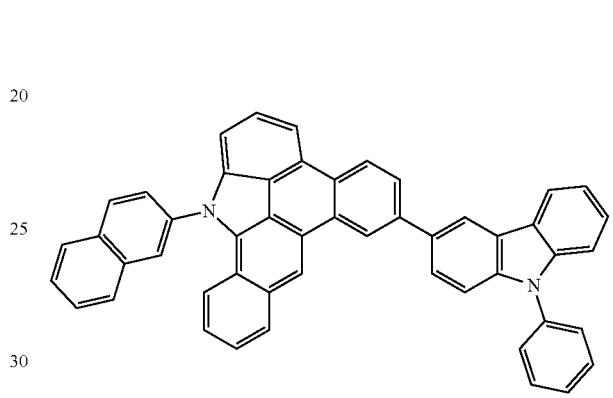
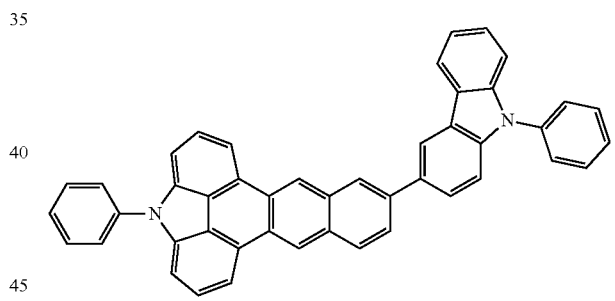
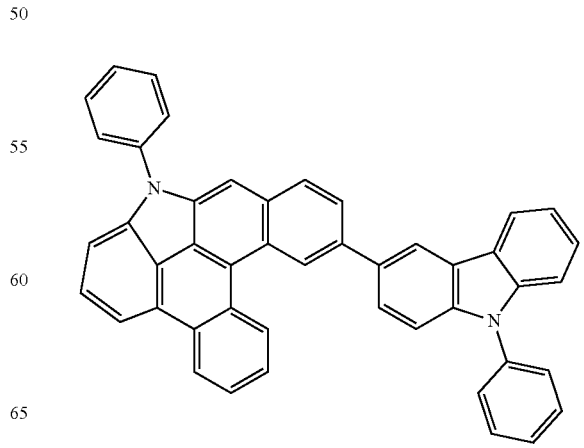

573
-continued
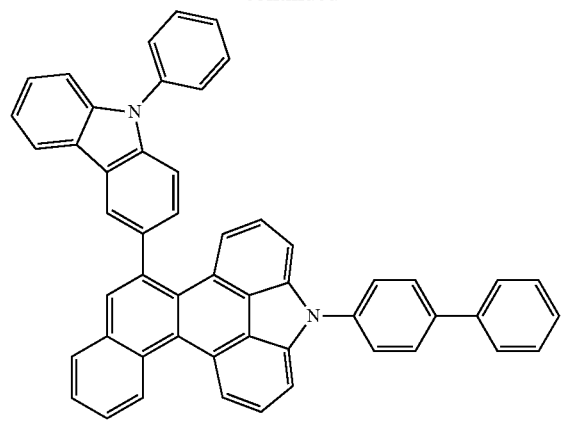
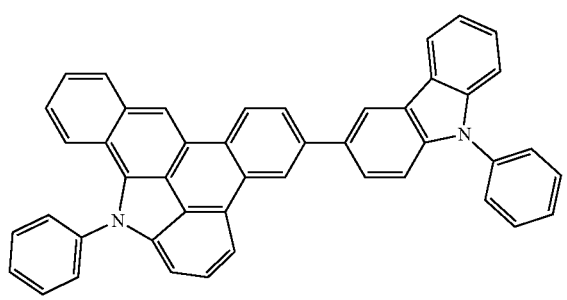
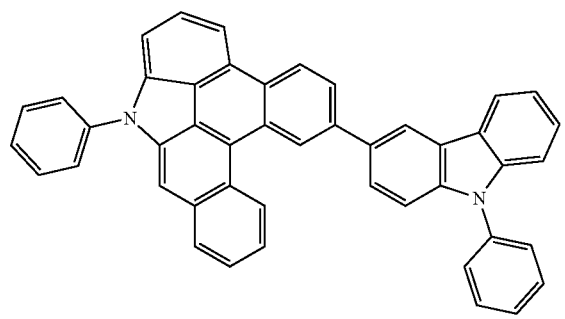
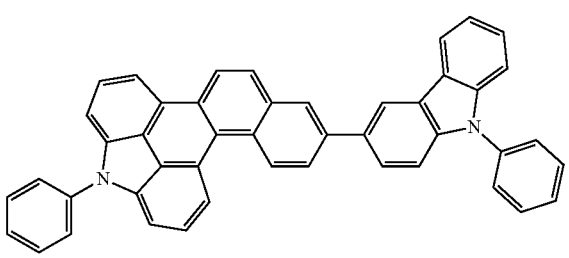
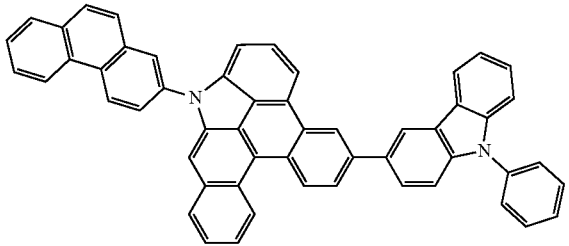
574
-continued
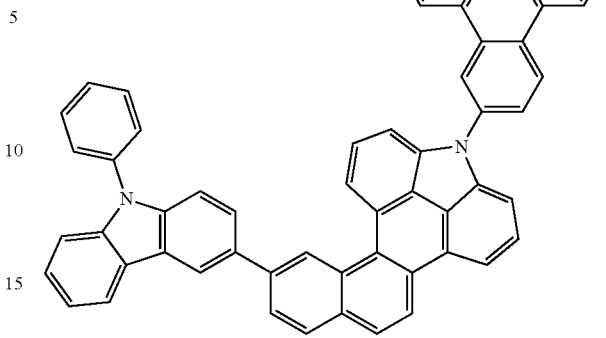
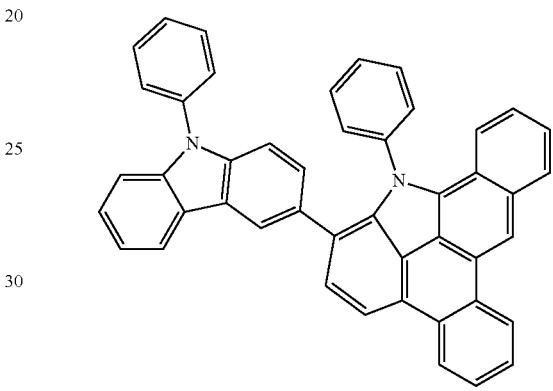
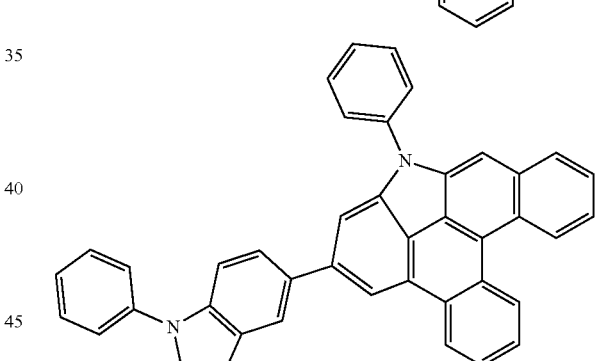
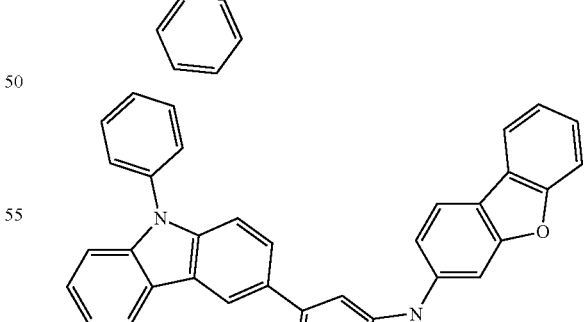
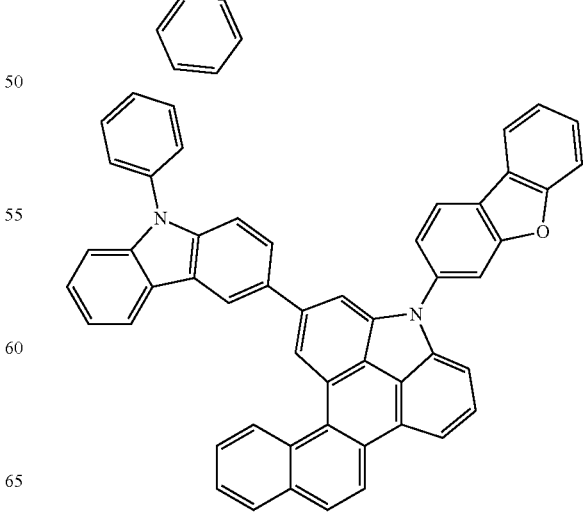

575
-continued
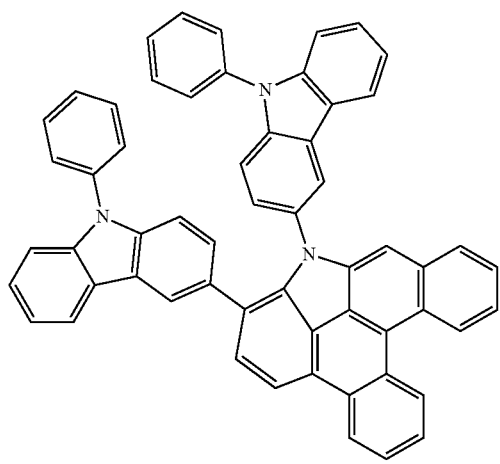
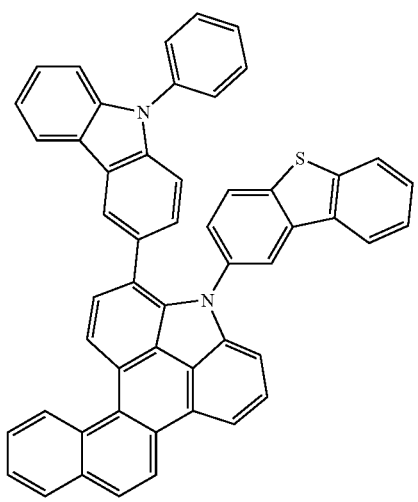
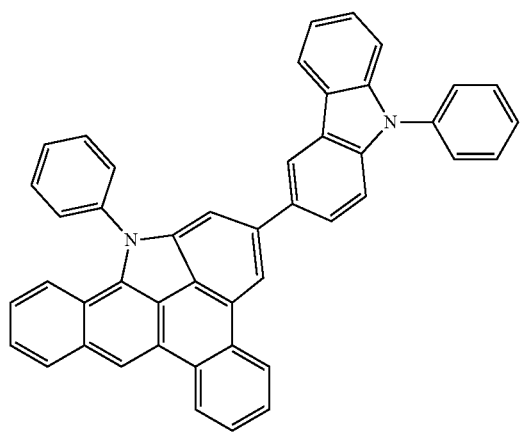
576
-continued
P1c
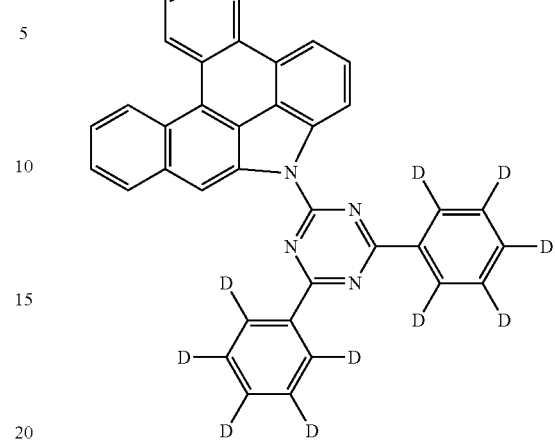
P1d
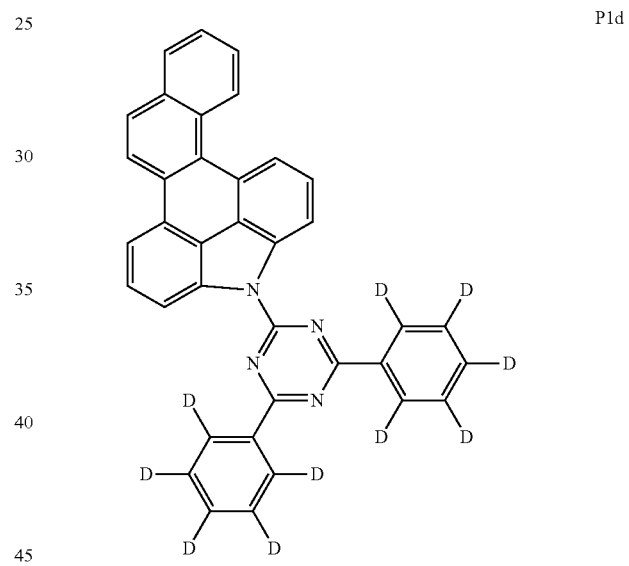
P1e
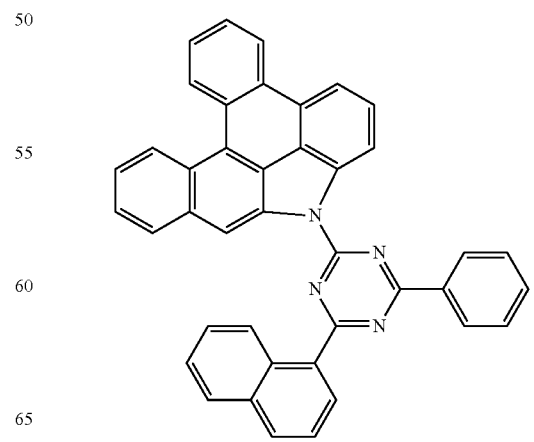

-continued
P1g
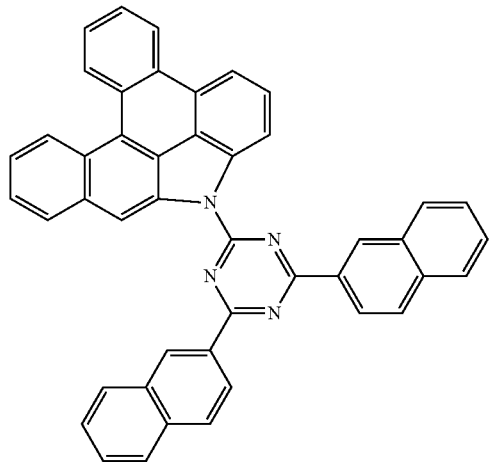
P1k
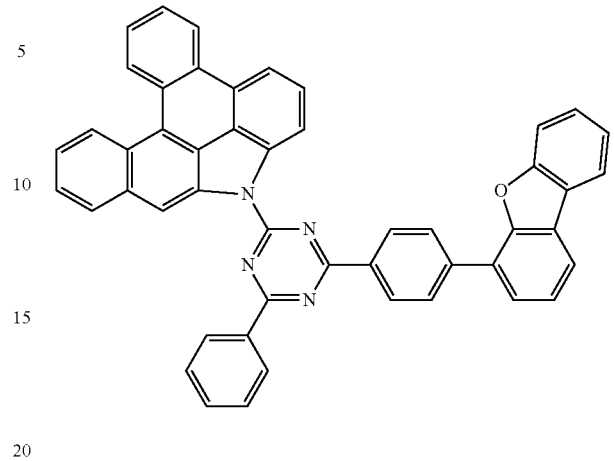
P1h
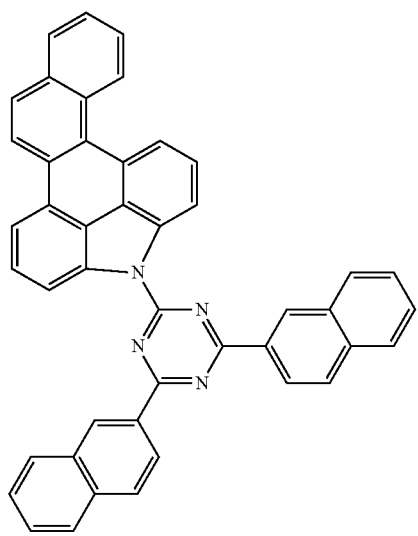
P1l
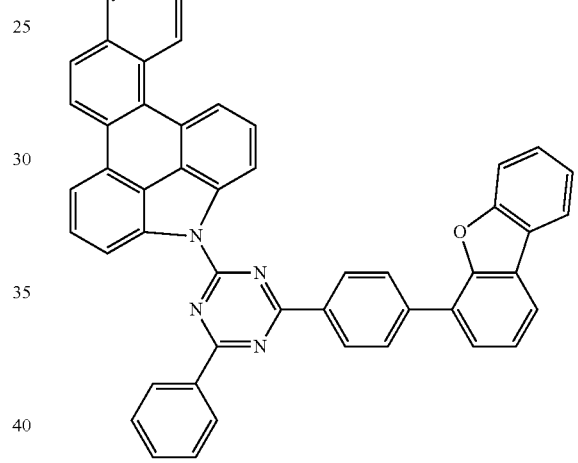
P1j
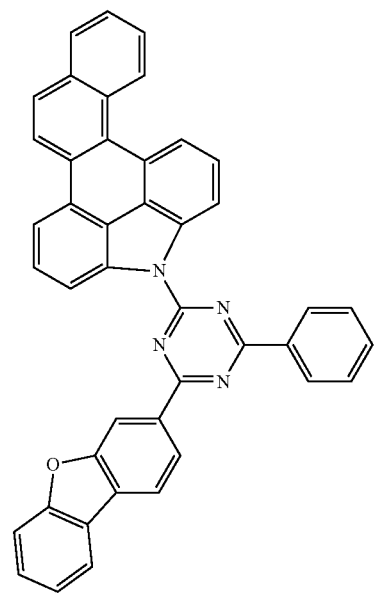
P1m
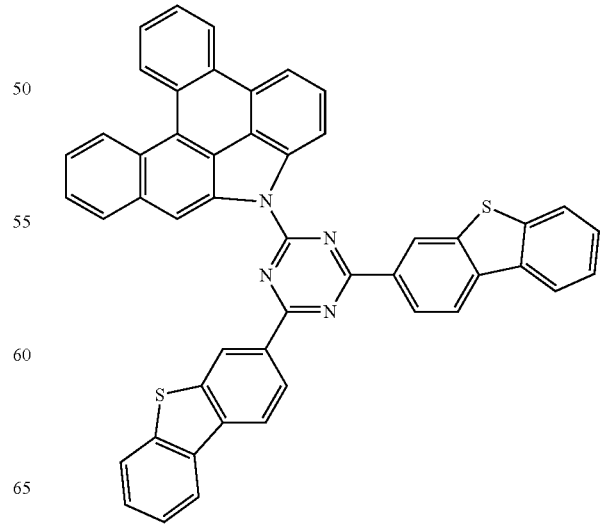

P1n
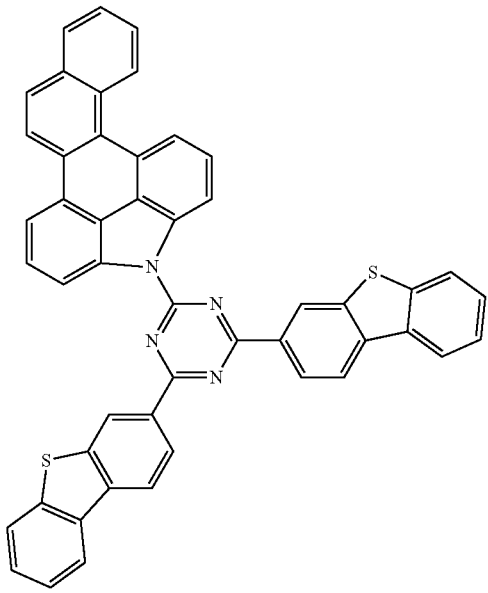
P1o
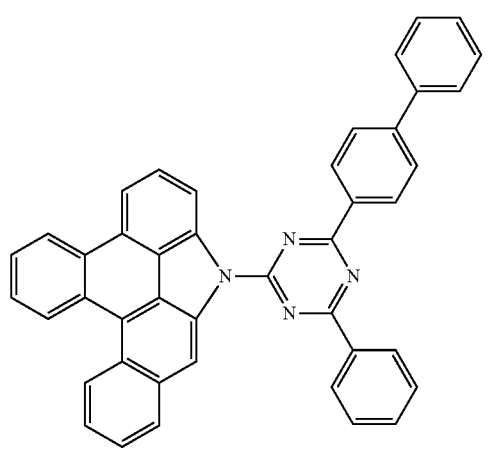
P1p
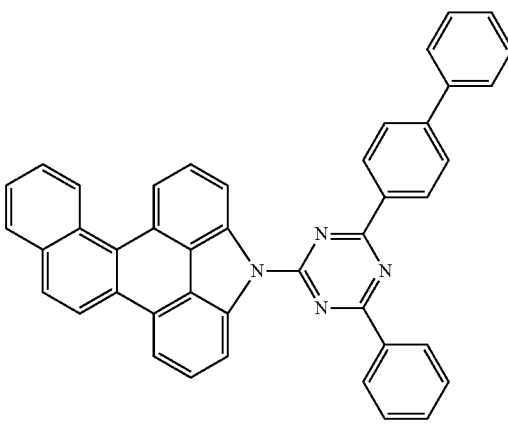
P1q
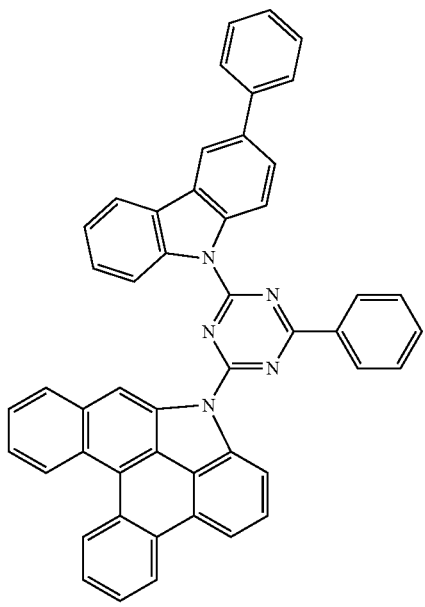
P1r
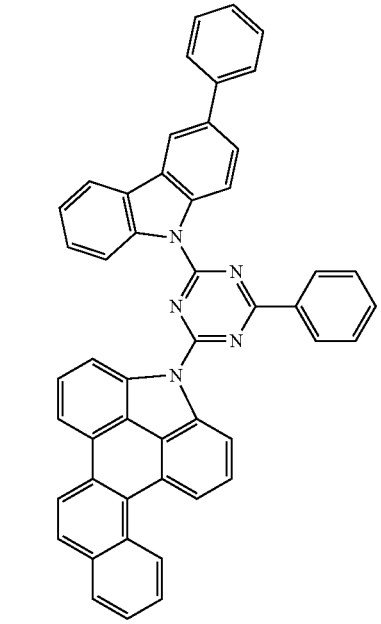
P1s
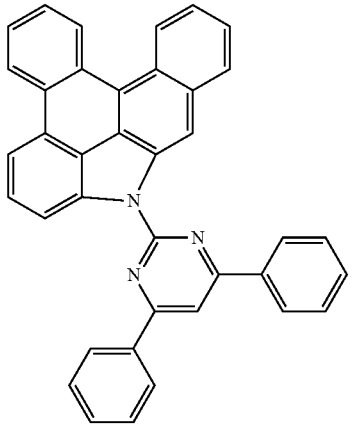

-continued
P1t
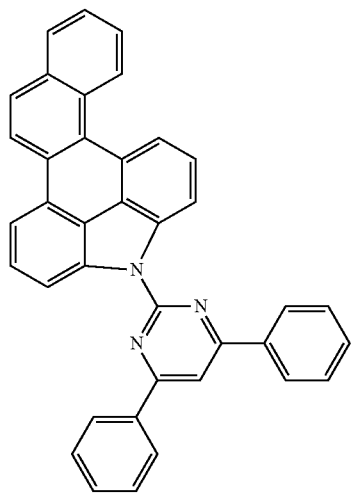
P1w
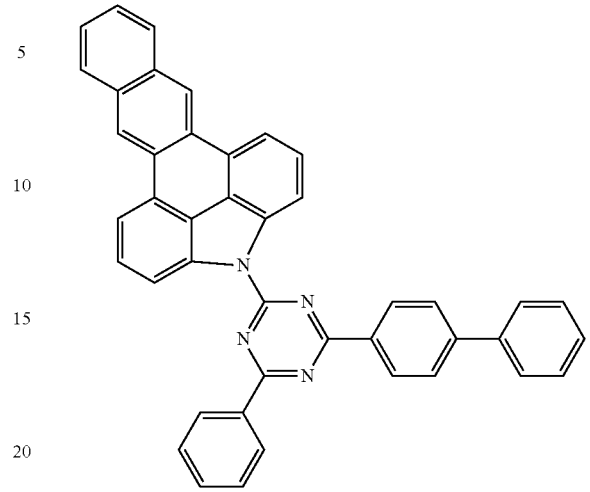
P1u
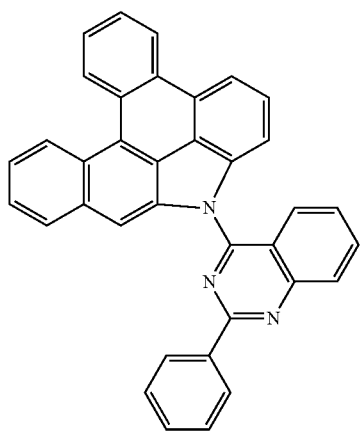
P1x
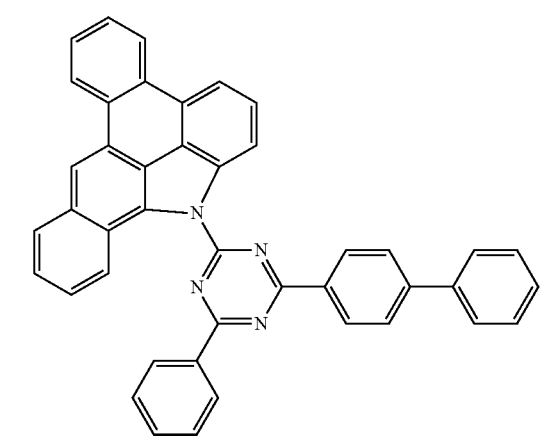
P1v
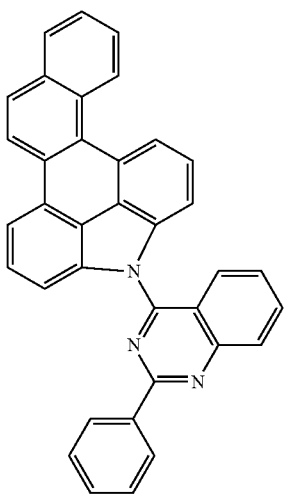
P1y
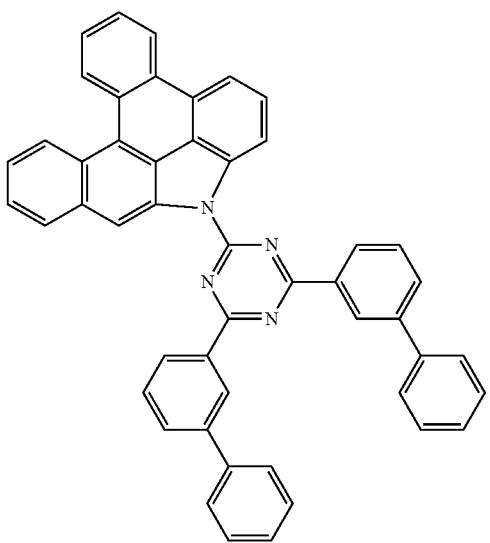

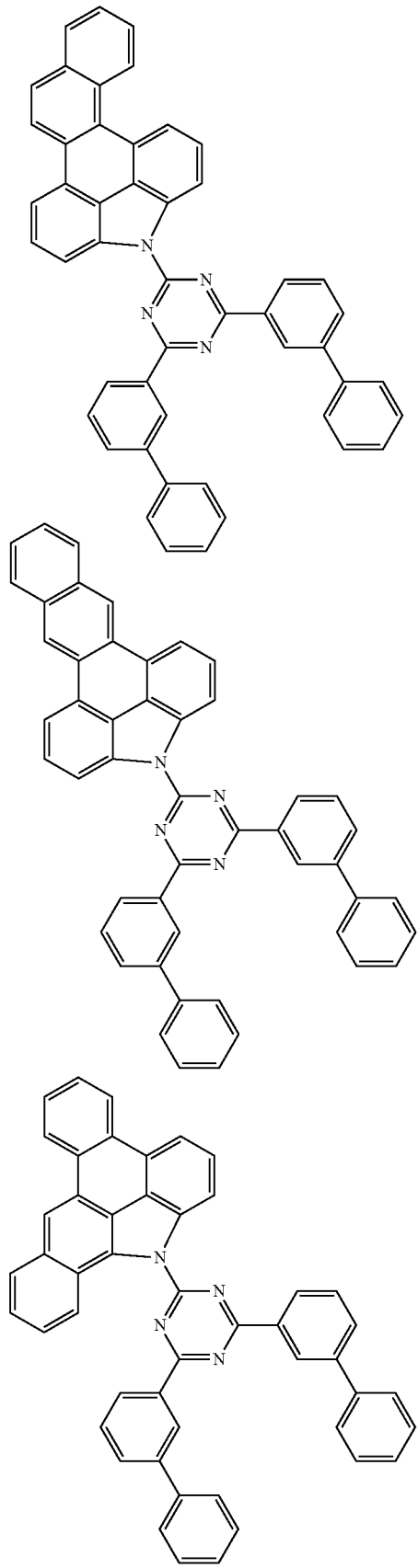
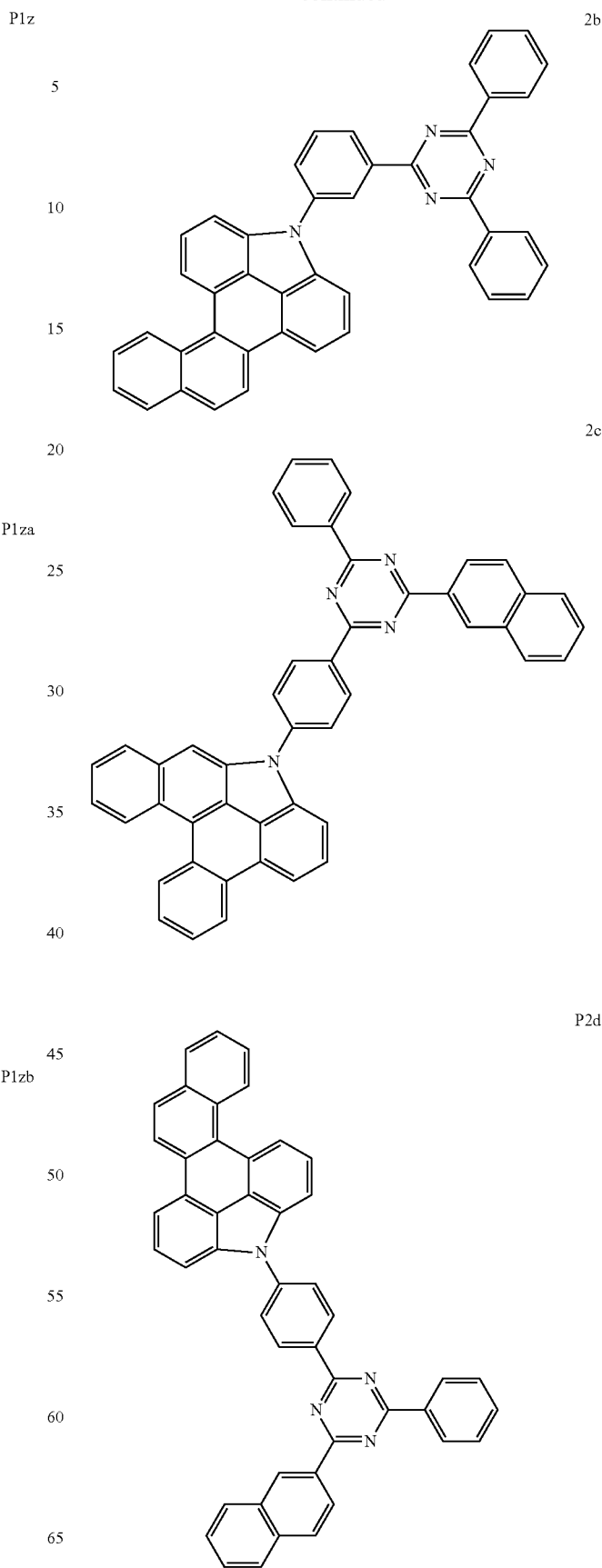

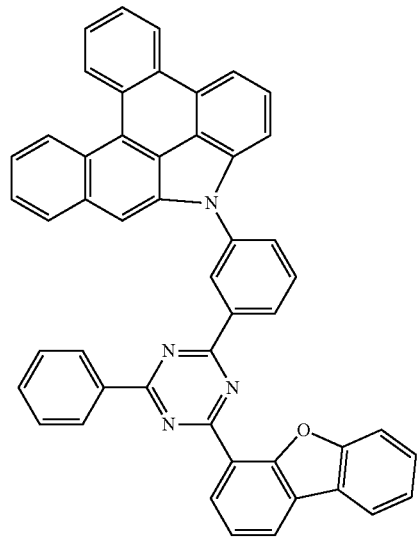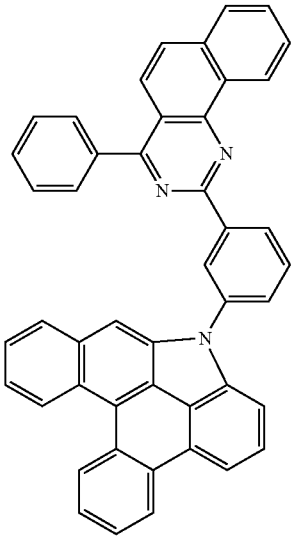

P2l-1
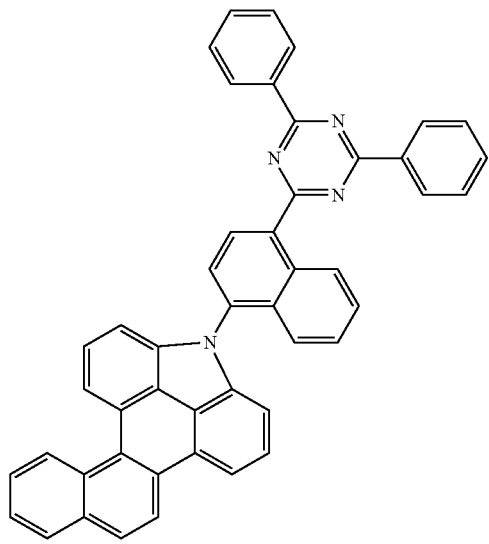
P2l-2
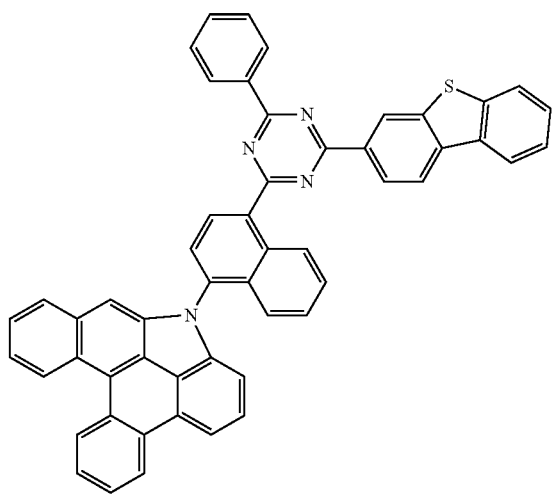
P2m
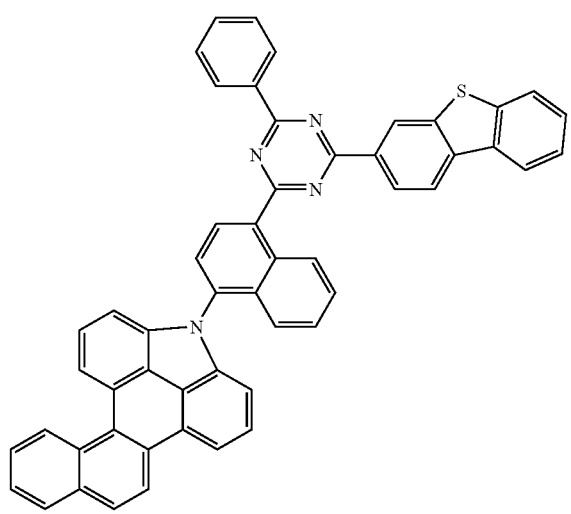
P2n
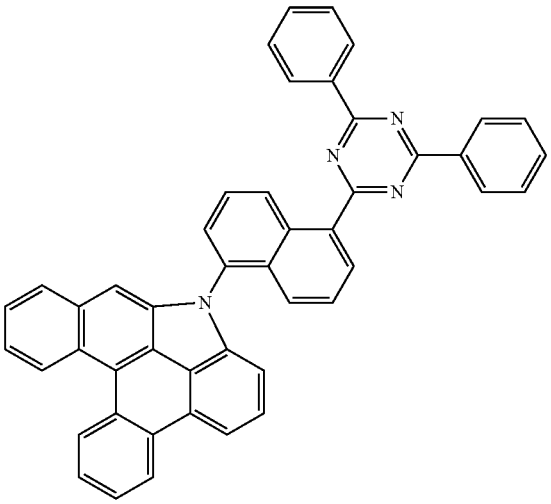
P2o
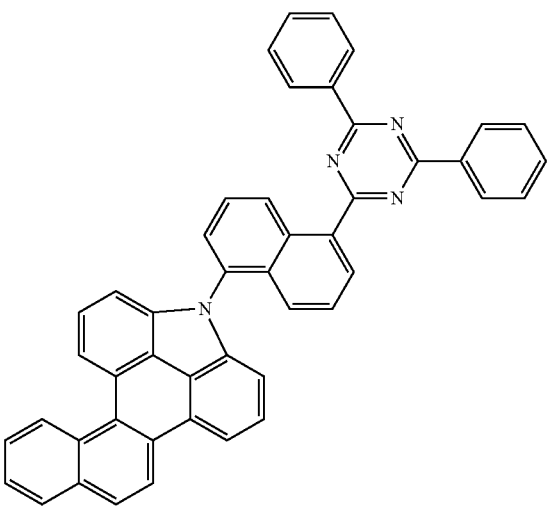
P2p
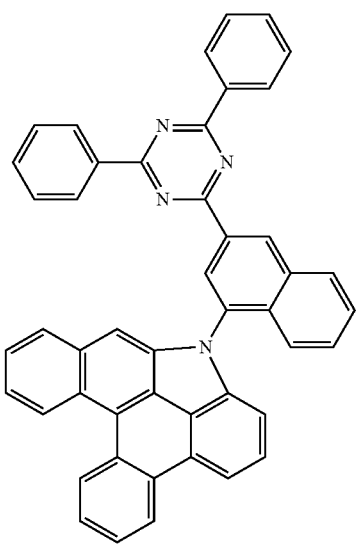

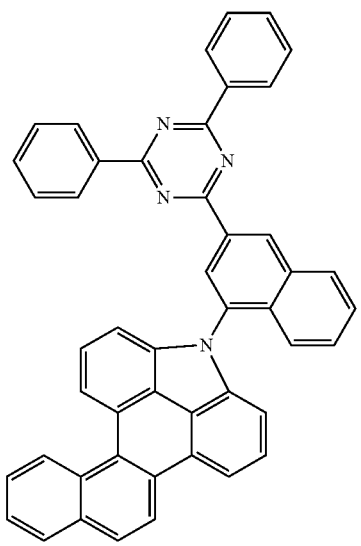
P2q
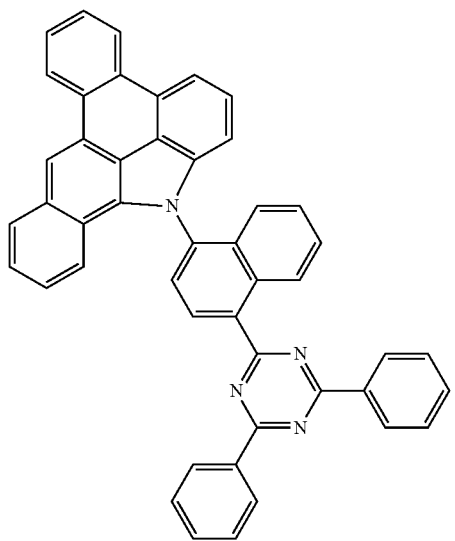
P2s
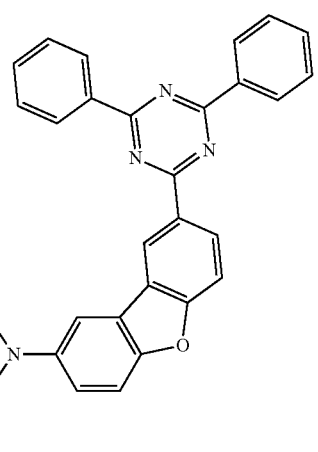
P2t
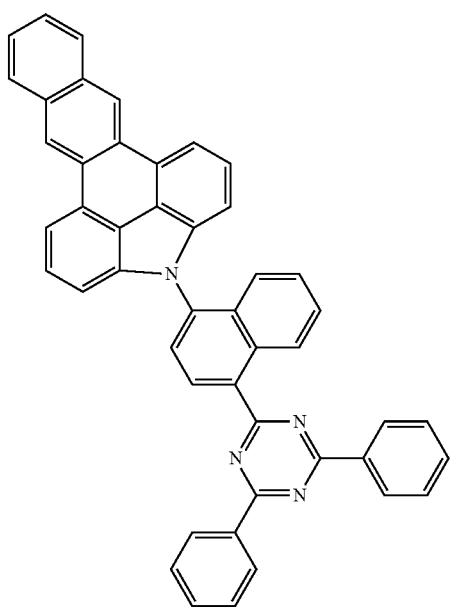
P2r
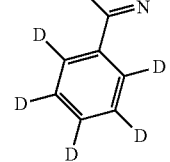
P2u P2v 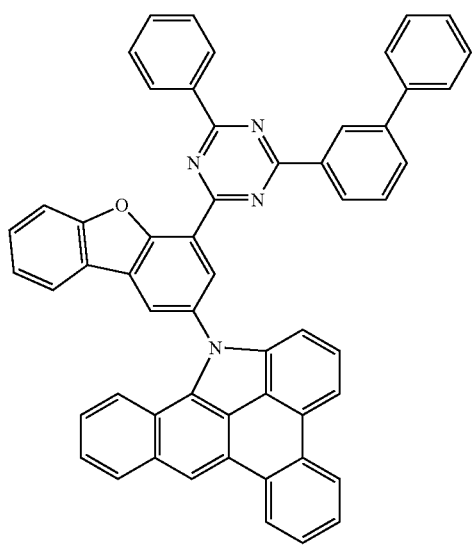
P2w 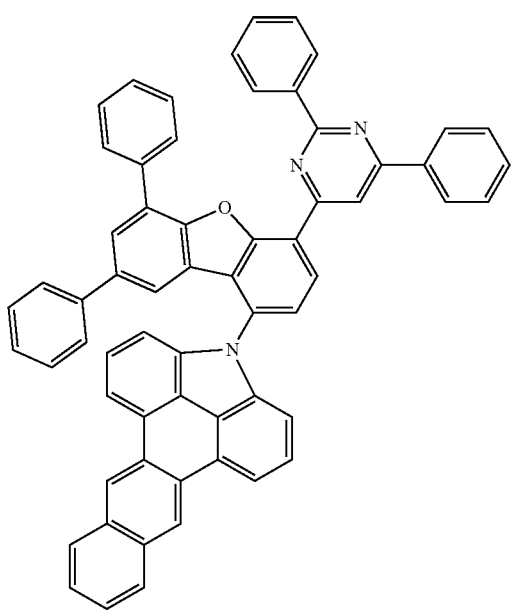
P2x 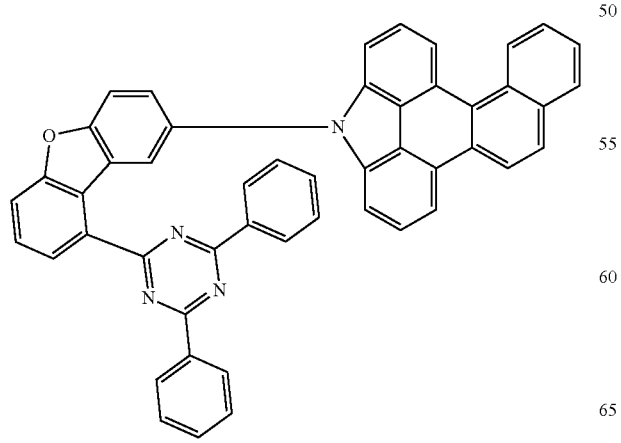
P2y 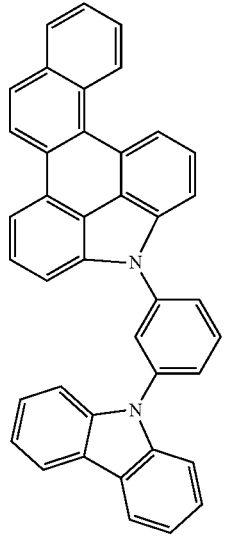
P2z 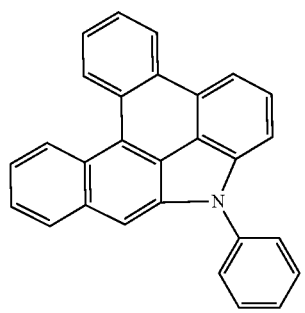
P2za 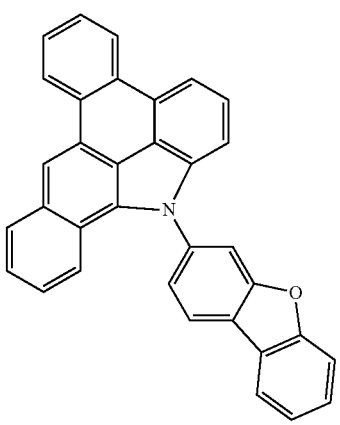

-continued
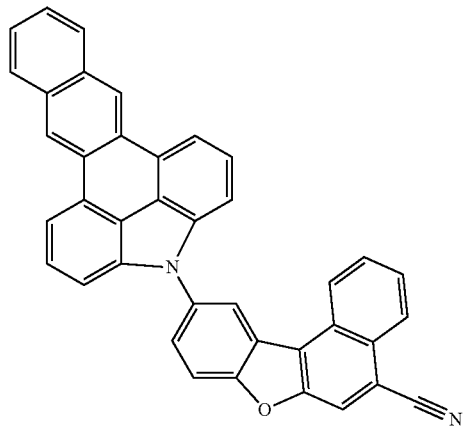
P2zb
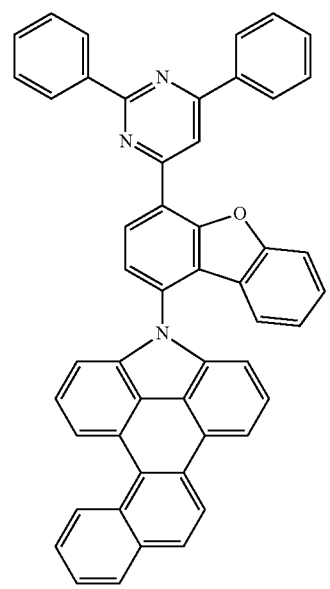
P2zc
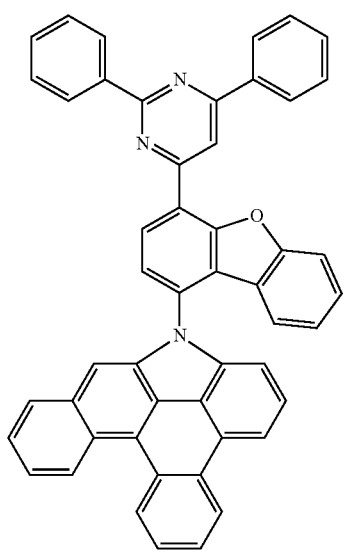
P2zd
-continued
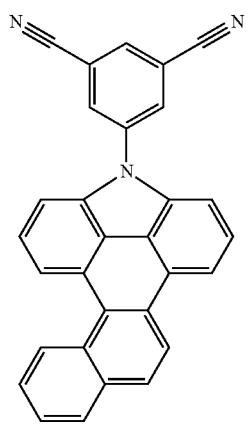
P2ze
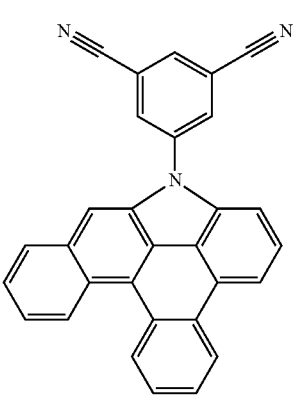
P2zf
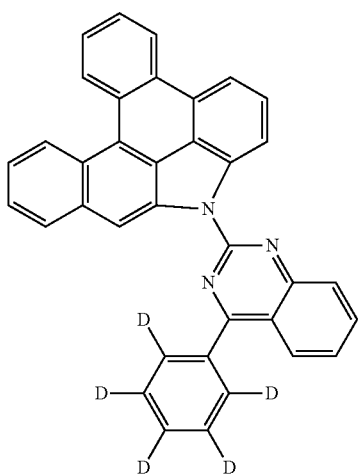
P3a 595
-continued
P3b
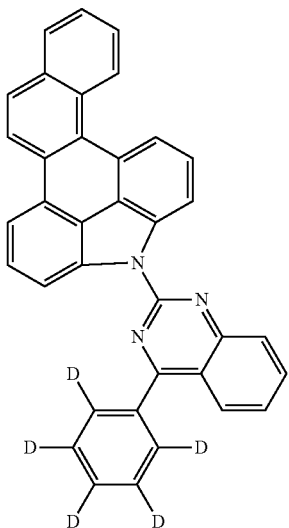
P3c
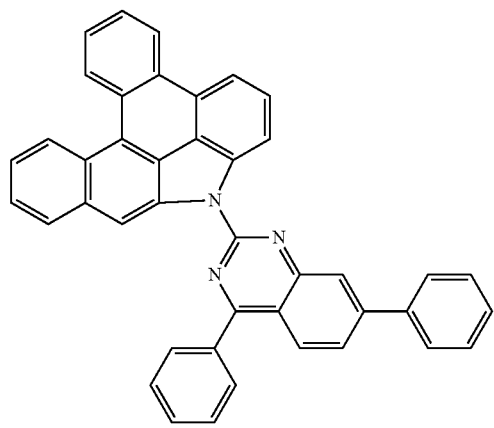
P3d
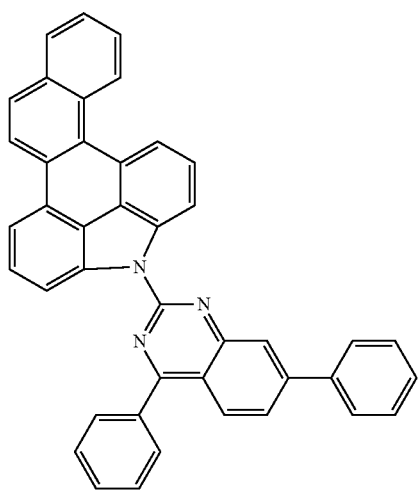
596
-continued
P3e
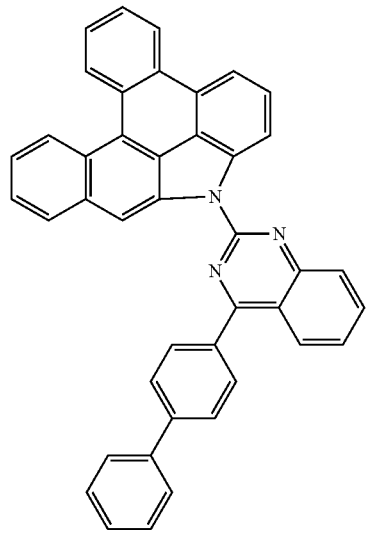
P3f
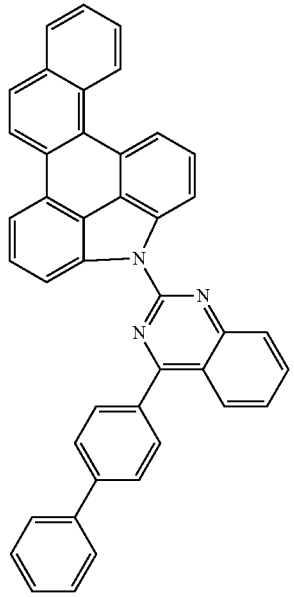
P3g
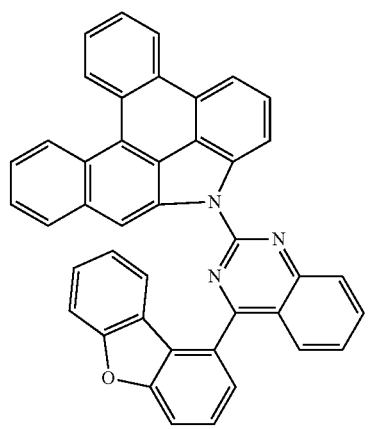

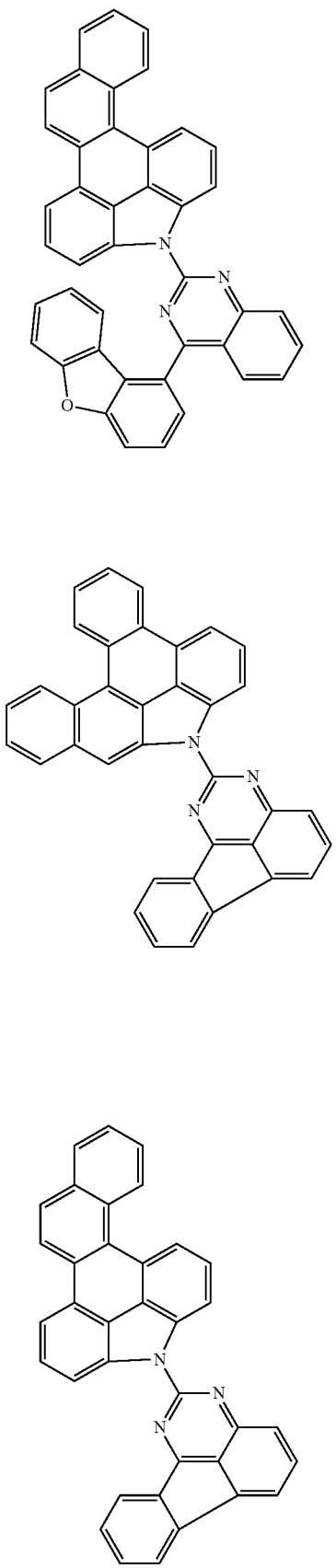
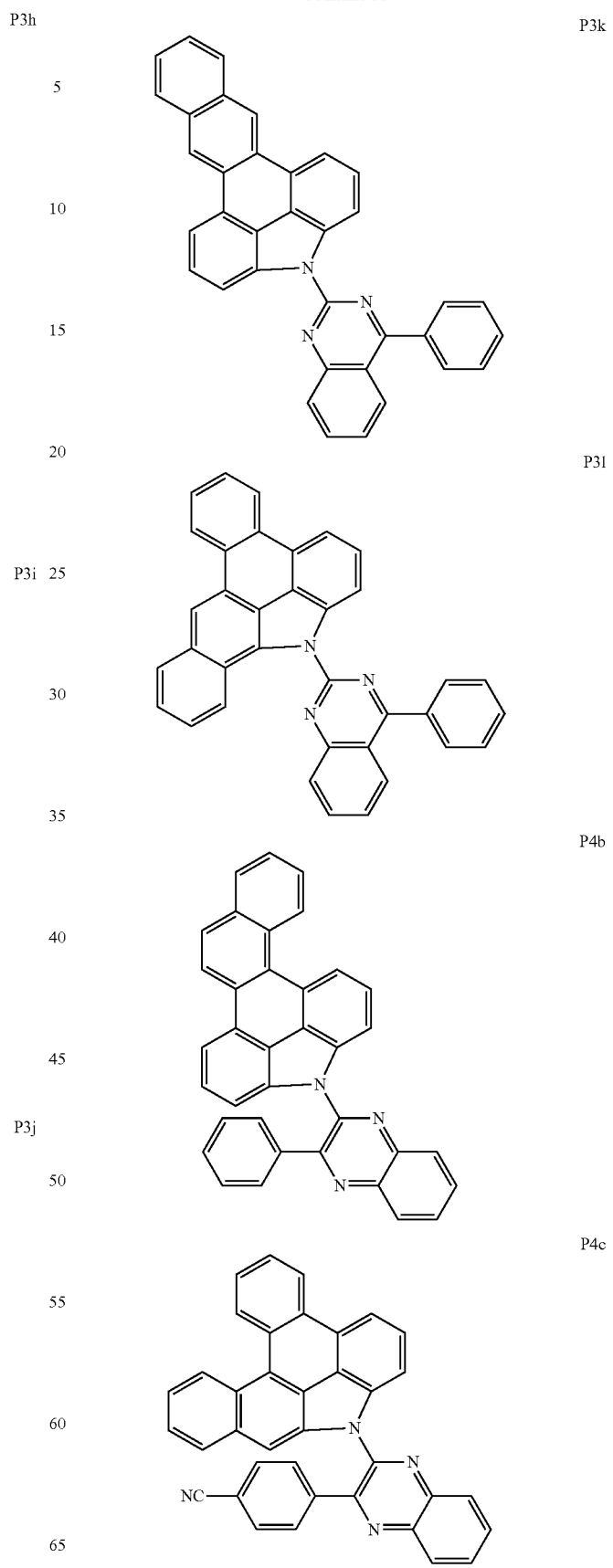

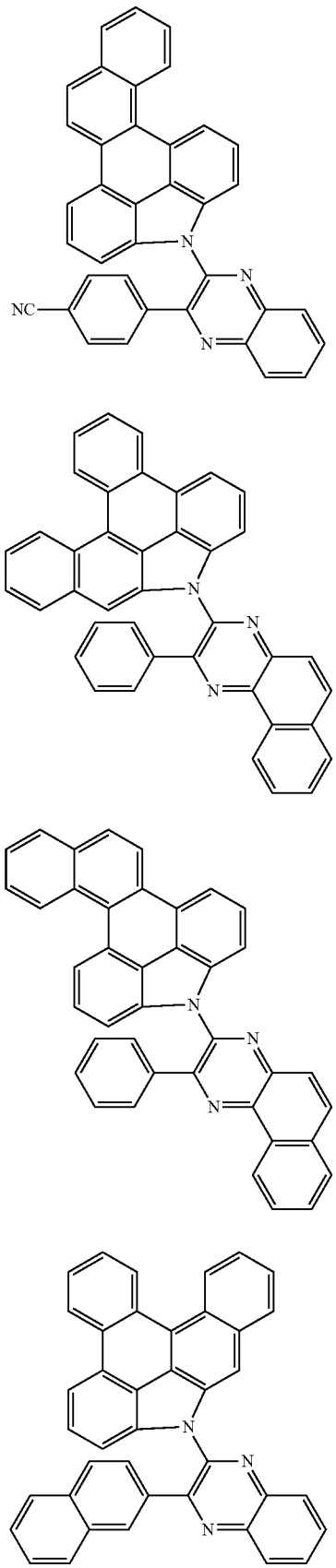
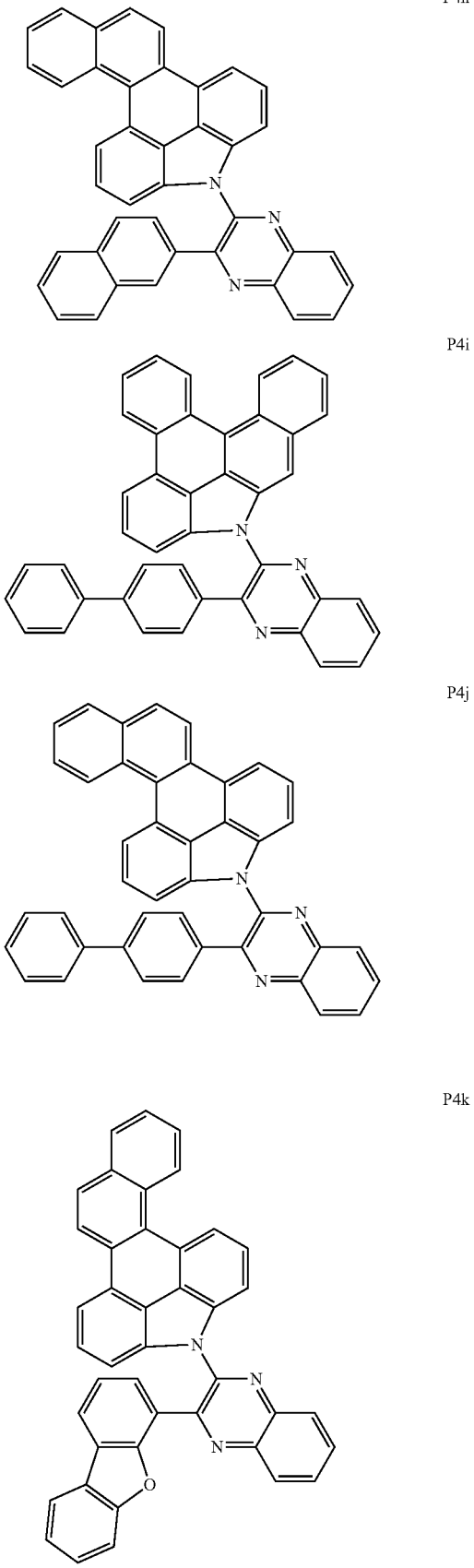

P4l
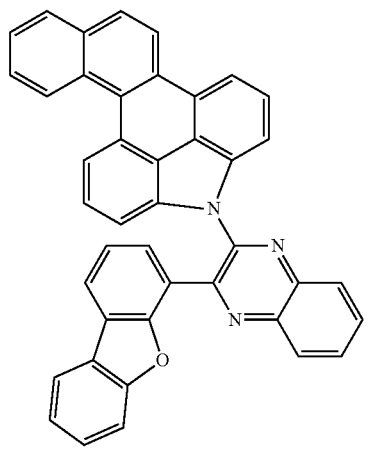
P4m
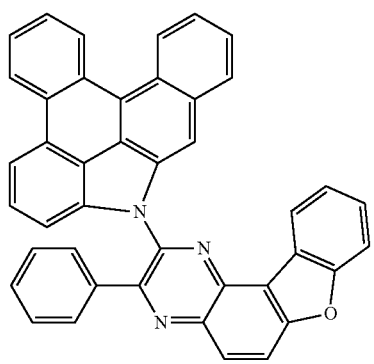
P4n
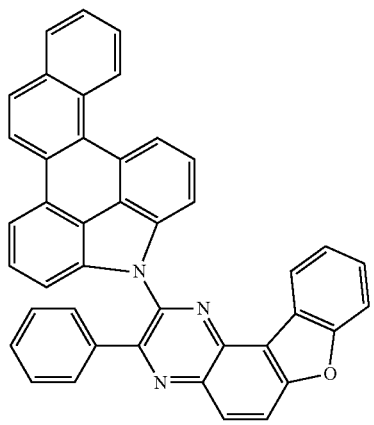 [SMILES: c1ccc(-c2nc3ccc4oc5ccccc5c4c3nc2-n2c3cccc4c5ccc6ccccc6c5c5cccc2c5c43)cc1]
P4o
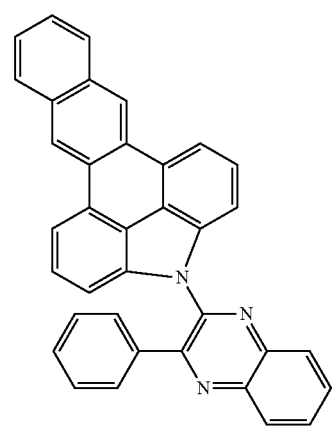 [SMILES: c1ccc(-c2nc3ccccc3nc2-n2c3cccc4c5cc6ccccc6cc5c5cccc2c5c43)cc1]
P5a
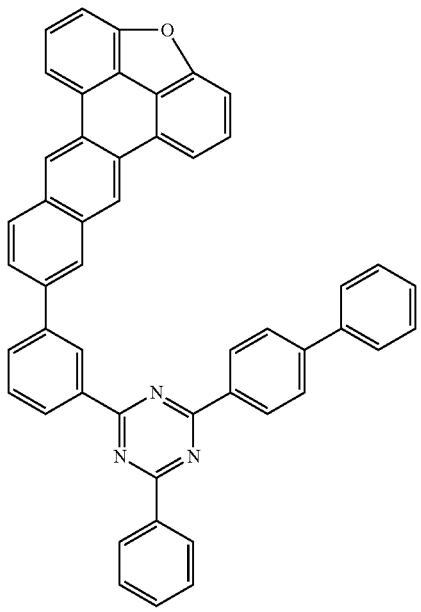
P5b
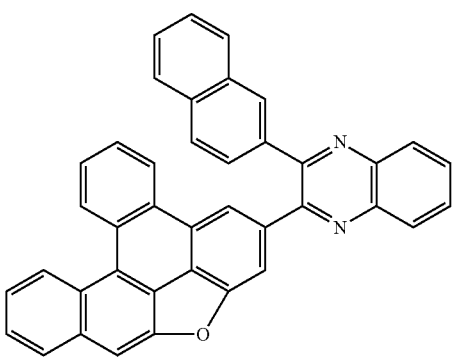 [SMILES: c1ccc2cc(-c3nc4ccccc4nc3-c3cc4oc5cc6ccccc6c6c7ccccc7c(c3)c4c56)ccc2c1]
P5c
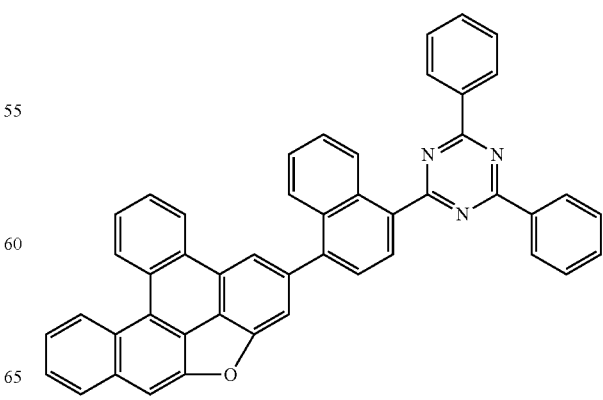

P5e
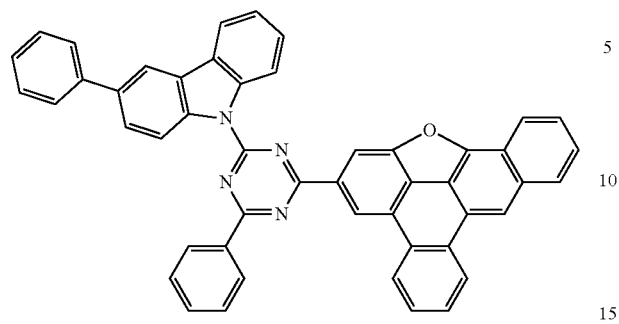
P5j
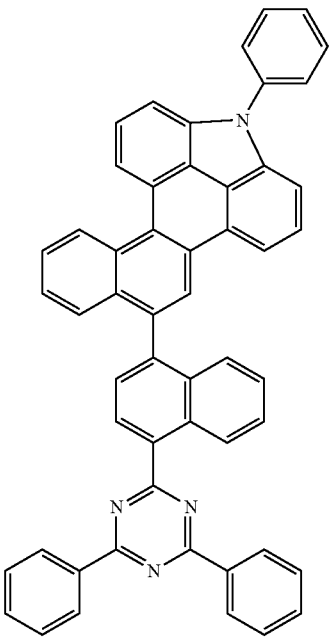
P5f
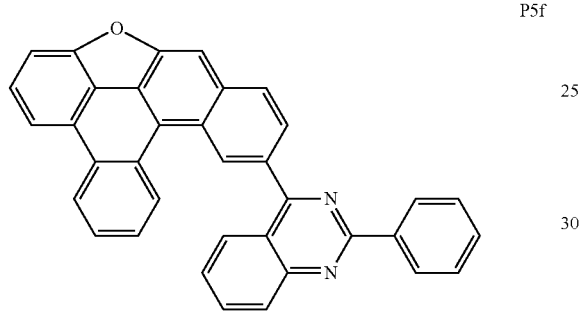
P5i
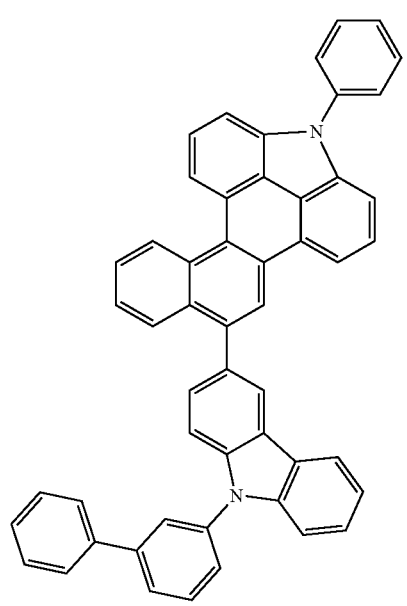 [SMILES: c1ccc(-c2cccc(-n3c4ccccc4c4cc(-c5cc6c7cccc8c7c7c(cccc7n8-c7ccccc7)c6c6ccccc56)ccc43)c2)cc1]
P5k
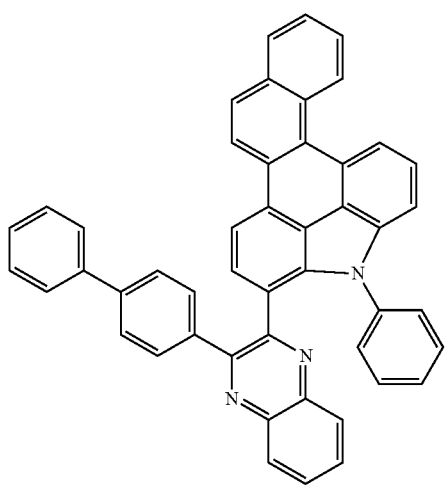 [SMILES: c1ccc(-c2ccc(-c3nc4ccccc4nc3-c3ccc4c5ccc6ccccc6c5c5cccc6c5c4c3n6-c3ccccc3)cc2)cc1]

P5l
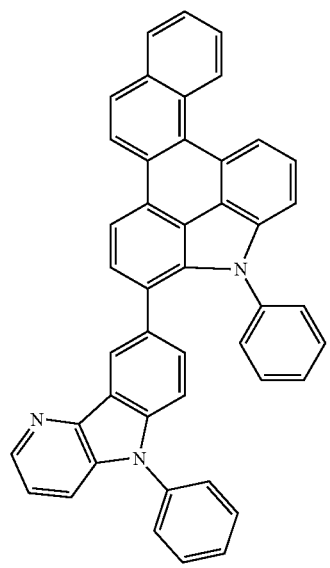 [SMILES: c1ccc(-n2c3ccc(-c4ccc5c6ccc7ccccc7c6c6cccc7c6c5c4n7-c4ccccc4)cc3c3ncccc32)cc1]
P5m
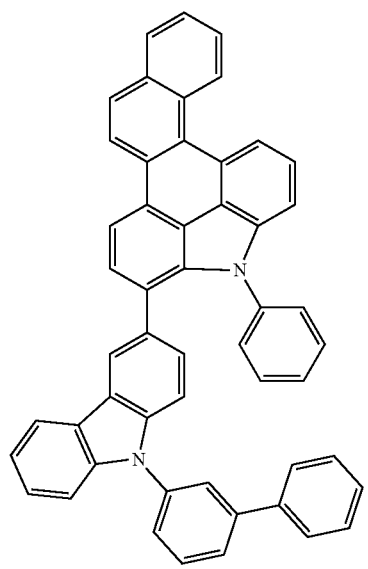 [SMILES: c1ccc(-c2cccc(-n3c4ccccc4c4cc(-c5ccc6c7ccc8ccccc8c7c7cccc8c7c6c5n8-c5ccccc5)ccc43)c2)cc1]
P5n
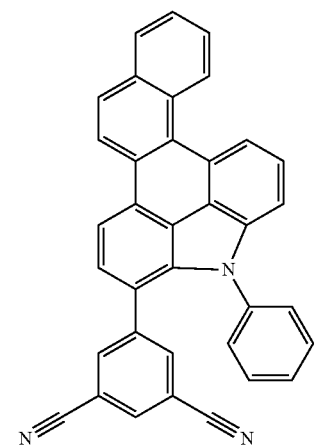
P5o
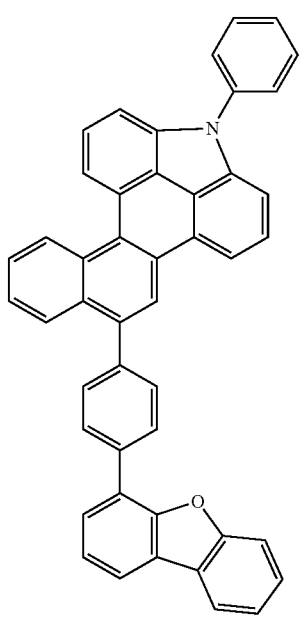
P5p
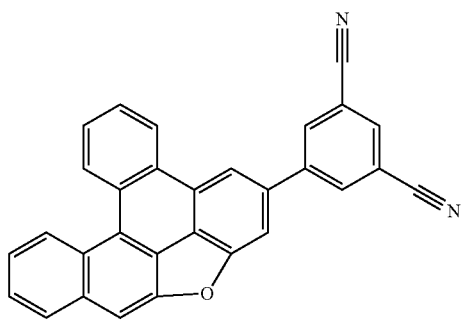 [SMILES: N#Cc1cc(C#N)cc(-c2cc3oc4cc5ccccc5c5c6ccccc6c(c2)c3c45)c1]
P5q
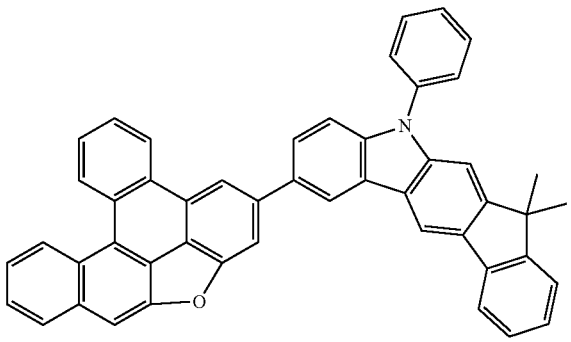 [SMILES: CC1(C)c2ccccc2-c2cc3c4cc(-c5cc6oc7cc8ccccc8c8c9ccccc9c(c5)c6c78)ccc4n(-c4ccccc4)c3cc21]

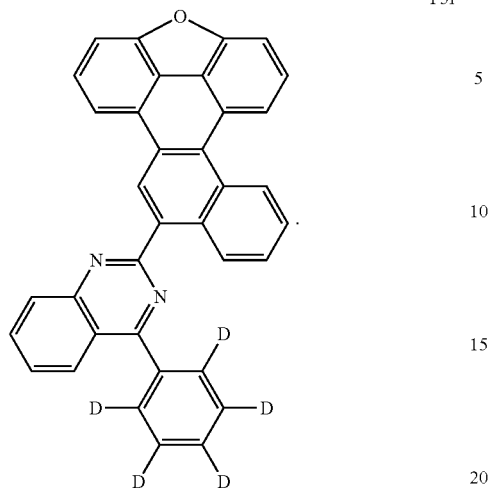
P5r
* * * * *